(12) United States Patent
Artis et al.

(10) Patent No.: US 11,814,404 B2
(45) Date of Patent: Nov. 14, 2023

(54) INHIBITORS OF COMPLEMENT FACTORS AND USES THEREOF

(71) Applicant: Annexon, Inc., Brisbane, CA (US)

(72) Inventors: Dean R. Artis, Kensington, CA (US); Colin P. Leslie, Pozzolengo (IT); Luca B. Mileo, San Giovanni Lupatoto (IT); Claudia Beato, Castel D'azzano (IT); Federico Sorana, Verona (IT); Bruno Di Guglielmo, Verona (IT); Chiara Padroni, Villafranca di Verona (IT)

(73) Assignees: ANNEXON, INC., South San Francisco, CA (US); APTUIT (VERONA) SRL, Verona (IT)

( * ) Notice: Subject to any disclaimer, the term of this patent is extended or adjusted under 35 U.S.C. 154(b) by 112 days.

(21) Appl. No.: 17/379,334

(22) Filed: Jul. 19, 2021

(65) Prior Publication Data

US 2022/0048930 A1 Feb. 17, 2022

Related U.S. Application Data

(60) Provisional application No. 63/054,064, filed on Jul. 20, 2020.

(51) Int. Cl.
| | | |
|---|---|---|
| *C07F 5/02* | (2006.01) | |
| *A61P 3/00* | (2006.01) | |
| *A61P 29/00* | (2006.01) | |
| *A61P 27/06* | (2006.01) | |
| *A61P 37/06* | (2006.01) | |
| *A61P 25/28* | (2006.01) | |
| *A61P 37/00* | (2006.01) | |

(52) U.S. Cl.
CPC ............... *C07F 5/025* (2013.01); *A61P 3/00* (2018.01); *A61P 25/28* (2018.01); *A61P 27/06* (2018.01); *A61P 29/00* (2018.01); *A61P 37/00* (2018.01); *A61P 37/06* (2018.01)

(58) Field of Classification Search
CPC .. C07F 5/025; A61P 3/00; A61P 25/28; A61P 27/02; A61P 27/06; A61P 29/00; A61P 37/00; A61P 37/06
USPC .......................................................... 514/64
See application file for complete search history.

(56) References Cited

U.S. PATENT DOCUMENTS

| | | | |
|---|---|---|---|
| 5,965,583 | A | 10/1999 | Beers et al. |
| 8,221,907 | B2 | 7/2012 | Kawamura et al. |
| 2009/0021149 | A1 * | 1/2009 | Kim ..................... C07D 333/18 548/440 |
| 2016/0263126 | A1 | 9/2016 | Kulikowski et al. |
| 2020/0227654 | A1 | 7/2020 | Zhang et al. |

FOREIGN PATENT DOCUMENTS

| | | | | |
|---|---|---|---|---|
| CN | 10957491 | * | 4/2019 | |
| CN | 111087387 | A | 5/2020 | |
| CN | 111423390 | A | 7/2020 | |
| CN | 111662309 | A | 9/2020 | |
| CN | 113045585 | A | 6/2021 | |
| KR | 20160025776 | A | 3/2016 | |
| KR | 20160059336 | * | 5/2016 | |
| KR | 10 2017/0049398 | A | 5/2017 | |
| KR | 20170058618 | A | 5/2017 | |
| WO | WO-2015/003146 | A1 | 1/2015 | |
| WO | WO-2015003146 | A1 * | 1/2015 | ............ A61K 31/69 |
| WO | WO 2016/113303 | * | 7/2016 | |
| WO | WO-2016/113303 | A1 | 7/2016 | |
| WO | WO-2019/240471 | A1 | 12/2019 | |
| WO | WO 2020032428 | * | 2/2020 | |

OTHER PUBLICATIONS

Carpenter et al., "Utilization of an Active Site Mutant Receptor for the Identification of Potent and Selective Atypical 5-HT2C Receptor Agonists," Journal of Medicinal Chemistry, 60(14): 6166-6190 (2017).
Dementiev et al., "Structures of human plasma b-factor XIIa cocrystallized with potent inhibitors," Blood Advances: Supplemental Information pp. 1-11 (2018).
Ishihara et al., "Rational Design of a New Chiral Lewis Acid Catalyst for Enantioselective Diels-Alder Reaction: Optically Active 2-Dichloroboryl-1, 1'-binaphthyl," Synlett, 10: 1053-1056 (1998).
Subasinghe et al., "A novel series of potent and selective small molecule inhibitor," Bioorganic & Medicinal Chemistry Letters, 14(12): 3043-3047 (2004).
Trinchera et al., "Synthesis of Previously Inaccessible Borylated Heterocycle Motifs Using Novel Boron-Containing Amphoteric Molecules," Angewandte Chemie International Edition, 127(31): 9166-9169 (2015).
CAS Registry No. 1100754-76-4 ; STN Entry Date Feb. 4, 2009.
International Search Report and Written Opinion for International Application No. PCT/US2023/010783 dated May 10 2023.
Bender et al., "Factor XII-Driven Inflammatory Reactions with Implications for Anaphylaxis," Frontiers in Immunology, 8: Article No. 1115 pp. 1-11 (2017).
Dementiev et al., "Structures of human plasma β-factor XIIa cocrystallized with potent inhibitors," Blood Advances, 2(5): 549-558 (2018).
International Search Report and Written Opinion for International Application No. PCT/US2021/042198 dated Oct. 28, 2021.
Kalinin., "Factor XII(a) inhibitors: a review of the patent literature," Expert Opinion on Therapeutic Patents: 1-22 (2021).
Naito et al., "Complement C1q Activates Canonical Wnt Signaling and Promotes Aging-Related Phenotypes," Cell, 149: 1298-1313 (2012).

(Continued)

*Primary Examiner* — Taylor V Oh
(74) *Attorney, Agent, or Firm* — Foley Hoag LLP; David P. Halstead; Lucas P. Watkins

(57) ABSTRACT

Disclosed are compounds of formula I and II and pharmaceutically acceptable salts thereof. Also disclosed are methods of treating a neurodegenerative disorder, an inflammatory disease, an autoimmune disease, an ophthalmic disease or a metabolic disorder using the compounds disclosed herein.

48 Claims, No Drawings

(56) References Cited

OTHER PUBLICATIONS

Schmaier et al., "Factor XII—What's important but not commonly thought about," Research and Practice in Thrombosis and Haemostasis, 3(4): 599-606 (2019).

Subasinghe et al., "A novel series of arylsulfonylthiophene-2-carboxamidine inhibitors of the complement component C1s," Bioorganic & Medicinal Chemistry Letters, 16(8): 2200-2204 (2006).

Subasinghe et al., "Design and synthesis of polyethylene glycol-modified biphenylsulfonyl-thiophene-carboxamidine inhibitors of the complement component C1s," Bioorganic & Medicinal Chemistry Letters, 22(16): 5303-5307 (2012).

Travins et al., "Biphenylsulfonyl-thiophene-carboxamidine inhibitors of the complement component C1s," Bioorganic & Medicinal Chemistry Letters, 18(5): 1603-1606 (2008).

\* cited by examiner

INHIBITORS OF COMPLEMENT FACTORS AND USES THEREOF

RELATED APPLICATIONS

This patent application claims priority to U.S. Provisional Patent Application No. 63/054,064, filed on Jul. 20, 2020, which is hereby incorporated by reference in its entirety.

BACKGROUND

The complement system refers to a group of proteins involved in the innate immune system. This helps or complements the ability of antibodies and phagocytic cells to clear pathogens from an organism. There are three cascades involved in this system, the classical, lectin and alternative pathways. Each is triggered by a different recognition event, and each results in the recruitment and activation of a sequence of proteins capable of tagging a cell surface and amplifying a process that can lead to cell lysis, damage or engulfment.

The classical pathway is activated by the binding of complement protein C1q directly to the cell surface or to proteins bound to the cell surface. In one of its primary functions, C1q can be recruited by antibodies specific to cell surface antigens. C1q is a large multimeric protein of 460 kDa consisting of 18 polypeptide chains (6 C1q A chains, 6 C1q B chains, and 6 C1q C chains). These chains form a large symmetric protein composed of three sections: the tail, arms and globular head regions. The single tail section divides into six symmetric arms, each of which terminates in a globular head. Most of the C1q circulating in blood carries a heterotetrameric complex of the complement proteins C1r and C1s, two serine proteases that bind to C1q initially as inactive zymogens. This large multichain assembly is known as C1-complex. Binding of the C1-complex to the surface of a cell or to the appropriate complement-binding epitope of a recruiting protein, such as that found in an antibody Fc region induces a conformational change that leads to a sequence of activation and amplification events. In response to binding. C1r is activated first, subsequently cleaving and activating C1s. Complement C4 is then recruited to the complex where it is incorporated and cleaved to C4b by C1s. This cleavage results in exposure of a moiety which can attach C4b to the cell surface covalently. This new complex subsequently recruits complement C2 where, in association with C4b, it is cleaved to C2a by C1s. The surface linked complex of C4b and C2a forms the C3-convertase, which drives the subsequent cleavage and surface linking of complement C3 and activates downstream steps of the complement cascade. A single C1-complex is capable of building multiple C3-convertase modules on the surface, resulting in a powerful amplification of the original targeting event.

These events can lead to tissue damage and cell clearance/destruction in normal function and in disease pathology. They have also been found to play a key role in pruning of synapses in normal neuronal development and in CNS-disease pathology. Such outcomes can be driven in various situations by the accumulation of C4 and C3 cleavage products on the surface, progression of the cascade to the terminal steps of membrane attack complex formation and/or pore-mediated lysis and accumulation of immune complexes containing early complement cascade components. In some cases, C1r and/or C1s expression may also be elevated through local induction as part of a biological response and the actions of these proteases may further contribute to the progression of disease pathology (see, for example Xavier et al Am. J. Renal Physiol, 2019).

The complement system is a central component of innate immunity and bridges the innate to the adaptive immune response. However, it can also turn its destructive capabilities against host cells. Aberrant activation or insufficient regulation of the complement cascade is involved in numerous diseases and pathological conditions. As a consequence, many neurodegenerative, inflammatory and autoimmune diseases are thought to be caused, or at least substantially driven, by unleashed complement factor activity.

For example, the cognitive abilities of humans, and especially of patients suffering from neurodegenerative diseases, are highly dependent on synapse formation. The formation of precise neuronal circuits during development is a highly regulated and dynamic process. Excess numbers of synapses are first generated to establish the initial wiring pattern of the brain, but the formation of mature, precise neuronal circuits requires the selective elimination and pruning of specific synapses. Neuronal activity plays a critical role in this refinement phase which utilizes targeting of early components of the classical complement cascade to effect this elimination.

However, premature synapse loss in neurodegenerative pathologies results in a loss of neuronal activity and aberrantly activates synaptic pruning, thereby leading to cognitive decline. In neurodegenerative diseases, such as Alzheimer's disease and glaucoma, complement factors, such as complement factor C1 and its subunits such as C1q, are expressed in neurons, where they act as signals for synapse elimination. See, e.g., U.S. Patent Publication Nos. US 2012/0195880 and US 2012/0328601. In the adult brain, synapse loss often occurs long before the pathology and clinical symptoms in many neurodegenerative diseases. Timely therapeutic intervention to prevent or reduce synapse loss may slow down or prevent progression of clinical symptoms of neurodegenerative diseases.

Therefore, inhibition or modulation of classical complement activity has been recognized as a promising therapeutic strategy. Thus, there is a need to discover and develop methods to inhibit or modulate the aberrant activity of these complement factors.

SUMMARY OF THE INVENTION

In certain aspects, the present disclosure provides compounds represented by formula I or II:

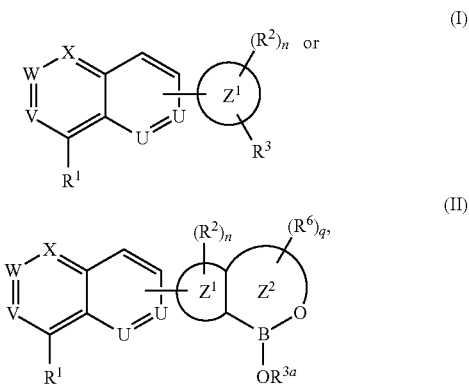

and pharmaceutically acceptable salts thereof, wherein:
R$^1$ is hydrogen, halogen, amino, hydroxyl, alkoxy, or alkylthio;
V and W are each independently CR$^a$ or N;
each R$^a$ independently is hydrogen, halogen, nitro, cyano, amino, hydroxyl, alkoxy, alkylthio, or alkyl;
X is CR$^b$ or N;
R$^b$ is hydrogen, halogen, nitro, cyano, amino, hydroxyl, alkoxy, alkylthio, alkyl, alkenyl, alkynyl, aralkyl, heteroaralkyl, carbocyclyl, heterocyclyl, aryl, or heteroaryl;
each U independently is N or CR$^c$;
each R$^c$ independently is hydrogen, halogen, alkoxy, or alkyl;
ring Z$^1$ is a five- or six-membered aryl or heteroaryl;
ring Z$^2$ is a five- or six-membered heterocycle;
each R$^2$ independently is halogen, nitro, cyano, amino, acylamino, amido, hydroxyl, alkoxy, alkylthio, acyl, amidino, azido, carbamoyl, carboxyl, carboxyester, guanidine, haloalkyl, haloalkoxy, heteroalkyl, imino, oxime, phosphonate, dialkylphosphine oxide, sulfonyl, sulfonamido, sulfonyl urea, sulfinyl, sulfinic acid, sulfonic acid, thiocyanate, thiocarbonyl, alkyl, aralkyl, heteroaralkyl, alkenyl, alkynyl, carbocyclyl, heterocyclyl, aryl, or heteroaryl; or two vicinal R$^2$, together with the intervening carbon atoms to which they attach, combine to form a 5- or 6-membered carbocycle, 5- or 6-membered heterocycle, 5- or 6-membered aryl, or 5- or 6-membered heteroaryl;
n is 0 or an integer selected from 1-4, as valency permits;
each R$^6$ independently is halogen, nitro, cyano, amino, acylamino, amido, hydroxyl, oxo, carboxyl, alkoxy, alkylthio, acyl, amidino, azido, carbamoyl, carboxyl, carboxyester, guanidine, haloalkyl, haloalkoxy, heteroalkyl, imino, oxime, phosphonate, dialkylphosphine oxide, sulfonyl, sulfonamido, sulfonyl urea, sulfinyl, sulfinic acid, sulfonic acid, thiocyanate, thiocarbonyl, alkyl, alkenyl, alkynyl, aralkyl, heteroaralkyl, carbocyclyl, heterocyclyl, aryl, or heteroaryl; or any two R$^6$, independently, together with the intervening carbon atom(s) to which they attach, combine to form a carbocycle or heterocycle;
q is 0 or an integer selected from 1-4, as valency permits;
R$^3$ is

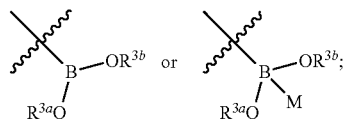

M is N(R$^8$)$_3$, N(R$^8$)$_2$, OR$^8$ or SR$^8$;
each R$^8$ is independently hydrogen, alkyl, aralkyl, heteroaralkyl, alkenyl, alkynyl, carbocyclyl, heterocyclyl, aryl, or heteroaryl; and
R$^{3a}$ and R$^{3b}$ independently are hydrogen, alkyl, acyl, alkenyl, alkynyl, aralkyl, heteroaralkyl, carbocyclyl, heterocyclyl, aryl, or heteroaryl; or R$^{3a}$ and R$^{3b}$, together with the boron atom and the two intervening oxygen atoms that separate them, combine to form a monocyclic or polycyclic heterocyclyl; or R$^{3a}$, R$^{3b}$, and M, together with the boron atom and the intervening atoms, combine to form a polycyclic heterocycle.

In certain aspects, the present disclosure provides pharmaceutical compositions comprising a compound provided herein and a pharmaceutically acceptable excipient.

In certain aspect, the present disclosure provides methods of making a compound provided herein.

In certain aspects, the present disclosure provides methods of treating diseases associated with complement activation in an individual in need thereof, comprising administering a therapeutically effective amount of a compound provided herein.

In certain aspects, the present disclosure provides methods of inhibiting C1s, comprising contacting the C1s with a compound disclosed herein. In certain aspects, the present disclosure provides methods of inhibiting activated C1s, comprising contacting the C1s with a compound disclosed herein.

DETAILED DESCRIPTION OF THE INVENTION

In one aspect, the current disclosure provides compounds of formula I or II:

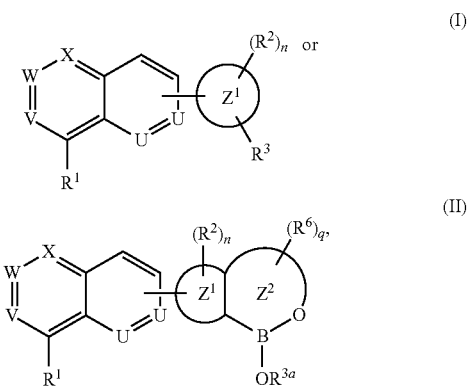

or a pharmaceutically acceptable salt thereof, wherein:
R$^1$ is hydrogen, halogen, amino, hydroxyl, alkoxy, or alkylthio;
V and W are each independently CR$^a$ or N;
each R$^a$ independently is hydrogen, halogen, nitro, cyano, amino, hydroxyl, alkoxy, alkylthio, or alkyl;
X is CR$^b$ or N;
R$^b$ is hydrogen, halogen, nitro, cyano, amino, hydroxyl, alkoxy, alkylthio, alkyl, alkenyl, alkynyl, aralkyl, heteroaralkyl, carbocyclyl, heterocyclyl, aryl, or heteroaryl;
each U independently is N or CR$^c$;
each R$^c$ independently is hydrogen, halogen, alkyl, or alkoxy;
ring Z$^1$ is a five- or six-membered aryl or heteroaryl;
ring Z$^2$ is a five- or six-membered heterocycle;
each R$^2$ independently is halogen, nitro, cyano, amino, acylamino, amido, hydroxyl, alkoxy, alkylthio, acyl, amidino, azido, carbamoyl, carboxyl, carboxyester, guanidine, haloalkyl, haloalkoxy, heteroalkyl, imino, oxime, phosphonate, dialkylphosphine oxide, sulfonyl, sulfonamido, sulfonyl urea, sulfinyl, sulfinic acid, sulfonic acid, thiocyanate, thiocarbonyl, alkyl, aralkyl, heteroaralkyl, alkenyl, alkynyl, carbocyclyl, heterocyclyl, aryl, or heteroaryl; or two vicinal R$^2$, together with the intervening carbon atoms to which they attach, combine to form a 5- or 6-membered carbocycle, 5- or 6-membered heterocycle, 5- or 6-membered aryl, or 5- or 6-membered heteroaryl;

n is 0 or an integer selected from 1-4, as valency permits;
each $R^6$ independently is halogen, nitro, cyano, amino, acylamino, amido, hydroxyl, oxo, carboxyl, alkoxy, alkylthio, acyl, amidino, azido, carbamoyl, carboxyl, carboxyester, guanidine, haloalkyl, haloalkoxy, heteroalkyl, imino, oxime, phosphonate, dialkylphosphine oxide, sulfonyl, sulfonamido, sulfonyl urea, sulfinyl, sulfinic acid, sulfonic acid, thiocyanate, thiocarbonyl, alkyl, alkenyl, alkynyl, aralkyl, heteroaralkyl, carbocyclyl, heterocyclyl, aryl, or heteroaryl; or any two $R^6$, independently, together with the intervening carbon atom(s) to which they attach, combine to form a carbocycle or heterocycle;

q is 0 or an integer selected from 1-4, as valency permits; $R^3$ is

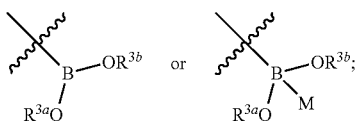

M is $N(R^8)_3$, $N(R^8)_2$, $OR^8$ or $SR^8$;

each $R^8$ is independently hydrogen, alkyl, aralkyl, heteroaralkyl, alkenyl, alkynyl, carbocyclyl, heterocyclyl, aryl, or heteroaryl; and $R^{3a}$ and $R^{3b}$ independently are hydrogen, alkyl, acyl, alkenyl, alkynyl, aralkyl, heteroaralkyl, carbocyclyl, heterocyclyl, aryl, or heteroaryl; or $R^{3a}$ and $R^{3b}$, together with the boron atom and the two intervening oxygen atoms that separate them, combine to form a monocyclic or polycyclic heterocyclyl; or $R^{3a}$, $R^{3b}$, and M, together with the boron atom and the intervening oxygen atoms, combine to form a polycyclic heterocycle.

It will be appreciated that because in formula II, $Z^1$ is an aromatic moiety, the shared bond between rings $Z^1$ and $Z^2$ has aromatic character.

In certain embodiments, the compound is represented by formula I-a or II-a:

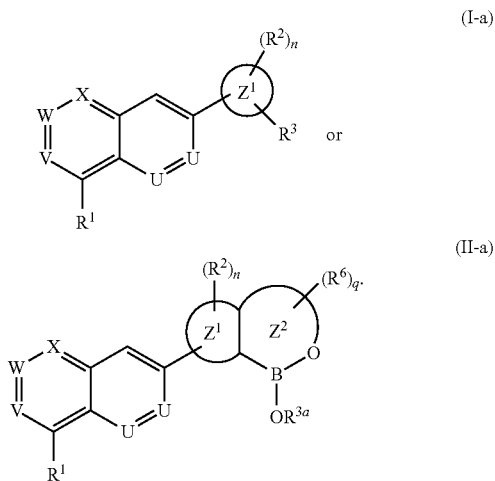

In certain preferred embodiments, $R^1$ is hydrogen, amino, hydroxyl, alkoxy, or alkylthio. In certain preferred embodiments, $R^1$ is hydroxyl or $C_{1-3}$ alkoxy. In certain preferred embodiments, $R^1$ is amino, preferably —NH$_2$ or —NHCH$_3$, such as NH$_2$.

In certain embodiments, each $R^2$ independently is halogen, nitro, cyano, amino, acylamino, amido, hydroxyl, alkoxy, alkylthio, phosphonate, dialkylphosphine oxide, alkyl, aralkyl, heteroaralkyl, alkenyl, alkynyl, carbocyclyl, heterocyclyl, aryl, or heteroaryl; or two vicinal $R^2$, together with the intervening carbon atoms to which they attach, combine to form a 5- or 6-membered carbocycle, 5- or 6-membered heterocycle, 5- or 6-membered aryl, or 5- or 6-membered heteroaryl.

In certain preferred embodiments, each $R^2$ independently is halogen, cyano, amino, acylamino, amido, hydroxyl, alkoxy, dialkylphosphine oxide, haloalkyl, sulfonyl, alkyl, carbocyclyl, heterocyclyl, aryl, aralkyl, heteroaralkyl or heteroaryl.

In certain embodiments, each $R^2$ independently is halogen, cyano, amino, acylamino, amido, hydroxyl, alkoxy, dialkylphosphine oxide, alkyl, carbocyclyl, heterocyclyl, aryl, aralkyl, heteroaralkyl or heteroaryl, e.g., —F, cyano, —N(H)C(O)R$^4$, —OCF$_3$, —OCH$_2$C(O)NR$^4$, —O(CH$_2$CH$_2$O)$_r$R$^4$, —CF$_3$, —CHF$_2$, —OCH$_3$, —P(=O)(CH$_3$)$_2$, —CH$_3$, —C$_2$H$_5$, cyclopropyl, tetrahydropyranyl or pyridinyl; wherein $R^4$ is alkyl, alkenyl, carbocyclyl, heterocyclyl, aryl or heteroaryl; and r is an integer selected from 1-6.

In certain embodiments, each $R^2$ independently is —F, cyano, —N(H)C(O)R$^4$, —OCF$_3$, —OCH$_2$C(O)N(R$^4$)$_2$, —O(CH$_2$CH$_2$O)$_r$R$^4$, —CF$_3$, —CHF$_2$, —OCH$_3$, —P(=O)(CH$_3$)$_2$, —CH$_3$, —C$_2$H$_5$, cyclopropyl, tetrahydropyranyl, 1,1-dioxo-1,2,5-thiadiazolidinyl or pyridinyl; wherein $R^4$ is alkyl, alkenyl, carbocyclyl, heterocyclyl, aryl or heteroaryl; and r is an integer selected from 1-6.

In certain embodiments, two vicinal $R^2$, together with the intervening carbon atoms to which they attach, combine to form a 5- or 6-membered carbocycle, 5- or 6-membered heterocycle, 5- or 6-membered aryl, or 5- or 6-membered heteroaryl. In certain preferred embodiments, two vicinal $R^2$, together with the intervening carbon atoms to which they attach, combine to form a 5- or 6-membered heteroaryl.

In certain embodiments, two vicinal $R^2$, together with the intervening carbon atoms to which they attach, combine to form a 5- or 6-membered heteroaryl ring. In some embodiments, the 5- or 6-membered heteroaryl ring is furan, pyrazole, indazole or oxazole.

In certain embodiments, two vicinal $R^2$, together with the intervening carbon atoms to which they attach, combine to form a 5- or 6-membered heterocycle. In some embodiments, the 5- or 6-membered heterocycle is tetrahydrofuran or tetrahydropyran, In certain embodiments, each $R^a$ independently is hydrogen, halogen, amino, hydroxyl, alkoxy, or alkyl, preferably hydrogen.

In certain embodiments, $R^b$ is hydrogen, halogen, alkyl, alkenyl, alkynyl, carbocyclyl, heterocyclyl, preferably hydrogen, $C_1$-$C_3$ alkyl, or cyclopropyl. In preferred embodiments, $R^b$ is methyl.

In certain embodiments, $R^c$ is hydrogen, halogen, or alkyl.

In certain embodiments, one of V, W, and X is N. In certain embodiments, two of V, W, and X are N. In certain embodiments, W and X are N and V is CR$^a$. In certain such embodiments, $R^a$ is hydrogen. In certain embodiments, V and W are N and X is CR$^b$. In certain such embodiments, $R^b$ is hydrogen or methyl. In certain embodiments, $R^b$ is methyl.

In certain embodiments, U is CR$^c$. In certain embodiments, $R^c$ is hydrogen, F, methyl, methoxy or Cl. In some preferred embodiments U is CH.

In certain embodiments, ring $Z^1$ is phenyl or a five- or six-membered heteroaryl. In certain preferred embodiments, ring $Z^1$ is phenyl. In such embodiments, for example, the compound may be represented by formula I-b or II-b:

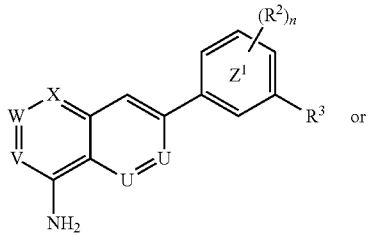
(I-b)

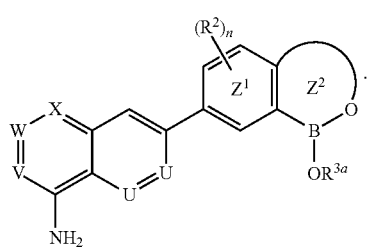
(II-b)

In certain embodiments, ring $Z^1$ is a five- or six-membered heteroaryl. In certain embodiments, ring $Z^1$ is a pyrazolyl. In certain embodiments, ring $Z^1$ is a pyridinyl. In such embodiments, for example, the compound may be represented by formula I-c or II-c:

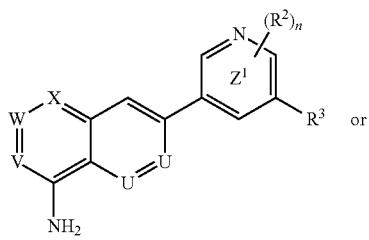
(I-c)

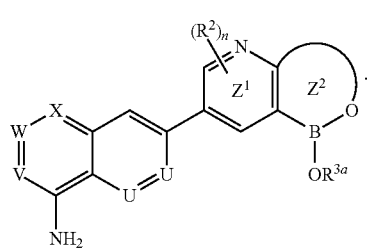
(II-c)

In certain embodiments, the compound is represented by formula I, for example by formula I-a, I-b or I-c. In certain embodiments, the compound is represented by formula I-c-1:

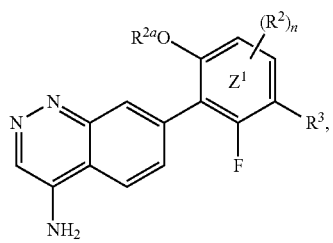
(I-c-1)

wherein n is 0, 1, or 2, and $R^{2a}$ is alkyl, aralkyl, heteroaralkyl, alkenyl, alkynyl, carbocyclyl, heterocyclyl, aryl, or heteroaryl.

In certain embodiments, the compound is represented by formula I-c-2:

(I-c-2)

wherein n is 0, 1, or 2, and $R^{2a}$ is alkyl, aralkyl, heteroaralkyl, alkenyl, alkynyl, carbocyclyl, heterocyclyl, aryl, or heteroaryl. In certain embodiments of formula (I-c-1) or (I-c-2), wherein $R^{2a}$ is methyl, difluoromethyl, —$CF_2CHF_2$, —$CHFCF_3$, —$CH_2CF_3$—$(CH_2CH_2O)_2CH_3$,

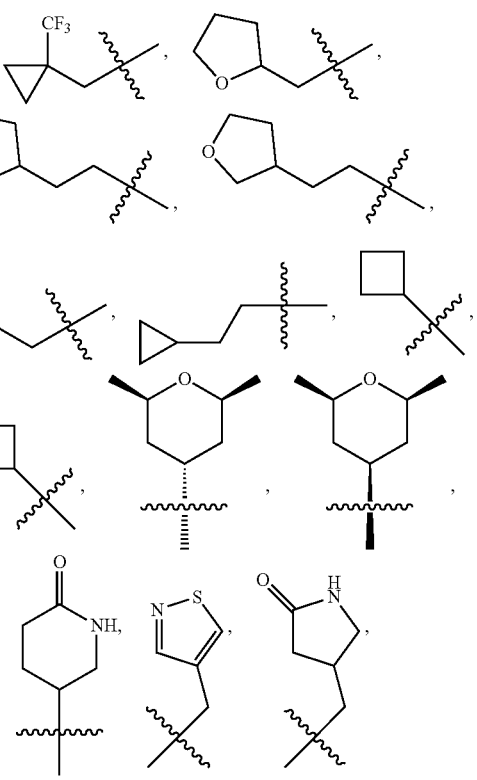

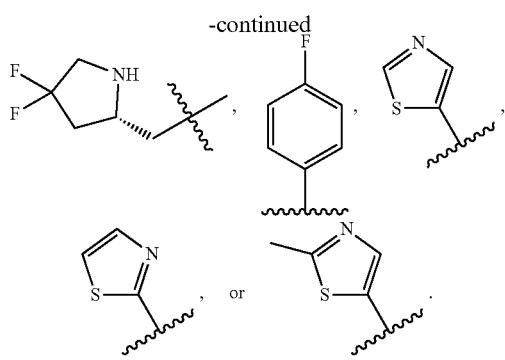

In certain embodiments of formula (I-c-1) or (I-c-2), $R^{2a}$ is methyl, difluoromethyl,

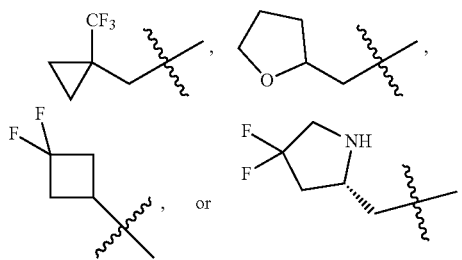

In certain embodiments of formula (I-c-1) or (I-c-2), $R^{2a}$ is

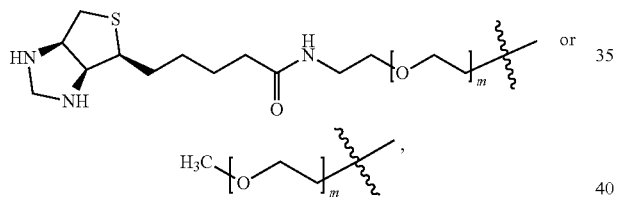

wherein m is an integer from 2 to 6.

In certain embodiments, $R^3$ is

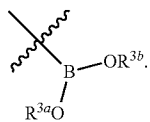

In other embodiments, $R^3$ is

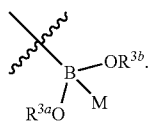

In certain embodiments, $R^{3a}$ and $R^{3b}$ independently are hydrogen, alkyl, acyl, alkenyl, alkynyl, aralkyl, heteroaralkyl, carbocyclyl, heterocyclyl, aryl, or heteroaryl. In certain preferred embodiments, $R^{3a}$ and $R^{3b}$ are hydrogen.

In certain embodiments, $R^{3a}$ and $R^{3b}$, together with the boron atom and the two intervening oxygen atoms that separate them, combine such that $R^3$ is a heterocyclyl, such as a five- or six-membered heterocyclyl. In certain such embodiments, $R^3$ may be represented as

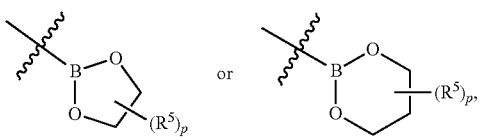

wherein:
each $R^5$ independently is halogen, nitro, cyano, amino, acylamino, amido, hydroxyl, oxo, carboxy, alkoxy, alkylthio, alkyl (e.g. carboxymethyl), aralkyl, heteroaralkyl, alkenyl, alkynyl, carbocyclyl, heterocyclyl, aryl, or heteroaryl; or any two $R^5$, independently, together with the intervening carbon atom(s) to which they attach, combine to form a carbocycle or heterocycle; and p is 0 or an integer selected from 1-6, as valency permits.
In certain such embodiments, wherein $R^3$ is

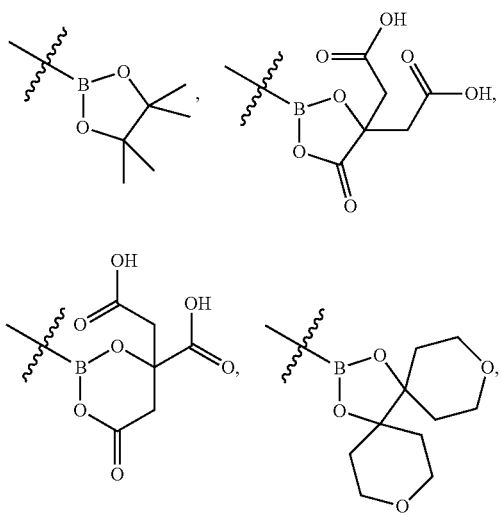

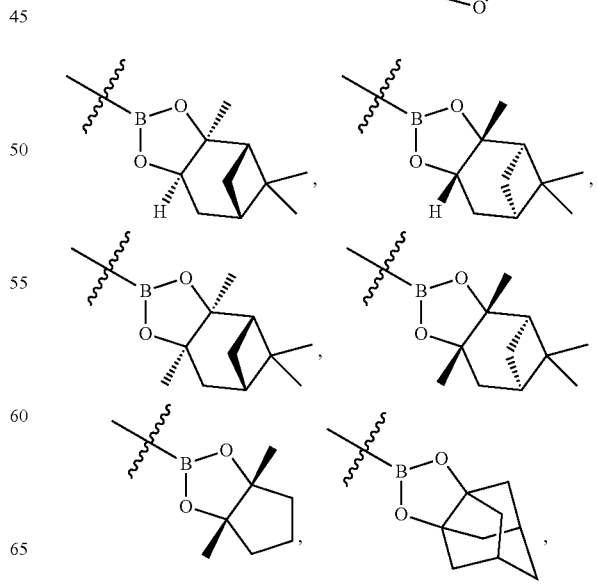

-continued

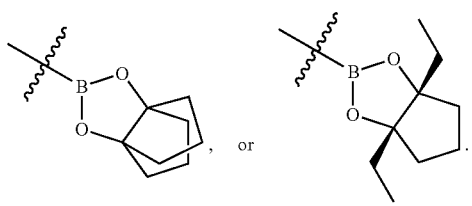

In certain such embodiments, R³ is

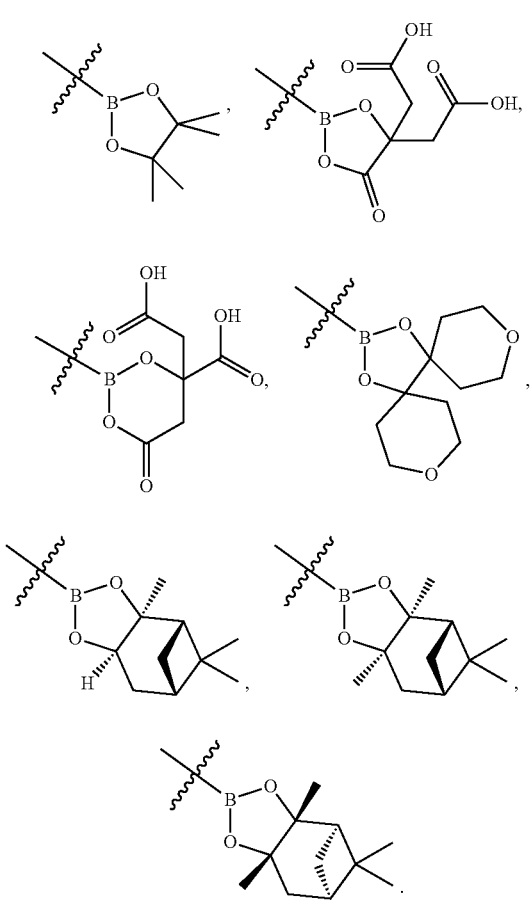

In certain embodiments, R³ is

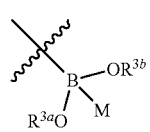

and R$^{3a}$, R$^{3b}$ and M, together with the boron atom and the intervening atoms, combine such that R³ is a polycyclic heterocycle. For example, R³ may be

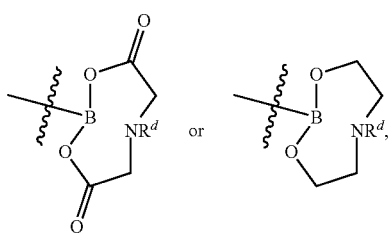

wherein R$^d$ is H or C$_1$-C$_4$ alkyl, preferably H or methyl, and more preferably H.

It will be appreciated that dative bonds may form in compounds comprising an atom with a lone electron pair (such as a Nitrogen atom) and a Boron atom. That is, the lone pair of electrons may coordinate with the empty orbital of boron. This may be indicated with an arrow from the donor atom to the boron, as shown below:

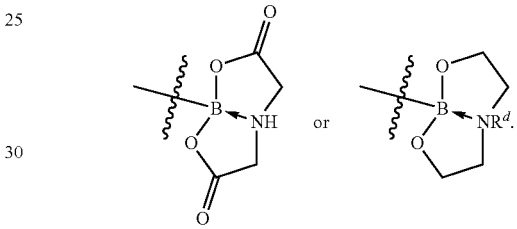

Such compounds may be represented with or without the dative bond; both representations refer to the same compound.

In certain embodiments, the compound is represented by formula II, for example formula II-a, II-b or II-c. In certain embodiments, the compound is represented by formula II-b-1, II-b-2, or II-b-3:

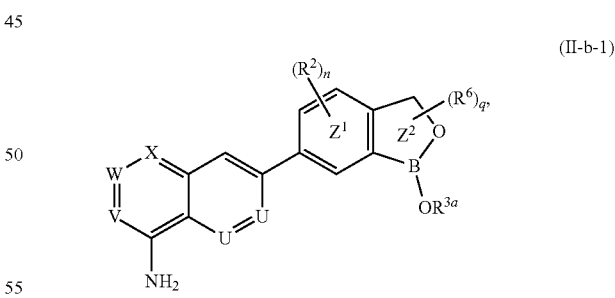

(II-b-1)

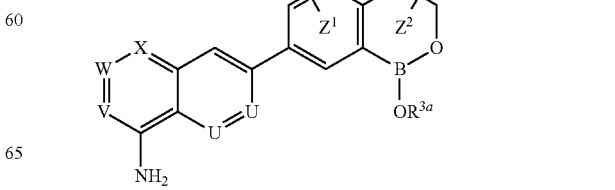

(II-b-2)

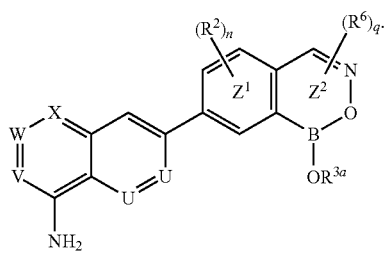
(II-b-3)
In certain embodiments, each $R^6$ independently is halogen, alkyl, or oxo.
In certain embodiments, ring $Z^2$ is
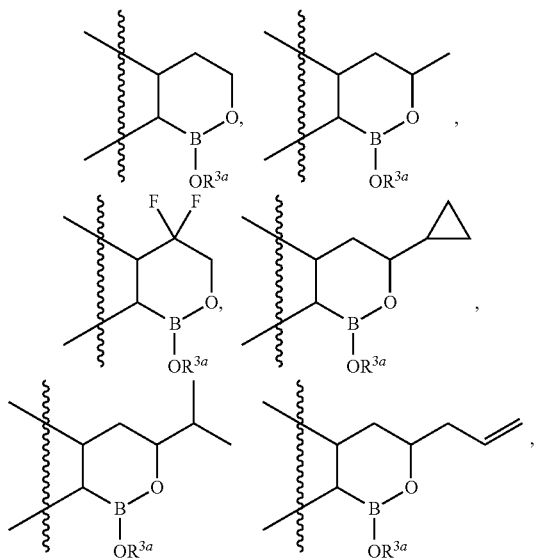
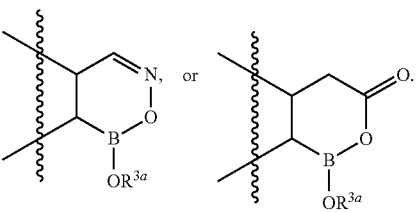
In certain embodiments, ring $Z^2$ is
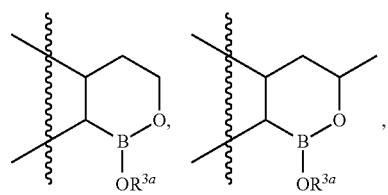
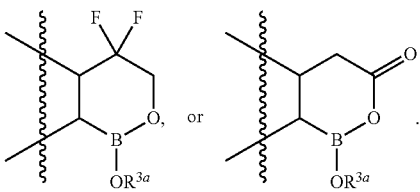
In certain preferred embodiments, $R^{3a}$ is hydrogen. In certain embodiments, $R^{3a}$ is methyl.
In certain embodiments, the compound is selected from:
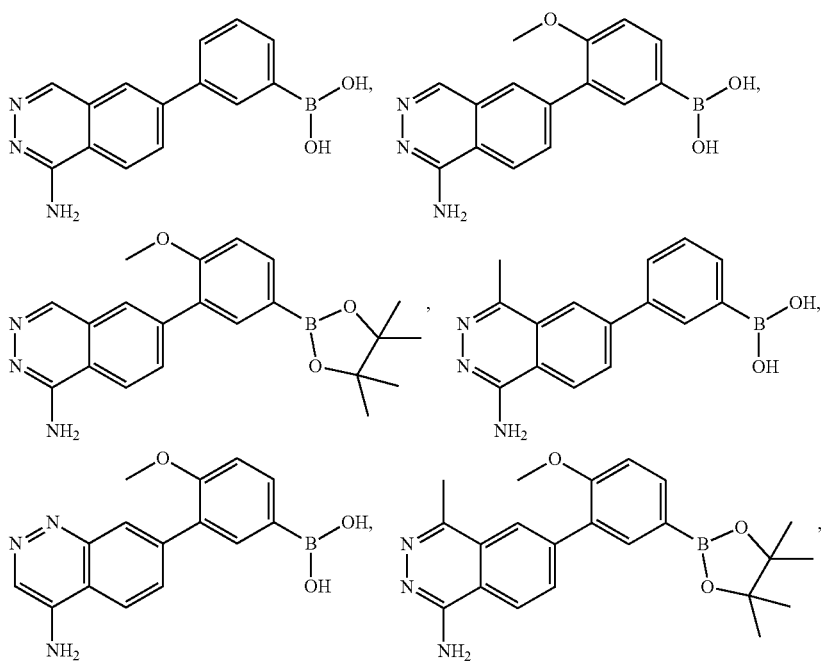

-continued
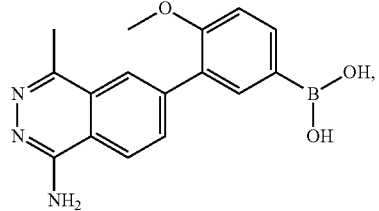 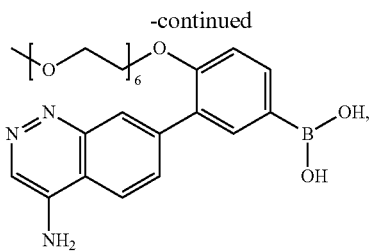
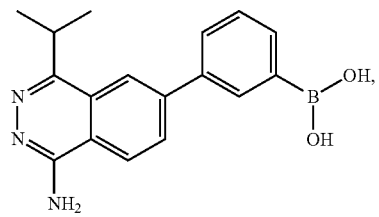 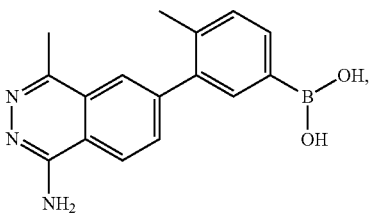
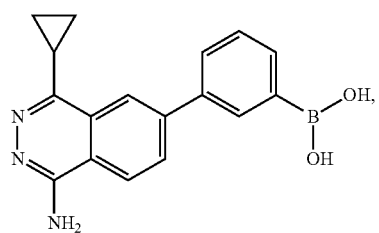 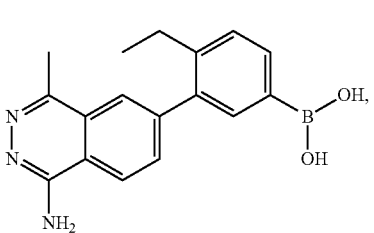
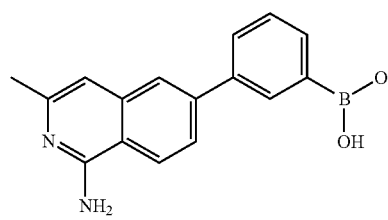 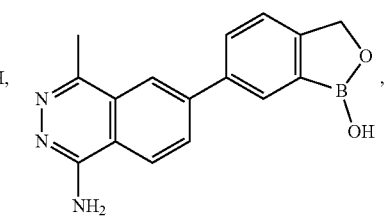
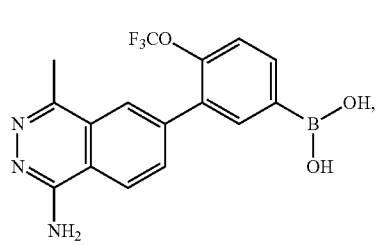 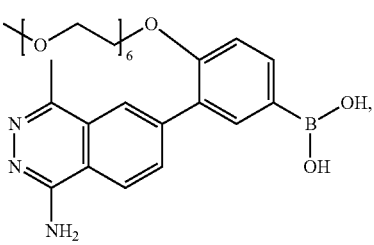
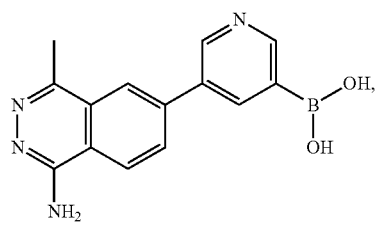 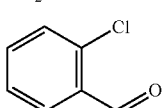
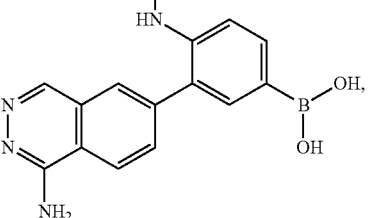
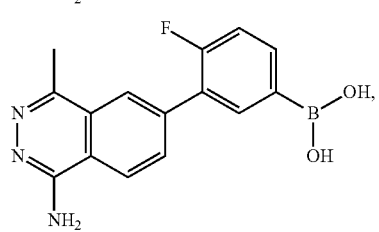 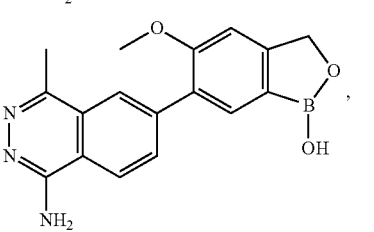

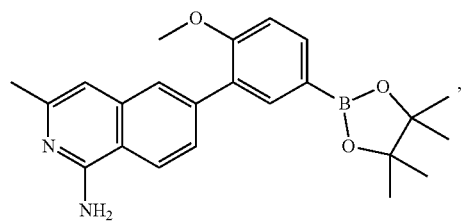
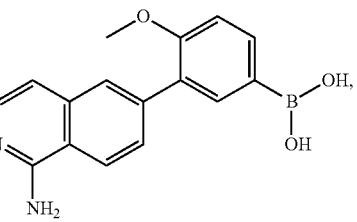
-continued
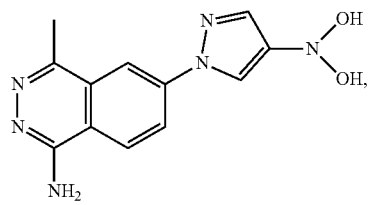
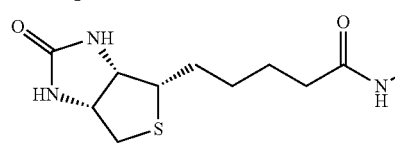
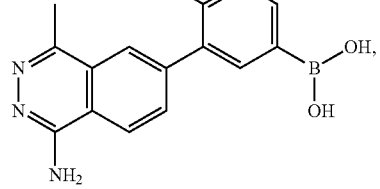
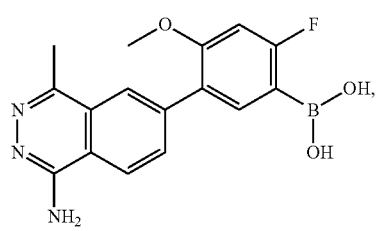
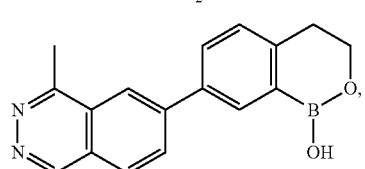
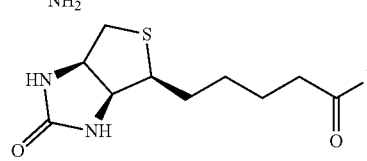
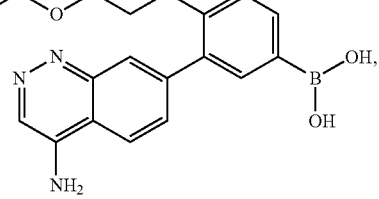
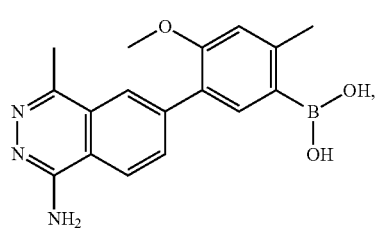
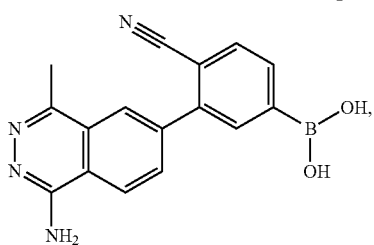
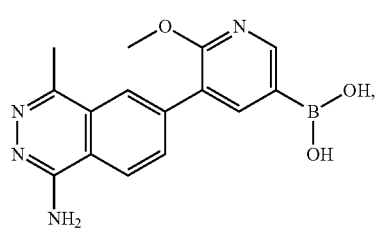
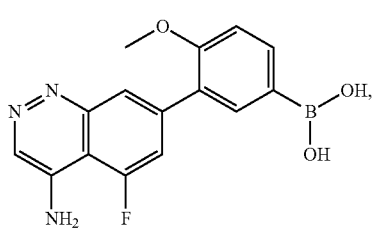
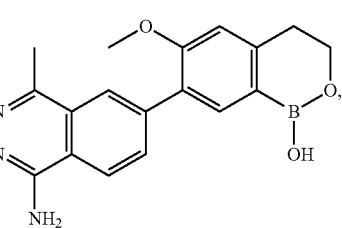

-continued
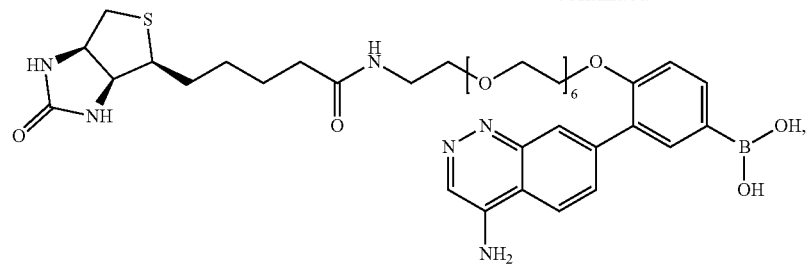
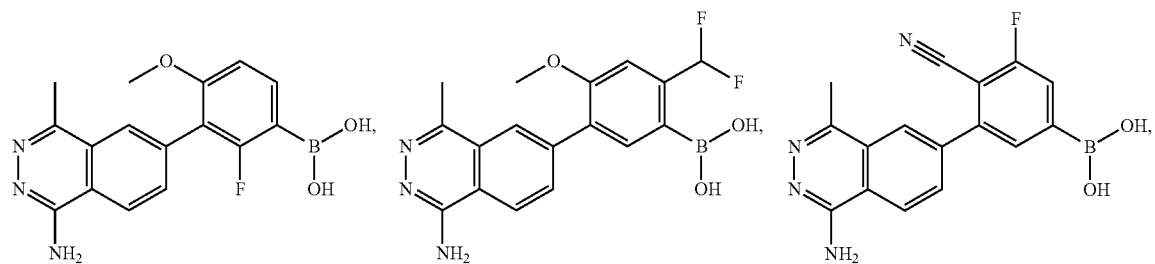
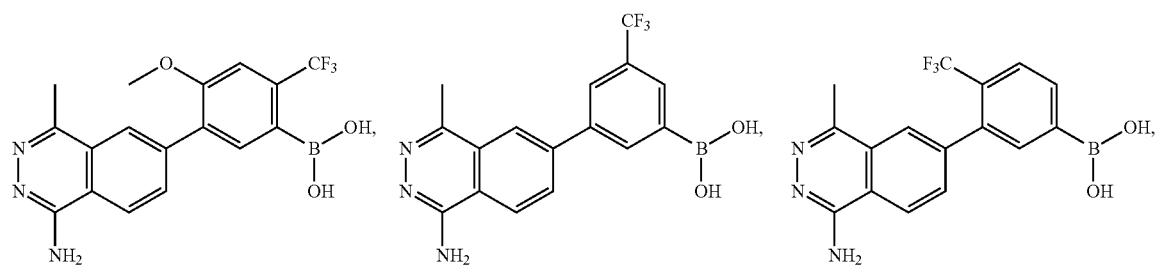
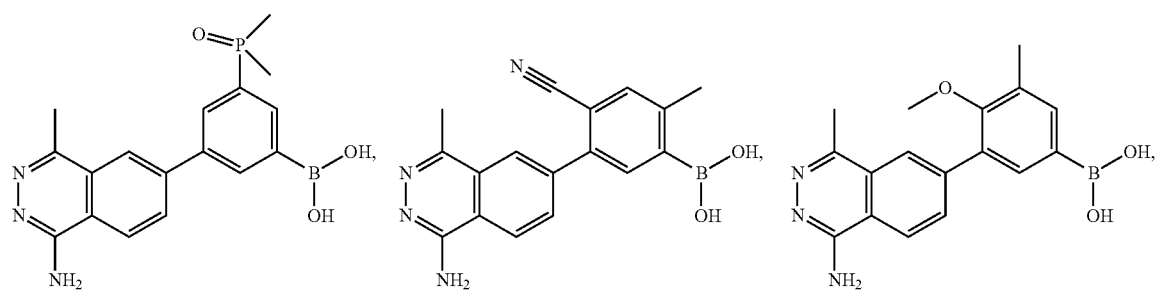
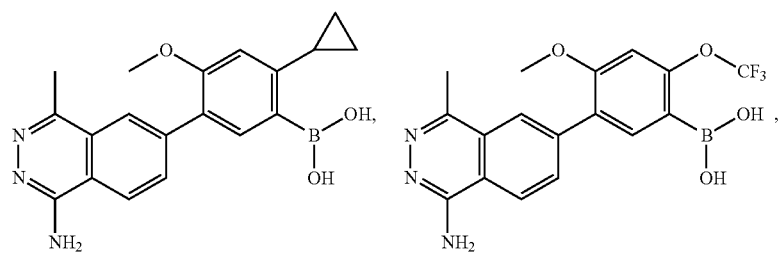
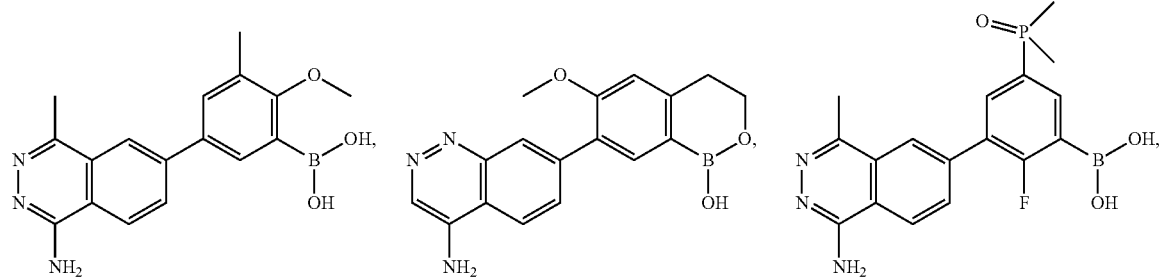

-continued
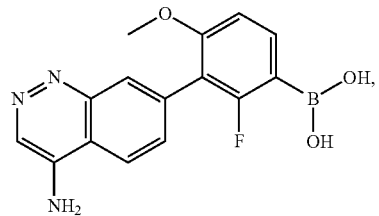 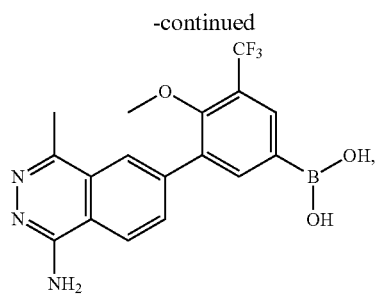 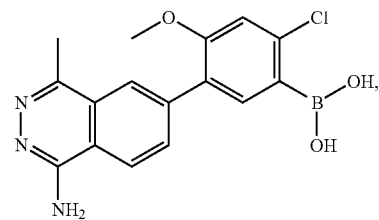
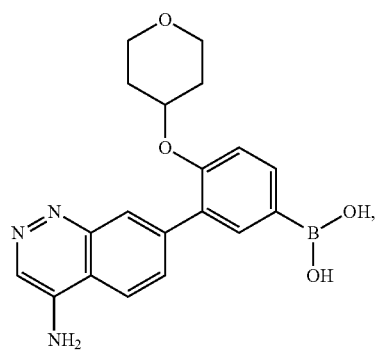 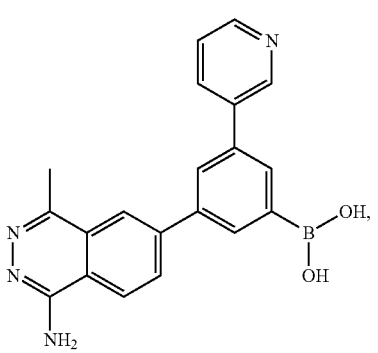
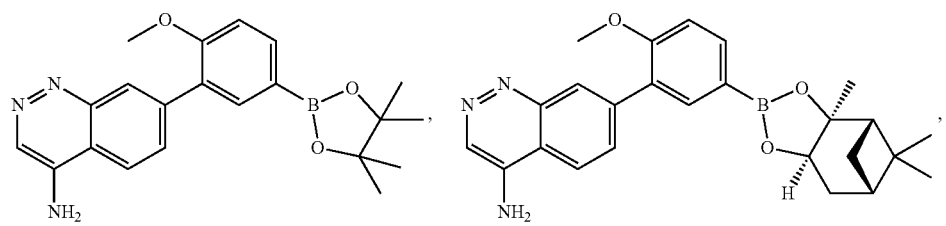
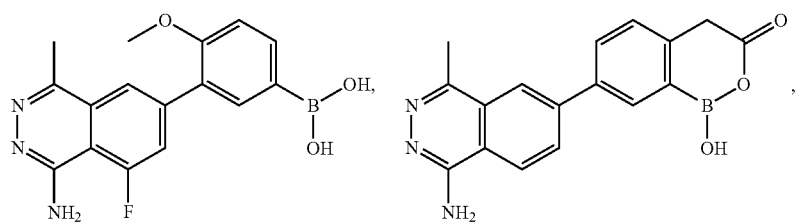
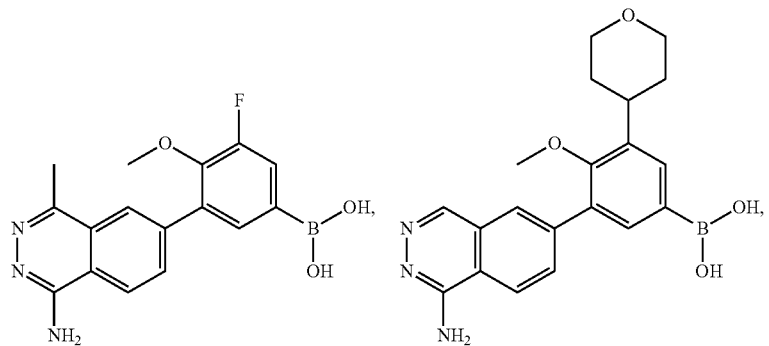

-continued
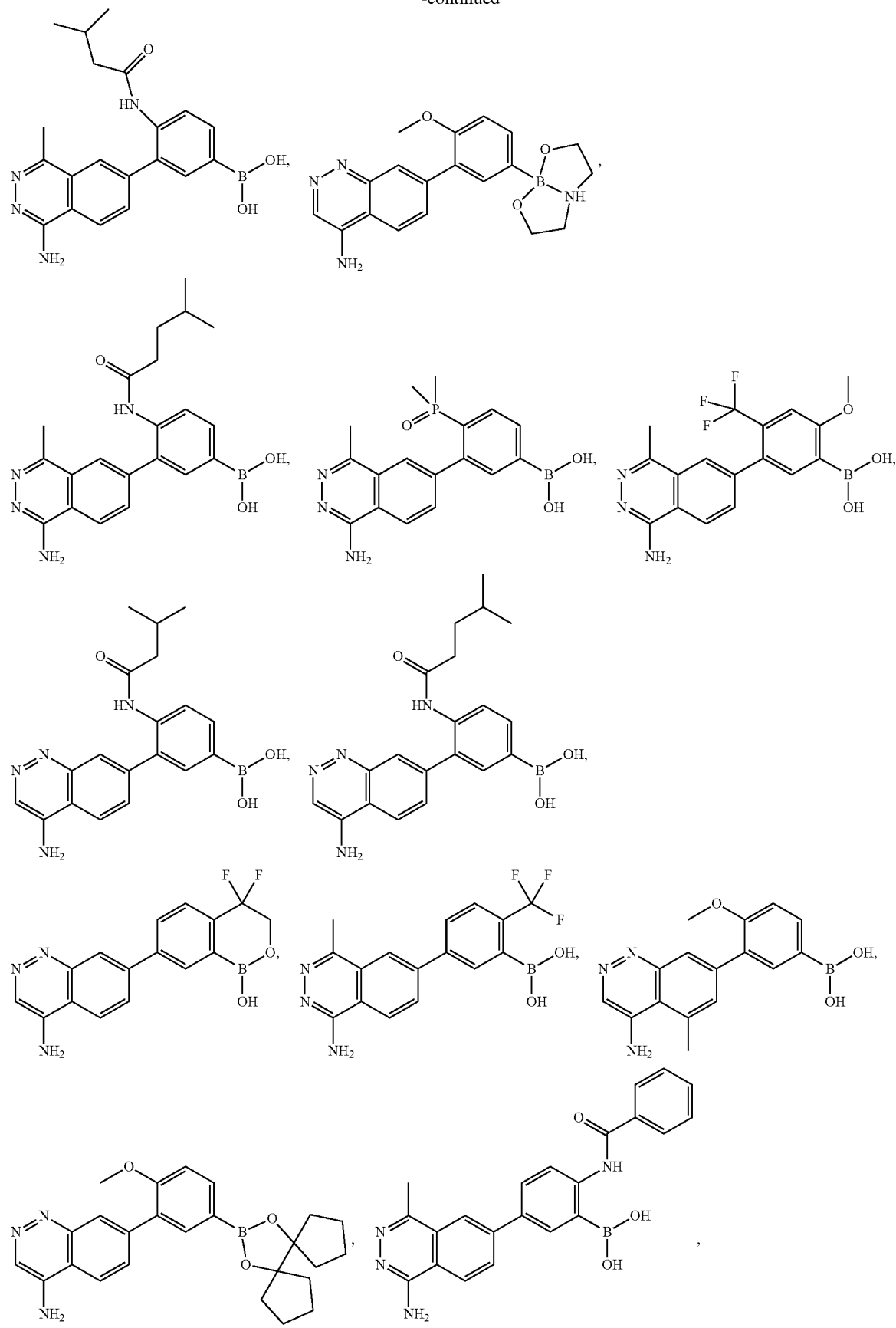

-continued
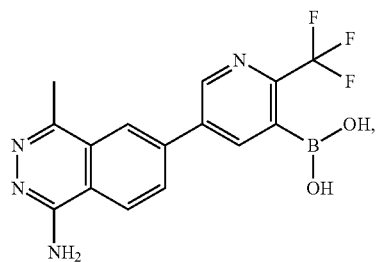 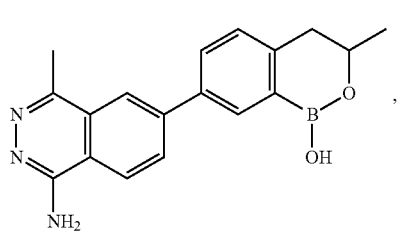
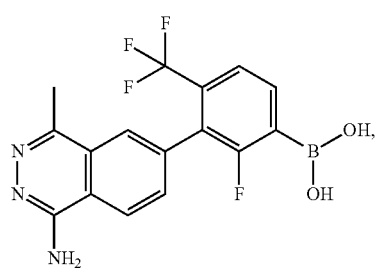 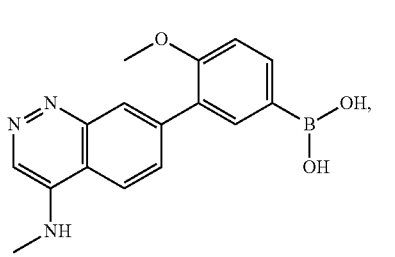 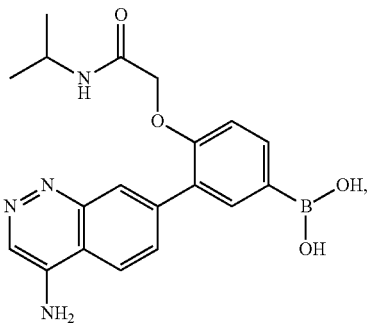
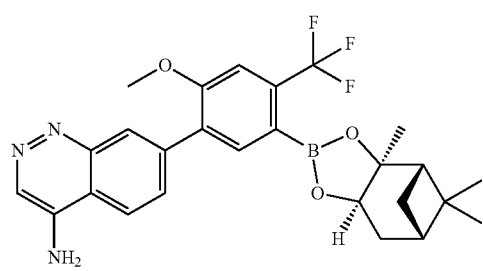 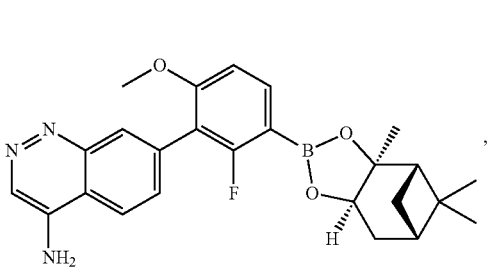
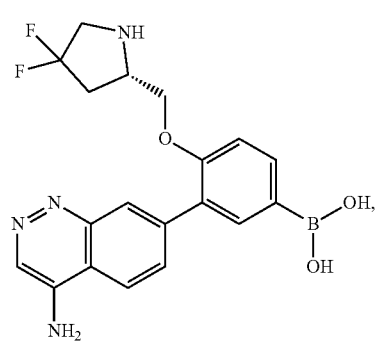 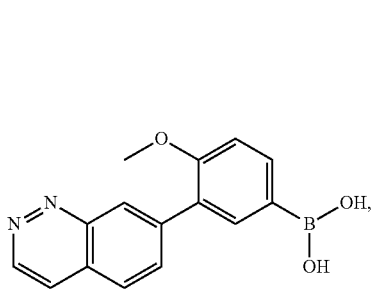 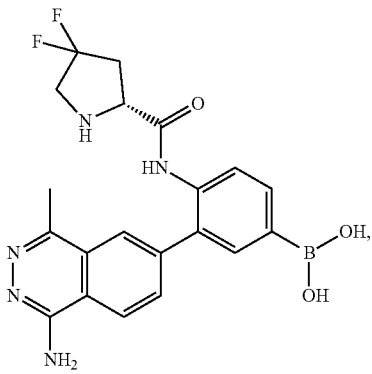
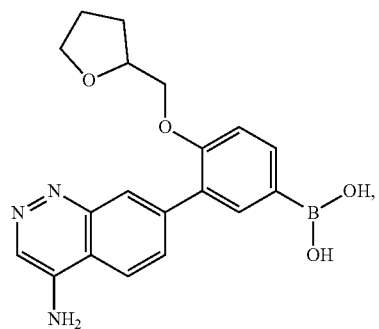 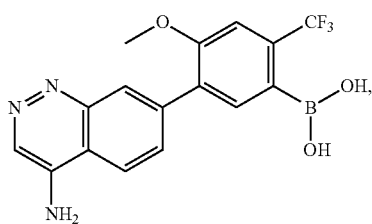 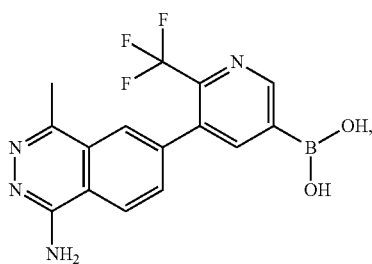

-continued
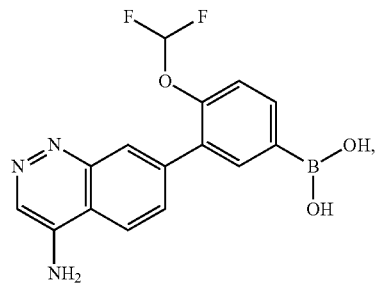
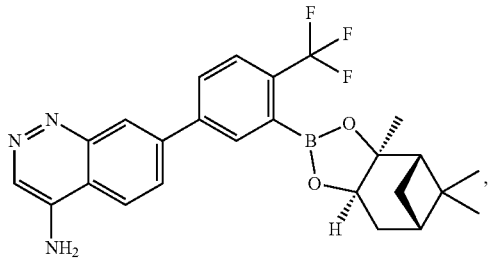
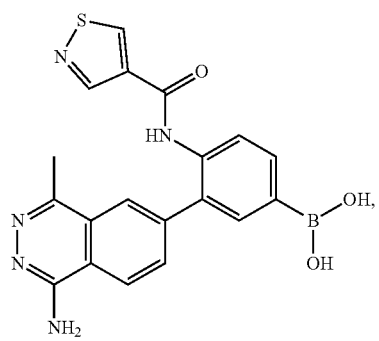
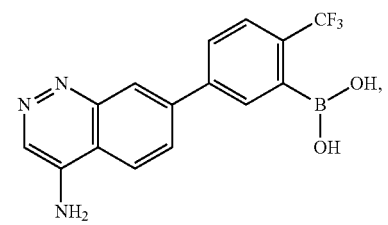
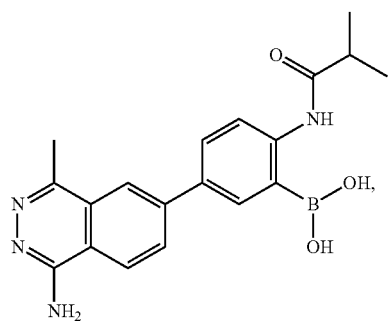
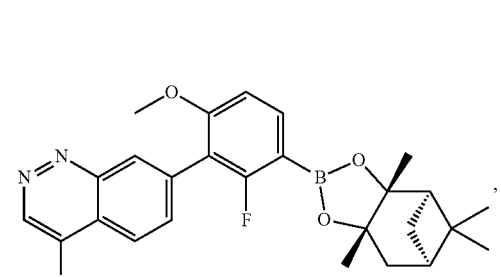
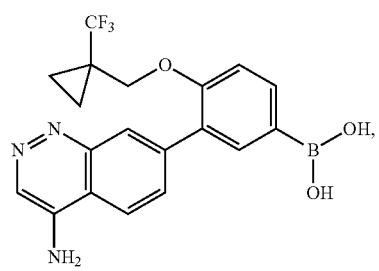
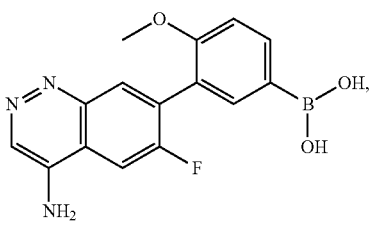
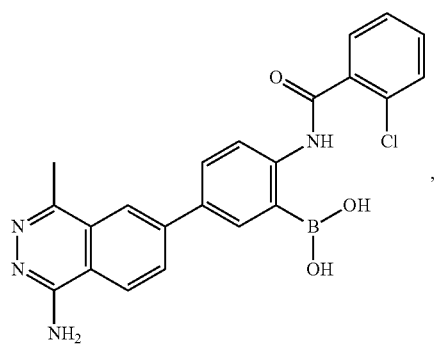
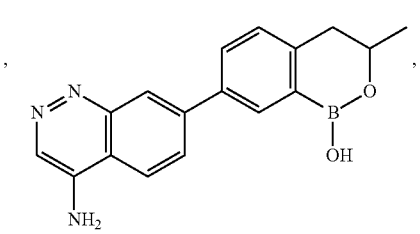

-continued
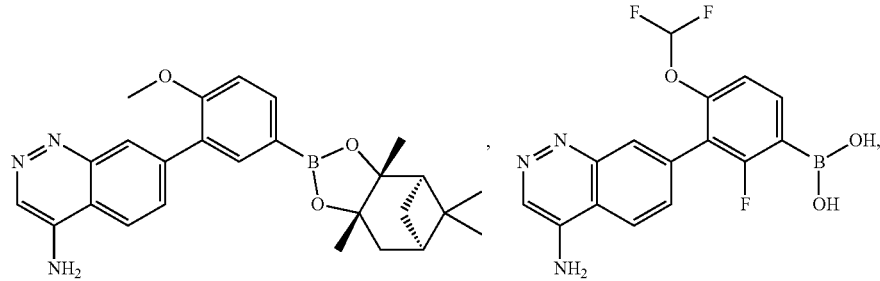
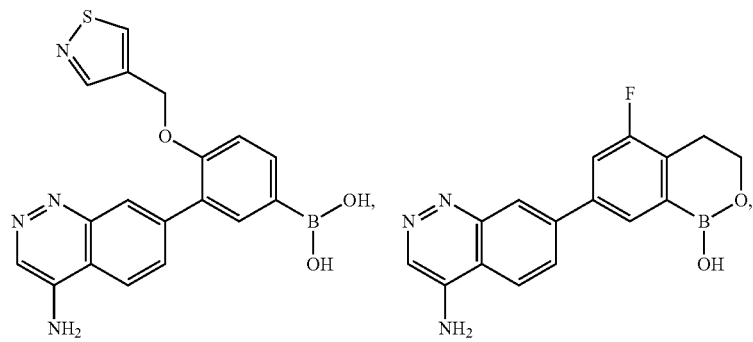
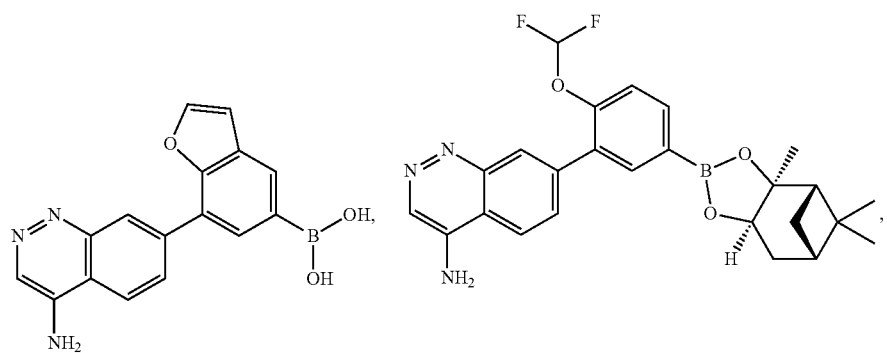
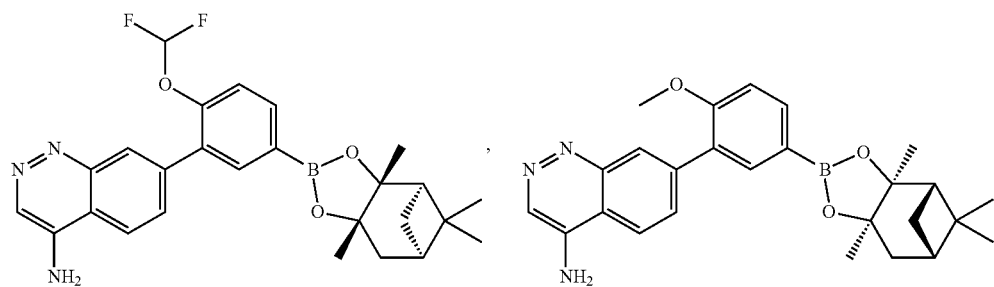
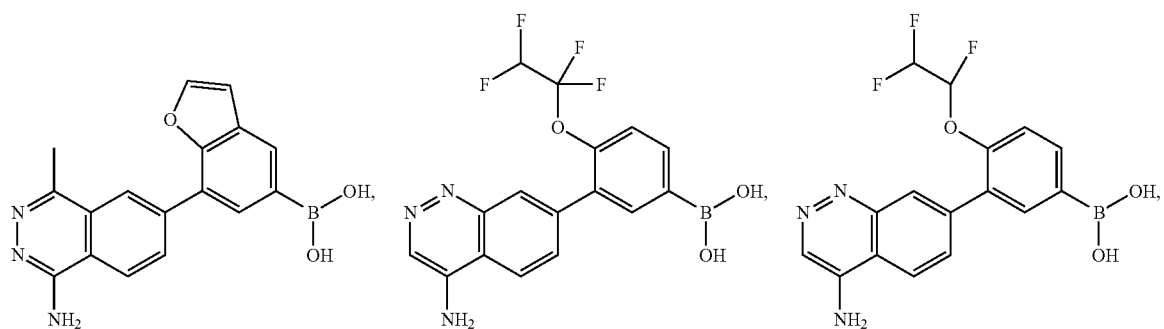

-continued
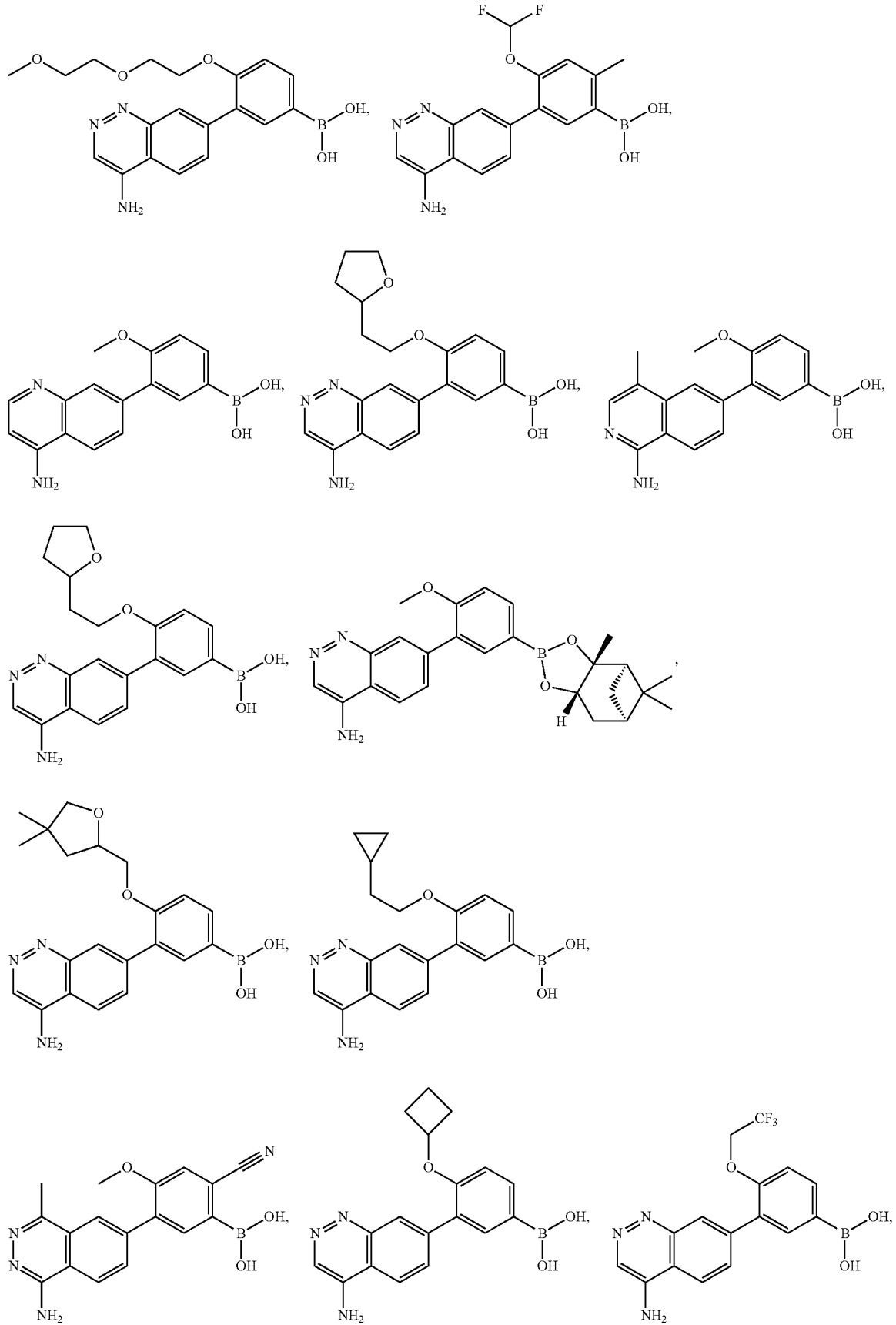

-continued
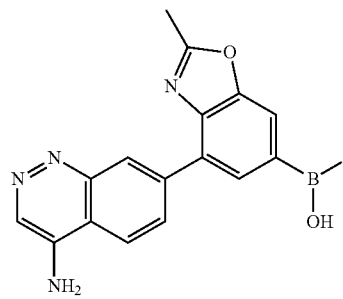 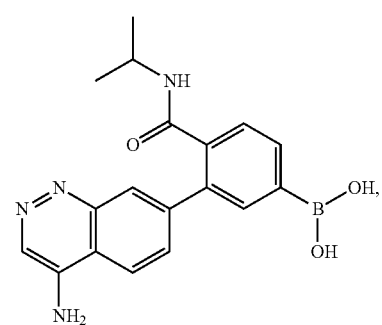 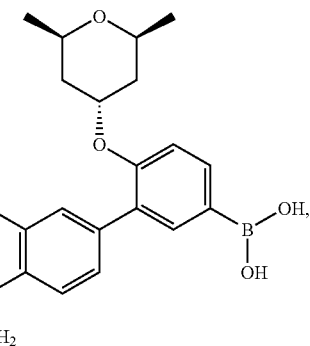
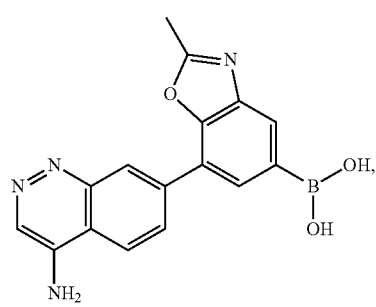 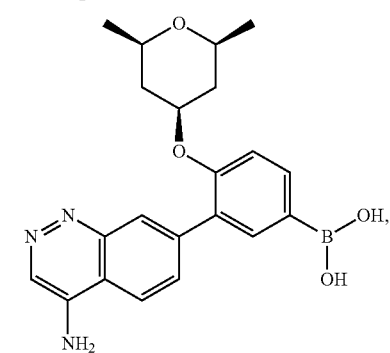
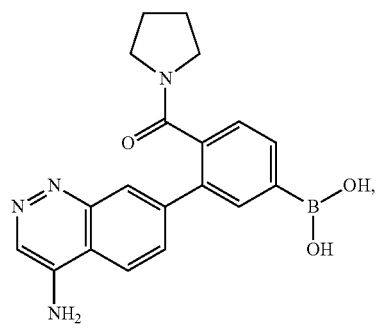 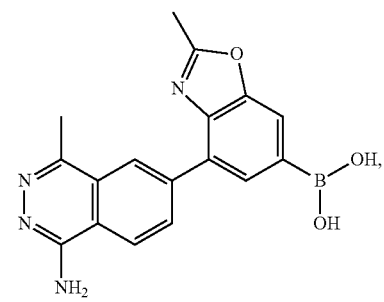
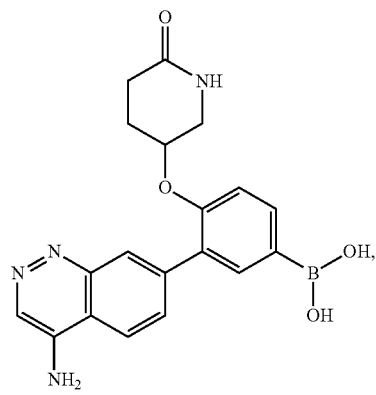 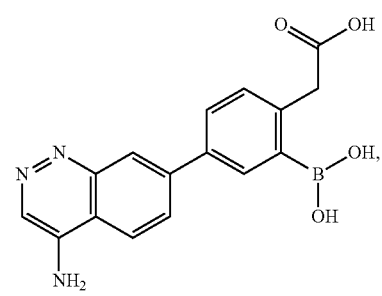 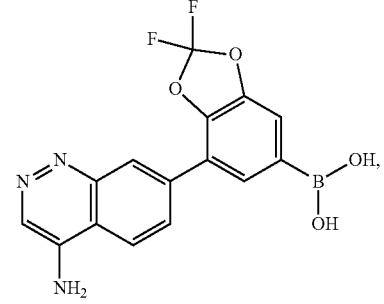
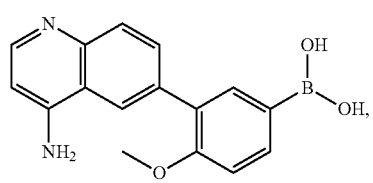 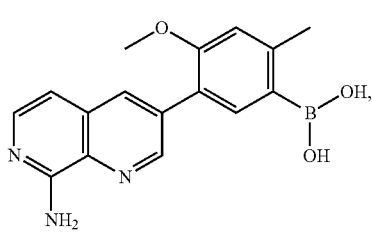 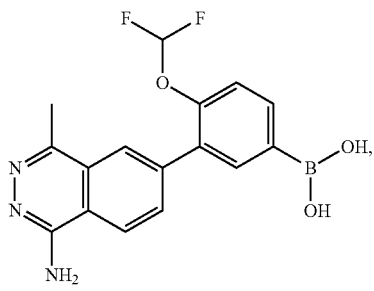

-continued
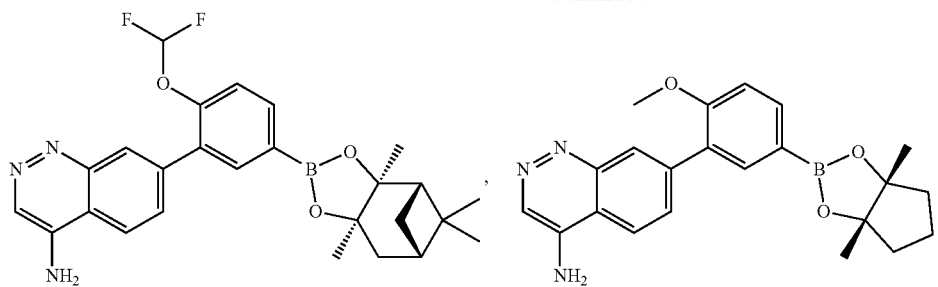
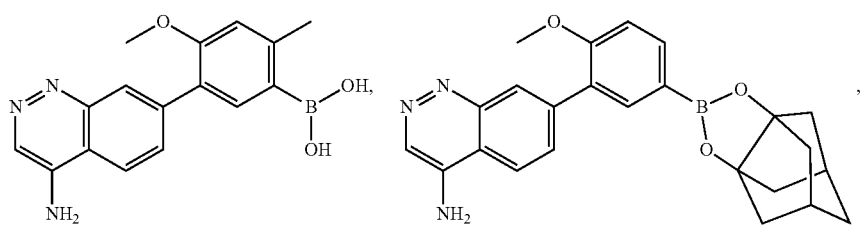
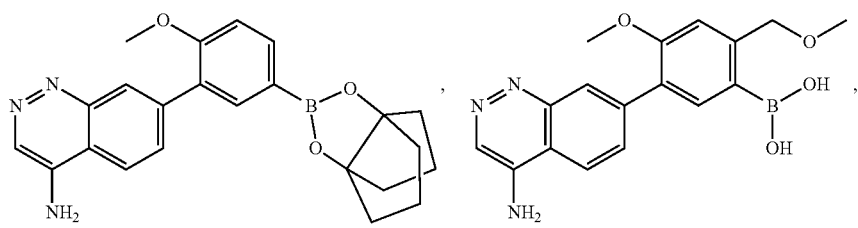
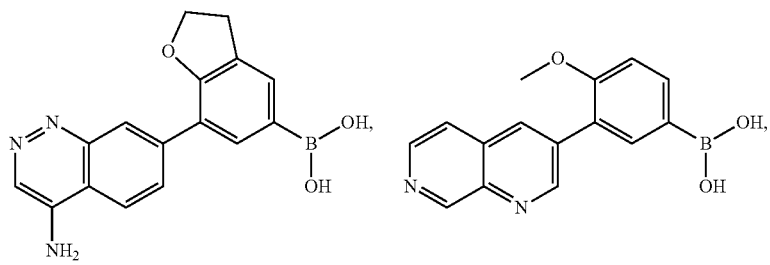
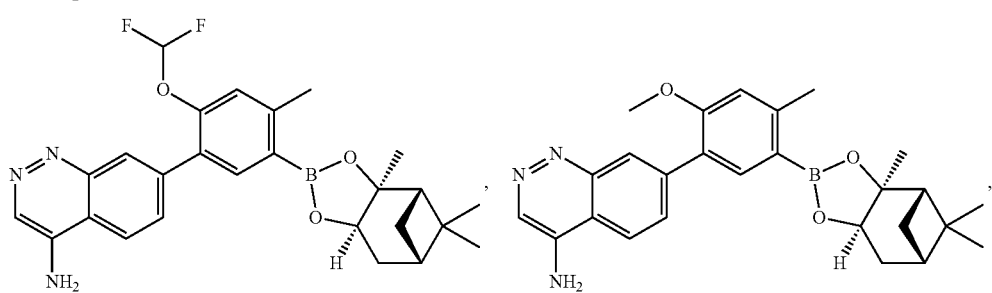
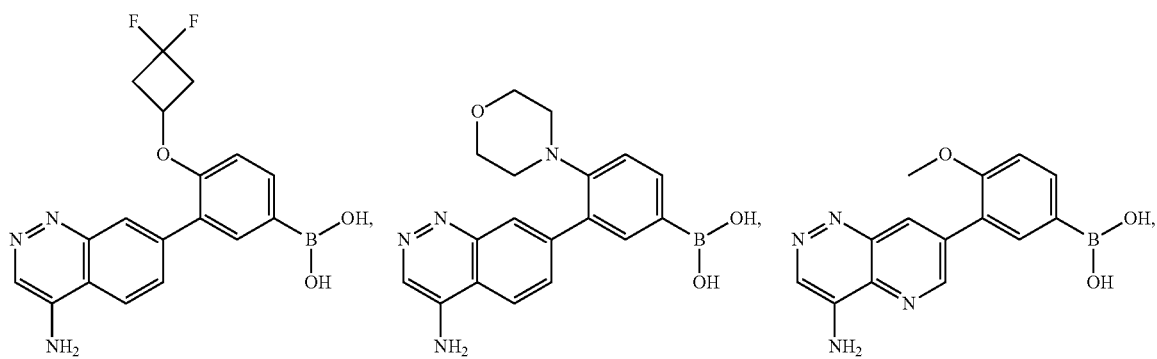

-continued
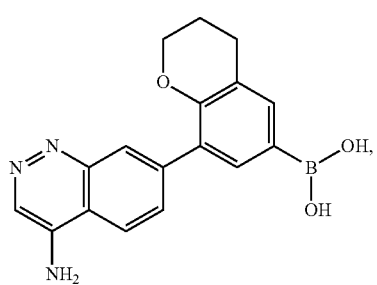
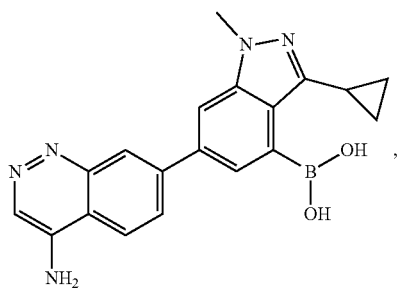
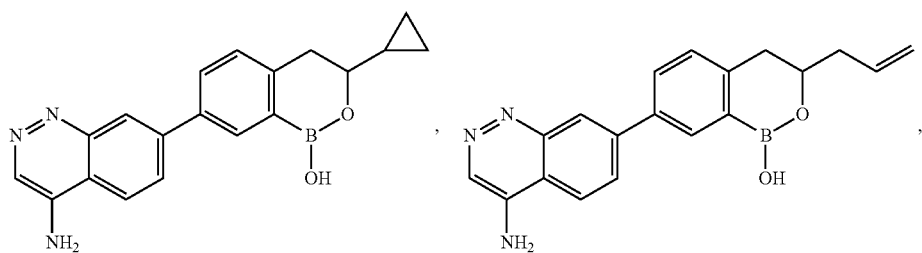
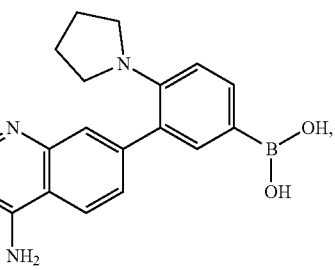
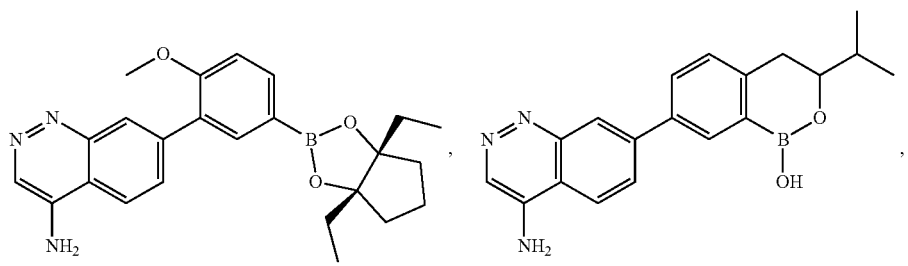
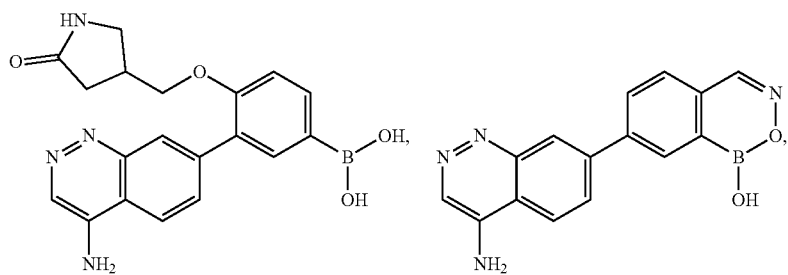
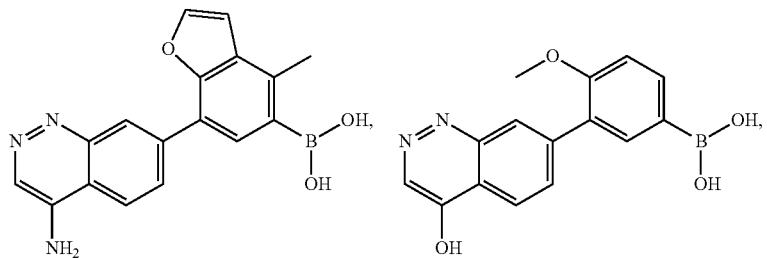

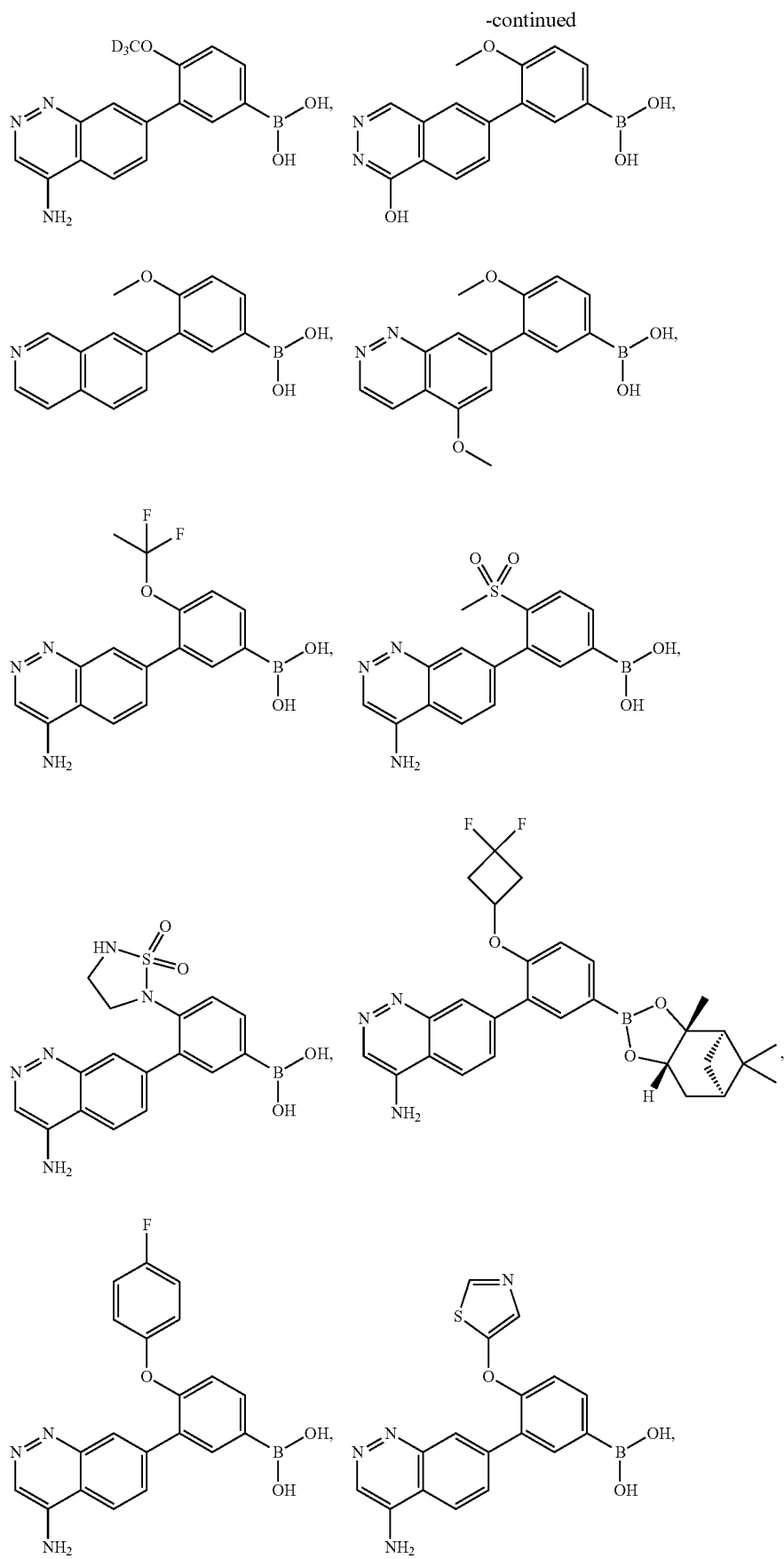

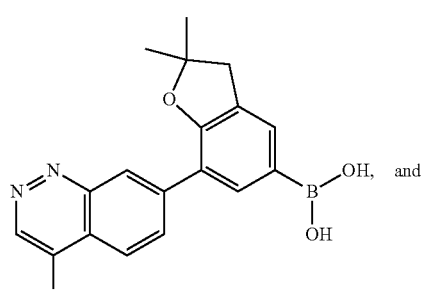
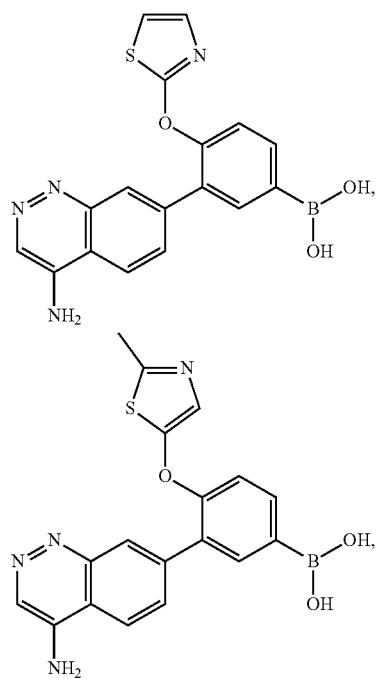

or a pharmaceutically acceptable salt thereof.

In certain embodiments, the pharmaceutically acceptable salt of any of the above-described compounds is a formic acid salt, methanesulfonic acid salt, ethane sulfonic acid salt, or maleic acid salt.

In certain aspects, the present disclosure provides pharmaceutical compositions, comprising the compound of any one of the preceding claims and a pharmaceutically acceptable excipient.

Definitions

Unless otherwise defined herein, scientific and technical terms used in this application shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well known and commonly used in the art.

The methods and techniques of the present disclosure are generally performed, unless otherwise indicated, according to conventional methods well known in the art and as described in various general and more specific references that are cited and discussed throughout this specification. See, e.g. "Principles of Neural Science", McGraw-Hill Medical, New York, N.Y. (2000); Motulsky, "Intuitive Biostatistics", Oxford University Press, Inc. (1995); Lodish et al., "Molecular Cell Biology, 4th ed", W. H. Freeman & Co., New York (2000); Griffiths et al., "Introduction to Genetic Analysis, 7th ed.", W. H. Freeman & Co., N.Y. (1999); and Gilbert et al., "Developmental Biology, 6th ed", Sinauer Associates, Inc., Sunderland, MA (2000).

Chemistry terms used herein, unless otherwise defined herein, are used according to conventional usage in the art, as exemplified by "McGraw-Hill Dictionary of Chemical Terms", Parker S., Ed., McGraw-Hill, San Francisco, C.A. (1985).

All of the above, and any other publications, patents and published patent applications referred to in this application are specifically incorporated by reference herein. In case of conflict, the present specification, including its specific definitions, will control.

The term "agent" is used herein to denote a chemical compound (such as an organic or inorganic compound, a mixture of chemical compounds), a biological macromolecule (such as a nucleic acid, an antibody, including parts thereof as well as humanized, chimeric and human antibodies and monoclonal antibodies, a protein or portion thereof, e.g., a peptide, a lipid, a carbohydrate), or an extract made from biological materials such as bacteria, plants, fungi, or animal (particularly mammalian) cells or tissues. Agents include, for example, agents whose structure is known, and those whose structure is not known. The ability of such agents to inhibit complement factors may render them suitable as "therapeutic agents" in the methods and compositions of this disclosure.

A "patient," "subject," or "individual" are used interchangeably and refer to either a human or a non-human animal. These terms include mammals, such as humans, primates, livestock animals (including bovines, porcines, etc.), companion animals (e.g., canines, felines, etc.) and rodents (e.g., mice and rats).

"Treating" a condition or patient refers to taking steps to obtain beneficial or desired results, including clinical results. As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount.

"Administering" or "administration of" a substance, a compound or an agent to a subject can be carried out using one of a variety of methods known to those skilled in the art. For example, a compound or an agent can be administered, intravenously, arterially, intradermally, intramuscularly, intraperitoneally, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods.

Appropriate methods of administering a substance, a compound or an agent to a subject will also depend, for example, on the age and/or the physical condition of the subject and the chemical and biological properties of the compound or agent (e.g., solubility, digestibility, bioavailability, stability and toxicity). In some embodiments, a compound or an agent is administered orally, e.g., to a subject by ingestion. In some embodiments, the orally administered compound or agent is in an extended release or slow release formulation, or administered using a device for such slow or extended release.

As used herein, the phrase "conjoint administration" refers to any form of administration of two or more different therapeutic agents such that the second agent is administered while the previously administered therapeutic agent is still effective in the body (e.g., the two agents are simultaneously effective in the patient, which may include synergistic effects of the two agents). For example, the different therapeutic compounds can be administered either in the same formulation or in separate formulations, either concomitantly or sequentially. Thus, an individual who receives such treatment can benefit from a combined effect of different therapeutic agents.

A "therapeutically effective amount" or a "therapeutically effective dose" of a drug or agent is an amount of a drug or an agent that, when administered to a subject will have the intended therapeutic effect. The full therapeutic effect does not necessarily occur by administration of one dose, and may occur only after administration of a series of doses. Thus, a therapeutically effective amount may be administered in one or more administrations. The precise effective amount needed for a subject will depend upon, for example, the subject's size, health and age, and the nature and extent of the condition being treated, such as cancer or MDS. The skilled worker can readily determine the effective amount for a given situation by routine experimentation.

As used herein, the terms "optional" or "optionally" mean that the subsequently described event or circumstance may occur or may not occur, and that the description includes instances where the event or circumstance occurs as well as instances in which it does not. For example, "optionally substituted alkyl" refers to the alkyl may be substituted as well as where the alkyl is not substituted.

It is understood that substituents and substitution patterns on the compounds of the present invention can be selected by one of ordinary skilled person in the art to result chemically stable compounds which can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

As used herein, the term "optionally substituted" refers to the replacement of one to six hydrogen radicals in a given structure with the radical of a specified substituent including, but not limited to: hydroxyl, hydroxyalkyl, alkoxy, halogen, alkyl, nitro, silyl, acyl, acyloxy, aryl, heteroaryl, cycloalkyl, heterocyclyl, amino, aminoalkyl, cyano, haloalkyl, haloalkoxy, —OCO—CH$_2$—O-alkyl, —OP(O)(O-alkyl)$_2$ or —CH$_2$—OP(O)(O-alkyl)$_2$. Preferably, "optionally substituted" refers to the replacement of one to four hydrogen radicals in a given structure with the substituents mentioned above. More preferably, one to three hydrogen radicals are replaced by the substituents as mentioned above. It is understood that the substituent can be further substituted.

As used herein, the term "alkyl" refers to saturated aliphatic groups, including but not limited to $C_1$-$C_{10}$ straight-chain alkyl groups or $C_1$-$C_{10}$ branched-chain alkyl groups. Preferably, the "alkyl" group refers to $C_1$-$C_6$ straight-chain alkyl groups or $C_1$-$C_6$ branched-chain alkyl groups. Most preferably, the "alkyl" group refers to $C_1$-$C_4$ straight-chain alkyl groups or $C_1$-$C_4$ branched-chain alkyl groups. Examples of "alkyl" include, but are not limited to, methyl, ethyl, 1-propyl, 2-propyl, n-butyl, sec-butyl, tert-butyl, 1-pentyl, 2-pentyl, 3-pentyl, neo-pentyl, 1-hexyl, 2-hexyl, 3-hexyl, 1-heptyl, 2-heptyl, 3-heptyl, 4-heptyl, 1-octyl, 2-octyl, 3-octyl or 4-octyl and the like. Moreover, the term "alkyl" as used throughout the specification, examples, and claims is intended to include both unsubstituted and substituted alkyl groups, the latter of which refers to alkyl moieties having substituents replacing a hydrogen on one or more carbons of the hydrocarbon backbone, including haloalkyl groups such as trifluoromethyl and 2,2,2-trifluoroethyl, etc.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "$C_{x-y}$" or "$C_x$-$C_y$", when used in conjunction with a chemical moiety, such as, acyl, acyloxy, alkyl, alkenyl, alkynyl, or alkoxy is meant to include groups that contain from x to y carbons in the chain. $C_0$alkyl indicates a hydrogen where the group is in a terminal position, a bond if internal. A $C_{1-6}$alkyl group, for example, contains from one to six carbon atoms in the chain.

The term "alkylamino", as used herein, refers to an amino group substituted with at least one alkyl group.

The term "alkylthio", as used herein, refers to a thiol group substituted with an alkyl group and may be represented by the general formula alkylS—.

The term "amide", as used herein, refers to a group

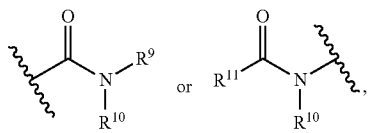

wherein $R^9$, $R^{10}$, and $R^{11}$, each independently represent a hydrogen or hydrocarbyl group, or $R^9$ and $R^{10}$ taken together with the N atom to which they are attached complete a heterocycle having from 4 to 8 atoms in the ring structure, or $R^{10}$ and $R^{11}$ taken together with the N atom to which they are attached complete a heterocycle having from 4 to 8 atoms in the ring structure.

The term "amidino", as used herein, refers to a group

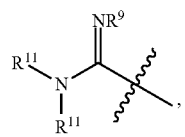

wherein $R^9$, $R^{10}$, and $R^{11}$, each independently represent a hydrogen or hydrocarbyl group, or $R^9$ and $R^{10}$ taken together with the N atom to which they are attached complete a heterocycle having from 4 to 8 atoms in the ring structure, or $R^{10}$ and $R^{11}$ taken together with the N atom to which they are attached complete a heterocycle having from 4 to 8 atoms in the ring structure.

The term "amido", as used herein, refers to a group

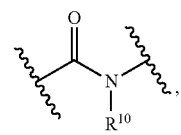

wherein $R^{10}$ represents a hydrogen or hydrocarbyl group.

The terms "amine" and "amino" are art-recognized and refer to both unsubstituted and substituted amines and salts thereof, e.g., a moiety that can be represented by

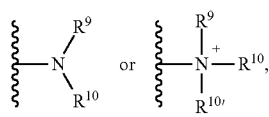

wherein $R^9$, $R^{10}$, and $R^{10'}$ each independently represent a hydrogen or a hydrocarbyl group, or $R^9$ and $R^{10}$ taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "azido" is art-recognized and refers to the group —$N_3$.

The term "carbamate" is art-recognized and refers to a group

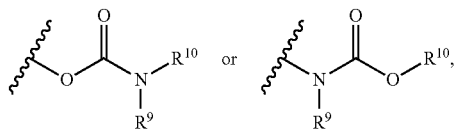

wherein $R^9$ and $R^{10}$ independently represent hydrogen or a hydrocarbyl group.

The term "carbocyclylalkyl", as used herein, refers to an alkyl group substituted with a carbocycle group.

The term "carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

The term "carbocyclylalkyl", as used herein, refers to an alkyl group substituted with a carbocycle group.

The term "carbonate" is art-recognized and refers to a group —$OCO_2$—.

The term "carboxy", as used herein, refers to a group represented by the formula —$CO_2H$.

The term "ester", as used herein, refers to a group —C(O)OR$^9$ wherein R$^9$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The term "haloalkyl" as used herein refers to an alkyl group wherein one or more hydrogens is replaced with a halogen.

The term "haloalkoxy" as used herein refers to an alkoxy group in which one or more hydrogen atoms is replaced with a halogen atom.

The terms "hetaralkyl" and "heteroaralkyl", as used herein, refers to an alkyl group substituted with a hetaryl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The term "heterocyclylalkyl", as used herein, refers to an alkyl group substituted with a heterocycle group.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and even trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to, aryl, heteroaryl, carbocycle, heterocycle, alkyl, alkenyl, alkynyl, and combinations thereof.

The term "hydroxyalkyl", as used herein, refers to an alkyl group substituted with a hydroxy group.

The term "imine" is art-recognized and refers to a group

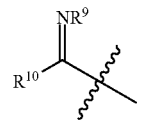

wherein R$^9$ is a hydrogen or a hydrocarbyl group, and R$^{10}$ represents a hydrocarbyl group, or R$^9$ and R$^{10}$ taken together with the N atom to which R$^9$ is attached complete a heterocycle having from 4 to 8 atoms in the ring structure.

The term "lower" when used in conjunction with a chemical moiety, such as, acyl, acyloxy, alkyl, alkenyl, alkynyl, or alkoxy is meant to include groups where there are ten or fewer atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The term "oxime" is art regognized and refers to the group

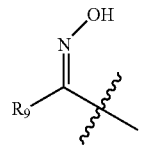

wherein R$^9$ represents hydrogen or a hydrocarbyl group.

The term "phosphonate" is art recognized and refers to the group

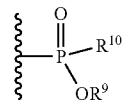

The term "dialkylphosphine oxide" is art recognized and refers to the group

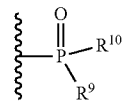

wherein R$^9$ and R$^{10}$ independently represents hydrogen or hydrocarbyl.

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "sulfate" is art-recognized and refers to the group —OSO$_3$H, or a pharmaceutically acceptable salt thereof.

The term "sulfonamide" is art-recognized and refers to the group represented by the general formulae

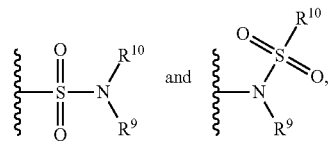

wherein R$^9$ and R$^{10}$ independently represents hydrogen or hydrocarbyl.

The term "sulfoxide" is art-recognized and refers to the group-S(O)—.

The term "sulfonate" is art-recognized and refers to the group SO$_3$H, or a pharmaceutically acceptable salt thereof.

The term "sulfone" is art-recognized and refers to the group —S(O)$_2$—.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

The term "thioalkyl", as used herein, refers to an alkyl group substituted with a thiol group.

The term "thioester", as used herein, refers to a group —C(O)SR$^9$ or —SC(O)R$^9$ wherein R$^9$ represents a hydrocarbyl.

The term "thioether", as used herein, is equivalent to an ether, wherein the oxygen is replaced with a sulfur.

The term "urea" is art-recognized and may be represented by the general formula

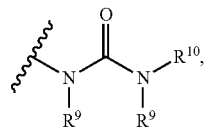

wherein R$^9$ and R$^{10}$ independently represent hydrogen or a hydrocarbyl.

The term "modulate" as used herein includes the inhibition or suppression of a function or activity (such as cell proliferation) as well as the enhancement of a function or activity.

The term "inhibit" as used herein includes the suppression of a function or activity. In certain embodiments, a compound disclosed herein inhibits a complement factor. Complement factor inhibition may be measured according to techniques known to those skilled in the art, such as an enzyme assay. For example, C1s inhibition can be determined according to the enzyme assay disclosed herein in Example 174. In some embodiments, a compound inhibits C1s when the PIC50 determined according to the procedure described in Example 174 is at least 5, at least 5.5, at least 6, at least 6.5, at least 7, at least 7.5, at least 8, at least 8.5, or at least 9.

The phrase "pharmaceutically acceptable" is art-recognized. In certain embodiments, the term includes compositions, excipients, adjuvants, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable salt" or "salt" is used herein to refer to an acid addition salt or a basic addition salt which is suitable for or compatible with the treatment of patients.

The term "pharmaceutically acceptable acid addition salt" as used herein means any non-toxic organic or inorganic salt of any base compounds represented by Formula I or IF Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of compounds of Formula I or II are more soluble in water and various hydrophilic organic solvents, and generally demonstrate higher melting points in comparison to their free base forms. The selection of the appropriate salt will be known to one skilled in the art. Other non-pharmaceutically acceptable salts, e.g., oxalates, may be used, for example, in the isolation of compounds of Formula I or II for laboratory use, or for subsequent conversion to a pharmaceutically acceptable acid addition salt.

The term "pharmaceutically acceptable basic addition salt" as used herein means any non-toxic organic or inorganic base addition salt of any acid compounds represented by Formula I or II or any of their intermediates. Illustrative inorganic bases which form suitable salts include lithium, sodium, potassium, calcium, magnesium, or barium hydroxide. Illustrative organic bases which form suitable salts include aliphatic, alicyclic, or aromatic organic amines such as methylamine, trimethylamine and picoline or ammonia. The selection of the appropriate salt will be known to a person skilled in the art.

Many of the compounds useful in the methods and compositions of this disclosure have at least one stereogenic center in their structure. This stereogenic center may be present in a R or a S configuration, said R and S notation is used in correspondence with the rules described in Pure Appl. Chem. (1976), 45, 11-30. The disclosure contemplates all stereoisomeric forms such as enantiomeric and diastereoisomeric forms of the compounds, salts, prodrugs or mixtures thereof (including all possible mixtures of stereoisomers). See, e.g., WO 01/062726.

Furthermore, certain compounds which contain alkenyl groups may exist as Z (zusammen) or E (entgegen) isomers. In each instance, the disclosure includes both mixture and separate individual isomers.

Some of the compounds may also exist in tautomeric forms. Such forms, although not explicitly indicated in the formulae described herein, are intended to be included within the scope of the present disclosure.

"Prodrug" or "pharmaceutically acceptable prodrug" refers to a compound that is metabolized, for example hydrolyzed or oxidized, in the host after administration to form the compound of the present disclosure (e.g., compounds of Formula I, II or II). Typical examples of prodrugs include compounds that have biologically labile or cleavable (protecting) groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound. Examples of prodrugs using ester or phosphoramidate as biologically labile or cleavable (protecting) groups are disclosed in U.S. Pat. Nos. 6,875,751, 7,585,851, and 7,964,580, the disclosures of which are incorporated herein by reference. The prodrugs of this disclosure are metabolized to produce a compound of Formula I or Formula II. The present disclosure includes within its scope, prodrugs of the compounds described herein. Conventional procedures for the selection and preparation of suitable prodrugs are described, for example, in "Design of Prodrugs" Ed. H. Bundgaard, Elsevier, 1985.

The phrase "pharmaceutically acceptable carrier" as used herein means a pharmaceutically acceptable material, composition or vehicle, such as a liquid or solid filter, diluent, excipient, solvent or encapsulating material useful for formulating a drug for medicinal or therapeutic use.

The term "Log of solubility", "Log S" or "log S" as used herein is used in the art to quantify the aqueous solubility of a compound. The aqueous solubility of a compound significantly affects its absorption and distribution characteristics. A low solubility often goes along with a poor absorption. Log S value is a unit stripped logarithm (base 10) of the solubility measured in mol/liter.

Pharmaceutical Compositions

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In preferred embodiments, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as a lotion, cream, or ointment. A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a selfemulsifying drug delivery system or a selfmicroemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

In some instances, the pharmaceutical composition may be a solid dispersion. The term "solid dispersion" refers to a system in a solid state comprising at least two components, wherein one component is dispersed throughout the other component or components. For example, the solid dispersion can be an amorphous solid dispersion. The tem "amorphous solid dispersion" as used herein, refers to stable solid dispersions comprising an amorphous drug substance and a polymer. By "amorphous drug substance," it is meant that the amorphous solid dispersion contains drug substance in a substantially amorphous solid state form.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); subcutaneously; transdermally (for example as a patch applied to the skin); and topically (for example, as a cream, ointment or spray applied to the skin). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; (11) a biocompatible polymer, such as those used to make amorphous solid dispersions, and (12) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans; and other mammals such as equines, cattle, swine, sheep, cats, and dogs; poultry; and pets in general.

In certain embodiments, compounds of the invention may be used alone or conjointly administered with another type of therapeutic agent.

The present disclosure includes the use of pharmaceutically acceptable salts (see Berge et al. (1977) "Pharmaceutical Salts", J. Pharm. Sci. 66: 1-19) of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxy ethyl)pyrrolidine, sodium, triethanolamine, tromethamine, and zinc salts. In certain embodiments, contemplated salts of the invention include, but are not limited to, Na, Ca, K, Mg, Zn or other metal salts. In certain embodiments, contemplated salts of the invention include, but are not limited to, 1-hydroxyl-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, 1-ascorbic acid, 1-aspartic acid, benzenesulfonic acid, benzoic acid, (+)-camphoric acid, (+)-camphor-10-sulfonic acid, capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, d-glucoheptonic acid, d-gluconic acid, d-glucuronic acid, glutamic acid, glutaric acid, glycerophosphoric acid, glycolic acid, hippuric acid, hydrobromic acid, hydrochloric acid, isobutyric acid, lactic acid, lactobionic acid, lauric acid, maleic acid, 1-malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, 1-pyroglutamic acid, salicylic acid, sebacic acid, stearic acid, succinic acid, sulfuric acid, 1-tartaric acid, thiocyanic acid, p-toluenesulfonic acid, trifluoroacetic acid, and undecylenic acid acid salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine Methods of Treatment In certain aspects, the present disclosure provides methods of treating a disease or condition associated with complement activation in an individual in need thereof, comprising administering a therapeutically effective amount of the compounds provided herein. While not being bound by theory, it is believed that the compounds disclosed herein act as C1s inhibitors and can therefore prevent complement activation, in turn treating diseases that associated with complement activation.

In certain embodiments, the disease or condition is selected from a neurodegenerative disorder, an inflammatory disease, an autoimmune disease, an ophthalmic disease, and a metabolic disorder. Those skilled in the art will readily appreciate that many diseases or conditions can fall into more than one of the aforementioned categories of diseases. For examples, conditions can be both neurological and autoimmune, autoimmune and inflammatory, ophthalmic and neurologic, and so on.

Diseases or conditions associated with complement activation that may be treated in accordance with the present methods include without limitation:

Alzheimer's disease, amyotrophic lateral sclerosis, multiple sclerosis, progressive multiple schlerosis, glaucoma, myotonic dystrophy, Guillain-Barre' syndrome, Myasthenia Gravis, spinal muscular atrophy, Down syndrome, Parkinson's disease, Huntington's disease, traumatic brain injury, epilepsy, frontotemporal dementia, diabetes, obesity, atherosclerosis, rheumatoid arthritis, acute respiratory distress syndrome, pemphigus, pemphigus vulgaris, pemphigus foliaceus, bullous pemphigoid, immune-mediated necrotizing myopathy, vitiligo, paraneoplastic syndromes, a vasculitis disease, hypocomplementemic urticarial vasculitis, chronic spontaneous urticaria, remote tissue injury after ischemia and reperfusion, complement activation during cardiopulmonary bypass surgery, dermatomyositis, lupus nephritis and resultant glomerulonephritis and vasculitis, kidney fibrosis, systemic lupus erythematosus, Hashimoto's thyroiditis, Addison's disease, Celiac disease, Crohn's disease, pernicious anemia, chronic idiopathic demyelinating polyneuropathy, multifocal motor neuropathy, heparin-induced thrombocytopenia, idiopathic thrombocytopenic purpura, cardioplegia-induced coronary endothelial dysfunction, type II membranoproliferative glomerulonephritis, IgA nephropathy, acute renal failure, cryoglobulemia, antiphospholipid syndrome, chronic open-angle glaucoma, acute closed angle glaucoma, macular degenerative diseases, wet age-related macular degeneration, dry age-related macular degeneration, geographic atrophy, choroidal neovascularization, uveitis, diabetic retinopathy, ischemia-related retinopathy, endophthalmitis, intraocular neovascular disease, diabetic macular edema, pathological myopia, von Hippel-Lindau disease, histoplasmosis of the eye, neuromyelitis optica, central retinal vein occlusion, corneal neovascularization, retinal neovascularization, Leber's hereditary optic neuropathy, optic neuritis, Behcet's retinopathy, ischemic optic neuropathy, retinal vasculitis, ANCA vasculitis, Wegener's granulomatosis, Purtscher retinopathy, Sjogren's dry eye disease, sarcoidosis, temporal arteritis, polyarteritis nodosa, allo-transplantation, hyperacute rejection, hemodialysis, chronic occlusive pulmonary distress syndrome, asthma, aspiration pneumonia, immune thrombocytopenia, autoimmune hemolytic anemia, cold agglutinin disease, warm autoimmune hemolytic anemia and coronary artery disease.

In certain embodiments, the disease or condition associated with complement activation that may be treated in accordance with the present methods includes Guillain-Barre' syndrome, amyotrophic lateral sclerosis (ALS), Huntington's disease (HD), geographic atrophy, cold agglutinin disease, warm autoimmune hemoltyic anemia, lupus nephritis, and multifocal motor neuropathy.

In certain embodiments, the disease or condition associated with complement activation that may be treated in accordance with the present methods is Guillain-Barre' syndrome. In certain embodiments, the disease or condition associated with complement activation that may be treated in accordance with the present methods is ALS. In certain embodiments, the disease or condition associated with complement activation that may be treated in accordance with the present methods is HD. In certain embodiments, the disease or condition associated with complement activation that may be treated in accordance with the present methods is geographic atrophy. In certain embodiments, the disease or condition associated with complement activation that may be treated in accordance with the present methods is cold agglutinin disease. In certain embodiments, the disease or condition associated with complement activation that may be treated in accordance with the present methods is warm autoimmune hemoltyic anemia. In certain embodiments, the disease or condition associated with complement activation that may be treated in accordance with the present methods is lupus nephritis. In certain embodiments, the disease or condition associated with complement activation that may be treated in accordance with the present methods is multifocal motor neuropathy.

In certain embodiments, the disease or condition is a neurodegenerative disorder, for example one associated with loss of synapses or loss of nerve connections, with synapse loss dependent on C1q, C1 complex, CR1, C3, CR3, C4, or CR4, with pathological activity-dependent synaptic loss, or with synapse phagocytosis by microglia. In certain embodiments, the neurodegenerative disorder is associated with dysregulation of C1s. In certain embodiments, the neurodegenerative disorder is associated with activation or dysregulation of C1s. In certain embodiments, the neurodegenerative disorder is associated with activation of C1s.

In certain embodiments, the neurodegenerative disorder is selected from Alzheimer's disease, amyotrophic lateral sclerosis (ALS), multiple sclerosis, progressive multiple schlerosis, glaucoma, myotonic dystrophy, Guillain-Barre' syndrome (GBS), Myasthenia Gravis, spinal muscular atrophy, Down syndrome, Parkinson's disease, Huntington's disease (HD), traumatic brain injury, epilepsy, age-related macular degeneration, immune-mediated necrotizing myopathy (IMNM) and frontotemporal dementia.

In certain embodiments, the neurodegenerative disorder is selected from Guillain-Barre' syndrome, Huntington's disease, amyotrophic lateral sclerosis, and geographic atrophy. Age-related macular degeneration (AMD) diseases include wet AMD and dry AMD. Furthermore, dry AMD involves early, intermediate and late stages, with the late stage being referred to as geographic atrophy, which refers to a progressive loss of cells in the retina.

In certain embodiments, the disease or condition is an inflammatory disease, an autoimmune disease, metabolic disorder, or an ophthalmic disease. In certain embodiments, the inflammatory disease, autoimmune disease, a metabolic disorder, or ophthalmic diesease is associated with activation or dysregulation of C1s.

In certain embodiments the inflammatory disease, autoimmune disease, metabolic disorder, or ophthalmic disease is is selected from diabetes, obesity, atherosclerosis, rheumatoid arthritis, acute respiratory distress syndrome, pemphigus vulgaris, pemphigus foliaceus, bullous pemphigoid, remote tissue injury after ischemia and reperfusion, complement activation during cardiopulmonary bypass surgery, dermatomyositis, pemphigus, lupus nephritis and resultant glomerulonephritis and vasculitis, kidney fibrosis, systemic lupus erythematosus, Hashimoto's thyroiditis, Addison's disease, Celiac disease, Crohn's disease, pernicious anaemia, immune-mediated necrotizing myopathy, vitiligo, paraneoplastic syndromes, a vasculitis disease, hypocomplementemic urticarial vasculitis, chronic spontaneous urticaria, chronic idiopathic demyelinating polyneuropathy, polymyalgia rheumatica, multifocal motor neuropathy, immune thrombocytopenia, heparin-induced thrombocytopenia, idiopathic thrombocytopenic purpura, cardioplegia-induced coronary endothelial dysfunction, type II membranoproliferative glomerulonephritis, IgA nephropathy, acute renal failure, cryoglobulemia, antiphospholipid syndrome, chronic open-angle glaucoma, acute closed angle glaucoma, macular degenerative diseases, wet age-related macular degeneration, dry age-related macular degeneration, geographic atrophy, choroidal neovascularization, uveitis, diabetic retinopathy, ischemia-related retinopathy, endophthalmitis, intraocular neovascular disease, diabetic macular edema, pathological myopia, von Hippel-Lindau disease, histoplasmosis of the eye, neuromyelitis optica, central retinal vein occlusion, corneal neovascularization, retinal neovascularization, Leber's hereditary optic neuropathy, optic neuritis, Behcet's retinopathy, ischemic optic neuropathy, retinal vasculitis, ANCA vasculitis, Wegener's granulomatosis, Purtscher retinopathy, Sjogren's dry eye disease, sarcoidosis, temporal arteritis, polyarteritis nodosa, multiple sclerosis, progressive multiple schlerosis, allo-transplantation, hyperacute rejection, hemodialysis, chronic occlusive pulmonary distress syndrome, asthma, aspiration pneumonia, immune thrombocytopenia, autoimmune hemolytic anemia, cold agglutinin disease, warm autoimmune hemolytic anemia, and coronary artery disease.

In some embodiments, the disease is cold agglutinin disease, warm autoimmune hemolytic anemia, geographic atrophy, lupus nephritis or multifocal motor neuropathy.

In certain embodiments, the disease is an autoimmune hemolytic anemia, such as cold agglutinin disease or warm autoimmune hemolytic anemia.

In certain aspects, the present disclosure provides methods of inhibiting C1s, comprising contacting the C1s with a compound disclosed herein. In certain aspects, the present disclosure provides methods of inhibiting activated C1s, comprising contacting the C1s with a compound disclosed herein.

In certain embodiments, contacting the C1s with the compound comprises administering the compound to an individual.

EXAMPLES

The invention now being generally described, it will be more readily understood by reference to the following examples which are included merely for purposes of illustration of certain aspects and embodiments of the present invention, and are not intended to limit the invention.

General Procedures

Liquid Chromatography-Mass Spectrometry Method a (LC-MS Method A)

Total ion current (TIC) and DAD UV chromatographic traces together with MS and UV spectra associated with the peaks were taken on a UPLC/MS Acquity™ system equipped with PDA detector and coupled to a Waters single quadrupole mass spectrometer operating in alternated positive and negative electrospray ionization mode. [LC/MS-ES (+/−): analyses performed using an Acquity UPLC™ CSH, C18 column (50×2.1 mm, 1.7 μm particle size), column temperature 40° C., mobile phase: A—water+0.1% HCOOH/B—CH$_3$CN+0.1% HCOOH, flow rate: 1.0 mL/min, runtime=2.0 min, gradient: t=0 min 3% B, t=1.5 min 99.9% B, t=1.9 min 99.9% B, t=2.0 min 3% B, stop time 2.0 min. Positive ES 100-1000, Negative ES 100-1000, UV detection DAD 210-350 nm.

Liquid Chromatography-Mass Spectrometry Method B (LC-MS Method B)

Total ion current (TIC) and DAD UV chromatographic traces together with MS and UV spectra associated with the peaks were taken on a UPLC/MS Acquity™ system equipped with PDA detector and coupled to a Waters single quadrupole mass spectrometer operating in alternated positive and negative electrospray ionization mode. [LC/MS-ES (+/−): analyses performed using an Acquity UPLC™ BEH, C18 column (50×2.1 mm, 1.7 μm particle size), column temperature 40° C., mobile phase: A—0.1% v/v aqueous ammonia solution pH 10/B—CH$_3$CN, flow rate: 1.0 mL/min, runtime=2.0 min, gradient: t=0 min 3% B, t=1.5 min 99.9% B, t=1.9 min 99.9% B, t=2.0 min 3% B, stop time 2.0 min. Positive ES 100-1000, Negative ES 100-1000, UV detection DAD 210-350 nm.

Analytical Methods $^1$H Nuclear magnetic resonance (NMR) spectroscopy was carried out using one of the following instruments: a Bruker Avance 400 instrument equipped with probe DUAL 400 MHz S1, a Bruker Avance 400 instrument equipped with probe 6 S1 400 MHz 5 mm $^1$H-$^{13}$C ID, a Bruker Avance III 400 instrument with nanobay equipped with probe Broadband BBFO 5 mm direct, a 400 MHz Agilent Direct Drive instrument with ID AUTO-X PFG probe, all operating at 400 MHz, or an Agilent VNMRS500 Direct Drive instrument equipped with a 5 mm Triple Resonance $^1$H{$^{13}$C/N} cryoprobe operating at 500 MHz. The spectra were acquired in the stated solvent at around room temperature unless otherwise stated. In all cases, NMR data were consistent with the proposed structures. Characteristic chemical shifts (δ) are given in parts-per-million using conventional abbreviations for designation of major peaks: e.g. s, singlet; d, doublet; t, triplet; q, quartet; dd, doublet of doublets; dt, doublet of triplets; br, broad.

Where thin layer chromatography (TLC) has been used it refers to silica gel TLC using silica gel F254 (Merck) plates, Rf is the distance travelled by the compound divided by the distance travelled by the solvent on a TLC plate. Column chromatography was performed using an automatic flash chromatography (Biotage SPI or Isolera) system over Biotage silica gel cartridges (KP-Sil, KP-NH, Sfar D or Sfar Amino D) or in the case of reverse phase column chromatography over Biotage C18 cartridges (KP-C18-HS or Sfar C18 D).

Compound Preparation

Where the preparation of starting materials is not described, these are commercially available, known in the literature, or readily obtainable by those skilled in the art using standard procedures. Where it is stated that compounds were prepared analogously to earlier examples or intermediates, it will be appreciated by the skilled person that the reaction time, number of equivalents of reagents and temperature can be modified for each specific reaction and that it may be necessary or desirable to employ different work-up or purification techniques. Where reactions are carried out using microwave irradiation, the microwave used is a Biotage Initiator. The actual power supplied varies during the course of the reaction in order to maintain a constant temperature.

Examples 1-171: Preparation of Exemplary Compounds

Example 1: [3-(1-aminophthalazin-6-yl)phenyl]boronic Acid (1)

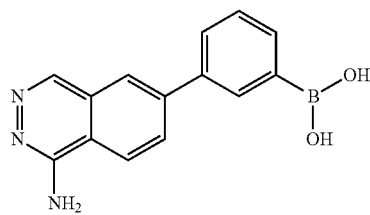 [SMILES: Nc1nncc2cc(-c3cccc(B(O)O)c3)ccc12]

To a solution of 6-[3-(4,4,5,5-tetramethyl-1,3,2-dioxaborolan-2-yl)phenyl]phthalazin-1-amine trifluoroacetic acid salt (89.0 mg, 0.190 mmol) in THF (2 mL), 1M hydrochloric acid solution (1.0 mL, 1 mmol) and sodium periodate (20.64 mg, 0.100 mmol) were added. The mixture was stirred at room temperature for 16 h and the volatiles were removed by evaporation. The residue was purified by column chromatography (KP-C18-HS, SNAP 12 g) eluting with a gradient of CH$_3$CN in water (+0.1% of HCOOH) from 2% to 80% to give [3-(1-aminophthalazin-6-yl)phenyl]boronic acid (20 mg, 0.075 mmol, 39.1% yield). $^1$H NMR (400 MHz, DMSO-d$_6$) δ 7.22 (br. s, 2H), 7.52 (t, J=7.53 Hz, 1H), 7.84-7.88 (m, 1H), 7.88-7.93 (m, 1H), 8.12-8.25 (m, 4H), 8.28 (t, J=1.55 Hz, 1H), 8.38 (d, J=8.35 Hz, 1H), 8.97 (d, J=0.79 Hz, 1H). LC-MS (Method A): r.t. 0.42 min, MS (ESI) m/z=266.2 [M+H]$^+$.

Example 2: [3-(1-aminophthalazin-6-yl)-4-methoxyphenyl]boronic Acid Formic Acid Salt (2)

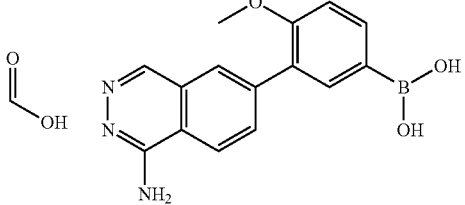

6-[2-Methoxy-5-(4,4,5,5-tetramethyl-1,3,2-dioxaborolan-2-yl)phenyl]phthalazin-1-amine trifluoroacetic acid salt (360.0 mg, 0.730 mmol) was dissolved in THF (21.6 mL) and 1M hydrochloric acid solution (10.26 mL, 10.26 mmol) was added. The mixture was stirred vigorously for 3 hours, then evaporated. The residue was purified by column chromatography (KP-C18-HS, 30 g) eluting with a gradient of CH$_3$CN in water (+0.1% of HCOOH) from 1% to 40%. Fractions containing the desired compound were collected and lyophilized to give [3-(1-amino-4-methylphthalazin-6-yl)-4-methoxyphenyl]boronic acid formic acid salt (46 mg, 0.149 mmol, 57.84% yield) as a white solid. $^1$H NMR (400 MHz, DMSO-d$_6$) δ 3.83 (s, 3H), 7.05 (br. s, 2H), 7.16 (d, J=8.17 Hz, 1H), 7.84-7.90 (m, 2H), 7.96-8.01 (m, 2H), 8.16 (s, HCOOH), 8.27 (d, J=8.40 Hz, 1H), 8.93 (s, 1H). LC-MS (Method A): r.t. 0.43 min, MS (ESI) m/z=296.2 [M+H]$^+$.

Example 3: 6-[2-methoxy-5-(4,4,5,5-tetramethyl-1,3,2-dioxaborolan-2-yl)phenyl]phthalazin-1-amine trifluoroacetic Acid Salt (3)

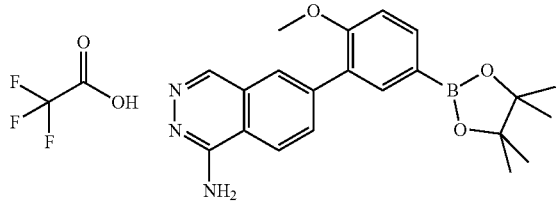 [SMILES: O=C(O)C(F)(F)F ; COc1ccc(B2OC(C)(C)C(C)(C)O2)cc1-c1ccc2c(N)nncc2c1]

A solution of N-[(2,4-dimethoxyphenyl)methyl]-6-[2-methoxy-5-(4,4,5,5-tetramethyl-1,3,2-dioxaborolan-2-yl)phenyl]phthalazin-1-amine (350.0 mg, 0.660 mmol) in DCM (4.71 mL) and trifluoroacetic acid (4.71 mL) was stirred for 2.5 hours at room temperature then it was concentrated under reduced pressure. The residue was suspended in Et$_2$O, stirred for 1 hour, filtered on a Hirsch funnel and dried to give 6-[2-methoxy-5-(4,4,5,5-tetramethyl-1,3,2-dioxaborolan-2-yl)phenyl]phthalazin-1-amine trifluoroacetic acid salt (350 mg, 0.712 mmol, 100% yield) as a pale-pink solid. $^1$H NMR (400 MHz, DMSO-d$_6$) δ 1.31 (s, 12H), 3.87 (s, 3H), 7.26 (d, J=8.42 Hz, 1H), 7.71 (d, J=1.65 Hz, 1H), 7.81 (dd, J=8.29, 1.69 Hz, 1H), 8.26 (dd, J=8.53, 1.79 Hz, 1H), 8.31 (d, J=1.74 Hz, 1H), 8.65 (d, J=8.56 Hz, 1H), 9.01 (s, 1H), 9.16 (br. s, 2H), 14.42 (br. s, TFA). LC-MS (Method A): r.t. 0.75 min, MS (ESI) m/z=378.3 [M+H]$^+$.

Example 4: [3-(1-amino-4-methylphthalazin-6-yl)phenyl]boronic Acid (4)

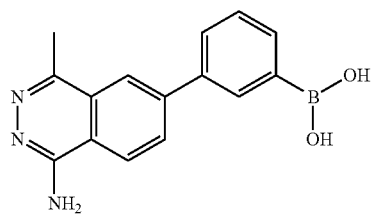 [SMILES: Cc1nnc(N)c2ccc(-c3cccc(B(O)O)c3)cc12]

A solution of [3-[1-[(2,4-dimethoxyphenyl)methylamino]-4-methylphthalazin-6-yl]phenyl]boronic acid (20 mg, 0.047 mmol) in DCM (0.250 mL) and trifluoroacetic acid (0.250 mL) was stirred for 2 hours at room temperature then it was concentrated under reduced pressure. The residue was purified by column chromatography (KP-C18-HS, 12 g) eluting with a gradient of CH$_3$CN in water (+0.1% of HCOOH) from 1% to 40%. Fractions containing the desired compound were collected and lyophilised to give [3-(1-amino-4-methylphthalazin-6-yl)phenyl]boronic acid (12 mg, 0.043 mmol, 92.29% yield) as a white solid. $^1$H NMR (400 MHz, DMSO-d$_6$) δ 2.79 (s, 3H), 7.54 (t, J=7.6 Hz, 1H), 7.62 (br. s, 2H), 7.89 (d, J=7.4 Hz, 1H), 7.97 (d, J=7.8 Hz, 1H), 8.22-8.34 (m, 5H), 8.45-8.52 (m, 1H). LC-MS (Method A): r.t. 0.46 min, MS (ESI) m/z=280.1 [M+H]$^+$.

Example 5: [3-(4-aminocinnolin-7-yl)-4-methoxyphenyl]boronic Acid (5)

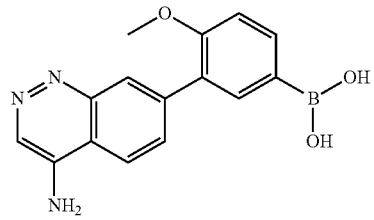 [SMILES: COc1ccc(B(O)O)cc1-c1ccc2c(N)cnnc2c1]

7-[2-Methoxy-5-(4,4,5,5-tetramethyl-1,3,2-dioxaborolan-2-yl)phenyl]cinnolin-4-amine trifluoroacetic acid (450.0 mg, 0.920 mmol) was dissolved in Et$_2$O (12 mL) and 2M hydrochloric acid solution (13.34 mL, 26.69 mmol) was added. The mixture was stirred vigorously for 1.5 hours. CH$_3$CN (10 mL) was added and the two phases (Et$_2$O/Water+CH$_3$CN) were separated. The water+CH$_3$CN phase was concentrated under reduced pressure and the residue was purified by column chromatography (KP-C18-HS, 60 g) eluting with a gradient of CH$_3$CN in water (+0.1% of HCOOH) from 2% to 25%. Fractions containing the compound were collected and lyophilized. The recovered solid was submitted to semi-preparative HPLC purification (Chiralcel OJ-H (25×0.46 cm), 5 µm, n-hexane/(EtOH+0.1% isopropylamine) 85/15% v/v). Fractions containing the desired compound were collected and evaporated under reduced pressure to give [3-(4-aminocinnolin-7-yl)-4-methoxyphenyl]boronic acid (65 mg, 0.220 mmol, 24.05% yield) as a pale yellow solid. ¹H NMR (400 MHz, DMSO-d₆+2 drops of TFA) δ 3.86 (s, 3H), 7.21 (d, J=8.78 Hz, 1H), 7.91-7.95 (m, 2H), 7.97 (dd, J=8.88, 1.63 Hz, 1H), 8.02 (d, J=1.55 Hz, 1H), 8.45-8.49 (m, 2H), 9.70 (s, 1H), 9.84 (s, 1H). LC-MS (Method A): r.t. 0.43 min, MS (ESI) m/z=296.2 [M+H]⁺.

Example 6: 6-[2-methoxy-5-(4,4,5,5-tetramethyl-1,3,2-dioxaborolan-2-yl)phenyl]-4-methylphthalazin-1-amine trifluoroacetic Acid Salt (6)

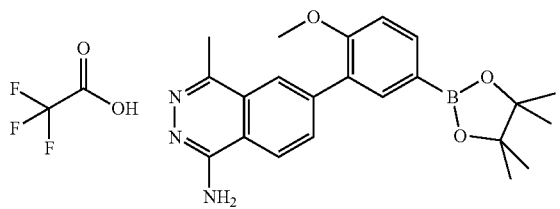 [SMILES: O=C(O)C(F)(F)F ; COc1ccc(B2OC(C)(C)C(C)(C)O2)cc1-c1ccc2c(N)nnc(C)c2c1]

N-[(2,4-Dimethoxyphenyl)methyl]-6-[2-methoxy-5-(4,4,5,5-tetramethyl-1,3,2-dioxaborolan-2-yl)phenyl]-4-methylphthalazin-1-amine (79.0 mg, 0.150 mmol) was dissolved in a mixture of trifluoroacetic acid (1 mL) and DCM (1 mL). The mixture was stirred at room temperature for 4 h and the volatiles were evaporated. The residue was dissolved in MeOH, and filtered through a short pad of Celite. The filtrate was evaporated and the obtained solid residue was triturated twice with Et₂O. The solid was dried under vacuum to give 6-[2-methoxy-5-(4,4,5,5-tetramethyl-1,3,2-dioxaborolan-2-yl)phenyl]-4-methylphthalazin-1-amine trifluoroacetic acid salt (35 mg, 0.069 mmol, 47.47% yield) as a white solid. ¹H NMR (400 MHz, DMSO-d₆) δ 1.30 (s, 12H), 2.74 (s, 3H), 3.84 (s, 3H), 7.24 (d, J=8.39 Hz, 1H), 7.69 (d, J=1.72 Hz, 1H), 7.80 (dd, J=8.39, 1.72 Hz, 1H), 8.19 (dd, J=8.52, 1.68 Hz, 1H), 8.23 (d, J=1.68 Hz, 1H), 8.62 (d, J=8.51 Hz, 1H), 8.85 (s, 2H). LC-MS (Method A): r.t. 0.78 min, MS (ESI) m/z=392.4 [M+H]⁺.

Example 7: [3-(1-amino-4-methylphthalazin-6-yl)-4-methoxyphenyl]boronic Acid Formic Acid Salt (7)

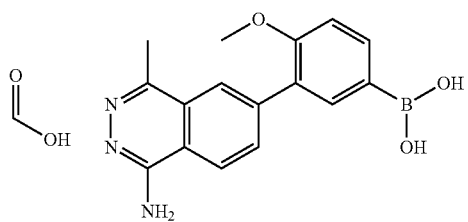 [SMILES: O=CO ; COc1ccc(B(O)O)cc1-c1ccc2c(N)nnc(C)c2c1]

6-[2-Methoxy-5-(4,4,5,5-tetramethyl-1,3,2-dioxaborolan-2-yl)phenyl]-4-methylphthalazin-1-amine trifluoroacetic acid salt (28.0 mg, 0.060 mmol) was suspended in Et₂O (2 mL) and 2M hydrochloric acid solution (0.83 mL, 0.830 mmol) was added. The mixture was stirred vigorously for 45 min and water (5 mL) and Et₂O (5 mL) were added. The layers were separated and the aqueous layer was washed with Et₂O (3×20 mL). The aqueous layer was evaporated and the residue was purified by column chromatography (KP-C18-HS, SNAP 12 g) eluting with a gradient of CH₃CN in water (+0.1% of HCOOH) from 1% to 40%. Fractions containing the desired compound were collected and evaporated under reduced pressure to give [3-(1-amino-4-methylphthalazin-6-yl)-4-methoxyphenyl]boronic acid formic acid salt (12 mg, 0.034 mmol, 60.98% yield) as a white solid. ¹H NMR (400 MHz, DMSO-d₆+2 drops of TFA) δ 2.74 (s, 3H) 3.85 (s, 3H) 7.20 (d, J=8.36 Hz, 1H) 7.86-7.97 (m, 2H) 8.13 (s, 1H from HCOOH) 8.23-8.32 (m, 2H) 8.69 (d, J=8.58 Hz, 1H) 9.14 (br. s, 2H). LC-MS (Method A): r.t. 0.47 min, MS (ESI) m/z=310.2 [M+H]⁺.

Example 8: [3-(4-aminocinnolin-7-yl)-4-[2-[2-[2-[2-[2-(2-methoxyethoxy)ethoxy]ethoxy]ethoxy]ethoxy]phenyl]boronic Acid (8)

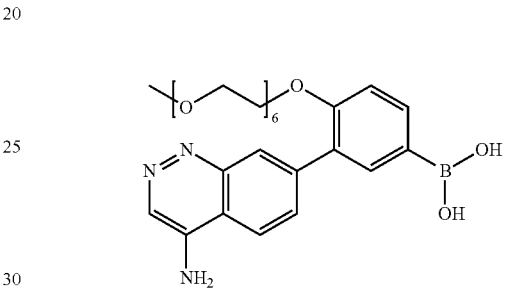

A solution of N-[(2,4-dimethoxyphenyl)methyl]-7-[2-[2-[2-[2-[2-[2-(2-methoxyethoxy)ethoxy]ethoxy]ethoxy]ethoxy]ethoxy]-5-(4,4,5,5-tetramethyl-1,3,2-dioxaborolan-2-yl)phenyl]cinnolin-4-amine (28.0 mg, 0.040 mmol) in DCM (2 mL) and trifluoroacetic acid (1 mL) was stirred for 5 hours at room temperature then was concentrated under reduced pressure. The residue was purified by column chromatography (KP-C18-HS, 12 g) eluting with a gradient of CH₃CN in water from 2% to 95%. Fractions containing the desired compound were collected and evaporated under reduced pressure to give [3-(4-aminocinnolin-7-yl)-4-[2-[2-[2-[2-(2-methoxyethoxy)ethoxy]ethoxy]ethoxy]ethoxy]phenyl]boronic acid (4.7 mg, 0.008 mmol, 23.76% yield) as a yellow powder that in air become a yellow gel. ¹H NMR (400 MHz, DMSO-d₆) δ 3.22 (s, 3H), 3.38-3.50 (m, 18H), 3.51-3.55 (m, 2H), 3.75 (t, J=4.68 Hz, 2H), 4.24 (t, J=5.77, 3.63 Hz, 2H), 7.21 (d, J=8.36 Hz, 1H), 7.90 (dd, J=8.24, 1.69 Hz, 1H), 7.95 (d, J=1.73 Hz, 1H), 8.01-8.08 (m, 4H), 8.41 (d, J=8.87 Hz, 1H), 8.51 (s, 1H). LC-MS (Method A): r.t. 0.51 min, MS (ESI) m/z=560.5 [M+H]⁺.

Example 9: [3-(1-amino-4-propan-2-ylphthalazin-6-yl)phenyl]boronic Acid Hydrochloric Acid Salt (9)

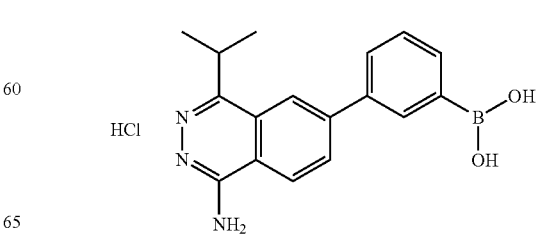

4-Propan-2-yl-6-[3-(4,4,5,5-tetramethyl-1,3,2-dioxaborolan-2-yl)phenyl]phthalazin-1-amine (23.0 mg, 0.060 mmol) was suspended in a 2M solution of hydrogen chloride in Et$_2$O (2.0 mL, 4 mmol) and water (50 μL) was added. The mixture was stirred for 30 min and additional water (1 mL) was added. The mixture was stirred for a further 10 min and the layers were separated. The aqueous layer was washed with Et$_2$O (2×1 mL) and then evaporated under reduced pressure to give [3-(1-amino-4-propan-2-ylphthalazin-6-yl)phenyl]boronic acid hydrochloric acid salt (11 mg, 0.032 mmol, 54.18% yield). $^1$H NMR (400 MHz, DMSO-d$_6$+2 drops of TFA) δ 1.36 (d, J=6.69 Hz, 6H), 3.97 (pent, J=6.69 Hz, 1H), 7.55 (t, J=7.57 Hz, 1H), 7.92 (d, J=7.36 Hz, 1H), 7.99 (d, J=7.68 Hz, 1H), 8.32 (s, 1H), 8.45 (d, J=8.72 Hz, 1H), 8.49 (s, 1H), 8.77 (d, J=8.58 Hz, 1H), 9.24 (br. s, 2H). LC-MS (Method A): r.t. 0.57 min, MS (ESI) m/z=308.3 [M+H]$^+$.

Example 10: [3-(1-amino-4-methylphthalazin-6-yl)-4-methylphenyl]boronic Acid Formic Acid Salt (10)

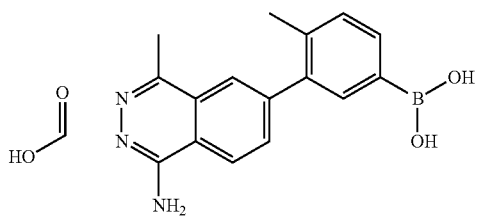

Trifluoroacetic acid (0.600 mL) was added to a solution of N-[(2,4-dimethoxyphenyl)methyl]-4-methyl-6-[2-methyl-5-(4,4,5,5-tetramethyl-1,3,2-dioxaborolan-2-yl)phenyl]phthalazin-1-amine (42.0 mg, 0.080 mmol) in DCM (0.600 mL). The reaction mixture was stirred at room temperature for 30 min, then the volatiles were removed. Et$_2$O (1 mL) was added and the mixture was stirred for 1 h at room temperature, then it was filtered. The filter cake was dissolved in DMSO and purified by column chromatography (KP-C18-HS, SNAP12) eluting with a gradient of MeCN (+0.1% of HCOOH) in water (+0.1% of HCOOH) from 2% to 50%. Appropriate fractions were collected and partially concentrated, then lyophilized to give [3-(1-amino-4-methylphthalazin-6-yl)-4-methylphenyl]boronic acid formic acid salt (9.12 mg, 0.026 mmol, 33.6% yield) as a white solid. NMR analysis showed a partial salification (~60%) of the title compound. $^1$H NMR (400 MHz, DMSO-d$_6$) δ 2.29 (s, 3H), 2.72 (s, 3H), 7.26 (br. s, 2H), 7.34 (d, J=8.36 Hz, 1H), 7.74-7.80 (m, 2H), 7.90-7.95 (m, 2H), 8.06 (br. s, 2H), 8.15 (s, 0.6H from HCOOH), 8.39 (d, J=8.14 Hz, 1H). LC-MS (Method A): r.t. 0.49 min, MS (ESI) m/z=294.26 [M+H]$^+$.

Example 11: [3-(1-amino-4-cyclopropylphthalazin-6-yl)phenyl]boronic Acid Formic Acid Salt (11)

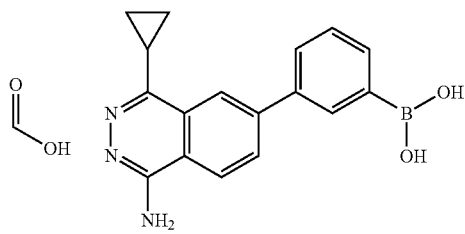 [SMILES: O=CO ; Nc1nnc(C2CC2)c2cc(-c3cccc(B(O)O)c3)ccc12]

A solution of [3-[4-cyclopropyl-1-[(2,4-dimethoxyphenyl)methylamino]phthalazin-6-yl]phenyl]boronic acid (50.0 mg, 0.110 mmol) in DCM (0.200 mL) and trifluoroacetic acid (0.200 mL) was stirred at room temperature for 1 hour then it was concentrated under reduced pressure. The residue was purified by column chromatography (KP-C18-HS 30 g) eluting with a gradient of CH$_3$CN in water (+0.1% of HCOOH) from 1% to 50%. Fractions containing the desired compound were collected and lyophilised to give [3-(1-amino-4-cyclopropylphthalazin-6-yl)phenyl]boronic acid formic acid salt (49 mg, 0.140 mmol, 127.07% yield) as a white solid. $^1$H NMR (400 MHz, DMSO-d$_6$+2 drops of TFA) δ 1.02-1.19 (m, 4H), 2.88 (ddd, J=13.20, 8.25, 5.06 Hz, 1H), 7.58 (t, J=7.58 Hz, 1H), 7.94 (d, J=7.40 Hz, 1H), 8.03 (dd, J=7.88, 1.99 Hz, 1H), 8.13 (s, 1H, HCOOH), 8.35 (s, 1H), 8.48 (dd, J=8.54, 1.73 Hz, 1H), 8.72-8.80 (m, 2H), 9.19 (s, 2H). LC-MS (Method A): r.t. 0.54 min, MS (ESI) m/z=352.1 [M+H]$^+$.

Example 12: [3-(1-amino-4-methylphthalazin-6-yl)-4-ethylphenyl]boronic Acid Formic Acid Salt (12)

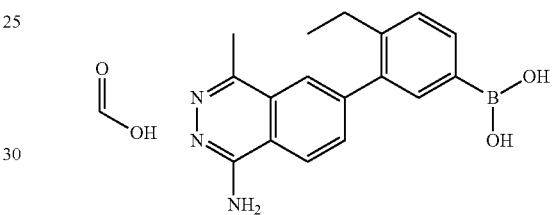

A solution of [3-[1-[(2,4-dimethoxyphenyl)methylamino]-4-methylphthalazin-6-yl]-4-ethylphenyl]boronic acid (36.0 mg, 0.080 mmol) in DCM (1.64 mL) and trifluoroacetic acid (1.64 mL) was stirred for 2 hours at room temperature then it was concentrated under reduced pressure. The residue was purified by column chromatography (KP-C18-HS, 12 g) eluting with a gradient of CH$_3$CN in water (+0.1% of HCOOH) from 1% to 40%. Fractions containing the desired compound were collected and lyophilized to give [3-(1-amino-4-methylphthalazin-6-yl)-4-ethylphenyl]boronic acid formic acid salt (22 mg, 0.062 mmol, 79.13% yield) as a white powder. $^1$H NMR (400 MHz, DMSO-d$_6$+2 drops of TFA) δ 1.07 (t, J=7.52 Hz, 3H), 2.60 (q, J=7.53 Hz, 2H), 2.74 (s, 3H), 7.41 (d, J=7.72 Hz, 1H), 7.72 (d, J=1.36 Hz, 1H), 7.86 (dd, J=7.70, 1.39 Hz, 1H), 8.12-8.17 (m, 2H), 8.14 (s, HCOOH), 8.73 (d, J=8.36 Hz, 1H), 9.15 (s, 2H). LC-MS (Method A): r.t. 0.54 min, MS (ESI) m/z=308.3 [M+H]$^+$.

Example 13: [3-(1-amino-3-methylisoquinolin-6-yl)phenyl]boronic Acid; Trifluoroacetic Acid Salt (13)

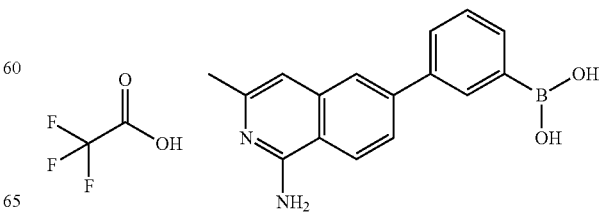

A mixture of N-[(2,4-dimethoxyphenyl)methyl]-3-methyl-6-[3-(4,4,5,5-tetramethyl-1,3,2-dioxaborolan-2-yl)phenyl]isoquinolin-1-amine (150.0 mg, 0.290 mmol) in trifluoroacetic acid (2 mL) and DCM (2 mL) was stirred at room temperature for 30 min, then it was concentrated. The residue was purified by column chromatography (KP-C18-HS, SNAP 30) eluting with a gradient of MeCN in water from 2% to 40%. Product containing fractions were concentrated to give a solid which was stripped with water and dried in the oven overnight to give [3-(1-amino-3-methyl-isoquinolin-6-yl)phenyl]boronic acid trifluoroacetic acid salt (53 mg, 0.135 mmol, 45.99% yield) as a white solid. $^1$H NMR (400 MHz, DMSO-$d_6$+2 drops of TFA) δ 2.48 (s, 3H), 7.10 (s, 1H), 7.54 (t, J=7.59 Hz, 1H), 7.87-7.94 (m, 2H), 8.06 (dd, J=8.80, 1.76 Hz, 1H), 8.14 (d, J=1.76 Hz, 1H), 8.28 (s, 1H), 8.62 (d, J=8.80 Hz, 1H), 8.86 (br. s, 2H), 13.29 (1H, br. s). LC-MS (Method A): r.t. 0.51 min, MS (ESI) m/z=279.26 [M+H]$^+$.

Example 14: 6-(1-hydroxy-3H-2,1-benzoxaborol-6-yl)-4-methylphthalazin-1-amine Formic Acid Salt (14)

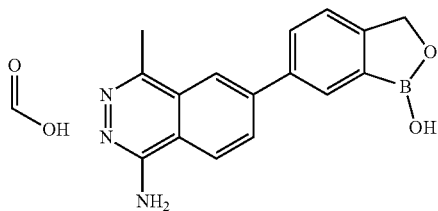

To a solution of N-[(2,4-dimethoxyphenyl)methyl]-4-methyl-6-[4-(oxan-2-yloxymethyl)-3-(4,4,5,5-tetramethyl-1,3,2-dioxaborolan-2-yl)phenyl]phthalazin-1-amine (78.0 mg, 0.120 mmol) in DCM (2 mL), trifluoroacetic acid (2 mL) was added. The mixture was stirred at room temperature for 1.5 h and then the volatiles were removed. The resulting solid was triturated with Et$_2$O, then purified by column chromatography (KP-C18-HS, SNAP 12 g) eluting with a gradient of CH$_3$CN (+0.1% of HCOOH) in water (+0.1% of HCOOH) from 1% to 40% to give 6-(1-hydroxy-3H-2,1-benzoxaborol-6-yl)-4-methylphthalazin-1-amine formic acid salt (18 mg, 0.053 mmol, 42.82% yield) as a white solid. $^1$H NMR (400 MHz, DMSO-$d_6$) δ 2.77 (s, 3H), 5.08 (s, 2H), 7.02 (s, 2H), 7.60 (d, J=7.94 Hz, 1H), 8.00 (dd, J=7.94, 1.85 Hz, 1H), 8.15 (s, 1H, from HCOOH), 8.17-8.23 (m, 3H), 8.36-8.43 (m, 1H), 9.29 (s, 1H). LC-MS (Method A): r.t. 0.50 min, MS (ESI) m/z=292.2 [M+H]$^+$.

Example 15: [3-(1-amino-4-methylphthalazin-6-yl)-4-(trifluoromethoxy)phenyl]boronic Acid (15)

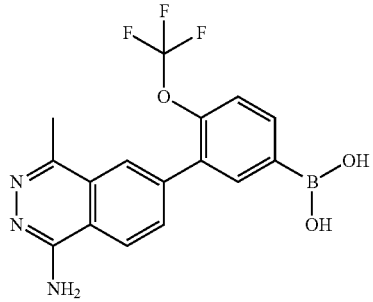 [SMILES: Cc1nnc(N)c2ccc(-c3cc(B(O)O)ccc3OC(F)(F)F)cc12]

A solution of [3-[1-[(2,4-dimethoxyphenyl)methylamino]-4-methylphthalazin-6-yl]-4-(trifluoromethoxy)phenyl]boronic acid (22.0 mg, 0.040 mmol) in DCM (1 mL) and trifluoroacetic acid (1 mL) was stirred for 1 hour at room temperature then it was concentrated under reduced pressure. The crude was submitted to semi-preparative HPLC purification (Chiralcel OJ-H (25×0.46 cm), 5 μm, n-hexane/(EtOH+0.1% isopropylamine) 85/15% v/v). Fractions containing the desired compound were collected and evaporated under reduced pressure to give [3-(1-amino-4-methylphthalazin-6-yl)-4-(trifluoromethoxy)phenyl]boronic acid (6 mg, 0.017 mmol, 38.55% yield) as a white powder. $^1$H NMR (400 MHz, DMSO-$d_6$+1 drop TFA) δ 2.75 (s, 3H), 7.57 (dd, J=8.24, 1.66 Hz, 1H), 8.03 (dd, J=8.24, 1.66 Hz, 1H), 8.10 (d, J=1.69 Hz, 1H), 8.27 (dd, J=8.52, 1.67 Hz, 1H), 8.33 (d, J=1.69 Hz, 1H), 8.77 (d, J=8.58 Hz, 1H), 9.19 (br. s, 2H). LC-MS (Method A): r.t. 0.59 min, MS (ESI) m/z=364.2 [M+H]$^+$.

Example 16: [3-(1-amino-4-methylphthalazin-6-yl)-4-[2-[2-[2-[2-[2-(2-methoxyethoxy)ethoxy]ethoxy]ethoxy]ethoxy]phenyl]boronic Acid (16)

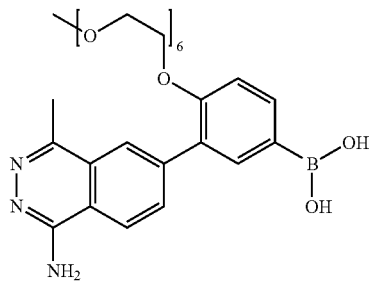

6-[2-[2-[2-[2-[2-[2-(2-Methoxyethoxy)ethoxy]ethoxy]ethoxy]ethoxy]ethoxy]-5-(4,4,5,5-tetramethyl-1,3,2-dioxaborolan-2-yl)phenyl]-4-methylphthalazin-1-amine trifluoroacetic acid salt (45.0 mg, 0.070 mmol) was suspended in Et$_2$O (2 mL) and 2M hydrochloric acid solution (1.0 mL, 2 mmol) was added. To aid solubility DCM (0.200 mL) was added and the viscous mixture became more homogeneous. The mixture was stirred vigorously for 1 hour, then evaporated and the residue was purified by column chromatography (KP-C18-HS, 2×12 g in series) eluting with a gradient of CH$_3$CN in water (+0.1% of HCOOH) from 2% to 30%. Fractions containing the desired compound were collected and lyophilised to give [3-(1-amino-4-methylphthalazin-6-yl)-4-[2-[2-[2-[2-[2-(2-methoxyethoxy)ethoxy]ethoxy]ethoxy]ethoxy]phenyl]boronic acid (16 mg, 0.028 mmol, 40.65% yield) as a white sticky solid that with time became a gel. NMR analysis showed a partial salification of the title compound (~45%). $^1$H NMR (400 MHz, DMSO-d$_6$+2 drops of TFA) δ 2.75 (s, 3H), 3.21 (s, 3H), 3.36-3.50 (m, 18H), 3.54 (dd, J=5.73, 3.22 Hz, 2H), 3.71-3.79 (m, 2H), 4.17-4.29 (m, 2H), 7.20 (d, J=8.35 Hz, 1H), 7.90 (dd, J=8.26, 1.69 Hz, 1H), 7.99 (d, J=1.66 Hz, 1H), 8.12 (s, 0.4H from HCOOH), 8.35 (dd, J=8.57, 1.67 Hz, 1H), 8.41 (d, J=1.64 Hz, 1H), 8.69 (d, J=8.60 Hz, 1H), 9.11 (s, 2H). LC-MS (Method A): r.t. 0.56 min, MS (ESI) m/z=574.52 [M+H]$^+$.

Example 17: [5-(1-amino-4-methylphthalazin-6-yl)pyridin-3-yl]boronic Acid (17)

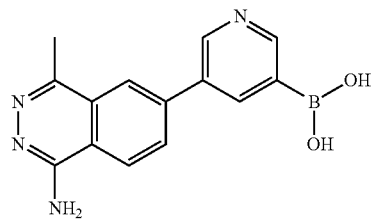 [SMILES: Cc1nnc(N)c2ccc(-c3cncc(B(O)O)c3)cc12]

To a solution of [5-[1-[(2,4-dimethoxyphenyl)methylamino]-4-methylphthalazin-6-yl]pyridin-3-yl]boronic acid (160.0 mg, 0.370 mmol) in DCM (4 mL), trifluoroacetic acid (4 mL) was added and the mixture was stirred at room temperature for 1 h. The volatiles were evaporated and the solid residue was triturated with twice with Et$_2$O. The solid residue was purified by column chromatography (KP-C18-HS, SNAP 12 g) eluting with a gradient of CH$_3$CN (+0.1% of HCOOH) in water (+0.1% of HCOOH) from 1% to 30% to give partially purified product which was purified further by column chromatography (KP-C18-HS, SNAP 12 g) eluting with a gradient of CH$_3$CN in basic water (10 mM ammonium bicarbonate aqueous solution adjusted to pH 10 with ammonia) from 1% to 20% to obtain [5-(1-amino-4-methylphthalazin-6-yl)pyridin-3-yl]boronic acid (17 mg, 0.061 mmol, 16.32% yield) as a white solid. $^1$H NMR (400 MHz, DMSO-d$_6$+2 drops of TFA) δ 2.82 (s, 3H), 8.62 (dd, J=8.58, 1.78 Hz, 1H), 8.69 (d, J=1.78 Hz, 1H), 8.85 (d, J=8.58 Hz, 1H), 9.12 (s, 1H), 9.31 (m, 3H), 9.57 (d, J=2.15 Hz, 1H). LC-MS (Method B): r.t. 0.31 min, MS (ESI) m/z=279.1 [M−H]$^−$.

Example 18: [3-(1-aminophthalazin-6-yl)-4-[(2-chlorobenzoyl)amino]phenyl]boronic Acid Formic Acid Salt (18)

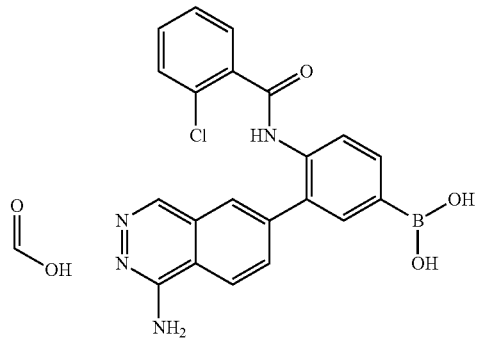 [SMILES: O=CO ; Nc1nncc2cc(-c3cc(B(O)O)ccc3NC(=O)c3ccccc3Cl)ccc12]

A solution of [4-benzamido-3-[1-[(2,4-dimethoxyphenyl)methylamino]phthalazin-6-yl]phenyl]boronic acid (46.97 mg, 0.090 mmol) in DCM (0.250 mL) and trifluoroacetic acid (0.250 mL) was stirred at room temperature for 1 hour then it was concentrated under reduced pressure. The residue was purified by column chromatography (KP-C18-HS, 12 g) eluting with a gradient of CH$_3$CN in water (+0.1% of HCOOH) from 1% to 50%. Fractions containing the desired compound were collected and lyophilised to give [3-(1-aminophthalazin-6-yl)-4-[(2-chlorobenzoyl)amino]phenyl]boronic acid formic acid salt as a white solid. $^1$H NMR (400 MHz, DMSO-d$_6$+2 drops of TFA) δ 7.32-7.51 (m, 4H), 7.61 (d, J=8.17 Hz, 1H), 7.95 (s, 2H), 8.05 (s, HCOOH), 8.23 (dd, J=8.50, 1.83 Hz, 1H), 8.30 (d, J=1.74 Hz, 1H), 8.72 (d, J=8.59 Hz, 1H), 9.02 (s, 1H), 9.37 (s, 2H), 10.29 (s, 1H), 14.57 (s, 1H). LC-MS (Method A): r.t. 0.46 min, MS (ESI) m/z=465.67 [M+H]$^+$.

Example 19: [3-(1-amino-4-methylphthalazin-6-yl)-4-ethylphenyl]boronic Acid Formic Acid Salt (19)

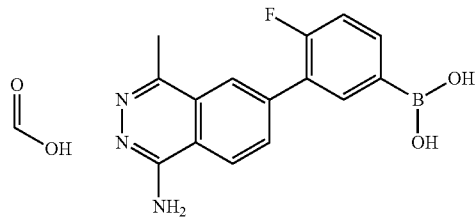 [SMILES: O=CO ; Cc1nnc(N)c2ccc(-c3cc(B(O)O)ccc3F)cc12]

A solution of [3-[1-[(2,4-dimethoxyphenyl)methylamino]-4-methylphthalazin-6-yl]-4-fluorophenyl]boronic acid (56.0 mg, 0.110 mmol) in DCM (3 mL) and trifluoroacetic acid (0.5 mL) was stirred for 2 hours at room temperature then it was concentrated under reduced pressure.

The residue was purified by column chromatography (KP-C18-HS, 2×12 g in series) eluting with a gradient of CH$_3$CN in water (+0.1% of HCOOH) from 2% to 95%. Fractions containing the desired compound were collected and lyophilized to give [3-(1-amino-4-methylphthalazin-6-yl)-4-fluorophenyl]boronic acid formic acid salt (16 mg, 0.047 mmol, 41.38% yield) as a white powder. $^1$H NMR (400 MHz, DMSO-d$_6$+1 drop TFA) δ 2.77 (s, 3H), 7.40 (dd, J=11.20, 8.29 Hz, 1H), 7.94-7.99 (m, 1H), 8.13 (s, 1H from HCOOH), 8.14 (dd, J=8.55, 1.83 Hz, 1H), 8.34 (td, J=8.55, 1.71 Hz, 1H), 8.37 (s, 1H), 8.77 (d, J=8.54 Hz, 1H), 9.19 (br. s, 2H). LC-MS (Method A): r.t. 0.49 min, MS (ESI) m/z=298.2 [M+H]$^+$.

Example 20: 6-(1-hydroxy-5-methoxy-3H-2,1-benzoxaborol-6-yl)-4-methylphthalazin-1-amine (20)

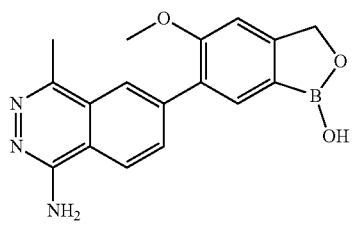 [SMILES: COc1cc2c(cc1-c1ccc3c(N)nnc(C)c3c1)B(O)OC2]

Trifluoroacetic acid (2 mL) was added to a solution of N-[(2,4-dimethoxyphenyl)methyl]-6-[2-methoxy-4-(oxan-2-yloxymethyl)-5-(4,4,5,5-tetramethyl-1,3,2-dioxaborolan-2-yl)phenyl]-4-methylphthalazin-1-amine (133.0 mg, 0.200 mmol) in DCM (2 mL). The mixture was stirred at room temperature for 1 h and the volatiles were evaporated. The residue was purified by column chromatography (KP-C18-HS, SNAP 12 g) eluting with a gradient of CH$_3$CN (+0.1% of HCOOH) in water (+0.1% of HCOOH) from 1% to 30% to give 6-(1-hydroxy-5-methoxy-3H-2,1-benzoxaborol-6-yl)-4-methylphthalazin-1-amine (28 mg, 0.087 mmol, 42.98% yield) as a white solid. NMR analysis showed a partial salification of the title compound (~22%). $^1$H NMR (400 MHz, DMSO-d$_6$+2 drops of TFA) δ 2.72 (s, 3H), 3.84 (s, 3H), 5.03 (s, 2H), 7.24 (s, 1H), 7.80 (s, 1H), 8.10 (s, 0.2H from HCOOH), 8.23 (dd, J=8.48, 1.63 Hz, 1H), 8.26 (d, J=1.63 Hz, 1H), 8.67 (d, J=8.48 Hz, 1H), 9.11 (br. s, 2H). LC-MS (Method A): r.t. 0.51 min, MS (ESI) m/z=322.3 [M+H]$^+$.

Example 21: 6-[2-methoxy-5-(4,4,5,5-tetramethyl-1,3,2-dioxaborolan-2-yl)phenyl]-3-methylisoquinolin-1-amine trifluoroacetic Acid Salt (21)

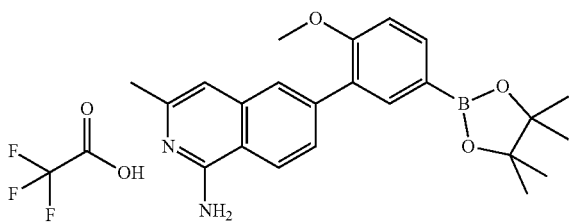

A mixture of N-[(2,4-dimethoxyphenyl)methyl]-6-[2-methoxy-5-(4,4,5,5-tetramethyl-1,3,2-dioxaborolan-2-yl)phenyl]-3-methylisoquinolin-1-amine (159.0 mg, 0.290 mmol) in DCM (2 mL) and trifluoroacetic acid (2 mL) was stirred at room temperature for 30 min. The volatiles were evaporated, Et$_2$O (4 mL) was added and the mixture was stirred for 1 h, then the solid was collected by filtration and washed with Et$_2$O to give 6-[2-methoxy-5-(4,4,5,5-tetramethyl-1,3,2-dioxaborolan-2-yl)phenyl]-3-methylisoquinolin-1-amine trifluoroacetic acid salt (162 mg, 0.321 mmol, 109.19% yield) as a pale pink solid. NMR analysis showed a partial salification (~65%) of the title compound. $^1$H NMR (400 MHz, DMSO-d$_6$) δ 1.30 (s, 12H), 2.46 (s, 3H), 3.84 (s, 3H), 7.10 (s, 1H), 7.22 (d, J=8.36 Hz, 1H), 7.65 (d, J=1.76 Hz, 1H), 7.77 (dd, J=8.36, 1.76 Hz, 1H), 7.79-7.83 (m, 1H), 7.92 (d, J=1.32 Hz, 1H), 8.52 (d, J=8.80 Hz, 1H), 8.66 (br. s, 2H), 13.10 (br. s, 0.65H from TFA). LC-MS (Method A): r.t. 0.82 min, MS (ESI) m/z=391.36 [M+H]$^+$.

Example 22: [3-(1-amino-3-methylisoquinolin-6-yl)-4-methoxyphenyl]boronic Acid (22)

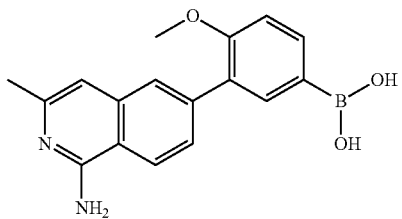 [SMILES: COc1ccc(B(O)O)cc1-c1ccc2c(N)nc(C)cc2c1]

A mixture of 6-[2-methoxy-5-(4,4,5,5-tetramethyl-1,3,2-dioxaborolan-2-yl)phenyl]-3-methylisoquinolin-1-amine trifluoroacetic acid salt (154.0 mg, 0.310 mmol) in 2M hydrochloric acid solution (3.82 mL, 7.63 mmol) and Et$_2$O (4 mL) was stirred at room temperature for 2.5 h. Et$_2$O was added and the phases were separated. The aqueous phase was concentrated and the residue was purified by column chromatography (KP-C18-HS, 2×SNAP 12 in series) with a gradient of MeCN (+0.1% of HCOOH) in water (+0.1% of HCOOH) from 2% to 60% to give [3-(1-amino-3-methylisoquinolin-6-yl)-4-methoxyphenyl]boronic acid (28 mg, 0.079 mmol, 25.89% yield) as a white solid. NMR analysis showed a partial salification of the title compound (~40%). $^1$H NMR (400 MHz, DMSO-d$_6$) δ 2.46 (s, 3H), 3.82 (s, 3H), 7.07 (s, 1H), 7.17 (d, J=8.14 Hz, 1H), 7.83 (dd, J=8.69, 1.65 Hz, 1H), 7.86-7.91 (m, 2H), 7.93 (d, J=1.54 Hz, 1H), 8.14 (s, 0.4H from HCOOH), 8.54 (d, J=8.80 Hz, 1H), 8.82 (br. s, 2H). LC-MS (Method A): r.t. 0.52 min, MS (ESI) m/z=309.23 [M+H]$^+$.

Example 23: [1-(1-amino-4-methylphthalazin-6-yl)pyrazol-4-yl]boronic Acid (23)

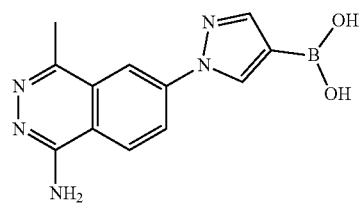 [SMILES: Cc1nnc(N)c2ccc(-n3cc(B(O)O)cn3)cc12]

A solution of [1-[1-[(2,4-dimethoxyphenyl)methylamino]-4-methylphthalazin-6-yl]pyrazol-4-yl]boronic acid (56.0 mg, 0.130 mmol) in DCM (3 mL) and trifluoroacetic acid (1 mL) was stirred for 2 hours at room temperature then it was concentrated under reduced pressure. The residue was purified by column chromatography (KP-C18-HS, 2×12 g in series) eluting with a gradient of CH$_3$CN in water (+0.10% of HCOOH) from 2% to 95% to give partially pure product. The compound was purified further by column chromatography (KP-C18-HS, 2×12 g in series) eluting with a gradient of CH$_3$CN in water (+0.1% of NH$_4$OH) from 2% to 95%. Fractions containing the desired compound were collected and lyophilized to give [1-(1-amino-4-methylphthalazin-6-yl)pyrazol-4-yl]boronic acid (12 mg, 0.045 mmol, 34.78% yield) as a white powder. $^1$H NMR (400 MHz, DMSO-d$_6$) δ 2.74 (s, 3H), 6.81 (s, 2H), 8.06 (s, 3H), 8.27 (d, J=2.08 Hz, 1H), 8.32-8.42 (m, 2H), 8.87 (s, 1H). LC-MS (Method A): r.t. 0.36 min, MS (ESI) m/z=270.3 [M+H]$^+$.

Example 24: [4-[2-[2-[2-[5-[(3aS,4S,6aR)-2-oxo-1,3,3a,4,6,6a-hexahydrothieno[3,4-d]imidazol-4-yl]pentanoylamino]ethoxy]ethoxy]ethoxy]-3-(1-amino-4-methylphthalazin-6-yl)phenyl]boronic Acid Formic Acid Salt (24)

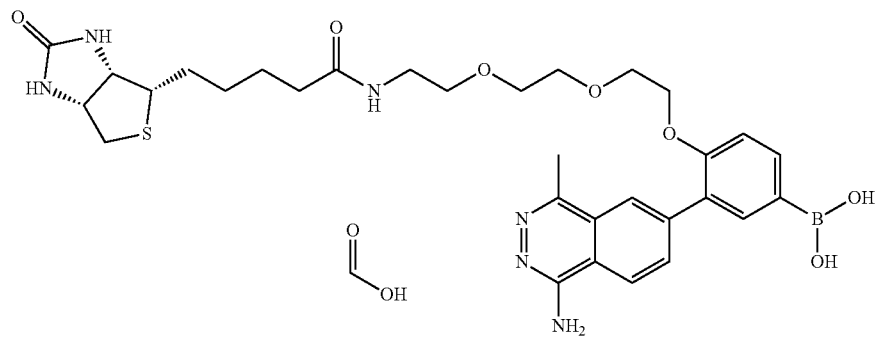 [SMILES: Cc1nnc(N)c2ccc(-c3cc(B(O)O)ccc3OCCOCCOCCNC(=O)CCCC[C@@H]3SC[C@@H]4NC(=O)N[C@@H]43)cc12 ; O=CO]

A suspension of 5-[(3aS,4S,6aR)-2-oxo-1,3,3a,4,6,6a-hexahydrothieno[3,4-d]imidazol-4-yl]-N-[2-[2-[2-[2-(1-amino-4-methylphthalazin-6-yl)-4-(4,4,5,5-tetramethyl-1,3,2-dioxaborolan-2-yl)phenoxy]ethoxy]ethoxy]ethyl]pentanamide (55.0 mg, 0.070 mmol) in 2M hydrochloric acid solution (0.04 mL, 0.070 mmol) and Et$_2$O (3.686 mL) was stirred at room temperature for 2 hours then it was evaporated under reduced pressure. The residue was purified by column chromatography (KP-C18-HS 30 g) eluting with a gradient of CH$_3$CN in water (+0.1% of HCOOH) from 1% to 60%. Appropriate fractions were collected and lyophilised to give [4-[2-[2-[2-[5-[(3aS,4S,6aR)-2-oxo-1,3,3a,4,6,6a-hexahydrothieno[3,4-d]imidazol-4-yl]pentanoylamino]ethoxy]ethoxy]ethoxy]-3-(1-amino-4-methylphthalazin-6-yl)phenyl]boronic acid formic acid salt (13 mg, 0.019 mmol, 24.86% yield) as a white solid. $^1$H NMR (400 MHz, DMSO-d$_6$) δ 1.07-1.39 (m, 2H), 1.41-1.67 (m, 3H), 2.04 (t, J=7.49 Hz, 2H), 2.53-2.61 (m, 3H), 2.72 (s, 3H), 2.80 (dd, J=12.19, 5.06 Hz, 1H), 3.05-3.09 (m, 1H), 3.10-3.17 (m, 2H), 3.43-3.49 (m, 2H), 3.49-3.56 (m, 2H), 3.71-3.75 (m, 2H), 4.09-4.14 (m, 1H), 4.18-4.24 (m, 2H), 4.25-4.31 (m, 1H), 6.34 (s, 1H), 6.46 (s, 1H), 6.83 (s, 2H), 7.17 (d, J=8.28 Hz, 1H), 7.76 (t, 1H), 7.84 (d, J=8.30 Hz, 1H), 7.94 (s, 1H), 8.02-8.06 (m, 3H), 8.13 (s, 1H, HCOOH), 8.17 (s, 1H), 8.27 (d, J=8.57 Hz, 1H). LC-MS (Method A): r.t. 0.51 min, MS (ESI) m/z=699.59 [M+H]$^+$.

Example 25: [5-(1-amino-4-methylphthalazin-6-yl)-2-fluoro-4-methoxyphenyl]boronic Acid (25)

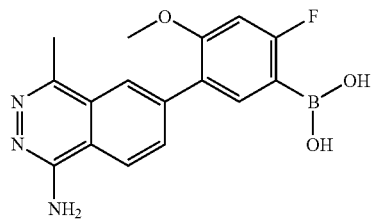 [SMILES: COc1cc(F)c(B(O)O)cc1-c1ccc2c(N)nnc(C)c2c1]

Trifluoroacetic acid (2.5 mL) was added to a solution of [5-[1-[(2,4-dimethoxyphenyl)methylamino]-4-methylphthalazin-6-yl]-2-fluoro-4-methoxyphenyl]boronic acid (140.0 mg, 0.290 mmol) in DCM (2.5 mL) and the mixture was stirred at room temperature for 1 h. The volatiles were evaporated and the residue was triturated with Et$_2$O. The residue was dissolved in MeOH and filtered over a short pad of Celite. The MeOH was evaporated and the residue was purified by column chromatography (KP-C18-HS, SNAP 12 g) eluting with a gradient of CH$_3$CN (+0.1% of HCOOH) in water (+0.1% of HCOOH) from 1% to 40% to give [5-(1-amino-4-methylphthalazin-6-yl)-2-fluoro-4-methoxyphenyl]boronic acid (23 mg, 0.070 mmol, 23.97% yield) as a white solid. NMR analysis showed a partial salification of the title compound (~21%). $^1$H NMR (400 MHz, DMSO-d$_6$+2 drops of TFA) δ 2.73 (s, 3H), 3.85 (s, 3H), 7.00 (d, J=11.41 Hz, 1H), 7.75 (d, J=7.21 Hz, 1H), 8.11 (s, 0.2H from HCOOH), 8.23 (dd, J=8.46, 1.63 Hz, 1H), 8.26 (d, J=1.63 Hz, 1H), 8.66 (d, J=8.46 Hz, 1H), 9.11 (br. s, 2H). LC-MS (Method A): r.t. 0.49 min, MS (ESI) m/z=328.2 [M+H]$^+$.

Example 26: 6-(1-hydroxy-3,4-dihydro-2,1-benzoxaborinin-7-yl)-4-methylphthalazin-1-amine Formic Acid Salt (26)

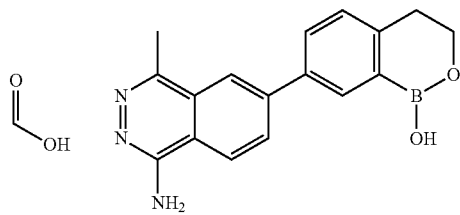 [SMILES: O=CO ; Cc1nnc(N)c2ccc(-c3ccc4c(c3)B(O)OCC4)cc12]

Trifluoroacetic acid (2.5 mL) was added to a solution of N-[(2,4-dimethoxyphenyl)methyl]-4-methyl-6-[4-[2-(oxan-2-yloxy)ethyl]-3-(4,4,5,5-tetramethyl-1,3,2-dioxaborolan-2-yl)phenyl]phthalazin-1-amine (50.0 mg, 0.080 mmol) in DCM (2.5 mL) and the mixture was stirred at room temperature for 1 h. The volatiles were evaporated and the residue was triturated with Et$_2$O. The residue was dissolved in MeOH and filtered over a short pad of Celite. The MeOH was evaporated and the residue was purified by column chromatography (KP-C18-HS, SNAP 12 g) eluting with a gradient of CH$_3$CN (+0.1% of HCOOH) in water (+0.1% of HCOOH) from 1% to 40% to give 6-(1-hydroxy-3,4-dihydro-2,1-benzoxaborinin-7-yl)-4-methylphthalazin-1-amine formic acid salt (13 mg, 0.037 mmol, 47.36% yield) as a white solid. $^1$H NMR (400 MHz, DMSO-d$_6$+2 drops of TFA) δ 2.80 (s, 3H), 2.96 (t, J=5.90 Hz, 2H), 4.12 (t, J=5.90 Hz, 2H), 7.42 (d, J=7.92 Hz, 1H), 8.00 (dd, J=7.92, 2.10 Hz, 1H), 8.11 (s, 1H from HCOOH), 8.23 (d, J=2.10 Hz, 1H), 8.40 (d, J=1.80 Hz, 1H), 8.45 (dd, J=8.58, 1.80 Hz, 1H), 8.74 (d, J=8.58 Hz, 1H), 9.12 (br. s, 2H). LC-MS (Method A): r.t. 0.54 min, MS (ESI) m/z=306.3 [M+H]$^+$.

Example 27: Giving [4-[2-[2-[2-[2-[5-[(3aS,4S,6aR)-2-oxo-1,3,3a,4,6,6a-hexahydrothieno[3,4-d]imidazol-4-yl]pentanoylamino]ethoxy]ethoxy]ethoxy]ethoxy]-3-(4-aminocinnolin-7-yl)phenyl]boronic Acid Formic Acid Salt (27)

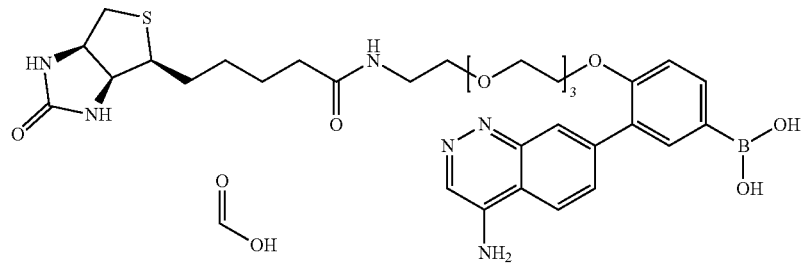

A solution of 5-[(3aS,4S,6aR)-2-oxo-hexahydro-1H-thieno[3,4-d]imidazol-4-yl]-N-{2-[2-(2-{2-[2-(4-aminocinnolin-7-yl)-4-(4,4,5,5-tetramethyl-1,3,2-dioxaborolan-2-yl)phenoxy]ethoxy}ethoxy)ethoxy]ethyl}pentanamide (200.0 mg) and 2M hydrochloric acid solution (2.5 mL, 5 mmol) in MeCN (2 mL) was stirred at room temperature for 2 hours. Then the mixture was washed with Et$_2$O and the aqueous phase was concentrated under reduced pressure. The residue was purified by column chromatography (KP-C18-HS 30 g) eluting with a gradient of CH$_3$CN in water (+0.1% of HCOOH) from 1% to 60%. Appropriate fractions were collected and lyophilised to give [4-[2-[2-[2-[2-[5-[(3aS,4S,6aR)-2-oxo-1,3,3a,4,6,6a-hexahydrothieno[3,4-d]imidazol-4-yl]pentanoylamino]ethoxy]ethoxy]ethoxy]ethoxy]-3-(4-aminocinnolin-7-yl)phenyl]boronic acid formic acid salt (37 mg, 0.051 mmol, 12.75% yield over three steps) as a white solid. $^1$H NMR (400 MHz, DMSO-d$_6$) δ 1.21-1.38 (m, 2H), 1.38-1.54 (m, 3H), 1.54-1.67 (m, 1H), 2.05 (t, J=7.42 Hz, 2H), 2.52-2.61 (m, 1H), 2.81 (dd, J=12.43, 5.07 Hz, 1H), 3.07 (ddd, J=8.49, 6.14, 4.38 Hz, 1H), 3.15 (q, J=5.80 Hz, 2H), 3.34 (t, J=5.89 Hz, 2H), 3.38-3.48 (m, 4H), 3.44-3.52 (m, 2H), 3.49-3.56 (m, 2H), 3.70-3.76 (m, 2H), 4.07-4.15 (m, 1H), 4.18-4.25 (m, 2H), 4.29 (dd, J=7.77, 5.03 Hz, 1H), 6.35 (s, 1H), 6.40 (s, 1H), 7.16 (d, J=8.35 Hz, 1H), 7.24 (s, 2H), 7.76-7.90 (m, 3H), 7.97 (d, J=1.75 Hz, 1H), 8.08 (s, 2H), 8.14-8.23 (m, 3H), 8.61 (s, 1H). LC-MS (Method B): r.t. 0.58 min, MS (ESI) m/z=729.62 [M+H]$^+$.

Example 28: [5-(1-amino-4-methylphthalazin-6-yl)-4-methoxy-2-methylphenyl]boronic Acid Formic Acid Salt (28)

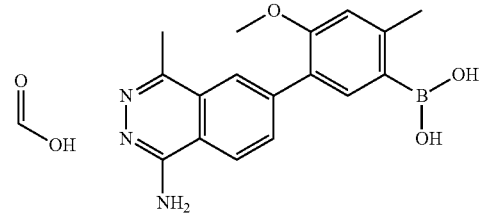 [SMILES: O=CO ; COc1cc(C)c(B(O)O)cc1-c1ccc2c(N)nnc(C)c2c1]

6-[2-Methoxy-4-methyl-5-(4,4,5,5-tetramethyl-1,3,2-dioxaborolan-2-yl)phenyl]-4-methylphthalazin-1-amine trifluoroacetic acid salt (140.0 mg, 0.270 mmol) was suspended in Et$_2$O (8 mL) and 2M hydrochloric acid solution (3.93 mL, 7.85 mmol) was added. The mixture was stirred vigorously for 1 hour, then evaporated. The residue was purified by column chromatography (KP-C18-HS, 12 g) eluting with a gradient of CH$_3$CN in water (+0.1% of HCOOH) from 1% to 30%. Fractions containing the desired compound were collected and lyophilized to give [5-(1-amino-4-methylphthalazin-6-yl)-4-methoxy-2-methylphenyl]boronic acid formic acid salt (24 mg, 0.065 mmol, 24.11% yield) as a white powder. $^1$H NMR (400 MHz, DMSO-d$_6$) δ 2.52 (s, 3H), 2.72 (s, 3H), 3.82 (s, 3H), 6.97 (s, 1H), 7.52 (br. s, 1H), 7.64 (s, 1H), 7.96 (br. s, 2H), 8.05-8.11 (m, 2H), 8.15 (s, 1H from HCOOH), 8.38 (d, J=8.50 Hz, 1H). LC-MS (Method A): r.t. 0.53 min, MS (ESI) m/z=324.2 [M+H]$^+$.

Example 29: [3-(1-amino-4-methylphthalazin-6-yl)-4-cyanophenyl]boronic Acid (29)

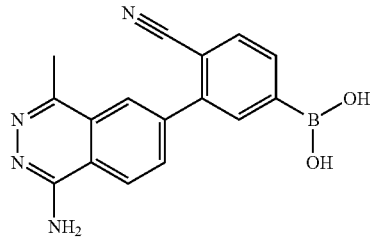 [SMILES: Cc1nnc(N)c2ccc(-c3cc(B(O)O)ccc3C#N)cc12]

Trifluoroacetic acid (1 mL) was added to a suspension of [4-cyano-3-[1-[(2,4-dimethoxyphenyl)methylamino]-4-methylphthalazin-6-yl]phenyl]boronic acid (35.0 mg, 0.080 mmol) in DCM (1 mL). The mixture was stirred at room temperature for 2 h, then the volatiles were removed. The residue was purified by column chromatography (KP-C18-HS, 2×SNAP 12 in series) eluting with a gradient of MeCN (+0.1% of HCOOH) in water (+0.1% of HCOOH) from 2% to 60% to give [3-(1-amino-4-methylphthalazin-6-yl)-4-cyanophenyl]boronic acid (7.9 mg, 0.026 mmol, 33.72% yield) as a white solid. $^1$H NMR (400 MHz, DMSO-d$_6$+2 drops of TFA) δ 2.78 (s, 3H), 8.05 (s, 1H), 8.13-8.19 (m, 2H), 8.40 (d, J=8.36 Hz, 1H), 8.49 (s, 1H), 8.81 (d, J=8.58 Hz, 1H). LC-MS (Method A): r.t. 0.47 min, MS (ESI) m/z=305.17 [M+H]$^+$.

Example 30: [5-(1-amino-4-methylphthalazin-6-yl)-6-methoxypyridin-3-yl]boronic Acid (30)

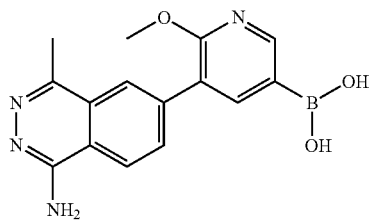 [SMILES: COc1ncc(B(O)O)cc1-c1ccc2c(N)nnc(C)c2c1]

A suspension of [5-[1-[(2,4-dimethoxyphenyl)methylamino]-4-methylphthalazin-6-yl]-6-methoxypyridin-3-yl]boronic acid (54.0 mg, 0.120 mmol) in DCM (1 mL) and trifluoroacetic acid (1 mL) was stirred at room temperature for 1 h, then it was concentrated. Et$_2$O (1 mL) was added to the residue and the mixture was stirred for 1 h, then it was filtered and washed with Et$_2$O. The filter cake was dissolved in DMSO and purified by column chromatography (KP-C18-HS, SNAP 12) eluting with a gradient of MeCN (+0.1% of HCOOH) in water (+0.1% of HCOOH) from 2% to 80% to give [5-(1-amino-4-methylphthalazin-6-yl)-6-methoxypyridin-3-yl]boronic acid (6.5 mg, 0.021 mmol, 17.87% yield) as a white solid. $^1$H NMR (400 MHz, methanol-d$_4$) δ 2.82 (s, 3H), 4.03 (s, 3H), 8.12 (br. s, 1H), 8.29 (dd, J=8.47, 1.65 Hz, 1H), 8.36-8.40 (m, 1H), 8.46 (d, J=8.36 Hz, 1H), 8.49 (br. s, 1H). LC-MS (Method A): r.t. 0.44 min, MS (ESI) m/z=311.15 [M+H]$^+$.

Example 31: [3-(4-amino-5-fluorocinnolin-7-yl)-4-methoxyphenyl]boronic Acid (31)

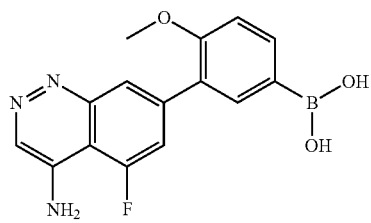 [SMILES: COc1ccc(B(O)O)cc1-c1cc(F)c2c(N)cnnc2c1]

A solution of N-[(2,4-dimethoxyphenyl)methyl]-5-fluoro-7-[2-methoxy-5-(4,4,5,5-tetramethyl-1,3,2-dioxaborolan-2-yl)phenyl]cinnolin-4-amine (90.0 mg, 0.130 mmol) in DCM (2 mL) and trifluoroacetic acid (2 mL) was stirred at room temperature for 2 days then it was concentrated under reduced pressure. The residue was purified by column chromatography (KP-C18-HS, 30 g) eluting with a gradient of CH$_3$CN in water (+0.1% of HCOOH) from 1% to 50%. Fractions containing the desired compound were collected and lyophilised to give [3-(4-amino-5-fluorocinnolin-7-yl)-4-methoxyphenyl]boronic acid (17 mg, 0.054 mmol, 41.13% yield) as a white solid. NMR analysis showed a partial salification of the title compound (~45%). $^1$H NMR (400 MHz, DMSO-d$_6$) δ 3.86 (s, 3H), 7.17 (d, J=8.34 Hz, 1H), 7.28 (s, 2H), 7.52 (d, J=13.74 Hz, 1H), 7.87 (dd, J=8.26, 1.72 Hz, 1H), 7.94-8.00 (m, 2H), 8.03 (s, 2H), 8.14 (s, 0.45H, HCOOH), 8.63 (s, 1H). LC-MS (Method A): r.t. 0.44 min, MS (ESI) m/z=314.09 [M+H]$^+$.

Example 32: 6-(1-hydroxy-6-methoxy-3,4-dihydro-2,1-benzoxaborinin-7-yl)-4-methylphthalazin-1-amine Formic Acid Salt (32)

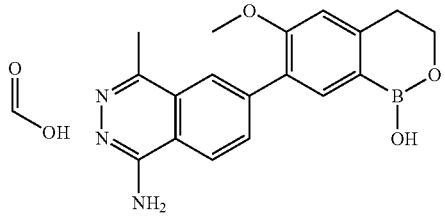

Trifluoroacetic acid (1 mL) was added to a suspension of N-[(2,4-dimethoxyphenyl)methyl]-6-[2-methoxy-4-[2-(oxan-2-yloxy)ethyl]-5-(4,4,5,5-tetramethyl-1,3,2-dioxaborolan-2-yl)phenyl]-4-methylphthalazin-1-amine (11.0 mg, 0.020 mmol) in DCM (1 mL). The mixture was stirred at room temperature for 2 h and the volatiles were evaporated. The residue was purified by column chromatography (KP-C18-HS, SNAP 12 g) eluting with a gradient of CH$_3$CN (+0.1% of HCOOH) in water (+0.1% of HCOOH) from 1% to 30% to give 6-(1-hydroxy-6-methoxy-3,4-dihydro-2,1-benzoxaborinin-7-yl)-4-methylphthalazin-1-amine formic acid salt (4 mg, 0.010 mmol, 63.88% yield) as a white solid. NMR and LC-MS analysis showed the presence of ~15% of 2-[4-(1-amino-4-methylphthalazin-6-yl)-3-methoxyphenyl]ethan-1-ol. $^1$H NMR (400 MHz, DMSO-d$_6$) δ 2.70 (s, 3H), 2.94 (t, J=5.88 Hz, 2H), 3.84 (s, 3H), 4.11 (t, J=5.88 Hz, 2H), 6.84 (s, 2H), 7.05 (s, 1H), 7.76 (s, 1H), 7.95 (dd, J=8.46, 1.70 Hz, 1H), 7.98 (d, J=1.70 Hz, 1H), 8.16 (s, 1H from HCOOH), 8.25 (d, J=8.46 Hz, 1H), 8.38 (s, 1H). LC-MS (Method A): r.t. 0.56 min, MS (ESI) m/z=336.3 [M+H]$^+$.

Example 33: [4-[2-[2-[2-[2-[2-[2-[5-[(3aS,4S,6aR)-2-oxo-1,3,3a,4,6,6a-hexahydrothieno[3,4-d]imidazol-4-yl]pentanoylamino]ethoxy]ethoxy]ethoxy]ethoxy]ethoxy]-3-(4-aminocinnolin-7-yl)phenyl]boronic Acid (33)

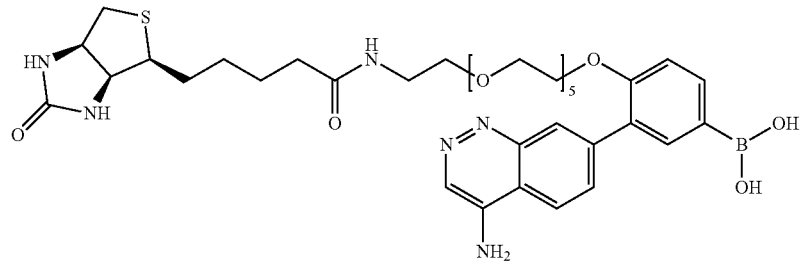

5-[(3aS,4S,6aR)-2-Oxo-hexahydro-1H-thieno[3,4-d]imidazol-4-yl]-N-{17-[2-(4-aminocinnolin-7-yl)-4-(4,4,5,5-tetramethyl-1,3,2-dioxaborolan-2-yl)phenoxy]-3,6,9,12,15-pentaoxaheptadecan-1-yl}pentanamide (60.0 mg, 0.070 mmol) was suspended in CH$_3$CN (1 mL) and 2M hydrochloric acid solution (960.75 uL, 1.92 mmol) was added. The mixture was stirred vigorously for 1 hour, then evaporated. The residue was purified by column chromatography (KP-C18-HS, 12 g) eluting with a gradient of CH$_3$CN in water (+0.1% of HCOOH) from 1% to 30%. Fractions containing the desired compound were collected and lyophilized to give [4-[2-[2-[2-[2-[2-[2-[5-[(3aS,4S,6aR)-2-oxo-1,3,3a,4,6,6a-hexahydrothieno[3,4-d]imidazol-4-yl]pentanoylamino]ethoxy]ethoxy]ethoxy]ethoxy]ethoxy]-3-(4-aminocinnolin-7-yl)phenyl]boronic acid (12.7 mg, 0.016 mmol, 23.42% yield) as a pale yellow solid. $^1$H NMR (400 MHz, DMSO-d$_6$+2 drops of TFA) δ 1.21-1.36 (m, 2H), 1.40-1.57 (m, 4H), 1.56-1.71 (m, 1H), 2.07 (t, J=7.39 Hz, 2H), 2.57-2.64 (m, 1H), 2.78-2.85 (m, 1H), 3.06-3.13 (m, 1H), 3.18 (q, J=5.71 Hz, 2H), 3.37 (t, J=5.89 Hz, 2H), 3.40-3.49 (m, 13H), 3.50-3.55 (m, 2H), 3.69-3.78 (m, 2H), 4.17 (dd, J=7.83, 4.45 Hz, 1H), 4.20-4.25 (m, 2H), 4.33-4.38 (m, 1H), 7.19 (d, J=8.36 Hz, 1H), 7.84 (t, J=5.61 Hz, 1H), 7.93-7.98 (m, 1H), 8.01-8.06 (m, 1H), 8.08 (s, 1H), 8.10 (s, 1H), 8.43-8.49 (m, 2H), 9.68 (s, 1H), 9.82 (s, 1H). LC-MS (Method A): r.t. 0.53 min, MS (ESI) m/z=771.8 [M+H]$^+$.

Example 34: [3-(1-amino-4-methylphthalazin-6-yl)-2-fluoro-4-methoxyphenyl]boronic Acid Formic Acid Salt (34)

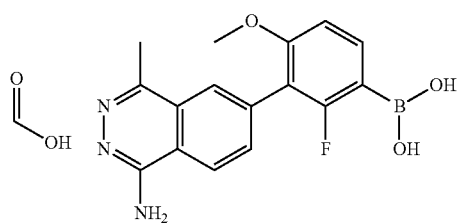

Step 1: Palladium(II) diacetate (5.59 mg, 0.020 mmol), 6-(3-chloro-2-fluoro-6-methoxyphenyl)-N-[(2,4-dimethoxyphenyl)methyl]-4-methylphthalazin-1-amine (233.0 mg, 0.500 mmol), dicyclohexyl-[2-[2,4,6-tri(propan-2-yl)phenyl]phenyl]phosphine (18.99 mg, 0.040 mmol), potassium acetate (146.61 mg, 1.49 mmol) and 4,4,5,5-tetramethyl-2-(4,4,5,5-tetramethyl-1,3,2-dioxaborolan-2-yl)-1,3,2-dioxaborolane (379.35 mg, 1.49 mmol) were dissolved in 1,4-dioxane (12.66 mL). The mixture was degassed with Ar for 10 min, then stirred at 90° C. for 18 hours. The mixture was filtered over a pad of Celite, washing with EtOAc and the filtrate was concentrated in vacuo. The residue was purified by column chromatography (KP-C18-HS, SNAP 30 g) eluting with a gradient of CH$_3$CN in water from 1% to 95% to give 140 mg of a mixture of [3-(1-{[(2,4-dimethoxyphenyl)methyl]amino}-4-methylphthalazin-6-yl)-2-fluoro-4-methoxyphenyl]boronic acid {LC-MS (Method A): r.t. 0.68 min, MS (ESI) m/z=478.4 [M+H]+} and N-[(2,4-dimethoxyphenyl)methyl]-6-[2-fluoro-6-methoxy-3-(4,4,5,5-tetramethyl-1,3,2-dioxaborolan-2-yl)phenyl]-4-methylphthalazin-1-amine {LC-MS (Method A): r.t. 0.94 min, MS (ESI) m/z=560.4 [M+H]$^+$}, which was used in the next step without further purification.

Step 2: The material obtained in Step 1 was dissolved in DCM (2 mL) and trifluoroacetic acid (2 mL) was added. The mixture was stirred at room temperature for 1 h and the volatiles were evaporated. The residue was dissolved in MeOH (20 mL) and filtered over a short pad of Celite. The filtrate was evaporated and the obtained solid was triturated with Et$_2$O. The solid residue was purified by column chromatography (KP-C18-HS, SNAP 12 g) eluting with a gradient of CH$_3$CN (+0.1% of HCOOH) in water (+0.1% of HCOOH) from 1% to 40% to give [3-(1-amino-4-methylphthalazin-6-yl)-2-fluoro-4-methoxyphenyl]boronic acid formic acid salt (29 mg, 0.078 mmol, 15.6% yield over two steps) as a white solid. $^1$H NMR (400 MHz, DMSO-d$_6$+2 drops of TFA) δ 2.67 (s, 3H), 3.77 (s, 3H), 7.00 (d, J=8.49 Hz, 1H), 7.63-7.83 (m, 1H), 8.08 (s, 1H), 8.10 (s, 0.5H from HCOOH), 8.18 (s, 1H), 8.69 (d, J=8.48 Hz, 1H), 9.11 (s, 2H). LC-MS (Method A): r.t. 0.47 min, MS (ESI) m/z=328.3 [M+H]$^+$.

Example 35: [5-(1-amino-4-methylphthalazin-6-yl)-2-(difluoromethyl)-4-methoxyphenyl]boronic Acid (35)

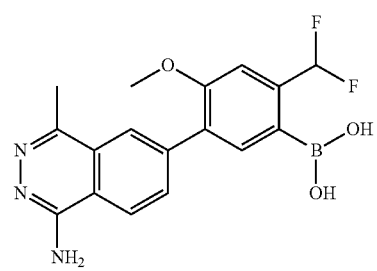 [SMILES: COc1cc(C(F)F)c(B(O)O)cc1-c1ccc2c(N)nnc(C)c2c1]

Palladium(II) diacetate (1.347 mg, 0.006 mmol), 6-[5-chloro-4-(difluoromethyl)-2-methoxyphenyl]-N-[(2,4-dimethoxyphenyl)methyl]-4-methylphthalazin-1-amine (60 mg, 0.120 mmol), potassium acetate (35.33 mg, 0.360 mmol), dicyclohexyl-[2-[2,4,6-tri(propan-2-yl)phenyl]phenyl]phosphine (5.721 mg, 0.012 mmol) and 4,4,5,5-tetramethyl-2-(4,4,5,5-tetramethyl-1,3,2-dioxaborolan-2-yl)-1,3,2-dioxaborolane (91.43 mg, 0.360 mmol) were dissolved in 1,4-dioxane (0.880 mL) in a microwave vial. The resulting mixture was degassed for 10 minutes with $N_2$ and then stirred at 75° C. for 2 h. It was then cooled to room temperature and filtered over Celite, washing with EtOAc. The filtrate was evaporated and the residue was solubilized in DCM (0.500 mL) and trifluoroacetic acid (0.500 mL). The resulting mixture was stirred at room temperature for 2 hours then it was concentrated under reduced pressure. The residue was purified by column chromatography (KP-C18-HS, 12 g) with a gradient from 1% to 40% of $CH_3CN$ in water. Fractions containing the desired compound were collected and lyophilised to give [5-(1-amino-4-methylphthalazin-6-yl)-2-(difluoromethyl)-4-methoxyphenyl]boronic acid (2.5 mg, 0.007 mmol, 5.8% yield) as a white solid. $^1H$ NMR (400 MHz, DMSO-$d_6$) δ 2.74 (s, 3H), 3.90 (s, 3H), 7.37 (s, 1H), 7.53 (t, J=56.3 Hz, 1H), 7.88 (s, 1H), 8.21-8.39 (m, 2H), 8.49 (s, 2H), 8.68 (d, J=8.52 Hz, 1H), 9.06 (br. s, 2H). LC-MS (Method A): r.t. 0.58 min, MS (ESI) m/z=360.1 [M+H]$^+$.

Example 36: [3-(1-amino-4-methylphthalazin-6-yl)-4-cyano-5-fluorophenyl]boronic Acid Formic Acid Salt (36)

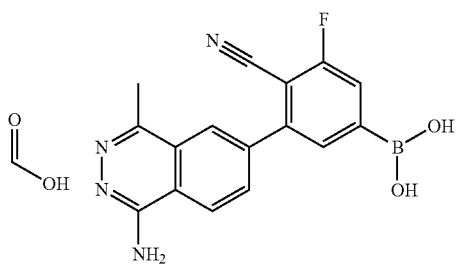

A solution of [4-cyano-3-[1-[(2,4-dimethoxyphenyl)methylamino]-4-methylphthalazin-6-yl]-5-fluorophenyl]boronic acid (45.0 mg, 0.100 mmol) in DCM (0.500 mL) and trifluoroacetic acid (0.500 mL) was stirred at room temperature for 3 hours then it was concentrated under reduced pressure. The residue was purified by column chromatography (KP-C18-HS, 11 g) eluting with a gradient of $CH_3CN$ in water (+0.1% of HCOOH) from 1% to 50%. Fractions containing the desired compound were collected and lyophilised to give [3-(1-amino-4-methylphthalazin-6-yl)-4-cyano-5-fluorophenyl]boronic acid formic acid salt (16 mg, 0.043 mmol, 45.61% yield) as a white solid. NMR analysis showed a partial salification of the title compound. $^1H$ NMR (400 MHz, DMSO-$d_6$+2 drops of TFA) δ 2.76 (s, 3H), 7.88 (d, J=9.6 Hz, 1H), 7.99 (s, 1H), 8.13 (s, 1H, HCOOH), 8.41 (d, J=8.4 Hz, 1H), 8.53 (s, 1H), 8.81 (d, J=8.5 Hz, 1H), 9.31 (s, 2H). LC-MS (Method A): r.t. 0.52 min, MS (ESI) m/z=369.13 [M+H]$^+$.

Example 37: [5-(1-amino-4-methylphthalazin-6-yl)-4-methoxy-2-(trifluoromethyl)phenyl]boronic Acid Formic Acid Salt (37)

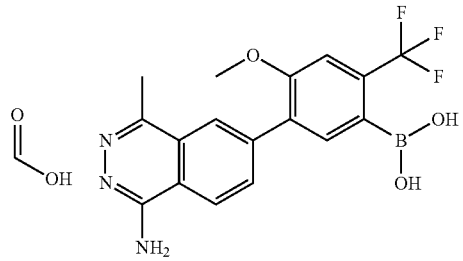

Step 1: Palladium(II) diacetate (5.14 mg, 0.020 mmol), 6-[5-chloro-2-methoxy-4-(trifluoromethyl)phenyl]-N-[(2,4-dimethoxyphenyl)methyl]-4-methylphthalazin-1-amine (237.0 mg, 0.460 mmol), dicyclohexyl-[2-[2,4,6-tri(propan-2-yl)phenyl]phenyl]phosphine (17.45 mg, 0.040 mmol), potassium acetate (134.72 mg, 1.37 mmol) and 4,4,5,5-tetramethyl-2-(4,4,5,5-tetramethyl-1,3,2-dioxaborolan-2-yl)-1,3,2-dioxaborolane (348.6 mg, 1.37 mmol) were dissolved in 1,4-dioxane (8 mL). The mixture was degassed with Ar for 10 min, then stirred at 90° C. for 18 hours. The mixture was filtered over a pad of Celite, washing with EtOAc. The filtrate was concentrated in vacuo and the residue was purified by column chromatography (KP-C18-HS, SNAP 30 g) eluting with a gradient of $CH_3CN$ in water from 1% to 95% to give 15 mg of a mixture of [5-(1-{[(2,4-dimethoxyphenyl)methyl]amino}-4-methylphthalazin-6-yl)-4-methoxy-2-(trifluoromethyl)phenyl]boronic acid and N-[(2,4-dimethoxyphenyl)methyl]-6-[2-methoxy-5-(4,4,5,5-tetramethyl-1,3,2-dioxaborolan-2-yl)-4-(trifluoromethyl)phenyl]-4-methylphthalazin-1-amine which was used in the next step without further purification.

Step 2: The mixture obtained in Step 1 was dissolved in DCM (1 mL) and trifluoroacetic acid (1 mL) was added. The mixture stirred at room temperature for 1 h and the volatiles were evaporated to give crude 6-[2-methoxy-5-(4,4,5,5-tetramethyl-1,3,2-dioxaborolan-2-yl)-4-(trifluoromethyl)phenyl]-4-methylphthalazin-1-amine trifluoroacetic salt.

Step 3: The crude material obtained in Step 2 was suspended in 2M hydrochloric acid solution (1.0 mL, 2 mmol) and $Et_2O$ (2 mL), and the mixture was stirred at room temperature for 20 min. Water (20 mL) was added and the layers were separated. The aqueous layer was washed with $Et_2O$ (3×20 mL) and evaporated. The residue was purified by column chromatography (KP-C18-HS, SNAP 12 g) eluting with a gradient of $CH_3CN$ (+0.1% of HCOOH) in water (+0.1% of HCOOH) from 1% to 40% to give [5-(1-amino-4-methylphthalazin-6-yl)-4-methoxy-2-(trifluoromethyl)phenyl]boronic acid formic acid salt (3.5 mg, 0.008 mmol, 1.74% yield over three steps) as a white solid. $^1H$ NMR (400 MHz, DMSO-$d_6$+TFA) δ 2.74 (s, 3H), 3.89 (s, 3H), 7.39 (s, 1H), 7.69 (s, 1H), 8.11 (s, 1H from HCOOH), 8.25-8.36 (m, 2H), 8.69 (d, J=9.08 Hz, 1H), 9.16 (s, 2H). LC-MS (Method A): r.t. 0.55 min, MS (ESI) m/z=378.1 [M+H]$^+$.

Example 38: 3-(1-amino-4-methylphthalazin-6-yl)-5-(trifluoromethyl)phenyl]boronic Acid (38)

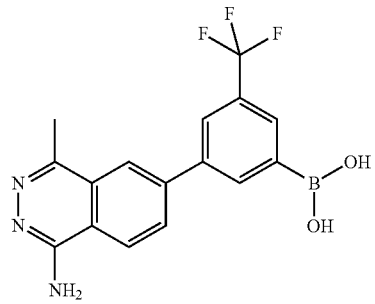 [SMILES: Cc1nnc(N)c2ccc(-c3cc(B(O)O)cc(C(F)(F)F)c3)cc12]

Trifluoroacetic acid (2 mL) was added to a solution of [3-[1-[(2,4-dimethoxyphenyl)methylamino]-4-methylphthalazin-6-yl]-5-(trifluoromethyl)phenyl]boronic acid (90.0 mg, 0.180 mmol) in DCM (2 mL). The mixture was stirred at room temperature for 1 h and the volatiles were evaporated. The residue was dissolved in MeOH and the precipitate was filtered over a short pad of Celite. The filtrate was evaporated and the solid obtained was triturated with Et$_2$O. The solid residue was purified by column chromatography (KP-C18-HS, SNAP 12 g) eluting with a gradient of CH$_3$CN (+0.1% of HCOOH) in water (+0.1% of HCOOH) from 1% to 50% to give [3-(1-amino-4-methylphthalazin-6-yl)-5-(trifluoromethyl)phenyl]boronic acid (20.5 mg, 0.059 mmol, 32.63% yield) as a white solid. NMR analysis showed a partial salification of the title compound (~20%). $^1$H NMR (400 MHz, DMSO-d$_6$+2 drops of TFA) δ 2.81 (s, 3H), 8.09 (s, 0.2H from HCOOH), 8.21 (s, 1H), 8.30 (s, 1H), 8.50 (d, J=1.44 Hz, 1H), 8.52 (dd, J=8.50, 1.81 Hz, 1H), 8.57 (s, 1H), 8.78 (d, J=8.51 Hz, 1H), 9.17 (s, 2H). LC-MS (Method A): r.t. 0.60 min, MS (ESI) m/z=348.2 [M+H]$^+$.

Example 39: [3-(1-amino-4-methylphthalazin-6-yl)-4-(trifluoromethyl)phenyl]boronic Acid Formic Acid Salt (39)

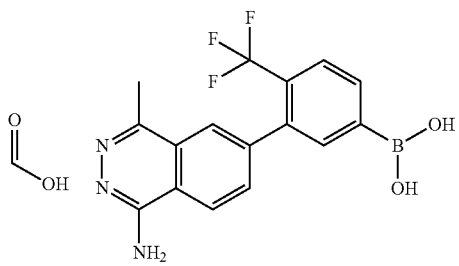

A solution of [3-[1-[(2,4-dimethoxyphenyl)methylamino]-4-methylphthalazin-6-yl]-4-(trifluoromethyl)phenyl]boronic acid (93.0 mg, 0.190 mmol) in DCM (0.500 mL) and trifluoroacetic acid (0.500 mL) was stirred at room temperature for 2 hours then it was concentrated under reduced pressure. The residue was purified by column chromatography (KP-C18-HS, 30 g) eluting with a gradient of CH$_3$CN in water (+0.1% of HCOOH) from 1% to 50%. Fractions containing the desired compound were collected and lyophilised to give [3-(1-amino-4-methylphthalazin-6-yl)-4-(trifluoromethyl)phenyl]boronic acid formic acid salt (50 mg, 0.127 mmol, 68.01% yield) as a white solid. $^1$H NMR (400 MHz, DMSO-d$_6$) δ 2.67 (s, 3H), 7.01 (br. s, 2H), 7.80-7.92 (m, 4H), 8.04 (d, J=7.85 Hz, 1H), 8.15 (s, 1H, HCOOH), 8.33 (d, J=8.42 Hz, 1H), 8.51 (br. s, 2H). LC-MS (Method A): r.t. 0.59 min, MS (ESI) m/z=394.4 [M+H]$^+$.

Example 40: [3-(1-amino-4-methylphthalazin-6-yl)-5-dimethylphosphorylphenyl]boronic Acid Formic Acid Salt (40)

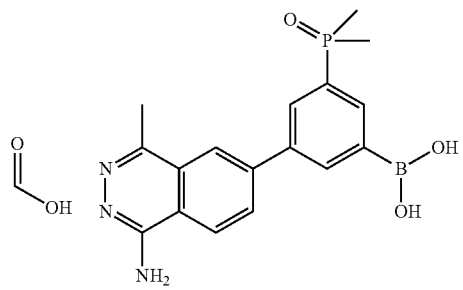

A solution of [3-[1-[(2,4-dimethoxyphenyl)methylamino]-4-methylphthalazin-6-yl]-5-dimethylphosphorylphenyl]boronic acid (94.0 mg, 0.190 mmol) in DCM (0.500 mL) and trifluoroacetic acid (0.500 mL) was stirred at room temperature for 2 hours then it was concentrated under reduced pressure. The residue was purified by column chromatography (KP-C18-HS, 30 g) eluting with a gradient of CH$_3$CN in water (+0.1% of HCOOH) from 1% to 50%. Fractions containing the desired compound were collected and lyophilised to give [3-(1-amino-4-methylphthalazin-6-yl)-5-dimethylphosphorylphenyl]boronic acid formic acid salt (37 mg, 0.092 mmol, 49.58% yield) as a white solid. $^1$H NMR (400 MHz, DMSO-d$_6$+TFA) δ 1.81 (s, 3H), 1.84 (s, 3H), 2.81 (s, 3H), 8.11 (s, 1H, HCOOH), 8.27-8.35 (m, 2H), 8.43-8.55 (m, 3H), 8.78 (d, J=8.60 Hz, 1H), 9.18 (s, 2H). LC-MS (Method A): r.t. 0.38 min, MS (ESI) m/z=402.4 [M+H]$^+$.

Example 41: [5-(1-amino-4-methylphthalazin-6-yl)-4-cyano-2-methylphenyl]boronic Acid (41)

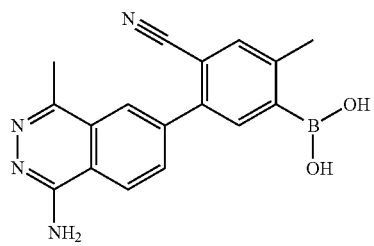 [SMILES: Cc1cc(C#N)c(-c2ccc3c(N)nnc(C)c3c2)cc1B(O)O]

Step 1: Trifluoroacetic acid (2 mL) was added to a solution of 2-[1-[(2,4-dimethoxyphenyl)methylamino]-4-methylphthalazin-6-yl]-5-methyl-4-(4,4,5,5-tetramethyl-1,3,2-dioxaborolan-2-yl)benzonitrile (123.42 mg, 0.220 mmol) in DCM (2 mL) and the mixture was stirred at room temperature for 1 h. The volatiles were evaporated and the residue was dissolved in MeOH (15 mL). The solution was filtered over a short pad of Celite and the volatiles were evaporated. The solid residue was triturated with Et₂O (3×5 mL) and dried under vacuum.

Step 2: The material obtained in Step 1 was suspended in Et₂O (2 mL) and 2M hydrochloric acid solution (2.0 mL, 0.300 mmol) and the mixture was stirred at room temperature for 30 min. The mixture was diluted with water (10 mL) and washed with Et₂O (3×10 mL). The aqueous layer was evaporated and the residue was purified by column chromatography (KP-C18-HS, SNAP 30 g) eluting with a gradient of CH₃CN (+0.1% of HCOOH) in water (+0.1% of HCOOH) from 1% to 30%. Fractions containing the desired compound were evaporated to give a white solid which was triturated with MeOH (3×0.5 mL) and dried under vacuum to give [5-(1-amino-4-methylphthalazin-6-yl)-4-cyano-2-methylphenyl]boronic acid (4.5 mg, 0.014 mmol, 6.4% yield over two steps) as a white solid. $^1$H NMR (400 MHz, DMSO-$d_6$+2 drops of TFA) δ 2.52 (s, 3H peak partially overlapped with DMSO-$d_6$ signal), 2.69-2.84 (m, 3H), 7.73-7.81 (m, 1H), 7.86 (s, 1H), 8.31-8.38 (m, 1H), 8.41 (br. s, 1H), 8.78 (d, J=8.51 Hz, 1H), 9.21 (br. s, 2H). LC-MS (Method A): r.t.: 0.51 min, MS (ESI) m/z=319.5 [M+H]$^+$.

Example 42: [3-(1-amino-4-methylphthalazin-6-yl)-4-methoxy-5-methylphenyl]boronic Acid Formic Acid Salt (42)

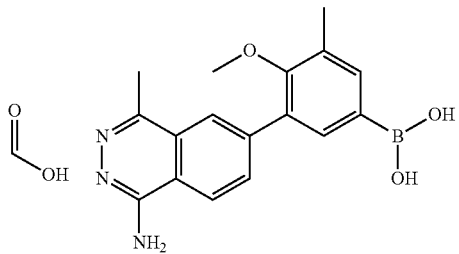

6-[2-Methoxy-3-methyl-5-(4,4,5,5-tetramethyl-1,3,2-dioxaborolan-2-yl)phenyl]-4-methylphthalazin-1-amine trifluoroacetic acid salt (94.0 mg, 0.230 mmol) was suspended in Et₂O (5 mL) and 2M hydrochloric acid solution (3.0 mL, 6 mmol) was added. To aid solubility DCM (50 uL) was added. The mixture was stirred vigorously for 2 hours, then evaporated. The residue was purified by column chromatography (KP-C18-HS, 30 g) eluting with a gradient of CH₃CN in water (+0.1% of HCOOH) from 2% to 95%. Fractions containing the desired compound were collected and lyophilized to give [3-(1-amino-4-methylphthalazin-6-yl)-4-methoxy-5-methylphenyl]boronic acid formic acid salt (50.42 mg, 0.137 mmol, 58.89% yield) as a white powder. $^1$H NMR (400 MHz, DMSO-$d_6$+2 drops of TFA) δ 2.33 (s, 3H), 2.75 (s, 3H), 3.38 (s, 3H), 7.78 (dd, J=16.2, 1.7 Hz, 2H), 8.12 (s, 0.58H from HCOOH), 8.30 (dd, J=8.5, 1.7 Hz, 1H), 8.34 (d, J=1.6 Hz, 1H), 8.72 (d, J=8.6 Hz, 1H), 9.14 (br. s, 2H). LC-MS (Method A): r.t. 0.52 min, MS (ESI) m/z=324.3 [M+H]$^+$.

Example 43: [5-(1-amino-4-methylphthalazin-6-yl)-2-cyclopropyl-4-methoxyphenyl]boronic Acid (43)

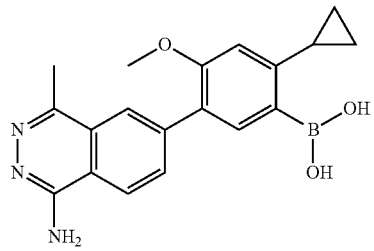 [SMILES: COc1cc(C2CC2)c(B(O)O)cc1-c1ccc2c(N)nnc(C)c2c1]

Palladium(II) diacetate (3.21 mg, 0.010 mmol), 6-(5-chloro-4-cyclopropyl-2-methoxyphenyl)-N-[(2,4-dimethoxyphenyl)methyl]-4-methylphthalazin-1-amine (140.0 mg, 0.290 mmol), dicyclohexyl-[2-[2,4,6-tri(propan-2-yl)phenyl]phenyl]phosphine (13.62 mg, 0.030 mmol), potassium acetate (84.12 mg, 0.860 mmol) and 4,4,5,5-tetramethyl-2-(4,4,5,5-tetramethyl-1,3,2-dioxaborolan-2-yl)-1,3,2-dioxaborolane (217.67 mg, 0.860 mmol) were dissolved in 1,4-dioxane (2.857 mL) in a microwave vial. The resulting mixture was degassed for 10 minutes with N₂ and stirred at 75° C. for 2 h. It was then cooled to room temperature and filtered over Celite, washing with EtOAc. The filtrate was evaporated and the residue was solubilized in DCM (0.500 mL) and trifluoroacetic acid (0.500 mL). The resulting mixture was stirred at room temperature for 2 hours then it was concentrated under reduced pressure. The residue was purified by column chromatography (KP-C18-HS, 12 g) eluting with a gradient of CH₃CN in water (+0.1% of HCOOH) from 1% to 50%. Fractions containing the desired compound were collected and lyophilised to give [5-(1-amino-4-methylphthalazin-6-yl)-2-cyclopropyl-4-methoxyphenyl]boronic acid (1.6 mg, 0.005 mmol, 9.869% yield) as a white solid. $^1$H NMR (400 MHz, DMSO-$d_6$+2 drops of TFA) δ 0.71-0.80 (m, 2H), 0.90-0.99 (m, 2H), 1.70 (s, 1H), 2.69 (s, 3H), 3.78 (s, 3H), 6.50 (s, 1H), 6.70 (m, 2H), 7.52 (s, 1H), 7.94 (dd, J=8.48, 1.70 Hz, 1H), 7.97 (d, J=1.74 Hz, 1H), 8.21 (d, J=8.52 Hz, 1H), 8.28 (br. s, 2H). LC-MS (Method A): r.t. 0.58 min, MS (ESI) m/z=350.3 [M+H]$^+$.

Example 44: [5-(1-amino-4-methylphthalazin-6-yl)-4-methoxy-2-(trifluoromethoxy)phenyl]boronic Acid (44)

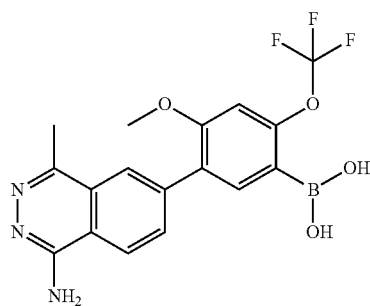 [SMILES: COc1cc(OC(F)(F)F)c(B(O)O)cc1-c1ccc2c(N)nnc(C)c2c1]

6-[2-Methoxy-5-(4,4,5,5-tetramethyl-1,3,2-dioxaborolan-2-yl)-4-(trifluoromethoxy)phenyl]-4-methylphthalazin-1-amine trifluoroacetic acid salt (180.0 mg, 0.180 mmol)

was suspended in Et$_2$O (10.64 mL) and 2M hydrochloric acid solution (2.35 mL, 4.7 mmol) was added. To aid solubility DCM (0.05 mL) was added and the viscous mixture became more homogeneous. The mixture was stirred vigorously for 5 hour, then evaporated and the residue was purified by column chromatography (KP-C18-HS, 12 g) eluting with a gradient of CH$_3$CN in water from 2% to 80%. Fractions containing the desired compound were collected and lyophilized to give [5-(1-amino-4-methylphthalazin-6-yl)-4-methoxy-2-(trifluoromethoxy)phenyl]boronic acid (2.13 mg, 0.005 mmol, 2.98% yield) as a white powder. $^1$H NMR (400 MHz, DMSO-d$_6$+2 drops of TFA) δ 2.74 (s, 3H), 3.87 (s, 3H), 7.10 (s, 1H), 7.78 (s, 1H), 8.28 (dd, J=8.5, 1.6 Hz, 1H), 8.31 (d, J=1.6 Hz, 1H), 8.69 (d, J=8.5 Hz, 1H), 9.14 (br. s, 2H). LC-MS (Method A): r.t. 0.60 min, MS (ESI) m/z=394.3 [M+H]$^+$.

Example 45: [5-(1-amino-4-methylphthalazin-6-yl)-2-methoxy-3-methylphenyl]boronic Acid (45)

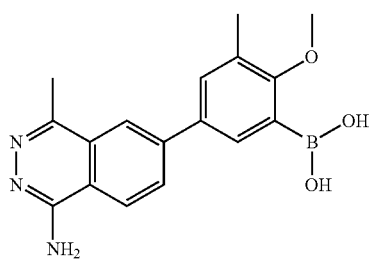 [SMILES: COc1c(C)cc(-c2ccc3c(N)nnc(C)c3c2)cc1B(O)O]

Trifluoroacetic acid (2 mL) was added to a solution of [5-[1-[(2,4-dimethoxyphenyl)methylamino]-4-methylphthalazin-6-yl]-2-methoxy-3-methylphenyl]boronic acid (41.0 mg, 0.090 mmol) in DCM (2 mL) and the mixture was stirred at room temperature for 1 h. The volatiles were evaporated and the residue was dissolved in MeOH. The solution was filtered over a short pad of Celite and the filtrate was evaporated. The residue was purified by column chromatography (KP-C18-HS, SNAP 30 g) eluting with a gradient of CH$_3$CN (+0.1% of HCOOH) in water (+0.1% of HCOOH) from 1% to 40%. The partially purified product obtained was submitted to semi-preparative HPLC purification (Column: Chiralcel OJ-H (25×2.0 cm), 5μ. Mobile phase: n-Hexane/(Ethanol+0.1% isopropylamine) 80/20% v/v. Flow rate: 17 ml/min) to give [5-(1-amino-4-methylphthalazin-6-yl)-2-methoxy-3-methylphenyl]boronic acid (4.5 mg, 0.014 mmol, 16.08% yield) as a white solid. $^1$H NMR (400 MHz, Methanol-d$_4$) δ 2.37 (s, 3H), 2.82 (s, 3H), 3.84 (s, 3H), 7.62 (br. s, 1H), 7.71 (d, J=2.45 Hz, 1H), 8.30-8.37 (m, 2H), 8.52-8.58 (m, 1H). LC-MS (Method A): r.t. 0.54 min, MS (ESI) m/z=324.23 [M+H]$^+$.

Example 46: 7-(1-hydroxy-6-methoxy-3,4-dihydro-2,1-benzoxaborinin-7-yl)cinnolin-4-amine trifluoroacetic Acid Salt (46)

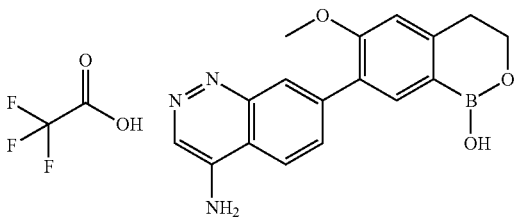

Step 1: Palladium(II) diacetate (3.36 mg, 0.010 mmol), 7-[5-chloro-2-methoxy-4-[2-(oxan-2-yloxy)ethyl]phenyl]-N-[(2,4-dimethoxyphenyl)methyl]cinnolin-4-amine (169.0 mg, 0.300 mmol), dicyclohexyl-[2-[2,4,6-tri(propan-2-yl)phenyl]phenyl]phosphine (11.43 mg, 0.020 mmol), potassium acetate (88.21 mg, 0.900 mmol) and 4,4,5,5-tetramethyl-2-(4,4,5,5-tetramethyl-1,3,2-dioxaborolan-2-yl)-1,3,2-dioxaborolane (228.25 mg, 0.900 mmol) were dissolved in 1,4-dioxane (4 mL). The mixture was degassed for 10 min with Ar, then stirred at 90° C. for 5 hours. The mixture was filtered over a pad of Celite, washing with EtOAc and the filtrate was concentrated in vacuo.

Step 2: The crude product obtained in Step 1 was suspended in DCM (4 mL) and trifluoroacetic acid (4 mL) was added. The mixture was stirred at room temperature for 4 h and the volatiles were evaporated. The residue was purified by column chromatography (KP-C18-HS, SNAP 30 g) eluting with a gradient of CH$_3$CN (+0.1% of HCOOH) in water (+0.1% of HCOOH) from 1% to 15%. The partially purified product obtained was submitted to semi-preparative HPLC purification (Column: Chiralcel OD-H (25×2.0 cm), 5 μm. Mobile phase: n-Hexane/(Ethanol+0.1% isopropylamine) 80/20% v/v. Flow rate: 17 ml/min). Fractions containing the desired compound were collected and evaporated. The residue was dissolved in MeOH (+5% of TFA) (5 mL) and water (5 mL) was added. The mixture was evaporated to give 7-(1-hydroxy-6-methoxy-3,4-dihydro-2,1-benzoxaborinin-7-yl)cinnolin-4-amine trifluoroacetic acid salt (5.7 mg, 0.013 mmol, 4.3% yield over two steps) as a pale yellow solid. $^1$H NMR (400 MHz, Methanol-d$_4$+2 drops of TFA) δ 3.01 (t, J=5.99 Hz, 2H), 3.90 (s, 3H), 4.25 (t, J=5.99 Hz, 2H), 7.02 (s, 1H), 7.73 (s, 1H), 7.96 (dd, J=8.86, 1.61 Hz, 1H), 8.00 (dd, J=1.61, 0.65 Hz, 1H), 8.31 (d, J=8.86 Hz, 1H), 8.43 (s, 1H). LC-MS (Method A): r.t. 0.51 min, MS (ESI) m/z=322.2 [M+H]$^+$.

Example 47: [3-(1-amino-4-methylphthalazin-6-yl)-5-dimethylphosphoryl-2-fluorophenyl]boronic Acid Formic Acid Salt (47)

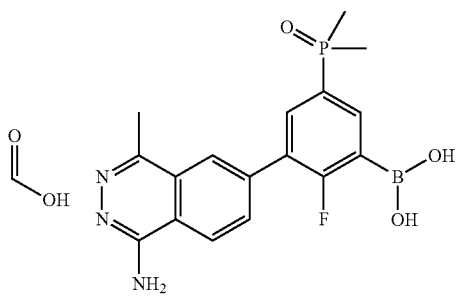

6-(3-Chloro-5-dimethylphosphoryl-2-fluorophenyl)-N-[(2,4-dimethoxyphenyl) methyl]-4-methylphthalazin-1-amine (75.0 mg, 0.150 mmol), 4,4,5,5-tetramethyl-2-(4,4,5,5-tetramethyl-1,3,2-dioxaborolan-2-yl)-1,3,2-dioxaborolane (111.18 mg, 0.440 mmol) and potassium acetate (42.97 mg, 0.440 mmol) were solubilized in 1,4-dioxane (1.558 mL). The resulting solution was degassed for 10 minutes with $N_2$ then palladium(II) diacetate (1.64 mg, 0.010 mmol) and dicyclohexyl-[2-[2,4,6-tri(propan-2-yl)phenyl]phenyl]phosphine (6.96 mg, 0.010 mmol) were added. The resulting reaction mixture was stirred at 75° C. for 2 hours then it was cooled to room temperature and filtered over Celite, washing with EtOAc. The filtrate was evaporated under reduced pressure and the residue was dissolved in dichloromethane (0.5 mL) and trifluoroacetic acid (0.8 mL). The resulting mixture was stirred for 2 hours at room temperature then it was concentrated under reduced pressure. The residue was purified by column chromatography (KP-C18-HS 30 g) eluting with a gradient of $CH_3CN$ in water (+0.1% of HCOOH) from 1% to 50%. Fractions containing the desired compound were collected and evaporated under reduced pressure to give [3-(1-amino-4-methylphthalazin-6-yl)-5-dimethylphosphoryl-2-fluorophenyl]boronic acid formic acid salt (8.5 mg, 0.020 mmol, 13.9% yield) as a white solid. $^1$H NMR (400 MHz, DMSO-$d_6$+2 drops of TFA) δ 1.74 (s, 3H), 1.78 (s, 3H), 2.77 (s, 3H), 8.08 (m, 2H), 8.13 (s, 1H, HCOOH), 8.30-8.43 (m, 2H), 8.78 (d, J=8.5 Hz, 1H), 9.23 (br. s, 2H). LC-MS (Method A): r.t. 0.36 min, MS (ESI) m/z=374.2 [M+H]$^+$.

Example 48: [3-(4-aminocinnolin-7-yl)-2-fluoro-4-methoxyphenyl]boronic Acid (48)

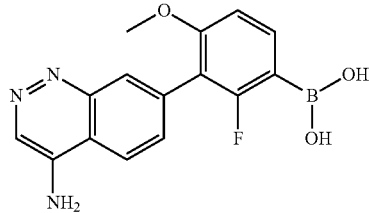 [SMILES: COc1ccc(B(O)O)c(F)c1-c1ccc2c(N)cnnc2c1]

Step 1: Palladium(II) diacetate (4.48 mg, 0.020 mmol), 7-(3-chloro-2-fluoro-6-methoxyphenyl)-N-[(2,4-dimethoxyphenyl)methyl]cinnolin-4-amine (181.0 mg, 0.400 mmol), dicyclohexyl-[2-[2,4,6-tri(propan-2-yl)phenyl]phenyl]phosphine (15.21 mg, 0.030 mmol), potassium acetate (117.41 mg, 1.2 mmol) and 4,4,5,5-tetramethyl-2-(4,4,5,5-tetramethyl-1,3,2-dioxaborolan-2-yl)-1,3,2-dioxaborolane (303.79 mg, 1.2 mmol) were dissolved in 1,4-dioxane (10 mL). The mixture was degassed with Ar for 10 min, then stirred at 50° C. for 9 hours. The mixture was filtered over a pad of Celite, washing with EtOAc and concentrated in vacuo.

Step 2: The crude material from Step 1 was dissolved in a mixture of DCM (2 mL) and trifluoroacetic acid (4 mL). The mixture was stirred at room temperature for 3 h and the volatiles were evaporated. The residue was dissolved in MeOH and loaded onto an SCX cartridge (5 g). The cartridge was washed with 4CV of MeOH, 2CV of MeOH/$H_2O$ (8:2) and 1CV with MeOH. The product was eluted from the SCX cartridge with 3CV of a 2M solution of $NH_3$ in MeOH. The volatiles were evaporated and the residue was purified by column chromatography (KP-C18-HS, SNAP 30 g) eluting with a gradient of $CH_3CN$ (+0.1% of HCOOH) in water (+0.1% of HCOOH) from 1% to 15% to give [3-(4-aminocinnolin-7-yl)-2-fluoro-4-methoxyphenyl]boronic acid (46 mg, 0.147 mmol, 56.75% yield over two steps) as a pale yellow solid. NMR analysis showed a partial salification of the title compound (~51%). $^1$H NMR (400 MHz, DMSO-$d_6$+TFA) δ 3.79 (s, 3H), 7.03 (d, J=8.53 Hz, 1H), 7.68-7.75 (m, 1H), 7.78 (d, J=8.78 Hz, 1H), 7.85 (s, 1H), 8.10 (s, 0.5H from HCOOH) 8.45-8.51 (m, 2H), 9.74 (s, 1H), 9.87 (s, 1H). LC-MS (Method A): r.t. 0.41 min, MS (ESI) m/z=314.7 [M+H]$^+$.

Example 49: [3-(1-amino-4-methylphthalazin-6-yl)-4-methoxy-5-(trifluoromethyl)phenyl]boronic Acid (49)

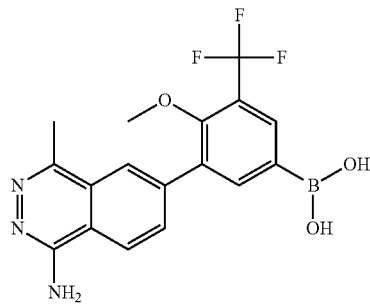 [SMILES: COc1c(-c2ccc3c(N)nnc(C)c3c2)cc(B(O)O)cc1C(F)(F)F]

A solution of [3-[1-[(2,4-dimethoxyphenyl)methylamino]-4-methylphthalazin-6-yl]-4-methoxy-5-(trifluoromethyl)phenyl]boronic acid (135.0 mg, 0.260 mmol) in DCM (3 mL) and trifluoroacetic acid (3 mL) was stirred for 2 hours at room temperature then it was concentrated under reduced pressure. The residue was purified by column chromatography (KP-C18-HS, 30 g) eluting with a gradient of $CH_3CN$ in water (+0.1% of HCOOH) from 2% to 95%. Fractions containing the desired compound were collected and evaporated under reduced pressure to give [3-(1-amino-4-methylphthalazin-6-yl)-4-methoxy-5-(trifluoromethyl)phenyl]boronic acid (40 mg, 0.106 mmol, 41.43% yield) as a white powder. $^1$H NMR (400 MHz, Methanol-$d_4$) δ 2.82 (s, 3H), 3.41 (s, 3H), 7.98 (br. s, 2H), 8.30-8.36 (m, 1H), 8.43 (d, J=1.7 Hz, 1H), 8.53 (dd, J=8.5, 0.6 Hz, 1H). LC-MS (Method A): r.t. 0.61 min, MS (ESI) m/z=378.2 [M+H]$^+$.

Example 50: [5-(1-amino-4-methylphthalazin-6-yl)-2-chloro-4-methoxyphenyl]boronic Acid (50)

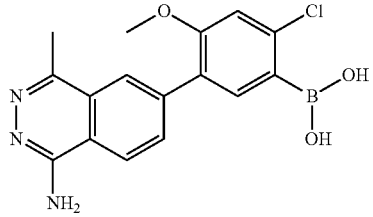 [SMILES: COc1cc(Cl)c(B(O)O)cc1-c1ccc2c(N)nnc(C)c2c1]

Step 1: 6-(5-Bromo-4-chloro-2-methoxyphenyl)-N-[(2,4-dimethoxyphenyl)methyl]-4-methylphthalazin-1-amine (139.0 mg, 0.260 mmol), potassium acetate (77.39 mg, 0.790 mmol), [1,1'-bis(diphenylphosphino)ferrocene]dichloropalladium(II) (9.64 mg, 0.010 mmol) and 4,4,5,5-tetramethyl-2-(4,4,5,5-tetramethyl-1,3,2-dioxaborolan-2-yl)-1,3,2-dioxaborolane (200.24 mg, 0.790 mmol) were dissolved in 1,4-dioxane (3.475 mL). The mixture was degassed with Ar for 10 min, then stirred at 100° C. for 40 hours. The mixture was cooled to room temperature, diluted with EtOAc and filtered over a short pad of Celite. The volatiles were evaporated to give a dark oil which was used in the next step without further purification.

Step 2: The crude material from Step 1 was combined with a similar crude material prepared by the same procedure described in Step 1 but starting with 41 mg of 6-(5-Bromo-4-chloro-2-methoxyphenyl)-N-[(2,4-dimethoxyphenyl)methyl]-4-methylphthalazin-1-amine. The combined crude material was dissolved in a mixture of DCM (4 mL) and trifluoroacetic acid (4 mL). The mixture was stirred at room temperature for 3 h and the volatiles were evaporated. The residue was dissolved in MeOH and loaded onto an SCX cartridge (5 g). The cartridge was washed with 4CV of MeOH, 2CV of MeOH/$H_2O$ (8:2) and 1CV with MeOH. The product was eluted from the SCX cartridge with 3CV of a 2M solution of $NH_3$ in MeOH. The volatiles were evaporated and the residue was purified by column chromatography (KP-C18-HS, SNAP 30 g) eluting with a gradient of $CH_3CN$ (+0.1% of HCOOH) in water (+0.1% of HCOOH) from 1% to 25% to give [5-(1-amino-4-methylphthalazin-6-yl)-2-chloro-4-methoxyphenyl]boronic acid (38 mg, 0.111 mmol, 32% yield over two steps) as a white solid. $^1$H NMR (400 MHz, DMSO-$d_6$+TFA) δ 2.71 (s, 3H), 3.83 (s, 3H), 7.17 (s, 1H), 7.63 (s, 1H), 8.20-8.26 (m, 2H), 8.66 (d, J=8.44 Hz, 1H), 9.10 (br. s, 2H). LC-MS (Method A): r.t. 0.53 min, MS (ESI) m/z=344.2 [M+H]$^+$.

Example 51: [3-(4-aminocinnolin-7-yl)-4-(oxan-4-yloxy)phenyl]boronic Acid Formic Acid Salt (51)

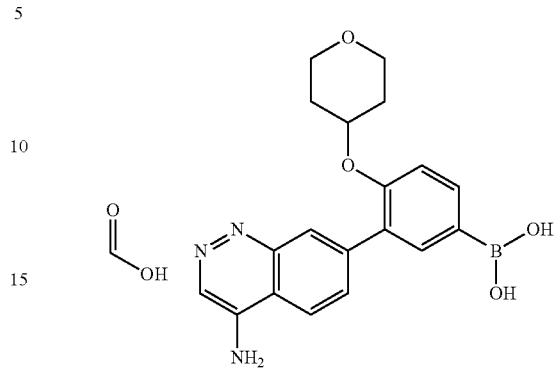

Step 1: Palladium(II) diacetate (3.08 mg, 0.010 mmol), 7-[5-chloro-2-(oxan-4-yloxy)phenyl]-N-[(2,4-dimethoxyphenyl)methyl]cinnolin-4-amine (134.0 mg, 0.270 mmol), dicyclohexyl-[2-[2,4,6-tri(propan-2-yl)phenyl]phenyl]phosphine (10.48 mg, 0.020 mmol), potassium acetate (80.88 mg, 0.820 mmol) and 4,4,5,5-tetramethyl-2-(4,4,5,5-tetramethyl-1,3,2-dioxaborolan-2-yl)-1,3,2-dioxaborolane (209.28 mg, 0.820 mmol) were dissolved in 1,4-dioxane (3.29 mL). The mixture was degassed with Ar for 10 min, then stirred at 85° C. for 4 hours. The mixture was filtered over a pad of Celite, washing with EtOAc and the filtrate was concentrated in vacuo.

Step 2: The crude material from Step 1 was dissolved in a mixture of DCM (2 mL) and trifluoroacetic acid (4 mL). The mixture was stirred at room temperature for 3 h and the volatiles were evaporated. The residue was dissolved in MeOH and loaded onto an SCX cartridge (5 g). The cartridge was washed with 4CV of MeOH, 2CV of MeOH/$H_2O$ (8:2) and 1CV of MeOH. The product was eluted from the SCX cartridge with 3CV of a 2M solution of $NH_3$ in MeOH. The volatiles were evaporated and the residue was purified by column chromatography (KP-C18-HS, SNAP 30 g) eluting with a gradient of $CH_3CN$ (+0.1% of HCOOH) in water (+0.1% of HCOOH) from 1% to 20% to give [3-(4-aminocinnolin-7-yl)-4-(oxan-4-yloxy)phenyl]boronic acid formic acid salt (38 mg, 0.092 mmol, 34% yield over two steps) as a yellow solid. $^1$H NMR (400 MHz, DMSO-$d_6$+2 drops TFA) δ 1.51-1.66 (m, 2H), 1.92-2.03 (m, 2H), 3.42-3.54 (m, 2H), 3.67-3.77 (m, 2H), 4.71-4.79 (m, 1H), 7.24 (d, J=8.44 Hz, 1H), 7.88 (dd, J=8.40, 1.51 Hz, 1H), 7.96 (d, J=1.51 Hz, 1H), 7.99 (dd, J=8.87, 1.34 Hz, 1H), 8.08 (d, J=1.20 Hz, 1H), 8.10 (s, 1H from HCOOH), 8.44-8.52 (m, 2H), 9.67 (s, 1H), 9.80 (s, 1H). LC-MS (Method A): r.t. 0.46 min, MS (ESI) m/z=366.2 [M+H]$^+$.

Example 52: [3-(1-amino-4-methylphthalazin-6-yl)-5-pyridin-3-ylphenyl]boronic Acid Formic Acid Salt (52)

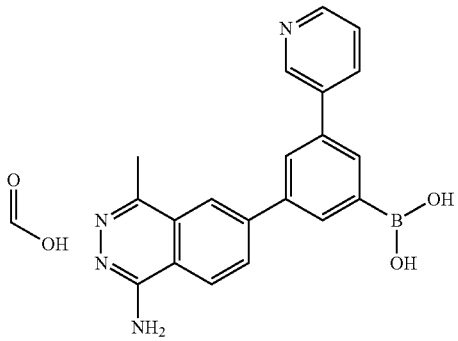

A solution of [3-[1-[(2,4-dimethoxyphenyl)methylamino]-4-methylphthalazin-6-yl]-5-pyridin-3-ylphenyl]boronic acid (55.0 mg, 0.110 mmol) in DCM (1 mL) and trifluoroacetic acid (1 mL) was stirred for 2 hours at room temperature then it was concentrated under reduced pressure. The resulting crude was purified by column chromatography (KP-C18-HS, 30 g) eluting with a gradient of $CH_3CN$ in water (+0.1% of HCOOH) from 2% to 95%. Fractions containing the desired compound were collected and evaporated under reduced pressure to give [3-(1-amino-4-methylphthalazin-6-yl)-5-pyridin-3-ylphenyl]boronic acid formic acid salt (6 mg, 0.015 mmol, 13.73% yield) as a yellow powder. $^1H$ NMR (400 MHz, Methanol-$d_4$) δ 2.87 (s, 3H), 7.55-7.63 (m, 1H), 8.00-8.16 (m, 3H), 8.25 (dt, J=8.0, 2.0 Hz, 1H), 8.39-8.54 (m, 5H), 8.58 (dd, J=4.9, 1.6 Hz, 1H), 8.95 (d, J=2.3, 0.9 Hz, 1H). LC-MS (Method A): r.t. 0.39 min, MS (ESI) m/z=357.3 $[M+H]^+$.

Example 53: 7-[2-methoxy-5-(4,4,5,5-tetramethyl-1,3,2-dioxaborolan-2-yl)phenyl]cinnolin-4-amine trifluoroacetic Acid Salt (53)

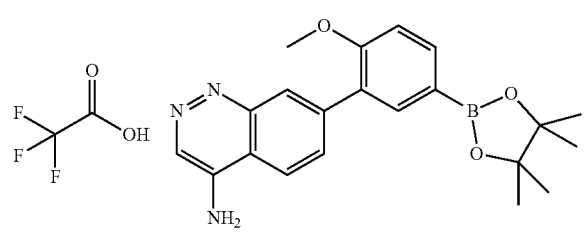

A solution of [3-(4-aminocinnolin-7-yl)-4-methoxyphenyl]boronic acid (100.0 mg, 0.240 mmol) and 2,3-dimethylbutane-2,3-diol (31.27 mg, 0.260 mmol) in dichloromethane (2 mL) and trifluoroacetic acid (0.500 mL) was stirred at room temperature for 2 hours then it was concentrated under reduced pressure to give an orange oil. This material was triturated with diethyl ether. The solvent was decanted and the resulting solid was taken up with dichloromethane. The volatiles were removed in vacuo to give 7-[2-methoxy-5-(4,4,5,5-tetramethyl-1,3,2-dioxaborolan-2-yl)phenyl]cinnolin-4-amine trifluoroacetic acid salt (111 mg, 0.226 mmol, 93.91% yield) as a yellow solid. $^1H$ NMR (400 MHz, DMSO-$d_6$) δ 1.31 (s, 12H), 3.88 (s, 3H), 7.27 (d, J=8.42 Hz, 1H), 7.72 (d, J=1.65 Hz, 1H), 7.81 (dd, J=8.27, 1.67 Hz, 1H), 7.94-7.99 (m, 2H), 8.45 (d, J=8.73 Hz, 1H), 8.49 (s, 1H), 9.64 (s, 2H). LC-MS (Method A): r.t. 0.73 min, MS (ESI) m/z=378.13 $[M+H]^+$.

Example 54: 7-{2-methoxy-5-[(1S,2S,6R,8S)-2,9,9-trimethyl-3,5-dioxa-4-boratricyclo[6.1.1.0$^{2,6}$]decan-4-yl]phenyl}cinnolin-4-amine (54)

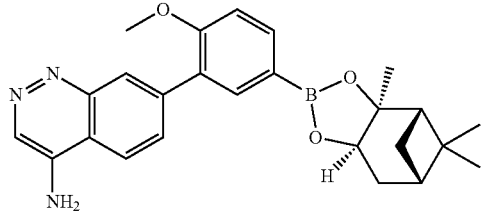 [SMILES: COc1ccc(B2O[C@@H]3C[C@@H]4C[C@@H](C4(C)C)[C@]3(C)O2)cc1-c1ccc2c(N)cnnc2c1]

A suspension of [3-(4-aminocinnolin-7-yl)-4-methoxyphenyl]boronic acid (100.0 mg, 0.340 mmol) and (1S,3R,4S,5S)-4,6,6-trimethylbicyclo[3.1.1]heptane-3,4-diol (57.69 mg, 0.340 mmol) in THF (4 mL) was stirred at room temperature for three hours (after 1 hour the suspension became a clear solution) then the mixture was concentrated in vacuo. The residue was triturated with diethyl ether, the solvent was decanted and the solid residue was collected and dried to give 7-{2-methoxy-5-[(1S,2S,6R,8S)-2,9,9-trimethyl-3,5-dioxa-4-boratricyclo[6.1.1.0$^{2,6}$]decan-4-yl]phenyl}cinnolin-4-amine (97 mg, 0.226 mmol, 66.67% yield) as an off white solid. $^1H$ NMR (400 MHz, Methanol-$d_4$) δ 0.94 (s, 3H), 1.24 (d, J=10.88 Hz, 1H), 1.35 (s, 3H), 1.51 (s, 3H), 1.93-2.02 (m, 2H), 2.15 (t, J=5.43 Hz, 1H), 2.26-2.34 (m, 1H), 2.48 (dd, J=13.17, 9.68 Hz, 1H), 3.91 (s, 3H), 4.52 (dd, J=8.79, 1.79 Hz, 1H), 7.19 (d, J=8.20 Hz, 1H), 7.80 (dd, J=8.79, 1.71 Hz, 1H), 7.82-7.88 (m, 2H), 8.14 (d, J=8.76 Hz, 1H), 8.18 (d, J=1.68 Hz, 1H), 8.60 (s, 1H). LC-MS (Method A): r.t. 0.90 min, MS (ESI) m/z=430.18 $[M+H]^+$.

Example 55: 3-(1-amino-8-fluoro-4-methylphthalazin-6-yl)-4-methoxyphenyl]boronic Acid (55)

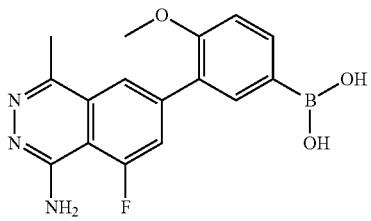 [SMILES: COc1ccc(B(O)O)cc1-c1cc(F)c2c(N)nnc(C)c2c1]

Palladium(II) diacetate (3.12 mg, 0.010 mmol), 6-(5-chloro-2-methoxyphenyl)-N-[(2,4-dimethoxyphenyl)methyl]-8-fluoro-4-methylphthalazin-1-amine (144.44 mg, 0.280 mmol), dicyclohexyl-[2-[2,4,6-tri(propan-2-yl)phenyl]phenyl]phosphine (13.24 mg, 0.030 mmol), potassium acetate (81.8 mg, 0.830 mmol) and 4,4,5,5-tetramethyl-2-(4,4,5,5-tetramethyl-1,3,2-dioxaborolan-2-yl)-1,3,2-dioxaborolane (211.65 mg, 0.830 mmol) were solved in 1,4-dioxane (2.653 mL) in a microwave vial. The resulting reaction mixture was stirred at 75° C. for 2 hours then it was cooled to room temperature and filtered over Celite, washing with EtOAc. The filtrate was evaporated under reduced pressure and the residue was dissolved in dichloromethane (1 mL) and trifluoroacetic acid (1 mL). The resulting mixture was stirred for 2 hours at room temperature then it was concentrated under reduced pressure. The residue was taken up with MeOH and this solution was loaded onto an SCX cartridge (5 g) which was washed with MeOH/H₂O (9:1) and then eluted with a 7M solution of ammonia in MeOH. The basic fractions were collected and evaporated under reduced pressure. The residue was purified by flash chromatography (KP-C18-HS 30 g) eluting with a gradient of CH₃CN (+0.1% of HCOOH) in water (+0.1% of HCOOH) from 1% to 70%. Appropriate fractions were collected and then lyophilised to give [3-(1-amino-8-fluoro-4-methylphthalazin-6-yl)-4-methoxyphenyl]boronic acid (25 mg, 0.076 mmol, 27.1% yield) as a white solid. ¹H NMR (400 MHz, DMSO-d₆) δ 2.72 (s, 3H), 3.85 (s, 3H), 6.59 (s, 2H), 7.18 (d, J=8.34 Hz, 1H), 7.82 (dd, J=13.51, 1.50 Hz, 1H), 7.83-7.91 (m, 2H), 7.93 (d, J=1.73 Hz, 1H), 8.04 (s, 2H). LC-MS (Method B): r.t. 0.64 min, MS (ESI) m/z=328.1 [M+H]⁺.

Example 56: 7-(1-amino-4-methylphthalazin-6-yl)-1-hydroxy-4H-2,1-benzoxaborinin-3-one trifluoroacetic Acid Salt (56)

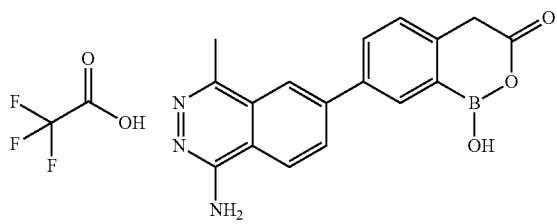

A 1M aqueous solution of LiOH (1.34 mL, 1.34 mmol) was added to a solution of ethyl 2-[4-(1-amino-4-methylphthalazin-6-yl)-2-(4,4,5,5-tetramethyl-1,3,2-dioxaborolan-2-yl)phenyl]acetate (150.0 mg, 0.340 mmol) in methanol (2 mL) and the mixture stirred at room temperature for 3 h. The mixture was quenched with 1M hydrochloric acid solution until the pH reached 6-7 and the volatiles were evaporated. The residue was purified by column chromatography (KP-C18-HS, SNAP 30 g) eluting with a gradient of CH₃CN (+0.1% of HCOOH) in water (+0.1% of HCOOH) from 1% to 30%. Fractions containing the desired compound were evaporated to give a solid which was triturated with MeOH (4×0.5 mL), dried under vacuum, dissolved in water (+10% of TFA) and dried under vacuum to give 7-(1-amino-4-methylphthalazin-6-yl)-1-hydroxy-4H-2,1-benzoxaborinin-3-one trifluoroacetic acid salt (15.8 mg, 0.036 mmol, 10.88% yield) as a white solid. ¹H NMR (400 MHz, DMSO-d₆+2 drops of TFA+2 drops of D₂O) δ 2.76 (s, 3H), 3.85 (s, 2H), 7.34 (d, J=8.00 Hz, 1H), 7.84 (dd, J=8.00, 2.18 Hz, 1H), 8.07 (d, J=2.18 Hz, 1H), 8.37 (d, J=1.24 Hz, 1H), 8.40 (dd, J=8.63, 1.64 Hz, 1H), 8.66 (d, J=8.56 Hz, 1H). LC-MS (Method A): r.t. 0.46 min, MS (ESI) m/z=320.1 [M+H]⁺.

Example 57: [3-(1-amino-4-methylphthalazin-6-yl)-5-fluoro-4-methoxyphenyl]boronic Acid trifluoroacetic Acid Salt (57)

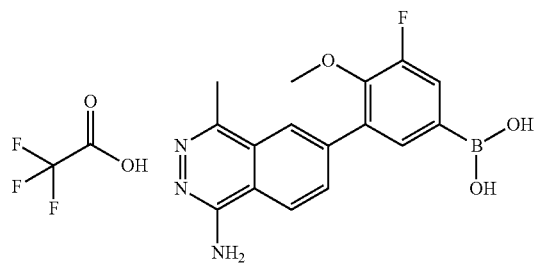

A mixture of [3-[1-[(2,4-dimethoxyphenyl)methylamino]-4-methylphthalazin-6-yl]-5-fluoro-4-methoxyphenyl]boronic acid (9 mg, 0.019 mmol) in DCM (0.50 mL) and trifluoroacetic acid (0.25 mL) was stirred at room temperature for 2 h, then the volatiles were removed. MeOH (1 mL) was added and the mixture was filtered over a pad of Celite, washing with MeOH. The volatiles were removed to give [3-[1-[(2,4-dimethoxyphenyl)methylamino]-4-methylphthalazin-6-yl]-5-fluoro-4-methoxyphenyl]boronic acid trifluoroacetic acid salt (9.0 mg, 0.020 mmol) as a white solid. ¹H NMR (400 MHz, DMSO-d₆) δ 2.76 (s, 3H), 3.81-3.84 (m, 3H), 7.72 (dd, J=12.43, 1.43 Hz, 1H), 7.78 (s, 1H), 8.20 (d, J=8.36 Hz, 1H), 8.25 (s, 1H), 8.30 (s, 2H), 8.63 (d, J=8.58 Hz, 1H), 14.23 (br. s, 1H). LC-MS (Method A): r.t. 0.53 min, MS (ESI) m/z=328.12 [M+H]⁺.

Example 58: [3-(4-aminocinnolin-7-yl)-4-methoxy-5-(oxan-4-yl)phenyl]boronic Acid (58)

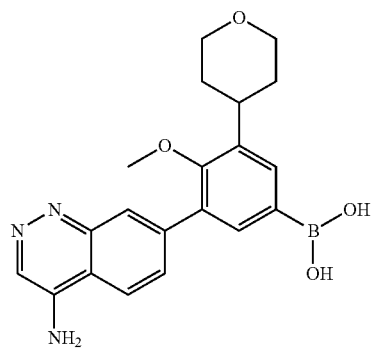 [SMILES: COc1c(-c2ccc3c(N)cnnc3c2)cc(B(O)O)cc1C1CCOCC1]

Palladium(II) diacetate (1.62 mg, 0.010 mmol), 7-[5-chloro-2-methoxy-3-(oxan-4-yl)phenyl]-N-[(2,4-dimethoxyphenyl)methyl]cinnolin-4-amine (75.0 mg, 0.140 mmol), dicyclohexyl-[2-[2,4,6-tri(propan-2-yl)phenyl]phenyl]phosphine (6.88 mg, 0.010 mmol), potassium acetate (42.46 mg, 0.430 mmol) and 4,4,5,5-tetramethyl-2-(4,4,5,5-tetramethyl-1,3,2-dioxaborolan-2-yl)-1,3,2-dioxaborolane (109.87 mg, 0.430 mmol) were solved in 1,4-dioxane (1.531 mL) in a microwave vial. The resulting reaction mixture was stirred at 80° C. for 2 hours then it was cooled to room temperature and filtered over Celite, washing with EtOAc. The filtrate was evaporated under reduced pressure and the residue was dissolved in dichloromethane (1 mL) and trifluoroacetic acid (1 mL). The resulting mixture was stirred for 2 hours at room temperature then it was concentrated under reduced pressure. The residue was taken up with MeOH and this solution was loaded onto an SCX cartridge (5 g) which was washed with MeOH/H$_2$O (9:1) and then eluted with a 7M solution of ammonia in MeOH. The basic fractions were collected and evaporated under reduced pressure. The residue was purified by column chromatography (KP-C18-HS, 30 g) eluting with a gradient of CH$_3$CN (+0.1% of HCOOH) in water (+0.1% of HCOOH) from 1% to 70. Appropriate fractions were collected and then lyophilised to give [3-(4-aminocinnolin-7-yl)-4-methoxy-5-(oxan-4-yl)phenyl]boronic acid (19 mg, 0.050 mmol, 34.74% yield) as a white solid. $^1$H NMR (400 MHz, Methanol-d$_4$) δ 1.75-1.84 (m, 2H), 1.83-1.99 (m, 3H), 3.45 (s, 3H), 3.60-3.69 (m, 2H), 4.07-4.14 (m, 2H), 7.60-7.75 (m, 2H), 8.06 (dd, J=8.86, 1.59 Hz, 1H), 8.08-8.11 (m, 2H), 8.41 (d, J=8.80 Hz, 1H), 8.49 (s, 1H). LC-MS (Method B): r.t. 0.61 min, MS (ESI) m/z=380.1 [M+H]$^+$.

Example 59: [3-(1-amino-4-methylphthalazin-6-yl)-4-(3-methylbutanoylamino)phenyl]boronic Acid Formic Acid Salt (59)

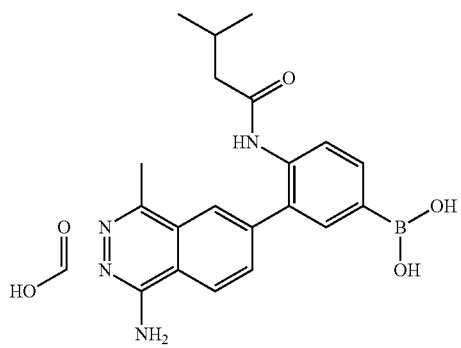

A mixture of N-[2-[1-[(2,4-dimethoxyphenyl)methylamino]-4-methylphthalazin-6-yl]-4-(4,4,5,5-tetramethyl-1,3,2-dioxaborolan-2-yl)phenyl]-3-methylbutanamide (47.0 mg, 0.080 mmol) in DCM (0.600 mL) and trifluoroacetic acid (0.600 mL) was stirred at room temperature for 1 h, then the volatiles were removed. The residue was dissolved in MeOH and loaded onto an SCX cartridge (2 g), that was slowly washed with MeOH/water (9:1) and then with MeOH, and then eluted with 2M ammonia in MeOH. The volatiles were removed and the residue was purified by column chromatography (KP-C18-HS, SNAP 18) eluting with a gradient of MeCN in water from 2% to 30% to give [3-(1-amino-4-methylphthalazin-6-yl)-4-(3-methylbutanoylamino)phenyl]boronic acid formic acid salt (10.2 mg, 0.024 mmol, 31.23% yield) as a white solid. $^1$H NMR (400 MHz, DMSO-d$_6$+2 drops of TFA) δ 0.75 (d, J=6.60 Hz, 6H), 1.86-1.91 (1H, m), 2.00 (d, J=7.04 Hz, 2H), 2.73 (s, 3H), 7.50 (d, J=7.92 Hz, 1H), 7.85-7.90 (m, 2H), 8.10-8.13 (m, 1H), 8.10-8.16 (m, 2H), 8.19 (d, J=1.54 Hz, 1H), 8.70 (d, J=8.58 Hz, 1H), 9.52 (s, 1H). LC-MS (Method A): r.t. 0.46 min, MS (ESI) m/z=379.18 [M+H]$^+$.

Example 60: 7-[5-(1,3,6,2-dioxazaborocan-2-yl)-2-methoxyphenyl]cinnolin-4-amine (60)

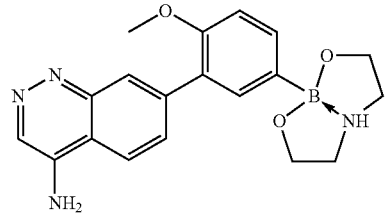 [SMILES: COc1ccc([B-]23OCC[NH+]2CCO3)cc1-c1ccc2c(N)cnnc2c1]

2-(2-Hydroxyethylamino)ethanol (16.24 uL, 0.170 mmol) was added to a suspension of [3-(4-aminocinnolin-7-yl)-4-methoxyphenyl]boronic acid (50.0 mg, 0.170 mmol) in THF (1 mL). The resulting mixture was stirred at 40° C. for three hours then it was evaporated in vacuo. The residue was triturated with acetonitrile and the resulting solid was filtered, washed with acetonitrile and dried to give 7-[5-(1,3,6,2-dioxazaborocan-2-yl)-2-methoxyphenyl]cinnolin-4-amine (37 mg, 0.102 mmol, 59.96% yield) as a white solid. $^1$H NMR (400 MHz, Methanol-d$_4$) δ 3.15-3.20 (m, 4H), 3.80-3.86 (m, 4H), 3.92 (s, 3H), 7.21 (d, J=8.37 Hz, 1H), 7.77 (s, 1H), 7.81 (d, J=8.42 Hz, 1H), 7.95 (dd, J=8.85, 1.66 Hz, 1H), 8.08 (d, J=1.59 Hz, 1H), 8.28 (d, J=8.83 Hz, 1H), 8.51 (s, 1H).

Example 61: [3-(1-amino-4-methylphthalazin-6-yl)-4-(4-methylpentanoylamino)phenyl]boronic Acid Formic Acid Salt (61)

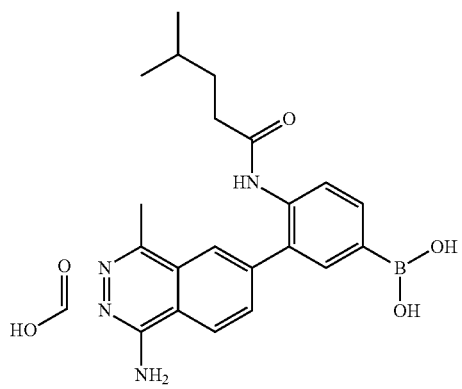

A mixture of N-[2-[1-[(2,4-dimethoxyphenyl)methylamino]-4-methylphthalazin-6-yl]-4-(4,4,5,5-tetramethyl-1,3,2-dioxaborolan-2-yl)phenyl]-4-methylpentanamide (42.0 mg, 0.070 mmol) in DCM (0.80 mL) and trifluoroacetic acid (0.50 mL) was stirred at room temperature for 1.5 h then the volatiles were removed. The residue was dissolved in MeOH and loaded onto an SCX cartridge (2 g), that was washed with MeOH/water (9:1) and then with MeOH, and then eluted with 2M ammonia in MeOH. The volatiles were removed and the residue was purified by column chromatography (Sfar C18) eluting with a gradient of MeCN (+0.1% HCOOH) in water (+0.1% HCOOH) from 2% to 30% to give [3-(1-amino-4-methylphthalazin-6-yl)-4-(4-methylpentanoylamino)phenyl]boronic acid formic acid salt (10 mg, 0.023 mmol, 33.93% yield) as white solid. $^1$H NMR (400 MHz, DMSO-d$_6$) δ 0.71-0.76 (m, 6H), 1.28 (br. s, 3H), 2.09-2.14 (m, 2H), 2.69 (s, 3H), 6.77 (br. s, 2H), 7.50 (d, J=7.92 Hz, 1H), 7.79-7.83 (m, 2H), 7.86 (s, 1H), 7.90 (d, J=1.32 Hz, 1H), 8.22 (br. s, 3H), 8.28 (d, J=8.58 Hz, 1H), 9.36 (s, 1H). LC-MS (Method A): r.t. 0.52 min, MS (ESI) m/z=393.2 [M+H]$^+$.

Example 62: [3-(1-amino-4-methylphthalazin-6-yl)-4-dimethylphosphorylphenyl]boronic Acid Formic Acid Salt (62)

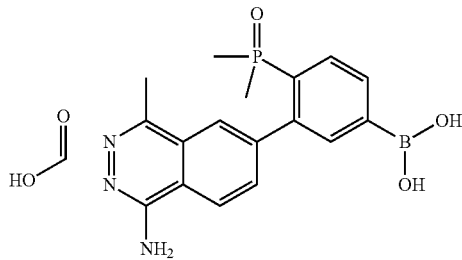

Palladium(II) diacetate (4.28 mg, 0.020 mmol), 6-(5-chloro-2-dimethylphosphorylphenyl)-N-[(2,4-dimethoxyphenyl)methyl]-4-methylphthalazin-1-amine (210.0 mg, 0.380 mmol), dicyclohexyl-[2-[2,4,6-tri(propan-2-yl)phenyl]phenyl]phosphine (14.53 mg, 0.030 mmol), potassium acetate (112.2 mg, 1.14 mmol) and 4,4,5,5-tetramethyl-2-(4,4,5,5-tetramethyl-1,3,2-dioxaborolan-2-yl)-1,3,2-dioxaborolane (290.33 mg, 1.14 mmol) were solved 1,4-dioxane (4 mL) in a microwave vial and the mixture was deoxygenated under N$_2$ for 10 minutes. Then the mixture was stirred at 75° C. for 1.5 hours. The mixture was filtered over a pad of Celite, washing with methanol and the filtrate was concentrated in vacuo. The residue was dissolved in DCM (3 mL) anf trifluoroacetic acid (3 mL) and stirred for 2 hours at room temperature. Then the mixture was evaporated in vacuo and the residue was dissolved in MeOH/H$_2$O (9:1), loaded onto an SCX cartridge and left absorbed on the SCX cartridge for 20 min. The cartridge was then washed with MeOH/H$_2$O (9:1) and eluted with 2 M methanolic ammonia solution. The basic fractions were evaporated and the residue was purified by column chromatography (KP-C18-HS, SNAP10) eluting with a gradient of MeCN (+0.1% HCOOH) in water (+0.1% HCOOH from 5% to 95%. The fractions containing product were combined and lyophilized to give [3-(1-amino-4-methylphthalazin-6-yl)-4-dimethylphosphorylphenyl]boronic acid formic acid salt (33.82 mg, 0.084 mmol, 22.12% yield) as a white solid. $^1$H NMR (400 MHz, DMSO-d$_6$+drop of TFA) δ 1.52 (s, 3H), 1.56 (s, 3H), 2.71 (s, 3H), 7.84 (d, J=3.94 Hz, 1H), 7.87-7.95 (m, 1H), 7.99-8.04 (m, 1H), 8.12 (s, HCOOH, 1H), 8.21 (dd, J=8.40, 1.69 Hz, 1H), 8.37 (d, J=1.65 Hz, 1H), 8.69 (d, J=8.44 Hz, 1H), 9.17 (br. s, 2H). LC-MS (Method A): r.t. 0.33 min, MS (ESI) m/z=356.1 [M+H]$^+$.

Example 63: [5-(1-amino-4-methylphthalazin-6-yl)-2-methoxy-4-(trifluoromethyl)phenyl]boronic Acid (63)

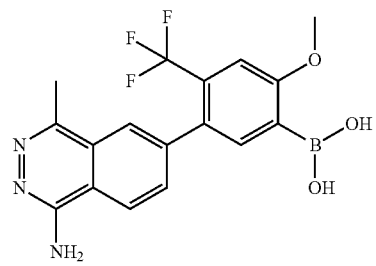 [SMILES: COc1cc(C(F)(F)F)c(-c2ccc3c(N)nnc(C)c3c2)cc1B(O)O]

Palladium(II) diacetate (3.68 mg, 0.020 mmol), 6-[5-chloro-4-methoxy-2-(trifluoromethyl)phenyl]-N-[(2,4-dimethoxyphenyl)methyl]-4-methylphthalazin-1-amine (170.0 mg, 0.330 mmol), dicyclohexyl-[2-[2,4,6-tri(propan-2-yl)phenyl]phenyl]phosphine (15.65 mg, 0.030 mmol), potassium acetate (96.64 mg, 0.980 mmol) and 4,4,5,5-tetramethyl-2-(4,4,5,5-tetramethyl-1,3,2-dioxaborolan-2-yl)-1,3,2-dioxaborolane (250.05 mg, 0.980 mmol) were dissolved in 1,4-dioxane (3.469 mL) in a microwave vial. The resulting reaction mixture was stirred at 80° C. for 2 hours, then it was cooled to room temperature and filtered over Celite, washing with EtOAc. The filtrate was evaporated under reduced pressure and the residue was dissolved in dichloromethane (1 mL) and trifluoroacetic acid (1 mL). The resulting mixture was stirred for 2 hours at room temperature then it was concentrated under reduced pressure. The residue was taken up with MeOH and this solution was loaded onto an SCX cartridge (5 g), which was washed with MeOH/H$_2$O (9:1) and then eluted with a 7M solution of ammonia in MeOH. The basic fractions were collected and evaporated under reduced pressure. The residue was purified by column chromatography (KP-C18-HS, 30 g) eluting with a gradient of MeCN (+0.1% HCOOH) in water (+0.1% HCOOH) from 1% to 70%. Appropriate fractions were collected and then lyophilised to give [5-(1-amino-4-methylphthalazin-6-yl)-2-methoxy-4-(trifluoromethyl)phenyl]boronic acid (52 mg, 0.138 mmol, 41% yield) as a white solid. $^1$H NMR (400 MHz, DMSO-d$_6$+2 drops of TFA) δ 2.70 (s, 3H), 3.95 (s, 3H), 7.37 (s, 1H), 7.56 (s, 1H), 8.00-8.11 (m, 1H), 8.11 (s, 1H), 8.70 (d, J=8.47 Hz, 1H), 9.19 (s, 2H). LC-MS (Method A): r.t. 0.59 min, MS (ESI) m/z=378.1 [M+H]$^+$.

Example 64: [3-(4-aminocinnolin-7-yl)-4-(3-methylbutanamido)phenyl]boronic Acid Formic Acid Salt (64)

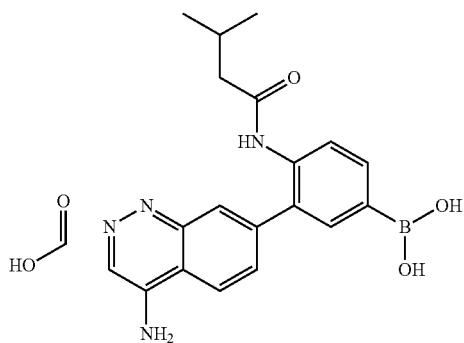

A mixture of N-[2-[4-[(2,4-dimethoxyphenyl)methylamino]cinnolin-7-yl]-4-(4,4,5,5-tetramethyl-1,3,2-dioxaborolan-2-yl)phenyl]-3-methylbutanamide (54.0 mg, 0.090 mmol) in DCM (1.5 mL) and trifluoroacetic acid (1 mL) was stirred overnight at room temperature, then the volatiles were removed. The residue was dissolved in MeOH/water (9:1) and loaded onto an SCX cartridge (2 g) that was washed with MeOH/water (9:1) and then eluted with 2M ammonia in MeOH. The volatiles were removed and the residue was purified by column chromatography (Sfar C18, 12 g) eluting with a gradient of MeCN (+0.1% HCOOH) in water (+0.1% HCOOH) from 2% to 20% to give [3-(4-aminocinnolin-7-yl)-4-(3-methylbutanoylamino)phenyl]boronic acid formic acid salt (22.1 mg, 0.054 mmol, 59.51% yield) as a white solid. $^1$H NMR (400 MHz, DMSO-$d_6$+1 drop of TFA) δ 0.74-0.82 (m, 6H), 1.85-1.96 (1H, m), 2.03 (d, J=7.04 Hz, 2H), 7.49 (d, J=7.92 Hz, 1H), 7.78-7.84 (m, 2H), 7.85-7.91 (m, 2H), 8.46-8.52 (m, 2H), 9.55 (1H, s), 9.76 (br. s, 1H), 9.88 (br. s, 1H). LC-MS (Method A): r.t. 0.41 min, MS (ESI) m/z=365.16 [M+H]$^+$.

Example 65: [3-(4-aminocinnolin-7-yl)-4-(4-methylpentanamido)phenyl]boronic Acid Formic Acid Salt (65)

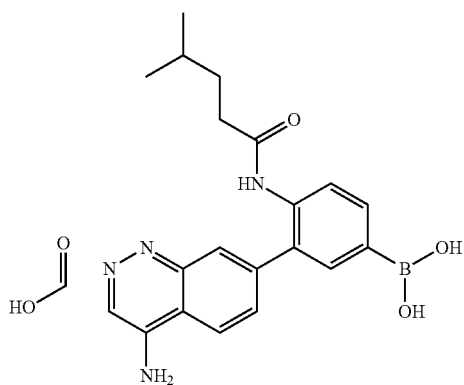

A mixture of N-[2-[4-[(2,4-dimethoxyphenyl)methylamino]cinnolin-7-yl]-4-(4,4,5,5-tetramethyl-1,3,2-dioxaborolan-2-yl)phenyl]-4-methylpentanamide (61.0 mg, 0.100 mmol) and trifluoroacetic acid (1 mL) in DCM (1.5 mL) was stirred overnight at room temperature, then the volatiles were removed. The residue was dissolved in MeOH/water (9:1) and loaded onto an SCX cartridge (2 g) that was washed with MeOH/water (9:1) and eluted with 2M ammonia in MeOH. The volatiles were removed and the residue was purified by column chromatography (Sfar C18, 12 g) eluting with a gradient of MeCN (+0.1% HCOOH) in water (+0.1% HCOOH) from 2% to 20% to give [3-(4-aminocinnolin-7-yl)-4-(4-methylpentanoylamino)phenyl]boronic acid formic acid salt (14.3 mg, 0.034 mmol, 33.74% yield) as a white solid. $^1$H NMR (400 MHz, DMSO-$d_6$+1 drop of TFA) δ 0.76 (d, J=6.16 Hz, 6H), 1.25-1.32 (m, 3H), 2.13 (t, J=7.15 Hz, 2H), 7.47 (d, J=7.92 Hz, 1H), 7.77-7.82 (m, 2H), 7.85-7.90 (m, 2H), 8.46-8.53 (m, 2H), 9.58 (s, 1H), 9.75 (br. s, 1H), 9.89 (br. s, 1H). LC-MS (Method A): r.t. 0.47 min, MS (ESI) m/z=379.18 [M+H]$^+$.

Example 66: 6-(4,4-difluoro-1-hydroxy-3H-2,1-benzoxaborinin-7-yl)-4-methylphthalazin-1-amine (66)

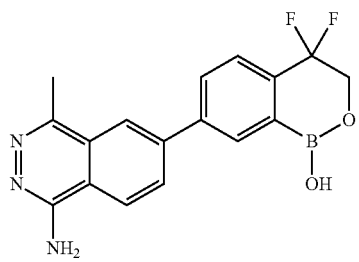 [SMILES: Cc1nnc(N)c2ccc(-c3ccc4c(c3)B(O)OCC4(F)F)cc12]

A mixture of 6-[4-[2-[tert-butyl(dimethyl)silyl]oxy-1,1-difluoroethyl]-3-chlorophenyl]-N-[(2,4-dimethoxyphenyl)methyl]-4-methylphthalazin-1-amine (66.0 mg, 0.110 mmol), 4,4,5,5-tetramethyl-2-(4,4,5,5-tetramethyl-1,3,2-dioxaborolan-2-yl)-1,3,2-dioxaborolane (54.58 mg, 0.210 mmol), cesium fluoride (32.65 mg, 0.210 mmol), trimethyl (2,2,2-trifluoroethoxy)silane (38.86 mg, 0.230 mmol) and dichlorobis(trimethylphosphine)nickel (0.61 mg, 0.002 mmol) were dissolved in THF (0.7 mL) in a microwave vial and degassed for 10 min with $N_2$. The mixture was heated to 100° C. under microwave irradiation for 3 hours in a microwave reactor. The mixture was then cooled to room temperature and filtered over a pad of Celite, washing with MeOH. The filtrate was evaporated and the residue was dissolved in DCM (4 mL) and trifluoroacetic acid (4 mL) and stirred for 2 hours at room temperature, then concentrated under reduced pressure. The residue was purified by column chromatography (KP-C18-HS, 30 g) eluting with a gradient of $CH_3CN$ in water (+0.1% of HCOOH) from 2% to 95%. Fractions containing the partially purified product were collected and evaporated. The recovered solid was submitted to semi-preparative HPLC purification (Chiralcel OJ-H (25×2.0 cm), 5 μm, n-hexane/(EtOH+0.1% isopropylamine) 60/40% v/v). Fractions containing the desired compound were collected and evaporated under reduced pressure to give 6-(4,4-difluoro-1-hydroxy-3H-2,1-benzoxaborinin-7-yl)-4-methylphthalazin-1-amine (2 mg, 0.006 mmol, 3.5% yield) as an off-white powder. $^1$H NMR (400 MHz, DMSO-$d_6$) δ 2.78 (s, 3H), 4.45 (t, J=12.37 Hz, 2H), 6.81 (s, 2H), 7.85 (d, J=8.03 Hz, 1H), 8.18-8.23 (m, 3H), 8.31 (s, 1H), 8.39 (d, J=8.42 Hz, 1H). LC-MS (Method A): r.t. 0.61 min, MS (ESI) m/z=342.1 [M+H]$^+$.

Example 67: [3-(4-amino-5-methylcinnolin-7-yl)-4-methoxyphenyl]boronic Acid (67)

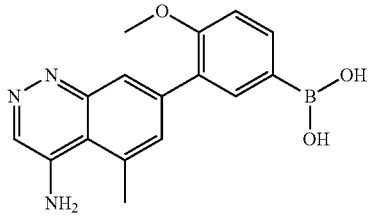 [SMILES: COc1ccc(B(O)O)cc1-c1cc(C)c2c(N)cnnc2c1]

A mixture of 7-(5-chloro-2-methoxyphenyl)-N-[(2,4-dimethoxyphenyl)methyl]-5-methylcinnolin-4-amine (205.0 mg, 0.460 mmol), 4,4,5,5-tetramethyl-2-(4,4,5,5-tetramethyl-1,3,2-dioxaborolan-2-yl)-1,3,2-dioxaborolane (347.11 mg, 1.37 mmol), dicyclohexyl-[2-[2,4,6-tri(propan-2-yl)phenyl]phenyl]phosphine (17.38 mg, 0.040 mmol), potassium acetate (134.15 mg, 1.37 mmol) and palladium(II) diacetate (5.11 mg, 0.020 mmol) were dissolved in 1,4-dioxane (4 mL) in a microwave vial and degassed for 15 min with $N_2$. The mixture was stirred at 75° C. for 1.5 hours, then it was cooled to room temperature and filtered over Celite, washing with MeOH. The filtrate was evaporated and the residue was dissolved in DCM (4 mL) and trifluoroacetic acid (4 mL) and stirred for 2 hours at room temperature, then concentrated under reduced pressure. The residue was dissolved in MeOH/$H_2O$ (9:1), loaded onto an SCX cartridge and left absorbed on the SCX cartridge for 20 min. The cartridge was then washed with MeOH/$H_2O$ (9:1) and eluted with 2 M methanolic ammonia solution. The basic fractions were evaporated and the residue was purified by column chromatography (KP-C18-HS, 12 g) eluting with a gradient of $CH_3CN$ in water (+0.1% of HCOOH) from 2% to 95%. Fractions containing the desired compound were collected and lyophilized. The recovered solid was submitted to semi-preparative HPLC purification (Chiralcel OJ-H (25× 2.0 cm), 5 μm, n-hexane/(EtOH+0.1% isopropylamine) 80/20% v/v). Fractions containing the desired compound were collected and lyophilized to give [3-(4-amino-5-methylcinnolin-7-yl)-4-methoxyphenyl]boronic acid (41 mg, 0.133 mmol, 34.2% yield) as a white powder. $^1$H NMR (400 MHz, DMSO-$d_6$+2 drops of TFA) δ 2.93 (s, 3H), 3.85 (s, 3H), 7.19 (d, J=8.27 Hz, 1H), 7.67 (s, 1H), 7.84 (d, J=1.65 Hz, 1H), 7.87-7.95 (m, 2H), 8.42 (s, 1H), 8.59 (s, 1H), 9.75 (s, 1H). LC-MS (Method A): r.t. 0.46 min, MS (ESI) m/z=310.1 [M+H]$^+$.

Example 68: [3-(1-amino-4-methylphthalazin-6-yl)-2-fluoro-4-(trifluoromethyl)phenyl]boronic Acid Formic Acid Salt (68)

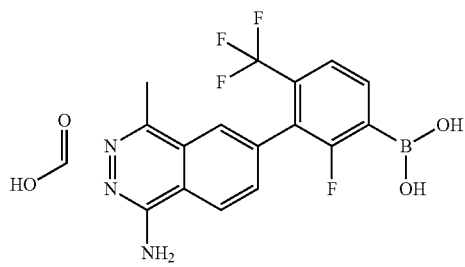

Palladium(II) diacetate (2.66 mg, 0.010 mmol), 6-[3-chloro-2-fluoro-6-(trifluoromethyl)phenyl]-N-[(2,4-dimethoxyphenyl)methyl]-4-methylphthalazin-1-amine (171.43 mg, 0.240 mmol), dicyclohexyl-[2-[2,4,6-tri(propan-2-yl)phenyl]phenyl]phosphine (11.31 mg, 0.020 mmol), potassium acetate (69.84 mg, 0.710 mmol) and 4,4,5,5-tetramethyl-2-(4,4,5,5-tetramethyl-1,3,2-dioxaborolan-2-yl)-1,3,2-dioxaborolane (180.71 mg, 0.710 mmol) were dissolved in 1,4-dioxane (2.449 mL) in a microwave vial and the mixture was deoxygenated under $N_2$ for 10 minutes. The resulting reaction mixture was stirred at 80° C. for 2 hours then it was cooled to room temperature and filtered over Celite, washing with EtOAc. The filtrate was evaporated under reduced pressure and the residue was dissolved in dichloromethane (1.5 mL) and trifluoroacetic acid (1.5 mL). The resulting mixture was stirred for 2 hours at room temperature then it was concentrated under reduced pressure. The residue was purified by column chromatography (Sfar C18, 30 g) eluting with a gradient of MeCN (+0.1% HCOOH) in water (+0.1% HCOOH) from 1% to 70%. Appropriate fractions were collected and then lyophilised to give [3-(1-amino-4-methylphthalazin-6-yl)-2-fluoro-4-(trifluoromethyl)phenyl]boronic formic acid salt (7 mg, 0.017 mmol, 7% yield) as a white solid. $^1$H NMR (400 MHz, DMSO-$d_6$) δ 2.65 (s, 3H), 6.86 (s, 2H), 7.71 (d, J=7.92 Hz, 1H), 7.74-7.89 (m, 2H), 7.89 (s, 1H), 8.17 (s, 1H, HCOOH), 8.32 (d, J=8.44 Hz, 1H), 8.63 (s, 2H). LC-MS (Method A): r.t. 0.56 min, MS (ESI) m/z=366.05 [M+H]$^+$.

Example 69: 7-[5-(11,13-dioxa-12-boradispiro[4.0.4$^6$.3$^5$]tridecan-12-yl)-2-methoxyphenyl]cinnolin-4-amine (69)

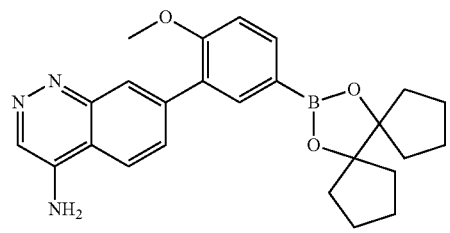 [SMILES: COc1ccc(B2OC3(CCCC3)C3(CCCC3)O2)cc1-c1ccc2c(N)cnnc2c1]

1-(1-Hydroxycyclopentyl)cyclopentan-1-ol (11.54 mg, 0.070 mmol) was added to a suspension of [3-(4-aminocinnolin-7-yl)-4-methoxyphenyl]boronic acid (20.0 mg, 0.070 mmol) in THF (1 mL). The resulting mixture was stirred at 40° C. for 3 h then it was evaporated in vacuo. The residue was triturated with diethyl ether and the resulting solid was filtered, washed with diethyl ether and dried to give 7-[5-(11,13-dioxa-12-boradispiro[4.0.4$^6$.3$^5$]tridecan-12-yl)-2-methoxyphenyl]cinnolin-4-amine (17 mg, 0.040 mmol, 58.43% yield) as an off white solid. $^1$H NMR (400 MHz, DMSO-$d_6$) δ 1.67-1.84 (m, 16H), 3.84 (s, 3H), 7.16-7.25 (m, 3H), 7.62-7.69 (m, 2H), 7.74 (dd, J=8.25, 1.68 Hz, 1H), 8.04 (d, J=1.72 Hz, 1H), 8.20 (d, J=8.75 Hz, 1H), 8.61 (s, 1H).

Example 70: [5-(1-amino-4-methylphthalazin-6-yl)-2-benzamidophenyl]boronic Acid (70)

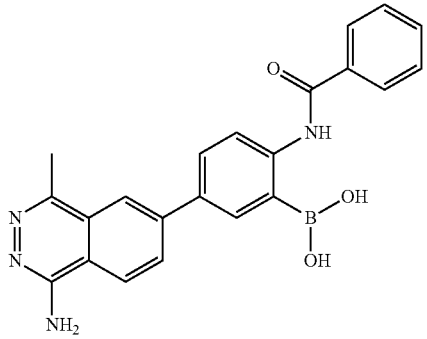 [SMILES: Cc1nnc(N)c2ccc(-c3ccc(NC(=O)c4ccccc4)c(B(O)O)c3)cc12]

A mixture of N-[2-chloro-4-[1-[(2,4-dimethoxyphenyl)methylamino]-4-methylphthalazin-6-yl]phenyl]benzamide (640.0 mg, 1.15 mmol), 4,4,5,5-tetramethyl-2-(4,4,5,5-tetramethyl-1,3,2-dioxaborolan-2-yl)-1,3,2-dioxaborolane (643.43 mg, 2.53 mmol), cesium fluoride (349.89 mg, 2.3 mmol), trimethyl(2,2,2-trifluoroethoxy)silane (416.53 mg, 2.42 mmol) and dichlorobis(trimethylphosphine)nickel (6.49 mg, 0.020 mmol) were dissolved in THF (11 mL) in a microwave vial and degassed for 10 min with $N_2$. The mixture was heated under microwave irradiation at 100° C. for 4.5 hours in a microwave reactor. Then it was cooled to room temperature, filtered over a pad of Celite, washing with MeOH and evaporated. The residue was purified by column chromatography (KP-C18-HS, 30 g) eluting with a gradient of $CH_3CN$ in water (+0.1% of HCOOH) from 2% to 95%. Fractions containing partially pure N-[4-(1-{[(2,4-dimethoxyphenyl)methyl]amino}-4-methylphthalazin-6-yl)-2-(4,4,5,5-tetramethyl-1,3,2-dioxaborolan-2-yl)phenyl]benzamide were collected and evaporated. The residue was dissolved in DCM (2 mL) and trifluoroacetic acid (2 mL) and stirred for 2 hours at room temperature. The reaction mixture was concentrated under reduced pressure and the residue was purified by column chromatography (KP-C18-HS, 12 g) eluting with a gradient of $CH_3CN$ in water (+0.1% of HCOOH) from 1% to 50%. Fractions containing the desired compound were collected and lyophilized to give [5-(1-amino-4-methylphthalazin-6-yl)-2-benzamidophenyl]boronic acid (18 mg, 0.045 mmol, 30.34% yield) as a yellow powder. $^1$H NMR (400 MHz, Methanol-$d_4$) δ 2.87 (s, 3H), 7.57 (d, J=8.36 Hz, 1H), 7.67-7.75 (m, 2H), 7.78-7.85 (m, 1H), 7.92 (dd, J=8.40, 2.27 Hz, 1H), 8.02 (d, J=2.21 Hz, 1H), 8.22-8.27 (m, 2H), 8.39 (dd, J=8.56, 1.81 Hz, 1H), 8.43 (d, J=1.52 Hz, 1H), 8.53 (d, J=8.56 Hz, 1H). LC-MS (Method A): r.t. 0.48 min, MS (ESI) m/z=399.1 [M+H]$^+$.

Example 71: [5-(1-amino-4-methylphthalazin-6-yl)-2-(trifluoromethyl)pyridin-3-yl]boronic Acid Formic Acid Salt (71)

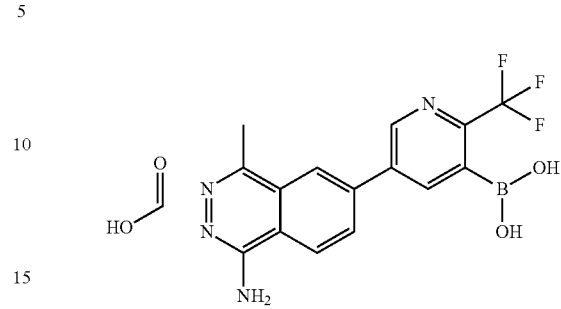

Trifluoroacetic acid (3.5 mL) was added to a solution of N-[(2,4-dimethoxyphenyl)methyl]-4-methyl-6-[5-(4,4,5,5-tetramethyl-1,3,2-dioxaborolan-2-yl)-6-(trifluoromethyl)pyridin-3-yl]phthalazin-1-amine (214.0 mg, 0.370 mmol) in DCM (3.5 mL) and mixture stirred at room temperature for 1 h, then the volatiles were evaporated. The residue was dissolved in MeOH and loaded onto an SCX cartridge (2 g) that was washed with MeOH/water (9:1) and then eluted with 1M ammonia in MeOH. The basic fractions were collected and evaporated under reduced pressure. The residue was purified by column chromatography (Sfar C18 D, 30 g) eluting with a gradient of MeCN (+0.1% HCOOH) in water (+0.1% HCOOH) from 1% to 30% to give [5-(1-amino-4-methylphthalazin-6-yl)-2-(trifluoromethyl)pyridin-3-yl]boronic acid formic acid salt (9.7 mg, 0.025 mmol, 6.675% yield) as a white solid. $^1$H NMR (400 MHz, DMSO-$d_6$+3 drops of TFA) δ 2.83 (s, 3H), 8.13 (s, 1H, HCOOH), 8.50-8.71 (m, 3H), 8.80 (d, J=9.30 Hz, 1H), 9.22 (s, 2H), 9.28 (d, J=2.32 Hz, 1H). LC-MS (Method A): r.t. 0.42 min, MS (ESI) m/z=349.10 [M+H]$^+$.

Examples 72 and 73: 6-(1-hydroxy-3-methyl-3,4-dihydro-2,1-benzoxaborinin-7-yl)-4-methylphthalazin-1-amine Enantiomer 1 (72) and Enantiomer 2 (73)

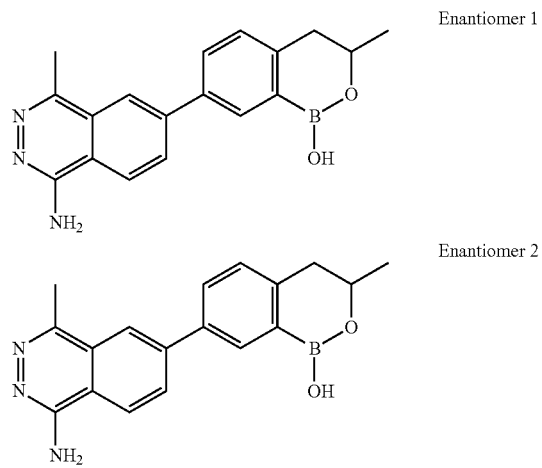

A mixture of 6-[4-[2-[tert-butyl(dimethyl)silyl]oxypropyl]-3-chlorophenyl]-N-[(2,4-dimethoxyphenyl)methyl]-4-methylphthalazin-1-amine (168.0 mg, 0.280 mmol), 4,4,5, 5-tetramethyl-2-(4,4,5,5-tetramethyl-1,3,2-dioxaborolan-2-yl)-1,3,2-dioxaborolane (216.1 mg, 0.850 mmol), dicyclohexyl-[2-[2,4,6-tri(propan-2-yl)phenyl]phenyl]phosphine (10.82 mg, 0.020 mmol), potassium acetate (83.52 mg, 0.850 mmol) and palladium(II) diacetate (3.18 mg, 0.010 mmol) were dissolved in 1,4-dioxane (3.47 mL) in a microwave vial and degassed for 10 min with $N_2$. The mixture was stirred at 75° C. for 1.5 hours, then it was cooled to room temperature and filtered over Celite, washing with MeOH. The filtrate was evaporated and the residue was dissolved in DCM (2 mL) and trifluoroacetic acid (2 mL) and stirred for 2 hours at room temperature, then concentrated under reduced pressure. The residue was purified by column chromatography (KP-C18-HS, 12 g) eluting with a gradient of $CH_3CN$ in water (+0.1% of HCOOH) from 1% to 60%. Appropriate fractions and evaporated. The recovered solid was submitted to semi-preparative chiral HPLC purification (Chiralpak AD-H (25×2.0 cm), 5 μm, n-hexane/(EtOH+0.1% isopropylamine) 88/12% v/v). Fractions containing the two separated enantiomers were collected separately and lyophilized to give enantiomer 1 6-(1-hydroxy-3-methyl-3,4-dihydro-2,1-benzoxaborinin-7-yl)-4-methylphthalazin-1-amine (1.46 mg, 0.005 mmol, 1.613% yield) as a white solid and enantiomer 2 6-(1-hydroxy-3-methyl-3,4-dihydro-2,1-benzoxaborinin-7-yl)-4-methylphthalazin-1-amine (1.4 mg, 0.004 mmol, 1.546% yield) as a white solid.

Enantiomer 1 characterization: $^1$H NMR (400 MHz, Methanol-$d_4$) δ 1.43 (d, J=6.27 Hz, 3H), 2.78-2.88 (m, 4H), 2.97 (dd, J=16.03, 3.42 Hz, 1H), 4.37-4.47 (m, 1H), 7.35 (d, J=7.89 Hz, 1H), 7.81 (dd, J=7.83, 2.17 Hz, 1H), 8.05 (d, J=2.13 Hz, 1H), 8.19 (dd, J=8.54, 1.80 Hz, 1H), 8.23-8.30 (m, 2H). LC-MS (Method A): r.t. 0.61 min, MS (ESI) m/z=320.1 [M+H]$^+$. Analytical chiral HPLC: Column Chiralpak AD-H (25×0.46 cm), 5 um Mobile phase n-Hexane/(Ethanol+0.1% isopropylamine) 88/12% v/v Flow rate 1.0 mL/min DAD 220 nm Loop 20 μL Enantiomer 1>99% a/a by UV (8.5 min) Enantiomer 2 traces.

Enantiomer 2 characterization: $^1$H NMR (400 MHz, Methanol-$d_4$) δ 1.43 (d, J=6.27 Hz, 3H), 2.78-2.88 (m, 4H), 2.97 (dd, J=16.03, 3.42 Hz, 1H), 4.37-4.47 (m, 1H), 7.35 (d, J=7.89 Hz, 1H), 7.81 (dd, J=7.83, 2.17 Hz, 1H), 8.05 (d, J=2.13 Hz, 1H), 8.19 (dd, J=8.54, 1.80 Hz, 1H), 8.23-8.30 (m, 2H). LC-MS (Method A): r.t. 0.61 min, MS (ESI) m/z=320.1 [M+H]$^+$. Analytical chiral HPLC: Column Chiralpak AD-H (25×0.46 cm), 5 um Mobile phase n-Hexane/(Ethanol+0.1% isopropylamine) 88/12% v/v Flow rate 1.0 mL/min DAD 220 nm Loop 20 μL Enantiomer 1 3.8% a/a by UV (8.7 min) Enantiomer 2 96.2% a/a by UV (10.0 min).

Example 74: [5-(1-amino-4-methylphthalazin-6-yl)-2-(trifluoromethyl)phenyl]boronic Acid Formic Acid Salt (74)

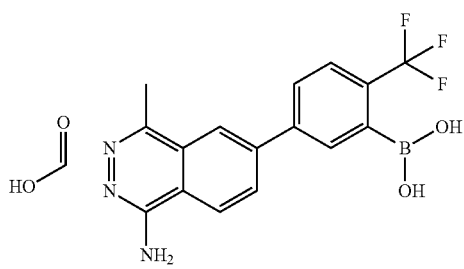

A mixture of N-[(2,4-dimethoxyphenyl)methyl]-4-methyl-6-[3-(4,4,5,5-tetramethyl-1,3,2-dioxaborolan-2-yl)-4-(trifluoromethyl)phenyl]phthalazin-1-amine (250.0 mg, 0.430 mmol) in DCM (1.5 mL) and trifluoroacetic acid (0.700 mL) was stirred overnight at room temperature, then the volatiles were removed. The residue was dissolved in MeOH and loaded onto an SCX cartridge (2 g) that was washed with MeOH/water (9:1) and then eluted with 2M ammonia in MeOH. The volatiles were removed and the residue was purified by column chromatography (Sfar C18 D, 12 g) eluting with a gradient of MeCN (+0.1% HCOOH) in water (+0.1% HCOOH) from 2% to 40% to give [5-(1-amino-4-methylphthalazin-6-yl)-2-(trifluoromethyl)phenyl] boronic acid formic acid salt (19.6 mg, 0.050 mmol, 11.56% yield) as a white solid. $^1$H NMR (400 MHz, DMSO-$d_6$+1 drop of TFA) δ 2.83 (s, 3H), 7.86 (d, J=8.36 Hz, 1H), 8.08-8.18 (m, 3H), 8.50 (d, J=1.32 Hz, 1H), 8.54 (dd, J=8.69, 1.65 Hz, 1H), 8.78 (d, J=8.58 Hz, 1H), 9.21 (br. s, 2H). LC-MS (Method A): r.t. 0.52 min, MS (ESI) m/z=348.08 [M+H]$^+$.

Example 75: [4-methoxy-3-[4-(methylamino)cinnolin-7-yl]phenyl]boronic Acid Formic Acid Salt (75)

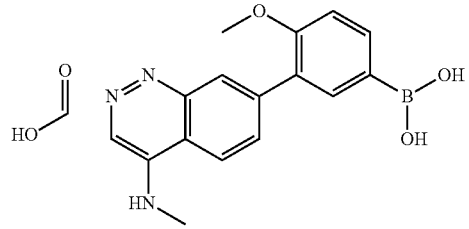

A mixture of 7-(5-chloro-2-methoxyphenyl)-N-[(2,4-dimethoxyphenyl)methyl]-N-methylcinnolin-4-amine (200.0 mg, 0.440 mmol), 4,4,5,5-tetramethyl-2-(4,4,5,5-tetramethyl-1,3,2-dioxaborolan-2-yl)-1,3,2-dioxaborolane (338.64 mg, 1.33 mmol), dicyclohexyl-[2-[2,4,6-tri(propan-2-yl)phenyl]phenyl]phosphine (16.95 mg, 0.040 mmol), potassium acetate (130.87 mg, 1.33 mmol) and palladium(II) diacetate (4.99 mg, 0.020 mmol) was dissolved in 1,4-dioxane (4 mL) in a microwave vial and degassed for 15 min with $N_2$. The mixture was stirred at 75° C. for 1.5 hours, then it was cooled to room temperature and filtered over Celite, washing with MeOH. The filtrate was evaporated and the residue was dissolved in DCM (3 mL) and trifluoroacetic acid (3 mL) and stirred for 1 hour at room temperature, then it was concentrated under reduced pressure. The residue was dissolved in MeOH/$H_2O$ (9:1) and loaded onto an SCX cartridge and left absorbed on the SCX cartridge for 20 min. The cartridge was then washed with MeOH/$H_2O$ (9:1) and eluted with 2 M methanolic ammonia solution. The basic fractions were evaporated and the residue was purified by column chromatography (KP-C18-HS, 30 g) eluting with a gradient of $CH_3CN$ in water (+0.1% of HCOOH) from 5% to 95%. Fractions containing the desired compound were collected and lyophilized to give [4-methoxy-3-[4-(methylamino)cinnolin-7-yl]phenyl]boronic acid formic acid salt (42 mg, 0.118 mmol, 26.6% yield) as a pale-yellow solid. $^1$H NMR (400 MHz, DMSO-$d_6$+2 drops of TFA) δ 3.30 (d, J=4.96 Hz, 3H), 3.86 (s, 3H), 7.21 (d, J=8.74 Hz, 1H), 7.89-7.96 (m, 2H), 8.00 (dd, J=8.83, 1.65 Hz, 1H), 8.05 (d, J=1.62 Hz, 1H), 8.13 (s, 1H from HCOOH), 8.47 (d, J=8.96

Hz, 1H), 8.71 (s, 1H), 10.14 (d, J=5.39 Hz, 1H). LC-MS (Method A): r.t. 0.45 min, MS (ESI) m/z=310.05 [M+H]⁺.

Example 76: [3-(4-aminocinnolin-7-yl)-4-[2-oxo-2-(propan-2-ylamino)ethoxy]phenyl]boronic Acid Formic Acid Salt (76)

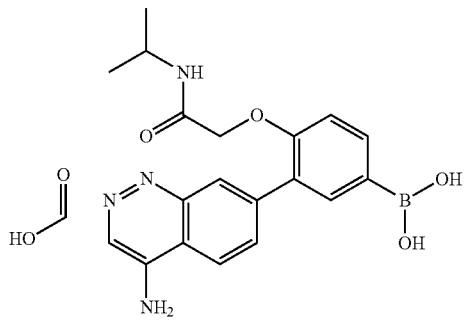

Palladium(II) diacetate (3.46 mg, 0.020 mmol), 2-[4-chloro-2-[4-[(2,4-dimethoxyphenyl)methylamino]cinnolin-7-yl]phenoxy]-N-propan-2-ylacetamide (160.68 mg, 0.310 mmol), dicyclohexyl-[2-[2,4,6-tri(propan-2-yl)phenyl]phenyl]phosphine (14.7 mg, 0.030 mmol), potassium acetate (90.8 mg, 0.930 mmol) and 4,4,5,5-tetramethyl-2-(4,4,5,5-tetramethyl-1,3,2-dioxaborolan-2-yl)-1,3,2-dioxaborolane (234.94 mg, 0.930 mmol) were dissolved in 1,4-dioxane (3.084 mL) in a microwave vial and the mixture was deoxygenated under N₂ for 10 min. The resulting reaction mixture was stirred at 80° C. for 2 hours, then it was cooled to room temperature and filtered over Celite, washing with EtOAc. The filtrate was evaporated under reduced pressure and the residue was dissolved in dichloromethane (1.5 mL) and trifluoroacetic acid (1.5 mL). The resulting mixture was stirred for 2 hours at room temperature then it was concentrated under reduced pressure. The residue was purified by column chromatography (Sfar C18 D, 30 g) eluting with a gradient of MeCN (+0.1% HCOOH) in water (+0.1% HCOOH) from 1% to 70%. Appropriate fractions were collected and then lyophilised to give [3-(4-aminocinnolin-7-yl)-4-[2-oxo-2-(propan-2-ylamino)ethoxy]phenyl]boronic acid formic acid salt (35 mg, 0.082 mmol, 26.45% yield) as a white solid. ¹H NMR (400 MHz, DMSO-d₆) δ 1.00 (d, J=6.60 Hz, 6H), 3.78-3.96 (m, 1H), 4.55 (s, 2H), 7.05 (d, J=8.36 Hz, 1H), 7.21 (s, 2H), 7.44 (d, J=7.81 Hz, 1H), 7.82 (dd, J=8.29, 1.71 Hz, 1H), 7.89 (dd, J=8.75, 1.82 Hz, 1H), 7.97 (d, J=1.71 Hz, 1H), 8.07 (s, 2H), 8.17 (s, from HCOOH, 1H), 8.19-8.28 (m, 2H), 8.62 (s, 1H). LC-MS (Method A): r.t. 0.52 min, MS (ESI) m/z=381.1 [M+H]⁺.

Example 77: 7-[2-methoxy-4-(trifluoromethyl)-5-[(1S,2S,6R,8S)-2,9,9-trimethyl-3,5-dioxa-4-boratricyclo[6.1.1.0²,⁶]decan-4-yl]phenyl]cinnolin-4-amine (77)

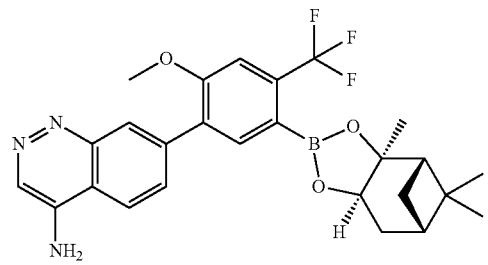 [SMILES: COc1cc(C(F)(F)F)c(B2O[C@@H]3C[C@@H]4C[C@@H](C4(C)C)[C@]3(C)O2)cc1-c1ccc2c(N)cnnc2c1]

Bis[(−)-pinanediolato]diboron (1.31 g, 3.67 mmol), 7-[5-bromo-2-methoxy-4-(trifluoromethyl)phenyl]-N-[(2,4-dimethoxyphenyl)methyl]cinnolin-4-amine (0.67 g, 1.22 mmol) and potassium acetate (0.36 g, 3.67 mmol) were dissolved 1,4-dioxane (12.22 mL) in a microwave vial and the mixture was deoxygenated under N₂ for 10 min. Then palladium(II) diacetate (13.72 mg, 0.060 mmol) and dicyclohexyl-[2-[2,4,6-tri(propan-2-yl)phenyl]phenyl]phosphine (46.6 mg, 0.100 mmol) was added and the mixture was deoxygenated under N₂ for another 10 min. The mixture was stirred at 110° C. for 10 hours. The mixture was filtered over a pad of Celite, washing with DCM and the filtrate was concentrated in vacuo. The red solid residue was dissolved in DCM (2.5 mL) and trifluoroacetic acid (2.5 mL) and stirred for 3 hours at room temperature, then it was evaporated in vacuo. The residue was taken up with MeOH and this solution was loaded onto an SCX cartridge (5 g) which was washed with MeOH and then eluted with a 7M solution of ammonia in MeOH. The basic fractions were collected and evaporated under reduced pressure. The residue was purified by column chromatography (Sfar C18 D, 30 g) eluting with a gradient of MeCN (+0.1% HCOOH) in water (+0.1% HCOOH) from 1% to 70%. Appropriate fractions were collected and lyophilised to give 7-[2-methoxy-4-(trifluoromethyl)-5-[(1S,2S,6R,8S)-2,9,9-trimethyl-3,5-dioxa-4-boratricyclo[6.1.1.0²,⁶]decan-4-yl]phenyl]cinnolin-4-amine (33 mg, 0.066 mmol, 5.4% yield) as a white solid. ¹H NMR (400 MHz, DMSO-d₆) δ 0.87 (s, 3H), 1.19 (d, J=10.75 Hz, 1H), 1.28 (s, 3H), 1.44 (s, 3H), 1.81-1.89 (m, 1H), 1.89-1.95 (m, 1H), 2.08 (t, J=5.50 Hz, 1H), 2.19-2.31 (m, 1H), 2.35-2.47 (m, 1H), 3.94 (s, 3H), 4.57 (dd, J=8.81, 2.02 Hz, 1H), 7.25 (s, 2H), 7.49 (s, 1H), 7.72 (dd, J=8.74, 1.79 Hz, 1H), 7.82 (s, 1H), 8.13 (d, J=1.74 Hz, 1H), 8.24 (d, J=8.77 Hz, 1H), 8.64 (s, 1H). LC-MS (Method A): r.t. 0.96 min, MS (ESI) m/z=396.33 [M+H]⁺.

Example 78: 7-{2-fluoro-6-methoxy-3-[(1S,2S,6R, 8S)-2,9,9-trimethyl-3,5-dioxa-4-boratricyclo [6.1.1.0$^{2,6}$]decan-4-yl]phenyl}cinnolin-4-amine (78)

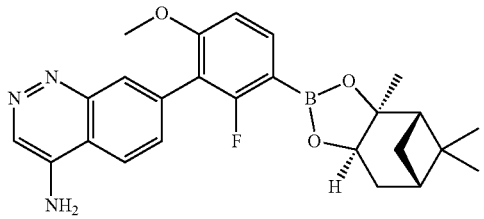 [SMILES: COc1ccc(B2O[C@@H]3C[C@@H]4C[C@@H](C4(C)C)[C@]3(C)O2)c(F)c1-c1ccc2c(N)cnnc2c1]

A suspension of [3-(4-aminocinnolin-7-yl)-2-fluoro-4-methoxyphenyl]boronic acid (82.0 mg, 0.260 mmol) and (1S,3R,4S,5S)-4,6,6-trimethylbicyclo[3.1.1]heptane-3,4-diol (43.7 mg, 0.260 mmol) in THF (3.214 mL) was stirred at room temperature for 1 h, then at 60° C. for 30 min and then it was evaporated in vacuo. The residue was triturated with Et$_2$O, filtered and washed with Et$_2$O. The resulting yellow powder was purified by coulmn chromatography (KP-sil silica gel, 2×SNAP10 in series) eluting with a gradient of EtOH in EtOAc from 0% to 20%. The appropriate fractions were concentrated and the residue was suspended in water and evaporated using a V10 evaporator to give 7-{2-fluoro-6-methoxy-3-[(1S,2S,6R,8S)-2,9,9-trimethyl-3,5-dioxa-4-boratricyclo[6.1.1.0$^{2,6}$]decan-4-yl]phenyl}cinnolin-4-amine (49.6 mg, 0.111 mmol, 43.2% yield) as a yellowish solid. $^1$H NMR (400 MHz, DMSO-d$_6$) δ 0.88 (s, 3H), 1.10 (d, J=10.78 Hz, 1H), 1.29 (s, 3H), 1.44 (s, 3H), 1.78-1.95 (m, 2H), 2.07-2.12 (m, 1H), 2.21-2.28 (m, 1H), 2.35-2.45 (m, 1H), 3.82 (s, 3H), 4.53 (d, J=6.82 Hz, 1H), 7.08 (d, J=8.58 Hz, 1H), 7.21 (s, 2H), 7.53 (d, J=8.58 Hz, 1H), 7.73 (dd, J=8.25, 7.15 Hz, 1H), 7.97 (s, 1H), 8.22 (d, J=8.80 Hz, 1H), 8.64 (s, 1H). LC-MS (Method A): r.t. 0.89 min, MS (ESI) m/z=448.24 [M+H]$^+$.

Example 79: [3-(4-aminocinnolin-7-yl)-4-[[(2S)-4,4-difluoropyrrolidin-2-yl]methoxy]phenyl]boronic Acid (79)

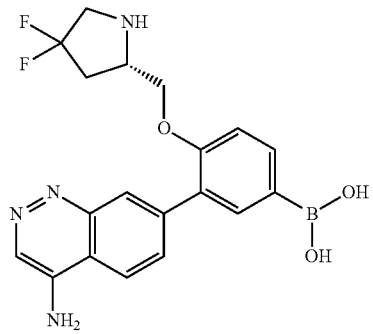 [SMILES: Nc1cnnc2cc(-c3cc(B(O)O)ccc3OC[C@@H]3CC(F)(F)CN3)ccc12]

Palladium(II) diacetate (3.5 mg, 0.020 mmol), tert-butyl (2S)-2-[[4-chloro-2-[4-[(2,4-dimethoxyphenyl)methylamino]cinnolin-7-yl]phenoxy]methyl]-4,4-difluoropyrrolidine-1-carboxylate (200.0 mg, 0.310 mmol), dicyclohexyl-[2-[2,4,6-tri(propan-2-yl)phenyl]phenyl]phosphine (14.87 mg, 0.030 mmol), potassium acetate (91.85 mg, 0.940 mmol) and 4,4,5,5-tetramethyl-2-(4,4,5,5-tetramethyl-1,3,2-dioxaborolan-2-yl)-1,3,2-dioxaborolane (237.66 mg, 0.940 mmol) were disolved in 1,4-dioxane (3.839 mL) in a microwave vial and the mixture was deoxygenated under N$_2$ for 10 minutes. The mixture was stirred at 80° C. for 2 hours then it was filtered over a pad of Celite, washing with MeOH and the filtrate was concentrated in vacuo. The residue was dissolved in DCM (2.5 mL) and trifluoroacetic acid (2.5 mL). The resulting mixture was stirred for 4 hours at room temperature then it was concentrated under reduced pressure. The residue was taken up with MeOH and this solution was loaded onto an SCX cartridge (5 g) which was washed with MeOH/H$_2$O (9:1) and then eluted with a 7M solution of ammonia in MeOH. The basic fractions were collected and evaporated under reduced pressure. The residue was purified by column chromatography (Sfar C18 D, 30 g) eluting with a gradient of MeCN (+0.1% ammonium hydroxide) in water (+0.1% ammonium hydroxide) from 1% to 70%. Appropriate fractions were collected and lyophilised to give [3-(4-aminocinnolin-7-yl)-4-[[(2S)-4,4-difluoropyrrolidin-2-yl]methoxy]phenyl]boronic acid (30 mg, 0.075 mmol, 13.73% yield) as a white solid. $^1$H NMR (400 MHz, DMSO-d$_6$) δ 1.96-2.15 (m, 1H), 2.23-2.36 (m, 1H), 2.89 (br. s, 1H), 3.00-3.20 (m, 2H), 3.53-3.63 (m, 1H), 3.97-4.13 (m, 2H), 7.12-7.19 (m, 3H), 7.79-7.87 (m, 2H), 7.97 (d, J=1.75 Hz, 1H), 8.00 (s, 2H), 8.16 (d, J=1.70 Hz, 1H), 8.19 (d, J=8.80 Hz, 1H), 8.61 (s, 1H). LC-MS (Method A): r.t. 0.58 min, MS (ESI) m/z=401.14 [M+H]$^+$.

Example 80: [3-(cinnolin-7-yl)-4-methoxyphenyl]boronic Acid (80)

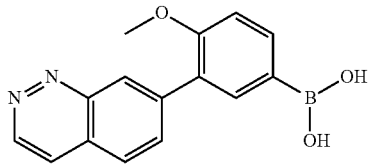 [SMILES: COc1ccc(B(O)O)cc1-c1ccc2ccnnc2c1]

Palladium(II) diacetate (8.92 mg, 0.040 mmol), 7-(5-chloro-2-methoxyphenyl)cinnoline (215.0 mg, 0.790 mmol), dicyclohexyl-[2-[2,4,6-tri(propan-2-yl)phenyl]phenyl]phosphine (30.29 mg, 0.060 mmol), potassium acetate (233.83 mg, 2.38 mmol) and 4,4,5,5-tetramethyl-2-(4,4,5,5-tetramethyl-1,3,2-dioxaborolan-2-yl)-1,3,2-dioxaborolane (605.04 mg, 2.38 mmol) were dissolved 1,4-dioxane (8 mL) in a microwave vial and the mixture was deoxygenated under N$_2$ for 10 min. The mixture was stirred at 75° C. for 1.5 hours then filtered over a pad of Celite, washing with MeOH and the filtrate was concentrated in vacuo. The residue was dissolved in MeOH/H$_2$O (9:1) and charged onto an SCX cartridge. The mixture was left to stand on the SCX cartridge for 20 min and then the cartridge was eluted sequentially with MeOH/H$_2$O (9:1) and 2 M methanolic ammonia solution. The basic fractions were evaporated and the residue was purified by column chromatography (Sfar C18 D, 2×6 g in series) eluting with a gradient of MeCN (+0.1% HCOOH) in water (+0.1% HCOOH) from 5% to 95%. The appropriate fractions were combined and lyophilized to give [3-(cinnolin-7-yl)-4-methoxyphenyl]boronic acid (19 mg, 0.068 mmol, 7.3% yield) as a pale-yellow solid. $^1$H NMR (400 MHz, DMSO-d$_6$) δ 3.86 (s, 3H), 7.19 (d, J=8.32 Hz, 1H), 7.88 (dd, J=8.26, 1.72 Hz, 1H), 7.95-

8.15 (m, 5H), 8.23 (d, J=5.79 Hz, 1H), 8.53 (s, 1H), 9.38 (d, J=5.78 Hz, 1H). LC-MS (Method A): r.t. 0.70 min, MS (ESI) m/z=281.05 [M+H]⁺.

Example 81: [3-(1-amino-4-methylphthalazin-6-yl)-4-[[(2S)-4,4-difluoropyrrolidine-2-carbonyl]amino]phenyl]boronic Acid (81)

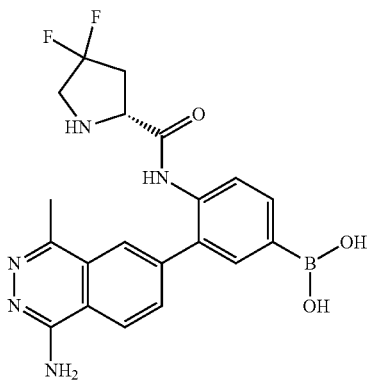 [SMILES: Cc1nnc(N)c2ccc(-c3cc(B(O)O)ccc3NC(=O)[C@H]3CC(F)(F)CN3)cc12]

A solution of 6-[2-amino-5-(4,4,5,5-tetramethyl-1,3,2-dioxaborolan-2-yl)phenyl]-N-[(2,4-dimethoxyphenyl)methyl]-4-methylphthalazin-1-amine (50.0 mg, 0.090 mmol), (2S)-4,4-difluoro-1-[(2-methylpropan-2-yl)oxycarbonyl]pyrrolidine-2-carboxylic acid (26.25 mg, 0.100 mmol), [dimethylamino(3-triazolo[4,5-b]pyridinyloxy)methylidene]-dimethylammonium hexafluorophosphate (39.73 mg, 0.100 mmol) and triethylamine (0.02 mL, 0.140 mmol) in DMF (1.5 mL) was stirred at 40° C. overnight then it was diluted with EtOAc. The organic phase was washed with water and brine, dried over Na₂SO₄, filtered and evaporated in vacuo. The residue was dissolved in dichloromethane (0.500 mL) and trifluoroacetic acid (0.500 mL). The resulting mixture was stirred at room temperature for three hours then it was evaporated in vacuo. The residue was taken up with MeOH and this solution was loaded onto an SCX cartridge (1 g) which was washed with MeOH/H₂O (9:1) and then eluted with a 7M solution of ammonia in MeOH. The basic fractions were collected and evaporated under reduced pressure. The residue was purified by column chromatography (Sfar C18 D, 12 g) eluting with MeCN (+0.1% ammonium hydroxide) in water (+0.1% ammonium hydroxide) from 1% to 70%. Appropriate fraction were collected and lyophilised. The recovered solid was submitted to semi-preparative HPLC purification (Chiralcel OJ-H (25×0.46 cm), 5 μm, n-hexane/(EtOH+0.1% isopropylamine) 60/40% v/v). Fractions containing the desired compound were collected and evaporated under reduced pressure to give [3-(1-amino-4-methylphthalazin-6-yl)-4-[[(2S)-4,4-difluoropyrrolidine-2-carbonyl]amino]phenyl]boronic acid (4 mg, 0.009 mmol, 9.9% yield) as a white solid. ¹H NMR (400 MHz, Methanol-d₄) δ 2.16-2.31 (m, 1H), 2.43-2.60 (m, 1H), 2.77-2.82 (m, 4H), 3.02-3.14 (m, 1H), 3.86-3.95 (m, 1H), 7.68 (s, 1H), 7.75 (d, J=8.10 Hz, 1H), 7.89-8.02 (m, 2H), 8.13 (d, J=1.69 Hz, 1H), 8.33 (d, J=8.47 Hz, 1H). LC-MS (Method B): r.t. 0.43 min, MS (ESI) m/z=428.08 [M+H]⁺.

Example 82: [3-(4-aminocinnolin-7-yl)-4-(oxolan-2-ylmethoxy)phenyl]boronic Acid Formic Acid Salt (82)

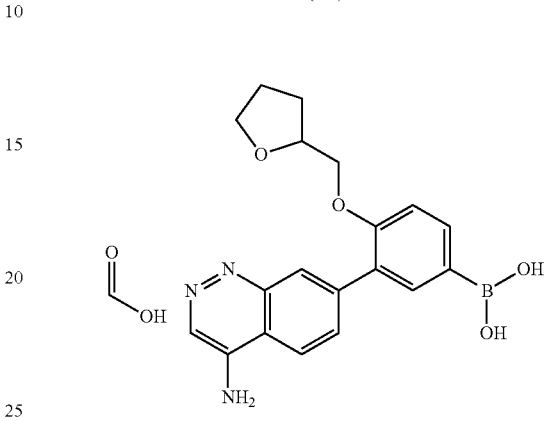

Palladium(II) diacetate (4.44 mg, 0.020 mmol), 7-[5-chloro-2-(oxolan-2-ylmethoxy)phenyl]-N-[(2,4-dimethoxyphenyl)methyl]cinnolin-4-amine (200.0 mg, 0.400 mmol), dicyclohexyl-[2-[2,4,6-tri(propan-2-yl)phenyl]phenyl]phosphine (18.84 mg, 0.040 mmol), potassium acetate (116.37 mg, 1.19 mmol) and 4,4,5,5-tetramethyl-2-(4,4,5,5-tetramethyl-1,3,2-dioxaborolan-2-yl)-1,3,2-dioxaborolane (301.12 mg, 1.19 mmol) were dissolved in 1,4-dioxane (3.839 mL) in a microwave vial and the mixture was deoxygenated under N₂ for 10 min. The mixture was stirred at 75° C. for 2 hours then it was filtered over a pad of Celite, washing with MeOH. The filtrate was concentrated in vacuo and the residue was dissolved in DCM (2 mL) and trifluoroacetic acid (2 mL) and stirred at room temperature overnight then it was evaporated in vacuo. The residue was taken up with MeOH and this solution was loaded onto an SCX cartridge (5 g). The mixture was left to stand on the SCX cartridge for 20 min then it was eluted sequentially with MeOH/H₂O (9:1) and 7M methanolic ammonia solution. The basic fractions were collected and evaporated under reduced pressure. The residue was purified by column chromatography (Sfar C18 D, 30 g) eluting with a gradient of MeCN (+0.1% HCOOH) in degassed water (+0.1% HCOOH) from 1% to 30%. Appropriate fractions were collected and lyophilised to give [3-(4-aminocinnolin-7-yl)-4-(oxolan-2-ylmethoxy)phenyl]boronic acid formic acid salt (33 mg, 0.080 mmol, 20% yield) as a white solid. ¹H NMR (400 MHz, DMSO-d₆) δ 1.59-1.82 (m, 3H), 1.85-2.00 (m, 1H), 3.52-3.75 (m, 2H), 4.00-4.17 (m, 3H), 7.14 (d, J=8.35 Hz, 1H), 7.19 (s, 2H), 7.78-7.86 (m, 2H), 7.96 (d, J=1.73 Hz, 1H), 8.00 (s, 2H), 8.12-8.24 (m, 2H+HCOOH, 1H), 8.60 (s, 1H). LC-MS (Method B): r.t. 0.49 min, MS (ESI) m/z=366.1 [M+H]⁺.

Example 83: [5-(4-aminocinnolin-7-yl)-4-methoxy-2-(trifluoromethyl)phenyl]boronic Acid Formic Acid Salt (83)

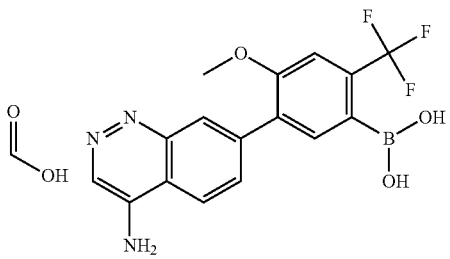

To a suspension of 7-[2-methoxy-4-(trifluoromethyl)-5-[(1S,2S,6R,8S)-2,9,9-trimethyl-3,5-dioxa-4-boratricyclo[6.1.1.0$^{2,6}$]decan-4-yl]phenyl]cinnolin-4-amine (20.0 mg, 0.040 mmol) in DCM (500 uL), were added methylboronic acid (9.63 mg, 0.160 mmol) and trifluoroacetic acid (25 uL). The resulting mixture was stirred at room temperature overnight. 3M hydrochloric acid solution (500.0 uL, 0.040 mmol) was added and the resulting mixture was stirred at 40° C. for 4 days. The mixture was diluted with MeOH and the resulting solution was loaded onto an SCX cartridge (1 g) which was washed with MeOH and then eluted with a 7M solution of ammonia in MeOH. The basic fractions were collected and evaporated under reduced pressure. The residue was purified by column chromatography (Sfar C18 D, 6 g) eluting with a gradient of MeCN (+0.1% HCOOH) in water (+0.1% HCOOH) from 1% to 70%. Appropriate fraction were collected and lyophilised to give [5-(4-aminocinnolin-7-yl)-4-methoxy-2-(trifluoromethyl)phenyl]boronic acid formic acid salt (8 mg, 0.020 mmol, 48.62% yield) as a white solid. $^1$H NMR (400 MHz, DMSO-d$_6$) δ 3.89 (s, 3H), 7.23 (s, 2H), 7.37 (s, 1H), 7.60 (s, 1H), 7.72 (dd, J=8.70, 1.79 Hz, 1H), 8.12-8.18 (m, 1H and HCOOH 1H), 8.23 (d, J=8.78 Hz, 1H), 8.33 (s, 2H), 8.62 (s, 1H). LC-MS (Method A): r.t. 0.50 min, MS (ESI) m/z=364.1 [M+H]$^+$.

Example 84: [5-(1-amino-4-methylphthalazin-6-yl)-6-(trifluoromethyl)pyridin-3-yl]boronic Acid (84)

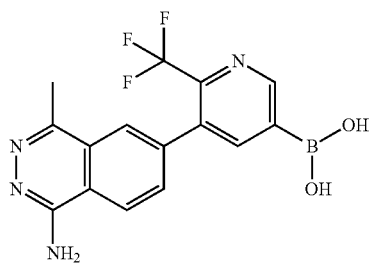 [SMILES: Cc1nnc(N)c2ccc(-c3cc(B(O)O)cnc3C(F)(F)F)cc12]

A mixture of 6-[5-chloro-2-(trifluoromethyl)pyridin-3-yl]-N-[(2,4-dimethoxyphenyl)methyl]-4-methylphthalazin-1-amine formic acid salt (182.66 mg, 0.340 mmol), 4,4,5,5-tetramethyl-2-(4,4,5,5-tetramethyl-1,3,2-dioxaborolan-2-yl)-1,3,2-dioxaborolane (260.15 mg, 1.02 mmol), potassium acetate (100.54 mg, 1.02 mmol), dicyclohexyl-[2-[2,4,6-tri(propan-2-yl)phenyl]phenyl]phosphine (13.02 mg, 0.030 mmol), and palladium(II) diacetate (3.83 mg, 0.020 mmol) in 1,4-dioxane (5 mL) was degassed under Ar for 10 min, then heated at 85° C. for 6 hours and 30 min. The mixture was filtered over a pad of Celite, washing with MeOH and the filtrate was concentrated under reduced pressure. The residue was dissolved in DCM (7 mL) and trifluoroacetic acid (7 mL) was added. The mixture was stirred at room temperature for 1 h. The volatiles were evaporated to give a brown solid residue that was dissolved in MeOH and loaded onto an SCX cartridge (5 g) which was washed three times with a 9:1 mixture of MeOH/H$_2$O and then eluted with a 7 M solution of ammonia in MeOH. The basic fractions were collected and evaporated under reduced pressure. The residue was purified by column chromatography (Sfar C18 D, 12 g) eluting with a gradient of MeCN in 10 mM aqueous ammonium bicarbonate aqueous solution adjusted to pH 10 with ammonia from 1% to 40%. The partially purified product obtained was submitted to semi-preparative HPLC purification (MDAP Waters with mass spectrometry detection (MS: ZQ2000). Column: xBridge C18 (30×100 mm, 3 μm). Conditions: [A2: 10 mM ammonium bicarbonate acqueous solution adjusted to pH 10 with ammonia]; [B2: MeCN]. Gradient: from 10.0% B2 to 50.0% B2 in 10 min (flow: 40.00 mL/min). Detection: UV/Vis+MS(ES+)) to give [5-(1-amino-4-methylphthalazin-6-yl)-6-(trifluoromethyl)pyridin-3-yl]boronic acid (11.5 mg, 0.033 mmol, 9.7% yield) as a white solid. $^1$H NMR (400 MHz, DMSO-d$_6$+TFA) δ 2.67 (s, 3H), 8.10 (dd, J=8.40, 1.24 Hz, 1H), 8.23 (d, J=1.38 Hz, 1H), 8.26 (s, 1H), 8.75 (d, J=8.47 Hz, 1H), 9.09 (s, 1H), 9.21 (br. s, 1H). LC-MS (Method A): r.t. 0.48 min, MS (ESI) m/z=349.10 [M+H]$^+$.

Example 85: [3-(4-aminocinnolin-7-yl)-4-(difluoromethoxy)phenyl]boronic Acid (85)

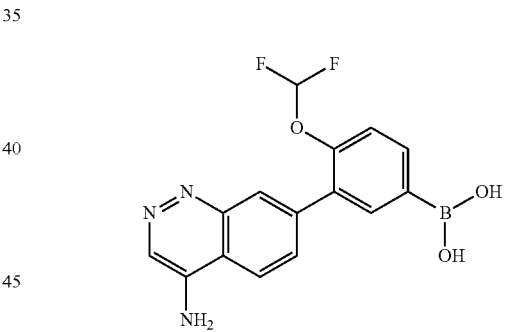

Palladium(II) diacetate (5.0 mg, 0.020 mmol), 7-[5-chloro-2-(difluoromethoxy)phenyl]-N-[(2,4-dimethoxyphenyl)methyl]cinnolin-4-amine (210.0 mg, 0.450 mmol), dicyclohexyl-[2-[2,4,6-tri(propan-2-yl)phenyl]phenyl]phosphine (16.97 mg, 0.040 mmol) and potassium acetate (131.03 mg, 1.34 mmol) were dissolved 1,4-dioxane (3.5 mL) in a microwave vial and the mixture was deoxygenated under N$_2$ for 10 min. 4,4,5,5-Tetramethyl-2-(4,4,5,5-tetramethyl-1,3,2-dioxaborolan-2-yl)-1,3,2-dioxaborolane (339.03 mg, 1.34 mmol) was added and the mixture was deoxygenated under N$_2$ for another 10 min. The mixture was then stirred at 70° C. for 90 min. The mixture was filtered over a pad of Celite, washing with EtOAc and the filtrate was concentrated in vacuo. The residue was dissolved in DCM (3 mL) and trifluoroacetic acid (1.8 mL) and the mixture was stirred overnight at room temperature. The volatiles were removed and the residue was dissolved in a 9:1 mixture of MeOH and H$_2$O, then loaded on an SCX cartridge (10 g) which was washed with a 9:1 mixture of MeOH and H$_2$O and then eluted with a 2M solution of ammonia in MeOH. The basic fractions were concentrated and the residue was purified by column chromatography (Sfar C18 D, 30 g) eluting with a gradient of MeOH (+0.1% HCOOH) in water (+0.1% HCOOH) from 2% to 50% to give [3-(4-aminocinnolin-7-yl)-4-(difluoromethoxy)phenyl]boronic acid (25.7 mg, 0.078 mmol, 17.3% yield) and as a white solid. $^1$H NMR (400 MHz, DMSO-d$_6$+1 drop of TFA) δ 7.32 (t, J=73.51 Hz, 1H), 7.38 (d, J=8.14 Hz, 1H), 7.93-8.03 (m, 4H), 8.51 (s, 1H), 8.53 (d, J=8.80 Hz, 1H), 9.72-9.97 (m, 2H). LC-MS (Method A): r.t. 0.48 min, MS (ESI) m/z=332.04 [M+H]$^+$.

Example 86: 7-[4-(trifluoromethyl)-3-[(1S,2S,6R,8S)-2,9,9-trimethyl-3,5-dioxa-4-boratricyclo[6.1.1.0$^{2,6}$]decan-4-yl]phenyl]cinnolin-4-amine (86)

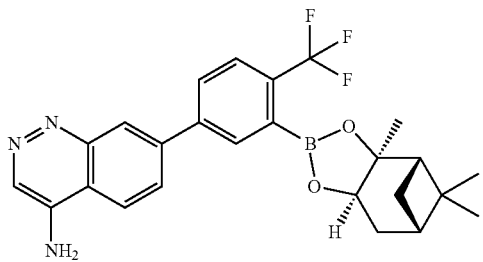 [SMILES: CC1(C)[C@@H]2C[C@H]3OB(c4cc(-c5ccc6c(N)cnnc6c5)ccc4C(F)(F)F)O[C@@]3(C)[C@H]1C2]

Bis[(+)-pinanediolato]diboron (259.35 mg, 0.720 mmol), 7-[3-chloro-4-(trifluoromethyl)phenyl]-N-[(2,4-dimethoxyphenyl)methyl]cinnolin-4-amine (130.0 mg, 0.240 mmol) and potassium acetate (71.08 mg, 0.720 mmol) were dissolved 1,4-dioxane (2.5 mL) in a microwave vial and the mixture was deoxygenated under N$_2$ for 10 min. Palladium (II) diacetate (2.71 mg, 0.010 mmol) and dicyclohexyl-[2-[2,4,6-tri(propan-2-yl)phenyl]phenyl]phosphine (9.21 mg, 0.020 mmol) was added and the mixture was deoxygenated under N$_2$ for another 10 min. Then the mixture was stirred at 80° C. for 4.5 hours. The mixture was filtered over a pad of Celite, washing with MeOH and the filtrate was concentrated. The residue was solubilized in DCM (2 mL) and trifluoroacetic acid (2 mL) was added. The mixture was stirred for 8 hours, then evaporated. The residue was solubilized in MeOH and loaded onto an SCX cartridge which was eluted first with MeOH and then with a 2M methanolic solution of ammonia. The basic fractions were evaporated and the residue was purified by column chromatography (Sfar C18 D, 2×6 g in series) eluting with a gradient of MeCN (+0.1% HCOOH) in water (+0.1% HCOOH) from 2% to 95%. The partially purified product obtained was submitted to semi-preparative HPLC purification (Column: Chiralpak IC (25×2.0 cm), 5 μm. Mobile phase n-Hexane/(Ethanol+0.1% isopropylamine) 80/20% v/v. Flow rate 17 ml/min). Fractions containing the desired compound were collected and evaporated. The residue was dissolved in MeCN/water and lyophilized to give 7-[4-(trifluoromethyl)-3-[(1S,2S,6R,8S)-2,9,9-trimethyl-3,5-dioxa-4-boratricyclo[6.1.1.0$^{2,6}$]decan-4-yl]phenyl]cinnolin-4-amine (3.2 mg, 0.007 mmol, 2.9% yield) as a white powder. $^1$H NMR (400 MHz, DMSO-d$_6$) δ 0.90 (s, 3H), 1.28 (d, J=10.80 Hz, 1H), 1.31 (s, 3H), 1.49 (s, 3H), 1.87-2.01 (m, 2H), 2.12 (t, J=5.46 Hz, 1H), 2.24-2.33 (m, 1H), 2.40-2.47 (m, 1H), 4.62 (dd, J=8.83, 2.08 Hz, 1H), 7.31 (s, 2H), 7.93 (d, J=8.23 Hz, 1H), 7.98 (dd, J=8.80, 1.91 Hz, 1H), 8.16 (d, J=8.57 Hz, 1H), 8.19 (s, 1H), 8.31-8.39 (m, 2H), 8.65 (s, 1H). LC-MS (Method A): r.t. 0.97 min, MS (ESI) m/z=468.23 [M+H]$^+$.

Example 87: [3-(1-amino-4-methylphthalazin-6-yl)-4-(1,2-thiazole-4-amido)phenyl]boronic Acid (87)

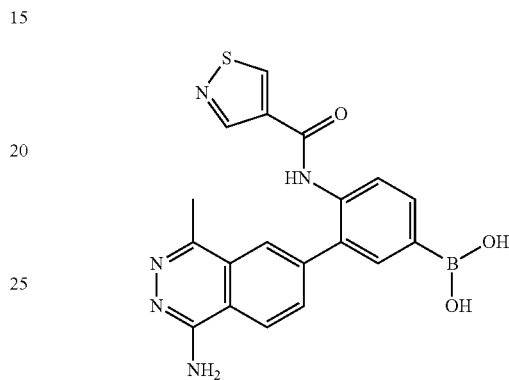

A solution of 1,2-thiazole-4-carboxylic acid (26.98 mg, 0.210 mmol), triethylamine (0.04 mL, 0.300 mmol) and [dimethylamino(3-triazolo[4,5-b]pyridinyloxy)methylidene]-dimethylammonium hexafluorophosphate (93.9 mg, 0.250 mmol) in DMF (1.5 mL) was stirred at room temperature for 1 hour, then 6-[2-amino-5-(4,4,5,5-tetramethyl-1,3,2-dioxaborolan-2-yl)phenyl]-N-[(2,4-dimethoxyphenyl)methyl]-4-methylphthalazin-1-amine (100.0 mg, 0.190 mmol) was added and the reaction mixture was stirred at 40° C. overnight. The reaction mixture was evaporated and the residue was purified by column chromatography (Sfar C18 D, 12 g) eluting with a gradient of MeCN in water from 5% to 70%. Appropriate fractions were evaporated. The residue was dissolved in DCM (1 mL) and trifluoroacetic acid (1 mL) and the resulting mixture was stirred at room temperature for 3 hours then it was evaporated in vacuo. The residue was taken up with MeOH/H$_2$O (9:1) and this solution was loaded onto an SCX cartridge (2 g) which was washed with MeOH/H$_2$O (9:1) and then eluted with a 7 M solution of ammonia in MeOH. The basic fractions were collected and evaporated under reduced pressure. The residue was purified by column chromatography (Sfar C18 D, 6 g) eluting with a gradient of MeCN in water from 5% to 60% to give [3-(1-amino-4-methylphthalazin-6-yl)-4-(1,2-thiazole-4-carbonylamino)phenyl]boronic acid (2.5 mg, 0.006 mmol, 3.248% yield) as a yellow solid. $^1$H NMR (400 MHz, DMSO-d$_6$+2 drops of TFA) δ 3.08 (s, 3H) 6.99-7.06 (m, 1H) 7.76 (s, 2H) 8.26-8.34 (m, 1H) 8.48-8.55 (m, 1H) 8.61-8.68 (m, 1H) 9.15 (s, 1H) 9.92 (s, 1H). LC-MS (Method A): r.t. 0.73 min, MS (ESI) m/z=406.1 [M+H]$^+$.

Example 88: [5-(4-aminocinnolin-7-yl)-2-(trifluoromethyl)phenyl]boronic Acid Formic Acid Salt (88)

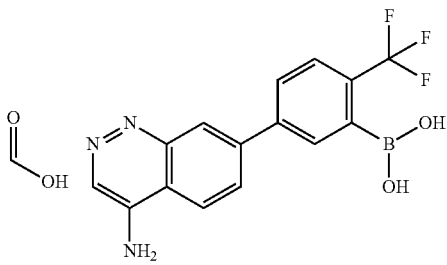

7-[4-(Trifluoromethyl)-3-[(1S,2S,6R,8S)-2,9,9-trimethyl-3,5-dioxa-4-boratricyclo[6.1.1.0$^{2,6}$]decan-4-yl]phenyl]cinnolin-4-amine (56.0 mg, 0.020 mmol) was dissolved in water (1 mL), MeCN (1 mL) and MeOH (1 mL) and formic acid (0.05 uL, 0.001 mmol) was added. The mixture was stirred at 40° C. for 3 days. Low conversion to the boronic acid product was observed. 6M Hydrochloric acid solution (2.0 mL, 12 mmol) was added and the mixture was stirred at 45° C. for 24 hours. The mixture was partially evaporated, then diluted with MeOH and loaded onto an SCX cartridge. The cartridge was eluted first with MeOH and then with a 2M methanolic solution of ammonia. Basic fractions were concentrated in vacuo and the residue was purified by column chromatography (Sfar C18 D, 2×SNAP 6 in series) eluting with a gradient of MeCN (+0.1% HCOOH) in water (+0.1% HCOOH) from 2% to 95%. Appropriate fractions were partially concentrated in vacuo and then lyophilized to give [5-(4-aminocinnolin-7-yl)-2-(trifluoromethyl)phenyl]boronic acid formic acid salt (3 mg, 0.008 mmol, 36.69% yield) as a pale-pink powder. $^1$H NMR (400 MHz, DMSO-d$_6$+2 drops of TFA) δ 7.88 (d, J=8.13 Hz, 1H), 7.96-8.06 (m, 2H), 8.12-8.16 (m, 1H plus 1H from HCOOH), 8.23 (d, J=8.88 Hz, 1H), 8.51 (s, 1H), 8.60 (d, J=8.88 Hz, 1H), 9.82 (s, 1H), 9.97 (s, 1H). LC-MS (Method A): r.t. 0.46 min, MS (ESI) m/z=334.07 [M+H]$^+$.

Example 89: [5-(1-amino-4-methylphthalazin-6-yl)-2-(2-methylpropanamido)phenyl]boronic Acid (89)

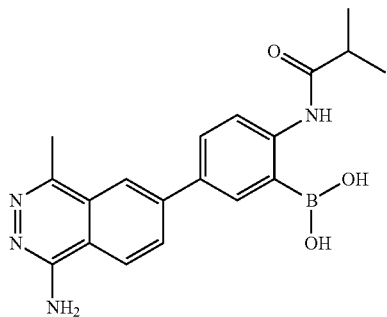 [SMILES: Cc1nnc(N)c2ccc(-c3ccc(NC(=O)C(C)C)c(B(O)O)c3)cc12]

[5-[1-[(2,4-Dimethoxyphenyl)methylamino]-4-methylphthalazin-6-yl]-2-(2-methylpropanoylamino)phenyl]boronic acid (56.0 mg, 0.110 mmol) was dissolved in DCM (1.371 mL) and trifluoroacetic acid (1.371 mL) was added. The mixture was stirred for 2 hours. The mixture was evaporated in vacuo and the residue was purified by column chromatography (Sfar C18 D, 2×SNAP6 in series) eluting with a gradient of MeCN (+0.1% HCOOH) in water (+0.1% HCOOH) from 1% to 50%. Appropriate fractions were collected and lyophilized to give partially pure product. This material was submitted to semi-preparative HPLC purification (Column: Chiralpak IC (25×2.0 cm), 5 μm, Mobile phase n-Hexane/(Ethanol/Methanol 1/1+0.1% isopropylamine) 50/50% v/v, Flow rate 17 ml/min). Fractions containing product were collected and lyophilized to give [5-(1-amino-4-methylphthalazin-6-yl)-2-(2-methylpropanoylamino)phenyl]boronic acid (4 mg, 0.011 mmol, 10.1% yield) as a white powder. $^1$H NMR (400 MHz, DMSO-d$_6$+2 drops of TFA) δ 1.27 (d, J=6.79 Hz, 6H), 2.81 (s, 3H), 3.01 (pentet, J=6.91 Hz, 1H), 7.36 (d, J=8.27 Hz, 1H), 7.95-8.05 (m, 2H), 8.37 (s, 1H), 8.44 (d, J=8.60 Hz, 1H), 8.75 (d, J=8.57 Hz, 1H), 9.17 (br. s, 2H). LC-MS (Method A): r.t. 0.38 min, MS (ESI) m/z=365.16 [M+H]$^+$.

Example 90: 7-{2-fluoro-6-methoxy-3-[(1R,2R,6S,8R)-2,6,9,9-tetramethyl-3,5-dioxa-4-boratricyclo[6.1.1.0$^{2,6}$]decan-4-yl]phenyl}cinnolin-4-amine (90)

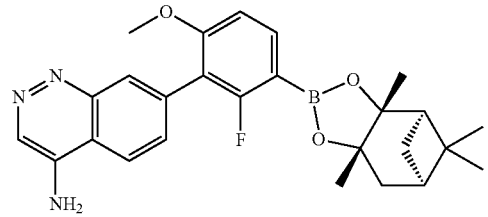 [SMILES: COc1ccc(B2O[C@@]3(C)C[C@H]4C[C@H](C4(C)C)[C@@]3(C)O2)c(F)c1-c1ccc2c(N)cnnc2c1]

A suspension of [3-(4-aminocinnolin-7-yl)-2-fluoro-4-methoxyphenyl]boronic acid (26.0 mg, 0.080 mmol) and (1R,3S,4R,5R)-3,4,6,6-tetramethylbicyclo[3.1.1]heptane-3,4-diol (15.3 mg, 0.080 mmol) in THF (0.830 mL) was stirred at 45° C. for three hours then it was evaporated in vacuo. The residue was purified by column chromatography (KP-sil silica gel, SNAP 10) eluting with a gradient of EtOH in EtOAc from 10% to 100% to give 7-{2-fluoro-6-methoxy-3-[(1R,2R,6S,8R)-2,6,9,9-tetramethyl-3,5-dioxa-4-boratricyclo[6.1.1.0$^{2,6}$]decan-4-yl]phenyl}cinnolin-4-amine (23 mg, 0.050 mmol, 60.03% yield) as an off white solid. $^1$H NMR (400 MHz, DMSO-d$_6$) δ 0.87 (s, 3H), 1.27 (s, 3H), 1.40 (s, 3H), 1.43 (s, 3H), 1.80-2.10 (m, 4H), 2.13-2.30 (m, 2H), 3.80 (s, 3H), 7.05 (d, J=8.50 Hz, 1H), 7.21 (s, 2H), 7.44-7.55 (m, 1H), 7.60-7.72 (m, 1H), 7.86-8.01 (m, 1H), 8.21 (d, J=8.74 Hz, 1H), 8.63 (s, 1H). LC-MS (Method A): r.t. 0.92 min, MS (ESI) m/z=462.3 [M+H]$^+$.

Example 91: [3-(4-aminocinnolin-7-yl)-4-{[1-(trifluoromethyl)cyclopropyl]methoxy}phenyl]boronic Acid Formic Acid Salt (91)

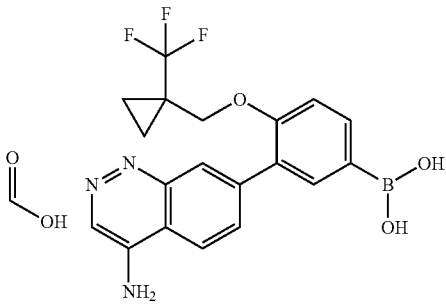

Palladium(II) diacetate (2.373 mg, 0.011 mmol), 7-[5-chloro-2-[[1-(trifluoromethyl)cyclopropyl]methoxy]phenyl]-N-[(2,4-dimethoxyphenyl)methyl]cinnolin-4-amine (115 mg, 0.211 mmol), dicyclohexyl-[2-[2,4,6-tri(propan-2-yl)phenyl]phenyl]phosphine (10 mg, 0.021 mmol), potassium acetate (62.24 mg, 0.634 mmol) and 4,4,5,5-tetramethyl-2-(4,4,5,5-tetramethyl-1,3,2-dioxaborolan-2-yl)-1,3,2-dioxaborolane (161.06 mg, 0.634 mmol) were dissolved in 1,4-dioxane (2.207 mL) in a microwave vial. The resulting reaction mixture was stirred at 75° C. for 2 hours, then it was cooled to room temperature and filtered over Celite, washing with EtOAc. The filtrate was evaporated under reduced pressure and the residue was dissolved in dichloromethane (1 mL) and trifluoroacetic acid (1 mL). The resulting mixture was stirred at room temperature overnight then it was concentrated under reduced pressure. The residue was taken up with MeOH and this solution was loaded onto an SCX cartridge (5 g). The mixture was left to stand on the SCX cartridge for 20 min then it was eluted sequentially with MeOH/H$_2$O (9:1) and a 7M solution of ammonia in MeOH. The basic fractions were collected and evaporated under reduced pressure. The residue was purified by column chromatography (Sfar C18 D, 30 g) eluting with a gradient of MeCN (+0.1% HCOOH) in degassed water (+0.1% HCOOH) from 1% to 30%. Appropriate fractions were collected and lyophilised to give [3-(4-aminocinnolin-7-yl)-4-[[1-(trifluoromethyl)cyclopropyl]methoxy]phenyl]boronic acid formic acid salt (26 mg, 0.058 mmol, 27.4% yield) as a white solid. $^1$H NMR (400 MHz, DMSO-d$_6$) δ 0.92-1.04 (m, 4H), 4.22 (s, 2H), 7.15 (d, J=8.39 Hz, 1H), 7.19 (s, 2H), 7.77-7.84 (m, 2H), 7.97 (d, J=1.71 Hz, 1H), 8.04 (s, 2H), 8.13-8.21 (m, 3H), 8.60 (s, 1H). LC-MS (Method A): r.t. 0.61 min, MS (ESI) m/z=404.1 [M+H]$^+$.

Example 92: [3-(4-amino-6-fluorocinnolin-7-yl)-4-methoxyphenyl]boronic Acid Formic Acid Salt (92)

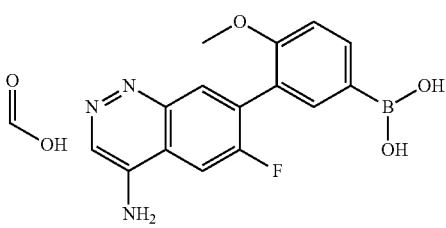

Palladium(II) diacetate (5.44 mg, 0.020 mmol), 7-(5-chloro-2-methoxyphenyl)-N-[(2,4-dimethoxyphenyl)methyl]-6-fluorocinnolin-4-amine (220.0 mg, 0.480 mmol), dicyclohexyl-[2-[2,4,6-tri(propan-2-yl)phenyl]phenyl]phosphine (23.11 mg, 0.050 mmol), potassium acetate (142.71 mg, 1.45 mmol) and 4,4,5,5-tetramethyl-2-(4,4,5,5-tetramethyl-1,3,2-dioxaborolan-2-yl)-1,3,2-dioxaborolane (0.37 g, 1.45 mmol) were dissolved in 1,4-dioxane (4.85 mL) in a microwave vial. The resulting reaction mixture was stirred at 75° C. for 2 hours, then it was cooled to room temperature and filtered over Celite, washing with EtOAc. The filtrate was evaporated under reduced pressure and the residue was dissolved in dichloromethane (1.5 mL) and trifluoroacetic acid (1.5 mL). The resulting mixture was stirred at room temperature overnight, then it was concentrated under reduced pressure. The residue was taken up with MeOH and this solution was loaded onto an SCX cartridge (5 g). The mixture was left to stand on the SCX cartridge for 20 min then it was eluted sequentially with MeOH/H$_2$O (9:1) and 7M methanolic ammonia solution. The basic fractions were collected and evaporated under reduced pressure. The residue was purified by column chromatography (Sfar C18 D, 30 g) eluting with a gradient of MeCN (+0.1% HCOOH) in water (+0.1% HCOOH) from 1% to 30%. Appropriate fractions were collected and lyophilised to give [3-(4-amino-6-fluorocinnolin-7-yl)-4-methoxyphenyl]boronic acid formic acid salt (45 mg, 0.125 mmol, 26% yield) as a white solid. $^1$H NMR (400 MHz, DMSO-d$_6$+2 drops of TFA) δ 3.80 (s, 3H), 7.18 (d, J=8.47 Hz, 1H), 7.78 (d, J=1.64 Hz, 1H), 7.87 (d, J=6.31 Hz, 1H), 7.97 (dd, J=8.30, 1.72 Hz, 1H), 8.11 (s, from HCOOH), 8.35 (d, J=10.26 Hz, 1H), 8.48 (s, 1H), 9.70-9.80 (m, 2H). LC-MS (Method A): r.t. 0.45 min, MS (ESI) m/z=314.1 [M+H]$^+$.

Example 93: [5-(1-amino-4-methylphthalazin-6-yl)-2-[(2-chlorobenzoyl)amino]phenyl]boronic Acid (93)

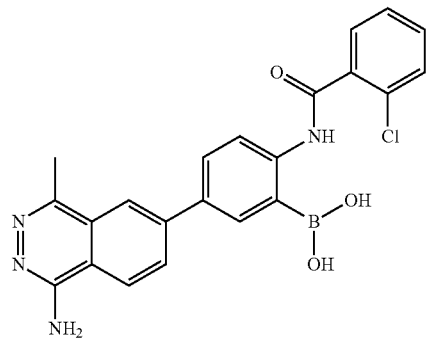 [SMILES: Cc1nnc(N)c2ccc(-c3ccc(NC(=O)c4ccccc4Cl)c(B(O)O)c3)cc12]

To a stirred solution of [2-amino-5-[1-[(2,4-dimethoxyphenyl)methylamino]-4-methylphthalazin-6-yl]phenyl]boronic acid (150.0 mg, 0.340 mmol) in dry THF (3.376 mL), 2-chlorobenzoyl chloride (43.16 uL, 0.340 mmol) was added dropwise. Then triethylamine (94.11 uL, 0.680 mmol) was added and the mixture was stirred overnight at room temperature under a N$_2$ atmosphere. Water was added and the resulting mixture was extracted three times with DCM. The combined organic phases were filtered over a hydrophobic frit (Phase separator) and evaporated. The residue was dissolved in DCM (3 mL) and trifluoroacetic acid (3 mL) was added. The mixture was stirred at room temperature for 4 hours, then evaporated in vacuo. The residue was purified by column chromatography (Sfar C18 D, 2×SNAP 6 in series) eluting with a gradient of MeCN (+0.1% HCOOH) in water (+0.1% HCOOH) from 1% to 50%. The partially purified product obtained was submitted to semi-preparative HPLC purification (MDAP Waters with mass spectrometry detection (MS: ZQ2000). Column: CSH C18 (30×100 mm, 3 μm). Conditions: [A1: Water+0.1% HCOOH]; [B1: MeCN]. Gradient: from 10.0% B1 to 60.0% B1 in 10 min (flow: 40.00 mL/min)). Fractions containing product were collected and lyophilized to give [5-(1-amino-4-methylphthalazin-6-yl)-2-[(2-chlorobenzoyl)amino]phenyl]boronic acid (6 mg, 0.014 mmol, 8.082% yield) as a pale-yellow powder. $^1$H NMR (400 MHz, Methanol-$d_4$+2 drops of TFA) δ 2.87 (s, 3H), 7.41 (d, J=8.34 Hz, 1H), 7.55-7.63 (m, 1H), 7.65-7.72 (m, 2H), 7.82 (d, J=7.67 Hz, 1H), 7.93 (dd, J=8.34, 2.25 Hz, 1H), 8.05 (d, J=2.22 Hz, 1H), 8.43 (dd, J=8.58, 1.78 Hz, 1H), 8.47 (d, J=1.73 Hz, 1H), 8.63 (d, J=8.56 Hz, 1H). LC-MS (Method A): r.t. 0.52 min, MS (ESI) m/z=433.18 [M+H]$^+$.

Examples 94 and 95: 7-(4-aminocinnolin-7-yl)-3-methyl-3,4-dihydro-1H-2,1-benzoxaborinin-1-ol Enantiomer 1 (94) and Enantiomer 2 (95)

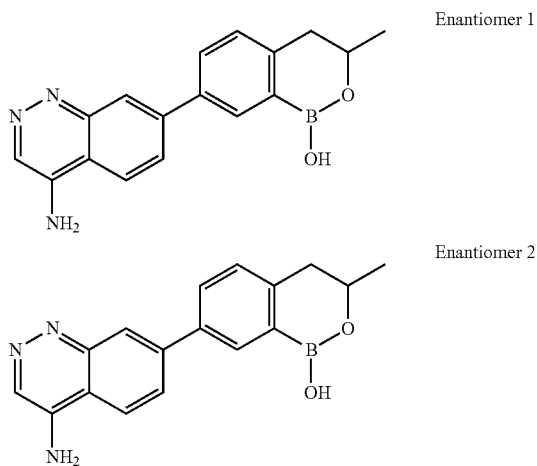

Palladium(II) diacetate (4.47 mg, 0.020 mmol), 7-[4-[2-[tert-butyl(dimethyl)silyl]oxypropyl]-3-chlorophenyl]-N-[(2,4-dimethoxyphenyl)methyl]cinnolin-4-amine (230.0 mg, 0.400 mmol), dicyclohexyl-[2-[2,4,6-tri(propan-2-yl)phenyl]phenyl]phosphine (15.17 mg, 0.030 mmol), potassium acetate (117.11 mg, 1.19 mmol) and bis[(+)-pinanediolato]diboron (427.32 mg, 1.19 mmol) were dissolved 1,4-dioxane (5 mL) in a microwave vial and the mixture was deoxygenated under N$_2$ for 10 min. Then the mixture was stirred at 80° C. for 20 hours. The mixture was filtered over Celite, washing three times with MeOH. The filtrate was concentrated in vacuo, then the residue was dissolved in DCM (30.95 mL) and trifluoroacetic acid (30.95 mL) was added. The mixture was stirred at room temperature for 6 hours, then evaporated and the residue was loaded onto an SCX cartridge. The cartridge was eluted first with MeOH and then with a 2M methanolic solution of ammonia. The basic fractions were evaporated and the residue was purified by column chromatography (Sfar C18 D, SNAP 30) eluting with a gradient of MeCN (+0.1% HCOOH) in water (+0.1% HCOOH) from 2% to 45%. Appropriate fractions were collected and lyophilized to give racemic 7-(1-hydroxy-3-methyl-3,4-dihydro-2,1-benzoxaborinin-7-yl)cinnolin-4-amine (18 mg) as a pale-yellow powder. This material was submitted to semi-preparative chiral HPLC purification (Column Chiralcel OD-H (25×2.0 cm), 5 μm, n-Hexane/(Ethanol+0.1% isopropylamine) 85/15% v/v, Flow rate 17 ml/min). Fractions containing the two separated enantiomers were collected separately and evaporated, the two residues were individually dissolved in MeCN/water and lyophilized to give enantiomer 1 7-(1-hydroxy-3-methyl-3,4-dihydro-2,1-benzoxaborinin-7-yl)cinnolin-4-amine (5.2 mg, 0.017 mmol, 4.25% yield) as a white powder and enantiomer 2 7-(1-hydroxy-3-methyl-3,4-dihydro-2,1-benzoxaborinin-7-yl)cinnolin-4-amine (5.7 mg, 0.019 mmol, 4.75% yield) as a white powder.

Enantiomer 1 characterization: $^1$H NMR (400 MHz, DMSO-$d_6$) δ 1.33 (d, J=6.16 Hz, 3H), 2.78 (dd, J=16.07, 10.12 Hz, 1H), 2.95 (dd, J=16.18, 3.19 Hz, 1H), 4.27-4.39 (m, 1H), 7.22 (s, 2H), 7.36 (d, J=7.92 Hz, 1H), 7.87-7.97 (m, 2H), 8.21 (d, J=1.98 Hz, 1H), 8.27-8.32 (m, 2H), 8.61 (s, 2H). LC-MS (Method A): r.t. 0.56 min, MS (ESI) m/z=306.25 [M+H]$^+$. Analytical chiral HPLC: Column Chiralcel OD-H (25×0.46 cm), 5 um Mobile phase n-Hexane/(Ethanol+0.1% isopropylamine) 85/15% v/v Flow rate 1.0 ml/min) DAD 220 nm Loop 20 μL Enantiomer 1 100% a/a by UV (14.8 min) Enantiomer 2 Not detected.

Enantiomer 2 characterization: $^1$H NMR (400 MHz, DMSO-$d_6$) δ 1.33 (d, J=6.16 Hz, 3H), 2.78 (dd, J=17.17, 10.10 Hz, 1H), 2.95 (dd, J=16.07, 3.30 Hz, 1H), 4.27-4.39 (m, 1H), 7.22 (s, 2H), 7.36 (d, J=7.92 Hz, 1H), 7.88-7.96 (m, 2H), 8.21 (d, J=1.98 Hz, 1H), 8.27-8.32 (m, 2H), 8.61 (s, 2H). LC-MS (Method A): r.t. 0.56 min, MS (ESI) m/z=306.29 [M+H]$^+$. Analytical chiral HPLC: Column Chiralcel OD-H (25×0.46 cm), 5 um Mobile phase n-Hexane/(Ethanol+0.1% isopropylamine) 85/15% v/v Flow rate 1.0 ml/min DAD 220 nm Loop 20 μL Enantiomer 1 1% a/a by UV (15.1 min) Enantiomer 2 99% a/a by UV (19.5 min).

Example 96: 7-{2-methoxy-5-[(1S,2R,6S,8S)-2,6-dimethyl-3,5-dioxa-4-boratricyclo[6.1.1.0$^{2,6}$]decan-4-yl]phenyl}cinnolin-4-amine (96)

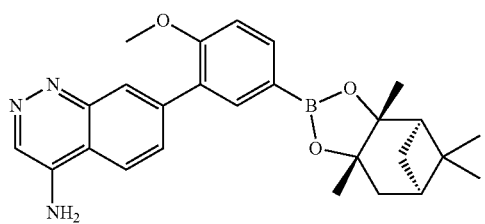 [SMILES: COc1ccc(B2O[C@@]3(C)C[C@H]4C[C@H](C4(C)C)[C@@]3(C)O2)cc1-c1ccc2c(N)cnnc2c1]

A suspension of [3-(4-aminocinnolin-7-yl)-4-methoxyphenyl]boronic acid (50.0 mg, 0.160 mmol) and (1R,3S,4R,5R)-3,4,6,6-tetramethylbicyclo[3.1.1]heptane-3,4-diol (29.35 mg, 0.160 mmol) in THF (1.5 mL) was stirred at 50° C. overnight then it was evaporated in vacuo. The residue was triturated with diethyl ether and the resulting solid was filtered, washed with diethyl ether and dried to give 7-{2-methoxy-5-[(1S,2R,6S,8S)-2,6-dimethyl-3,5-dioxa-4-boratricyclo[6.1.1.0$^{2,6}$]decan-4-yl]phenyl}cinnolin-4-amine (50 mg, 0.113 mmol, 70.81% yield) as an off white solid. $^1$H NMR (400 MHz, DMSO-$d_6$) δ 0.88 (s, 3H), 1.27 (s, 3H), 1.28-1.33 (m, 1H), 1.41 (s, 3H), 1.44 (s, 3H), 1.89-2.01 (m, 2H), 2.04 (t, J=5.60 Hz, 1H), 2.09-2.20 (m, 1H), 2.27 (dd, J=14.85, 4.27 Hz, 1H), 3.84 (s, 3H), 7.17-7.27 (m, 3H), 7.64-7.70 (m, 2H), 7.72 (dd, J=8.23, 1.69 Hz, 1H), 8.05 (d, J=1.76 Hz, 1H), 8.20 (d, J=8.71 Hz, 1H), 8.60 (s, 1H). LC-MS (Method A): r.t. 0.92 min, MS (ESI) m/z=444.3 [M+H]⁺.

Example 97: [3-(4-aminocinnolin-7-yl)-4-(difluoromethoxy)-2-fluorophenyl]boronic Acid Formic Acid Salt (97)

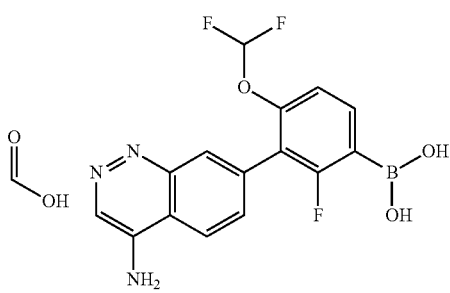

Step 1: Palladium(II) diacetate (2.68 mg, 0.010 mmol), 7-[3-chloro-6-(difluoromethoxy)-2-fluorophenyl]-N-[(2,4-dimethoxyphenyl)methyl]cinnolin-4-amine (117.0 mg, 0.240 mmol), dicyclohexyl-[2-[2,4,6-tri(propan-2-yl)phenyl]phenyl]phosphine (9.11 mg, 0.020 mmol), potassium acetate (70.32 mg, 0.720 mmol) and 4,4,5,5-tetramethyl-2-(4,4,5,5-tetramethyl-1,3,2-dioxaborolan-2-yl)-1,3,2-dioxaborolane (181.95 mg, 0.720 mmol) were dissolved in 1,4-dioxane (1.95 mL) in a microwave vial and the mixture was degassed with Ar for 10 min. The mixture was then stirred at 90° C. for 4 hours. The mixture was filtered, washing with MeOH and the filtrate was concentrated in vacuo. LC-MS (Method A): r.t. 0.92 min, MS (ESI) m/z=582.3 [M+H]⁺.

Step 2: The crude material from Step 1 was dissolved in DCM (1.76 mL) and trifluoroacetic acid (1.06 mL) and the mixture was stirred overnight at room temperature then it was concentrated under reduced pressure. The residue was dissolved in MeOH/H₂O (9:1) and loaded onto an SCX cartridge (5 g). The cartridge was washed with MeOH/H₂O (9:1) and the product was eluted from the SCX cartridge with a 2 M solution of NH₃ in MeOH. The basic fractions were evaporated and the residue was purified by column chromatography (KP-C18-HS, 30 g) eluting with a gradient of MeCN (+0.1% of HCOOH) in water (+0.1% of HCOOH) from 2% to 20%. Fractions containing the desired compound were collected and lyophilised to give [3-(4-aminocinnolin-7-yl)-4-(difluoromethoxy)-2-fluorophenyl]boronic acid formic acid salt (15.9 mg, 0.040 mmol, 7.3% yield) as a white solid. ¹H NMR (400 MHz, DMSO-d₆+2 drops of TFA) δ 7.24 (d, J=8.36 Hz, 1H), 7.30 (t, J=73.07 Hz, 1H), 7.74-7.87 (m, 2H), 7.89 (s, 1H), 8.13 (s, 1H from HCOOH), 8.84-8.57 (m, 2H), 9.83 (br s, 1H), 9.95 (br s, 1H). LC-MS (Method A): r.t. 0.41 min, MS (ESI) m/z=350.02 [M+H]⁺.

Example 98: [3-(4-aminocinnolin-7-yl)-4-[(1,2-thiazol-4-yl)methoxy]phenyl]boronic Acid (98)

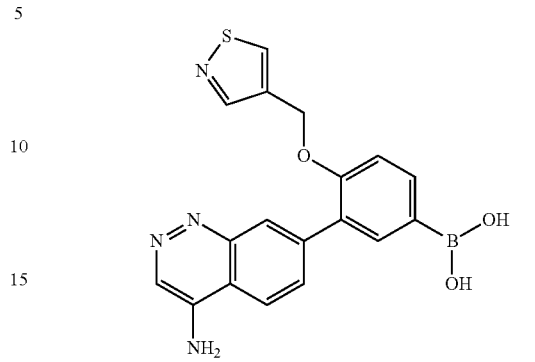

Step 1: Palladium(II) diacetate (4.74 mg, 0.020 mmol), 7-[5-chloro-2-(1,2-thiazol-4-ylmethoxy)phenyl]-N-[(2,4-dimethoxyphenyl)methyl]cinnolin-4-amine (219.0 mg, 0.420 mmol), dicyclohexyl-[2-[2,4,6-tri(propan-2-yl)phenyl]phenyl]phosphine (16.09 mg, 0.030 mmol), potassium acetate (124.23 mg, 1.27 mmol) and 4,4,5,5-tetramethyl-2-(4,4,5,5-tetramethyl-1,3,2-dioxaborolan-2-yl)-1,3,2-dioxaborolane (321.46 mg, 1.27 mmol) were dissolved in 1,4-dioxane (4.635 mL). The mixture was degassed with Ar for 10 min, then stirred at 75° C. for 6 hours. The mixture was filtered over a pad of Celite, washing with EtOAc and the filtrate was concentrated in vacuo.

Step 2: The crude material from Step 1 was dissolved in a mixture of DCM (3 mL) and trifluoroacetic acid (3 mL). The mixture was stirred at room temperature overnight and the volatiles were evaporated. The residue was dissolved in MeOH and loaded onto an SCX cartridge (5 g). The cartridge was washed with MeOH/H₂O (9:1) then the product was eluted from the SCX cartridge with a 2M solution of NH₃ in MeOH. The volatiles were evaporated and the residue was purified by column chromatography (KP-C18-HS, SNAP 30 g) eluting with a gradient of CH₃CN (+0.1% of HCOOH) in water (+0.1% of HCOOH) from 2% to 30%. Fractions containing the partially purified product were collected and evaporated. The recovered solid was submitted to semi-preparative HPLC purification (Chiralcel OJ-H (25×2.0 cm), 5 μm, n-hexane/(EtOH+0.1% isopropylamine), 70/30% v/v). Fractions containing the desired compound were collected and evaporated under reduced pressure. The residue was dissolved in CH₃CN and water and lyophilized to give 3-(4-aminocinnolin-7-yl)-4-(1,2-thiazol-4-ylmethoxy)phenyl]boronic acid (18 mg, 0.048 mmol, 11.3% yield) as a white powder. ¹H NMR (400 MHz, DMSO-d₆+2 drops TFA) δ 5.36 (s, 2H), 7.34 (d, J=8.76 Hz, 1H), 7.89-7.98 (m, 2H), 8.00-8.06 (m, 2H), 8.39-8.53 (m, 2H), 8.66 (s, 1H), 9.03 (s, 1H), 9.70 (s, 1H), 9.82 (s, 1H). LC-MS (Method A): r.t. 0.47 min, MS (ESI) m/z=379.12 [M+H]⁺.

Example 99: 7-(4-aminocinnolin-7-yl)-5-fluoro-3,4-dihydro-1H-2,1-benzoxaborinin-1-ol Formic Acid Salt (99)

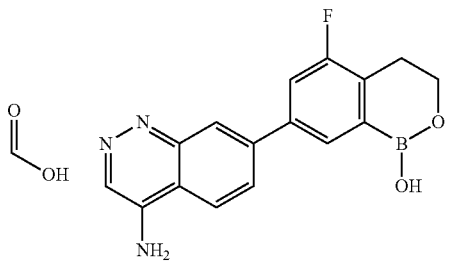

Step 1: Palladium(II) diacetate (6.23 mg, 0.028 mmol), 7-[4-[2-[tert-butyl(dimethyl)silyl]oxyethyl]-3-chloro-5-fluorophenyl]-N-[(2,4-dimethoxyphenyl)methyl]cinnolin-4-amine (323.0 mg, 0.555 mmol), dicyclohexyl-[2-[2,4,6-tri(propan-2-yl)phenyl]phenyl]phosphine (21.16 mg, 0.045 mmol), potassium acetate (163.35 mg, 1.66 mmol) and bis[(+)-pinanendiolato]diboron (596.02 mg, 1.66 mmol) were dissolved in 1,4-dioxane (6.46 mL). The mixture was degassed with Ar for 10 min, then stirred at 80° C. for 24 hours. The mixture was filtered over a pad of Celite, washing with MeOH and the filtrate was concentrated in vacuo.

Step 2: The crude material from Step 1 was dissolved in a mixture of DCM (6 mL) and trifluoroacetic acid (6 mL). The mixture was stirred at room temperature for 6 hours and the volatiles were evaporated. The residue was dissolved in MeOH and loaded onto an SCX cartridge (10 g). The cartridge was washed with MeOH then the product was eluted from the SCX cartridge with a 2M solution of $NH_3$ in MeOH. The volatiles were evaporated and the residue was purified by column chromatography (KP-C18-HS, SNAP 30 g) eluting with a gradient of $CH_3CN$ (+0.1% of HCOOH) in water (+0.1% of HCOOH) from 2% to 45%. Fractions containing the product were collected and lyophilized to give 7-(5-fluoro-1-hydroxy-3,4-dihydro-2,1-benzoxaborinin-7-yl)cinnolin-4-amine formic acid salt (19 mg, 0.054 mmol, 9.7%) as a white powder. $^1$H NMR (400 MHz, DMSO-$d_6$+2 drops of TFA) δ 2.94 (t, J=5.96 Hz, 2H), 4.15 (t, J=5.97 Hz, 2H), 7.26 (s, 2H), 7.84 (dd, J=10.92, 1.82 Hz, 1H), 7.97 (dd, J=8.82, 1.96 Hz, 1H), 8.09 (d, J=1.80 Hz, 1H), 8.14 (s, 1H from HCOOH), 8.30 (d, J=8.82 Hz, 1H), 8.35 (d, J=1.88 Hz, 1H), 8.61 (s, 1H), 8.80 (br. s, 1H). LC-MS (Method A): r.t. 0.52 min, MS (ESI) m/z=310.15 [M+H]$^+$.

Example 100: [7-(4-aminocinnolin-7-yl)-1-benzofuran-5-yl]boronic Acid Formic Acid Salt (100)

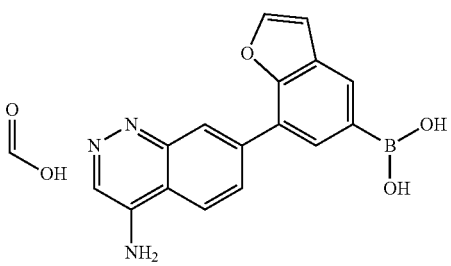

Step 1: Palladium(II) diacetate (3.47 mg, 0.020 mmol), 7-(5-chloro-1-benzofuran-7-yl)-N-[(2,4-dimethoxyphenyl)methyl]cinnolin-4-amine (138.0 mg, 0.310 mmol), dicyclohexyl-[2-[2,4,6-tri(propan-2-yl)phenyl]phenyl]phosphine (11.8 mg, 0.020 mmol), potassium acetate (91.12 mg, 0.930 mmol) and 4,4,5,5-tetramethyl-2-(4,4,5,5-tetramethyl-1,3,2-dioxaborolan-2-yl)-1,3,2-dioxaborolane (235.77 mg, 0.930 mmol) were dissolved in 1,4-dioxane (2.3 mL) in a microwave vial and the mixture was degassed with Ar for 10 minutes. The mixture was then stirred at 70° C. for 1.5 hour. The mixture was filtered, washing with MeOH and the filtrate was concentrated in vacuo. LC-MS (Method A): r.t. 0.96 min, MS (ESI) m/z=538.3 [M+H]$^+$.

Step 2: The crude material from Step 1 was dissolved in DCM (2.5 mL) and trifluoroacetic acid (1.5 mL) and the mixture was stirred overnight at room temperature then it was concentrated under reduced pressure. The residue was dissolved in MeOH/$H_2O$ (9:1) and loaded onto an SCX cartridge (5 g). The cartridge was washed with MeOH/$H_2O$ (9:1) and the product was eluted from the SCX cartridge with a 2 M solution of $NH_3$ in MeOH. The basic fractions were evaporated and the residue was purified by column chromatography (KP-C18-HS, 30 g) eluting with a gradient of $CH_3CN$ (+0.1% of HCOOH) in water (+0.1% of HCOOH) from 2% to 20%. Fractions containing the desired compound were collected concentrated to give [7-(4-aminocinnolin-7-yl)-1-benzofuran-5-yl]boronic acid formic acid salt (22.7 mg, 0.065 mmol, 7.569% yield) as a yellow solid. $^1$H NMR (400 MHz, DMSO-$d_6$+2 drops of TFA) δ 7.15 (d, J=2.20 Hz, 1H), 8.12 (s, 1H from HCOOH), 8.15 (d, J=2.20 Hz, 1H), 8.24 (s, 1H), 8.27 (s, 1H), 8.35 (dd, J=9.02, 1.54 Hz, 1H), 8.48-8.51 (m, 2H), 8.61 (d, J=9.02 Hz, 1H), 9.76 (s, 1H), 9.93 (s, 1H). LC-MS (Method A): r.t. 0.48 min, MS (ESI) m/z=306.2 [M+H]$^+$.

Example 101: 7-[2-(difluoromethoxy)-5-[(1S,2S,6R,8S)-2,9,9-trimethyl-3,5-dioxa-4-boratricyclo[6.1.1.0$^{2,6}$]decan-4-yl]phenyl]cinnolin-4-amine (101)

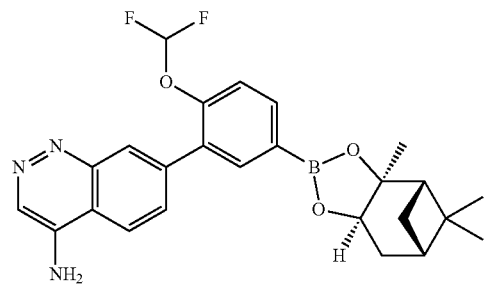 [SMILES: CC1(C)[C@@H]2C[C@H]3OB(c4ccc(OC(F)F)c(-c5ccc6c(N)cnnc6c5)c4)O[C@@]3(C)[C@H]1C2]

A suspension of [3-(4-aminocinnolin-7-yl)-4-(difluoromethoxy)phenyl]boronic acid (700.0 mg, 2.11 mmol) and (1S,3R,4S,5S)-4,6,6-trimethylbicyclo[3.1.1]heptane-3,4-diol (359.96 mg, 2.11 mmol) in THF (28 mL) was stirred at 45° C. overnight, then the mixture was concentrated in vacuo. The residue was triturated with diethyl ether. The solid was collected by filtration and dried in an oven at 45° C. for 48 h to give 7-{2-difluoromethoxy-5-[(1S,2S,6R,8S)-2,9,9-trimethyl-3,5-dioxa-4-boratricyclo[6.1.1.02,6]decan-4-yl]phenyl}cinnolin-4-amine (658 mg, 1.414 mmol, 66.88% yield) as a white solid. $^1$H NMR (400 MHz, DMSO-$d_6$) δ 0.88 (s, 3H), 1.07-1.13 (m, 1H), 1.29 (3H, s), 1.46 (3H, s), 1.87 (d, J=14.75 Hz, 1H) 1.92 (br. s, 1H), 2.11

(t, J=5.50 Hz, 1H), 2.20-2.28 (m, 1H), 2.41 (dd, J=14.31, 8.80 Hz, 1H), 4.57 (dd, J=8.69, 1.65 Hz, 1H), 7.25 (s, 2H), 7.31 (t, J=72.8 Hz 1H) 7.41 (d, J=8.58 Hz, 1H), 7.69 (dd, J=8.80, 1.76 Hz, 1H), 7.81-7.86 (m, 2H), 8.10 (d, J=1.54 Hz, 1H), 8.26 (d, J=8.80 Hz, 1H), 8.65 (s, 1H). LC-MS (Method A): r.t. 0.92 min, MS (ESI) m/z=466.25 [M+H]+.

Example 102: 7-[2-(difluoromethoxy)-5-[(1R,2R, 6S,8R)-2,6,9,9-tetramethyl-3,5-dioxa-4-boratricyclo [6.1.1.0$^{2,6}$]decan-4-yl]phenyl]cinnolin-4-amine (102)

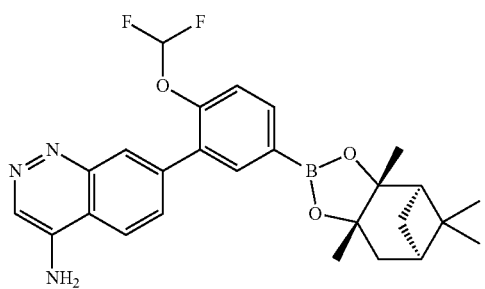 [SMILES: CC1(C)[C@@H]2C[C@H]1[C@@]1(C)OB(c3ccc(OC(F)F)c(-c4ccc5c(N)cnnc5c4)c3)O[C@@]1(C)C2]

A suspension of [3-(4-aminocinnolin-7-yl)-4-(difluoromethoxy)phenyl]boronic acid (50.0 mg, 0.150 mmol) and (1R,3S,4R,5R)-3,4,6,6-tetramethylbicyclo[3.1.1]heptane-3,4-diol (27.27 mg, 0.150 mmol) in THF (1.5 mL) was stirred at 50° C. overnight and then it was evaporated in vacuo. The residue was triturated with diethyl ether, the solvent was decanted and the solid residue was collected and dried to give 7-[2-(difluoromethoxy)-5-[(1R,2R,6S,8R)-2,6,9,9-tetramethyl-3,5-dioxa-4-boratricyclo[6.1.1.0$^{2,6}$]decan-4-yl] phenyl]cinnolin-4-amine (45 mg, 0.094 mmol, 63.43% yield) as an off white solid. $^1$H NMR (400 MHz, DMSO-d$_6$) δ 0.89 (s, 3H), 1.28 (s, 3H), 1.30 (d, J=10.68 Hz, 1H), 1.43 (s, 3H), 1.47 (s, 3H), 1.91-2.03 (m, 2H), 2.06 (t, J=5.59 Hz, 1H), 2.11-2.22 (m, 1H), 2.29 (dd, J=14.88, 4.23 Hz, 1H), 7.25 (br. s, 2H), 7.30 (t, J=73.55 Hz, 1H), 7.39 (d, J=8.55 Hz, 1H), 7.68 (dd, J=8.73, 1.81 Hz, 1H), 7.80 (m, 2H), 8.09 (d, J=1.78 Hz, 1H), 8.26 (d, J=8.78 Hz, 1H), 8.65 (s, 1H). LC-MS (Method A): r.t. 0.96 min, MS (ESI) m/z=480.3 [M+H]+.

Example 103: 7-{2-methoxy-5-[(1S,2S,6R,8S)-2,6, 9,9-tetramethyl-3,5-dioxa-4-boratricyclo[6.1.1.0$^{2,6}$] decan-4-yl]phenyl}cinnolin-4-amine (103)

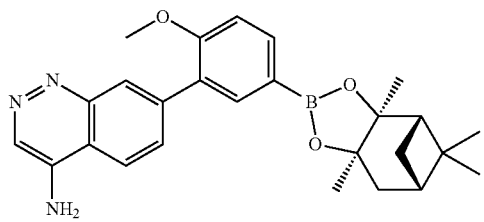 [SMILES: COc1ccc(B2O[C@]3(C)C[C@@H]4C[C@@H](C4(C)C)[C@]3(C)O2)cc1-c1ccc2c(N)cnnc2c1]

A suspension of [3-(4-aminocinnolin-7-yl)-4-methoxyphenyl]boronic acid (50.0 mg, 0.170 mmol) and (1S,3R,4S, 5S)-3,4,6,6-tetramethylbicyclo[3.1.1]heptane-3,4-diol (31.22 mg, 0.170 mmol) in THF (1.597 mL) was stirred at 50° C. for 24 hours. No formation of product was observed. MeOH (0.1 mL) was added and the mixture become a clear solution. The reaction was stirred for 24 hours then it was evaporated in vacuo. The residue was loaded onto an SCX cartridge that was eluted first with MeOH and then with 2M methanolic NH$_3$ solution. The basic fractions were evaporated and the residue was dissolved in MeCN/H$_2$O and lyophilised to give 7-{2-methoxy-5-[(1S,2S,6R,8S)-2,6,9,9-tetramethyl-3,5-dioxa-4-boratricyclo[6.1.1.0$^{2,6}$]decan-4-yl] phenyl}cinnolin-4-amine (60 mg, 0.135 mmol, 79.87% yield) as a white solid. $^1$H NMR (400 MHz, DMSO-d$_6$) δ 0.89 (s, 3H), 1.28 (s, 3H), 1.32 (d, J=10.59 Hz, 1H), 1.42 (s, 3H), 1.46 (s, 3H), 1.90-2.02 (m, 2H), 2.03-2.09 (m, 1H), 2.10-2.21 (m, 1H), 2.28 (dd, J=14.76, 4.16 Hz, 1H), 3.85 (s, 3H), 7.13-7.23 (m, 3H), 7.65-7.75 (m, 3H), 8.06 (d, J=1.72 Hz, 1H), 8.20 (d, J=8.77 Hz, 1H), 8.62 (s, 1H). LC-MS (Method A): r.t. 0.94 min, MS (ESI) m/z=444.27 [M+H]+.

Example 104: [7-(1-amino-4-methylphthalazin-6-yl)-1-benzofuran-5-yl]boronic Acid (104)

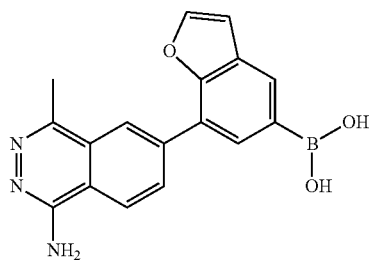 [SMILES: Cc1nnc(N)c2ccc(-c3cc(B(O)O)cc4ccoc34)cc12]

Step 1: Palladium(II) diacetate (1.81 mg, 0.010 mmol), 6-(5-chloro-1-benzofuran-7-yl)-N-[(2,4-dimethoxyphenyl) methyl]-4-methylphthalazin-1-amine (74.0 mg, 0.160 mmol), dicyclohexyl-[2-[2,4,6-tri(propan-2-yl)phenyl]phenyl]phosphine (6.14 mg, 0.010 mmol) and potassium acetate (47.37 mg, 0.480 mmol) were dissolved 1,4-dioxane (1.5 mL) in a microwave vial and the mixture was degassed with Ar for 10 minutes. 4,4,5,5-Tetramethyl-2-(4,4,5,5-tetramethyl-1,3,2-dioxaborolan-2-yl)-1,3,2-dioxaborolane (122.57 mg, 0.480 mmol) was added and the mixture was degassed under Ar for another 10 minutes. The mixture was then stirred at 75° C. for 3 hours. The mixture was filtered, washing with methanol and the filtrate was concentrated in vacuo. LC-MS (Method A): r.t. 0.99 min, MS (ESI) m/z=552.3 [M+H]+.

Step 2: The crude material from Step 1 was dissolved in DCM (1.25 mL) and trifluoroacetic acid (0.75 mL) and the mixture was stirred overnight at room temperature then it was concentrated under reduced pressure. The residue was dissolved in MeOH/H$_2$O (9:1) and loaded onto an SCX cartridge (2 g). The cartridge was washed with MeOH/H$_2$O (9:1) and the product was eluted from the SCX cartridge with a 2 M solution of NH$_3$ in MeOH. The basic fractions were evaporated and the residue was purified by column chromatography (KP-C18-HS, 12 g) eluting with a gradient of MeCN in water (+0.1% of HCOOH) from 2% to 20%. Fractions containing the desired compound were collected and lyophilised to give [7-(1-amino-4-methylphthalazin-6-yl)-1-benzofuran-5-yl]boronic acid (15 mg, 0.047 mmol, 29.4% yield) as a white solid. $^1$H NMR (400 MHz, DMSO-d$_6$+2 drops TFA) δ 2.81 (s, 3H), 7.15 (d, J=2.2 Hz, 1H), 8.11-8.17 (m, 1H), 8.23 (s, 1H), 8.26 (s, 1H), 8.65 (dd, J=8.58, 1.54 Hz, 1H), 8.68 (d, J=1.32 Hz, 1H), 8.81 (d, J=8.58 Hz, 1H), 9.22 (br. s, 2H). LC-MS (Method A): r.t. 0.53 min, MS (ESI) m/z=320.2 [M+H]⁺.

Example 105: [3-(4-aminocinnolin-7-yl)-4-(1,1,2,2-tetrafluoroethoxy)phenyl]boronic Acid Formic Acid Salt (105)

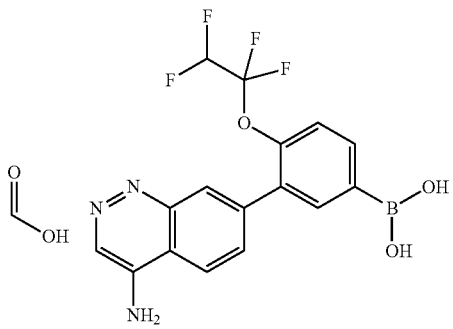

Palladium(II) diacetate (5.38 mg, 0.020 mmol), 7-[5-chloro-2-(1,1,2,2-tetrafluoroethoxy)phenyl]-N-[(2,4-dimethoxyphenyl)methyl]cinnolin-4-amine (250.0 mg, 0.480 mmol), dicyclohexyl-[2-[2,4,6-tri(propan-2-yl)phenyl]phenyl]phosphine (22.84 mg, 0.050 mmol), potassium acetate (141.04 mg, 1.44 mmol) and 4,4,5,5-tetramethyl-2-(4,4,5,5-tetramethyl-1,3,2-dioxaborolan-2-yl)-1,3,2-dioxaborolane (360 mg, 1.44 mmol) were dissolved in 1,4-dioxane (4.79 mL) in a microwave vial and degassed for 10 min with $N_2$. The resulting reaction mixture was stirred at 75° C. for 2 hours then it was cooled to room temperature and filtered over Celite, washing with EtOAc. The filtrate was evaporated under reduced pressure and the residue was dissolved in dichloromethane (2 mL) and trifluoroacetic acid (2 mL). The resulting mixture was stirred for 4 hours at room temperature then it was concentrated under reduced pressure. The residue was taken up with MeOH and this solution was loaded onto an SCX cartridge (5 g) which was washed with MeOH/$H_2O$ (9:1) and then eluted with a 7M solution of ammonia in MeOH. The basic fractions were collected and evaporated under reduced pressure. The residue was purified by column chromatography (KP-C18-HS, 30 g) eluting with a gradient of MeCN (+0.1% of HCOOH) in water (+0.1% of HCOOH) from 1% to 70%. Appropriate fractions were collected and lyophilised to give [3-(4-aminocinnolin-7-yl)-4-(1,1,2,2-tetrafluoroethoxy)phenyl]boronic acid formic acid salt (21 mg, 0.049 mmol, 10.1% yield) as a white solid. ¹H NMR (400 MHz, DMSO-$d_6$) δ 6.51 (t, J=51.90 Hz, 1H), 7.24 (s, 2H), 7.44-7.52 (m, 1H), 7.67 (dd, J=8.75, 1.81 Hz, 1H), 7.93 (dd, J=8.20, 1.71 Hz, 1H), 8.10 (d, J=1.71 Hz, 1H), 8.12 (d, J=1.77 Hz, 1H), 8.17 (s, from HCOOH), 8.25 (d, J=8.75 Hz, 1H), 8.33 (s, 2H), 8.64 (s, 1H). LC-MS (Method A): r.t. 0.54 min, MS (ESI) m/z=382.4 [M+H]⁺.

Example 106: [3-(4-aminocinnolin-7-yl)-4-(1,2,2,2-tetrafluoroethoxy)phenyl]boronic Acid (106)

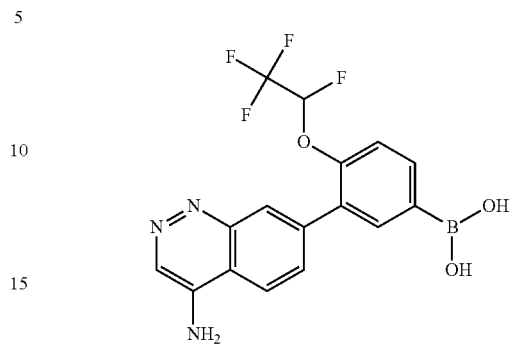

Step 1: A mixture of 7-[5-chloro-2-(1,2,2,2-tetrafluoroethoxy)phenyl]-N-[(2,4-dimethoxyphenyl)methyl]cinnolin-4-amine (100.0 mg, 0.190 mmol), 4,4,5,5-tetramethyl-2-(4,4,5,5-tetramethyl-1,3,2-dioxaborolan-2-yl)-1,3,2-dioxaborolane (145.97 mg, 0.570 mmol) and potassium acetate (56.41 mg, 0.570 mmol) in 1,4-dioxane (2.8 mL) was degassed under argon for 10 minutes then dicyclohexyl-[2-[2,4,6-tri(propan-2-yl)phenyl]phenyl]phosphine (7.31 mg, 0.020 mmol) and palladium(II) diacetate (2.15 mg, 0.010 mmol) were added and the mixture stirred at 70° C. for 1 hour. The temperature was then raised to 85° C. and the mixture was stirred for 26 hours. The reaction mixture was allowed to cool to room temperature and filtered over a pad of Celite, washing with MeOH and EtOAc, and the filtrate was concentrated in vacuo. LC-MS (Method A): r.t. 1.00 min, MS (ESI) m/z=614.2 [M+H]⁺.

Step 2: The crude material from Step 1 was combined with a similar crude isolated from an analogous reaction performed on 27 mg of 7-[5-chloro-2-(1,2,2,2-tetrafluoroethoxy)phenyl]-N-[(2,4-dimethoxyphenyl)methyl]cinnolin-4-amine. This material was dissolved in trifluoroacetic acid (2 mL) and DCM (2 mL) and the mixture was stirred at room temperature for 6 hours, then the volatiles were removed under reduced pressure. The residue was dissolved in MeOH/$H_2O$ (9:1), then loaded onto an SCX cartridge (5 g), which was washed with MeOH/$H_2O$ (9:1) and then eluted with a 2M solution of ammonia in MeOH. The basic fractions were collected and evaporated under reduced pressure. The residue was purified twice by column chromatography (Sfar C18 D, 12 g) eluting with a gradient of MeCN (+0.1% HCOOH) in water (+0.1% HCOOH) from 1% to 25%. The appropriate fractions were collected and lyophilized. The residue was submitted to semi-preparative HPLC purification (CSH C18 (30×100 mm, 3 μm); gradient of MeCN in water+0.1% HCOOH from 18.0% to 30.0%) to give [3-(4-aminocinnolin-7-yl)-4-(1,2,2,2-tetrafluoroethoxy)phenyl]boronic acid (6.5 mg, 0.017 mmol, 8.9% yield) as a white solid. ¹H NMR (400 MHz, DMSO-$d_6$+3 drops of TFA) δ 6.90 (dd, J=56.91, 3.01 Hz, 1H), 7.41 (d, J=8.17 Hz, 1H), 7.88 (dd, J=8.84, 1.51 Hz, 1H), 7.93 (d, J=1.35 Hz, 1H), 7.98-8.02 (m, 2H), 8.06 (s, 0.12H from HCOOH), 8.47 (s, 1H), 8.50 (d, J=8.88 Hz, 1H), 9.72 (s, 1H), 9.84 (s, 1H). LC-MS (Method A): r.t. 0.55 min, MS (ESI) m/z=382.1 [M+H]⁺.

Example 107: [3-(4-aminocinnolin-7-yl)-4-[2-(2-methoxyethoxy)ethoxy]phenyl]boronic Acid Formic Acid Salt (107)

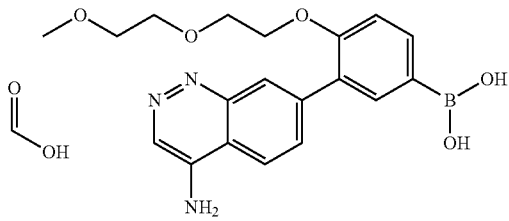 [SMILES: O=CO ; COCCOCCOc1ccc(B(O)O)cc1-c1ccc2c(N)cnnc2c1]

Palladium(II) diacetate (3.0 mg, 0.010 mmol), 7-[5-chloro-2-[2-(2-methoxyethoxy)ethoxy]phenyl]-N-[(2,4-dimethoxyphenyl)methyl]cinnolin-4-amine (140.0 mg, 0.270 mmol), dicyclohexyl-[2-[2,4,6-tri(propan-2-yl)phenyl]phenyl]phosphine (10.19 mg, 0.020 mmol), potassium acetate (78.66 mg, 0.800 mmol) and 4,4,5,5-tetramethyl-2-(4,4,5,5-tetramethyl-1,3,2-dioxaborolan-2-yl)-1,3,2-dioxaborolane (203.54 mg, 0.800 mmol) were dissolved in 1,4-dioxane (3.5 mL) in a microwave vial and degassed for 10 min with $N_2$. The resulting reaction mixture was stirred at 80° C. for 1 hour then it was cooled to room temperature and filtered over Celite, washing with EtOAc. The filtrate was evaporated under reduced pressure and the residue was dissolved in dichloromethane (3 mL) and trifluoroacetic acid (3 mL). The resulting mixture was stirred overnight at room temperature then it was evaporated in vacuo. The residue was dissolved in MeOH/$H_2O$ (9:1), loaded onto an SCX cartridge and the cartridge was left to stand for 20 min. The cartridge was then washed with MeOH/$H_2O$ (9:1) and the product was eluted with 7 M methanolic ammonia solution. The basic fractions were collected and evaporated under reduced pressure. The residue was purified by flash chromatography (Sfar C18 D, 12 g) eluting with a gradient of MeCN (+0.1% of HCOOH) in water (+0.1% of HCOOH) from 1% to 15%. Appropriate fractions were collected and lyophilised to give [3-(4-aminocinnolin-7-yl)-4-[2-(2-methoxyethoxy)ethoxy]phenyl]boronic acid formic acid salt (45 mg, 0.105 mmol, 38.88% yield) as a white powder. $^1$H NMR (400 MHz, DMSO-$d_6$) δ 3.17 (s, 3H), 3.37-3.43 (m, 2H), 3.49-3.54 (m, 2H), 3.66-3.79 (m, 2H), 4.18-4.25 (m, 2H), 7.16 (d, J=8.36 Hz, 1H), 7.21 (s, 2H), 7.81-7.87 (m, 2H), 7.97 (d, J=1.73 Hz, 1H), 8.01 (s, 2H), 8.15 (s, 1H from HCOOH), 8.17-8.20 (m, 2H), 8.61 (s, 1H). LC-MS (Method A): r.t. 0.47 min, MS (ESI) m/z=384.2 [M+H]$^+$.

Example 108: [5-(4-aminocinnolin-7-yl)-4-(difluoromethoxy)-2-methylphenyl]boronic Acid (108)

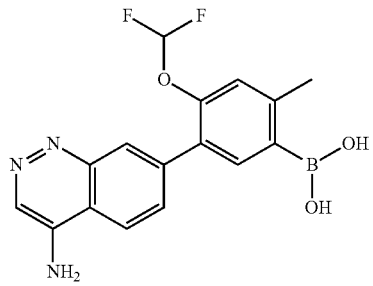 [SMILES: Cc1cc(OC(F)F)c(-c2ccc3c(N)cnnc3c2)cc1B(O)O]

Step 1: A mixture of 7-[5-chloro-2-(difluoromethoxy)-4-methylphenyl]-N-[(2,4-dimethoxyphenyl)methyl]cinnolin-4-amine (100.0 mg, 0.210 mmol), 4,4,5,5-tetramethyl-2-(4,4,5,5-tetramethyl-1,3,2-dioxaborolan-2-yl)-1,3,2-dioxaborolane (156.78 mg, 0.620 mmol), potassium acetate (60.59 mg, 0.620 mmol) in 1,4-dioxane (3.75 mL) was degassed under Ar for 10 minutes, then dicyclohexyl-[2-[2,4,6-tri(propan-2-yl)phenyl]phenyl]phosphine (7.85 mg, 0.020 mmol) and palladium(II) diacetate (2.31 mg, 0.010 mmol) were added and the mixture was stirred at 70° C. for 1 hour. The temperature was then raised to 95° C. and the mixture was stirred overnight. The mixture was allowed to cool to room temperature, diluted with MeOH and filtered over Celite, washing with MeOH and EtOAc, and the filtrate was concentrated in vacuo. LC-MS (Method A): r.t. 1.01 min, MS (ESI) m/z=578.2 [M+H]$^+$.

Step 2: The crude material from Step 1 was dissolved in trifluoroacetic acid (2 mL) and DCM (2 mL) and the mixture stirred at room temperature for 6 hours. The volatiles were removed under reduced pressure and the residue was dissolved in MeOH/$H_2O$ (9:1), then loaded onto an SCX cartridge (5 g), which was washed with MeOH/$H_2O$ (9:1) and then eluted with a 2M solution of ammonia in MeOH. The basic fractions were collected and evaporated under reduced pressure. The residue was purified by column chromatography (Sfar C18 D, 12 g), eluting with a gradient of MeCN (+0.1% of HCOOH) in water (+0.1% of HCOOH) from 1% to 30%. The appropriate fractions were collected and lyophilized to give a light yellow solid that was submitted to semi-preparative HPLC purification (Chiralpak AS-H (25×2.0 cm), 5 μm, n-hexane/(EtOH+0.1% isopropylamine), 80/20% v/v) to give [5-(4-aminocinnolin-7-yl)-4-(difluoromethoxy)-2-methylphenyl]boronic acid (7.4 mg, 0.021 mmol, 10.0% yield) as a white solid. $^1$H NMR (400 MHz, DMSO-$d_6$+6 drops of TFA) δ 2.49-2.51 (s, 3H peak obscured by DMSO-$d_5$ solvent peak), 7.07 (t, J=74.08 Hz, 1H), 7.10 (s, 1H), 7.70 (s, 1H), 7.88 (d, J=9.86 Hz, 1H), 7.94 (s, 1H), 8.02 (s, 0.26H from HCOOH), 8.43 (d, J=2.52 Hz, 1H), 8.47 (d, J=8.70 Hz, 1H), 9.64 (s, 1H), 9.79 (s, 1H). LC-MS (Method A): r.t. 0.51 min, MS (ESI) m/z=346.1 [M+H]$^+$.

Example 109: [3-(4-aminoquinolin-7-yl)-4-methoxyphenyl]boronic Acid Formic Acid Salt (109)

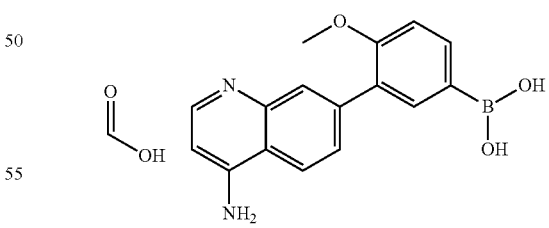

Palladium(II) diacetate (5.16 mg, 0.020 mmol), 7-(5-chloro-2-methoxyphenyl)-N-[(2,4-dimethoxyphenyl)methyl]quinolin-4-amine (200.0 mg, 0.460 mmol), dicyclohexyl-[2-[2,4,6-tri(propan-2-yl)phenyl]phenyl]phosphine (17.54 mg, 0.040 mmol), potassium acetate (135.39 mg, 1.38 mmol) and 4,4,5,5-tetramethyl-2-(4,4,5,5-tetramethyl-1,3,2-dioxaborolan-2-yl)-1,3,2-dioxaborolane (350.33 mg, 1.38 mmol) were dissolved in 1,4-dioxane (5 mL) in a microwave vial and degassed for 10 min with $N_2$. The resulting reaction mixture was stirred at 80° C. for 2 hours then it was cooled to room temperature and filtered over Celite, washing with EtOAc. The filtrate was evaporated under reduced pressure and the residue was dissolved in dichloromethane (3 mL) and trifluoroacetic acid (2 mL). The resulting mixture was stirred overnight at room temperature then it was evaporated in vacuo. The residue was dissolved in MeOH/H$_2$O (9:1), loaded onto an SCX cartridge and the cartridge was left to stand for 20 min. The cartridge was then washed with MeOH/H$_2$O (9:1) and eluted with 7 M methanolic ammonia solution. The basic fractions were collected and evaporated under reduced pressure. The residue was purified by column chromatography (Sfar C18 D, 12 g) eluting with a gradient of MeCN (+0.1% of HCOOH) in water (+0.1% of HCOOH) from 1% to 15%. Appropriate fractions were collected and lyophilised to give [3-(4-aminoquinolin-7-yl)-4-methoxyphenyl]boronic acid formic acid salt (38 mg, 0.112 mmol, 24.34% yield) as a white powder. $^1$H NMR (400 MHz, DMSO-d$_6$) δ 3.85 (s, 3H), 6.79 (dd, J=6.93, 1.03 Hz, 1H), 7.19 (m, 1H), 7.83 (dd, J=8.78, 1.66 Hz, 1H), 7.88-7.93 (m, 2H), 8.01 (d, J=1.66 Hz, 1H), 8.13 (s, 1H from HCOOH), 8.39-8.47 (m, 2H), 8.89-8.98 (m, 2H). LC-MS (Method A): r.t. 0.46 min, MS (ESI) m/z=295.2 [M+H]$^+$.

Example 110: [3-(4-aminocinnolin-7-yl)-4-[2-(oxolan-2-yl)ethoxy]phenyl]boronic Acid (110)

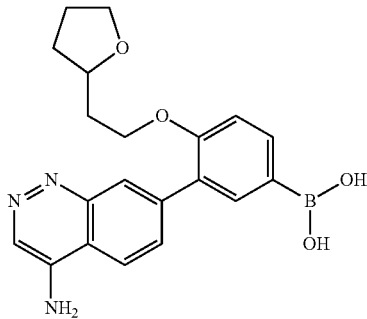 [SMILES: Nc1cnnc2cc(-c3cc(B(O)O)ccc3OCCC3CCCO3)ccc12]

Palladium(II) diacetate (3.89 mg, 0.020 mmol), 7-[5-chloro-2-[2-(oxolan-2-yl)ethoxy]phenyl]-N-[(2,4-dimethoxyphenyl)methyl]cinnolin-4-amine (180.0 mg, 0.346 mmol), dicyclohexyl-[2-[2,4,6-tri(propan-2-yl)phenyl]phenyl]phosphine (16.5 mg, 0.030 mmol), potassium acetate (101.91 mg, 1.04 mmol) and 4,4,5,5-tetramethyl-2-(4,4,5,5-tetramethyl-1,3,2-dioxaborolan-2-yl)-1,3,2-dioxaborolane (263.7 mg, 1.04 mmol) were dissolved in 1,4-dioxane (3.45 mL) in a microwave vial and degassed for 10 min with N$_2$. The resulting reaction mixture was stirred at 80° C. for 2 hours then it was cooled to room temperature and filtered over Celite, washing with EtOAc. The filtrate was evaporated under reduced pressure and the residue was dissolved in dichloromethane (1.5 mL) and trifluoroacetic acid (1.5 mL). The resulting mixture was stirred for 4 hours at room temperature then it was concentrated under reduced pressure. The residue was taken up with MeOH and this solution was loaded onto an SCX cartridge (5 g) which was washed with MeOH/H$_2$O (9:1) and then eluted with a 7M solution of ammonia in MeOH. The basic fractions were collected and evaporated under reduced pressure. The residue was purified by column chromatography (KP-C18-HS, 30 g) eluting with a gradient of MeCN (+0.1% of HCOOH) in water (+0.1% of HCOOH) from 1% to 70%. Appropriate fractions were collected and lyophilised to give [3-(4-aminocinnolin-7-yl)-4-[2-(oxolan-2-yl)ethoxy]phenyl]boronic acid (40 mg, 0.105 mmol, 30.3% yield) as a pale yellow solid. $^1$H NMR (400 MHz, DMSO-d$_6$+2 drops of TFA) δ 1.28-1.49 (m, 1H), 1.64-1.79 (m, 2H), 1.79-1.94 (m, 3H), 3.54 (q, J=7.43 Hz, 1H), 3.69 (q, J=7.16 Hz, 1H), 3.82 (quin, J=6.77 Hz, 1H), 4.07-4.18 (m, 2H), 7.13 (d, J=8.12 Hz, 1H), 7.83-8.06 (m, 4H), 8.36-8.51 (m, 2H), 9.62 (br. s, 1H), 9.76 (br. s, 1H). LC-MS (Method A): r.t. 0.53 min, MS (ESI) m/z=380.3 [M+H]$^+$.

Example 111: [3-(1-amino-4-methylisoquinolin-6-yl)-4-methoxyphenyl]boronic Acid

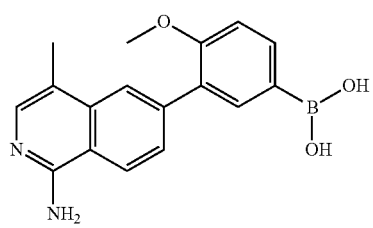 [SMILES: COc1ccc(B(O)O)cc1-c1ccc2c(N)ncc(C)c2c1]

Palladium(II) diacetate (3.5 mg, 0.020 mmol), 6-(5-chloro-2-methoxyphenyl)-N-[(2,4-dimethoxyphenyl)methyl]-4-methylisoquinolin-1-amine (140.0 mg, 0.310 mmol), dicyclohexyl-[2-[2,4,6-tri(propan-2-yl)phenyl]phenyl]phosphine (14.87 mg, 0.030 mmol), potassium acetate (91.81 mg, 0.940 mmol) and 4,4,5,5-tetramethyl-2-(4,4,5,5-tetramethyl-1,3,2-dioxaborolan-2-yl)-1,3,2-dioxaborolane (0.24 g, 0.940 mmol) were dissolved in 1,4-dioxane (3.11 mL) in a microwave vial and degassed for 10 min with N$_2$. The resulting reaction mixture was stirred at 80° C. for 2 hours then it was cooled to room temperature and filtered over Celite, washing with EtOAc. The filtrate was evaporated under reduced pressure and the residue was dissolved in dichloromethane (1.5 mL) and trifluoroacetic acid (1.5 mL). The resulting mixture was stirred for 4 hours at room temperature then it was concentrated under reduced pressure. The residue was taken up with MeOH and this solution was loaded onto an SCX cartridge (5 g) which was washed with MeOH/H$_2$O (9:1) and then eluted with a 7M solution of ammonia in MeOH. The basic fractions were collected and evaporated under reduced pressure. The residue was purified by column chromatography (KP-C18-HS, 30 g) eluting with a gradient of MeCN (+0.1% of HCOOH) in water (+0.1% of HCOOH) from 1% to 70%. Appropriate fractions were collected and lyophilised to give [3-(1-amino-4-methylisoquinolin-6-yl)-4-methoxyphenyl]boronic acid (28 mg, 0.091 mmol, 29.4% yield) as a white solid. $^1$H NMR (400 MHz, DMSO-d$_6$) δ 2.36 (s, 3H), 3.81 (s, 3H), 6.64 (s, 2H), 7.13 (d, J=8.27 Hz, 1H), 7.61 (dd, J=8.62, 1.67 Hz, 1H), 7.65 (s, 1H), 7.77-8.07 (m, 4H), 8.17 (s, 1H), 8.21 (d, J=8.64 Hz, 1H). LC-MS (Method A): r.t. 0.53 min, MS (ESI) m/z=309.2 [M+H]$^+$.

Example 112: [3-(4-aminocinnolin-7-yl)-4-[2-(oxolan-3-yl)ethoxy]phenyl]boronic Acid Formic Acid Salt (112)

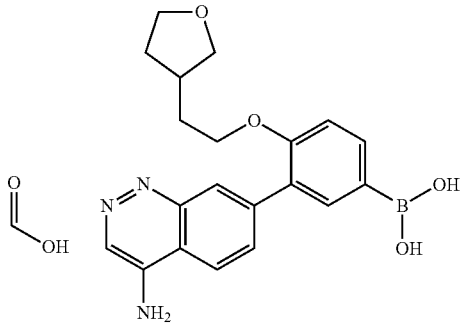

Palladium(II) diacetate (3.24 mg, 0.010 mmol), 7-[5-chloro-2-[2-(oxolan-3-yl)ethoxy]phenyl]-N-[(2,4-dimethoxyphenyl)methyl]cinnolin-4-amine (150.0 mg, 0.290 mmol), dicyclohexyl-[2-[2,4,6-tri(propan-2-yl)phenyl]phenyl]phosphine (11.0 mg, 0.020 mmol), potassium acetate (84.93 mg, 0.870 mmol) and 4,4,5,5-tetramethyl-2-(4,4,5,5-tetramethyl-1,3,2-dioxaborolan-2-yl)-1,3,2-dioxaborolane (219.75 mg, 0.870 mmol) were dissolved in 1,4-dioxane (3 mL) in a microwave vial and degassed for 10 min with $N_2$. The resulting reaction mixture was stirred at 80° C. for 1 hour then it was cooled to room temperature and filtered over Celite, washing with EtOAc. The filtrate was evaporated under reduced pressure and the residue was dissolved in dichloromethane (2.5 mL) and trifluoroacetic acid (2.5 mL). The resulting mixture was stirred overnight at room temperature then it was evaporated in vacuo. The residue was dissolved in MeOH/$H_2O$ (9:1), loaded onto an SCX cartridge and the cartridge was left to stand for 20 min. The cartridge was then washed with MeOH/$H_2O$ (9:1) and eluted with 7 M methanolic ammonia solution. The basic fractions were collected and evaporated under reduced pressure. The residue was purified by column chromatography (Sfar C18 D, 12 g) eluting with a gradient of MeCN (+0.1% of HCOOH) in water (+0.1% of HCOOH) from 1% to 15%. Appropriate fractions were collected and lyophilised to give [3-(4-aminocinnolin-7-yl)-4-[2-(oxolan-3-yl)ethoxy]phenyl]boronic acid formic acid salt (45 mg, 0.106 mmol, 36.55% yield) as a white powder. $^1$H NMR (400 MHz, DMSO-$d_6$+2 drops of TFA) δ 1.38-1.55 (m, 1H), 1.72-1.85 (m, 2H), 1.89-2.01 (m, 1H), 2.16-2.27 (m, 1H), 3.16-3.25 (m, 1H), 3.52-3.61 (m, 1H), 3.61-3.74 (m, 2H), 4.08-4.16 (m, 2H), 7.21 (d, J=8.27 Hz, 1H), 7.87-7.95 (m, 2H), 7.97-8.05 (m, 2H), 8.13 (s, 1H from HCOOH), 8.44-8.51 (m, 2H), 9.71 (br. s, 1H), 9.83 (br. s, 1H). LC-MS (Method A): r.t. 0.51 min, MS (ESI) m/z=380.3 [M+H]$^+$.

Example 113: 7-{2-methoxy-5-[(1R,2R,6S,8R)-2,9,9-trimethyl-3,5-dioxa-4-boratricyclo[6.1.1.0$^{2,6}$]decan-4-yl]phenyl}cinnolin-4-amine (113)

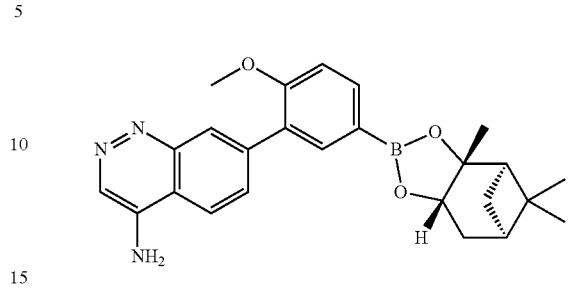

A suspension of [3-(4-aminocinnolin-7-yl)-4-methoxyphenyl]boronic acid (50.0 mg, 0.170 mmol) and (1R,3S,4R,5R)-3,6,6-trimethylbicyclo[3.1.1]heptane-3,4-diol (28.85 mg, 0.170 mmol) in THF (1.5 mL) was stirred at 50° C. overnight and then it was evaporated in vacuo. The residue was triturated with diethyl ether, the solvent was decanted and the solid residue was collected and dried in the oven at 50° C. overnight. $^1$H NMR showed the presence of residual diethyl ether, so the solid was suspensed in cyclohexane, filtered and dried to give 7-{2-methoxy-5-[(1R,2R,6S,8R)-2,9,9-trimethyl-3,5-dioxa-4-boratricyclo[6.1.1.0$^{2,6}$]decan-4-yl]phenyl}cinnolin-4-amine (36 mg, 0.084 mmol, 49.49% yield) as white solid. $^1$H NMR (400 MHz, DMSO-$d_6$) δ 0.88 (s, 3H), 1.07-1.12 (m, 1H), 1.29 (s, 3H), 1.45 (s, 3H), 1.80-1.96 (m, 2H), 2.10 (t, J=5.47 Hz, 1H), 2.16-2.29 (m, 1H), 2.35-2.46 (m, 1H), 3.86 (s, 3H), 4.53 (dd, J=8.68, 1.81 Hz, 1H), 7.19 (br. s, 2H), 7.23 (d, J=8.36 Hz, 1H), 7.67-7.73 (m, 2H), 7.77 (dd, J=8.25, 1.69 Hz, 1H), 8.08 (d, J=1.73 Hz, 1H), 8.21 (d, J=8.79 Hz, 1H), 8.62 (s, 1H). LC-MS (Method A): r.t. 0.91 min, MS (ESI) m/z=430.3 [M+H]$^+$.

Example 114: [3-(4-aminocinnolin-7-yl)-4-[(4,4-dimethyloxolan-2-yl)methoxy]phenyl]boronic Acid (114)

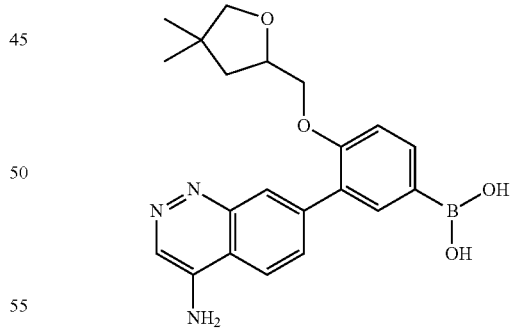

Step 1: Palladium(II) diacetate (4.77 mg, 0.020 mmol), 7-[5-chloro-2-[(4,4-dimethyloxolan-2-yl)methoxy]phenyl]-N-[(2,4-dimethoxyphenyl)methyl]cinnolin-4-amine (227.0 mg, 0.430 mmol), dicyclohexyl-[2-[2,4,6-tri(propan-2-yl)phenyl]phenyl]phosphine (16.21 mg, 0.030 mmol), potassium acetate (125.14 mg, 1.28 mmol) and 4,4,5,5-tetramethyl-2-(4,4,5,5-tetramethyl-1,3,2-dioxaborolan-2-yl)-1,3,2-dioxaborolane (323.81 mg, 1.28 mmol) were dissolved in 1,4-dioxane (5 mL). The mixture was degassed with $N_2$ for 10 min, then stirred at 75° C. for 6 hours. The mixture was filtered over a pad of Celite, washing with MeOH and the filtrate was concentrated in vacuo.

Step 2: The crude material from Step 1 was dissolved in a mixture of DCM (3.11 mL) and trifluoroacetic acid (3.11 mL). The mixture was stirred at room temperature overnight and the volatiles were evaporated. The residue was dissolved in MeOH and loaded onto an SCX cartridge (10 g). The cartridge was washed with MeOH/H$_2$O (9:1) then the product was eluted from the SCX cartridge with a 2M solution of NH$_3$ in MeOH. The volatiles were evaporated and the residue was purified by column chromatography (KP-C18-HS, SNAP 30 g) eluting with a gradient of CH$_3$CN (+0.1% of HCOOH) in water (+0.1% of HCOOH) from 2% to 30%. Appropriate fractions were collected and lyophilized to give partially pure product. This material was submitted to semi-preparative HPLC purification (Chiralpak AD-H (25×2.0 cm), 5 μm, n-Hexane/(Ethanol/Methanol 1/1+0.1% isopropylamine) 75/25% v/v). Fractions containing product were collected and evaporated under reduced pressure, then the residue was dissolved in CH$_3$CN and water and lyophilized to give [3-(4-aminocinnolin-7-yl)-4-[(4,4-dimethyloxolan-2-yl)methoxy]phenyl]boronic acid (45.21 mg, 0.115 mmol, 27.05% yield) as a white powder. $^1$H NMR (400 MHz, DMSO-d$_6$+2 drops of TFA) δ 0.92 (s, 3H), 1.01 (s, 3H), 1.42-1.54 (m, 1H), 1.64-1.79 (m, 1H), 3.23-3.37 (m, 2H), 4.00-4.18 (m, 2H), 4.24-4.33 (m, 1H), 7.20 (d, J=8.37 Hz, 1H), 7.89-7.94 (m, 2H), 7.98 (d, J=1.53 Hz, 1H), 8.03 (dd, J=8.87, 1.55 Hz, 1H), 8.46-8.51 (m, 2H), 9.70 (s, 1H), 9.83 (s, 1H). LC-MS (Method A): r.t. 0.58 min, MS (ESI) m/z=394.16 [M+H]$^+$.

Example 115: [3-(4-aminocinnolin-7-yl)-4-(2-cyclopropylethoxy)phenyl]boronic Acid Formic Acid Salt (115)

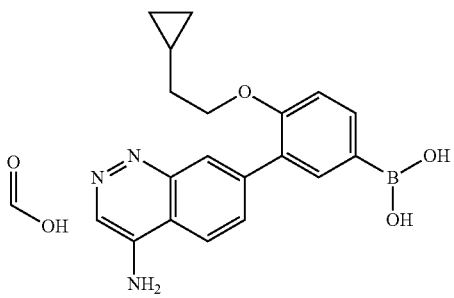

Step 1: A mixture of 7-[5-chloro-2-(2-cyclopropylethoxy)phenyl]-N-[(2,4-dimethoxyphenyl)methyl]cinnolin-4-amine (292.0 mg, 0.600 mmol), 4,4,5,5-tetramethyl-2-(4,4,5,5-tetramethyl-1,3,2-dioxaborolan-2-yl)-1,3,2-dioxaborolane (453.99 mg, 1.79 mmol) and potassium acetate (175.45 mg, 1.79 mmol) in 1,4-dioxane (6.5 mL) was degassed for 10 minutes under argon, then dicyclohexyl-[2-[2,4,6-tri(propan-2-yl)phenyl]phenyl]phosphine (22.73 mg, 0.050 mmol) and palladium(II) diacetate (6.69 mg, 0.030 mmol) were added and the mixture stirred at 80° C. for 2 hours. The mixture was allowed to cool to room temperature then diluted with MeOH and filtered over Celite, washing with MeOH and EtOAc, and the filtrate was evaporated under reduced pressure. LC-MS (Method A): r.t. 1.05 min, MS (ESI) m/z=582.4 [M+H]$^+$.

Step 2: The crude material from Step 1 was dissolved in trifluoroacetic acid (4 mL) and DCM (6 mL) and the mixture was stirred at room temperature for 3 hours, then the volatiles were removed under reduced pressure. The residue was dissolved in MeOH/H$_2$O (9:1) and loaded onto an SCX cartridge (10 g), which was washed with MeOH/H$_2$O (9:1) and then eluted with a 7 M solution of ammonia in MeOH. The basic fractions were collected and evaporated under reduced pressure and the residue was purified by column chromatography (Sfar C18 D, 30 g) eluting with a gradient of MeCN (+0.1% of HCOOH) in water (+0.1% of HCOOH) from 1% to 35%. The appropriate fractions were collected and lyophilized to give [3-(4-aminocinnolin-7-yl)-4-(2-cyclopropylethoxy)phenyl]boronic acid formic acid salt (91 mg, 0.230 mmol, 38.3% yield) as an off-white solid. $^1$H NMR (400 MHz, DMSO-d$_6$+3 drops of TFA) δ −0.13-0.17 (m, 2H), 0.21-0.59 (m, 2H), 0.76 (dtt, J=12.02, 7.32, 3.71 Hz, 1H), 1.61 (q, J=6.45 Hz, 2H), 4.14 (t, J=6.42 Hz, 2H), 7.20 (d, J=8.32 Hz, 1H), 7.84-7.95 (m, 2H), 7.97-8.03 (m, 2H), 8.12 (s, 0.56H, HCOOH), 8.47 (d, J=8.77 Hz, 1H), 8.47 (s, 1H), 9.69 (s, 1H), 9.81 (s, 1H). LC-MS (Method A): r.t. 0.62 min, MS (ESI) m/z=350.3 [M+H]$^+$.

Example 116: [5-(1-amino-4-methylphthalazin-6-yl)-2-cyano-4-methoxyphenyl]boronic Acid Formic Acid Salt (116)

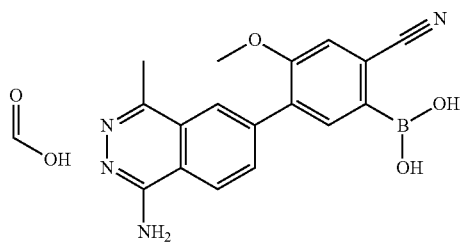

Step 1: A mixture of 2-chloro-4-[1-[(2,4-dimethoxyphenyl)methylamino]-4-methylphthalazin-6-yl]-5-methoxybenzonitrile (169 mg, 0.280 mmol), 4,4,5,5-tetramethyl-2-(4,4,5,5-tetramethyl-1,3,2-dioxaborolan-2-yl)-1,3,2-dioxaborolane (214.15 mg, 0.840 mmol), and potassium acetate (82.76 mg, 0.840 mmol) in 1,4-dioxane (5 mL) was degassed for 10 minutes under argon, then dicyclohexyl-[2-[2,4,6-tri(propan-2-yl)phenyl]phenyl]phosphine (10.72 mg, 0.020 mmol), and palladium(II) diacetate (3.16 mg, 0.010 mmol) were added and the mixture was stirred at 85° C. for 2 hours. The mixture was allowed to cool to room temperature then diluted with MeOH and filtered over Celite, washing with MeOH and EtOAc, and the filtrate was evaporated in vacuo. LC-MS (Method A): r.t. 0.68 min, MS (ESI) m/z=485.3 [M+H]$^+$.

Step 2: The crude material from Step 1 was dissolved in trifluoroacetic acid (1.8 mL) and DCM (3 mL) and the mixture stirred at room temperature for 3 hours, then the volatiles were removed under reduced pressure. The residue was dissolved in MeOH/H$_2$O (9:1), then loaded onto an SCX cartridge (5 g), which was washed with MeOH/H$_2$O (9:1) and then eluted with a 2M solution of ammonia in MeOH. The basic fractions were collected and evaporated under reduced pressure. The residue was purified by column chromatography (Sfar C18 D, 30 g) eluting with a gradient of MeCN (+0.1% of HCOOH) in water (+0.1% of HCOOH) from 1% to 25%. The appropriate fractions were collected and lyophilized to give an off-white solid that was submitted to semi-preparative HPLC purification (CSH C18 (30×100 mm, 3 μm), gradient of MeCN in Water+0.1% of HCOOH from 1.0% to 40.0) to give [5-(1-amino-4-methylphthalazin-6-yl)-2-cyano-4-methoxyphenyl]boronic acid formic acid salt (10 mg, 0.026 mmol, 9.3% yield) as a white solid. $^1$H NMR (400 MHz, DMSO-d$_6$+5 drops of TFA) δ 2.72 (s, 3H), 3.89 (s, 3H), 7.59 (s, 1H), 7.94 (s, 1H), 8.09 (s, 1H from HCOOH), 8.27 (dd, J=8.55, 1.57 Hz, 1H), 8.32 (d, J=1.42 Hz, 1H), 8.70 (d, J=8.52 Hz, 1H), 9.15 (s, 2H). LC-MS (Method A): r.t. 0.48 min, MS (ESI) m/z=335.1 [M+H]$^+$.

Example 117: [3-(4-aminocinnolin-7-yl)-4-cyclobutoxyphenyl]boronic Acid (117)

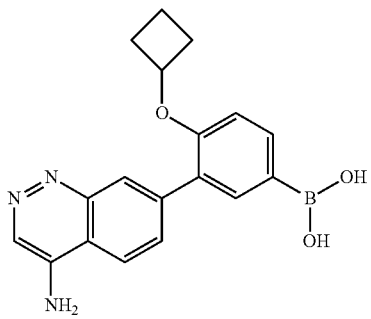 [SMILES: Nc1cnnc2cc(-c3cc(B(O)O)ccc3OC3CCC3)ccc12]

Palladium(II) diacetate (3.3 mg, 0.010 mmol), 7-(5-chloro-2-cyclobutyloxyphenyl)-N-[(2,4-dimethoxyphenyl)methyl]cinnolin-4-amine (140.0 mg, 0.290 mmol), dicyclohexyl-[2-[2,4,6-tri(propan-2-yl)phenyl]phenyl]phosphine (14.02 mg, 0.030 mmol), potassium acetate (86.6 mg, 0.880 mmol), and 4,4,5,5-tetramethyl-2-(4,4,5,5-tetramethyl-1,3,2-dioxaborolan-2-yl)-1,3,2-dioxaborolane (224.08 mg, 0.880 mmol) were dissolved in 1,4-dioxane (2.7 mL) in a microwave vial and degassed for 10 min with N$_2$. The resulting reaction mixture was stirred at 80° C. for 2 hours then it was cooled to room temperature and filtered over Celite, washing with EtOAc. The filtrate was evaporated under reduced pressure and the residue was dissolved in dichloromethane (2 mL) and trifluoroacetic acid (2 mL). The resulting mixture was stirred for 4 hours at room temperature then it was concentrated under reduced pressure. The residue was taken up with MeOH and this solution was loaded onto an SCX cartridge (5 g) which was washed with MeOH/H$_2$O (9:1) and then eluted with a 7M solution of ammonia in MeOH. The basic fractions were collected and evaporated under reduced pressure. The residue was purified by column chromatography (KP-C18-HS, 30 g) eluting with a gradient of MeCN (+0.1% of HCOOH) in water (+0.1% of HCOOH) from 1% to 70%. Appropriate fractions were collected and lyophilised to give [3-(4-aminocinnolin-7-yl)-4-cyclobutyloxyphenyl]boronic acid (34 mg, 0.101 mmol, 34.8% yield) as a white solid. $^1$H NMR (400 MHz, DMSO-d$_6$+3 drops of TFA) δ 1.61-1.70 (m, 1H), 1.71-1.82 (m, 1H), 1.97-2.09 (m, 2H), 2.38-2.48 (m, 2H), 4.72-4.85 (m, 1H), 6.97 (d, J=8.38 Hz, 1H), 7.85 (d, J=8.21 Hz, 1H), 7.95 (s, 1H), 7.99 (d, J=8.93 Hz, 1H), 8.09 (d, J=4.23 Hz, 1H), 8.42-8.48 (m, 2H), 9.64 (br. s, 1H), 9.78 (br. s, 1H). LC-MS (Method A): r.t. 0.56 min, MS (ESI) m/z=336.1 [M+H]$^+$.

Example 118: [3-(4-aminocinnolin-7-yl)-4-(2,2,2-trifluoroethoxy)phenyl]boronic Acid Formic Acid Salt (118)

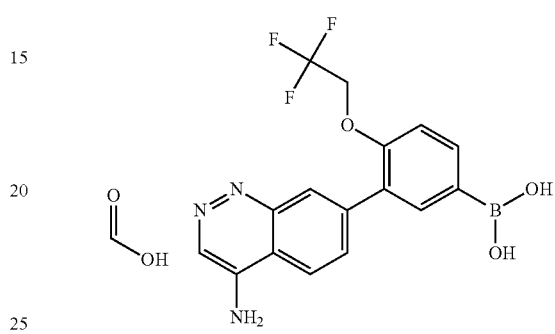

Palladium(II) diacetate (2.63 mg, 0.010 mmol), 7-[5-chloro-2-(2,2,2-trifluoroethoxy)phenyl]-N-[(2,4-dimethoxyphenyl)methyl]cinnolin-4-amine (118.0 mg, 0.230 mmol), dicyclohexyl-[2-[2,4,6-tri(propan-2-yl)phenyl]phenyl]phosphine (8.93 mg, 0.020 mmol), potassium acetate (68.95 mg, 0.700 mmol) and 4,4,5,5-tetramethyl-2-(4,4,5,5-tetramethyl-1,3,2-dioxaborolan-2-yl)-1,3,2-dioxaborolane (178.4 mg, 0.700 mmol) were dissolved in 1,4-dioxane (2.5 mL) in a microwave vial and degassed for 10 min with N$_2$. The resulting reaction mixture was stirred at 80° C. for 1 hour then it was cooled to room temperature and filtered over Celite, washing with EtOAc. The filtrate was evaporated under reduced pressure and the residue was dissolved in dichloromethane (3 mL) and trifluoroacetic acid (2 mL). The resulting mixture was stirred overnight at room temperature then it was evaporated in vacuo. The residue was dissolved in MeOH/H$_2$O (9:1), loaded onto an SCX cartridge and the cartridge was left to stand for 20. The cartridge was then washed with MeOH/H$_2$O (9:1) and eluted with 7 M methanolic ammonia solution. The basic fractions were collected and evaporated under reduced pressure. The residue was purified by column chromatography (Sfar C18 D, 12 g) eluting with a gradient of MeCN (+0.1% of HCOOH) in water (+0.1% of HCOOH) from 5% to 20%. Appropriate fractions were collected and lyophilised to give [3-(4-aminocinnolin-7-yl)-4-(2,2,2-trifluoroethoxy)phenyl]boronic acid formic acid salt (32 mg, 0.078 mmol, 33.91% yield). $^1$H NMR (400 MHz, DMSO-d$_6$+2 drops of TFA) δ 4.88 (q, J=8.78 Hz, 2H), 7.32 (d, J=8.79 Hz, 1H), 7.87-8.01 (m, 4H), 8.13 (s, 1H from HCOOH), 8.43-8.53 (m, 2H), 9.74 (br. s, 1H), 9.84 (br. s, 1H). LC-MS (Method A): r.t. 0.52 min, MS (ESI) m/z=364.1 [M+H]$^+$.

Example 119: [4-(4-aminocinnolin-7-yl)-2-methyl-1,3-benzoxazol-6-yl]boronic Acid Formic Acid Salt (119)

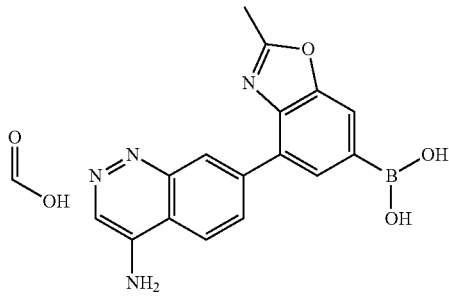

Step 1: A mixture of 7-(6-chloro-2-methyl-1,3-benzoxazol-4-yl)-N-[(2,4-dimethoxyphenyl)methyl]cinnolin-4-amine (136.0 mg, 0.300 mmol), potassium acetate (86.87 mg, 0.890 mmol) and 4,4,5,5-tetramethyl-2-(4,4,5,5-tetramethyl-1,3,2-dioxaborolan-2-yl)-1,3,2-dioxaborolane (224.79 mg, 0.890 mmol) were dissolved in 1,4-dioxane (8.435 mL) and the mixture was degassed with Ar for 10 minutes. Palladium(II) diacetate (3.31 mg, 0.010 mmol) was added and the mixture was degassed for 10 minutes then stirred at 75° C. for 1 hour. The mixture was allowed to cool to room temperature then diluted with EtOAc and MeOH, filtered and the filtrate was concentrated in vacuo. LC-MS (Method A): r.t. 0.93 min, MS (ESI) m/z=553.3 [M+H]$^+$.

Step 2: The crude material from Step 1 was dissolved in DCM (2 mL) and trifluoroacetic acid (2 mL) and stirred overnight at room temperature then the reaction mixture was concentrated under reduced pressure. The residue was dissolved in MeOH/H$_2$O (9:1) and loaded onto an SCX cartridge (5 g). The cartridge was washed with MeOH/H$_2$O (9:1) and the product was eluted from the SCX cartridge with a 2 M solution of NH$_3$ in MeOH. The basic fractions were evaporated and the residue was purified by column chromatography (KP-C18-HS, 6 g+6 g in series) eluting with a gradient of CH$_3$CN (+0.1% of HCOOH) in water (+0.1% of HCOOH) from 2% to 20%. Appropriate fractions were collected and lyophilised to give [4-(4-aminocinnolin-7-yl)-2-methyl-1,3-benzoxazol-6-yl]boronic acid formic acid salt (5.4 mg, 0.015 mmol, 5% yield) as a yellowish solid. $^1$H NMR (400 MHz, DMSO-d$_6$+3 drops of TFA) δ 2.71 (s, 3H), 8.11 (s, 1H), 8.14 (s, 1H from HCOOH), 8.29 (s, 1H), 8.43 (d, J=10.56 Hz, 1H), 8.49 (s, 1H), 8.59 (d, J=9.02 Hz, 1H), 8.71 (d, J=1.54 Hz, 1H), 9.73 (br. s, 1H), 9.89 (br. s, 1H). LC-MS (Method A): r.t. 0.43 min, MS (ESI) m/z=321.1 [M+H]$^+$.

Example 120: [3-(4-aminocinnolin-7-yl)-4-(propan-2-ylcarbamoyl)phenyl]boronic Acid Formic Acid Salt (120)

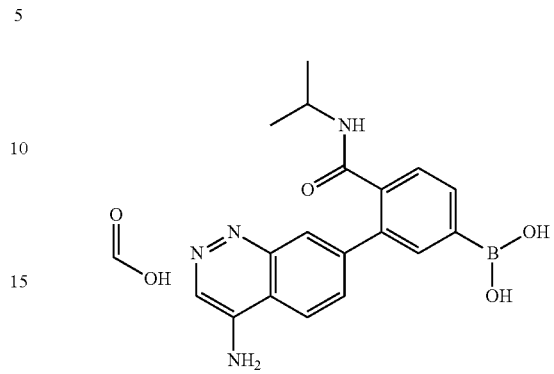

Step 1: Palladium(II) diacetate (2.06 mg, 0.010 mmol), 4-chloro-2-[4-[(2,4-dimethoxyphenyl)methylamino]cinnolin-7-yl]-N-propan-2-ylbenzamide formic acid salt (90 mg, 0.169 mmol), dicyclohexyl-[2-[2,4,6-tri(propan-2-yl)phenyl]phenyl]phosphine (6.99 mg, 0.010 mmol), potassium acetate (53.97 mg, 0.550 mmol) and 4,4,5,5-tetramethyl-2-(4,4,5,5-tetramethyl-1,3,2-dioxaborolan-2-yl)-1,3,2-dioxaborolane (139.65 mg, 0.550 mmol) were dissolved in 1,4-dioxane (3 mL). The mixture was degassed with N$_2$ for 10 min, then stirred at 75° C. for 3 hours. The mixture was filtered over a pad of Celite, washing with MeOH and the filtrate was concentrated in vacuo.

Step 2: The crude material from Step 1 was dissolved in a mixture of DCM (1 mL) and trifluoroacetic acid (1 mL). The mixture was stirred at room temperature overnight and the volatiles were evaporated. The residue was dissolved in MeOH and loaded onto an SCX cartridge (10 g). The cartridge was washed with MeOH/H$_2$O (9:1) then the product was eluted from the SCX cartridge with a 2M solution of NH$_3$ in MeOH. The volatiles were evaporated and the residue was purified by column chromatography (KP-C18-HS, 2×SNAP 12 g in series) eluting with a gradient of CH$_3$CN (+0.1% of HCOOH) in water (+0.1% of HCOOH) from 2% to 25%. Appropriate fractions were collected and lyophilized to give [3-(4-aminocinnolin-7-yl)-4-(propan-2-ylcarbamoyl)phenyl]boronic acid formic acid salt (12 mg, 0.030 mmol, 17.7% yield) as a white powder. $^1$H NMR (400 MHz, DMSO-d$_6$+2 drops of TFA) δ 0.93 (d, J=6.60 Hz, 6H), 3.82-3.93 (m, 1H), 7.50 (d, J=7.51 Hz, 1H), 7.77 (dd, J=8.75, 1.66 Hz, 1H), 7.83 (d, J=1.63 Hz, 1H), 7.89-7.96 (m, 2H), 8.11 (s, 0.77H from HCOOH), 8.21 (d, J=7.81 Hz, 1H), 8.43-8.49 (m, 2H), 9.74 (s, 1H), 9.86 (s, 1H). LC-MS (Method A): r.t. 0.36 min, MS (ESI) m/z=351.26 [M+H]$^+$.

Example 121: [3-(4-aminocinnolin-7-yl)-4-{[(2R,4s,6S)-2,6-dimethyloxan-4-yl]oxy}phenyl]boronic Acid (121)

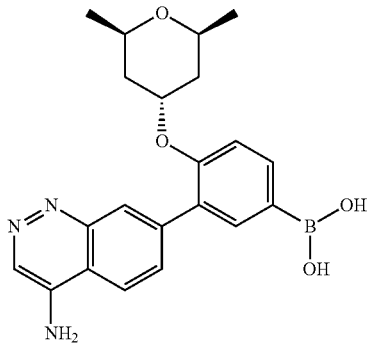 [SMILES: C[C@@H]1C[C@@H](Oc2ccc(B(O)O)cc2-c2ccc3c(N)cnnc3c2)C[C@H](C)O1]

Step 1: Palladium(II) diacetate (4.41 mg, 0.020 mmol), 7-(5-chloro-2-{[(2R,4s,6S)-2,6-dimethyloxan-4-yl]oxy}phenyl)-N-[(2,4-dimethoxyphenyl)methyl]cinnolin-4-amine (210.0 mg, 0.390 mmol), potassium acetate (115.77 mg, 1.18 mmol) and 4,4,5,5-tetramethyl-2-(4,4,5,5-tetramethyl-1,3,2-dioxaborolan-2-yl)-1,3,2-dioxaborolane (299.56 mg, 1.18 mmol) were dissolved in 1,4-dioxane (13 mL) and the mixture was degassed with Ar for 10 minutes. The mixture was then stirred at 75° C. for 3 hours. The mixture was filtered, washing with methanol and the filtrate was concentrated in vacuo. LC-MS (Method A): r.t. 0.98 min, MS (ESI) m/z=426.5 [M+H]$^+$.

Step 2: The crude material from Step 1 was dissolved in DCM (3 mL) and trifluoroacetic acid (3 mL) was stirred for 10 h at room temperature then it was concentrated under reduced pressure. The residue was dissolved in MeOH/H$_2$O (9:1) and loaded onto an SCX cartridge (5 g). The cartridge was washed with MeOH/H$_2$O (9:1) and the product was eluted from the SCX cartridge with a 2 M solution of NH$_3$ in MeOH. The basic fractions were evaporated and the residue was purified by column chromatography (KP-C18-HS, 12 g+12 g in series) eluting with a gradient of CH$_3$CN (+0.1% of HCOOH) in water (+0.1% of HCOOH) from 2% to 20%. Fractions containing the desired compound were collected and lyophilised to give [3-(4-aminocinnolin-7-yl)-4-{[(2R,4s,6S)-2,6-dimethyloxan-4-yl]oxy}phenyl]boronic acid (58 mg, 0.147 mmol, 37.7% yield) as a white solid. $^1$H NMR (400 MHz, DMSO-d$_6$) δ 0.91-1.02 (m, 6H), 1.31-1.43 (m, 2H), 1.80 (br. d, J=12.6 Hz, 2H), 3.51-3.65 (m, 2H), 4.89 (quin, J=2.5 Hz, 1H), 7.15 (d, J=8.5 Hz, 1H), 7.21 (br. s, 2H), 7.78-7.84 (m, 2H), 7.97 (d, J=1.6 Hz, 1H), 8.02 (br. s, 2H), 8.12-8.25 (m, 2H), 8.61 (s, 1H). LC-MS (Method A): r.t. 0.52 min, MS (ESI) m/z=394.2 [M+H]$^+$.

Example 122: [7-(4-aminocinnolin-7-yl)-2-methyl-1,3-benzoxazol-5-yl]boronic Acid Formic Acid Salt (122)

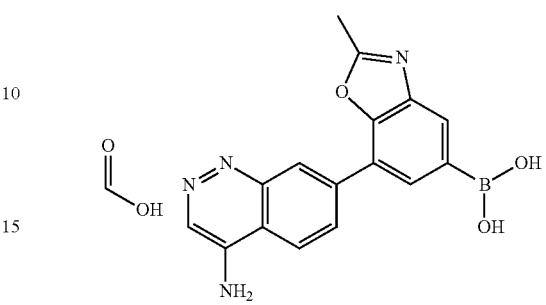

Step 1: Palladium(II) diacetate (0.66 mg, 0 mmol), 7-(5-chloro-2-methyl-1,3-benzoxazol-7-yl)-N-[(2,4-dimethoxyphenyl)methyl]cinnolin-4-amine (27.0 mg, 0.060 mmol), potassium acetate (17.25 mg, 0.180 mmol) and 4,4,5,5-tetramethyl-2-(4,4,5,5-tetramethyl-1,3,2-dioxaborolan-2-yl)-1,3,2-dioxaborolane (44.63 mg, 0.180 mmol) were dissolved in 1,4-dioxane (1.6 mL) and the mixture was degassed with Ar for 10 minutes. The mixture was then stirred at 75° C. for 1 hour. The mixture was filtered, washing with methanol and the filtrate was concentrated in vacuo. LC-MS (Method A): r.t. 0.88 min, MS (ESI) m/z=553.3 [M+H]$^+$.

Step 2: The crude material from Step 1 was dissolved in DCM (2 mL) and trifluoroacetic acid (1 mL) and stirred overnight at room temperature then it was concentrated under reduced pressure. The residue was dissolved in MeOH/H$_2$O (9:1) and loaded onto an SCX cartridge (2 g). The cartridge was washed with MeOH/H$_2$O (9:1) and the product was eluted from the SCX cartridge with a 2 M solution of NH$_3$ in MeOH. The basic fractions were evaporated and the residue was purified by column chromatography (KP-C18-HS, 6 g+6 g in series) eluting with a gradient of CH$_3$CN (+0.1% of HCOOH) in water (+0.1% of HCOOH) from 2% to 20%. Appropriate fractions were collected and lyophilised to give [7-(4-aminocinnolin-7-yl)-2-methyl-1,3-benzoxazol-5-yl]boronic acid formic acid salt (2.5 mg, 0.007 mmol, 11.7% yield) as a brownish solid. $^1$H NMR (400 MHz, DMSO-d$_6$+drops of TFA) δ 2.71 (s, 3H), 8.14 (s, 1H from HCOOH), 8.22 (s, 1H), 8.27 (s, 1H), 8.35 (dd, J=9.02, 1.32 Hz, 1H), 8.45 (d, J=1.10 Hz, 1H), 8.52 (s, 1H), 8.62 (d, J=9.02 Hz, 1H), 9.80 (br. s, 1H), 9.97 (br. s, 1H). LC-MS (Method A): r.t. 0.42 min, MS (ESI) m/z=321.1 [M+H]$^+$.

Example 123: [3-(4-aminocinnolin-7-yl)-4-{[(2R,4R,6S)-2,6-dimethyloxan-4-yl]oxy}phenyl]boronic Acid Formic Acid Salt (123)

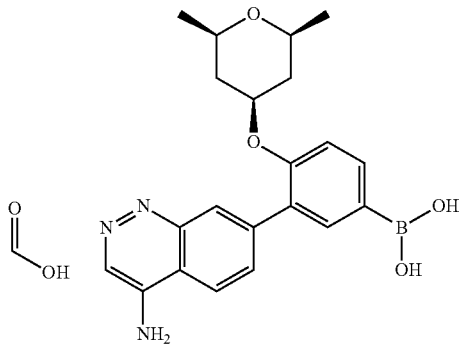

Step 1: Palladium(II) diacetate (2.71 mg, 0.010 mmol), 7-(5-chloro-2-{[(2R,4r,6S)-2,6-dimethyloxan-4-yl]oxy}phenyl)-N-[(2,4-dimethoxyphenyl)methyl]cinnolin-4-amine formic acid salt (140.0 mg, 0.240 mmol), potassium acetate (71.06 mg, 0.720 mmol) and 4,4,5,5-tetramethyl-2-(4,4,5,5-tetramethyl-1,3,2-dioxaborolan-2-yl)-1,3,2-dioxaborolane (183.87 mg, 0.720 mmol) were dissolved in 1,4-dioxane (8.7 mL) and the mixture was degassed with Ar for 10 minutes. The mixture was then stirred at 75° C. for 90 minutes. The mixture was filtered, washing with methanol and the filtrate was concentrated in vacuo. LC-MS (Method A): r.t. 1.00 min, MS (ESI) m/z=626.4 [M+H]$^+$.

Step 2: The crude material from Step 1 was dissolved in DCM (2 mL) and trifluoroacetic acid (2 mL) and stirred overnight at room temperature then concentrated under reduced pressure. The residue was dissolved in MeOH/H$_2$O (9:1) and loaded onto an SCX cartridge (5 g). The cartridge was washed with MeOH/H$_2$O (9:1) and the product was eluted from the SCX cartridge with a 2 M solution of NH$_3$ in MeOH. The basic fractions were evaporated and the residue was purified by column chromatography (KP-C18-HS, 12 g+12 g in series) eluting with a gradient of CH$_3$CN (+0.1% of HCOOH) in water (+0.1% of HCOOH) from 2% to 20%. Appropriate factions were collected and lyophilised to give [3-(4-aminocinnolin-7-yl)-4-{[(2R,4r,6S)-2,6-dimethyloxan-4-yl]oxy}phenyl]boronic acid formic acid salt (10.3 mg, 0.023 mmol, 9.6% yield) as a white solid. $^1$H NMR (400 MHz, DMSO-d$_6$+drops of TFA) δ 1.08-1.20 (m, 8H), 2.11 (dd, J=11.88, 4.40 Hz, 2H), 3.53-3.62 (m, 2H), 4.69-4.79 (m, 1H), 7.31 (d, J=8.58 Hz, 1H), 7.89 (dd, J=8.36, 1.76 Hz, 1H), 7.96 (d, J=1.54 Hz, 1H), 7.98 (dd, J=8.80, 1.54 Hz, 1H), 8.08 (d, J=1.32 Hz, 1H), 8.13 (s, 1H from HCOOH), 8.45-8.50 (m, 2H), 9.69 (s, 1H), 9.81 (s, 1H). LC-MS (Method A): r.t. 0.54 min, MS (ESI) m/z=394.2 [M+H]$^+$.

Example 124: [3-(4-aminocinnolin-7-yl)-4-(pyrrolidine-1-carbonyl)phenyl]boronic Acid (124)

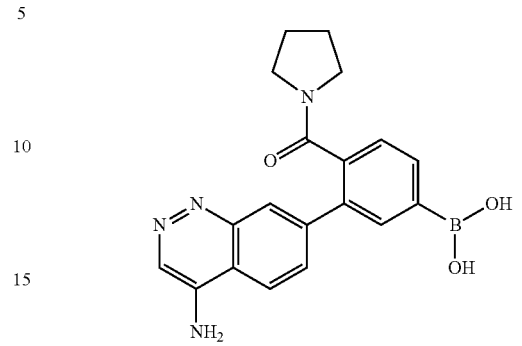

Step 1: Palladium(II) diacetate (3.24 mg, 0.010 mmol), [4-chloro-2-[4-[(2,4-dimethoxyphenyl)methylamino]cinnolin-7-yl]phenyl]-pyrrolidin-1-ylmethanone (145 mg, 0.290 mmol), dicyclohexyl-[2-[2,4,6-tri(propan-2-yl)phenyl]phenyl]phosphine (10.99 mg, 0.020 mmol), potassium acetate (84.87 mg, 0.860 mmol) and 4,4,5,5-tetramethyl-2-(4,4,5,5-tetramethyl-1,3,2-dioxaborolan-2-yl)-1,3,2-dioxaborolane (219.61 mg, 0.860 mmol) were dissolved in 1,4-dioxane (3.5 mL). The mixture was degassed with N$_2$ for 10 min, then stirred at 75° C. for 3 hours. The mixture was filtered over a pad of Celite, washing with MeOH and the filtrate was concentrated in vacuo.

Step 2: The crude material from Step 1 was dissolved in a mixture of DCM (2 mL) and trifluoroacetic acid (2 mL). The mixture was stirred at room temperature overnight and the volatiles were evaporated. The residue was dissolved in MeOH and loaded onto an SCX cartridge (10 g). The cartridge was washed with MeOH/H$_2$O (9:1) then the product was eluted from the SCX cartridge with a 2M solution of NH$_3$ in MeOH. The volatiles were evaporated and the residue was purified by column chromatography (KP-C18-HS, SNAP 30 g) eluting with a gradient of CH$_3$CN (+0.1% of HCOOH) in water (+0.1% of HCOOH) from 2% to 30%. Appropriate fractions were collected and lyophilized to give partially pure product. This material was submitted to semi-preparative HPLC purification (Column: Chiralpak AD-H (25×2.0 cm), 5 μm, mobile phase n-hexane/(EtOH+0.1% isopropylamine) 70/30% v/v, flow rate 17 ml/min). Fractions containing product were collected and evaporated under reduced pressure. The residue was dissolved in CH$_3$CN and water and lyophilized to give [3-(4-aminocinnolin-7-yl)-4-(pyrrolidine-1-carbonyl)phenyl]boronic acid (22 mg, 0.061 mmol, 21.07% yield) as a white powder. $^1$H NMR (400 MHz, DMSO-d$_6$+2 drops of TFA) δ 1.56-1.72 (m, 4H), 2.96 (t, J=6.55 Hz, 2H), 3.30 (t, J=6.74 Hz, 2H), 7.47 (dd, J=7.61, 1.78 Hz, 1H), 7.80-7.87 (m, 2H), 7.97 (dd, J=7.57, 1.14 Hz, 1H), 8.02 (s, 1H), 8.47-8.52 (m, 2H), 9.78 (s, 1H), 9.90 (s, 1H). LC-MS (Method A): r.t. 0.40 min, MS (ESI) m/z=363.22 [M+H]$^+$.

Example 125: [4-(1-amino-4-methylphthalazin-6-yl)-2-methyl-1,3-benzoxazol-6-yl]boronic Acid Formic Acid Salt (125)

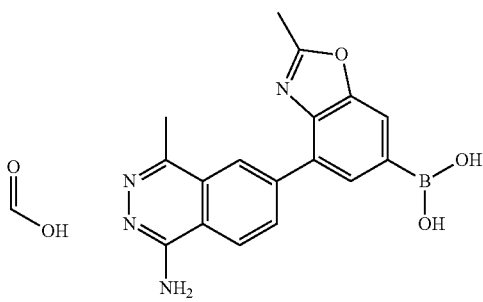 [SMILES: O=CO ; Cc1nc2c(-c3ccc4c(N)nnc(C)c4c3)cc(B(O)O)cc2o1]

Step 1: Palladium(II) diacetate (2.03 mg, 0.010 mmol), 6-(6-chloro-2-methyl-1,3-benzoxazol-4-yl)-N-[(2,4-dimethoxyphenyl)methyl]-4-methylphthalazin-1-amine (86.0 mg, 0.180 mmol), potassium acetate (53.31 mg, 0.540 mmol) and 4,4,5,5-tetramethyl-2-(4,4,5,5-tetramethyl-1,3,2-dioxaborolan-2-yl)-1,3,2-dioxaborolane (137.95 mg, 0.540 mmol) were dissolved in 1,4-dioxane (5.3 mL) and the mixture was degassed with Ar for 10 minutes. The mixture was then stirred at 75° C. for 1 hour. The reaction mixture was filtered, washing with methanol and the filtrate was concentrated in vacuo. LC-MS (Method A): r.t. 0.97 min, MS (ESI) m/z=567.3 [M+H]$^+$.

Step 2: The crude material from Step 1 was dissolved in DCM (2 mL) and trifluoroacetic acid (2 mL) and stirred overnight at room temperature then concentrated under reduced pressure. The residue was dissolved in MeOH/H$_2$O (9:1) and loaded onto an SCX cartridge (2 g). The cartridge was washed with MeOH/H$_2$O (9:1) and the product was eluted from the SCX cartridge with a 2 M solution of NH$_3$ in MeOH. The basic fractions were evaporated and the crude was submitted to semi-preparative HPLC purification [CSH C18 (2.1×50 mm, 1.7 μm), gradient of MeCN (+0.1% of HCOOH) in water (+0.1% of HCOOH) from 3% to 99.9%]. Appropriate fractions were collected and lyophilised to give [4-(1-amino-4-methylphthalazin-6-yl)-2-methyl-1,3-benzoxazol-6-yl]boronic acid formic acid salt (16.1 mg, 0.042 mmol, 23.3% yield) as white solid. $^1$H NMR (400 MHz, DMSO-d$_6$+drops of TFA) δ 2.71 (s, 3H), 2.80 (s, 3H), 8.10-8.14 (m, 1H and 1H from HCOOH), 8.32 (s, 1H), 8.79 (s, 2H), 8.88 (s, 1H), 9.18 (br. s, 2H). LC-MS (Method A): r.t. 0.50 min, MS (ESI) m/z=335.2 [M+H]$^+$.

Example 126: [3-(4-aminocinnolin-7-yl)-4-[(6-oxopiperidin-3-yl)oxy]phenyl]boronic Acid (126)

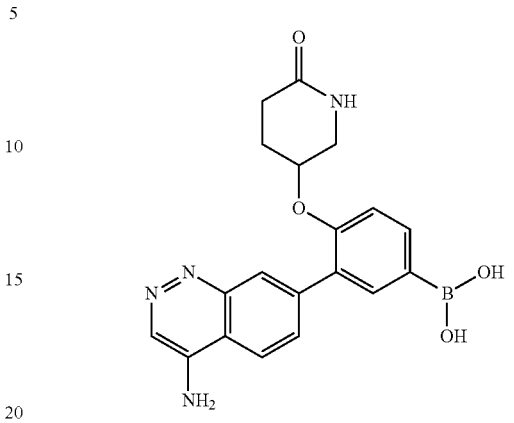

Palladium(II) diacetate (3.68 mg, 0.020 mmol), 5-[4-chloro-2-[[(2,4-dimethoxyphenyl)methylamino]cinnolin-7-yl]phenoxy]piperidin-2-one (170.0 mg, 0.330 mmol), dicyclohexyl-[2-[2,4,6-tri(propan-2-yl)phenyl]phenyl]phosphine (15.62 mg, 0.030 mmol), potassium acetate (96.44 mg, 0.980 mmol) and 4,4,5,5-tetramethyl-2-(4,4,5,5-tetramethyl-1,3,2-dioxaborolan-2-yl)-1,3,2-dioxaborolane (249.54 mg, 0.980 mmol) were dissolved in 1,4-dioxane (3.2 mL) in a microwave vial and degassed for 10 min with N$_2$. The resulting reaction mixture was stirred at 80° C. for 2 hours then it was cooled to room temperature and filtered over Celite, washing with EtOAc. The filtrate was evaporated under reduced pressure and the residue was dissolved in dichloromethane (2 mL) and trifluoroacetic acid (2 mL). The resulting mixture was stirred for 4 hours at room temperature then it was concentrated under reduced pressure. The residue was taken up with MeOH and this solution was loaded onto an SCX cartridge (5 g) which was washed with MeOH/H$_2$O (9:1) and then eluted with a 7M solution of ammonia in MeOH. The basic fractions were collected and evaporated under reduced pressure. The residue was purified by column chromatography (KP-C18-HS, 30 g) eluting with a gradient of MeCN (+0.1% of HCOOH) in water (+0.1% of HCOOH) from 1% to 70%. Appropriate fractions were collected and lyophilised to give 10 mg of partially purified product. This material was further purified by column chromatography (KP-C18-HS, 12 g) eluting with a gradient of MeCN (+0.1% of NH$_4$OH) in water (+0.1% of NH$_4$OH) from 1% to 70%. Appropriate fractions were collected and lyophilised to give [3-(4-aminocinnolin-7-yl)-4-(6-oxopiperidin-3-yl)oxyphenyl]boronic acid (3.5 mg, 0.009 mmol, 2.7% yield) as a white solid. $^1$H NMR (400 MHz, DMSO-d$_6$) δ 1.92-2.08 (m, 2H), 2.09-2.20 (m, 2H), 3.25-3.48 (m, 2H together with signal from water), 4.84-4.96 (m, 1H), 7.18 (s, 2H), 7.24 (d, J=8.42 Hz, 1H), 7.31-7.34 (m, 1H), 7.73 (dd, J=8.75, 1.78 Hz, 1H), 7.84 (dd, J=8.24, 1.74 Hz, 1H), 7.98 (d, J=1.73 Hz, 1H), 8.01-8.10 (br. s, 2H), 8.12 (d, J=1.71 Hz, 1H), 8.16 (d, J=8.82 Hz, 1H), 8.61 (s, 1H). LC-MS (Method B): r.t. 0.41 min, MS (ESI) m/z=379.2 [M+H]$^+$.

Example 127: 2-[4-(4-aminocinnolin-7-yl)-2-(dihydroxyboranyl)phenyl]acetic Acid (127)

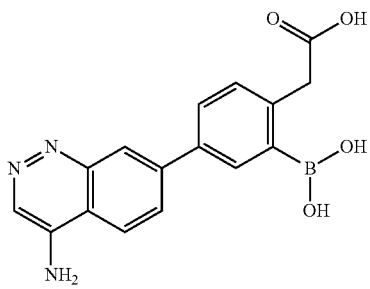 [SMILES: Nc1cnnc2cc(-c3ccc(CC(=O)O)c(B(O)O)c3)ccc12]

Step 1: A mixture of N-[(2,4-dimethoxyphenyl)methyl]-7-(4,4,5,5-tetramethyl-1,3,2-dioxaborolan-2-yl)cinnolin-4-amine (0.93 g, 2.2 mmol), tert-butyl 2-{4-chloro-2-[(1S,2S,6R,8S)-2,9,9-trimethyl-3,5-dioxa-4-boratricyclo[6.1.1.0$^{2,6}$]decan-4-yl]phenyl}acetate (0.89 g, 2.2 mmol), potassium dihydrogen phosphate (299.4 mg, 2.2 mmol) and tripotassium phosphate (933.99 mg, 4.4 mmol) in 1,4-dioxane (35 mL) and water (8 mL) was degassed for 10 min under argon, then [1,1'-bis(di-tert-butylphosphino)ferrocene]dichloropalladium(II) (143.83 mg, 0.220 mmol) was added and the mixture was heated at 85° C. for 4 hours. The mixture was allowed to cool to room temperature, diluted with EtOAc and filtered over Celite, washing with EtOAc. The filtrate was concentrated under reduced pressure and the residue was purified by column chromatography (Sfar Amino D, 55 g) eluting with a gradient of EtOAc in cyclohexane from 0% to 100% to give crude tert-butyl 2-[4-(4-{[(2,4-dimethoxyphenyl)methyl]amino}cinnolin-7-yl)-2-[(1S,2S,6R,8S)-2,9,9-trimethyl-3,5-dioxa-4-boratricyclo[6.1.1.02,6]decan-4-yl]phenyl]acetate (730 mg) as a light brown solid. Purity by LC-MS was ~62%. This material was used in the next step without further purification. LC-MS (Method A): r.t. 1.19 min, MS (ESI) m/z=664.3 [M+H]$^+$.

Step 2: The material from step 1 was dissolved in DCM (6 mL) and trifluoroacetic acid (3 mL) and the mixture stirred for 3 hours at room temperature. The volatiles were removed under reduced pressure and the residue thus obtained was submitted to semi-preparative HPLC purification [first purification conditions (CSH C18 (2.1×50 mm, 1.7 µm), gradient of MeCN in water (+0.1% of HCOOH) from 3% to 99.9%; second purification conditions Kinetex 1.7 um EVO C18 100A (2.1×50 mm, 1.7 µm), gradient of MeCN in 10 mM aqueous ammonium bicarbonate solution adjusted to pH 10 with ammonia from 3% to 99.9%). Appropriate fractions were lyophilized to give 2-[4-(4-aminocinnolin-7-yl)-2-boronophenyl]acetic acid partially salified as its ammonium salt (15.5 mg, 0.048 mmol) as a light yellow solid. $^1$H NMR (400 MHz, DMSO-d$_6$+3 drops of TFA) δ 3.79 (s, 2H), 7.31 (d, J=8.14 Hz, 1H), 7.75 (s, 1H), 7.93-8.21 (m, 3H), 8.46 (s, 1H), 8.53 (d, J=8.95 Hz, 1H), 9.70 (s, 1H), 9.86 (s, 1H). LC-MS (Method A): r.t. 0.47 min, MS (ESI) m/z=324.1 [M+H]$^+$.

Example 128: [7-(4-aminocinnolin-7-yl)-2,2-difluoro-2H-1,3-benzodioxol-5-yl]boronic Acid (128)

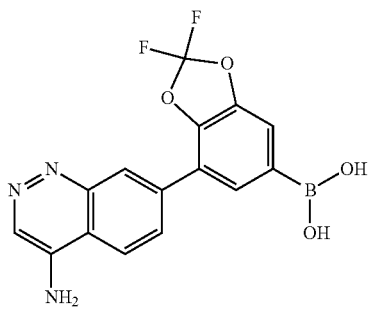 [SMILES: Nc1cnnc2cc(-c3cc(B(O)O)cc4c3OC(F)(F)O4)ccc12]

Step 1: Palladium(II) diacetate (4.62 mg, 0.020 mmol), 7-(6-chloro-2,2-difluoro-1,3-benzodioxol-4-yl)-N-[(2,4-dimethoxyphenyl)methyl]cinnolin-4-amine (200 mg, 0.410 mmol), dicyclohexyl-[2-[2,4,6-tri(propan-2-yl)phenyl]phenyl]phosphine (15.7 mg, 0.030 mmol), potassium acetate (121.19 mg, 1.23 mmol), and 4,4,5,5-tetramethyl-2-(4,4,5,5-tetramethyl-1,3,2-dioxaborolan-2-yl)-1,3,2-dioxaborolane (313.59 mg, 1.23 mmol) were dissolved in 1,4-dioxane (5 mL). The mixture was degassed with N$_2$ for 10 min, then stirred at 75° C. for 3 hours. The mixture was filtered over a pad of Celite, washing with MeOH and the filtrate was concentrated in vacuo.

Step 2: The crude material from Step 1 was dissolved in a mixture of DCM (3 mL) and trifluoroacetic acid (3 mL). The mixture was stirred at room temperature overnight and the volatiles were evaporated. The residue was dissolved in MeOH and loaded onto an SCX cartridge (10 g). The cartridge was washed with MeOH/H$_2$O (9:1) then the product was eluted from the SCX cartridge with a 2M solution of NH$_3$ in MeOH. The volatiles were evaporated and the residue was purified by column chromatography (KP-C18-HS, SNAP 30 g) eluting with a gradient of CH$_3$CN (+0.1% of HCOOH) in water (+0.1% of HCOOH) from 2% to 30% to give partially pure product. This material was purified further by column chromatography (KP-C18-HS, SNAP 11 g) eluting with a gradient of CH$_3$CN in water (+0.1% of ammonium hydroxide) from 5% to 85%. Appropriate fractions were collected and lyophilized to give [7-(4-aminocinnolin-7-yl)-2,2-difluoro-1,3-benzodioxol-5-yl]boronic acid (31 mg, 0.090 mmol, 21.82% yield) as a white powder. $^1$H NMR (400 MHz, DMSO-d$_6$+2 drops of TFA) δ 7.80 (s, 1H), 8.12 (s, 1H), 8.18 (dd, J=8.92, 1.82 Hz, 1H), 8.25 (d, J=1.66 Hz, 1H), 8.50 (s, 1H), 8.61 (d, J=8.96 Hz, 1H), 9.83 (s, 1H), 9.99 (s, 1H). $^{19}$F NMR (377 MHz, DMSO-d$_6$) δ −48.74. LC-MS (Method A): r.t. 0.93 min, MS (ESI) m/z=346.08 [M+H]$^+$.

Example 129: [3-(4-aminoquinolin-6-yl)-4-methoxyphenyl]boronic Acid Formic Acid Salt (129)

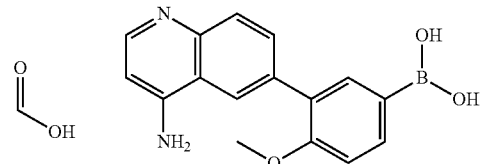

Step 1: Palladium(II) diacetate (14.16 mg, 0.060 mmol), 6-(5-chloro-2-methoxyphenyl)-N-[(2,4-dimethoxyphenyl)methyl]quinolin-4-amine (590.0 mg, 1.26 mmol), potassium acetate (371.45 mg, 3.78 mmol) and 4,4,5,5-tetramethyl-2-(4,4,5,5-tetramethyl-1,3,2-dioxaborolan-2-yl)-1,3,2-dioxaborolane (961.14 mg, 3.78 mmol) were dissolved in 1,4-dioxane (34 mL) and the mixture was degassed with Ar for 10 minutes. The mixture was then stirred overnight at 75° C. The reaction was not complete, so further palladium(II) diacetate (3.54 mg, 0.015 mmol), potassium acetate (92.94 mg, 0.95 mmol) and 4,4,5,5-tetramethyl-2-(4,4,5,5-tetramethyl-1,3,2-dioxaborolan-2-yl)-1,3,2-dioxaborolane (240.28 mg, 0.95 mmol) were added and the mixture was stirred at 90° C. for another 4 hours. The reaction mixture was filtered, washing with methanol and the filtrate was concentrated in vacuo. LC-MS (Method A): r.t. 0.94 min, MS (ESI) m/z=527.3 [M+H]$^+$.

Step 2: The crude material from Step 1 was dissolved in DCM (3 mL) and trifluoroacetic acid (3 mL) and stirred overnight at room temperature then it was concentrated under reduced pressure. The residue was dissolved in MeOH/H$_2$O (9:1) and loaded onto an SCX cartridge (20 g). The cartridge was washed with MeOH/H$_2$O (9:1) and the product was eluted from the SCX cartridge with a 2 M solution of NH$_3$ in MeOH. The basic fractions were evaporated and the residue was purified by column chromatography (KP-C18-HS, 12 g+12 g in series) eluting with a gradient of CH$_3$CN (+0.1% of HCOOH) in water (+0.1% of HCOOH) from 2% to 30%. Appropriate fractions were collected and lyophilised to give [3-(4-aminoquinolin-6-yl)-4-methoxyphenyl]boronic acid formic acid salt (53.6 mg, 0.158 mmol, 12.5% yield) as a white solid. $^1$H NMR (400 MHz, DMSO-d$_6$+drops of TFA) δ 3.79 (d, J=1.54 Hz, 3H), 6.78 (d, J=6.82 Hz, 1H), 7.08-7.16 (m, 1H), 7.82-7.91 (m, 3H), 8.04-8.13 (m, 2H), 8.33-8.42 (m, 1H), 8.48 (d, J=1.32 Hz, 1H), 8.91 (br. s, 2H). LC-MS (Method A): r.t. 0.44 min, MS (ESI) m/z=295.1 [M+H]$^+$.

Example 130: [3-(8-amino-1,7-naphthyridin-3-yl)-4-methoxyphenyl]boronic Acid Formic Acid Salt (130)

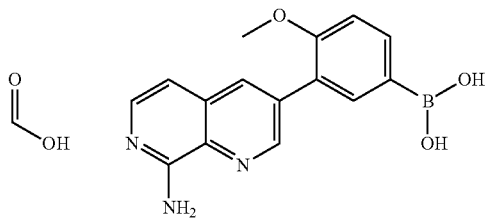 [SMILES: O=CO ; COc1ccc(B(O)O)cc1-c1cnc2c(N)nccc2c1]

Palladium(II) diacetate (4.12 mg, 0.020 mmol), 3-(5-chloro-2-methoxyphenyl)-N-[(2,4-dimethoxyphenyl)methyl]-1,7-naphthyridin-8-amine (160.0 mg, 0.370 mmol), dicyclohexyl-[2-[2,4,6-tri(propan-2-yl)phenyl]phenyl]phosphine (14.0 mg, 0.030 mmol), potassium acetate (108.07 mg, 1.1 mmol), and 4,4,5,5-tetramethyl-2-(4,4,5,5-tetramethyl-1,3,2-dioxaborolan-2-yl)-1,3,2-dioxaborolane (279.63 mg, 1.1 mmol) were dissolved in 1,4-dioxane (3.5 mL) in a microwave vial and degassed for 10 min with N$_2$. The resulting reaction mixture was stirred at 80° C. for 1 hour then it was cooled to room temperature and filtered over Celite, washing with MeOH. The filtrate was evaporated under reduced pressure and the residue was dissolved in dichloromethane (4 mL) and trifluoroacetic acid (3 mL). The resulting mixture was stirred overnight at room temperature then it was evaporated in vacuo. The residue was dissolved in MeOH/H$_2$O (9:1), loaded onto an SCX cartridge and the cartridge was left to stand for 20 min. The cartridge was then washed with MeOH/H$_2$O (9:1) and eluted with 7 M methanolic ammonia solution. The basic fractions were collected and evaporated under reduced pressure. The residue was purified by column chromatography (Sfar C18 D, 12 g) eluting with a gradient of MeCN (+0.1% of HCOOH) in water (+0.1% of HCOOH) from 5% to 20%. Appropriate fractions were collected and lyophilised to give [3-(8-amino-1,7-naphthyridin-3-yl)-4-methoxyphenyl]boronic acid formic acid salt (87 mg, 0.255 mmol, 68.91% yield) as a white solid. $^1$H NMR (400 MHz, DMSO-d$_6$) δ 6.90 (br. s, 2H), 6.97 (d, J=5.73 Hz, 1H), 7.18 (d, J=8.21 Hz, 1H), 7.84-7.92 (m, 3H), 8.02 (br. s, 2H), 8.15 (s, 1H from HCOOH), 8.20 (d, J=2.16 Hz, 1H), 8.90 (d, J=2.11 Hz, 1H). LC-MS (Method A): r.t. 0.46 min, MS (ESI) m/z=296.2 [M+H]$^+$.

Example 131: [3-(1-amino-4-methylphthalazin-6-yl)-4-(difluoromethoxy)phenyl]boronic Acid Formic Acid Salt (131)

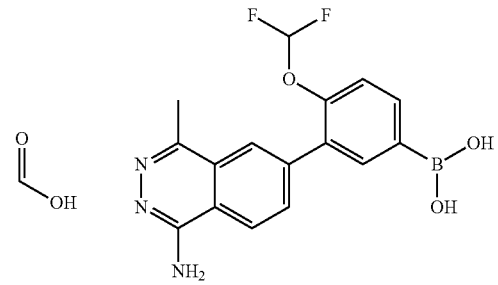 [SMILES: O=CO ; Cc1nnc(N)c2ccc(-c3cc(B(O)O)ccc3OC(F)F)cc12]

Palladium(II) diacetate (2.31 mg, 0.010 mmol), 6-[5-chloro-2-(difluoromethoxy)phenyl]-N-[(2,4-dimethoxyphenyl)methyl]-4-methylphthalazin-1-amine (100.0 mg, 0.210 mmol), dicyclohexyl-[2-[2,4,6-tri(propan-2-yl)phenyl]phenyl]phosphine (7.85 mg, 0.020 mmol), potassium acetate (60.59 mg, 0.620 mmol), and 4,4,5,5-tetramethyl-2-(4,4,5,5-tetramethyl-1,3,2-dioxaborolan-2-yl)-1,3,2-dioxaborolane (156.78 mg, 0.620 mmol) were dissolved in 1,4-dioxane (2.2 mL) in a microwave vial and degassed for 10 min with N$_2$. The resulting reaction mixture was stirred at 80° C. for 1 hour then it was cooled to room temperature and filtered over Celite, washing with MeOH. The filtrate was evaporated under reduced pressure and the residue was dissolved in dichloromethane (3 mL) and trifluoroacetic acid (2 mL). The resulting mixture was stirred overnight at room temperature then it was evaporated in vacuo. The residue was dissolved in MeOH/H$_2$O (9:1), loaded onto an SCX cartridge (10 g) and the cartridge was left to stand for 20 min. The cartridge was then washed with MeOH/H$_2$O (9:1) and eluted with 7 M methanolic ammonia solution. The basic fractions were collected and evaporated under reduced pressure. The residue was purified by flash chromatography (Sfar C18 D, 12 g) eluting with a gradient of MeCN (+0.1% of HCOOH) in water (+0.1% of HCOOH) from 5% to 20%. Appropriate fractions were collected and lyophilised to give [3-(1-amino-4-methylphthalazin-6-yl)-4-(difluoromethoxy)phenyl]boronic acid formic acid salt (31 mg, 0.079 mmol, 37.61% yield) as a white solid. $^1$H NMR (400 MHz, DMSO-d$_6$+2 drops of TFA) δ 2.74 (s, 3H), 7.32 (t, J=73.56

Hz, 1H), 7.37 (d, J=8.21 Hz, 1H), 7.97 (dd, J=8.24, 1.71 Hz, 1H), 8.05 (d, J=1.70 Hz, 1H), 8.13 (s, 1H from HCOOH), 8.26 (dd, J=8.52, 1.71 Hz, 1H), 8.33 (d, J=1.68 Hz, 1H), 8.74 (d, J=8.55 Hz, 1H), 9.16 (br. s, 2H).

Example 132: 7-[2-(difluoromethoxy)-5-[(1S,2S,6R,8S)-2,6,9,9-tetramethyl-3,5-dioxa-4-boratricyclo[6.1.1.0$^{2,6}$]decan-4-yl]phenyl]cinnolin-4-amine (132)

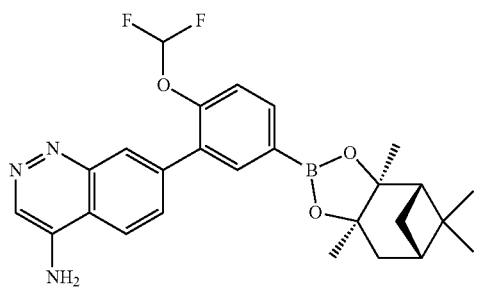 [SMILES: CC1(C)[C@H]2C[C@@H]1[C@]1(C)OB(c3ccc(OC(F)F)c(-c4ccc5c(N)cnnc5c4)c3)O[C@]1(C)C2]

A suspension of [3-(4-aminocinnolin-7-yl)-4-(difluoromethoxy)phenyl]boronic acid (60.0 mg, 0.180 mmol) and (1S,3R,4S,5S)-3,4,6,6-tetramethylbicyclo[3.1.1]heptane-3,4-diol (32.73 mg, 0.180 mmol) in THF (1.9 mL) was stirred overnight at 50° C., then the mixture was concentrated in vacuo. The residue was triturated with diethyl ether (2 mL) for two hours, the solvent was decanted and the solid residue was collected and dried in the oven at 50° C. to give 7-[2-(difluoromethoxy)-5-[(1S,2S,6R,8S)-2,6,9,9-tetramethyl-3,5-dioxa-4-boratricyclo[6.1.1.0$^{2,6}$]decan-4-yl]phenyl]cinnolin-4-amine (58.2 mg, 0.121 mmol, 67.5% yield) as a white solid. $^1$H NMR (400 MHz, DMSO-d$_6$) δ 0.89 (s, 3H), 1.28 (s, 3H), 1.30 (d, J=10.78 Hz, 1H), 1.43 (s, 3H), 1.47 (s, 3H), 1.92-2.03 (m, 2H), 2.06 (t, J=5.61 Hz, 1H), 2.13-2.22 (m, 1H), 2.29 (dd, J=14.75, 4.18 Hz, 1H), 7.25 (s, 2H), 7.30 (t, J=73.73 Hz, 1H), 7.39 (d, J=8.58 Hz, 1H), 7.68 (dd, J=8.58, 1.76 Hz, 1H), 7.78-7.82 (s, 2H), 8.09 (d, J=1.54 Hz, 1H), 8.26 (d, J=8.58 Hz, 1H), 8.65 (s, 1H). LC-MS (Method A): r.t. 0.96 min, MS (ESI) m/z=480.4 [M+H]$^+$.

Example 133: 7-{5-[(3aR,6aS)-3a,6a-dimethyl-hexahydrocyclopenta[d][1,3,2]dioxaborol-2-yl]-2-methoxyphenyl}cinnolin-4-amine (133)

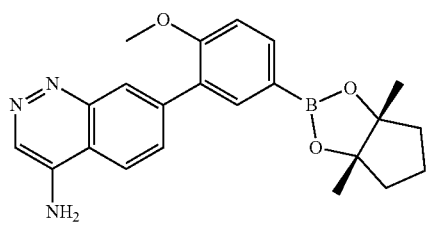 [SMILES: COc1ccc(B2O[C@]3(C)CCC[C@]3(C)O2)cc1-c1ccc2c(N)cnnc2c1]

A suspension of [3-(4-aminocinnolin-7-yl)-4-methoxyphenyl]boronic acid (50.0 mg, 0.170 mmol) and (1R,2S)-1,2-dimethylcyclopentane-1,2-diol (22.06 mg, 0.170 mmol) in THF (2.4 mL) was stirred overnight at 45° C., then the mixture was concentrated in vacuo. The residue was triturated with diethyl ether (2.5 mL) for one hour, the solvent was decanted and the solid residue was collected and dried in the oven at 50° C. to give 7-{5-[(3aR,6aS)-3a,6a-dimethyl-hexahydrocyclopenta[d][1,3,2]dioxaborol-2-yl]-2-methoxyphenyl}cinnolin-4-amine (54.3 mg, 0.139 mmol, 82.33% yield) as a white solid. $^1$H NMR (400 MHz, DMSO-d$_6$) δ 1.37 (s, 6H), 1.49-1.70 (m, 4H), 1.96 (dd, J=12.32, 5.06 Hz, 2H), 3.86 (s, 3H), 7.17-7.23 (m, 3H), 7.66-7.71 (m, 2H), 7.73 (dd, J=8.14, 1.76 Hz, 1H), 8.07 (d, J=1.76 Hz, 1H), 8.20 (d, J=8.80 Hz, 1H), 8.62 (s, 1H). LC-MS (Method A): r.t. 0.76 min, MS (ESI) m/z=390.3 [M+H]$^+$.

Example 134: [5-(4-aminocinnolin-7-yl)-4-methoxy-2-methylphenyl]boronic Acid Formic Acid Salt (134)

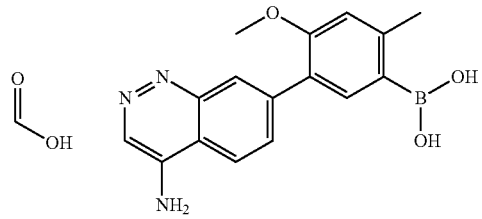 [SMILES: O=CO ; COc1cc(C)c(B(O)O)cc1-c1ccc2c(N)cnnc2c1]

Step 1: Palladium(II) diacetate (8.36 mg, 0.040 mmol), 7-(5-chloro-2-methoxy-4-methylphenyl)-N-[(2,4-dimethoxyphenyl)methyl]cinnolin-4-amine (335.0 mg, 0.740 mmol), potassium acetate (219.21 mg, 2.23 mmol) and 4,4,5,5-tetramethyl-2-(4,4,5,5-tetramethyl-1,3,2-dioxaborolan-2-yl)-1,3,2-dioxaborolane (567.22 mg, 2.23 mmol) were dissolved in 1,4-dioxane (12.5 mL) and the mixture was degassed with Ar for 10 minutes. The mixture was then stirred overnight at 95° C. The mixture was filtered, washing with methanol and the filtrate was concentrated in vacuo. LC-MS (Method A): r.t. 0.99 min, MS (ESI) m/z=542.4 [M+H]$^+$.

Step 2: The crude material from Step 1 was dissolved in DCM (8 mL) and trifluoroacetic acid (6.5 mL) and stirred for seven hours at room temperature then it was concentrated under reduced pressure. The residue was dissolved in MeOH/H$_2$O (9:1) and loaded onto an SCX cartridge (20 g). The cartridge was washed with MeOH/H$_2$O (9:1) and the product was eluted from the SCX cartridge with a 2 M solution of NH$_3$ in MeOH. The basic fractions were evaporated and the residue was purified by column chromatography (KP-C18-HS, 12 g+12 g in series) eluting with a gradient of CH$_3$CN (+0.1% of HCOOH) in water (+0.1% of HCOOH) from 2% to 30%. Appropriate fractions were collected and concentrated to give [5-(4-aminocinnolin-7-yl)-4-methoxy-2-methylphenyl]boronic acid formic acid salt (19 mg, 0.053 mmol, 7.2% yield) as a yellow solid. $^1$H NMR (400 MHz, DMSO-d$_6$+drops of TFA) δ 2.53 (s, 3H), 3.84 (s, 3H), 6.97-7.01 (m, 1H), 7.67 (s, 1H), 7.88-8.06 (m, 2H), 8.11 (s, 1H from HCOOH), 8.39-8.47 (m, 2H), 9.64 (br. s, 1H), 9.79 (br. s, 1H). LC-MS (Method A): r.t. 0.47 min, MS (ESI) m/z=310.1 [M+H]$^+$.

Example 135: 7-(5-{2,4-dioxa-3-boratetracyclo[5.3.1.1⁵,⁹.0¹,⁵]dodecan-3-yl}-2-methoxyphenyl)cinnolin-4-amine (135)

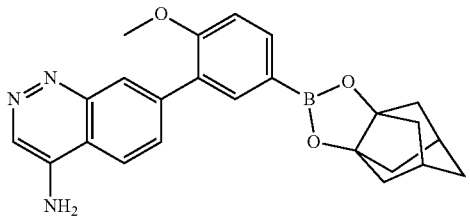 [SMILES: COc1ccc(B2OC34CC5CC(C3)CC4(C5)O2)cc1-c1ccc2c(N)cnnc2c1]

A suspension of [3-(4-aminocinnolin-7-yl)-4-methoxyphenyl]boronic acid (30.0 mg, 0.100 mmol) and tricyclo[3.3.1.0³,⁷]nonane-3,7-diol (20.38 mg, 0.130 mmol) in THF (2.5 mL) was stirred overnight at 50° C., then the mixture was concentrated in vacuo. The residue was triturated with diethyl ether (3 mL) for four hours, the solvent was decanted and the solid residue was collected and dried to give 7-(5-{2,4-dioxa-3-boratetracyclo[5.3.1.1⁵,⁹.0¹,⁵]dodecan-3-yl}-2-methoxyphenyl)cinnolin-4-amine (15.9 mg, 0.038 mmol, 37.84% yield) as a white solid. ¹H NMR (400 MHz, DMSO-d₆) δ 1.49 (br. s, 2H), 1.95 (d, J=10.56 Hz, 4H), 2.09 (d, J=10.12 Hz, 4H), 2.47-2.49 (m, 2H), 3.86 (s, 3H), 7.19 (s, 2H), 7.23 (d, J=8.36 Hz, 1H), 7.69 (dd, J=8.69, 1.65 Hz, 1H), 7.73 (d, J=1.54 Hz, 1H), 7.78 (dd, J=8.25, 1.65 Hz, 1H), 8.08 (d, J=1.54 Hz, 1H), 8.21 (d, J 8.80 Hz, 1H), 8.62 (s, 1H). LC-MS (Method A): r.t. 0.43 min, MS (ESI) m/z=296.2 [peak corresponding to the corresponding boronic acid formed via in situ hydrolysis, M+H]⁺.

Example 136: 7-{2-methoxy-5-[(1s,5s)-2,4-dioxa-3-boratricyclo[3.3.3.0¹,⁵]undecan-3-yl]phenyl}cinnolin-4-amine (136)

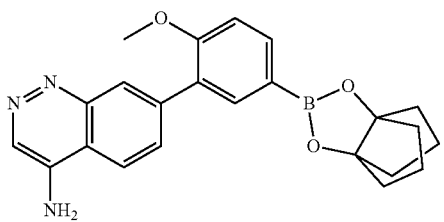 [SMILES: COc1ccc(B2OC34CCCC3(CCC4)O2)cc1-c1ccc2c(N)cnnc2c1]

A mixture of [3-(4-aminocinnolin-7-yl)-4-methoxyphenyl]boronic acid (25 mg, 0.080 mmol) and 1,2,3,4,5,6-hexahydropentalene-3a,6a-diol (40.16 mg, 0.080 mmol) in THF (1.25 mL) was stirred at 45° C. for 48 hours. The volatiles were removed under reduced pressure and the resulting residue was dissolved in MeOH and loaded onto an SCX cartridge. The cartridge was eluted first with MeOH and then with a 2M methanolic NH₃ solution to elute the boronic ester product. Basic fractions were evaporated and the residue was purified by column chromatography (KP-C18-HS, SNAP 30 g) eluting with a gradient of CH₃CN (+0.1% of HCOOH) in water (+0.1% of HCOOH) from 2% to 30%. Appropriate fractions were collected and lyophilized to give 7-{2-methoxy-5-[(1s,5s)-2,4-dioxa-3-boratricyclo[3.3.3.0¹,⁵]undecan-3-yl]phenyl}cinnolin-4-amine (7.17 mg, 0.018 mmol, 21.09% yield) as a pale-yellow powder. ¹H NMR (400 MHz, Chloroform-d) δ 1.62-1.91 (m, 8H), 1.99-2.08 (m, 4H), 3.88 (s, 3H), 4.76 (s, 2H), 7.05 (d, J=8.32 Hz, 1H), 7.75 (d, J=8.74 Hz, 1H), 7.80-7.90 (m, 2H), 7.94 (d, J=1.68 Hz, 1H), 8.53 (d, J=1.72 Hz, 1H), 8.75 (s, 1H). LC-MS (Method A): r.t. 0.79 min, MS (ESI) m/z=402.29 [M+H]⁺.

Example 137: [5-(4-aminocinnolin-7-yl)-4-methoxy-2-(methoxymethyl)phenyl]boronic Acid Formic Acid Salt (137)

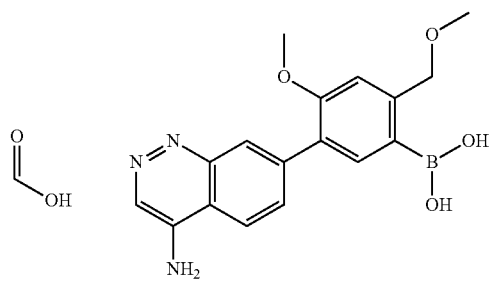 [SMILES: O=CO ; COCc1cc(OC)c(-c2ccc3c(N)cnnc3c2)cc1B(O)O]

Step 1: Palladium(II) diacetate (4.91 mg, 0.020 mmol), 7-[5-chloro-2-methoxy-4-(methoxymethyl)phenyl]-N-[(2,4-dimethoxyphenyl)methyl]cinnolin-4-amine (210.0 mg, 0.440 mmol), dicyclohexyl-[2-[2,4,6-tri(propan-2-yl)phenyl]phenyl]phosphine (16.69 mg, 0.040 mmol), potassium acetate (128.82 mg, 1.31 mmol), and 4,4,5,5-tetramethyl-2-(4,4,5,5-tetramethyl-1,3,2-dioxaborolan-2-yl)-1,3,2-dioxaborolane (333.32 mg, 1.31 mmol) were dissolved in 1,4-dioxane (5 mL). The mixture was degassed with N₂ for 10 min, then stirred at 75° C. for 20 hours. The mixture was filtered over a pad of Celite, washing with MeOH and the filtrate was concentrated in vacuo.

Step 2: The crude material from Step 1 was dissolved in a mixture of DCM (3 mL) and trifluoroacetic acid (3 mL). The mixture was stirred at room temperature overnight and the volatiles were evaporated. The residue was dissolved in MeOH and loaded onto an SCX cartridge (10 g). The cartridge was washed with MeOH/H₂O (9:1) then the product was eluted from the SCX cartridge with a 2M solution of NH₃ in MeOH. The volatiles were evaporated and the residue was purified by column chromatography (KP-C18-HS, SNAP 30 g) eluting with a gradient of CH₃CN (+0.1% of HCOOH) in water (+0.1% of HCOOH) from 2% to 30% to give [5-(4-aminocinnolin-7-yl)-4-methoxy-2-(methoxymethyl)phenyl]boronic acid formic acid salt (7.05 mg, 0.018 mmol, 4.1% yield) as a pale-yellow powder. ¹H NMR (400 MHz, DMSO-d₆+2 drops of TFA) δ 3.37 (s, 3H), 3.87 (s, 3H), 4.69 (s, 2H), 7.22 (s, 1H), 7.72 (s, 1H), 7.99 (dd, J=8.87, 1.65 Hz, 1H), 8.04 (d, J=1.57 Hz, 1H), 8.13 (s, 0.59H from HCOOH), 8.45-8.49 (m, 2H), 9.69 (s, 1H), 9.83 (s, 1H). LC-MS (Method A): r.t. 0.46 min, MS (ESI) m/z=340.19 [M+H]⁺.

Example 138: [7-(4-aminocinnolin-7-yl)-2,3-dihydro-1-benzofuran-5-yl]boronic Acid Formic Acid Salt (138)

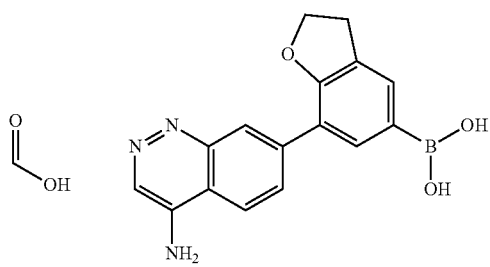 [SMILES: O=CO ; Nc1cnnc2cc(-c3cc(B(O)O)cc4c3OCC4)ccc12]

Step 1: Palladium(II) diacetate (3.63 mg, 0.020 mmol), 7-(5-chloro-2,3-dihydro-1-benzofuran-7-yl)-N-[(2,4-dimethoxyphenyl)methyl]cinnolin-4-amine (145.0 mg, 0.320 mmol), dicyclohexyl-[2-[2,4,6-tri(propan-2-yl)phenyl]phenyl]phosphine (12.35 mg, 0.030 mmol), potassium acetate (95.31 mg, 0.970 mmol), and 4,4,5,5-tetramethyl-2-(4,4,5,5-tetramethyl-1,3,2-dioxaborolan-2-yl)-1,3,2-dioxaborolane (246.62 mg, 0.970 mmol) were dissolved in 1,4-dioxane (4 mL). The mixture was degassed with $N_2$ for 10 min, then stirred at 75° C. for 3 hours. The mixture was filtered over a pad of Celite, washing with MeOH and the filtrate was concentrated in vacuo.

Step 2: The crude material from Step 1 was dissolved in a mixture of DCM (3 mL) and trifluoroacetic acid (3 mL). The mixture was stirred at room temperature overnight and the volatiles were evaporated. The residue was dissolved in MeOH and loaded onto an SCX cartridge (10 g). The cartridge was washed with MeOH/$H_2O$ (9:1) then the product was eluted from the SCX cartridge with a 2M solution of $NH_3$ in MeOH. The volatiles were evaporated and the residue was purified by column chromatography (KP-C18-HS, 2×SNAP 12 g in series) eluting with a gradient of $CH_3CN$ (+0.1% of HCOOH) in water (+0.1% of HCOOH) from 2% to 30% to give [7-(4-aminocinnolin-7-yl)-2,3-dihydro-1-benzofuran-5-yl]boronic acid formic acid salt (43 mg, 0.122 mmol, 37.61% yield) as a yellow powder. $^1$H NMR (400 MHz, DMSO-$d_6$+2 drops of TFA) δ 3.30 (t, J=8.72 Hz, 2H), 4.72 (t, J=8.76 Hz, 2H), 7.79 (d, J=1.23 Hz, 1H), 8.05 (d, J=1.28 Hz, 1H), 8.13 (s, 0.86H from HCOOH), 8.19 (dd, J=9.02, 1.69 Hz, 1H), 8.33 (d, J=1.61 Hz, 1H), 8.46 (s, 1H), 8.51 (d, J=9.01 Hz, 1H), 9.69 (s, 1H), 9.84 (s, 1H). LC-MS (Method A): r.t. 0.45 min, MS (ESI) m/z=308.12 [M+H]$^+$.

Example 139: [4-methoxy-3-(1,7-naphthyridin-3-yl)phenyl]boronic Acid (139)

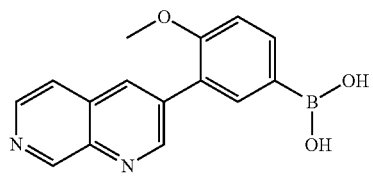 [SMILES: COc1ccc(B(O)O)cc1-c1cnc2cnccc2c1]

Palladium(II) diacetate (0.83 mg, 0.004 mmol), 3-(5-chloro-2-methoxyphenyl)-1,7-naphthyridine (20.0 mg, 0.070 mmol), dicyclohexyl-[2-[2,4,6-tri(propan-2-yl)phenyl]phosphine (2.82 mg, 0.010 mmol), potassium acetate (21.75 mg, 0.220 mmol), and 4,4,5,5-tetramethyl-2-(4,4,5,5-tetramethyl-1,3,2-dioxaborolan-2-yl)-1,3,2-dioxaborolane (56.28 mg, 0.220 mmol) were dissolved in 1,4-dioxane (0.8 mL) in a microwave vial and degassed for 10 min with $N_2$. The resulting reaction mixture was stirred at 80° C. for 2 hours then it was cooled to room temperature and filtered over Celite, washing with MeOH. The filtrate was evaporated under reduced pressure and the residue was dissolved in MeOH/$H_2O$ (9:1), loaded onto an SCX cartridge and the cartridge was left to stand for 20 min. The cartridge was then washed with MeOH/$H_2O$ (9:1) and eluted with 1M methanolic ammonia solution. The basic fractions were collected and evaporated under reduced pressure. The residue was purified by flash chromatography (Sfar C18 D, 6 g) eluting with a gradient of MeCN (+0.1% of HCOOH) in water (+0.1% of HCOOH) from 5% to 20%. Appropriate fractions were collected and lyophilised to give [4-methoxy-3-(1,7-naphthyridin-3-yl)phenyl]boronic acid (7.5 mg, 0.027 mmol, 36.24% yield) as a pale-yellow solid. $^1$H NMR (400 MHz, DMSO-$d_6$) δ 3.87 (s, 3H), 7.21 (d, J=8.34 Hz, 1H), 7.89-7.98 (m, 3H), 8.01 (s, 2H), 8.50 (dd, J=2.14, 0.85 Hz, 1H), 8.64 (d, J=5.56 Hz, 1H), 9.20 (d, J=2.13 Hz, 1H), 9.42 (d, J=0.97 Hz, 1H). LC-MS (Method A): r.t. 0.55 min, MS (ESI) m/z=281.2 [M+H]$^+$.

Example 140: 7-[2-(difluoromethoxy)-4-methyl-5-[(1S,2S,6R,8S)-2,9,9-trimethyl-3,5-dioxa-4-boratricyclo[6.1.1.0$^{2,6}$]decan-4-yl]phenyl]cinnolin-4-amine (140)

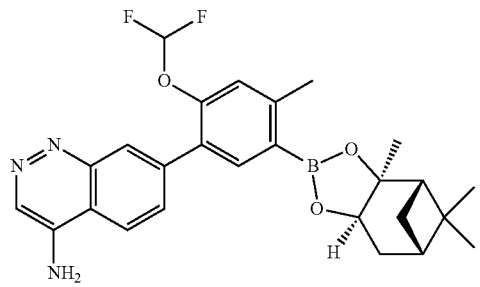 [SMILES: Cc1cc(OC(F)F)c(-c2ccc3c(N)cnnc3c2)cc1B1O[C@@H]2C[C@@H]3C[C@@H](C3(C)C)[C@]2(C)O1]

7-[2-(Difluoromethoxy)-4-methyl-5-[(1S,2S,6R,8S)-2,9,9-trimethyl-3,5-dioxa-4-boratricyclo[6.1.1.0$^{2,6}$]decan-4-yl]phenyl]-N-[(2,4-dimethoxyphenyl)methyl]cinnolin-4-amine (850.0 mg, 1.35 mmol) was dissolved in DCM (5 mL) and trifluoroacetic acid (4 mL) and the mixture stirred at room temperature for 4 hours. The volatiles were evaporated under reduced pressure. The residue was dissolved in MeOH/$H_2O$ (9:1), then loaded onto an SCX cartridge (5 g), which was washed with MeOH/$H_2O$ (9:1) and then eluted with a 7 M solution of ammonia in MeOH. The basic fractions were collected and evaporated under reduced pressure and the residue was purified twice by column chromatography (Sfar C18 D, 30 g) eluting with a gradient of MeCN (+0.1% of HCOOH) in water (+0.1% of HCOOH) from 2% to 50% to give 7-[2-(difluoromethoxy)-4-methyl-5-[(1S,2S,6R,8S)-2,9,9-trimethyl-3,5-dioxa-4-boratricyclo[6.1.1.0$^{2,6}$]decan-4-yl]phenyl]cinnolin-4-amine (38 mg, 0.079 mmol, 5.871% yield) as a light brown solid. $^1$H NMR (400 MHz, DMSO-$d_6$) δ 0.87 (s, 3H), 1.12 (d, J=10.64 Hz, 1H), 1.28 (s, 3H), 1.45 (s, 3H), 1.77-2.00 (m, 2H), 2.09 (t, J=5.46 Hz, 1H), 2.18-2.31 (m, 1H), 2.35-2.44 (m, 1H), 2.57 (s, 3H), 4.55 (dd, J=8.70, 1.89 Hz, 1H), 7.21 (s, 1H), 7.23 (s, 2H), 7.28 (t, J=73.69 Hz, 1H), 7.65 (dd, J=8.78, 1.80 Hz, 1H), 7.80 (s, 1H), 8.05 (d, J=1.73 Hz, 1H), 8.24 (d, J=8.69 Hz, 1H), 8.63 (s, 1H). LC-MS (Method A): r.t. 0.98 min, MS (ESI) m/z=480.3 [M+H]⁺.

Example 141: 7-{2-methoxy-4-methyl-5-[(1S,2S, 6R,8S)-2,9,9-trimethyl-3,5-dioxa-4-boratricyclo [6.1.1.0$^{2,6}$]decan-4-yl]phenyl}cinnolin-4-amine (141)

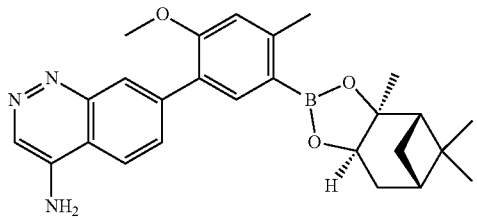 [SMILES: COc1cc(C)c(B2O[C@@H]3C[C@@H]4C[C@@H](C4(C)C)[C@]3(C)O2)cc1-c1ccc2c(N)cnnc2c1]

Step 1: Palladium(II) diacetate (6.43 mg, 0.030 mmol), 7-(5-chloro-2-methoxy-4-methylphenyl)-N-[(2,4-dimethoxyphenyl)methyl]cinnolin-4-amine (280.0 mg, 0.570 mmol), potassium acetate (168.57 mg, 1.72 mmol) and bis[(+)-pinanediolato]diboron (615.06 mg, 1.72 mmol) were dissolved in 1,4-dioxane (10 mL) and the mixture was degassed with Ar for 10 minutes. The mixture was then stirred overnight at 85° C. The mixture was diluted with MeOH, filtered and concentrated in vacuo. LC-MS (Method A): r.t. 1.12 min, MS (ESI) m/z=594.4 [M+H]⁺.

Step 2: The crude material from Step 1 was dissolved in DCM (6 mL) and trifluoroacetic acid (6 mL) was stirred overnight at room temperature. The volatiles were removed and the residue was dissolved in MeOH, then loaded onto an SCX cartridge (20 g). The cartridge was washed with MeOH and eluted with 2M solution of ammonia in MeOH. The basic fractions were concentrated and the residue was purified by column chromatography (KP-C18-HS, 30 g) eluting with a gradient of MeCN (+0.1% of HCOOH) in water (+0.1% of HCOOH) from 2% to 60%. Appropriate fractions were concentrated to give partially purified product (16 mg) that was submitted to semi-preparative HPLC purification (CSH C18 (100×30 mm), 3 μm, gradient of MeCN in water (+0.1% of HCOOH) from 43% to 45% in 10 min, flow 40 mL/min). Appropriate fractions were collected and lyophilised to give 7-{2-methoxy-4-methyl-5-[(1S,2S,6R,8S)-2,9, 9-trimethyl-3,5-dioxa-4-boratricyclo[6.1.1.0$^{2,6}$]decan-4-yl] phenyl}cinnolin-4-amine (6.4 mg, 0.014 mmol, 0.659% yield) as a yellowish solid. ¹H NMR (400 MHz, DMSO-d₆) δ 0.87 (s, 3H), 1.11 (d, J=10.7 Hz, 1H), 1.28 (s, 3H), 1.44 (s, 3H), 1.81-1.88 (m, 1H), 1.89-1.94 (m, 1H), 2.08 (t, J=5.5 Hz, 1H), 2.17-2.29 (m, 1H), 2.37-2.43 (m, 1H), 2.56 (s, 3H), 3.84 (s, 3H), 4.51 (dd, J=8.6, 1.6 Hz, 1H), 7.03 (s, 1H), 7.18 (s, 2H), 7.66 (dd, J=8.7, 1.8 Hz, 1H), 7.69 (s, 1H), 8.03 (d, J=1.6 Hz, 1H), 8.18 (d, J=8.7 Hz, 1H), 8.60 (s, 1H). LC-MS (Method A): r.t. 1.01 min, MS (ESI) m/z=444.3 [M+H]⁺.

Example 142: [3-(4-aminocinnolin-7-yl)-4-(3,3-difluorocyclobutoxy)phenyl]boronic Acid Formic Acid Salt (142)

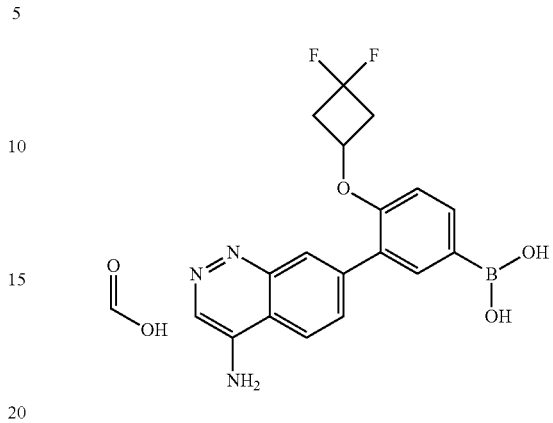

Step 1: Palladium(II) diacetate (3.33 mg, 0.010 mmol), 7-[5-chloro-2-(3,3-difluorocyclobutyl)oxyphenyl]-N-[(2,4-dimethoxyphenyl)methyl]cinnolin-4-amine (152.0 mg, 0.300 mmol), potassium acetate (87.41 mg, 0.890 mmol) and 4,4,5,5-tetramethyl-2-(4,4,5,5-tetramethyl-1,3,2-dioxaborolan-2-yl)-1,3,2-dioxaborolane (226.19 mg, 0.890 mmol) were dissolved in 1,4-dioxane (8 mL) and the mixture was degassed with Ar for 10 minutes. The mixture was then stirred at 95° C. for 1 hour. The mixture was filtered, washing with MeOH and the filtrate was concentrated in vacuo. LC-MS (Method A): r.t. 0.98 min, MS (ESI) m/z=604.4 [M+H]⁺.

Step 2: The crude material from Step 1 was dissolved in DCM (5 mL) and trifluoroacetic acid (4 mL) and stirred for four hours at room temperature then concentrated under reduced pressure. The residue was dissolved in MeOH/H₂O (9:1) and loaded onto an SCX cartridge (10 g). The cartridge was washed with MeOH/H₂O (9:1) and the product was eluted from the SCX cartridge with a 2 M solution of NH₃ in MeOH. The basic fractions were evaporated and the residue was purified by column chromatography (KP-C18-HS, 12 g+12 g in series) eluting with a gradient of CH₃CN (+0.1% of HCOOH) in water (+0.1% of HCOOH) from 2% to 20%. Appropriate fractions were concentrated to give [3-(4-aminocinnolin-7-yl)-4-(3,3-difluorocyclobutyl)oxyphenyl]boronic acid formic acid salt (83 mg, 0.199 mmol, 66.3% yield) as a yellowish solid. ¹H NMR (400 MHz, DMSO-d₆+drops of TFA) δ 2.66-2.79 (m, 2H), 3.19-3.32 (m, 2H), 4.84-4.94 (m, 1H), 7.09 (d, J=8.36 Hz, 1H), 7.91 (dd, J=8.25, 1.65 Hz, 1H), 7.98 (d, J=1.54 Hz, 1H), 8.03 (dd, J=8.80, 1.54 Hz, 1H), 8.08 (d, J=1.32 Hz, 1H), 8.14 (s, 1H from HCOOH), 8.46-8.52 (m, 2H), 9.71 (br. s, 1H), 9.83 (br. s, 1H). LC-MS (Method A): r.t. 0.54 min, MS (ESI) m/z=372.2 [M+H]⁺.

Example 143: [3-(4-aminocinnolin-7-yl)-4-(morpholin-4-yl)phenyl]boronic Acid Formic Acid Salt (143)

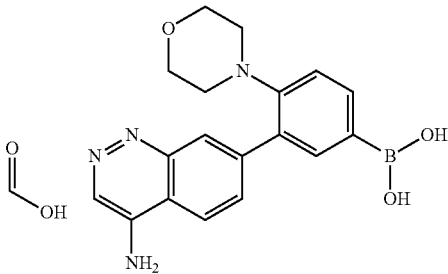

Step 1: Palladium(II) diacetate (2.29 mg, 0.010 mmol), 7-(5-chloro-2-morpholin-4-ylphenyl)-N-[(2,4-dimethoxyphenyl)methyl]cinnolin-4-amine (100.0 mg, 0.200 mmol), dicyclohexyl-[2-[2,4,6-tri(propan-2-yl)phenyl]phenyl]phosphine (7.77 mg, 0.020 mmol), potassium acetate (59.97 mg, 0.610 mmol), and 4,4,5,5-tetramethyl-2-(4,4,5,5-tetramethyl-1,3,2-dioxaborolan-2-yl)-1,3,2-dioxaborolane (155.16 mg, 0.610 mmol) were dissolved in 1,4-dioxane (3 mL). The mixture was degassed with $N_2$ for 10 min, then stirred at 75° C. for 2 hours. The mixture was filtered over a pad of Celite, washing with MeOH and the filtrate was concentrated in vacuo.

Step 2: The crude material from Step 1 was dissolved in a mixture of DCM (3 mL) and trifluoroacetic acid (3 mL). The mixture was stirred overnight at room temperature and the volatiles were evaporated. The residue was dissolved in MeOH and loaded onto an SCX cartridge (10 g). The cartridge was washed with MeOH/$H_2O$ (9:1) then the product was eluted from the SCX cartridge with a 2M solution of $NH_3$ in MeOH. The volatiles were evaporated and the residue was purified by column chromatography (KP-C18-HS, 2×SNAP 12 g in series) eluting with a gradient of $CH_3CN$ (+0.1% of HCOOH) in water (+0.1% of HCOOH) from 2% to 30% to give [3-(4-aminocinnolin-7-yl)-4-morpholin-4-ylphenyl]boronic acid formic acid salt (24 mg, 0.061 mmol, 33.93% yield) as a yellow powder. $^1$H NMR (400 MHz, DMSO-$d_6$+2 drops of TFA) δ 2.80 (t, J=4.56 Hz, 4H), 3.45-3.56 (m, 4H), 7.14 (d, J=8.07 Hz, 1H), 7.82 (d, J=1.60 Hz, 1H), 7.86 (dd, J=8.08, 1.63 Hz, 1H), 8.08-8.19 (m, 2H+1H of HCOOH), 8.43-8.50 (m, 2H), 9.68 (s, 1H), 9.79 (s, 1H). LC-MS (Method A): r.t. 0.43 min, MS (ESI) m/z=351.20 [M+H]$^+$.

Example 144: (3-{4-aminopyrido[3,2-c]pyridazin-7-yl}-4-methoxyphenyl)boronic Acid (144)

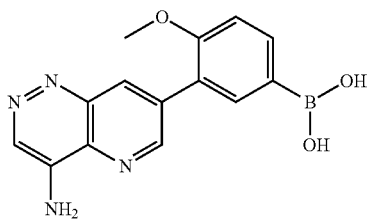 [SMILES: COc1ccc(B(O)O)cc1-c1cnc2c(N)cnnc2c1]

Step 1: A mixture of 7-(5-chloro-2-methoxyphenyl)-N-[(2,4-dimethoxyphenyl)methyl]pyrido[3,2-c]pyridazin-4-amine (54.0 mg, 0.110 mmol), 4,4,5,5-tetramethyl-2-(4,4,5,5-tetramethyl-1,3,2-dioxaborolan-2-yl)-1,3,2-dioxaborolane (86.63 mg, 0.340 mmol) and potassium acetate (33.48 mg, 0.340 mmol) in 1,4-dioxane (1.5 mL) was degassed for 10 minutes under argon, then dicyclohexyl-[2-[2,4,6-tri(propan-2-yl)phenyl]phenyl]phosphine (4.34 mg, 0.010 mmol) and palladium diacetate (1.28 mg, 0.010 mmol) were added and the mixture was stirred at 90° C. for 6 hours. Then additional 4,4,5,5-tetramethyl-2-(4,4,5,5-tetramethyl-1,3,2-dioxaborolan-2-yl)-1,3,2-dioxaborolane (43.32 mg, 0.170 mmol), dicyclohexyl-[2-[2,4,6-tri(propan-2-yl)phenyl]phenyl]phosphine (2.17 mg, 0.005 mmol) and palladium diacetate (0.64 mg, 0.005 mmol) were added and the mixture was stirred at 90° C. for another 15 hours. UPLC-MS analysis indicated a considerable amount of unreacted 7-(5-chloro-2-methoxyphenyl)-N-[(2,4-dimethoxyphenyl)methyl]pyrido[3,2-c]pyridazin-4-amine was still present. The reaction mixture was filtered over Celite, washing with MeOH and EtOAc. The filtrate was concentrated under reduced pressure and the residue was redissolved in 1,4-dioxane (1.5 mL), 4,4,5,5-tetramethyl-2-(4,4,5,5-tetramethyl-1,3,2-dioxaborolan-2-yl)-1,3,2-dioxaborolane (86.63 mg, 0.340 mmol) and potassium acetate (33.48 mg, 0.340 mmol) were added and the mixture was deoxygenated for 10 minutes under argon. Then dicyclohexyl-[2-[2,4,6-tri(propan-2-yl)phenyl]phenyl]phosphine (4.34 mg, 0.010 mmol) and palladium diacetate (1.28 mg, 0.010 mmol) were added and the mixture was stirred at 95° C. for 24 hours. The mixture was allowed to cool to room temperature and filtered over Celite, washing with MeOH and EtOAc, and the filtrate was concentrated in vacuo. LC-MS (Method A): r.t. 0.92 min, MS (ESI) m/z=529.3 [M+H]$^+$.

Step 2: The crude material from Step 1 was dissolved in DCM (2 mL) and trifluoroacetic acid (2 mL) and the mixture was stirred for 2 hours at room temperature, then further trifluoroacetic acid (1 mL) was added and the mixture was stirred for an additional 3 hours. The volatiles were removed under reduced pressure. The residue was dissolved in MeOH/$H_2O$ (9:1), then loaded onto an SCX cartridge (5 g), which was washed with MeOH/$H_2O$ (9:1) and then eluted with a 7 M solution of ammonia in MeOH. The basic fractions were collected and evaporated under reduced pressure and the residue purified by column chromatography (Sfar C18 D, 30 g) eluting with a gradient of MeCN (+0.1% of HCOOH) in water (+0.1% of HCOOH) from 1% to 25%. Appropriate fractions were collected and lyophilized. The recovered solid was submitted to semi-preparative HPLC purification (Chiralcel OJ-H (25×0.46 cm), 5 μm, n-hexane/(EtOH+0.1% isopropylamine) 70/30% v/v). Appropriate fractions were collected and concentrated in vacuo, then the solid residue was dissolved in MeCN/water and lyophilized to give [3-(4-aminopyrido[3,2-c]pyridazin-7-yl)-4-methoxyphenyl]boronic acid (2.1 mg, 0.007 mmol, 6.4% yield) as a light yellow solid. $^1$H NMR (400 MHz, DMSO-$d_6$+3 drops of TFA) δ 3.88 (s, 3H), 7.23 (d, J=8.28 Hz, 1H), 7.89-8.07 (m, 2H), 8.35 (d, J=1.91 Hz, 1H), 8.62 (s, 1H), 9.23 (d, J=1.89 Hz, 1H), 9.83 (s, 1H), 9.99 (s, 1H). LC-MS (Method A): r.t. 0.42 min, MS (ESI) m/z=297.2 [M+H]$^+$.

Example 145: [8-(4-aminocinnolin-7-yl)-3,4-dihydro-2H-chromen-6-yl]boronic Acid Formic Acid Salt (145)

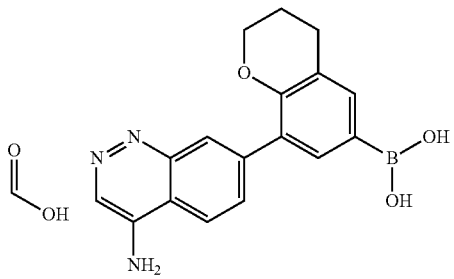

Step 1: Palladium(II) diacetate (2.19 mg, 0.010 mmol), 7-(6-chloro-3,4-dihydro-2H-chromen-8-yl)-N-[(2,4-dimethoxyphenyl)methyl]cinnolin-4-amine (90.0 mg, 0.190 mmol), potassium acetate (57.36 mg, 0.580 mmol), dicyclohexyl-[2-[2,4,6-tri(propan-2-yl)phenyl]phenyl]phosphine (7.43 mg, 0.020 mmol) and 4,4,5,5-tetramethyl-2-(4,4,5,5-tetramethyl-1,3,2-dioxaborolan-2-yl)-1,3,2-dioxaborolane (148.43 mg, 0.580 mmol) were dissolved in 1,4-dioxane (5 mL) and the mixture was degassed with Ar for 10 minutes. The mixture was then stirred at 95° C. for 1 hour. The mixture was filtered, washing with methanol and the filtrate was concentrated in vacuo. LC-MS (Method A): r.t. 0.98 min, MS (ESI) m/z=554.4 [M+H]$^+$.

Step 2: The crude material from Step 1 was dissolved in DCM (3 mL) and trifluoroacetic acid (2 mL) and stirred for seven hours at room temperature then it was concentrated under reduced pressure. The residue was dissolved in MeOH/H$_2$O (9:1) and loaded onto an SCX cartridge (5 g). The cartridge was washed with MeOH/H$_2$O (9:1) and the product was eluted from the SCX cartridge a 2 M solution of NH$_3$ in MeOH. The basic fractions were evaporated and the residue was purified by column chromatography (KP-C18-HS, 12 g+12 g in series) eluting with a gradient of CH$_3$CN (+0.1% of HCOOH) in water (+0.1% of HCOOH) from 2% to 15%. Appropriate fractions were collected and concentrated to give [8-(4-aminocinnolin-7-yl)-3,4-dihydro-2H-chromen-6-yl]boronic acid formic acid salt (27 mg, 0.074 mmol, 38.9% yield) as a yellow solid. $^1$H NMR (400 MHz, DMSO-d$_6$+drops of TFA) δ 1.95-2.04 (m, 2H), 2.86 (t, J=6.38 Hz, 2H), 4.19-4.28 (t, J=4.80 Hz, 2H), 7.65 (s, 1H), 7.74 (d, J=1.32 Hz, 1H), 7.97 (dd, J=8.80, 1.54 Hz, 1H), 8.02 (d, J=1.32 Hz, 1H), 8.14 (s, 1H from HCOOH), 8.44-8.49 (m, 2H), 9.68 (br. s, 1H), 9.83 (br. s, 1H). LC-MS (Method A): r.t. 0.48 min, MS (ESI) m/z=322.1 [M+H]$^+$.

Example 146: [6-(4-aminocinnolin-7-yl)-3-cyclopropyl-1-methyl-1H-indazol-4-yl]boronic Acid (146)

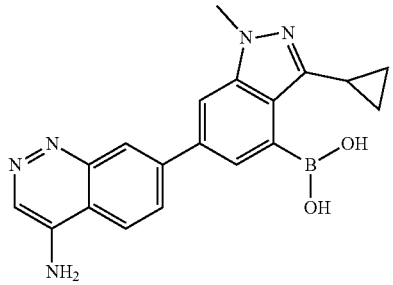 [SMILES: Cn1nc(C2CC2)c2c(B(O)O)cc(-c3ccc4c(N)cnnc4c3)cc21]

Palladium(II) diacetate (1.8 mg, 0.010 mmol), 7-(4-chloro-3-cyclopropyl-1-methylindazol-6-yl)-N-[(2,4-dimethoxyphenyl)methyl]cinnolin-4-amine (80.0 mg, 0.160 mmol), dicyclohexyl-[2-[2,4,6-tri(propan-2-yl)phenyl]phenyl]phosphine (6.1 mg, 0.010 mmol), potassium acetate (47.11 mg, 0.480 mmol), and 4,4,5,5-tetramethyl-2-(4,4,5,5-tetramethyl-1,3,2-dioxaborolan-2-yl)-1,3,2-dioxaborolane (121.89 mg, 0.480 mmol) were dissolved in 1,4-dioxane (1.6 mL) in a microwave vial and degassed for 10 min with N$_2$. The resulting reaction mixture was stirred at 80° C. for 4 hours then it was cooled to room temperature and filtered over Celite, washing with MeOH. The filtrate was evaporated under reduced pressure and the residue was dissolved in dichloromethane (3 mL) and trifluoroacetic acid (3 mL). The resulting mixture was stirred overnight at room temperature then concentrated under reduced pressure. The residue was dissolved in MeOH/H$_2$O (9:1), loaded onto an SCX cartridge and the cartridge was left to stand for 20 min. The cartridge was then washed with MeOH/H$_2$O (9:1) and eluted with 7 M methanolic ammonia solution. The basic fractions were collected and evaporated under reduced pressure. The residue was purified by column chromatography (Sfar C18 D, 12 g) eluting with a gradient of CH$_3$CN (+0.1% of HCOOH) in water (+0.1% of HCOOH) from 1% to 10%. Appropriate fractions were collected and evaporated under reduced pressure. The residue was submitted to semi-preparative HPLC purification (Chiralpak AD-H (25×0.46 cm), 5 μm, n-hexane/(EtOH+0.1% isopropylamine) 80/20% v/v). Appropriate fractions were collected and concentrated to give [6-(4-aminocinnolin-7-yl)-3-cyclopropyl-1-methylindazol-4-yl]boronic acid (3 mg, 0.008 mmol, 5% yield) as a pale-yellow powder. $^1$H NMR (400 MHz, DMSO-d$_6$+TFA) δ 0.86-0.98 (m, 4H), 2.52-2.57 (m, 1H), 4.02 (s, 3H), 7.61 (d, J=1.58 Hz, 1H), 8.07 (d, J=1.60 Hz, 1H), 8.20 (d, J=1.66 Hz, 1H), 8.32 (dd, J=8.92, 1.70 Hz, 1H), 8.49 (s, 1H), 8.58 (d, J=8.95 Hz, 1H), 9.74 (br. s, 1H), 9.90 (br. s, 1H). LC-MS (Method A): r.t. 0.45 min, MS (ESI) m/z=360.24 [M+H]$^+$.

Examples 147 and 148: 7-(3-cyclopropyl-1-hydroxy-3,4-dihydro-2,1-benzoxaborinin-7-yl)cinnolin-4-amine (147) and 7-(1-hydroxy-3-prop-2-enyl-3,4-dihydro-2,1-benzoxaborinin-7-yl)cinnolin-4-amine (148)

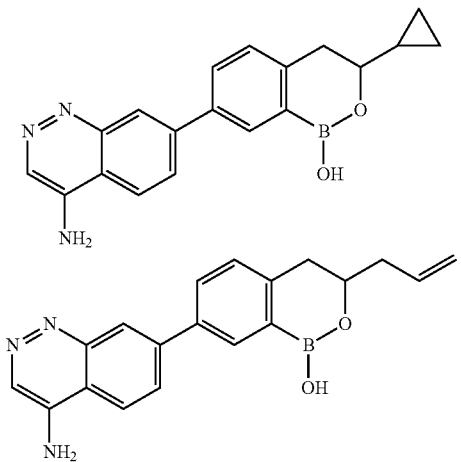

Step 1: A mixture of tert-butyl(2-{4-chloro-2-[(1S,2S,6R,8S)-2,9,9-trimethyl-3,5-dioxa-4-boratricyclo[6.1.1.0$^{2,6}$]decan-4-yl]phenyl}-1-cyclopropylethoxy)dimethylsilane (220.04 mg, 0.450 mmol), N-[(2,4-dimethoxyphenyl)methyl]-7-(4,4,5,5-tetramethyl-1,3,2-dioxaborolan-2-yl)cinnolin-4-amine (189.59 mg, 0.450 mmol) and aqueous 2M sodium carbonate solution (450.0 uL, 0.900 mmol) in 1,2-dimethoxyethane (3 mL) was degassed for 10 minutes under argon. Then [1,1'-bis(di-tert-butylphosphino)ferrocene]dichloropalladium(II) (29.42 mg, 0.050 mmol) was added and the resulting mixture was stirred at 85° C. for 2 hours. The reaction mixture was filtered over Celite, washing with EtOAc and MeOH and the filtrate was evaporated in vacuo. LC-MS (Method A): r.t. 1.51 min, MS (ESI) m/z=748.4 [M+H]$^+$.

Step 2: The crude material from Step 1 was dissolved in trifluoroacetic acid (2.5 mL) and DCM (3 mL) and stirred at room temperature for 17 hours, then it was evaporated in vacuo. The residue was taken up in MeOH and loaded onto an SCX cartridge (5 g) which was washed with MeOH and then eluted with a 7M solution of ammonia in MeOH. The basic fractions were collected and evaporated under reduced pressure. The residue was purified by flash chromatography (Sfar C18 D, 30 g), eluting with a gradient of MeCN (+0.1% of HCOOH) in water (+0.1% of HCOOH) from 1% to 35%. Appropriate fractions were collected and lyophilised to give 14 mg of a white solid that was submitted to semi-preparative HPLC purification (xBridge C18 (30×100 mm, 3 μm), gradient of MeCN in 10 mM ammonium bicarbonate acqueous solution adjusted to pH 10 with ammonia from 30.0% to 35.0%. Two different product peaks were collected and the appropriate fractions from each peak were lyophilized separately to give 7-(3-cyclopropyl-1-hydroxy-3,4-dihydro-2,1-benzoxaborinin-7-yl)cinnolin-4-amine (4 mg, 0.012 mmol, 2.7% yield) as a white solid. $^1$H NMR (400 MHz, DMSO-d$_6$) δ 0.25-0.44 (m, 2H), 0.44-0.58 (m, 2H), 1.07 (dtd, J=13.03, 8.21, 4.87 Hz, 1H), 2.94 (dd, J=16.13, 9.84 Hz, 1H), 3.03 (dd, J=16.11, 3.72 Hz, 1H), 3.53 (ddd, J=9.66, 8.04, 3.74 Hz, 1H), 7.21 (s, 2H), 7.38 (d, J=7.92 Hz, 1H), 7.86-7.96 (m, 2H), 8.18 (d, J=2.12 Hz, 1H), 8.24-8.34 (m, 2H), 8.60 (s, 1H).

LC-MS (Method A): r.t. 0.65 min, MS (ESI) m/z=332.3 [M+H]$^+$.

and 7-(1-hydroxy-3-prop-2-enyl-3,4-dihydro-2,1-benzoxaborinin-7-yl)cinnolin-4-amine (7 mg, 0.021 mmol, 4.7% yield) as a white solid. $^1$H NMR (400 MHz, DMSO-d$_6$) δ 2.35-2.45 (m, 2H), 2.81 (dd, J=16.13, 10.20 Hz, 1H), 2.93 (dd, J=16.23, 3.46 Hz, 1H), 4.24 (dtd, J=9.84, 6.22, 3.55 Hz, 1H), 5.03-5.23 (m, 2H), 5.93 (ddt, J=17.11, 10.26, 6.96 Hz, 1H), 7.20 (s, 2H), 7.36 (d, J=7.92 Hz, 1H), 7.83-8.00 (m, 2H), 8.22 (d, J=2.13 Hz, 1H), 8.26-8.34 (m, 2H), 8.60 (s, 1H), 8.66 (s, 1H). LC-MS (Method A): r.t. 0.64 min, MS (ESI) m/z=332.2 [M+H]$^+$.

Example 149: [5-(4-aminocinnolin-7-yl)-1-benzofuran-7-yl]boronic Acid Formic Acid Salt (149)

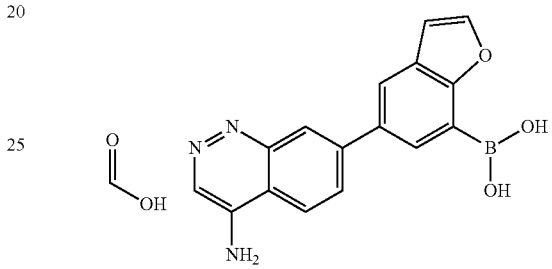

Step 1: Palladium(II) diacetate (2.77 mg, 0.010 mmol), 7-(7-chloro-1-benzofuran-5-yl)-N-[(2,4-dimethoxyphenyl)methyl]cinnolin-4-amine (110.0 mg, 0.250 mmol), potassium acetate (72.63 mg, 0.740 mmol), dicyclohexyl-[2-[2,4,6-tri(propan-2-yl)phenyl]phenyl]phosphine (9.41 mg, 0.020 mmol), and 4,4,5,5-tetramethyl-2-(4,4,5,5-tetramethyl-1,3,2-dioxaborolan-2-yl)-1,3,2-dioxaborolane (187.93 mg, 0.740 mmol) were dissolved in 1,4-dioxane (6.11 mL) and the mixture was degassed with Ar for 10 minutes. The mixture was then stirred at 95° C. for 1.5 hour. The mixture was filtered, washing with methanol and the filtrate was concentrated in vacuo. LC-MS (Method A): r.t. 0.91 min, MS (ESI) m/z=538.3 [M+H]$^+$.

Step 2: The crude material from Step 1 was dissolved in DCM (3 mL) and trifluoroacetic acid (2 mL) was stirred overnight at room temperature then it was concentrated under reduced pressure. The residue was dissolved in MeOH/H$_2$O (9:1) and loaded onto an SCX cartridge (5 g). The cartridge was washed with MeOH/H$_2$O (9:1) and the product was eluted from the SCX cartridge with a 2 M solution of NH$_3$ in MeOH. The basic fractions were evaporated and the residue was purified by column chromatography (KP-C18-HS silica gel, 2×12 g in series) eluting with a gradient of MeCN (+0.1% of HCOOH) in water (+0.1% of HCOOH) from 2% to 15%. Fractions containing the desired compound were collected and concentrated to give 5-(4-aminocinnolin-7-yl)-1-benzofuran-7-yl]boronic acid formic acid salt (3.7 mg, 0.011 mmol, 4.4% yield) as a yellow solid. $^1$H NMR (400 MHz, DMSO-d$_6$+drops of TFA) δ 7.06 (d, J=2.20 Hz, 1H), 8.05 (d, J=1.98 Hz, 1H), 8.10 (d, J=2.42 Hz, 1H), 8.11 (d, J=1.76 Hz, 1H), 8.13 (s, 1H from HCOOH), 8.20 (d, J=1.98 Hz, 1H), 8.25 (dd, J=9.02, 1.54 Hz, 1H), 8.48 (s, 1H), 8.55 (d, 1H), 9.72 (s, 1H), 9.87 (s, 1H). LC-MS (Method A): r.t. 0.46 min, MS (ESI) m/z=306.1 [M+H]$^+$.

Example 150: [3-(4-aminocinnolin-7-yl)-4-(pyrrolidin-1-yl)phenyl]boronic Acid Formic Acid Salt (150)

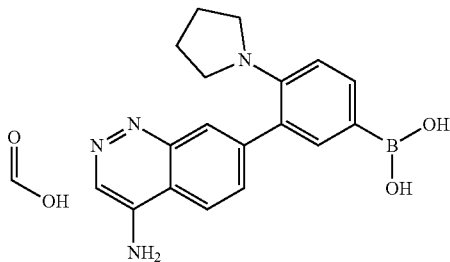

Step 1: A mixture of 7-[5-chloro-2-(pyrrolidin-1-yl)phenyl]-N-[(2,4-dimethoxyphenyl)methyl]cinnolin-4-amine (79.0 mg, 0.170 mmol), 4,4,5,5-tetramethyl-2-(4,4,5,5-tetramethyl-1,3,2-dioxaborolan-2-yl)-1,3,2-dioxaborolane (126.71 mg, 0.500 mmol) and potassium acetate (48.97 mg, 0.500 mmol) in 1,4-dioxane (3 mL) was degassed for 10 minutes under argon, then dicyclohexyl-[2-[2,4,6-tri(propan-2-yl)phenyl]phenyl]phosphine (6.34 mg, 0.010 mmol) and palladium(II) diacetate (1.87 mg, 0.010 mmol) were added and the mixture was stirred at 90° C. for 15 hours. Then additional 4,4,5,5-tetramethyl-2-(4,4,5,5-tetramethyl-1,3,2-dioxaborolan-2-yl)-1,3,2-dioxaborolane (63.36 mg, 0.250 mmol), potassium acetate (24.49 mg, 0.250 mmol), dicyclohexyl-[2-[2,4,6-tri(propan-2-yl)phenyl]phenyl]phosphine (3.17 mg, 0.005 mmol) and palladium(II) diacetate (0.94 mg, 0.005 mmol) were added and the mixture was stirred for 2 hours at 100° C. The mixture was allowed to cool to room temperature then filtered over Celite, washing with MeOH and EtOAc, and the filtrate was concentrated in vacuo. LC-MS (Method A): r.t. 1.01 min, MS (ESI) m/z=567.4 [M+H]$^+$.

Step 2: The crude material from Step 1 was dissolved in trifluoroacetic acid (2 mL) and DCM (3 mL). The resulting mixture was stirred at room temperature for 7 hours, then additional trifluoroacetic acid (2 mL) was added and the mixture was stirred for a further 24 hours. The volatiles were removed under reduced pressure. The residue was taken up in MeOH/water (9:1) and the solution was loaded onto an SCX cartridge (10 g) which was washed with MeOH/water and then eluted with a 7M solution of ammonia in MeOH. The basic fractions were collected and evaporated under reduced pressure. The residue was purified by column chromatography (Sfar C18 D, 30 g) eluting with a gradient of MeCN (+0.1% of HCOOH) in water (+0.1% of HCOOH) from 1% to 30%. The appropriate fractions were collected and lyophilised to give [3-(4-aminocinnolin-7-yl)-4-(pyrrolidin-1-yl)phenyl]boronic acid formic acid salt (12 mg, 0.032 mmol, 4.705% yield) as an orange solid. $^1$H NMR (400 MHz, DMSO-d$_6$+TFA) δ 1.69-1.77 (m, 4H), 2.92-2.99 (m, 4H), 6.96 (d, J=8.36 Hz, 1H), 7.71 (d, J=1.54 Hz, 1H), 7.75 (dd, J=8.40, 1.62 Hz, 1H), 7.77 (d, J=1.34 Hz, 1H), 7.82 (dd, J=8.79, 1.47 Hz, 1H), 8.07 (s, 1H from HCOOH), 8.42 (d, J=8.76 Hz, 1H), 8.44 (s, 1H), 9.61 (s, 1H), 9.76 (s, 1H). LC-MS (Method A): r.t. 0.53 min, MS (ESI) m/z=335.3 [M+H]$^+$.

Example 151: 7-{5-[(3aR,6aS)-3a,6a-diethyl-hexahydrocyclopenta[d][1,3,2]dioxaborol-2-yl]-2-methoxyphenyl}cinnolin-4-amine (151)

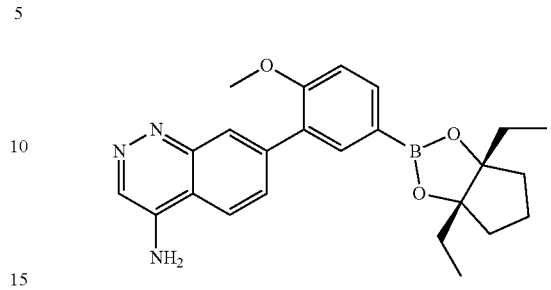

A mixture of [3-(4-aminocinnolin-7-yl)-4-methoxyphenyl]boronic acid (50.0 mg, 0.170 mmol) and 1,2-diethylcyclopentane-1,2-diol (32.77 mg, 0.190 mmol) in THF (2.5 mL) was stirred at 50° C. for 16 hours, then MeOH (500 uL) was added and the solution was left to stir for 1 hour. The volatiles were removed under reduced pressure and the residue was triturated in diethyl ether (2.5 mL). The solid was filtered off, washed with diethylether and dried under vacuum for 24 hours to give 7-{5-[(3aR,6aS)-3a,6a-diethyl-hexahydrocyclopenta[d][1,3,2]dioxaborol-2-yl]-2-methoxyphenyl}cinnolin-4-amine (50 mg, 0.120 mmol, 70.71% yield) as an off-white solid. $^1$H NMR (400 MHz, DMSO-d$_6$) δ 1.04 (t, J=7.28 Hz, 6H), 1.40-1.63 (m, 6H), 1.64-1.79 (m, 2H), 1.93-2.00 (m, 2H), 3.84 (s, 3H), 7.18 (s, 2H), 7.20 (d, J=8.29 Hz, 1H), 7.66-7.71 (m, 2H), 7.74 (dd, J=8.21, 1.68 Hz, 1H), 8.05 (d, J=1.72 Hz, 1H), 8.20 (d, J=8.77 Hz, 1H), 8.61 (s, 1H). LC-MS (Method A): r.t. 0.91 min, MS (ESI) m/z=418.3 [M+H]$^+$.

Example 152 and 153: 7-(4-aminocinnolin-7-yl)-3-(propan-2-yl)-3,4-dihydro-1H-2,1-benzoxaborinin-1-ol Enantiomer 1 (152) and Enantiomer 2 (153)

Enantiomer 1

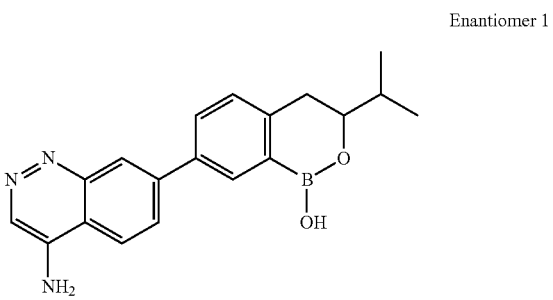

Enantiomer 2

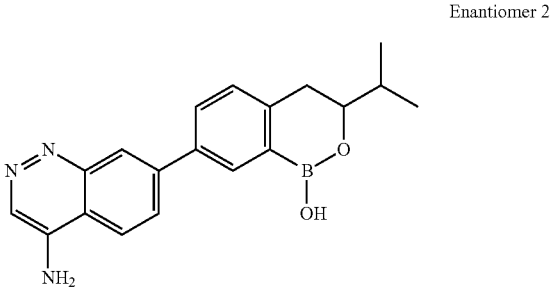

Step 1: A solution of tert-butyl[(1-{4-chloro-2-[(1S,2S,6R,8S)-2,9,9-trimethyl-3,5-dioxa-4-boratricyclo[6.1.1.0$^{2,6}$]

decan-4-yl]phenyl}-3-methylbutan-2-yl)oxy]dimethylsilane (131.11 mg, 0.270 mmol), N-[(2,4-dimethoxyphenyl)methyl]-7-(4,4,5,5-tetramethyl-1,3,2-dioxaborolan-2-yl)cinnolin-4-amine (125.0 mg, 0.300 mmol) and aqueous 2N sodium carbonate solution (296.7 uL, 0.590 mmol) in 1,2-dimethoxyethane (3 mL) was degassed for 10 min with $N_2$. Then [1,1'-bis(di-tert-butylphosphino)ferrocene]dichloropalladium(II) (19.4 mg, 0.030 mmol) was added and the reaction mixture was heated to 85° C. for 2 hours. The mixture was filtered over a pad of Celite, washing with MeOH and the filtrate was concentrated in vacuo.

Step 2: The crude material from Step 1 was dissolved in a mixture of DCM (2 mL) and trifluoroacetic acid (2 mL). The mixture was stirred at room temperature overnight and the volatiles were evaporated in vacuo. The residue was purified by column chromatography (KP-C18-HS, 2×SNAP 12 g in series) eluting with a gradient of $CH_3CN$ (+0.1% of HCOOH) in water (+0.1% of HCOOH) from 2% to 25%. Appropriate fractions were collected and lyophilized. The recovered solid was submitted to semi-preparative HPLC purification (Chiralpak OD-H (25×0.46 cm), 5 µm, n-hexane/(EtOH+0.1% isopropylamine) 85/15% v/v). Fractions containing the two separated enantiomers were collected separately and lyophilized to give 7-(1-hydroxy-3-propan-2-yl-3,4-dihydro-2,1-benzoxaborinin-7-yl)cinnolin-4-amine enantiomer 1 (3.12 mg, 0.009 mmol, 3.156% yield) as a white solid and 7-(1-hydroxy-3-propan-2-yl-3,4-dihydro-2,1-benzoxaborinin-7-yl)cinnolin-4-amine enantiomer 2 (3.55 mg, 0.011 mmol, 3.591% yield) as a white solid.

Enantiomer 1 characterization: $^1$H NMR (400 MHz, DMSO-$d_6$) δ 0.99 (d, J=6.74 Hz, 3H), 1.02 (d, J=6.70 Hz, 3H), 1.77-1.88 (m, 1H), 2.74-2.95 (m, 2H), 3.89 (ddd, J=10.23, 6.27, 3.74 Hz, 1H), 7.21 (s, 2H), 7.39 (d, J=7.92 Hz, 1H), 7.88-7.97 (m, 2H), 8.23 (d, J=2.11 Hz, 1H), 8.26-8.32 (m, 2H), 8.61 (s, 1H). LC-MS (Method A): r.t. 0.69 min, MS (ESI) m/z=334.19 [M+H]$^+$. Analytical chiral HPLC: Column Chiralpak OD-H (25×0.46 cm), 5 um, Mobile phase n-Hexane/(Ethanol+0.1% isopropylamine) 85/15% v/v, flow rate 1.0 mL/min, Enantiomer 1=100% a/a by UV (12.6 min) Enantiomer 2 not detected.

Enantiomer 2 characterization: $^1$H NMR (400 MHz, DMSO-$d_6$) δ 0.99 (d, J=6.74 Hz, 3H), 1.02 (d, J=6.70 Hz, 3H), 1.77-1.88 (m, 1H), 2.74-2.95 (m, 2H), 3.81-3.94 (m, 1H), 7.21 (s, 2H), 7.39 (d, J=7.92 Hz, 1H), 7.88-7.97 (m, 2H), 8.23 (d, J=2.11 Hz, 1H), 8.26-8.32 (m, 2H), 8.61 (s, 1H). LC-MS (Method A): r.t. 0.69 min, MS (ESI) m/z=334.18 [M+H]$^+$. Analytical chiral HPLC: Column Chiralpak OD-H (25×0.46 cm), 5 um, mobile phase n-Hexane/(Ethanol+0.1% isopropylamine) 85/15% v/v, flow rate 1.0 mL/min, Enantiomer 1=1.3% a/a by UV (12.6 min) Enantiomer 2=98.7% a/a by UV (15.4 min).

Example 154 and 155: [3-(4-aminocinnolin-7-yl)-4-[(5-oxopyrrolidin-3-yl)methoxy]phenyl]boronic Acid Enantiomer 1 (154) and Enantiomer 2 (155)

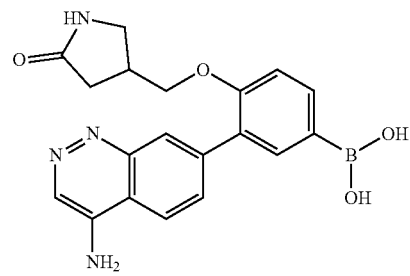

Enantiomer 1

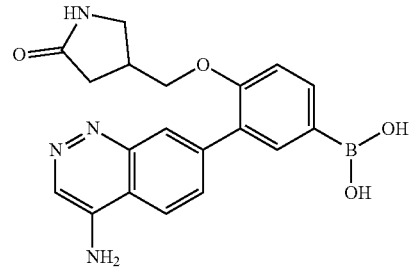

Enantiomer 2

Palladium(II) diacetate (3.89 mg, 0.020 mmol), 4-[[4-chloro-2-[4-[(2,4-dimethoxyphenyl)methylamino]cinnolin-7-yl]phenoxy]methyl]pyrrolidin-2-one (180.0 mg, 0.350 mmol), dicyclohexyl-[2-[2,4,6-tri(propan-2-yl)phenyl]phenyl]phosphine (16.53 mg, 0.030 mmol), potassium acetate (102.11 mg, 1.04 mmol), and 4,4,5,5-tetramethyl-2-(4,4,5,5-tetramethyl-1,3,2-dioxaborolan-2-yl)-1,3,2-dioxaborolane (264.22 mg, 1.04 mmol) were dissolved in 1,4-dioxane (3.468 mL) in a microwave vial and degassed for 10 min with $N_2$. The resulting reaction mixture was stirred at 80° C. for 2 hours then it was cooled to room temperature and filtered over Celite, washing with EtOAc. The filtrate was evaporated under reduced pressure and the residue was dissolved in dichloromethane (1 mL) and trifluoroacetic acid (1 mL). The resulting mixture was stirred for 4 hours at room temperature then evaporated in vacuo. The residue was dissolved in MeOH/$H_2O$ (9:1), loaded onto an SCX cartridge and the cartridge was left to stand for 20 min. The cartridge was then washed with MeOH/$H_2O$ (9:1) and eluted with 2 M methanolic ammonia solution. The basic fractions were collected and evaporated under reduced pressure. The residue was purified by semi-preparative HPLC (xBridge C18 (30×100 mm, 3 µm). gradient of MeCN in 10 mM aqueous ammonium bicarbonate solution adjusted to pH 10 with ammonia from 10.0% to 30.0% in 10 min; flow: 40.00 mL/min). Appropriate fractions were collected and evaporated. The recovered solid was submitted to semi-preparative chiral HPLC purification (Chiralpak AS-H (25×0.46 cm), 5 µm, n-hexane/(EtOH+0.1% isopropylamine) 70/30% v/v). Fractions containing the two separated enantiomers were collected separately and lyophilized to give [3-(4-aminocinnolin-7-yl)-4-[(5-oxopyrrolidin-3-yl)methoxy]phenyl]boronic acid enantiomer 1 (3.7 mg, 0.010 mmol, 2.85% yield) as a white solid and [3-(4-aminocinnolin-7-yl)-4-[(5-oxopyrrolidin-3-yl)methoxy]phenyl]boronic acid enantiomer 2 (3.9 mg, 0.011 mmol, 3.14% yield) as a white solid.

Enantiomer 1 characterization: $^1$H NMR (400 MHz, DMSO-$d_6$) δ 2.02 (dd, J=16.65, 7.45 Hz, 1H), 2.22 (dd, J=16.63, 8.94 Hz, 1H), 2.70-2.81 (m, 1H), 3.06 (dd, J=9.74, 6.12 Hz, 1H), 3.26-3.29 (m, 1H), 4.02-4.12 (m, 2H), 7.12-7.21 (m, 3H), 7.50 (s, 1H), 7.76 (dd, J=8.78, 1.77 Hz, 1H), 7.83 (dd, J=8.25, 1.73 Hz, 1H), 7.96 (d, J=1.72 Hz, 1H), 8.02 (s, 2H), 8.15 (d, J=1.71 Hz, 1H), 8.19 (d, J=8.75 Hz, 1H), 8.61 (s, 1H). LC-MS (Method A): r.t. 0.38 min, MS (ESI) m/z=379.2 [M+H]$^+$. Analytical chiral HPLC: Column Chiralpak AS-H (25×0.46 cm), 5 um, mobile phase n-Hexane/(Ethanol+0.1% isopropylamine) 70/30% v/v, flow rate 2.5 mL/min, Enantiomer 1=98% a/a by UV (14.3 min) Enantiomer 2=2% a/a by UV (20.3 min).

Enantiomer 2 characterization: $^1$H NMR (400 MHz, DMSO-$d_6$) δ 2.02 (dd, J=16.65, 7.45 Hz, 1H), 2.22 (dd, J=16.63, 8.94 Hz, 1H), 2.70-2.81 (m, 1H), 3.06 (dd, J=9.74, 6.12 Hz, 1H), 3.26-3.29 (m, 1H), 4.02-4.12 (m, 2H), 7.12-7.21 (m, 3H), 7.50 (s, 1H), 7.76 (dd, J=8.78, 1.77 Hz, 1H), 7.83 (dd, J=8.25, 1.73 Hz, 1H), 7.96 (d, J=1.72 Hz, 1H), 8.02 (s, 2H), 8.15 (d, J=1.71 Hz, 1H), 8.19 (d, J=8.75 Hz, 1H), 8.61 (s, 1H). LC-MS (Method A): r.t. 0.38 min, MS (ESI) m/z=379.2 [M+H]$^+$. Analytical chiral HPLC: Column Chiralpak AS-H (25×0.46 cm), 5 um, mobile phase n-Hexane/(Ethanol+0.1% isopropylamine) 88/12% v/v, flow rate 2.5 mL/min, Enantiomer 1=9.5% a/a by UV (14.3 min) Enantiomer 2=90.5% a/a by UV (20.3 min).

Example 156: 7-(4-aminocinnolin-7-yl)-1H-2,3,1-benzoxazaborinin-1-ol Formic Acid Salt (156)

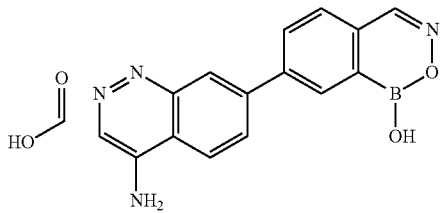

N-[(2,4-Dimethoxyphenyl)methyl]-7-(1-hydroxy-2,3,1-benzoxazaborinin-7-yl)cinnolin-4-amine (27.0 mg, 0.060 mmol) was dissolved in DCM (1.5 mL) and trifluoroacetic acid (1.5 mL) and the mixture was stirred at room temperature for 4 hours, then it was concentrated under reduced pressure. The residue was purified by column chromatography (KP-C18-HS, 2×6 g in series) eluting with a gradient of CH$_3$CN (+0.1% of HCOOH) in water (+0.1% of HCOOH) from 2% to 20%. Fractions containing the desired compound were concentrated to give 7-(1-hydroxy-2,3,1-benzoxazaborinin-7-yl)cinnolin-4-amine formic acid salt (4 mg, 0.012 mmol, 19.41% yield) as a whitish solid. $^1$H NMR (400 MHz, DMSO-$d_6$) δ 7.71 (br s, 2H), 7.94 (d, J=7.92 Hz, 1H), 8.06-8.10 (dd, J=8.80, 1.80 Hz, 1H), 8.14 (s, 1H from HCOOH), 8.36 (dd, J=8.14, 1.98 Hz, 1H), 8.38-8.44 (m, 2H), 8.63 (s, 2H), 8.75 (s, 1H), 9.56 (br s, 1H). LC-MS (Method A): r.t. 0.41 min, MS (ESI) m/z=291.1 [M+H]$^+$.

Example 157: [7-(4-aminocinnolin-7-yl)-4-methyl-1-benzofuran-5-yl]boronic Acid (157)

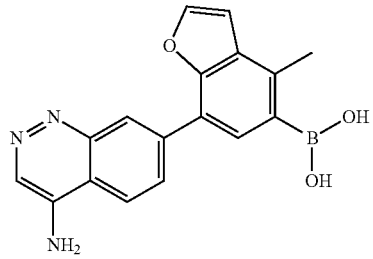 [SMILES: Cc1c(B(O)O)cc(-c2ccc3c(N)cnnc3c2)c2occc12]

Step 1: Palladium(II) diacetate (3.05 mg, 0.010 mmol), 7-(5-chloro-4-methyl-1-benzofuran-7-yl)-N-[(2,4-dimethoxyphenyl)methyl]cinnolin-4-amine (125.0 mg, 0.270 mmol), dicyclohexyl-[2-[2,4,6-tri(propan-2-yl)phenyl]phenyl]phosphine (10.37 mg, 0.020 mmol), potassium acetate (80.02 mg, 0.820 mmol), and 4,4,5,5-tetramethyl-2-(4,4,5,5-tetramethyl-1,3,2-dioxaborolan-2-yl)-1,3,2-dioxaborolane (207.05 mg, 0.820 mmol) were dissolved in 1,4-dioxane (6.9 mL) in a microwave vial and the mixture was degassed with Ar for 10 minutes. The mixture was then stirred at 100° C. for 1 hour. The mixture was filtered, washing with MeOH and the filtrate was concentrated in vacuo. LC-MS (Method A): r.t. 1.03 min, MS (ESI) m/z=552.3 [M+H]$^+$.

Step 2: The crude material from Step 1 was dissolved in DCM (3 mL) and trifluoroacetic acid (2.5 mL) and the mixture was stirred overnight at room temperature then concentrated under reduced pressure. The residue was dissolved in MeOH/H$_2$O (9:1) and loaded onto an SCX cartridge (5 g). The cartridge was washed with MeOH/H$_2$O (9:1) and the product was eluted from the SCX cartridge with a 2 M solution of NH$_3$ in MeOH. The basic fractions were evaporated and the residue was purified by column chromatography (KP-C18-HS, 2×12 g in series) eluting with a gradient of CH$_3$CN (+0.1% of HCOOH) in water (+0.1% of HCOOH) from 2% to 30%. Appropriate fractions were collected and concentrated. The recovered solid was submitted to semi-preparative HPLC purification (Chiralpak IC (25×2.0 cm), 5 μm, n-hexane/(EtOH+0.1% isopropylamine) 75/25% v/v). Appropriate fractions were collected and evaporated under reduced pressure to give [7-(4-aminocinnolin-7-yl)-4-methyl-1-benzofuran-5-yl]boronic acid (2.6 mg, 0.008 mmol, 3.0% yield) as a yellowish solid. $^1$H NMR (400 MHz, DMSO-$d_6$+2 drops of TFA) δ 2.71 (s, 3H), 7.21 (d, J=2.42 Hz, 1H), 7.94 (s, 1H), 8.13 (d, J=2.20 Hz, 1H), 8.36 (dd, J=9.13, 1.65 Hz, 1H), 8.47-8.50 (m, 2H), 8.58 (d, J=9.02 Hz, 1H), 9.73 (br. s, 1H), 9.89 (br. s, 1H). LC-MS (Method A): r.t. 0.51 min, MS (ESI) m/z=320.1 [M+H]$^+$.

Example 158: [3-(4-hydroxycinnolin-7-yl)-4-methoxyphenyl]boronic Acid (158)

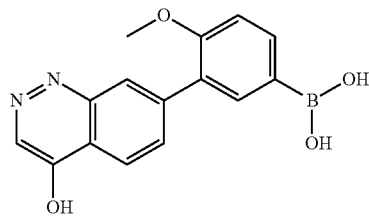 [SMILES: COc1ccc(B(O)O)cc1-c1ccc2c(O)cnnc2c1]

The crude reaction mixture from a preparation of Intermediate 19 starting with 50 g of 7-(5-chloro-2-methoxyphenyl)-N-[(2,4-dimethoxyphenyl)methyl]cinnolin-4-amine following a similar procedure to that described above was cooled in an ice bath and H₂O was added causing precipitation of Intermediate 19. The mixture was stirred for 10 minutes and filtered. The filtrate was concentrated, quenched with saturated aqueous NH₄Cl solution and extracted three times with EtOAc. The combined organic phases were washed with brine, dried over Na₂SO₄, filtered and evaporated under reduced pressure. A small aliquot of the residue was taken up with MeOH and was loaded onto an SCX cartridge which was washed with MeOH and then eluted with a 7 M methanolic ammonia solution. The basic fractions were collected and evaporated under reduced pressure. The residue was purified by flash chromatography (Sfar C18 D, 12 g) eluting with a gradient of MeCN (+0.1% of HCOOH) in water (+0.1% of HCOOH) from 1% to 70%. Appropriate fractions were collected and lyophilized. The recovered solid was submitted to semi-preparative chiral HPLC purification (MDAP Waters with mass spectrometry detection (MS: ZQ2000), xBridge C18 (30×100 mm, 3 μm), gradient of MeCN in 10 mM aqueous ammonium bicarbonate solution adjusted to pH 10 with ammonia from 10.0% to 30.0% in 10 min, flow: 40.00 mL/min). Appropriate fractions were collected and lyophilized to give [3-(4-hydroxycinnolin-7-yl)-4-methoxyphenyl]boronic acid (7 mg, 0.024 mmol, 0.179% yield) as a white solid. ¹H NMR (400 MHz, DMSO-d₆) δ 3.82 (s, 3H), 7.13 (d, J=8.21 Hz, 1H), 7.58 (dd, J=8.47, 1.43 Hz, 1H), 7.72-7.75 (m, 1H), 7.78 (s, 1H), 7.85-7.90 (m, 2H), 8.06 (d, J=8.48 Hz, 1H). LC-MS (Method A): r.t. 0.43 min, MS (ESI) m/z=297.1 [M+H]⁺.

Example 159: [3-(4-aminocinnolin-7-yl)-4-(²H₃)methoxyphenyl]boronic Acid Formic Acid Salt (159)

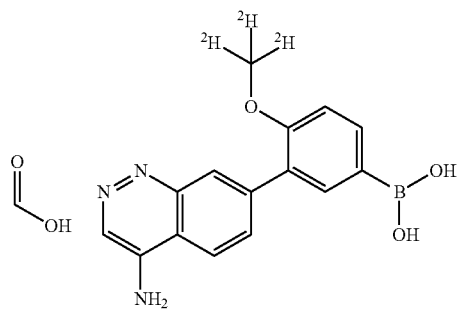

Step 1: A mixture of 7-[5-chloro-2-(²H₃)methoxyphenyl]-N-[(2,4-dimethoxyphenyl)methyl]cinnolin-4-amine (690.0 mg, 1.57 mmol), 4,4,5,5-tetramethyl-2-(4,4,5,5-tetramethyl-1,3,2-dioxaborolan-2-yl)-1,3,2-dioxaborolane (1.2 g, 4.72 mmol) and potassium acetate (462.84 mg, 4.72 mmol) in 1,4-dioxane (20 mL) was degassed for 10 minutes under argon. Dicyclohexyl-[2-[2,4,6-tri(propan-2-yl)phenyl]phenyl]phosphine (59.95 mg, 0.130 mmol) and palladium(II) diacetate (17.65 mg, 0.080 mmol) were added and the mixture was stirred at 85° C. for 2 hours. The mixture was allowed to cool to room temperature, filtered over Celite, washing with MeOH and EtOAc and the filtrate concentrated in vacuo. LC-MS (Method A): r.t. 0.92 min, MS (ESI) m/z=531.4 [M+H]⁺.

Step 2: The crude material from Step 1 was dissolved in DCM (5 mL) and trifluoroacetic acid (5 mL) and the mixture was stirred for 24 hours, then the volatiles were removed under reduced pressure. The residue was dissolved in MeOH/water (9:1) and loaded onto 2 SCX cartridges (10 g each) each of which was washed with MeOH and then eluted with a 7M solution of ammonia in MeOH. The basic fractions from both cartridges were collected and evaporated under reduced pressure. The residue was purified by flash chromatography (Sfar C18 D, 60 g) eluting with a gradient of MeCN (+0.1% of HCOOH) in water (+0.1% of HCOOH) from 1% to 35%. Appropriate fractions were collected and lyophilized to give [3-(4-aminocinnolin-7-yl)-4-(²H₃)methoxyphenyl]boronic acid in a mixture with 6% of the corresponding pinacolate ester. This material was dissolved in MeOH/water (9:1) and loaded onto an SCX cartridge (10 g) which was washed with MeOH and then eluted with a 7M solution of ammonia in MeOH. The basic fractions were collected and evaporated under reduced pressure and the residue was purified by flash chromatography (Sfar C18 D, 30 g) eluting with a gradient of MeCN (+0.1% of HCOOH) in water (+0.1% of HCOOH) from 1% to 35%. Appropriate fractions were collected and lyophilized to give [3-(4-aminocinnolin-7-yl)-4-(²H₃)methoxyphenyl]boronic acid formic acid salt (122 mg, 0.355 mmol, 22.61% yield) as a light yellow solid. ¹H NMR (400 MHz, DMSO-d₆+TFA) δ 7.12 (d, J=8.19 Hz, 1H), 7.84-7.95 (m, 3H), 8.01 (d, J=1.56 Hz, 1H), 8.04 (s, 1H), 8.39-8.49 (m, 2H), 9.60 (s, 1H), 9.75 (s, 1H). LC-MS (Method A): r.t. 0.43 min, MS (ESI) m/z=299.1 [M+H]⁺.

Example 160: [3-(1-hydroxyphthalazin-6-yl)-4-methoxyphenyl]boronic Acid (160)

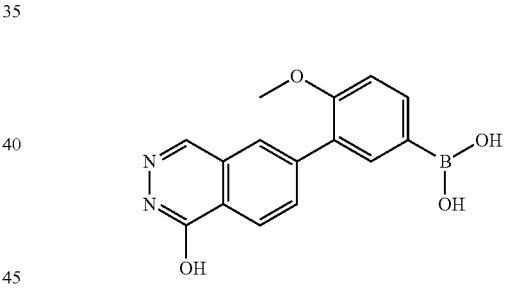

Palladium(II) diacetate (4.7 mg, 0.020 mmol), 6-(5-chloro-2-methoxyphenyl)phthalazin-1-ol (120.0 mg, 0.420 mmol), dicyclohexyl-[2-[2,4,6-tri(propan-2-yl)phenyl]phenyl]phosphine (19.95 mg, 0.040 mmol), potassium acetate (123.23 mg, 1.26 mmol), and 4,4,5,5-tetramethyl-2-(4,4,5,5-tetramethyl-1,3,2-dioxaborolan-2-yl)-1,3,2-dioxaborolane (318.85 mg, 1.26 mmol) were dissolved in 1,4-dioxane (4.18 mL) in a microwave vial and degassed for 10 min with N₂. The resulting reaction mixture was stirred at 80° C. for 2 hours then it was cooled to room temperature and filtered over Celite, washing with EtOAc. The filtrate was evaporated under reduced pressure and the residue was dissolved in dichloromethane (1.5 mL) and trifluoroacetic acid (1.5 mL). The resulting mixture was stirred for 4 hours at room temperature then evaporated in vacuo. The residue was purified by column chromatography (Sfar C18 D, 30 g) eluting with a gradient of MeCN (+0.1% of HCOOH) in water (+0.1% of HCOOH) from 1% to 70%. Appropriate fraction were collected and lyophilised to give [4-methoxy-3-(1-oxo-2H-phthalazin-6-yl)phenyl]boronic acid (9 mg, 0.030 mmol, 7.14% yield) as a white solid. ¹H NMR (500

MHz, DMSO-d$_6$) δ 3.82 (s, 3H), 7.16 (d, J=8.1 Hz, 1H), 7.82-7.90 (m, 2H), 7.96 (dd, J=8.4, 1.5 Hz, 1H), 7.99-8.06 (m, 3H), 8.24 (d, J=8.2 Hz, 1H), 8.40 (s, 1H), 12.63 (s, 1H). LC-MS (Method A): r.t. 0.66 min, MS (ESI) m/z=297.5 [M+H]$^+$.

Example 161: [3-(isoquinolin-7-yl)-4-methoxyphenyl]boronic Acid (161)

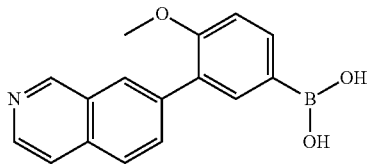 [SMILES: COc1ccc(B(O)O)cc1-c1ccc2ccncc2c1]

Palladium(II) diacetate (8.24 mg, 0.040 mmol), 7-(5-chloro-2-methoxyphenyl)isoquinoline (198.0 mg, 0.730 mmol), dicyclohexyl-[2-[2,4,6-tri(propan-2-yl)phenyl]phenyl]phosphine (34.99 mg, 0.070 mmol), potassium acetate (216.12 mg, 2.2 mmol), and 4,4,5,5-tetramethyl-2-(4,4,5,5-tetramethyl-1,3,2-dioxaborolan-2-yl)-1,3,2-dioxaborolane (559.23 mg, 2.2 mmol) were dissolved in 1,4-dioxane (3.561 mL) in a microwave vial and degassed for 10 min with N$_2$. The resulting reaction mixture was stirred at 80° C. for 2 hours then it was cooled to room temperature and filtered over Celite, washing with MeOH. The filtrate was evaporated under reduced pressure and the residue was dissolved in MeOH/H$_2$O (9:1), loaded onto an SCX cartridge and the cartridge was left to stand for 20 min. The cartridge was then washed with MeOH/H$_2$O (9:1) and eluted with 2 M methanolic ammonia solution. The basic fractions were collected and evaporated under reduced pressure. The residue was column chromatography (Sfar C18 D, 30 g) eluting with a gradient of MeCN (+0.1% of HCOOH) in water (+0.1% of HCOOH) from 1% to 70%. Appropriate fractions were collected and lyophilized to give (3-isoquinolin-7-yl-4-methoxyphenyl)boronic acid (36 mg, 0.129 mmol, 17.57% yield) as a white solid. $^1$H NMR (400 MHz, DMSO-d$_6$+2 drops of TFA) δ 3.82 (s, 3H), 7.15 (d, J=8.30 Hz, 1H), 7.87-7.97 (m, 2H), 8.31 (d, J=8.71 Hz, 1H), 8.38 (dd, J=8.64, 1.72 Hz, 1H), 8.48 (d, J=6.43 Hz, 1H), 8.61-8.67 (m, 2H), 9.90 (s, 1H). LC-MS (Method A): r.t. 0.43 min, MS (ESI) m/z=280.1 [M+H]$^+$.

Example 162: [4-methoxy-3-(5-methoxycinnolin-7-yl)phenyl]boronic Acid 162

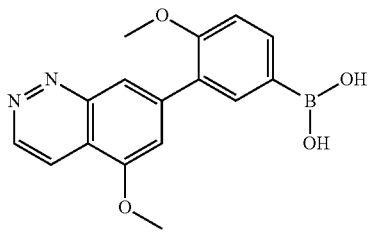 [SMILES: COc1ccc(B(O)O)cc1-c1cc(OC)c2ccnnc2c1]

Palladium(II) diacetate (4.11 mg, 0.020 mmol), 7-(5-chloro-2-methoxyphenyl)-5-methoxycinnoline (110.0 mg, 0.370 mmol), dicyclohexyl-[2-[2,4,6-tri(propan-2-yl)phenyl]phenyl]phosphine (13.95 mg, 0.030 mmol), potassium acetate (107.69 mg, 1.1 mmol), and 4,4,5,5-tetramethyl-2-(4,4,5,5-tetramethyl-1,3,2-dioxaborolan-2-yl)-1,3,2-dioxaborolane (278.65 mg, 1.1 mmol) were dissolved in 1,4-dioxane (4 mL). The mixture was degassed with N$_2$ for 10 min, then stirred at 75° C. for 2 hours. The mixture was filtered over a pad of Celite, washing with EtOAc and the filtrate was concentrated in vacuo. The residue was suspended in DCM (2.129 mL) and trifluoroacetic acid (2.129 mL) and stirred overnight. The mixture was concentrated in vacuo and the residue was dissolved in MeOH and loaded onto an SCX cartridge. The cartridge was washed with MeOH/H$_2$O (9:1) then the product was eluted from the SCX cartridge with a 2M solution of NH$_3$ in MeOH. The volatiles were evaporated and the residue was purified by column chromatography (KP-C18-HS, 2×SNAP 12 g in series) eluting with a gradient of CH$_3$CN (+0.1% of HCOOH) in water (+0.1% of HCOOH) from 2% to 50%. Appropriate fractions were collected and lyophilized to give [4-methoxy-3-(5-methoxycinnolin-7-yl)phenyl]boronic acid (3.5 mg, 0.011 mmol, 3.086% yield) as a pale-yellow powder. $^1$H NMR (400 MHz, DMSO-d$_6$+2 drops TFA) δ 3.87 (s, 3H), 4.09 (s, 3H), 7.20 (d, J=8.37 Hz, 1H), 7.49 (s, 1H), 7.90 (dd, J=8.25, 1.69 Hz, 1H), 8.00 (d, J=1.71 Hz, 1H), 8.12 (s, 1H), 8.43-8.50 (m, 1H), 9.43 (d, J=5.95 Hz, 1H). LC-MS (Method A): r.t. 0.76 min, MS (ESI) m/z=311.16 [M+H]$^+$.

Example 163: [3-(4-aminocinnolin-7-yl)-4-(1,1-difluoroethoxy)phenyl]boronic Acid Formic Acid Salt (163)

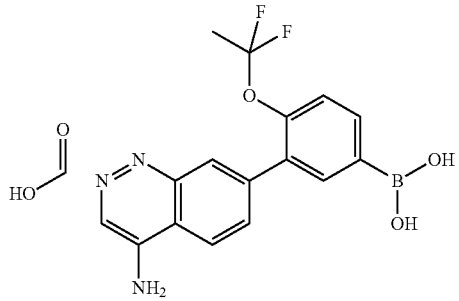

Step 1: Palladium(II) diacetate (3.47 mg, 0.020 mmol), 7-[5-chloro-2-(1,1-difluoroethoxy)phenyl]-N-[(2,4-dimethoxyphenyl)methyl]cinnolin-4-amine (150.0 mg, 0.310 mmol), dicyclohexyl-[2-[2,4,6-tri(propan-2-yl)phenyl]phenyl]phosphine (11.77 mg, 0.020 mmol), potassium acetate (90.89 mg, 0.930 mmol), and 4,4,5,5-tetramethyl-2-(4,4,5,5-tetramethyl-1,3,2-dioxaborolan-2-yl)-1,3,2-dioxaborolane (235.17 mg, 0.930 mmol) were dissolved in 1,4-dioxane (5 mL). The mixture was degassed with N$_2$ for 10 min, then stirred at 75° C. for 2 hours. The mixture was filtered over a pad of Celite, washing with MeOH and the filtrate was concentrated in vacuo.

Step 2: The crude material from Step 1 was dissolved in a mixture of DCM (3 mL) and trifluoroacetic acid (3 mL). The mixture was stirred at room temperature overnight and the volatiles were evaporated. The residue was dissolved in MeOH and loaded onto an SCX cartridge. The cartridge was washed with MeOH/H$_2$O (9:1) and then the product was eluted from the SCX cartridge with a 2M solution of NH$_3$ in MeOH. The volatiles were evaporated and the residue was purified by column chromatography (KP-C18-HS, 2×SNAP 12 g in series) eluting with a gradient of CH$_3$CN (+0.1% of HCOOH) in water (+0.1% of HCOOH) from 2% to 20%. Appropriate fractions were collected and lyophilized to give [3-(4-aminocinnolin-7-yl)-4-(1,1-difluoroethoxy)phenyl]boronic acid formic acid salt (23 mg, 0.059 mmol, 19.0% yield) as a white solid. $^1$H NMR (400 MHz, DMSO-$d_6$+2 drops TFA) δ 1.83 (t, J=13.81 Hz, 3H), 7.45 (d, J=8.15 Hz, 1H), 7.90-8.00 (m, 3H), 8.03 (s, 1H), 8.13 (s, 0.73H from HCOOH), 8.50 (s, 1H), 8.54 (d, J=8.86 Hz, 1H), 9.79 (s, 1H), 9.92 (s, 1H). LC-MS (Method A): r.t. 0.52 min, MS (ESI) m/z=346.10 [M+H]$^+$.

Example 164: [3-(4-aminocinnolin-7-yl)-4-methanesulfonylphenyl]boronic Acid Formic Acid Salt (164)

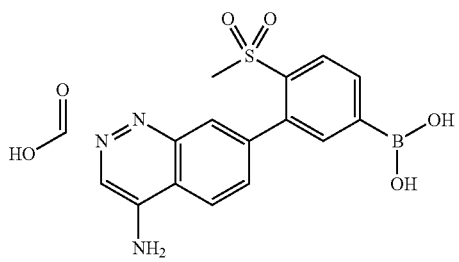

Palladium(II) diacetate (6.61 mg, 0.030 mmol), 7-(5-chloro-2-methylsulfonylphenyl)-N-[(2,4-dimethoxyphenyl)methyl]cinnolin-4-amine (285.0 mg, 0.590 mmol), dicyclohexyl-[2-[2,4,6-tri(propan-2-yl)phenyl]phenyl]phosphine (28.07 mg, 0.060 mmol), potassium acetate (173.38 mg, 1.77 mmol), and 4,4,5,5-tetramethyl-2-(4,4,5,5-tetramethyl-1,3,2-dioxaborolan-2-yl)-1,3,2-dioxaborolane (448.62 mg, 1.77 mmol) were dissolved in 1,4-dioxane (5.6 mL) in a microwave vial and degassed for 10 min with N$_2$. The resulting reaction mixture was stirred at 80° C. for 6 hours then it was cooled to room temperature and filtered over Celite, washing with EtOAc. The filtrate was evaporated under reduced pressure and the residue was dissolved in dichloromethane (2.5 mL) and trifluoroacetic acid (2.5 mL). The resulting mixture was stirred for 4 hours at room temperature then evaporated in vacuo. The residue was dissolved in MeOH/H$_2$O (9:1), loaded onto an SCX cartridge and the cartridge was left to stand for 20 min. The cartridge was then washed with MeOH/H$_2$O (9:1) and eluted with 2 M methanolic ammonia solution. The basic fractions were collected and evaporated under reduced pressure. The residue was purified by column chromatography (Sfar C18 D, 30 g) eluting with a gradient of MeCN (+0.1% of HCOOH) in water (+0.1% of HCOOH) from 1% to 25%. Appropriate fractions were collected and lyophilised to give [3-(4-aminocinnolin-7-yl)-4-methylsulfonylphenyl]boronic acid formic acid salt (55 mg, 0.141 mmol, 23.89% yield) as a white solid. $^1$H NMR (400 MHz, DMSO-$d_6$+2 drops of TFA) δ 3.06 (s, 3H), 7.80-7.89 (m, 3H), 8.12 (s, 1H from HCOOH), 8.13-8.14 (m, 2H), 8.48 (d, J=8.71 Hz, 1H), 8.52 (s, 1H), 9.83 (br. s, 1H), 9.96 (br. s, 1H). LC-MS (Method A): r.t. 0.33 min, MS (ESI) m/z=343.39 [M+H]$^+$.

Example 165: [3-(4-aminocinnolin-7-yl)-4-(1,1-dioxo-1,2,5-thiadiazolidin-2-yl)phenyl]boronic Acid (165)

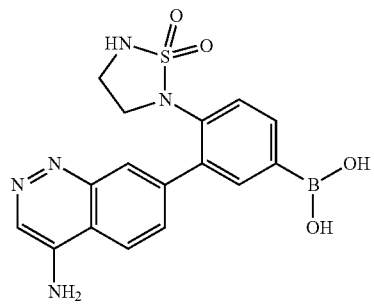 [SMILES: Nc1cnnc2cc(-c3cc(B(O)O)ccc3N3CCNS3(=O)=O)ccc12]

Palladium(II) diacetate (3.51 mg, 0.020 mmol), tert-butyl 5-[4-chloro-2-[4-[(2,4-dimethoxyphenyl)methylamino]cinnolin-7-yl]phenyl]-1,1-dioxo-1,2,5-thiadiazolidine-2-carboxylate (196.0 mg, 0.310 mmol), dicyclohexyl-[2-[2,4,6-tri(propan-2-yl)phenyl]phenyl]phosphine (14.92 mg, 0.031 mmol), potassium acetate (92.16 mg, 0.940 mmol), and 4,4,5,5-tetramethyl-2-(4,4,5,5-tetramethyl-1,3,2-dioxaborolan-2-yl)-1,3,2-dioxaborolane (238.48 mg, 0.940 mmol) were dissolved in 1,4-dioxane (3.13 mL) in a microwave vial and degassed for 10 min with N$_2$. The resulting reaction mixture was stirred at 90° C. for 2 hours then it was cooled to room temperature and filtered over Celite, washing with EtOAc. The filtrate was evaporated under reduced pressure and the residue was dissolved in dichloromethane (2 mL) and trifluoroacetic acid (2 mL). The resulting mixture was stirred for 4 hours at room temperature then was evaporated in vacuo. The residue was dissolved in MeOH/H$_2$O (9:1), loaded onto an SCX cartridge and the cartridge was left to stand for 20 min. The cartridge was then washed with MeOH/H$_2$O (9:1) and eluted with 2 M methanolic ammonia solution. The basic fractions were collected and evaporated under reduced pressure. The residue was purified by column chromatography (Sfar C18 D, 12 g) eluting with a gradient of MeCN (+0.1% of HCOOH) in water (+0.1% of HCOOH) from 1% to 25%. Appropriate fractions were collected and evaporated under reduced pressure. This residue was submitted to semi-preparative HPLC purification [CSH C18 (30×100 mm, 3 μm), gradient of MeCN in water (+0.1% of HCOOH) from 3.0% to 20.0% in 10 min, flow: 40.00 mL/min]. Appropriate fractions were collected and lyophilized to give [3-(4-aminocinnolin-7-yl)-4-(1,1-dioxo-1,2,5-thiadiazolidin-2-yl)phenyl]boronic acid (3.5 mg, 0.009 mmol, 2.9% yield) as a yellow solid. $^1$H NMR (400 MHz, DMSO-$d_6$+2 drops of TFA) δ 3.34 (t, J=6.41 Hz, 2H), 3.68 (t, J=6.41 Hz, 2H), 7.68 (d, J=8.01 Hz, 1H), 7.89-8.00 (m, 4H), 8.46-8.49 (m, 1H), 8.50 (s, 1H), 9.72 (s, 1H), 9.85 (s, 1H). LC-MS (Method B): r.t. 0.3 min, MS (ESI) m/z=386.18 [M+H]$^+$.

Example 166: 7-[2-(3,3-difluorocyclobutoxy)-5-[(1R,2R,6S,8R)-2,9,9-trimethyl-3,5-dioxa-4-boratricyclo[6.1.1.0$^{2,6}$]decan-4-yl]phenyl]cinnolin-4-amine; Formic Acid (166)

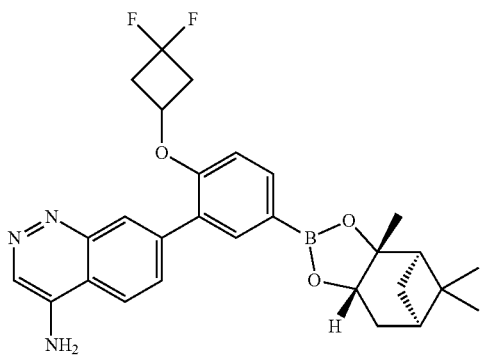 [SMILES: CC1(C)[C@H]2C[C@@H]3OB(c4ccc(OC5CC(F)(F)C5)c(-c5ccc6c(N)cnnc6c5)c4)O[C@]3(C)[C@@H]1C2]

A mixture of [3-(4-aminocinnolin-7-yl)-4-(3,3-difluorocyclobutyl)oxyphenyl]boronic acid formic acid salt (38.0 mg, 0.090 mmol) and (1R,3S,4R,5R)-4,6,6-trimethylbicyclo[3.1.1]heptane-3,4-diol (15.51 mg, 0.090 mmol) in THF (0.997 mL) was stirred overnight at 50° C. The volatiles were removed and crude was tritured with diethyl ether to give 7-[2-(3,3-difluorocyclobutoxy)-5-[(1R,2R,6S,8R)-2,9,9-trimethyl-3,5-dioxa-4-boratricyclo[6.1.1.0$^{2,6}$]decan-4-yl]phenyl]cinnolin-4-amine (33 mg, 0.065 mmol, 71.69% yield) as a white solid. $^1$H NMR (400 MHz, Methanol-d$_4$) δ 0.94 (s, 3H), 1.17-1.33 (m, 1H), 1.35 (s, 3H), 1.51 (s, 3H), 1.91-2.03 (m, 2H), 2.10-2.18 (m, 1H), 2.26-2.36 (m, 1H), 2.42-2.54 (m, 1H), 2.65-2.80 (m, 2H), 3.08-3.24 (m, 2H), 4.52 (d, J=8.47 Hz, 1H), peak for 1H at ~4.8 ppm obscured by solvent peak, 7.03 (d, J=8.24 Hz, 1H), 7.81-7.92 (m, 3H), 8.13-8.23 (m, 2H), 8.60 (s, 1H). LC-MS (Method B): r.t. 0.96 min, MS (ESI) m/z=506.2 [M+H]$^+$.

Example 167: [3-(4-aminocinnolin-7-yl)-4-(4-fluorophenoxy)phenyl]boronic Acid Formic Acid Salt (167)

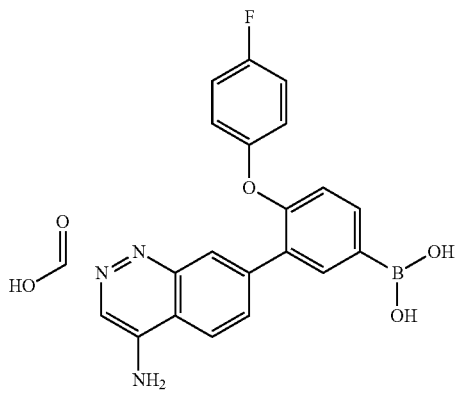

Step 1: Palladium(II) diacetate (4.79 mg, 0.020 mmol), 7-[5-chloro-2-(4-fluorophenoxy)phenyl]-N-[(2,4-dimethoxyphenyl)methyl]cinnolin-4-amine (220 mg, 0.430 mmol), dicyclohexyl-[2-[2,4,6-tri(propan-2-yl)phenyl]phenyl]phosphine (20.33 mg, 0.040 mmol), potassium acetate (125.54 mg, 1.28 mmol), and 4,4,5,5-tetramethyl-2-(4,4,5,5-tetramethyl-1,3,2-dioxaborolan-2-yl)-1,3,2-dioxaborolane (324.83 mg, 1.28 mmol) were dissolved in 1,4-dioxane (5 mL). The mixture was degassed with N$_2$ for 10 min, then stirred at 75° C. for 2 hours. The mixture was filtered over a pad of Celite, washing with MeOH and the filtrate was concentrated in vacuo.

Step 2: The crude material from Step 1 was dissolved in a mixture of DCM (4 mL) and trifluoroacetic acid (4 mL). The mixture was stirred at room temperature overnight and the volatiles were evaporated. The residue was dissolved in MeOH and loaded onto an SCX cartridge. The cartridge was washed with MeOH/H$_2$O (9:1) and then the product was eluted from the SCX cartridge with a 2M solution of NH$_3$ in MeOH. The volatiles were evaporated and the residue was purified by column chromatography (KP-C18-HS, 2×SNAP 12 g in series) eluting with a gradient of MeCN (+0.1% of HCOOH) in water (+0.1% of HCOOH) from 2% to 15%. Appropriate fractions were collected and lyophilized to give [3-(4-aminocinnolin-7-yl)-4-(4-fluorophenoxy)phenyl]boronic acid formic acid salt (82.62 mg, 0.196 mmol, 34.54% yield) as a white solid. $^1$H NMR (400 MHz, DMSO-d$_6$+2 drops of TFA) δ 6.94 (d, J=8.24 Hz, 1H), 7.07-7.14 (m, 2H), 7.18-7.26 (m, 2H), 7.90 (dd, J=8.26, 1.66 Hz, 1H), 8.05 (dd, J=8.88, 1.64 Hz, 1H), 8.08 (d, J=1.66 Hz, 1H), 8.11 (d, J=1.60 Hz, 1H), 8.13 (s, 0.76H from HCOOH), 8.46-8.51 (m, 2H), 9.73 (s, 1H), 9.86 (s, 1H). LC-MS (Method A): r.t. 0.62 min, MS (ESI) m/z=376.10 [M+H]$^+$.

Example 168: [3-(4-aminocinnolin-7-yl)-4-(1,3-thiazol-5-yloxy)phenyl]boronic Acid Formic Acid Salt (168)

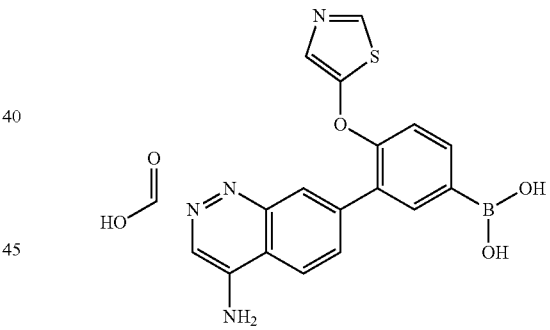

Palladium(II) diacetate (3.73 mg, 0.020 mmol), 7-[5-chloro-2-(1,3-thiazol-5-yloxy)phenyl]-N-[(2,4-dimethoxyphenyl)methyl]cinnolin-4-amine (168.0 mg, 0.330 mmol), dicyclohexyl-[2-[2,4,6-tri(propan-2-yl)phenyl]phenyl]phosphine (15.86 mg, 0.030 mmol), potassium acetate (97.95 mg, 1 mmol) and 4,4,5,5-tetramethyl-2-(4,4,5,5-tetramethyl-1,3,2-dioxaborolan-2-yl)-1,3,2-dioxaborolane (253.44 mg, 1 mmol) were dissolved in 1,2-dimethoxyethane (3.327 mL) in a microwave vial and degassed for 10 min with N$_2$. The resulting reaction mixture was stirred at 80° C. for 2 hours, then it was cooled to room temperature and filtered over Celite, washing with EtOAc. The filtrate was evaporated under reduced pressure and the residue was dissolved in dichloromethane (1.5 mL) and trifluoroacetic acid (1.5 mL). The resulting mixture was stirred overnight at room temperature then evaporated in vacuo. The residue was dissolved in MeOH/H$_2$O (9:1), loaded onto an SCX cartridge and the cartridge was left to stand for 20 min. The cartridge was then washed with MeOH/H$_2$O (9:1) and eluted with 2 M methanolic ammonia solution. The basic fractions were collected and evaporated under reduced pressure. The residue was purified by column chromatography (Sfar C18 D, 30 g) eluting with a gradient of MeCN (+0.1% of HCOOH) in water (+0.1% of HCOOH) from 1% to 70%. Appropriate fractions were collected and lyophilised to give [3-(4-aminocinnolin-7-yl)-4-(1,3-thiazol-5-yloxy)phenyl]boronic acid formic acid salt (25 mg, 0.061 mmol, 18.48% yield) as a white powder. $^1$H NMR (400 MHz, DMSO-d$_6$+2 drops of TFA) δ 7.20 (d, J=8.27 Hz, 1H), 7.58 (d, J=0.95 Hz, 1H), 7.94 (dd, J=8.30, 1.67 Hz, 1H), 8.01 (dd, J=8.85, 1.62 Hz, 1H), 8.06 (m, 2H), 8.10 (s, from HCOOH), 8.47 (s, 1H), 8.51 (d, J=8.90 Hz, 1H), 8.74 (d, J=0.92 Hz, 1H), 9.74 (br. s, 1H), 9.88 (br. s, 1H). LC-MS (Method A): r.t. 0.45 min, MS (ESI) m/z=365.12 [M+H]$^+$.

Example 169 [3-(4-aminocinnolin-7-yl)-4-(1,3-thiazol-2-yloxy)phenyl]boronic Acid Formic Acid Salt (169)

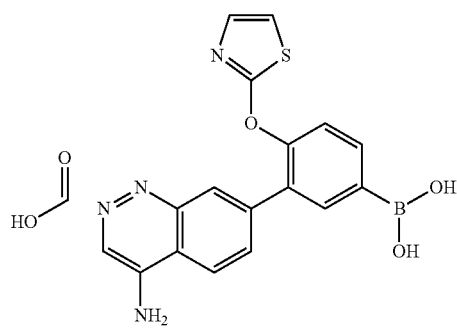

Step 1: Palladium(II) diacetate (3.8 mg, 0.020 mmol), 7-[5-chloro-2-(1,3-thiazol-2-yloxy)phenyl]-N-[(2,4-dimethoxyphenyl)methyl]cinnolin-4-amine (171 mg, 0.340 mmol), dicyclohexyl-[2-[2,4,6-tri(propan-2-yl)phenyl]phenyl]phosphine (16.14 mg, 0.030 mmol), potassium acetate (99.7 mg, 1.02 mmol) and 4,4,5,5-tetramethyl-2-(4,4,5,5-tetramethyl-1,3,2-dioxaborolan-2-yl)-1,3,2-dioxaborolane (257.97 mg, 1.02 mmol) were dissolved in 1,4-dioxane (3.88 mL). The mixture was degassed with N$_2$ for 10 min, then stirred at 75° C. for 2 hours. The mixture was filtered over a pad of Celite, washing with MeOH and the filtrate was concentrated in vacuo.

Step 2: The crude material from Step 1 was dissolved in a mixture of DCM (4 mL) and trifluoroacetic acid (4 mL). The mixture was stirred at room temperature overnight and the volatiles were evaporated. The residue was dissolved in MeOH and loaded onto an SCX cartridge. The cartridge was washed with MeOH/H$_2$O (9:1) and then the product was eluted from the SCX cartridge with a 2M solution of NH$_3$ in MeOH. The volatiles were evaporated and the residue was purified by column chromatography (KP-C18-HS, 2×SNAP 12 g in series) eluting with a gradient of CH$_3$CN (+0.1% of HCOOH) in water (+0.1% of HCOOH) from 1% to 15%. Fractions containing the desired compound were collected and lyophilized to give [3-(4-aminocinnolin-7-yl)-4-(1,3-thiazol-2-yloxy)phenyl]boronic acid formic acid salt (15 mg, 0.037 mmol, 6.415% yield) as a white solid. $^1$H NMR (400 MHz, DMSO-d$_6$+2 drops of TFA) δ 7.16 (d, J=3.89 Hz, 1H), 7.19 (d, J=3.86 Hz, 1H), 7.49 (d, J=8.19 Hz, 1H), 7.95 (dd, J=8.87, 1.66 Hz, 1H), 7.98-8.03 (m, 2H), 8.10 (d, J=1.67 Hz, 1H), 8.13 (s, 0.59H from HCOOH), 8.47 (s, 1H), 8.50 (d, J=8.88 Hz, 1H), 9.77 (s, 1H), 9.89 (s, 1H). LC-MS (Method A): r.t. 0.47 min, MS (ESI) m/z=365.13 [M+H]$^+$.

Example 170: [7-(4-aminocinnolin-7-yl)-2,2-dimethyl-2,3-dihydro-1-benzofuran-5-yl]boronic Acid Formic Acid Salt (170)

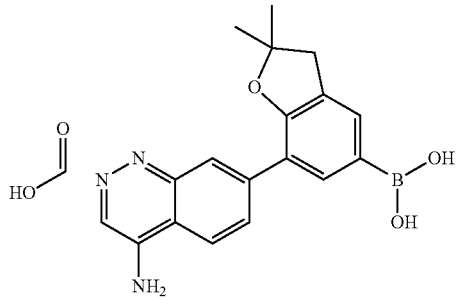

Palladium(II) diacetate (3.66 mg, 0.020 mmol), 7-(5-chloro-2,2-dimethyl-3H-1-benzofuran-7-yl)-N-[(2,4-dimethoxyphenyl)methyl]cinnolin-4-amine (155.0 mg, 0.330 mmol), dicyclohexyl-[2-[2,4,6-tri(propan-2-yl)phenyl]phenyl]phosphine (15.52 mg, 0.030 mmol), potassium acetate (95.88 mg, 0.980 mmol) and 4,4,5,5-tetramethyl-2-(4,4,5,5-tetramethyl-1,3,2-dioxaborolan-2-yl)-1,3,2-dioxaborolane (248.09 mg, 0.980 mmol) were dissolved in 1,2-dimethoxyethane (3.069 mL) in a microwave vial and degassed for 10 minutes with N$_2$. The resulting reaction mixture was stirred at 80° C. for 2 hours then it was cooled to room temperature and filtered over Celite, washing with EtOAc. The filtrate was evaporated under reduced pressure and the residue was dissolved in dichloromethane (1.5 mL) and trifluoroacetic acid (1.5 mL). The resulting mixture was stirred overnight at room temperature then evaporated in vacuo. The residue was dissolved in MeOH/H$_2$O (9:1), loaded onto an SCX cartridge and the cartridge was left to stand for 20 min. The cartridge was then washed with MeOH/H$_2$O (9:1) and eluted with 2 M methanolic ammonia solution. The basic fractions were collected and evaporated under reduced pressure. The residue was purified by column chromatography (Sfar C18 D, 30 g) eluting with a gradient of MeCN (+0.1% of HCOOH) in water (+0.1% of HCOOH) from 1% to 70%). Appropriate fractions were collected and lyophilized to give [7-(4-aminocinnolin-7-yl)-2,2-dimethyl-3H-1-benzofuran-5-yl]boronic acid formic acid salt (58 mg, 0.152 mmol, 46.06% yield) as a white solid. $^1$H NMR (400 MHz, DMSO-d$_6$) δ 1.51 (s, 6H), 3.11 (s, 2H), 7.74 (s, 1H), 8.04 (s, 1H), 8.11 (s, from HCOOH), 8.16 (dd, J=8.85, 1.62 Hz, 1H), 8.33 (d, J=1.79 Hz, 1H), 8.46 (s, 1H), 8.50 (d, J=9.00 Hz, 1H), 9.65 (br. s, 1H), 9.79 (br. s, 1H). LC-MS (Method A): r.t. 0.53 min, MS (ESI) m/z=336.13 [M+H]$^+$.

Example 171: [3-(4-aminocinnolin-7-yl)-4-(2-methylthiazol-5-yl)oxy-phenyl]boronic Acid Formic Acid Salt (171)

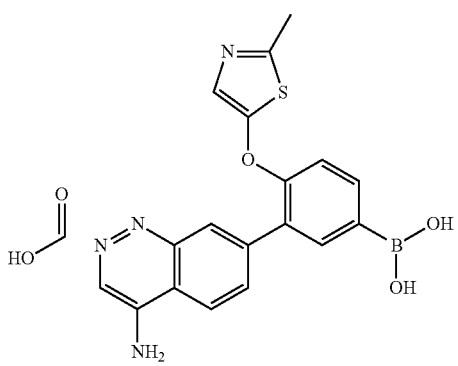

Palladium(II) diacetate (2.7 mg, 0.010 mmol), 7-[5-chloro-2-(2-methylthiazol-5-yl)oxy-phenyl]-N-[(2,4-dimethoxyphenyl)methyl]cinnolin-4-amine (125.0 mg, 0.240 mmol), dicyclohexyl-[2-[2,4,6-tri(propan-2-yl)phenyl]phenyl]phosphine (11.48 mg, 0.020 mmol), potassium acetate (70.91 mg, 0.720 mmol), and 4,4,5,5-tetramethyl-2-(4,4,5,5-tetramethyl-1,3,2-dioxaborolan-2-yl)-1,3,2-dioxaborolane (183.48 mg, 0.720 mmol) were dissolved in 1,2-dimethoxyethane (2.475 mL) in a microwave vial and degassed for 10 min with $N_2$. The resulting reaction mixture was stirred at 80° C. for 2 hours then it was cooled to room temperature and filtered over Celite, washing with EtOAc. The filtrate was evaporated under reduced pressure and the residue was dissolved in dichloromethane (1.5 mL) and trifluoroacetic acid (1.5 mL). The resulting mixture was stirred overnight at room temperature then was evaporated in vacuo. The residue was dissolved in MeOH/$H_2O$ (9:1), loaded onto an SCX cartridge and the cartridge was left to stand for 20 min. The cartridge was then washed with MeOH/$H_2O$ (9:1) and eluted with 2 M methanolic ammonia solution. The basic fractions were collected and evaporated under reduced pressure. The residue was purified by column chromatography (Sfar C18 D, 12 g) eluting with a gradient of MeCN (+0.1% of HCOOH) in water (+0.1% of HCOOH) from 1% to 70%. Appropriate fractions were collected and lyophilized to give [3-(4-aminocinnolin-7-yl)-4-(2-methylthiazol-5-yl)oxy-phenyl]boronic acid formic acid salt (32 mg, 0.075 mmol, 31.25% yield) as a white powder. $^1$H NMR (400 MHz, DMSO-$d_6$+2 drops TFA) δ 2.57 (s, 3H), 7.22 (d, J=8.28 Hz, 1H), 7.35 (s, 1H), 7.94 (dd, J=8.29, 1.69 Hz, 1H), 8.02 (dd, J=8.85, 1.63 Hz, 1H), 8.04-8.07 (m, 2H), 8.13 (s, from HCOOH), 8.49 (s, 1H), 8.53 (d, J=8.88 Hz, 1H), 9.77 (br. s, 1H), 9.91 (br. s, 1H). LC-MS (Method A): r.t. 0.48 min, MS (ESI) m/z=379.17 [M+H]$^+$.

Example 172: Preparation of Exemplary Intermediates

Intermediate 1: 6-bromo-1-chlorophthalazine

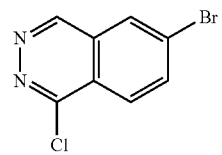 [SMILES: Clc1nncc2cc(Br)ccc12]

A solution of 6-bromophthalazin-1(2H)-one (3.2 g, 14.22 mmol) in phosphorus oxychloride (20.8 mL, 222.47 mmol) was stirred at 100° C. for 1 h. Then the phosphorus oxychloride was removed under reduced pressure. The residue was cooled in an ice bath and then quenched with 2N aqueous NaOH solution until the pH was basic. The resulting yellow solid was filtered off and washed with water to afford 6-bromo-1-chlorophthalazine (3.15 g, 12.94 mmol, 91% yield). $^1$H NMR (400 MHz, DMSO-$d_6$) δ 8.23 (d, J=8.80 Hz, 1H), 8.32 (dd, J=8.87, 1.97 Hz, 1H), 8.61 (d, J=1.93 Hz, 1H), 9.68 (s, 1H). LC-MS (Method A): r.t. 0.84 min, MS (ESI) m/z=243.09 and 245.1 [M+H]$^+$.

Intermediate 2: 6-bromo-N-[(2,4-dimethoxyphenyl)methyl]phthalazin-1-amine

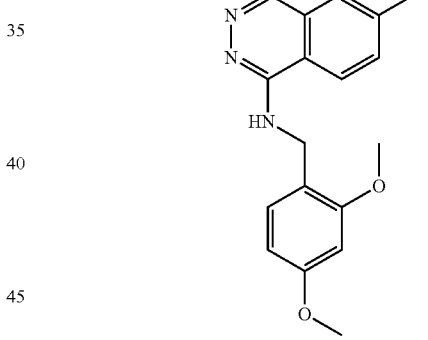

To a solution of 6-bromo-1-chlorophthalazine (500 mg, 2.05 mmol) in ethanol (9 mL) was added (2,4-dimethoxyphenyl)methanamine (0.460 mL, 3.08 mmol). The resulting mixture was stirred at 80° C. for 12 hours then it was cooled to room temperature and concentrated under reduced pressure. The residue was taken up with EtOAc and the organic phase was washed with water and brine, dried over sodium sulfate, filtered and concentrated under reduced pressure. The residue was purified by column chromatography (KP silica gel, SNAP 50) eluting with a gradient of EtOAc in dichloromethane from 10% to 70% to give 6-bromo-N-[(2,4-dimethoxyphenyl)methyl]phthalazin-1-amine (450 mg, 1.202 mmol, 58.56% yield) as a yellow solid. $^1$H NMR (400 MHz, DMSO-$d_6$) δ 3.74 (s, 3H), 3.84 (s, 3H), 4.67 (d, J=5.52 Hz, 2H), 6.44 (dd, J=8.36, 2.39 Hz, 1H), 6.58 (d, J=2.42 Hz, 1H), 7.13 (d, J=8.33 Hz, 1H), 7.84 (t, J=5.60 Hz, 1H), 8.04 (dd, J=8.80, 2.06 Hz, 1H), 8.22 (d, J=2.04 Hz, 1H), 8.34 (d, J=8.86 Hz, 1H), 8.87 (s, 1H). LC-MS (Method A): r.t. 0.64 min, MS (ESI) m/z=374.07 and 376.03 [M+H]$^+$.

Intermediate 3: 6-(3-chlorophenyl)-N-[(2,4-dimethoxyphenyl)methyl]phthalazin-1-amine

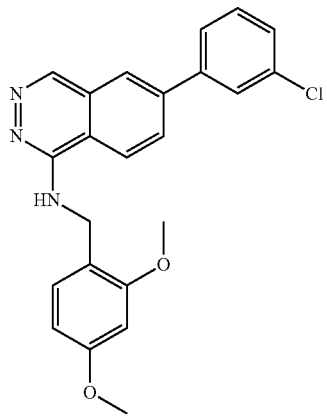 [SMILES: COc1ccc(CNc2nncc3cc(-c4cccc(Cl)c4)ccc23)c(OC)c1]

A mixture of (3-chlorophenyl)boronic acid (125.35 mg, 0.800 mmol), 6-bromo-N-[(2,4-dimethoxyphenyl)methyl]phthalazin-1-amine (300.0 mg, 0.800 mmol), [1,1'-bis(di-tert-butylphosphino)ferrocene]dichloropalladium(II) (52.41 mg, 0.080 mmol) in 1,2-dimethoxyethane (6 mL) and aqueous 2N sodium carbonate solution (1.6 mL, 1.6 mmol) was degassed for 10 min with Ar. The mixture was stirred at 85° C. for 3 hours, then it was cooled to room temperature and filtered over Celite, washing with EtOAc and the solvent was evaporated. The residue was purified by column chromatography (KP-NH silica gel, SNAP 28 g) eluting with a gradient of EtOAc in DCM from 0% to 50% to give 6-(3-chlorophenyl)-N-[(2,4-dimethoxyphenyl)methyl]phthalazin-1-amine (240 mg, 0.591 mmol, 73.76% yield, purity 67%) as a pale-brown oil. This material was used in the next step without further purification. LC-MS (Method A): r.t. 0.80 min, MS (ESI) m/z=406.3 [M+H]$^+$.

Intermediate 4: N-[(2,4-dimethoxyphenyl)methyl]-6-[3-(4,4,5,5-tetramethyl-1,3,2-dioxaborolan-2-yl)phenyl]phthalazin-1-amine

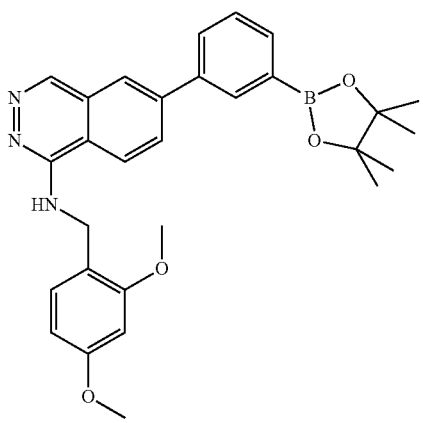 [SMILES: COc1ccc(CNc2nncc3cc(-c4cccc(B5OC(C)(C)C(C)(C)O5)c4)ccc23)c(OC)c1]

Palladium(II) diacetate (4.45 mg, 0.020 mmol), 6-(3-chlorophenyl)-N-[(2,4-dimethoxyphenyl)methyl]phthalazin-1-amine (240.0 mg, 0.400 mmol), dicyclohexyl-[2-[2,4,6-tri(propan-2-yl)phenyl]phenyl]phosphine (15.11 mg, 0.030 mmol) and potassium acetate (116.64 mg, 1.19 mmol) were dissolved in 1,4-dioxane (2.5 mL) in a microwave vial and the mixture was degassed with Ar for 10 minutes. 4,4,5,5-tetramethyl-2-(4,4,5,5-tetramethyl-1,3,2-dioxaborolan-2-yl)-1,3,2-dioxaborolane (301.81 mg, 1.19 mmol) was added and the mixture was degassed under Ar for another 10 minutes. The mixture was then stirred at 80° C. for 2 hours. The mixture was filtered over a pad of Celite, washing with methanol and the filtrate was concentrated in vacuo. The resulting residue was purified by column chromatography (KP-C18-HS, SNAP 30 g) eluting with a gradient of CH$_3$CN in water from 5% to 95% to give N-[(2,4-dimethoxyphenyl)methyl]-6-[3-(4,4,5,5-tetramethyl-1,3,2-dioxaborolan-2-yl)phenyl]phthalazin-1-amine (116 mg, 0.233 mmol, 58.87% yield) as a white solid. NMR analysis showed the presence of ~35% of the corresponding boronic acid and ~15% of free pinacol inside. $^1$H NMR (400 MHz, DMSO-d$_6$) δ 1.34 (s, 12H), 3.73 (s, 3H), 3.85 (s, 3H), 4.70 (d, J=5.38 Hz, 2H), 6.44 (dd, J=8.32, 2.29 Hz, 1H), 6.59 (d, J=2.29 Hz, 1H), 7.14 (d, J=8.32 Hz, 1H), 7.58 (t, J=7.60 Hz, 1H), 7.74-7.81 (m, 2H), 7.99 (ddd, J=7.80, 2.12, 1.25 Hz, 1H), 8.07 (br. s, 1H), 8.19 (dd, J=8.67, 1.96 Hz, 1H), 8.23 (d, J=2.16 Hz, 1H), 8.47 (d, J=8.69 Hz, 1H), 9.00 (d, J=0.75 Hz, 1H). LC-MS (Method A): r.t. 0.91 min, MS (ESI) m/z=498.4 [M+H]$^+$.

Intermediate 5: 6-[3-(4,4,5,5-tetramethyl-1,3,2-dioxaborolan-2-yl)phenyl]phthalazin-1-amine trifluoroacetic Acid Salt

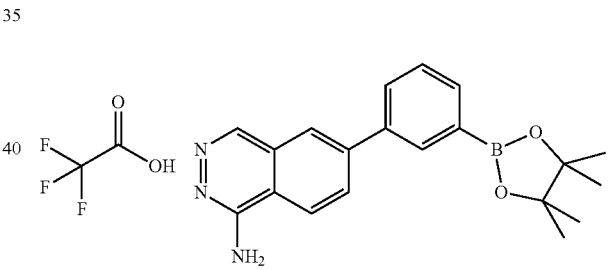

N-[(2,4-Dimethoxyphenyl)methyl]-6-[3-(4,4,5,5-tetramethyl-1,3,2-dioxaborolan-2-yl)phenyl]phthalazin-1-amine (116.0 mg, 0.230 mmol) was dissolved in a mixture of DCM (3 mL) and trifluoroacetic acid (0.600 mL) and the mixture was stirred at room temperature for 18 h. The volatiles were evaporated and the residue was purified by column chromatography (KP-C18-HS, SNAP 12 g) eluting with a gradient of CH$_3$CN in water from 2% to 80% to give 6-[3-(4,4,5,5-tetramethyl-1,3,2-dioxaborolan-2-yl)phenyl]phthalazin-1-amine trifluoroacetic acid salt (89 mg, 0.193 mmol, 82.74% yield) as a white solid. NMR analysis showed the presence of ~17% of the corresponding boronic acid inside. $^1$H NMR (400 MHz, DMSO-d$_6$) δ 1.34 (s, 12H), 7.63 (t, J=7.62 Hz, 1H), 7.83 (dt, J=7.38, 1.20 Hz, 1H), 8.05 (ddd, J=7.84, 2.15, 1.20 Hz, 1H), 8.13 (br. s, 1H), 8.49 (dd, J=8.59, 1.97 Hz, 1H), 8.56 (d, J=1.90 Hz, 1H), 8.73 (d, J=8.58 Hz, 1H), 9.03 (s, 1H), 9.25 (br. s, 2H). LC-MS (Method A): r.t. 0.74 min, MS (ESI) m/z=348.3 [M+H]$^+$.

Intermediate 6: 6-(5-chloro-2-methoxyphenyl)-N-[(2,4-dimethoxyphenyl)methyl]phthalazin-1-amine

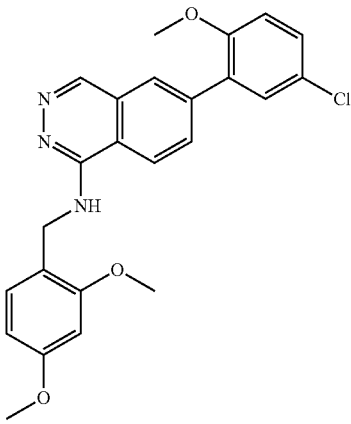 [SMILES: COc1ccc(CNc2nncc3cc(-c4cc(Cl)ccc4OC)ccc23)c(OC)c1]

A mixture of 5-chloro-2-methoxyphenylboronic acid (298.85 mg, 1.6 mmol) and 6-bromo-N-[(2,4-dimethoxyphenyl)methyl]phthalazin-1-amine (400.0 mg, 1.07 mmol) in 1,2-dimethoxyethane (8 mL) and aqueous 2N sodium carbonate solution (1.03 mL, 2.06 mmol) was degassed for 10 min with $N_2$. Then, [1,1'-bis(di-tert-butylphosphino)ferrocene]dichloropalladium(II) (69.88 mg, 0.107 mmol) was added. The mixture was stirred at 80° C. for 5 hours, then it was cooled to room temperature and filtered over Celite, washing with MeOH. The filtrate was evaporated and the residue was purified by column chromatography (KP-NH silica gel, SNAP 55) eluting with a gradient of MeOH in DCM from 0% to 10% to give 6-(5-chloro-2-methoxyphenyl)-N-[(2,4-dimethoxyphenyl)methyl]phthalazin-1-amine (495 mg, 1.136 mmol, 100% yield) as a yellow oil. $^1$H NMR (400 MHz, DMSO-d$_6$) δ 3.74 (s, 3H), 3.82 (s, 3H), 3.85 (s, 3H), 4.71 (d, J=5.48 Hz, 2H), 6.44 (dd, J=8.36, 2.41 Hz, 1H), 6.59 (d, J=2.38 Hz, 1H), 7.13 (d, J=8.35 Hz, 1H), 7.22 (d, J=8.62 Hz, 1H), 7.47-7.52 (m, 2H), 7.77 (t, J=5.73 Hz, 1H), 8.00 (dd, J=8.56, 1.84 Hz, 1H), 8.04 (d, J=1.75 Hz, 1H), 8.40 (d, J=8.58 Hz, 1H), 8.92 (d, J=0.77 Hz, 1H). LC-MS (Method A): r.t. 0.83 min, MS (ESI) m/z=436.3 [M+H]$^+$.

Intermediate 7: N-[(2,4-dimethoxyphenyl)methyl]-6-[2-methoxy-5-(4,4,5,5-tetramethyl-1,3,2-dioxaborolan-2-yl)phenyl]phthalazin-1-amine

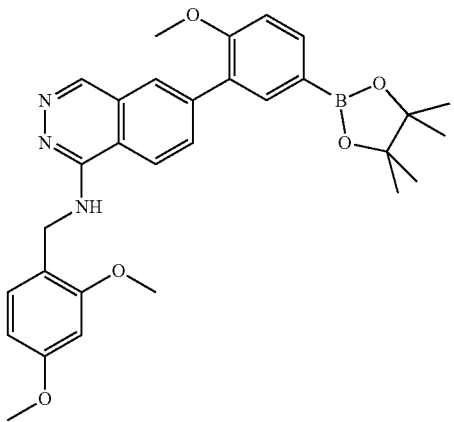

A mixture of 6-(5-chloro-2-methoxyphenyl)-N-[(2,4-dimethoxyphenyl)methyl]phthalazin-1-amine (450.0 mg, 1.03 mmol), 4,4,5,5-tetramethyl-2-(4,4,5,5-tetramethyl-1,3,2-dioxaborolan-2-yl)-1,3,2-dioxaborolane (786.46 mg, 3.1 mmol), dicyclohexyl-[2-[2,4,6-tri(propan-2-yl)phenyl]phenyl]phosphine (39.37 mg, 0.080 mmol), potassium acetate (303.94 mg, 3.1 mmol) and palladium(II) diacetate (11.59 mg, 0.050 mmol) were dissolved in 1,4-dioxane (5.46 mL) in a microwave vial and degassed for 10 min with $N_2$. The mixture was stirred at 70° C. for 2 hours, then it was cooled to room temperature and filtered over Celite, washing with MeOH. The filtrate was evaporated and the residue was purified by column chromatography (KP-C18-HS, 30 g) eluting with a gradient of $CH_3CN$ in water from 5% to 95%. Fractions containing the desired compound were collected and evaporated under reduced pressure to give N-[(2,4-dimethoxyphenyl)methyl]-6-[2-methoxy-5-(4,4,5,5-tetramethyl-1,3,2-dioxaborolan-2-yl)phenyl]phthalazin-1-amine (300 mg, 0.569 mmol, 55.10% yield) as a white powder. $^1$H NMR (400 MHz, DMSO-d$_6$) δ 1.30 (s, 12H), 3.74 (s, 3H), 3.85 (s, 3H), 3.86 (s, 3H), 4.71 (d, J=5.44 Hz, 2H), 6.44 (dd, J=8.36, 2.42 Hz, 1H), 6.60 (d, J=2.38 Hz, 1H), 7.14 (d, J=8.29 Hz, 1H), 7.21 (d, J=8.38 Hz, 1H), 7.67 (d, J=1.72 Hz, 1H), 7.72-7.78 (m, 2H), 7.95-8.03 (m, 2H), 8.38 (d, J=8.48 Hz, 1H), 8.95 (s, 1H). LC-MS (Method A): r.t. 0.92 min, MS (ESI) m/z=528.4 [M+H]$^+$.

Intermediate 8: methyl 4-bromo-2-iodobenzoate

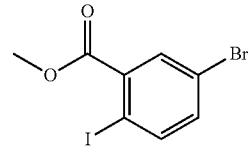

Sulfuric acid (13.89 mL, 260.56 mmol) was added to 4-bromo-2-iodobenzoic acid (25.0 g, 76.47 mmol) in methanol (287.36 mL) and the reaction mixture was heated to reflux overnight. The reaction mixture was left to reach room temperature and neutralized with solid $NaHCO_3$. The volatiles were removed in vacuum and the residue was partitioned between a saturated aqueous solution of $NaHCO_3$ and EtOAc (700 mL). The aqueous phase was extracted 3 times. The combined organic phases were dried over anhydrous sodium sulfate and concentrated to give methyl 4-bromo-2-iodobenzoate (22.96 g, 67.33 mmol, 88.05% yield) as an orange oil. $^1$H NMR (400 MHz, DMSO-d$_6$) δ 3.86 (s, 3H), 7.64-7.68 (m, 1H), 7.72-7.76 (m, 1H), 8.24 (d, J=1.98 Hz, 1H). LC-MS (Method A): r.t. 1.23 min, MS (ESI) m/z=340.93 and 342.93 [M+H]$^+$.

Intermediate 9: methyl 2-acetyl-4-bromobenzoate

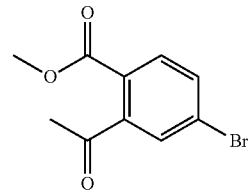

A 2.0M solution of isopropylmagnesium chloride in THF (35.19 mL, 70.37 mmol) was added dropwise at −78° C. to a solution of methyl 4-bromo-2-iodobenzoate (21.81 g, 63.98 mmol) in THF (221.7 mL). After 30 minutes acetic acid acetyl ester (7.86 mL, 83.17 mmol) was added at the same temperature. After addition was complete, the reaction mixture was stirred at room temperature for 2 hours then it was quenched with a saturated aqueous solution of ammonium chloride and extracted three times with EtOAc. The combined organic phases were washed with brine, filtered and evaporated in vacuo. The residue was purified by column chromatography (KP-Sil silica gel, SNAP 750) eluting with a gradient of EtOAc in cyclohexane from 5% to 25% to give methyl 2-acetyl-4-bromobenzoate (13.8 g, 53.69 mmol, 83.92% yield) as a yellowish oil. $^1$H NMR (400 MHz, DMSO-d$_6$) δ 2.52 (s, 3H), 3.81 (s, 3H), 7.72-7.76 (m, 1H), 7.82-7.86 (m, 1H), 7.88 (d, J=1.76 Hz, 1H). LC-MS (Method A): r.t. 0.98 min, MS (ESI) m/z=257.14 and 259.07 [M+H]$^+$.

Intermediate 10:
6-bromo-4-methyl-2H-phthalazin-1-one

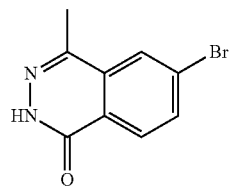

To a solution of methyl 2-acetyl-4-bromobenzoate (13.8 g, 53.68 mmol) in ethanol (89.47 mL) was added hydrazine hydrate (12.35 mL, 161.04 mmol). The resulting mixture was stirred at 85° C. overnight then it was cooled to room temperature and concentrated in vacuo. The residue was triturated with MeCN (20 mL) and filtered, washing with MeCN to give 6-bromo-4-methyl-2H-phthalazin-1-one (12.27 g, 51.3 mmol, 95.57% yield) as a white solid. $^1$H NMR (400 MHz, DMSO-d$_6$) δ 2.52 (s, 3H), 8.02 (dd, J=8.36, 1.98 Hz, 1H), 8.14 (d, J=1.54 Hz, 1H), 8.16 (d, J=8.58 Hz, 1H), 12.53 (br. s, 1H). LC-MS (Method A): r.t. 0.77 min, MS (ESI) m/z=239.06 and 241.07 [M+H]$^+$.

Intermediate 11:
6-bromo-1-chloro-4-methylphthalazine

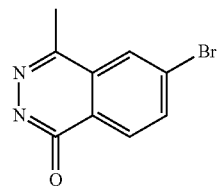

A solution of 6-bromo-4-methyl-2H-phthalazin-1-one (12.27 g, 49.27 mmol) in phosphorus(V) oxychloride (34.55 mL, 369.53 mmol) was stirred at 100° C. for 1.5 h. The phosphorus(V) oxychloride was removed under reduced pressure. The residue was cooled in an ice bath and 2N aqueous NaOH solution was added until the mixture was basic. The resulting precipitate was filtered, washed with water, dried and collected to give 6-bromo-1-chloro-4-methylphthalazine (13.77 g, 53.48 mmol, 108.54% yield). $^1$H NMR (400 MHz, DMSO-d$_6$) δ 2.93 (s, 3H), 8.20-8.23 (m, 1H), 8.29-8.33 (m, 1H), 8.57 (d, J=1.54 Hz, 1H). LC-MS (Method A): r.t. 0.91 min, MS (ESI) m/z=257 and 258.99 [M+H]$^+$.

Intermediate 12: 6-bromo-N-[(2,4-dimethoxyphenyl)methyl]-4-methylphthalazin-1-amine

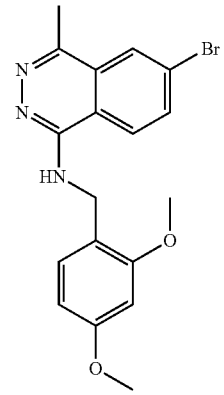 [SMILES: COc1ccc(CNc2nnc(C)c3cc(Br)ccc23)c(OC)c1]

To a solution of 6-bromo-1-chloro-4-methylphthalazine (13.77 g, 51.87 mmol) in ethanol (212.78 mL) was added (2,4-dimethoxyphenyl)methanamine (15.35 mL, 103.74 mmol) and the resulting mixture was stirred at 85° C. for 5 days. The volatiles were evaporated and the residue was purified by column chromatography (the residue was split into 2 halves, each of which was purified as described then product containing fractions from both columns were combined) (KP-Sil silica gel, SNAP 340 and SNAP 100 in series) eluting with a gradient of EtOAc in cyclohexane from 30% to 100% and then 3% MeOH in EtOAc to give 6-bromo-N-[(2,4-dimethoxyphenyl)methyl]-4-methylphthalazin-1-amine (14.77 g, 38.05 mmol, 73.35% yield) as a yellow foam. $^1$H NMR (400 MHz, DMSO-d$_6$) δ 2.66 (s, 3H), 3.73 (s, 3H), 3.83 (s, 3H), 4.63 (d, J=5.50 Hz, 2H), 6.43 (dd, J=8.36, 2.42 Hz, 1H), 6.58 (d, J=2.42 Hz, 1H), 7.11 (d, J=8.36 Hz, 1H), 7.66 (t, J=5.72 Hz, 1H), 8.05 (dd, J=8.69, 2.09 Hz, 1H), 8.19 (d, J=1.98 Hz, 1H), 8.32-8.37 (m, 1H). LC-MS (Method A): r.t. 0.65 min, MS (ESI) m/z=388.21 and 390.21 [M+H]$^+$.

Intermediate 13: 6-(3-chlorophenyl)-N-[(2,4-dimethoxyphenyl)methyl]-4-methylphthalazin-1-amine

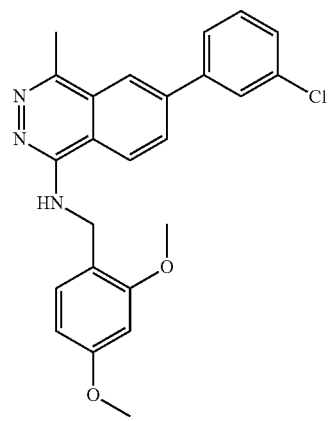 [SMILES: COc1ccc(CNc2nnc(C)c3cc(-c4cccc(Cl)c4)ccc23)c(OC)c1]

A mixture of 6-bromo-N-[(2,4-dimethoxyphenyl)methyl]-4-methylphthalazin-1-amine (100.0 mg, 0.260 mmol), (3-chlorophenyl)boronic acid (48.33 mg, 0.310 mmol) in 1,2-dimethoxyethane (2 mL) and aqueous 2N sodium carbonate solution (260 uL, 0.520 mmol) was degassed for 10 minutes with $N_2$. Then [1,1'-bis(di-tert-butylphosphino)ferrocene]dichloropalladium(II) (16.84 mg, 0.030 mmol) was added and the resulting reaction mixture was stirred at 70° C. for 1 hour. Then it was cooled to room temperature and filtered over Celite, washing with EtOAc. The filtrate was evaporated and the residue was purified by column chromatography (KP silica gel, SNAP 25) eluting with a gradient of methanol in dichloromethane from 1% to 20% to give 6-(3-chlorophenyl)-N-[(2,4-dimethoxyphenyl)methyl]-4-methylphthalazin-1-amine (55 mg, 0.131 mmol, 50.86% yield) as an off white solid. LC-MS (Method A): r.t. 0.84 min, MS (ESI) m/z=420.9 [M+H]$^+$.

Intermediate 14: [3-[1-[(2,4-dimethoxyphenyl)methylamino]-4-methylphthalazin-6-yl]phenyl]boronic Acid

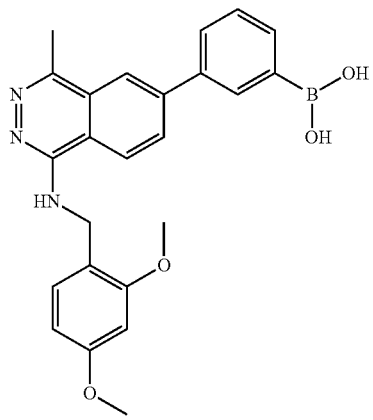 [SMILES: COc1ccc(CNc2nnc(C)c3cc(-c4cccc(B(O)O)c4)ccc23)c(OC)c1]

6-(3-Chlorophenyl)-N-[(2,4-dimethoxyphenyl)methyl]-4-methylphthalazin-1-amine (53.0 mg, 0.130 mmol), 4,4,5,5-tetramethyl-2-(4,4,5,5-tetramethyl-1,3,2-dioxaborolan-2-yl)-1,3,2-dioxaborolane (96.16 mg, 0.380 mmol) and potassium acetate (37.16 mg, 0.380 mmol) were solubilised in 1,4-dioxane (0.437 mL). The resulting solution was degassed for 10 minutes with $N_2$ then palladium(II) diacetate (1.42 mg, 0.010 mmol) and dicyclohexyl-[2-[2,4,6-tri(propan-2-yl)phenyl]phenyl]phosphine (6.02 mg, 0.010 mmol) were added. The resulting reaction mixture was stirred at 105° C. for 1 h then it was cooled to room temperature and filtered over Celite, washing with EtOAc. The filtrate was evaporated and the residue was purified by column chromatography (KP-C18-HS, 30 g) eluting with a gradient of $CH_3CN$ in water (+0.1% of HCOOH) from 1% to 50%. Fractions containing the desired compound were collected and evaporated under reduced pressure. The residue was triturated with $Et_2O$, filtered and dried to give [3-[1-[(2,4-dimethoxyphenyl)methylamino]-4-methylphthalazin-6-yl]phenyl]boronic acid (20 mg, 0.047 mmol, 36.91% yield) as a white solid. $^1$H NMR (400 MHz, DMSO-$d_6$) δ 2.77 (s, 3H), 3.73 (s, 3H), 3.85 (s, 3H), 4.67 (d, J=5.6 Hz, 2H), 6.44 (dd, J=8.4, 2.4 Hz, 1H), 6.59 (d, J=2.4 Hz, 1H), 7.14 (d, J=8.3 Hz, 1H), 7.53 (t, J=7.5 Hz, 1H), 7.61 (s, 1H), 7.83-7.90 (m, 1H), 7.91-7.99 (m, 1H), 8.21 (d, J=11.2 Hz, 4H), 8.29 (d, J=1.8 Hz, 1H), 8.48 (d, J=8.5 Hz, 1H). LC-MS (Method A): r.t. 0.67 min, MS (ESI) m/z=430.3 [M+H]$^+$.

Intermediate 15: 7-bromocinnolin-1-ium-4-ol hydrochloride

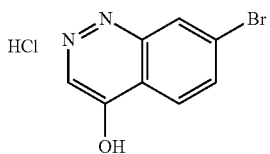 [SMILES: Cl ; Oc1cnnc2cc(Br)ccc12]

1-(2-Amino-4-bromophenyl)ethanone (10.0 g, 46.72 mmol) was dissolved in concentrated hydrochloric acid solution (270.02 mL, 3240.2 mmol) and water (51 mL) and cooled to −5° C. in an ice/brine bath. After 15 min, a solution of sodium nitrite (3380.0 mg, 48.99 mmol) in water (17 mL) was slowly added dropwise. The reaction was stirred for 30 min at −5° C., then for 30 min at room temperature and then the temperature was slowly raised to 60° C. The reaction mixture was heated at 60° C. for 2 h, then it was cooled to room temperature and the resulting precipitate was filtered, washed with water, dried in the oven at 50° C. overnight to give 7-bromocinnolin-1-ium-4-ol hydrochloride (7.463 g, 28.54 mmol, 61.09% yield) as a brownish powder. $^1$H NMR (400 MHz, DMSO-$d_6$) δ 7.57 (dd, J=8.58, 1.76 Hz, 1H), 7.76-7.80 (m, 2H), 7.96 (d, J=8.58 Hz, 1H), 13.50 (br. s, 1H). LC-MS (Method A): r.t. 0.66 min, MS (ESI) m/z=224.98 and 226.97 [M+H]$^+$.

Intermediate 16: 7-bromo-4-chlorocinnoline

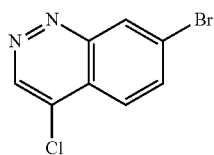 [SMILES: Clc1cnnc2cc(Br)ccc12]

A solution of 7-bromocinnolin-1-ium-4-ol hydrochloride (7.85 g, 29.73 mmol) in phosphorus(V) oxychloride (24.0 mL, 256.7 mmol) was stirred at 90° C. for 4 h. The reaction was cooled to room temperature and the excess phosphorus (V) oxychloride was removed in vacuo.

The residue was dissolved in DCM and the resulting mixture was cooled to 0° C., then a saturated aqueous solution of $NaHCO_3$ was added. The phases were separated, and the organic phase was washed with brine, dried over sodium sulfate, filtered and concentrated. The residue was purified by column chromatography (KP-Sil silica gel, SNAP 340 g) eluting with a gradient of EtOAc in cyclohexane from 2% to 10% to give 7-bromo-4-chlorocinnoline (4.875 g, 20.02 mmol, 67.35% yield) as an orange foam. $^1$H NMR (400 MHz, DMSO-$d_6$) δ 8.18-8.21 (m, 2H), 8.85 (t, J=1.21 Hz, 1H), 9.66 (s, 1H). LC-MS (Method A): r.t. 0.97 min, MS (ESI) m/z=242.97 and 244.97 [M+H]$^+$.

Intermediate 17: 7-bromo-N-[(2,4-dimethoxyphenyl)methyl]cinnolin-4-amine

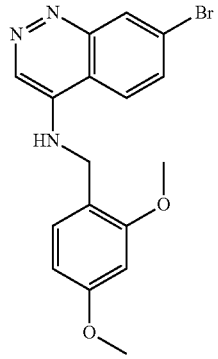 [SMILES: COc1ccc(CNc2cnnc3cc(Br)ccc23)c(OC)c1]

(2,4-Dimethoxyphenyl)methanamine (5.55 mL, 37.54 mmol) was added to a solution of 7-bromo-4-chlorocinnoline (4.06 g, 15.02 mmol) in ethanol (60.94 mL) and the resulting mixture was stirred at 110° C. for 2.5 h. Further (2,4-dimethoxyphenyl)methanamine (1 mL) was added and the mixture was stirred at 110° C. for 2.5 h. The reaction mixture was cooled to room temperature and concentrated in vacuo. The residue was taken up with EtOAc and the suspension was filtered on a Hirsch funnel. The recovered powder was purified by column chromatography (KP-Sil silica gel, SNAP 340) eluting with a gradient of MeOH in DCM from 0 to 10% to give 7-bromo-N-[(2,4-dimethoxyphenyl)methyl]cinnolin-4-amine (5.667 g, 15.14 mmol, 100.85% yield) as a yellow solid. $^1$H NMR (400 MHz, DMSO-$d_6$) δ 3.74 (s, 3H), 3.87 (s, 3H), 4.50 (d, J=5.72 Hz, 2H), 6.46-6.52 (m, 1H), 6.62 (d, J=2.42 Hz, 1H), 7.15 (d, J=8.36 Hz, 1H), 7.78 (dd, J=8.91, 2.09 Hz, 1H), 8.16 (t, J=5.72 Hz, 1H), 8.29 (d, J=1.98 Hz, 1H), 8.32 (d, J=9.24 Hz, 1H), 8.54 (s, 1H). LC-MS (Method A): r.t. 0.63 min, MS (ESI) m/z=374.05 and 376.08 [M+H]$^+$.

Intermediate 18: 7-(5-chloro-2-methoxyphenyl)-N-[(2,4-dimethoxyphenyl)methyl]cinnolin-4-amine

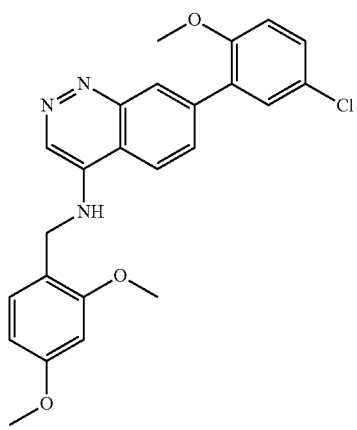 [SMILES: COc1ccc(CNc2cnnc3cc(-c4cc(Cl)ccc4OC)ccc23)c(OC)c1]

A mixture of 5-chloro-2-methoxyphenylboronic acid (547.9 mg, 2.94 mmol) and 7-bromo-N-[(2,4-dimethoxyphenyl)methyl]cinnolin-4-amine (1.0 g, 2.67 mmol) in 1,2-dimethoxyethane (20 mL) and aqueous 2N sodium carbonate solution (1.34 mL, 2.67 mmol) was degassed for 10 min with N$_2$. Then, [1,1'-bis(di-tert-butylphosphino)ferrocene]dichloropalladium(II) (174.69 mg, 0.270 mmol) was added. The mixture was stirred at 80° C. for 6 hours, then it was cooled to room temperature and filtered over Celite, washing with MeOH. The filtrate was evaporated and the residue was purified by column chromatography (KP-NH silica gel, SNAP 100) eluting with a gradient of MeOH in DCM from 0% to 5% to give 7-(5-chloro-2-methoxyphenyl)-N-[(2,4-dimethoxyphenyl)methyl]cinnolin-4-amine (1 g, 2.294 mmol, 85.85% yield) as an orange solid. $^1$H NMR (400 MHz, DMSO-$d_6$) δ 3.74 (s, 3H), 3.83 (s, 3H), 3.89 (s, 3H), 4.52 (d, J=6.08 Hz, 2H), 6.48 (dd, J=8.37, 2.42 Hz, 1H), 6.64 (d, J=2.42 Hz, 1H), 7.16 (d, J=8.33 Hz, 1H), 7.23 (d, J=8.85 Hz, 1H), 7.48 (dd, J=8.79, 2.68 Hz, 1H), 7.53 (d, J=2.67 Hz, 1H), 7.77 (dd, J=8.78, 1.85 Hz, 1H), 8.03 (t, J=5.98 Hz, 1H), 8.18 (d, J=1.77 Hz, 1H), 8.37 (d, J=8.78 Hz, 1H), 8.48 (s, 1H). LC-MS (Method A): r.t. 0.83 min, MS (ESI) m/z=436.3 [M+H]$^+$.

Intermediate 19: N-[(2,4-dimethoxyphenyl)methyl]-7-[2-methoxy-5-(4,4,5,5-tetramethyl-1,3,2-dioxaborolan-2-yl)phenyl]cinnolin-4-amine

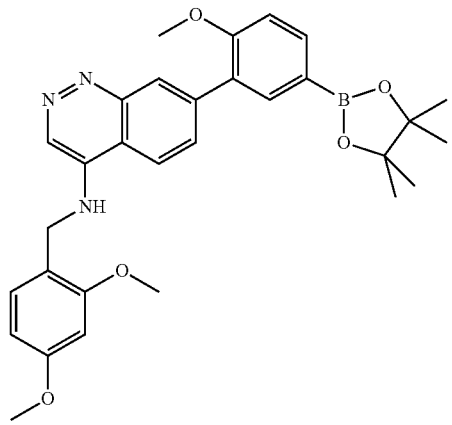 [SMILES: COc1ccc(CNc2cnnc3cc(-c4cc(B5OC(C)(C)C(C)(C)O5)ccc4OC)ccc23)c(OC)c1]

A mixture of 7-(5-chloro-2-methoxyphenyl)-N-[(2,4-dimethoxyphenyl)methyl]cinnolin-4-amine (1.0 g, 2.29 mmol), 4,4,5,5-tetramethyl-2-(4,4,5,5-tetramethyl-1,3,2-dioxaborolan-2-yl)-1,3,2-dioxaborolane (1747.69 mg, 6.88 mmol), dicyclohexyl-[2-[2,4,6-tri(propan-2-yl)phenyl]phenyl]phosphine (87.49 mg, 0.180 mmol), potassium acetate (675.43 mg, 6.88 mmol) and palladium(II) diacetate (25.75 mg, 0.110 mmol) were dissolved in 1,4-dioxane (20 mL) in a microwave vial and degassed for 10 min with N$_2$. The mixture was stirred at 75° C. for 2 hours, then it was cooled to room temperature and filtered over Celite, washing with MeOH. The filtrate was evaporated and the residue was purified by column chromatography (KP-C18-HS, 60 g) eluting with a gradient of CH$_3$CN in water from 4% to 95%. Fractions containing the desired compound were collected and evaporated under reduced pressure to give N-[(2,4-dimethoxyphenyl)methyl]-7-[2-methoxy-5-(4,4,5,5-tetramethyl-1,3,2-dioxaborolan-2-yl)phenyl]cinnolin-4-amine (500 mg, 0.948 mmol, 41.32% yield) as a brownish powder. $^1$H NMR (400 MHz, DMSO-$d_6$) δ 1.31 (s, 12H), 3.75 (s, 3H), 3.86 (s, 3H), 3.89 (s, 3H), 4.52 (d, J=5.86 Hz, 2H), 6.48 (dd, J=8.37, 2.41 Hz, 1H), 6.64 (d, J=2.36 Hz, 1H), 7.16 (d, J=8.40 Hz, 1H), 7.22 (d, J=8.36 Hz, 1H), 7.70 (d, J=1.68 Hz, 1H), 7.74 (d, J=1.68 Hz, 1H), 7.76 (d, J=1.74 Hz, 1H), 8.02 (t, J=6.16 Hz, 1H), 8.12 (d, J=1.78 Hz, 1H), 8.35 (d, J=8.80 Hz, 1H), 8.48 (s, 1H). LC-MS (Method A): r.t. 0.92 min, MS (ESI) m/z=528.5 [M+H]⁺.

Intermediate 20: 7-[2-methoxy-5-(4,4,5,5-tetramethyl-1,3,2-dioxaborolan-2-yl)phenyl]cinnolin-4-amine trifluoroacetic Acid Salt

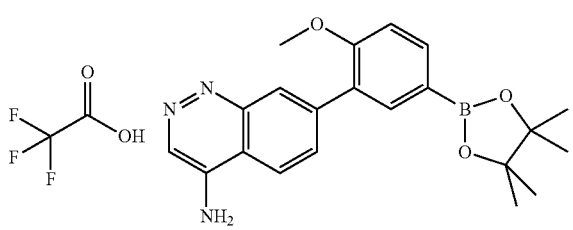

A solution of N-[(2,4-dimethoxyphenyl)methyl]-7-[2-methoxy-5-(4,4,5,5-tetramethyl-1,3,2-dioxaborolan-2-yl)phenyl]cinnolin-4-amine (500.0 mg, 0.920 mmol) in DCM (5 mL) and trifluoroacetic acid (4.5 mL) was stirred for 3.5 hours at room temperature then it was concentrated under reduced pressure. The residue was dissolved in DCM/MeOH (1/1, 20 mL) and filtered over Celite. The filtrate was evaporated to give 7-[2-methoxy-5-(4,4,5,5-tetramethyl-1,3,2-dioxaborolan-2-yl)phenyl]cinnolin-4-amine trifluoroacetic acid salt (450 mg, 0.916 mmol, 99.61% yield) as a brown sticky oil. ¹H NMR (400 MHz, DMSO-d₆) δ 1.31 (s, 12H), 3.88 (s, 3H), 7.27 (d, J=8.35 Hz, 1H), 7.72 (d, J=1.64 Hz, 1H), 7.81 (dd, J=8.29, 1.68 Hz, 1H), 7.94-8.00 (m, 2H), 8.46 (d, J=9.30 Hz, 1H), 8.48 (s, 1H). LC-MS (Method A): r.t. 0.73 min, MS (ESI) m/z=378.4 [M+H]⁺.

Intermediate 21: 6-(5-chloro-2-methoxyphenyl)-N-[(2,4-dimethoxyphenyl)methyl]-4-methylphthalazin-1-amine

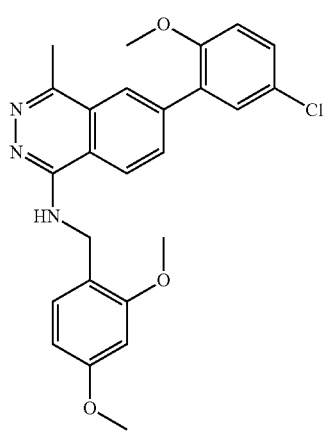

A mixture of 5-chloro-2-methoxyphenylboronic acid (192.04 mg, 1.03 mmol), 6-bromo-N-[(2,4-dimethoxyphenyl)methyl]-4-methylphthalazin-1-amine (400.0 mg, 1.03 mmol) and [1,1'-bis(di-tert-butylphosphino)ferrocene]dichloropalladium(II) (67.35 mg, 0.100 mmol) in 1,2-dimethoxyethane (8 mL) and aqueous 2N sodium carbonate solution (1.03 mL, 2.06 mmol) was degassed for 10 min with Ar. The mixture was stirred at 80° C. for 1 hour, then it was cooled to room temperature and filtered over Celite, washing with EtOAc. The filtrate was evaporated under reduced pressure and the residue was purified by column chromatography (KP-NH silica gel, SNAP 55) eluting with a gradient of a mixture of EtOAc/DCM (3:7) in cyclohexane from 0% to 100% to give 6-(5-chloro-2-methoxyphenyl)-N-[(2,4-dimethoxyphenyl)methyl]-4-methylphthalazin-1-amine (398 mg, 0.885 mmol, 85.86% yield) as a yellow oil. ¹H NMR (400 MHz, DMSO-d₆) δ 2.70 (s, 3H) 3.73 (s, 3H) 3.82 (s, 3H) 3.85 (s, 3H) 4.67 (d, J=5.72 Hz, 2H) 6.43 (dd, J=8.36, 2.42 Hz, 1H) 6.58 (d, J=2.42 Hz, 1H) 7.12 (d, J=8.36 Hz, 1H) 7.22 (d, J=9.02 Hz, 1H) 7.49 (dd, J=8.80, 2.86 Hz, 1H) 7.56 (d, J=2.64 Hz, 1H) 7.59 (t, J=5.72 Hz, 1H) 8.00 (dd, J=8.58, 1.76 Hz, 1H) 8.03 (d, J=1.54 Hz, 1H) 8.39 (d, J=8.58 Hz, 1H). LC-MS (Method A): r.t. 0.86 min, MS (ESI) m/z=450.4 [M+H]⁺.

Intermediate 22: N-[(2,4-dimethoxyphenyl)methyl]-6-[2-methoxy-5-(4,4,5,5-tetramethyl-1,3,2-dioxaborolan-2-yl)phenyl]-4-methylphthalazin-1-amine

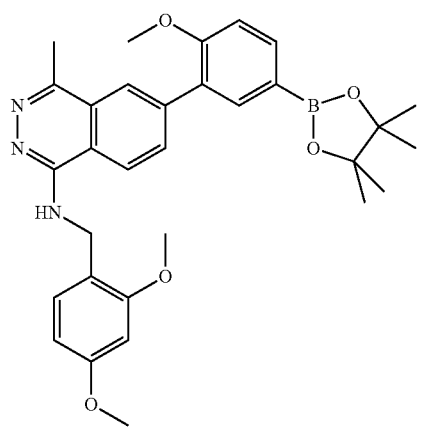 [SMILES: COc1ccc(CNc2nnc(C)c3cc(-c4cc(B5OC(C)(C)C(C)(C)O5)ccc4OC)ccc23)c(OC)c1]

Palladium(II) diacetate (4.99 mg, 0.020 mmol), 6-(5-chloro-2-methoxyphenyl)-N-[(2,4-dimethoxyphenyl)methyl]-4-methylphthalazin-1-amine (200.0 mg, 0.440 mmol), dicyclohexyl-[2-[2,4,6-tri(propan-2-yl)phenyl]phenyl]phosphine (16.95 mg, 0.040 mmol), potassium acetate (130.87 mg, 1.33 mmol) and 4,4,5,5-tetramethyl-2-(4,4,5,5-tetramethyl-1,3,2-dioxaborolan-2-yl)-1,3,2-dioxaborolane (338.64 mg, 1.33 mmol) were dissolved in 1,4-dioxane (3.143 mL). The mixture was degassed with Ar for 10 min, then stirred at 80° C. for 4 hours. The mixture was filtered over a pad of Celite, washing with methanol and concentrated in vacuo. The residue was purified by column chromatography (KP-C18-HS, 30 g) eluting with a gradient of CH₃CN in water from 1% to 90% to give N-[(2,4-dimethoxyphenyl)methyl]-6-[2-methoxy-5-(4,4,5,5-tetramethyl-1,3,2-dioxaborolan-2-yl)phenyl]-4-methylphthalazin-1-amine (79 mg, 0.146 mmol, 32.82% yield) as a white solid. ¹H NMR (400 MHz, DMSO-d₆) δ 1.30 (s, 12H), 2.68 (s, 3H), 3.73 (s, 3H), 3.83 (s, 3H), 3.84 (s, 3H), 4.67 (d, J=5.56 Hz, 2H), 6.43 (dd, J=8.38, 2.41 Hz, 1H), 6.58 (d, J=2.37 Hz, 1H), 7.12 (d, J=8.35 Hz, 1H), 7.21 (d, J=8.41 Hz, 1H), 7.57 (t, J=5.64 Hz, 1H), 7.65 (d, J=1.72 Hz, 1H), 7.76 (dd, J=8.29, 1.71 Hz, 1H), 7.93 (dd, J=8.54, 1.74 Hz, 1H), 7.97 (d, J=1.74 Hz, 1H), 8.38 (d, J=8.57 Hz, 1H). LC-MS (Method A): r.t. 0.95 min, MS (ESI) m/z=542.5 [M+H]⁺

Intermediate 23: 2-bromo-4-chloro-1-[2-[2-[2-[2-[2-(2-methoxyethoxy)ethoxy]ethoxy]ethoxy]ethoxy]ethoxy]benzene

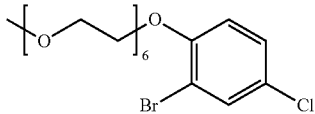

A mixture of mPEG6-bromide (333.36 mg, 0.930 mmol), 2-bromo-4-chlorophenol (175.0 mg, 0.840 mmol) and potassium carbonate (233.18 mg, 1.69 mmol) in dry DMF (2.34 mL) was stirred at 50° C. for 8 hours. The reaction mixture was diluted with water (25 mL) and extracted with EtOAc (3×20 mL). The combined organic phases were washed with brine (25 mL), dried over sodium sulphate and concentrated under reduced pressure. The residue was purified by column chromatography (KP-NH silica gel, SNAP 28) eluting with a gradient of EtOAc in cyclohexane from 5% to 100% to give 2-bromo-4-chloro-1-[2-[2-[2-[2-[2-(2-methoxyethoxy)ethoxy]ethoxy]ethoxy]ethoxy]benzene (385 mg, 0.793 mmol, 93.95% yield) as a colourless oil. $^1$H NMR (400 MHz, DMSO-$d_6$) δ 3.24 (s, 3H), 3.40-3.44 (m, 2H), 3.49-3.56 (m, 16H), 3.61-3.64 (m, 2H), 3.76-3.79 (m, 2H), 4.16-4.20 (m, 2H), 7.16 (d, J=8.88 Hz, 1H), 7.41 (dd, J=8.84, 2.60 Hz, 1H), 7.69 (d, J=2.60 Hz, 1H). LC-MS (Method A): r.t. 1.13 min, MS (ESI) m/z=485.3 and 487.3 [M+H]$^+$.

Intermediate 24: [4-[(2,4-dimethoxyphenyl)methylamino]cinnolin-7-yl]boronic Acid

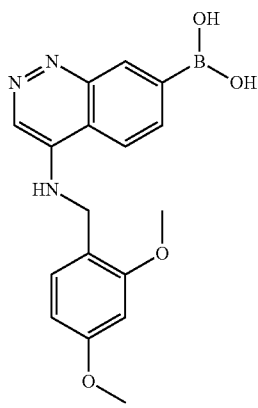 [SMILES: COc1ccc(CNc2cnnc3cc(B(O)O)ccc23)c(OC)c1]

A mixture of 7-bromo-N-[(2,4-dimethoxyphenyl)methyl]cinnolin-4-amine (600.0 mg, 1.6 mmol), 4,4,5,5-tetramethyl-2-(4,4,5,5-tetramethyl-1,3,2-dioxaborolan-2-yl)-1,3,2-dioxaborolane (1221.42 mg, 4.81 mmol), dicyclohexyl-[2-[2,4,6-tri(propan-2-yl)phenyl]phenyl]phosphine (61.15 mg, 0.130 mmol), potassium acetate (472.04 mg, 4.81 mmol) and palladium(II) diacetate (18.0 mg, 0.080 mmol) were dissolved in 1,4-dioxane (16 mL) in a microwave vial and degassed for 10 min with Ar. The mixture was stirred at 80° C. for 2 hours, then it was cooled to room temperature and filtered over Celite, washing with MeOH. The filtrate was evaporated and the residue was purified by column chromatography (KP-C18-HS, 60 g) eluting with a gradient of MeCN in water from 2% to 95%. Fractions containing the desired compound were collected and evaporated under reduced pressure to give [4-[(2,4-dimethoxyphenyl)methylamino]cinnolin-7-yl]boronic acid (520 mg, 1.533 mmol, 95.63% yield) as a brown gel. LC-MS (Method A): r.t. 0.55 min, MS (ESI) m/z=340.3 [M+H]$^+$.

Intermediate 25: 7-[5-chloro-2-[2-[2-[2-[2-[2-(2-methoxyethoxy)ethoxy]ethoxy]ethoxy]ethoxy]ethoxy]phenyl]-N-[(2,4-dimethoxyphenyl)methyl]cinnolin-4-amine

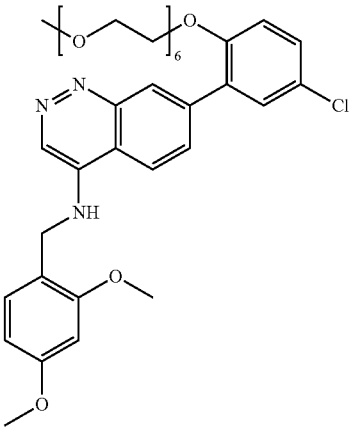

A mixture of [4-[(2,4-dimethoxyphenyl)methylamino]cinnolin-7-yl]boronic acid (181.52 mg, 0.540 mmol) and 2-bromo-4-chloro-1-[2-[2-[2-[2-[2-(2-methoxyethoxy)ethoxy]ethoxy]ethoxy]ethoxy]ethoxy]benzene (200.0 mg, 0.410 mmol) in 1,2-dimethoxyethane (9.47 mL) and aqueous 2N sodium carbonate solution (205.85 uL, 0.410 mmol) was degassed for 10 min with $N_2$. Then, [1,1'-bis(di-tert-butylphosphino)ferrocene]dichloropalladium(II) (26.92 mg, 0.040 mmol) was added. The mixture was stirred at 80° C. for 12 hours, then it was cooled to room temperature and filtered over Celite, washing with MeOH. The filtrate was evaporated and the residue was purified by column chromatography (KP-NH silica gel, SNAP 28) eluting with a gradient of MeOH in DCM from 0% to 8% to give 7-[5-chloro-2-[2-[2-[2-[2-[2-(2-methoxyethoxy)ethoxy]ethoxy]ethoxy]ethoxy]ethoxy]phenyl]-N-[(2,4-dimethoxyphenyl)methyl]cinnolin-4-amine (140 mg, 0.200 mmol, 48.56% yield). LC-MS (Method A): r.t. 0.84 min, MS (ESI) m/z=700.6 [M+H]$^+$.

Intermediate 26: N-[(2,4-dimethoxyphenyl)methyl]-7-[2-[2-[2-[2-[2-[2-(2-methoxyethoxy)ethoxy]ethoxy]ethoxy]ethoxy]ethoxy]-5-(4,4,5,5-tetramethyl-1,3,2-dioxaborolan-2-yl)phenyl]cinnolin-4-amine

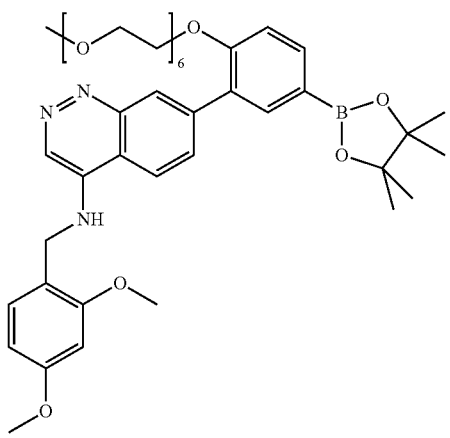

A mixture of 7-[5-chloro-2-[2-[2-[2-[2-[2-(2-methoxyethoxy)ethoxy]ethoxy]ethoxy]ethoxy]phenyl]-N-[(2,4-dimethoxyphenyl)methyl]cinnolin-4-amine (160.0 mg, 0.110 mmol), 4,4,5,5-tetramethyl-2-(4,4,5,5-tetramethyl-1,3,2-dioxaborolan-2-yl)-1,3,2-dioxaborolane (87.04 mg, 0.340 mmol), dicyclohexyl-[2-[2,4,6-tri(propan-2-yl)phenyl]phenyl]phosphine (4.36 mg, 0.010 mmol), potassium acetate (33.64 mg, 0.340 mmol) and palladium(II) diacetate (1.28 mg, 0.010 mmol) were dissolved in 1,4-dioxane (5.6 mL) in a microwave vial and degassed for 15 min with $N_2$. The mixture was stirred at 75° C. for 2 hours, then it was cooled to room temperature and filtered over Celite, washing with MeOH. The filtrate was evaporated and the residue was purified by column chromatography (KP-C18-HS, 30 g) eluting with a gradient of $CH_3CN$ in water from 2% to 95%. Fractions containing the desired compound were collected and evaporated under reduced pressure to give N-[(2,4-dimethoxyphenyl)methyl]-7-[2-[2-[2-[2-[2-[2-(2-methoxyethoxy)ethoxy]ethoxy]ethoxy]ethoxy]-5-(4,4,5,5-tetramethyl-1,3,2-dioxaborolan-2-yl)phenyl]cinnolin-4-amine (29 mg, 0.037 mmol, 32.06% yield) as a brown gel. $^1$H NMR (400 MHz, DMSO-$d_6$) δ 1.31 (s, 12H), 3.21 (d, J=0.96 Hz, 3H), 3.36-3.56 (m, 20H), 3.70-3.77 (m, 5H), 3.89 (s, 3H), 4.23 (q, J=5.77, 4.99 Hz, 2H), 4.52 (d, J=5.83 Hz, 2H), 6.48 (dd, J=8.42, 2.40 Hz, 1H), 6.64 (d, J=2.38 Hz, 1H), 7.16 (dd, J=8.38, 2.11 Hz, 2H), 7.73 (d, J=1.67 Hz, 1H), 7.80-7.88 (m, 1H), 7.88-7.93 (m, 1H), 7.95-8.01 (m, 1H), 8.04 (s, 1H), 8.33 (dd, J=8.89, 3.89 Hz, 1H), 8.47 (d, J=3.74 Hz, 1H). LC-MS (Method A): r.t. 0.92 min, MS (ESI) m/z=592.7 [M+H]$^+$.

Intermediate 27: methyl 4-bromo-2-(2-methylpropanoyl)benzoate

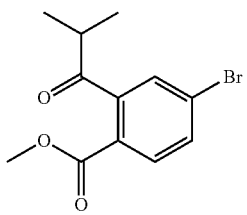 [SMILES: COC(=O)c1ccc(Br)cc1C(=O)C(C)C]

To a solution of methyl 4-bromo-2-iodobenzoate (1.0 g, 2.93 mmol) in THF (10 mL) cooled to −78° C., a 2.0M solution of isopropyl magnesium chloride in THF (1.61 mL, 3.23 mmol) was added. After 15 minutes, 2-methylpropanoic acid (2-methyl-1-oxopropyl) ester (0.63 mL, 3.81 mmol) was added dropwise at the same temperature and then the reaction mixture was stirred at room temperature for 2 h. The mixture was quenched with saturated ammonium chloride solution and extracted three times with EtOAc. The combined organic phases were washed with brine, filtered and evaporated in vacuo. The residue was purified by column chromatography (KP-Sil, SNAP 50 g) eluting with a gradient of EtOAc in cyclohexane from 0% to 20% to give methyl 4-bromo-2-(2-methylpropanoyl)benzoate (800 mg, 2.806 mmol, 95.66% yield) as a white solid. $^1$H NMR (400 MHz, DMSO-$d_6$) δ 1.08 (d, J=6.89 Hz, 6H), 3.13 (hept, J=6.89 Hz, 1H), 3.79 (s, 3H), 7.74 (dd, J=1.75, 0.67 Hz, 1H), 7.80-7.82 (m, 2H). LC-MS (Method A): r.t. 1.16 min, MS (ESI) m/z=285.1 and 287.1 [M+H]$^+$.

Intermediate 28: 6-bromo-4-propan-2-yl-2H-phthalazin-1-one

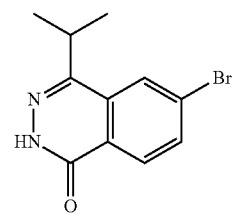

To a solution of methyl 4-bromo-2-(2-methylpropanoyl)benzoate (800.0 mg, 2.81 mmol) in ethanol (4.651 mL), hydrazine hydrate (0.65 mL, 8.42 mmol) was added. The resulting mixture was stirred at 85° C. for 4 hours then cooled to room temperature and concentrated in vacuo. The residue was triturated with EtOAc (10 mL) and $CH_3CN$ (10 mL) and the resulting solid was dried under vacuum to give 6-bromo-4-propan-2-yl-2H-phthalazin-1-one (600 mg, 2.246 mmol, 80.06% yield) as a white solid. $^1$H NMR (400 MHz, DMSO-$d_6$) δ 1.24 (d, J=6.75 Hz, 6H), 3.57 (hept, J=6.74 Hz, 1H), 8.00 (dd, J=8.46, 1.85 Hz, 1H), 8.18 (d, J=8.46 Hz, 1H), 8.23 (d, J=1.85 Hz, 1H), 12.59 (s, 1H). LC-MS (Method A): r.t. 0.99 min, MS (ESI) m/z=267.1 and 269.1 [M+H]$^+$.

Intermediate 29: 6-bromo-1-chloro-4-propan-2-ylphthalazine

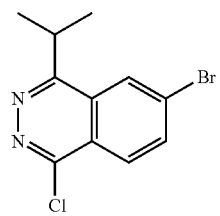

A solution of 6-bromo-4-propan-2-yl-2H-phthalazin-1-one (600.0 mg, 2.25 mmol) in POCl$_3$ (2.1 mL, 22.46 mmol) was stirred at 100° C. for 1 h. The mixture was then cooled in an ice bath and 2N sodium hydroxide solution was carefully added until the mixture was basic, at which point the formation of a precipitate was observed. The precipitate was filtered and washed with water to afford 6-bromo-1-chloro-4-propan-2-ylphthalazine (590 mg, 2.066 mmol, 91.98% yield) as a yellow solid. $^1$H NMR (400 MHz, DMSO-$d_6$) δ 1.39 (d, J=6.71 Hz, 6H), 4.01 (hept, J=6.80 Hz, 1H), 8.23 (d, J=8.81 Hz, 1H), 8.29 (d, J=8.81 Hz, 1H), 8.60-8.74 (m, 1H). LC-MS (Method A): r.t. 1.15 min, MS (ESI) m/z=285.1 and 287.1 [M+H]$^+$.

Intermediate 30: 6-bromo-N-[(2,4-dimethoxyphenyl)methyl]-4-propan-2-ylphthalazin-1-amine

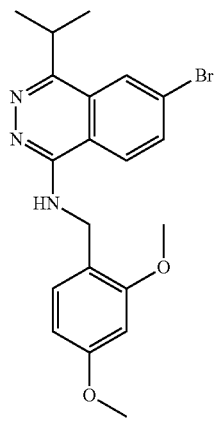 [SMILES: COc1ccc(CNc2nnc(C(C)C)c3cc(Br)ccc23)c(OC)c1]

To a solution of 6-bromo-1-chloro-4-propan-2-ylphthalazine (590.0 mg, 2.07 mmol) in ethanol (9.44 mL), (2,4-dimethoxyphenyl)methanamine (0.61 mL, 4.13 mmol) was added and the resulting mixture was stirred at 90° C. for 48 h. The volatiles were evaporated and the resulting solid residue was triturated with Et$_2$O. The residue was purified by column chromatography (KP-NH silica gel, SNAP 110 g) eluting with a gradient of EtOAc in cyclohexane from 0% to 60% to give 6-bromo-N-[(2,4-dimethoxyphenyl)methyl]-4-propan-2-ylphthalazin-1-amine (676 mg, 1.624 mmol, 78.59% yield) as a white solid. $^1$H NMR (400 MHz, DMSO-d$_6$) δ 1.29 (d, J=6.80 Hz, 6H), 3.65-3.75 (m, 1H), 3.72 (s, 3H), 3.83 (s, 3H), 4.64 (d, J=5.51 Hz, 2H), 6.43 (dd, J=8.34, 2.40 Hz, 1H), 6.57 (d, J=2.38 Hz, 1H), 7.12 (d, J=8.33 Hz, 1H), 7.68 (t, J=5.65 Hz, 1H), 8.03 (dd, J=8.80, 1.90 Hz, 1H), 8.27 (d, J=1.90 Hz, 1H), 8.35 (d, J=8.83 Hz, 1H). LC-MS (Method A): r.t. 0.78 min, MS (ESI) m/z=416.2 and 418.2 [M+H]$^+$.

Intermediate 31: 6-(3-chlorophenyl)-N-[(2,4-dimethoxyphenyl)methyl]-4-propan-2-ylphthalazin-1-amine

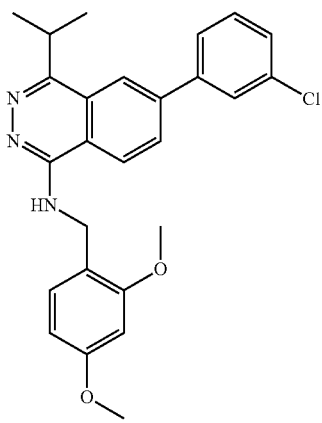 [SMILES: COc1ccc(CNc2nnc(C(C)C)c3cc(-c4cccc(Cl)c4)ccc23)c(OC)c1]

A mixture of (3-chlorophenyl)boronic acid (75.12 mg, 0.480 mmol), 6-bromo-N-[(2,4-dimethoxyphenyl)methyl]-4-propan-2-ylphthalazin-1-amine (200.0 mg, 0.480 mmol) and [1,1'-bis(di-tert-butylphosphino)ferrocene]dichloropalladium(II) (31.41 mg, 0.050 mmol) in 1,2-dimethoxyethane (4 mL) and aqueous 2N sodium carbonate solution (0.48 mL, 0.960 mmol) was degassed for 10 min with Ar. The mixture was stirred at 85° C. for 3 h. Then the mixture was cooled to room temperature and filtered over Celite, washing with EtOAc. The solvent was evaporated and the residue was purified by column chromatography (KP-NH silica gel, SNAP 28 g) eluting with a gradient of a mixture DCM/EtOAc (7:3) in cyclohexane from 0% to 100% to give 6-(3-chlorophenyl)-N-[(2,4-dimethoxyphenyl)methyl]-4-propan-2-ylphthalazin-1-amine (148 mg, 0.330 mmol, 68.77% yield) as a white solid. LC-MS analysis showed the presence of an impurity (~16%). $^1$H NMR (400 MHz, DMSO-d$_6$) δ 1.34 (d, J=6.73 Hz, 6H), 3.73 (s, 3H), 3.85 (s, 3H), 3.87-3.97 (m, 1H), 4.67 (d, J=5.66 Hz, 2H), 6.43 (dd, J=8.37, 2.34 Hz, 1H), 6.58 (d, J=2.36 Hz, 1H), 7.13 (d, J=8.33 Hz, 1H), 7.50-7.55 (m, 1H), 7.58 (t, J=7.76 Hz, 1H), 7.63-7.67 (m, 1H), 7.87 (dt, J=7.56, 1.49 Hz, 1H), 7.99 (t, J=1.89 Hz, 1H), 8.21 (dd, J=8.67, 1.77 Hz, 1H), 8.30 (d, J=1.77 Hz, 1H), 8.49 (d, J=8.67 Hz, 1H). LC-MS (Method A): r.t. 0.94 min, MS (ESI) m/z=448.3[M+H]$^+$.

Intermediate 32: 4-propan-2-yl-6-[3-(4,4,5,5-tetramethyl-1,3,2-dioxaborolan-2-yl)phenyl]phthalazin-1-amine

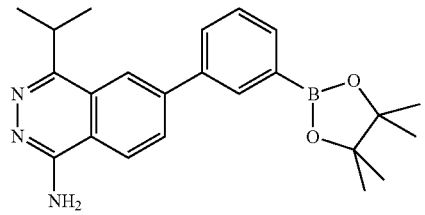 [SMILES: CC(C)c1nnc(N)c2ccc(-c3cccc(B4OC(C)(C)C(C)(C)O4)c3)cc12]

Step 1: Palladium(II) diacetate (3.71 mg, 0.020 mmol), 6-(3-chlorophenyl)-N-[(2,4-dimethoxyphenyl)methyl]-4-propan-2-ylphthalazin-1-amine (148.0 mg, 0.330 mmol), dicyclohexyl-[2-[2,4,6-tri(propan-2-yl)phenyl]phenyl]phosphine (12.6 mg, 0.030 mmol), potassium acetate (97.27 mg, 0.990 mmol) and 4,4,5,5-tetramethyl-2-(4,4,5,5-tetramethyl-1,3,2-dioxaborolan-2-yl)-1,3,2-dioxaborolane (251.7 mg, 0.990 mmol) were dissolved in 1,4-dioxane (2.326 mL). The mixture was degassed with Ar for 10 min, then stirred at 100° C. for 2 hours. The mixture was cooled to room temperature and filtered over a pad of Celite, washing with methanol. The filtrate was concentrated in vacuo and the residue was purified by column chromatography (KP-C18-HS, SNAP 30 g) eluting with a gradient of CH$_3$CN (+0.1% of HCOOH) in water (+0.1% of HCOOH) from 1% to 40% to give a mixture of N-[(2,4-dimethoxyphenyl)methyl]-4-(propan-2-yl)-6-[3-(4,4,5,5-tetramethyl-1,3,2-dioxaborolan-2-yl)phenyl]phthalazin-1-amine and [3-(1-{[(2,4-dimethoxyphenyl)methyl]amino}-4-(propan-2-yl)phthalazin-6-yl)phenyl]boronic acid. This mixture was used in the next step without further purification. LC-MS (Method A): r.t.$_{boronic\ acid}$ 0.77 min, MS (ESI) m/z=458.4[M+H]$^+$; r.t.$_{boronic\ ester}$ 1.04 min, MS (ESI) m/z=540.5 [M+H]$^+$.

Step 2: To a solution of the mixture from Step 1 (50.0 mg, 0.110 mmol) in DCM (2 mL), trifluoroacetic acid (2 mL) was added and mixture was stirred at room temperature for 2 h. The volatiles were evaporated and the residue was purified by column chromatography (KP-C18-HS, SNAP 12 g) eluting with a gradient of $CH_3CN$ (+0.1% of HCOOH) in water (+0.1% of HCOOH) from 2% to 50% to give 4-propan-2-yl-6-[3-(4,4,5,5-tetramethyl-1,3,2-dioxaborolan-2-yl)phenyl]phthalazin-1-amine (23 mg, 0.059 mmol, 54.04% yield) as a white solid. LC-MS analysis showed the presence of boronic acid inside. LC-MS (Method A): r.t. 0.88 min, MS (ESI) m/z=390.4 $[M+H]^+$.

Intermediate 33: 6-(5-chloro-2-methylphenyl)-N-[(2,4-dimethoxyphenyl)methyl]-4-methylphthalazin-1-amine

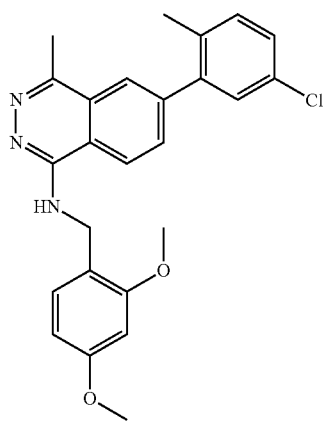 [SMILES: COc1ccc(CNc2nnc(C)c3cc(-c4cc(Cl)ccc4C)ccc23)c(OC)c1]

A mixture of 6-bromo-N-[(2,4-dimethoxyphenyl)methyl]-4-methylphthalazin-1-amine (200.0 mg, 0.520 mmol) and (5-chloro-2-methylphenyl)boronic acid (87.78 mg, 0.520 mmol) in aqueous 2N sodium carbonate solution (0.26 mL, 0.520 mmol) and 1,2-dimethoxyethane (3 mL) was degassed for 10 min. [1,1'-Bis(di-tert-butylphosphino)ferrocene]dichloropalladium(II) (33.68 mg, 0.050 mmol) was added and the mixture was degassed for 10 min, then stirred at 70° C. for 90 min. The mixture was left to reach room temperature, then diluted with EtOAc and filtered. The filtrate was concentrated and the residue was purified by column chromatography (KP-C18-HS, SNAP 30) eluting with a gradient of MeCN in water from 2% to 80 to give 6-(5-chloro-2-methylphenyl)-N-[(2,4-dimethoxyphenyl)methyl]-4-methylphthalazin-1-amine (164 mg, 0.378 mmol, 73.37% yield) as a brownish foam. $^1$H NMR (400 MHz, DMSO-$d_6$) δ 2.25 (s, 3H), 2.69 (s, 3H), 3.74 (s, 3H), 3.85 (s, 3H), 4.68 (d, J=5.28 Hz, 2H), 6.44 (dd, J=8.36, 2.42 Hz, 1H), 6.59 (d, J=2.20 Hz, 1H), 7.13 (d, J=8.36 Hz, 1H), 7.41-7.45 (m, 3H), 7.64 (t, J=5.83 Hz, 1H), 7.89 (dd, J=8.47, 1.65 Hz, 1H), 7.92 (d, J=1.32 Hz, 1H), 8.44 (d, J=8.36 Hz, 1H). LC-MS (Method A): r.t. 0.88 min, MS (ESI) m/z=434.39 $[M+H]^+$.

Intermediate 34: N-[(2,4-dimethoxyphenyl)methyl]-4-methyl-6-[2-methyl-5-(4,4,5,5-tetramethyl-1,3,2-dioxaborolan-2-yl)phenyl]phthalazin-1-amine

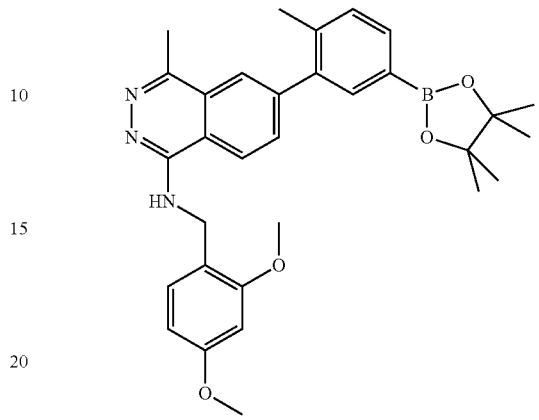

A mixture of 6-(5-chloro-2-methylphenyl)-N-[(2,4-dimethoxyphenyl)methyl]-4-methylphthalazin-1-amine (164.0 mg, 0.380 mmol), 4,4,5,5-tetramethyl-2-(4,4,5,5-tetramethyl-1,3,2-dioxaborolan-2-yl)-1,3,2-dioxaborolane (287.92 mg, 1.13 mmol) and potassium diacetate (111.27 mg, 1.13 mmol) in 1,4-dioxane (2.5 mL) was degassed for 10 min, then palladium(II) diacetate (4.24 mg, 0.020 mmol) and dicyclohexyl-[2-[2,4,6-tri(propan-2-yl)phenyl]phenyl]phosphine (14.41 mg, 0.030 mmol) were added. The mixture was degassed for 10 min, then stirred at 70° C. for 2.5 h. The mixture was left to reach room temperature, diluted with EtOAc and filtered. The volatiles were removed and the residue was purified by column chromatography (KP-C18-HS, SNAP30) eluting with a gradient of MeCN in water from 2% to 95% to give N-[(2,4-dimethoxyphenyl)methyl]-4-methyl-6-[2-methyl-5-(4,4,5,5-tetramethyl-1,3,2-dioxaborolan-2-yl)phenyl]phthalazin-1-amine (42 mg, 0.080 mmol, 21.15% yield) as a white solid. Purity by LC-MS was ~70%. This material was used in the next step without further purification. LC-MS (Method A): r.t. 0.97 min, MS (ESI) m/z=526.49 $[M+H]^+$.

Intermediate 35: methyl 4-bromo-2-(cyclopropanecarbonyl)benzoate

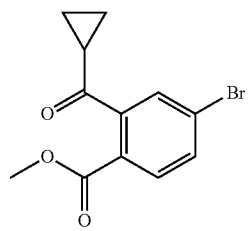 [SMILES: COC(=O)c1ccc(Br)cc1C(=O)C1CC1]

To a solution of methyl 4-bromo-2-iodobenzoate (1.6 g, 4.69 mmol) in THF (16.26 mL), a 2 M solution of isopropylmagnesium chloride in THF (2.58 mL, 5.16 mmol) was added dropwise at −78° C. After 30 minutes cyclopropanecarboxylic anhydride (0.67 mL, 6.1 mmol) was added at the same temperature. After addition was complete the reaction mixture was stirred at room temperature for 2 hours. It was then quenched with a saturated solution of ammonium chloride and extracted three times with EtOAc. The combined organic phases were washed with brine, dried over anhydrous sodium sulfate, filtered and concentrated under reduced pressure. The residue was purified by column chromatography (KP silica gel, SNAP 340) eluting with a gradient of EtOAc in cyclohexane from 2% to 40% to give methyl 4-bromo-2-(cyclopropanecarbonyl)benzoate (1.108 g, 3.914 mmol, 83.39% yield) as a yellow oil. $^1$H NMR (400 MHz, DMSO-$d_6$) δ 1.05-1.14 (m, 4H), 2.40 (tt, J=6.7, 5.5 Hz, 1H), 3.80 (s, 3H), 7.76 (dd, J=8.2, 0.5 Hz, 1H), 7.80-7.89 (m, 2H). LC-MS (Method A): r.t. 1.08 min. MS (ESI) m/z of product not observed due to poor ionization.

Intermediate 36:
6-bromo-4-cyclopropyl-2H-phthalazin-1-one

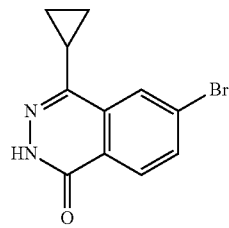

To a solution of methyl 4-bromo-2-(cyclopropanecarbonyl)benzoate (1.11 g, 3.91 mmol) in ethanol (7 mL), hydrazine hydrate (900.0 uL, 11.72 mmol) was added. The resulting mixture was stirred at 90° C. for 4 hours then it was cooled to room temperature and concentrated under reduced pressure. The residue was triturated with CH$_3$CN (10 mL). The resulting solid was filtered and dried under vacuum to give 6-bromo-4-cyclopropyl-2H-phthalazin-1-one (946 mg, 3.568 mmol, 91.34% yield) as a white solid. $^1$H NMR (400 MHz, DMSO-$d_6$) δ 0.83-0.94 (m, 2H), 0.91-1.02 (m, 2H), 2.46 (tt, J=8.1, 5.0 Hz, 1H), 8.04 (dd, J=8.5, 1.9 Hz, 1H), 8.16 (d, J=8.5 Hz, 1H), 8.44 (d, J=1.9 Hz, 1H), 12.49 (s, 1H). LC-MS (Method A): r.t. 0.92 min, MS (ESI) m/z=265.1 and 267.1 [M+H]$^+$.

Intermediate 37:
6-bromo-1-chloro-4-cyclopropylphthalazine

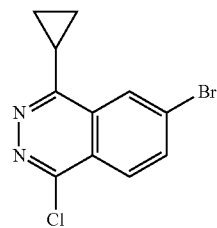 [SMILES: Clc1nnc(C2CC2)c2cc(Br)ccc12]

A solution of 6-bromo-4-cyclopropyl-2H-phthalazin-1-one (946.0 mg, 3.57 mmol) in phosphorus oxychloride (5.0 mL, 53.48 mmol) was stirred at 100° C. for 1 h. Then the phosphorus oxychloride was removed under reduced pressure. The residue was cooled in an ice bath and then quenched with 2N aqueous NaOH solution until the pH was basic. The resulting mixture was extracted three times with EtOAc. The combined organic phases were washed with brine, dried over sodium sulfate, filtered and concentrated under reduced pressure. The residue was purified by column chromatography (KP silica gel, SNAP 100) eluting with a gradient of EtOAc in cyclohexane from 5% to 50% to give 6-bromo-1-chloro-4-cyclopropylphthalazine (700 mg, 2.469 mmol, 69.18% yield) as a white solid. $^1$H NMR (400 MHz, DMSO-$d_6$) δ 1.19 (tdd, J=7.27, 4.93, 2.57 Hz, 2H), 1.25 (dt, J=5.33, 2.71 Hz, 2H), 2.96 (tt, J=8.12, 4.90 Hz, 1H), 8.21 (d, J=8.78 Hz, 1H), 8.31 (dd, J=8.81, 1.87 Hz, 1H), 8.87 (d, J=1.88 Hz, 1H). LC-MS (Method A): r.t. 1.11 min, MS (ESI) m/z=283.1 and 285.1 [M+H]$^+$.

Intermediate 38: 6-bromo-4-cyclopropyl-N-[(2,4-dimethoxyphenyl)methyl]phthalazin-1-amine

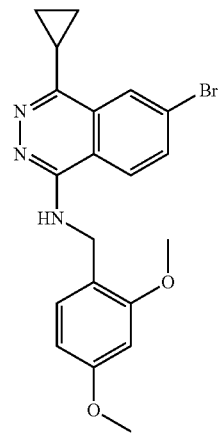 [SMILES: COc1ccc(CNc2nnc(C3CC3)c3cc(Br)ccc23)c(OC)c1]

To a solution of 6-bromo-1-chloro-4-cyclopropylphthalazine (700.0 mg, 2.47 mmol) in ethanol (10.16 mL), (2,4-dimethoxyphenyl)methanamine (1.11 mL, 7.41 mmol) was added. The resulting mixture was stirred at 80° C. for 40 hours then it was cooled to room temperature and concentrated under reduced pressure. The residue was taken up with EtOAc and the organic phase was washed with water and brine, dried over sodium sulfate, filtered and concentrated under reduced pressure. The residue was purified by column chromatography (KP silica gel, SNAP 50) eluting with a gradient of MeOH in dichloromethane from 1% to 15% to give 6-bromo-4-cyclopropyl-N-[(2,4-dimethoxyphenyl)methyl]phthalazin-1-amine (766 mg, 1.849 mmol, 74.89% yield) as a white solid. $^1$H NMR (400 MHz, DMSO-$d_6$) δ 0.91-1.03 (m, 4H), 2.52-2.61 (m, 1H), 3.73 (s, 3H), 3.83 (s, 3H), 4.62 (d, J=5.54 Hz, 2H), 6.42 (dd, J=8.36, 2.40 Hz, 1H), 6.57 (d, J=2.39 Hz, 1H), 7.10 (d, J=8.33 Hz, 1H), 7.67 (t, J=5.60 Hz, 1H), 8.06 (dd, J=8.80, 1.99 Hz, 1H), 8.34 (d, J=8.85 Hz, 1H), 8.49 (d, J=2.01 Hz, 1H). LC-MS (Method A): r.t. 0.75 min, MS (ESI) m/z=414.2 and 416.2 [M+H]$^+$.

Intermediate 39: 6-(3-chlorophenyl)-4-cyclopropyl-N-[(2,4-dimethoxyphenyl)methyl]phthalazin-1-amine

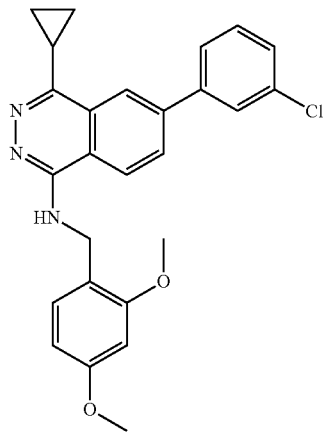 [SMILES: COc1ccc(CNc2nnc(C3CC3)c3cc(-c4cccc(Cl)c4)ccc23)c(OC)c1]

A mixture of 6-bromo-4-cyclopropyl-N-[(2,4-dimethoxyphenyl)methyl]phthalazin-1-amine (180.0 mg, 0.430 mmol), (3-chlorophenyl)boronic acid (74.73 mg, 0.480 mmol) in 1,2-dimethoxyethane (4 mL) and aqueous 2N sodium carbonate solution (434.47 uL, 0.870 mmol) was degassed for 10 minutes with $N_2$. Then [1,1'-bis(di-tert-butylphosphino)ferrocene]dichloropalladium(II) (28.4 mg, 0.040 mmol) was added and the resulting reaction mixture was stirred at 70° C. for 1 hour. It was then cooled to room temperature and filtered over Celite, washing with EtOAc. The filtrate was evaporated and the residue was purified by column chromatography (KP silica gel, SNAP 25) eluting with a gradient of MeOH in dichloromethane from 1% to 20% to give 6-(3-chlorophenyl)-4-cyclopropyl-N-[(2,4-dimethoxyphenyl)methyl]phthalazin-1-amine (185 mg, 0.415 mmol, 95.49% yield) as an off white solid. $^1$H NMR (400 MHz, DMSO-$d_6$) δ 0.94-1.09 (m, 4H), 2.79 (ddd, J=13.40, 8.07, 5.04 Hz, 1H), 3.73 (s, 3H), 3.84 (s, 3H), 4.66 (d, J=5.56 Hz, 2H), 6.43 (dd, J=8.36, 2.42 Hz, 1H), 6.58 (d, J=2.41 Hz, 1H), 7.11 (d, J=8.36 Hz, 1H), 7.54 (ddd, J=7.99, 2.01, 1.22 Hz, 1H), 7.59 (t, J=7.78 Hz, 1H), 7.64 (t, J=5.75 Hz, 1H), 7.90 (dt, J=7.65, 1.45 Hz, 1H), 8.02 (t, J=1.85 Hz, 1H), 8.24 (dd, J=8.65, 1.87 Hz, 1H), 8.49 (d, J=8.61 Hz, 1H), 8.55 (d, J=1.85 Hz, 1H). LC-MS (Method A): r.t. 0.92 min, MS (ESI) m/z=446.9 [M+H]$^+$.

Intermediate 40: [3-[4-cyclopropyl-1-[(2,4-dimethoxyphenyl)methylamino]phthalazin-6-yl]phenyl]boronic Acid

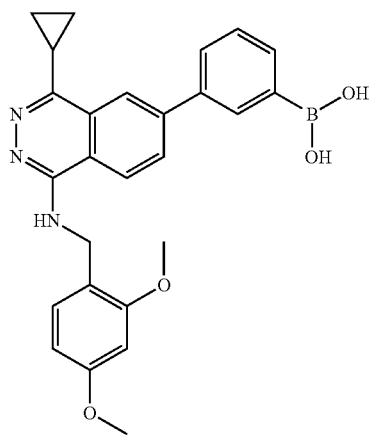 [SMILES: COc1ccc(CNc2nnc(C3CC3)c3cc(-c4cccc(B(O)O)c4)ccc23)c(OC)c1]

6-(3-Chlorophenyl)-4-cyclopropyl-N-[(2,4-dimethoxyphenyl)methyl]phthalazin-1-amine (185.0 mg, 0.410 mmol), 4,4,5,5-tetramethyl-2-(4,4,5,5-tetramethyl-1,3,2-dioxaborolan-2-yl)-1,3,2-dioxaborolane (316.04 mg, 1.24 mmol) and potassium acetate (122.14 mg, 1.24 mmol) were solubilised in 1,4-dioxane (1.435 mL). The solution was degassed for 10 minutes with $N_2$ then palladium(II) diacetate (4.66 mg, 0.020 mmol) and dicyclohexyl-[2-[2,4,6-tri(propan-2-yl)phenyl]phenyl]phosphine (19.78 mg, 0.040 mmol) were added. The resulting reaction mixture was stirred at 105° C. for 30 minutes then it was cooled to room temperature and filtered over Celite, washing with EtOAc. The filtrate was evaporated and the residue was purified by column chromatography (KP-C18-HS, 30 g) eluting with a gradient of $CH_3CN$ in water (+0.1% of HCOOH) from 1% to 50%. Fractions containing the desired compound were collected and evaporated under reduced pressure. The residue was triturated with $Et_2O$, filtered and dried to give [3-[4-cyclopropyl-1-[(2,4-dimethoxyphenyl)methylamino]phthalazin-6-yl]phenyl]boronic acid (50 mg, 0.110 mmol, 26.47% yield) as an off white solid. $^1$H NMR (400 MHz, DMSO-$d_6$) δ 0.95-1.06 (m, 2H), 1.06-1.21 (m, 2H), 2.67-2.77 (m, 1H), 3.73 (s, 3H), 3.85 (s, 3H), 4.66 (d, J=5.57 Hz, 2H), 6.43 (dd, J=8.29, 2.40 Hz, 1H), 6.58 (d, J=2.39 Hz, 1H), 7.13 (d, J=8.36 Hz, 1H), 7.49-7.63 (m, 1H), 7.84-7.92 (m, 1H), 7.95 (d, J=8.45 Hz, 1H), 8.18-8.27 (m, 2H), 8.30 (s, 1H), 8.45-8.54 (m, 2H). LC-MS (Method A): r.t. 0.74 min, MS (ESI) m/z=456.3 [M+H]$^+$.

Intermediate 41: [1-[(2,4-dimethoxyphenyl)methylamino]-4-methylphthalazin-6-yl]boronic Acid

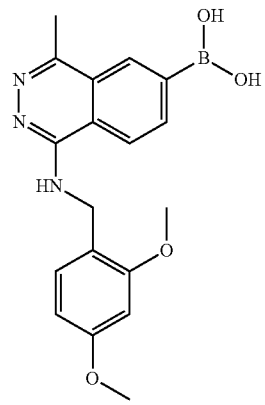 [SMILES: COc1ccc(CNc2nnc(C)c3cc(B(O)O)ccc23)c(OC)c1]

6-Bromo-N-[(2,4-dimethoxyphenyl)methyl]-4-methylphthalazin-1-amine (3.0 g, 7.73 mmol), 4,4,5,5-tetramethyl-2-(4,4,5,5-tetramethyl-1,3,2-dioxaborolan-2-yl)-1,3,2-dioxaborolane (5886.42 mg, 23.18 mmol) and potassium acetate (2274.92 mg, 23.18 mmol) were dissolved 1,4-dioxane (100 mL) and the mixture was deoxygenated with $N_2$ for 10 min. Dicyclohexyl-[2-[2,4,6-tri(propan-2-yl)phenyl]phenyl]phosphine (294.68 mg, 0.620 mmol) and palladium(II) diacetate (86.74 mg, 0.390 mmol) were added and the mixture was deoxygenated with $N_2$ for another 10 min. Then the mixture was stirred at 90° C. overnight. The mixture was left to reach room temperature, then diluted with EtOAc and filtered. The volatiles were removed and the residue was purified by column chromatography (KP-C18-HS, 2×SNAP 120 in series) eluting with a gradient of MeCN (+0.1% of HCOOH) in water (+0.1% of HCOOH) from 2% to 90% to give [1-[(2,4-dimethoxyphenyl)methylamino]-4-methylphthalazin-6-yl]boronic acid (2.52 g, 7.135 mmol, 92.34% yield) as a brownish solid. $^1$H NMR (400 MHz, DMSO-d$_6$) δ 2.69 (s, 3H), 3.73 (s, 3H), 3.84 (s, 3H), 4.64 (d, J=5.50 Hz, 2H), 6.42 (dd, J=8.36, 2.42 Hz, 1H), 6.58 (d, J=2.42 Hz, 1H), 7.11 (d, J=8.36 Hz, 1H), 7.50 (s, 1H), 8.19 (d, J=7.26 Hz, 1H), 8.30 (d, J=8.14 Hz, 1H), 8.44 (s, 1H), 8.49 (s, 2H). LC-MS (Method A): r.t. 0.55 min, MS (ESI) m/z=354.32 [M+H]$^+$.

Intermediate 42: 6-(5-chloro-2-ethylphenyl)-N-[(2,4-dimethoxyphenyl)methyl]-4-methylphthalazin-1-amine

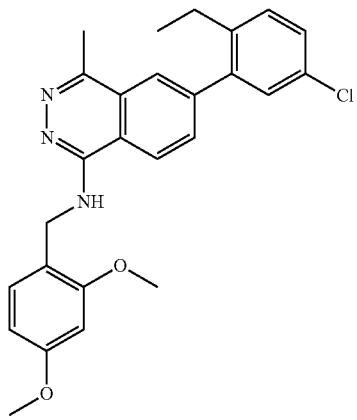 [SMILES: CCc1ccc(Cl)cc1-c1ccc2c(NCc3ccc(OC)cc3OC)nnc(C)c2c1]

A mixture of [1-[(2,4-dimethoxyphenyl)methylamino]-4-methylphthalazin-6-yl]boronic acid (198.78 mg, 0.560 mmol) and 4-chloro-1-ethyl-2-iodobenzene (150.0 mg, 0.560 mmol) in 1,2-dimethoxyethane (7 mL) and aqueous 2N sodium carbonate solution (281.42 uL, 0.560 mmol) was degassed for 10 min with N$_2$. Then, [1,1'-bis(di-tert-butylphosphino)ferrocene]dichloropalladium(II) (36.8 mg, 0.060 mmol) was added. The mixture was stirred at 80° C. for 12 hours, then it was cooled to room temperature and filtered over Celite, washing with MeOH. The filtrate was evaporated and the residue was purified by column chromatography (KP-NH silica gel, SNAP 55) eluting with a gradient of MeOH in DCM from 0% to 5% to give 6-(5-chloro-2-ethylphenyl)-N-[(2,4-dimethoxyphenyl)methyl]-4-methylphthalazin-1-amine (129 mg, 0.288 mmol, 51.16% yield) as a brown powder. $^1$H NMR (400 MHz, DMSO-d$_6$) δ 1.04 (t, J=7.53 Hz, 3H), 2.56 (q, J=7.63 Hz, 2H), 2.69 (s, 3H), 3.74 (s, 3H), 3.85 (s, 3H), 4.68 (d, J=5.40 Hz, 2H), 6.44 (dd, J=8.35, 2.41 Hz, 1H), 6.59 (d, J=2.35 Hz, 1H), 7.14 (d, J=8.34 Hz, 1H), 7.38 (d, J=2.09 Hz, 1H), 7.45 (s, 1H), 7.46 (d, J=2.10 Hz, 1H), 7.64 (t, J=5.74 Hz, 1H), 7.85 (dd, J=8.40, 1.74 Hz, 1H), 7.90 (d, J=1.68 Hz, 1H), 8.45 (d, J=8.49 Hz, 1H). LC-MS (Method A): r.t. 0.91 min, MS (ESI) m/z=448.3 [M+H]$^+$.

Intermediate 43: [3-[1-[(2,4-dimethoxyphenyl)methylamino]-4-methylphthalazin-6-yl]-4-ethylphenyl]boronic Acid

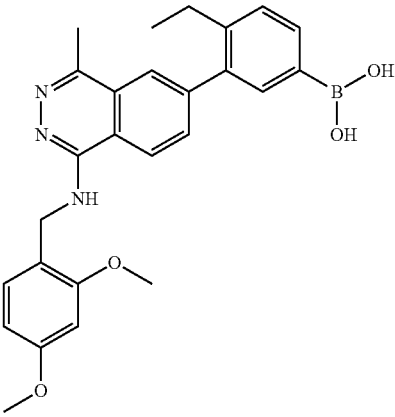 [SMILES: CCc1ccc(B(O)O)cc1-c1ccc2c(NCc3ccc(OC)cc3OC)nnc(C)c2c1]

A mixture of 6-(5-chloro-2-ethylphenyl)-N-[(2,4-dimethoxyphenyl)methyl]-4-methylphthalazin-1-amine (129.0 mg, 0.290 mmol), 4,4,5,5-tetramethyl-2-(4,4,5,5-tetramethyl-1,3,2-dioxaborolan-2-yl)-1,3,2-dioxaborolane (219.38 mg, 0.860 mmol), dicyclohexyl-[2-[2,4,6-tri(propan-2-yl)phenyl]phenyl]phosphine (10.98 mg, 0.020 mmol), potassium acetate (84.78 mg, 0.860 mmol) and palladium(II) diacetate (3.23 mg, 0.010 mmol) was dissolved in 1,4-dioxane (1.57 mL) in a microwave vial and degassed for 10 min with N$_2$. The mixture was stirred at 75° C. for 2 hours, then it was cooled to room temperature and filtered over Celite, washing with MeOH. The filtrate was evaporated and the residue was purified by column chromatography (KP-C18-HS, 30 g) eluting with a gradient of CH$_3$CN in water from 2% to 95%. Fractions containing the desired compound were collected and evaporated under reduced pressure to give [3-[1-[(2,4-dimethoxyphenyl)methylamino]-4-methylphthalazin-6-yl]-4-ethylphenyl]boronic acid (36 mg, 0.079 mmol, 27.34% yield) as a white powder. $^1$H NMR (400 MHz, DMSO-d$_6$) δ 1.07 (t, J=7.52 Hz, 3H), 2.60 (q, J=7.51 Hz, 2H), 2.68 (s, 3H), 3.74 (s, 3H), 3.85 (s, 3H), 4.68 (d, J=5.52 Hz, 2H), 6.44 (dd, J=8.36, 2.42 Hz, 1H), 6.59 (d, J=2.42 Hz, 1H), 7.15 (d, J=8.36 Hz, 1H), 7.38 (d, J=7.73 Hz, 1H), 7.61 (t, J=5.75 Hz, 1H), 7.72 (d, J=1.34 Hz, 1H), 7.79-7.87 (m, 3H), 8.05 (s, 2 OH), 8.44 (d, J=8.41 Hz, 1H). LC-MS (Method A): r.t. 0.74 min, MS (ESI) m/z=558.3 [M+H]$^+$.

Intermediate 44: 6-bromo-1-chloro-3-methylisoquinoline

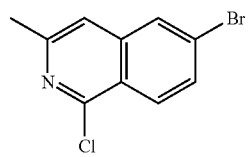

A mixture of 6-bromo-3-methyl-2H-isoquinolin-1-one (1000.0 mg, 4.2 mmol) and phosphorus(V) oxychloride (6.0 mL, 64.18 mmol) was stirred at 100° C. for 1 h, then it was left to reach room temperature and concentrated. 2M aqueous NaOH solution was added at 0° C. and the precipitate was filtered and washed with water tio give 6-bromo-1-chloro-3-methylisoquinoline (858 mg, 3.345 mmol, 79.63% yield) as a yellowish powder. $^1$H NMR (400 MHz, DMSO-d$_6$) δ 2.59 (s, 3H), 7.70 (s, 1H), 7.87 (dd, J=9.02, 1.98 Hz, 1H), 8.15 (d, J=9.02 Hz, 1H), 8.30 (d, J=1.98 Hz, 1H). LC-MS (Method A): r.t. 1.28 min, MS (ESI) m/z=256.06 and 258.06 [M+H]$^+$.

Intermediate 45: 6-bromo-N-[(2,4-dimethoxyphenyl)methyl]-3-methylisoquinolin-1-amine

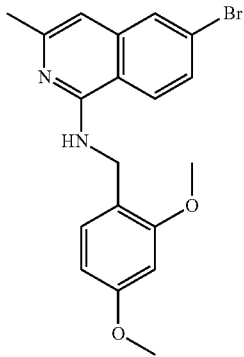 [SMILES: COc1ccc(CNc2nc(C)cc3cc(Br)ccc23)c(OC)c1]

A mixture of 6-bromo-1-chloro-3-methylisoquinoline (858.0 mg, 3.34 mmol) and (2,4-dimethoxyphenyl)methanamine (0.5 mL, 3.34 mmol) in ethanol (13.38 mL) was stirred at 100° C. and then for 6 h at 120° C. The mixture was heated to 120° C. under microwave irradiation in a microwave reactor (5×20 min). The volatiles were evaporated and EtOAc and water were added. The phases were separated and the organic phase was washed with brine, dried over sodium sulfate, filtered and concentrated. The residue was purified by column chromatography (KP-Sil silica gel SNAP 50) eluting with a gradient of EtOAc in cyclohexane from 2% to 30% to give 6-bromo-N-[(2,4-dimethoxyphenyl)methyl]-3-methylisoquinolin-1-amine (238 mg, 0.615 mmol, 18.37% yield) as a yellowish oil. $^1$H NMR (400 MHz, DMSO-d$_6$) δ 2.31 (s, 3H), 3.73 (s, 3H), 3.83 (s, 3H), 4.61 (d, J=5.50 Hz, 2H), 6.44 (dd, J=8.36, 2.42 Hz, 1H), 6.56 (d, J=2.20 Hz, 1H), 6.70 (s, 1H), 7.14 (d, J=8.14 Hz, 1H), 7.51 (dd, J=8.91, 2.09 Hz, 1H), 7.66 (t, J=5.72 Hz, 1H), 7.85 (d, J=1.98 Hz, 1H), 8.22 (1H, d, J=8.80 Hz). LC-MS (Method A): r.t. 0.74 min, MS (ESI) m/z=387.2 and 389.2 [M+H]$^+$.

Intermediate 46: 6-(3-chlorophenyl)-N-[(2,4-dimethoxyphenyl]-3-methylisoquinolin-1-amine

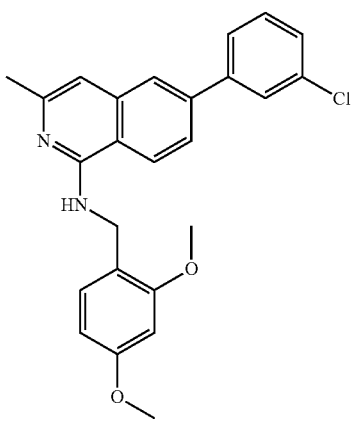 [SMILES: COc1ccc(CNc2nc(C)cc3cc(-c4cccc(Cl)c4)ccc23)c(OC)c1]

A mixture of 6-bromo-N-[(2,4-dimethoxyphenyl)methyl]-3-methylisoquinolin-1-amine (238.0 mg, 0.610 mmol) and (3-chlorophenyl)boronic acid (96.1 mg, 0.610 mmol) in 1,2-dimethoxyethane (4 mL) and aqueous 2N sodium carbonate solution (0.307 mL) was degassed for 10 min, then [1,1'-bis(di-tert-butylphosphino)ferrocene]dichloropalladium(II) (401.77 mg, 0.610 mmol) was added. The mixture was degassed for 10 min and then stirred at 70° C. for 80 min. The mixture was left to reach room temperature, then it was diluted with EtOAc and filtered. The volatiles were removed and the residue was purified by column chromatography (KP-C18-HS, SNAP 30) eluting with a gradient of MeCN in water from 2% to 100% to give 6-(3-chlorophenyl)-N-[(2,4-dimethoxyphenyl)methyl]-3-methylisoquinolin-1-amine (160 mg, 0.382 mmol, 62.15% yield) as a yellowish oil. $^1$H NMR (400 MHz, DMSO-d$_6$) δ 2.33 (s, 3H), 3.73 (s, 3H), 3.84 (s, 3H), 4.65 (d, J=5.72 Hz, 2H), 6.45 (dd, J=8.47, 2.31 Hz, 1H), 6.57 (d, J=2.42 Hz, 1H), 6.80 (s, 1H), 7.16 (d, J=8.36 Hz, 1H), 7.47-7.51 (m, 1H), 7.53-7.58 (m, 1H), 7.63 (t, J=5.72 Hz, 1H) 7.74 (dd, J=8.69, 1.87 Hz, 1H), 7.79 (dt, J=7.92, 1.32 Hz, 1H), 7.87 (t, J=1.87 Hz, 1H), 7.94 (d, J=1.76 Hz, 1H), 8.36 (d, J=8.80 Hz, 1H). LC-MS (Method A): r.t. 0.91 min, MS (ESI) m/z=419.3 [M+H]$^+$.

Intermediate 47: N-[(2,4-dimethoxyphenyl)methyl]-3-methyl-6-[3-(4,4,5,5-tetramethyl-1,3,2-dioxaborolan-2-yl)phenyl]isoquinolin-1-amine

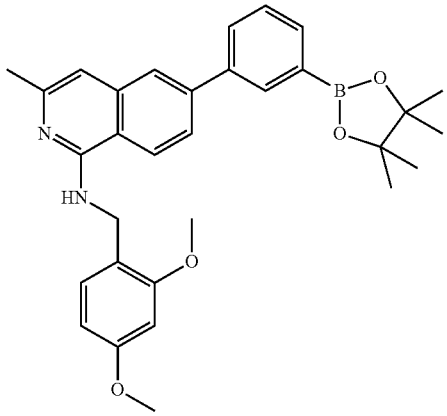

A mixture of 6-(3-chlorophenyl)-N-[(2,4-dimethoxyphenyl)methyl]-3-methylisoquinolin-1-amine (160.0 mg, 0.380 mmol), potassium acetate (112.45 mg, 1.15 mmol) and 4,4,5,5-tetramethyl-2-(4,4,5,5-tetramethyl-1,3,2-dioxaborolan-2-yl)-1,3,2-dioxaborolane (290.97 mg, 1.15 mmol) in 1,4-dioxane (3 mL) was degassed for 10 min. Palladium(II) diacetate (4.29 mg, 0.020 mmol) and dicyclohexyl-[2-[2,4,6-tri(propan-2-yl)phenyl]phenyl]phosphine (14.57 mg, 0.030 mmol) were added and the reaction mixture was stirred at 70° C. for 2.5 h, then it was left to reach room temperature. EtOAc was added and the mixture was filtered, then the volatiles were removed. The residue was purified by column chromatography (KP-C18-HS, SNAP 30) eluting with a gradient of MeCN in water from 2% to 100% to give N-[(2,4-dimethoxyphenyl)methyl]-3-methyl-6-[3-(4,4,5,5-tetramethyl-1,3,2-dioxaborolan-2-yl)phenyl]isoquinolin-1-amine (150 mg, 0.294 mmol, 76.94% yield) as a yellowish solid. $^1$H NMR (400 MHz, DMSO-d$_6$) δ 1.34 (s, 12H), 2.33 (s, 3H), 3.74 (s, 3H), 3.85 (s, 3H), 4.66 (d, J=5.72 Hz, 2H), 6.45 (dd, J=8.36, 2.42 Hz, 1H), 6.58 (d, J=2.42 Hz, 1H), 6.84 (s, 1H), 7.17 (d, J=8.14 Hz, 1H), 7.52-7.57 (m, 1H), 7.60 (t, J=5.83 Hz, 1H), 7.66-7.70 (m, 1H), 7.73 (d, J=7.26 Hz, 1H), 7.86 (d, J=1.76 Hz, 1H), 7.92 (d, J=7.70 Hz, 1H), 8.01 (s, 1H), 8.35 (d, J=8.80 Hz, 1H). LC-MS (Method A): r.t. 1.00 min, MS (ESI) m/z=511.48 [M+H]$^+$.

Intermediate 48: (4-bromo-2-chlorophenyl)methanol

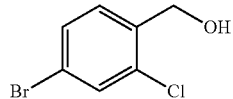

To a solution of 4-bromo-2-chlorobenzoic acid (1.0 g, 4.25 mmol) in THF (15 mL) cooled to 0° C., a 1M solution of borane in THF (8.92 mL, 8.92 mmol) was added dropwise. The mixture was then stirred at room temperature for 18 h, then cooled again to 0° C. and water (25 mL) was added dropwise, followed by saturated aqueous NaHCO$_3$ solution (25 mL, dropwise). EtOAc (50 mL) was added and the layers were separated. The organic phase was washed with brine, and filtered over a short pad of silica gel, washing with EtOAc. The volatiles were evaporated to give (4-bromo-2-chlorophenyl)methanol (1 g, 4.52 mmol, 106.31% yield) as a viscous oil. This crude compound was used in the next step without further purification. $^1$H NMR (400 MHz, DMSO-d$_6$) δ 4.51 (d, J=5.63 Hz, 2H), 5.47 (t, J=5.63 Hz, 1H), 7.48 (d, J=8.25 Hz, 1H), 7.57 (dd, J=8.25, 1.98 Hz, 1H), 7.66 (d, J=1.98 Hz, 1H). LC-MS (Method A): r.t. 0.97 min, MS (ESI) m/z of product not observed due to poor ionization.

Intermediate 49: 2-[(4-bromo-2-chlorophenyl)methoxy]oxane

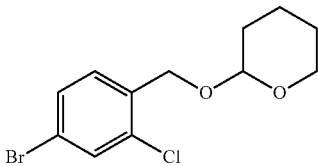 [SMILES: Clc1cc(Br)ccc1COC1CCCCO1]

3,4-Dihydro-2H-pyran (0.62 mL, 6.77 mmol) and 4-methylbenzenesulfonic acid hydrate (42.94 mg, 0.230 mmol) were added to a solution of (4-bromo-2-chlorophenyl)methanol (1.0 g, 4.52 mmol) in DCM (15 mL). The mixture was stirred at room temperature for 48 h, diluted with DCM (40 mL) and washed with aqueous saturated NaHCO$_3$ solution. The organic phase was dried over Na$_2$SO$_4$, filtered and the solvent was evaporated. The residue was purified by column chromatography (KP-Sil, SNAP 25 g) eluting with a gradient of EtOAc in cyclohexane from 0% to 15% to give 2-[(4-bromo-2-chlorophenyl)methoxy]oxane (1.2 g, 3.927 mmol, 86.97% yield) as an oil. $^1$H NMR (400 MHz, DMSO-d$_6$) δ 1.42-1.92 (m, 6H), 3.44-3.54 (m, 1H), 3.73-3.83 (m, 1H), 4.50 (d, J=13.30 Hz, 1H), 4.69 (d, J=13.30 Hz, 1H), 4.72-4.79 (m, 1H), 7.44-7.51 (m, 1H), 7.58 (dd, J=8.26, 1.98 Hz, 1H), 7.73 (d, J=1.98 Hz, 1H). LC-MS (Method A): r.t. 1.43 min, MS (ESI) m/z of product not observed due to poor ionization.

Intermediate 50: 2-[3-chloro-4-(oxan-2-yloxymethyl)phenyl]-4,4,5,5-tetramethyl-1,3,2-dioxaborolane

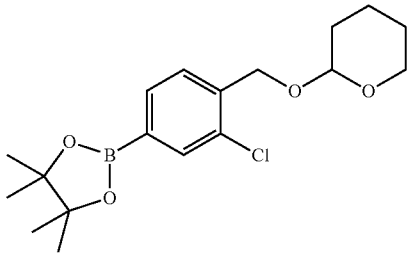 [SMILES: CC1(C)OB(c2ccc(COC3CCCCO3)c(Cl)c2)OC1(C)C]

A vial was charged with 2-[(4-bromo-2-chlorophenyl)methoxy]oxane (350.0 mg, 1.15 mmol), potassium acetate (567.78 mg, 5.73 mmol), 4,4,5,5-tetramethyl-2-(4,4,5,5-tetramethyl-1,3,2-dioxaborolan-2-yl)-1,3,2-dioxaborolane (436.25 mg, 1.72 mmol), [1,1'-bis(diphenylphosphino)ferrocene]dichloropalladium(II) complex with dichloromethane (93.76 mg, 0.110 mmol) and 1,4-dioxane (10 mL). The mixture was degassed with Ar for 10 min and then stirred at 80° C. for 3 h. The mixture was cooled to room temperature and filtered through a short pad of Celite, washing with EtOAc. The volatiles were evaporated and the residue was purified by column chromatography (KP-Sil, SNAP 100 g) eluting with a gradient of a EtOAc in cyclohexane from 0% to 10% to give 2-[3-chloro-4-(oxan-2-yloxymethyl)phenyl]-4,4,5,5-tetramethyl-1,3,2-dioxaborolane (400 mg, 1.134 mmol, 99.04% yield) as a viscous oil. $^1$H NMR (400 MHz, DMSO-d$_6$) δ 1.17 (s, 12H), 1.41-1.83 (m, 6H), 3.45-3.53 (m, 1H), 3.78 (ddd, J=11.26, 8.15, 3.21 Hz, 1H), 4.56 (d, J=13.66 Hz, 1H), 4.69-4.88 (m, 2H), 7.55 (d, J=7.52 Hz, 1H), 7.61 (s, 1H), 7.62-7.67 (m, 1H). LC-MS (Method A): r.t. 1.54 min, MS (ESI) m/z of product not observed due to poor ionization.

Intermediate 51: 6-[3-chloro-4-(oxan-2-yloxymethyl)phenyl]-N-[(2,4-dimethoxyphenyl)methyl]-4-methylphthalazin-1-amine

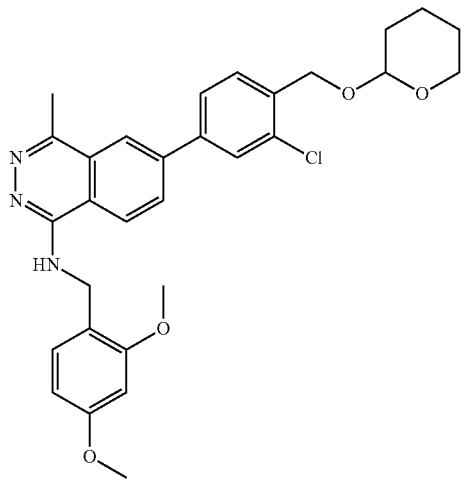 [SMILES: COc1ccc(CNc2nnc(C)c3cc(-c4ccc(COC5CCCCO5)c(Cl)c4)ccc23)c(OC)c1]

A mixture of 2-[3-chloro-4-(oxan-2-yloxymethyl)phenyl]-4,4,5,5-tetramethyl-1,3,2-dioxaborolane (272.49 mg, 0.770 mmol), 6-bromo-N-[(2,4-dimethoxyphenyl)methyl]-4-methylphthalazin-1-amine (300.0 mg, 0.770 mmol), [1,1'-bis(di-tert-butylphosphino)ferrocene]dichloropalladium(II) (50.51 mg, 0.080 mmol) in 1,2-dimethoxyethane (6 mL) and aqueous 2N sodium carbonate solution (0.77 mL, 1.55 mmol) was degassed for 10 min with Ar. The mixture was stirred at 80° C. for 1 hour, then it was cooled to room temperature and filtered over Celite, washing with EtOAc. The solvent was evaporated and the residue was purified by column chromatography (KP-NH silica gel, SNAP 28 g) eluting with a gradient of EtOAc/DCM (1:1) in cyclohexane from 0% to 100% to give 6-[3-chloro-4-(oxan-2-yloxymethyl)phenyl]-N-[(2,4-dimethoxyphenyl)methyl]-4-methylphthalazin-1-amine (240 mg, 0.449 mmol, 58.16% yield) as a yellow oil. $^1$H NMR (400 MHz, DMSO-$d_6$) δ 1.44-1.86 (m, 6H), 2.76 (s, 3H), 3.48-3.57 (m, 1H), 3.72 (s, 3H), 3.79-3.86 (m, 1H), 3.84 (s, 3H), 4.62 (d, J=13.16 Hz, 1H), 4.66 (d, J=5.50 Hz, 2H), 4.76-4.87 (m, 2H), 6.42 (dd, J=8.35, 2.37 Hz, 1H), 6.58 (d, J=2.37 Hz, 1H), 7.12 (d, J=8.35 Hz, 1H), 7.63 (t, J=5.70 Hz, 1H), 7.68 (d, J=8.02 Hz, 1H), 7.90 (dd, J=8.02, 1.87 Hz, 1H), 8.03 (d, J=1.87 Hz, 1H), 8.21-8.25 (m, 2H), 8.47 (d, J=9.28 Hz, 1H). LC-MS (Method A): r.t. 0.94 min, MS (ESI) m/z=534.4 [M+H]$^+$.

Intermediate 52: N-[(2,4-dimethoxyphenyl)methyl]-4-methyl-6-[4-(oxan-2-yloxymethyl)-3-(4,4,5,5-tetramethyl-1,3,2-dioxaborolan-2-yl)phenyl]phthalazin-1-amine

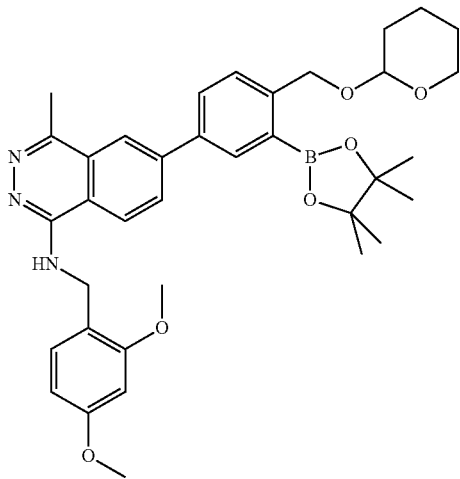 [SMILES: COc1ccc(CNc2nnc(C)c3cc(-c4ccc(COC5CCCCO5)c(B5OC(C)(C)C(C)(C)O5)c4)ccc23)c(OC)c1]

Palladium(II) diacetate (3.87 mg, 0.020 mmol), 6-[3-chloro-4-(oxan-2-yloxymethyl)phenyl]-N-[(2,4-dimethoxyphenyl)methyl]-4-methylphthalazin-1-amine (184.0 mg, 0.340 mmol), dicyclohexyl-[2-[2,4,6-tri(propan-2-yl)phenyl]phenyl]phosphine (13.14 mg, 0.030 mmol), potassium acetate (101.44 mg, 1.03 mmol) and 4,4,5,5-tetramethyl-2-(4,4,5,5-tetramethyl-1,3,2-dioxaborolan-2-yl)-1,3,2-dioxaborolane (262.48 mg, 1.03 mmol) were dissolved in 1,4-dioxane (10 mL). The mixture was degassed with Ar for 10 min, then stirred at 75° C. for 3 hours. The mixture was filtered over a pad of Celite, washing with EtOAc. The filtrate was concentrated in vacuo and the residue was purified by column chromatography (KP-C18-HS, SNAP 30 g) eluting with a gradient of CH$_3$CN in water from 1% to 95% to give N-[(2,4-dimethoxyphenyl)methyl]-4-methyl-6-[4-(oxan-2-yloxymethyl)-3-(4,4,5,5-tetramethyl-1,3,2-dioxaborolan-2-yl)phenyl]phthalazin-1-amine (78 mg, 0.125 mmol, 36.19% yield) as a pale yellow solid. $^1$H NMR (400 MHz, DMSO-$d_6$) δ 1.34 (s, 12H), 1.43-1.84 (m, 6H), 2.74 (s, 3H), 3.45-3.54 (m, 1H), 3.73 (s, 3H), 3.79-3.87 (m, 1H), 3.84 (s, 3H), 4.67 (d, J=5.37 Hz, 2H), 4.72 (t, J=3.39 Hz, 1H), 4.76 (d, J=12.31 Hz, 1H), 4.89 (d, J=12.31 Hz, 1H), 6.43 (dd, J=8.36, 2.42 Hz, 1H), 6.58 (d, J=2.42 Hz, 1H), 7.12 (d, J=8.36 Hz, 1H), 7.57-7.70 (m, 2H), 7.96 (dd, J=7.96, 2.16 Hz, 1H), 8.01 (d, J=2.16 Hz, 1H), 8.10-8.12 (m, 1H), 8.14 (dd, J=8.54, 1.87 Hz, 1H), 8.47 (d, J=8.53 Hz, 1H). LC-MS (Method A): r.t. 1.03 min, MS (ESI) m/z=626.6 [M+H]$^+$.

Intermediate 53: 6-[5-chloro-2-(trifluoromethoxy)phenyl]-N-[(2,4-dimethoxyphenyl)methyl]-4-methylphthalazin-1-amine Formic Acid Salt

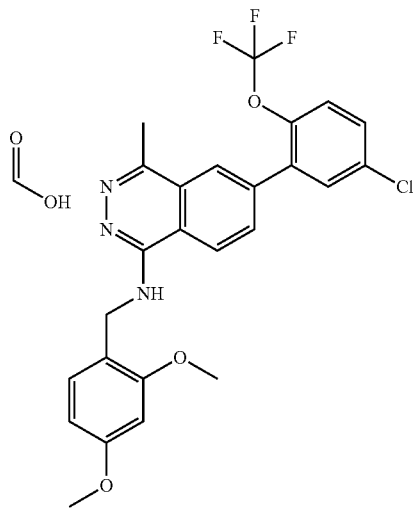

A mixture of [5-chloro-2-(trifluoromethoxy)phenyl]boronic acid (160.96 mg, 0.670 mmol) and 6-bromo-N-[(2,4-dimethoxyphenyl)methyl]-4-methylphthalazin-1-amine (200.0 mg, 0.520 mmol) in 1,2-dimethoxyethane (3 mL) and aqueous 2N sodium carbonate solution (257.56 uL, 0.520 mmol) was degassed for 10 min with N$_2$. Then, [1,1'-bis(di-tert-butylphosphino)ferrocene]dichloropalladium(II) (33.68 mg, 0.050 mmol) was added. The mixture was stirred at 70° C. for 5 hours, then it was cooled to room temperature and filtered over Celite, washing with MeOH. The filtrate was evaporated and the residue was purified by column chromatography (KP-NH silica gel, SNAP 55) eluting with a gradient of MeOH in DCM from 0% to 10% to give a partially pure product. The mixture was purified further by column chromatography (KP-C18-HS, 30 g) eluting with a gradient of CH$_3$CN in water (+0.1% of HCOOH) from 2% to 95%. Fractions containing the desired compound were collected and evaporated under reduced pressure to give 6-[5-chloro-2-(trifluoromethoxy)phenyl]-N-[(2,4-dimethoxyphenyl)methyl]-4-methylphthalazin-1-amine formic acid salt (146 mg, 0.290 mmol, 56.25% yield) as a white foam. $^1$H NMR (400 MHz, DMSO-$d_6$) δ 2.71 (s, 3H), 3.74 (s, 3H), 3.85 (s, 3H), 4.67 (s, 2H), 6.44 (dd, J=8.36, 2.42 Hz, 1H), 6.59 (d, J=2.41 Hz, 1H), 7.15 (d, J=8.29 Hz, 1H), 7.60-7.64 (m, 1H), 7.69 (dd, J=8.80, 2.63 Hz, 1H), 7.88 (d, J=2.60 Hz, 1H), 8.01 (dd, J=8.57, 1.76 Hz, 1H), 8.11 (d, J=1.73 Hz, 1H), 8.15 (s, HCOOH), 8.48 (d, J=8.57 Hz, 1H). LC-MS (Method A): r.t. 0.90 min, MS (ESI) m/z=504.3 [M+H]$^+$.

Intermediate 54: [3-[1-[(2,4-dimethoxyphenyl)methylamino]-4-methylphthalazin-6-yl]-4-(trifluoromethoxy)phenyl]boronic Acid

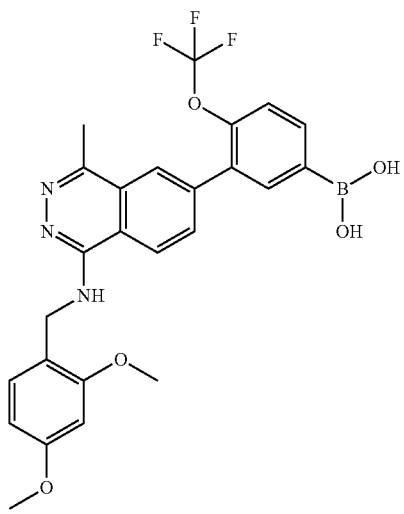 [SMILES: COc1ccc(CNc2nnc(C)c3cc(-c4cc(B(O)O)ccc4OC(F)(F)F)ccc23)c(OC)c1]

A mixture of 6-[5-chloro-2-(trifluoromethoxy)phenyl]-N-[(2,4-dimethoxyphenyl)methyl]-4-methylphthalazin-1-amine (146.0 mg, 0.290 mmol), 4,4,5,5-tetramethyl-2-(4,4,5,5-tetramethyl-1,3,2-dioxaborolan-2-yl)-1,3,2-dioxaborolane (220.73 mg, 0.870 mmol), dicyclohexyl-[2-[2,4,6-tri(propan-2-yl)phenyl]phenyl]phosphine (11.05 mg, 0.020 mmol), potassium acetate (85.31 mg, 0.870 mmol) and palladium (II) diacetate (3.25 mg, 0.010 mmol) was dissolved in 1,4-dioxane (1.77 mL) in a microwave vial and degassed for 10 min with $N_2$. The mixture was stirred at 70° C. for 2 hours, then it was cooled to room temperature and filtered over Celite, washing with MeOH. The filtrate was evaporated and the residue was purified by column chromatography (KP-C18-HS, 12 g) eluting with a gradient of $CH_3CN$ in water (+0.1% of HCOOH) from 1% to 40%. Fractions containing the desired compound were collected and evaporated under reduced pressure to give [3-[1-[(2,4-dimethoxyphenyl)methylamino]-4-methylphthalazin-6-yl]-4-(trifluoromethoxy)phenyl]boronic acid (22 mg, 0.043 mmol, 14.79% yield) as a colorless oil. LC-MS (Method A): r.t. 0.78 min, MS (ESI) m/z=514.4 [M+H]⁺.

Intermediate 55: 6-[5-chloro-2-[2-[2-[2-[2-[2-(2-methoxyethoxy)ethoxy]ethoxy]ethoxy]ethoxy]ethoxy]phenyl]-N-[(2,4-dimethoxyphenyl)methyl]-4-methylphthalazin-1-amine Formic Acid Salt

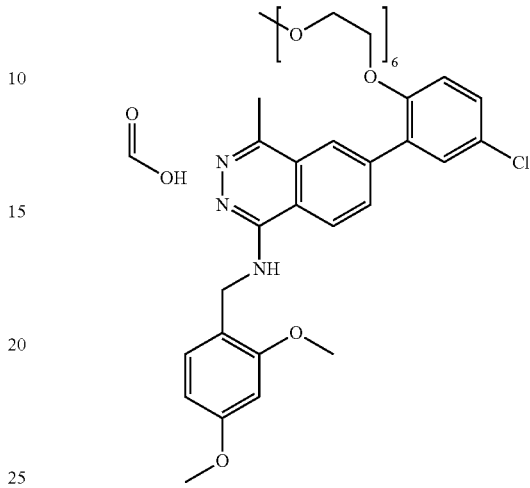

A mixture of [1-[(2,4-dimethoxyphenyl)methylamino]-4-methylphthalazin-6-yl]boronic acid (191.93 mg, 0.540 mmol) and 2-bromo-4-chloro-1-[2-[2-[2-[2-[2-(2-methoxyethoxy)ethoxy]ethoxy]ethoxy]ethoxy]ethoxy]benzene (330.0 mg, 0.680 mmol) in 1,2-dimethoxyethane (9 mL) and aqueous 2N sodium carbonate solution (339.65 uL, 0.680 mmol) was degassed for 10 min with $N_2$. Then, [1,1'-bis(di-tert-butylphosphino)ferrocene]dichloropalladium(II) (44.41 mg, 0.070 mmol) was added. The mixture was stirred at 80° C. for 20 hours, then it was cooled to room temperature and filtered over Celite, washing with MeOH. The filtrate was evaporated and the residue was purified by column chromatography (KP-NH silica gel, SNAP 28) eluting with a gradient of MeOH in DCM from 0% to 8% to give partially pure product. The mixture was purified further by column chromatography (KP-C18-HS, 30 g) eluting with a gradient of $CH_3CN$ in water (+0.1% of HCOOH) from 2% to 95%. Fractions containing the desired compound were collected and evaporated under reduced pressure to give 6-[5-chloro-2-[2-[2-[2-[2-(2-methoxyethoxy)ethoxy]ethoxy]ethoxy]ethoxy]ethoxy]phenyl]-N-[(2,4-dimethoxyphenyl)methyl]-4-methylphthalazin-1-amine formic acid salt (200 mg, 0.280 mmol, 41.22% yield) as a yellow oil. ¹H NMR (400 MHz, DMSO-$d_6$) δ 2.71 (s, 3H), 3.21 (s, 3H), 3.37-3.53 (m, 20H), 3.69-3.73 (m, 2H), 3.73 (s, 3H), 3.85 (s, 3H), 4.13-4.22 (m, 2H), 4.67 (s, 2H), 6.43 (dd, J=8.36, 2.41 Hz, 1H), 6.58 (d, J=2.41 Hz, 1H), 7.13 (d, J=8.34 Hz, 1H), 7.24 (d, J=8.91 Hz, 1H), 7.46 (dd, J=8.82, 2.73 Hz, 1H), 7.60 (d, J=2.67 Hz, 1H), 8.08 (dd, J=8.57, 1.75 Hz, 1H), 8.15 (d, J=1.68 Hz, 1H), 8.15 (s, HCOOH), 8.39 (d, J=8.58 Hz, 1H). LC-MS (Method A): r.t. 0.86 min, MS (ESI) m/z=714.6 [M+H]⁺.

Intermediate 56: N-[(2,4-dimethoxyphenyl)methyl]-6-[2-[2-[2-[2-[2-[2-(2-methoxyethoxy)ethoxy]ethoxy]ethoxy]ethoxy]ethoxy]-5-(4,4,5,5-tetramethyl-1,3,2-dioxaborolan-2-yl)phenyl]-4-methylphthalazin-1-amine

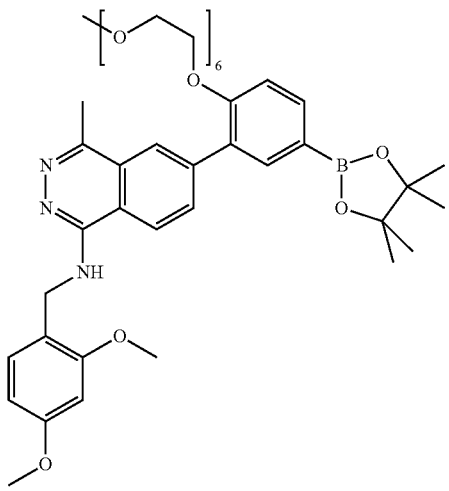

A mixture of 6-[5-chloro-2-[2-[2-[2-[2-[2-(2-methoxyethoxy)ethoxy]ethoxy]ethoxy]ethoxy]ethoxy]phenyl]-N-[(2,4-dimethoxyphenyl)methyl]-4-methylphthalazin-1-amine formic acid salt (180.0 mg, 0.250 mmol), 4,4,5,5-tetramethyl-2-(4,4,5,5-tetramethyl-1,3,2-dioxaborolan-2-yl)-1,3,2-dioxaborolane (191.99 mg, 0.760 mmol), dicyclohexyl-[2-[2,4,6-tri(propan-2-yl)phenyl]phenyl]phosphine (9.61 mg, 0.020 mmol), potassium acetate (74.2 mg, 0.760 mmol) and palladium(II) diacetate (2.83 mg, 0.010 mmol) were dissolved in 1,4-dioxane (3.8 mL) in a microwave vial and degassed for 10 min with $N_2$. The mixture was stirred at 75° C. for 1.5 hours, then it was cooled to room temperature and filtered over Celite, washing with MeOH. The filtrate was evaporated and the residue was purified by column chromatography (KP-C18-HS, 30 g) eluting with a gradient of $CH_3CN$ in water from 2% to 95%. Fractions containing the desired compound were collected and evaporated under reduced pressure to give N-[(2,4-dimethoxyphenyl)methyl]-6-[2-[2-[2-[2-[2-[2-(2-methoxyethoxy)ethoxy]ethoxy]ethoxy]ethoxy]ethoxy]-5-(4,4,5,5-tetramethyl-1,3,2-dioxaborolan-2-yl)phenyl]-4-methylphthalazin-1-amine containing some 6-[2-[2-[2-[2-[2-[2-(2-methoxyethoxy)ethoxy]ethoxy]ethoxy]ethoxy]ethoxy]phenyl]-N-[(2,4-dimethoxyphenyl)methyl]-4-methylphthalazin-1-amine (57 mg, 0.071 mmol, 28.07% yield) as a brown/orange gel. LC-MS (Method A): r.t. 0.93 min, MS (ESI) m/z=806.8 [M+H]$^+$.

Intermediate 57: 6-[2-[2-[2-[2-[2-[2-(2-methoxyethoxy)ethoxy]ethoxy]ethoxy]ethoxy]ethoxy]-5-(4,4,5,5-tetramethyl-1,3,2-dioxaborolan-2-yl)phenyl]-4-methylphthalazin-1-amine trifluoroacetic Acid Salt

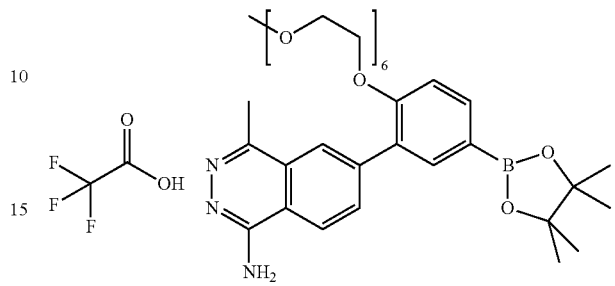

A solution of N-[(2,4-dimethoxyphenyl)methyl]-6-[2-[2-[2-[2-[2-[2-(2-methoxyethoxy)ethoxy]ethoxy]ethoxy]ethoxy]ethoxy]-5-(4,4,5,5-tetramethyl-1,3,2-dioxaborolan-2-yl)phenyl]-4-methylphthalazin-1-amine (57.0 mg, 0.070 mmol) in DCM (4 mL) and trifluoroacetic acid (0.5 mL) was stirred for 2 hours at room temperature then was concentrated under reduced pressure. The residue was dissolved in MeOH and filtered over Celite. The organic phase was evaporated to give 6-[2-[2-[2-[2-[2-[2-(2-methoxyethoxy)ethoxy]ethoxy]ethoxy]ethoxy]ethoxy]-5-(4,4,5,5-tetramethyl-1,3,2-dioxaborolan-2-yl)phenyl]-4-methylphthalazin-1-amine trifluoroacetic acid salt containing some 6-[2-[2-[2-[2-[2-[2-(2-methoxyethoxy)ethoxy]ethoxy]ethoxy]ethoxy]ethoxy]phenyl]-N-[(2,4-dimethoxyphenyl)methyl]-4-methylphthalazin-1-amine that was already present in the starting material (45 mg, 0.069 mmol, 97.03% yield) as a colourless oil. $^1$H NMR (400 MHz, DMSO-$d_6$) δ 1.31 (s, 12H), 2.76 (s, 3H), 3.22 (s, 3H), 3.31-3.69 (m, 20H), 3.69-3.78 (m, 2H), 4.20-4.29 (m, 2H), 7.27 (d, J=8.30 Hz, 1H), 7.74-7.82 (m, 2H), 8.25-8.46 (m, 2H), 8.68 (dd, J=8.39, 3.57 Hz, 1H), 9.16 (br. s, 2H). LC-MS (Method A): r.t. 0.80 min, MS (ESI) m/z=656.6 [M+H]$^+$.

Intermediate 58: 6-(5-chloropyridin-3-yl)-N-[(2,4-dimethoxyphenyl)methyl]-4-methylphthalazin-1-amine

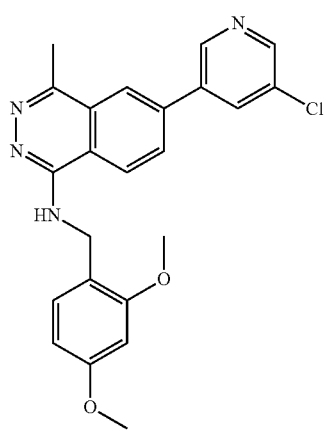 [SMILES: COc1ccc(CNc2nnc(C)c3cc(-c4cncc(Cl)c4)ccc23)c(OC)c1]

A mixture of (5-chloro-3-pyridinyl)boronic acid (154.01 mg, 0.980 mmol), 6-bromo-N-[(2,4-dimethoxyphenyl)

methyl]-4-methylphthalazin-1-amine (400.0 mg, 0.980 mmol) and [1,1'-bis(di-tert-butylphosphino)ferrocene]dichloropalladium(II) (63.99 mg, 0.100 mmol) in 1,2-dimethoxyethane (6.514 mL) and aqueous 2N sodium carbonate solution (0.98 mL, 1.96 mmol) was degassed for 10 min with Ar. The mixture was stirred at 80° C. for 3 hours, then cooled to room temperature and filtered over Celite, washing with EtOAc. The volatiles were evaporated and the residue was purified by column chromatography (KP-NH silica gel, SNAP 30 g) eluting with a gradient of DCM/EtOAc (1:1) in cyclohexane from 0% to 100% to give 6-(5-chloropyridin-3-yl)-N-[(2,4-dimethoxyphenyl)methyl]-4-methylphthalazin-1-amine (325 mg, 0.772 mmol, 78.9% yield) as a white solid. $^1$H NMR (400 MHz, DMSO-$d_6$) δ 2.77 (s, 3H), 3.73 (s, 4H), 3.84 (s, 3H), 4.66 (d, J=5.41 Hz, 2H), 6.42 (dd, J=8.35, 2.39 Hz, 1H), 6.58 (d, J=2.39 Hz, 1H), 7.12 (d, J=8.35 Hz, 1H), 7.66 (t, J=5.71 Hz, 1H), 8.31 (dd, J=8.58, 1.87 Hz, 1H), 8.34 (d, J=1.87 Hz, 1H), 8.51 (d, J=8.58 Hz, 1H), 8.55 (t, J=2.18 Hz, 1H), 8.72 (d, J=2.28 Hz, 1H), 9.11 (d, J=1.97 Hz, 1H). LC-MS (Method A): r.t. 0.70 min, MS (ESI) m/z=421.3 [M+H]$^+$.

Intermediate 59: [5-[1-[(2,4-dimethoxyphenyl)methylamino]-4-methylphthalazin-6-yl]pyridin-3-yl]boronic Acid

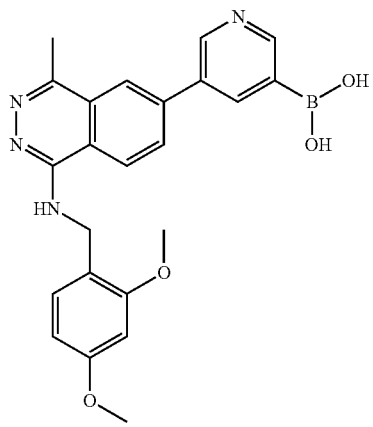 [SMILES: COc1ccc(CNc2nnc(C)c3cc(-c4cncc(B(O)O)c4)ccc23)c(OC)c1]

Palladium(II) diacetate (8.67 mg, 0.040 mmol), 6-(5-chloropyridin-3-yl)-N-[(2,4-dimethoxyphenyl)methyl]-4-methylphthalazin-1-amine (325.0 mg, 0.770 mmol), dicyclohexyl-[2-[2,4,6-tri(propan-2-yl)phenyl]phenyl]phosphine (29.45 mg, 0.060 mmol), potassium acetate (227.34 mg, 2.32 mmol) and 4,4,5,5-tetramethyl-2-(4,4,5,5-tetramethyl-1,3,2-dioxaborolan-2-yl)-1,3,2-dioxaborolane (588.26 mg, 2.32 mmol) were dissolved in 1,4-dioxane (6.734 mL). The mixture was degassed with Ar for 10 min, then stirred at 75° C. for 3 hours. The mixture was filtered over a pad of Celite, washing with EtOAc and the filtrate was concentrated in vacuo. The residue was purified by column chromatography (KP-C18-HS, SNAP 60 g) eluting with a gradient of CH$_3$CN (+0.1% HCOOH) in water (+0.1% HCOOH) from 1% to 40% to give [5-[1-[(2,4-dimethoxyphenyl)methylamino]-4-methylphthalazin-6-yl]pyridin-3-yl]boronic acid (160 mg, 0.372 mmol, 48.16% yield) as a brown solid. LC-MS (Method A): r.t. 0.49 min, MS (ESI) m/z=431.3 [M+H]$^+$.

Intermediate 60: 2,4-bis(4,4,5,5-tetramethyl-1,3,2-dioxaborolan-2-yl)aniline

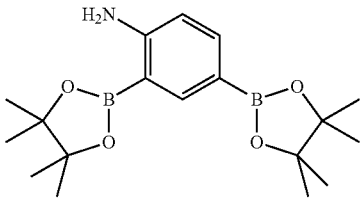

4-(4,4,5,5-Tetramethyl-1,3,2-dioxaborolan-2-yl)aniline (250.0 mg, 1.14 mmol) was dissolved in THF (1.1 mL) in a microwawe vial then 4,4,5,5-tetramethyl-1,3,2-dioxaborolane (0.36 mL, 2.51 mmol) was added. The reaction vessel was degassed for 10 minutes with N$_2$ and then stirred at room temperature for 1 hour. 3,4,7,8-Tetramethyl-1,10-phenanthroline (8.09 mg, 0.030 mmol) and (1Z,5Z)-cycloocta-1,5-diene iridium methyloxonium (11.41 mg, 0.020 mmol) were added and the reaction vessel was sealed and heated at 80° C. for 16 h. The reaction mixture was allowed to return to room temperature and then it was exposed to air, diluted with methanol and concentrated under reduced pressure. The residue was purified by column chromatography (KP silica gel, SNAP 50) eluting with a gradient of EtOAc in cyclohexane from 5% to 45% to give 2,4-bis(4,4,5,5-tetramethyl-1,3,2-dioxaborolan-2-yl)aniline (290 mg, 0.840 mmol, 73.65% yield) as a white solid. $^1$H NMR (400 MHz, DMSO-$d_6$) δ 1.25 (s, 12H), 1.30 (s, 12H), 5.85 (s, 2H), 6.55 (d, J=8.24 Hz, 1H), 7.41 (dd, J=8.22, 1.72 Hz, 1H), 7.80 (d, J=1.76 Hz, 1H). LC-MS (Method A): r.t. 1.36 min, MS (ESI) m/z=346 [M+H]$^+$.

Intermediate 61: N-[2,4-bis(4,4,5,5-tetramethyl-1,3,2-dioxaborolan-2-yl)phenyl]-2-chlorobenzamide

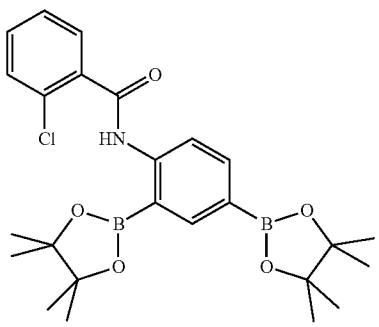 [SMILES: CC1(C)OB(c2ccc(NC(=O)c3ccccc3Cl)c(B3OC(C)(C)C(C)(C)O3)c2)OC1(C)C]

2-Chlorobenzoyl chloride (0.08 mL, 0.550 mmol) was added dropwise to a mixture of 2,4-bis(4,4,5,5-tetramethyl-1,3,2-dioxaborolan-2-yl)aniline (190.0 mg, 0.550 mmol) and triethylamine (0.08 mL, 0.610 mmol) in DCM (2.85 mL). The resulting mixture was stirred at room temperature overnight. After addition of water and dichloromethane the phases were separated. The aqueous phase was extracted further with dichloromethane. The combined organic phases were washed with water, a saturated solution of NaHCO$_3$ and brine, dried over sodium sulfate, filtered and concentrated under reduced pressure to give N-[2,4-bis(4,4,5,5-tetramethyl-1,3,2-dioxaborolan-2-yl)phenyl]-2-chlorobenzamide (260 mg, 0.538 mmol, 97.64% yield) as a white solid. LC-MS (Method A): r.t. 1.54 min, MS (ESI) m/z=484.6 [M+H]⁺.

Intermediate 62: [4-[(2-chlorobenzoyl)amino]-3-[1-[(2,4-dimethoxyphenyl)methylamino]phthalazin-6-yl]phenyl]boronic Acid

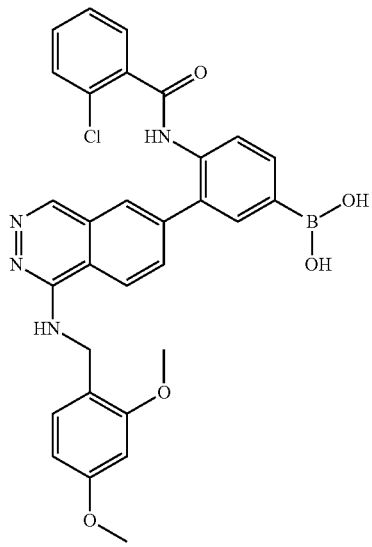 [SMILES: COc1ccc(CNc2nncc3cc(-c4cc(B(O)O)ccc4NC(=O)c4ccccc4Cl)ccc23)c(OC)c1]

A mixture of cesium carbonate (471.62 mg, 1.45 mmol), N-[2,4-bis(4,4,5,5-tetramethyl-1,3,2-dioxaborolan-2-yl)phenyl]-2-chlorobenzamide (350 mg, 724 mmol) and 6-bromo-N-[(2,4-dimethoxyphenyl)methyl]phthalazin-1-amine (135.42 mg, 0.360 mmol) in 1,4-dioxane (5.868 mL) was degassed for 10 minutes with N₂. Then [1,1'-bis(di-tert-butylphosphino)ferrocene]dichloropalladium(II) (47.32 mg, 0.070 mmol) was added and the resulting reaction mixture was stirred at room temperature for 1 hour then filtered over Celite, washing with EtOAc. The filtrate was concentrated under reduced pressure and the residue was purified by column chromatography (KP-C18-HS, 60 g) eluting with a gradient of CH₃CN in water (+0.1% of HCOOH) from 1% to 60%. Fractions containing the desired compound were collected and evaporated. The residue was taken up with EtOAc and the organic phase was washed with a saturated solution of NaHCO₃ and brine, dried over sodium sulfate, filtered and concentrated under reduced pressure to give [4-[(2-chlorobenzoyl)amino]-3-[1-[(2,4-dimethoxyphenyl)methylamino]phthalazin-6-yl]phenyl]boronic acid (50 mg, 0.087 mmol, 12.1% yield) as an off white solid. LC-MS (Method A): r.t. 0.66 min, MS (ESI) m/z=569.8 [M+H]⁺.

Intermediate 63: 6-(5-chloro-2-fluorophenyl)-N-[(2,4-dimethoxyphenyl)methyl]-4-methylphthalazin-1-amine

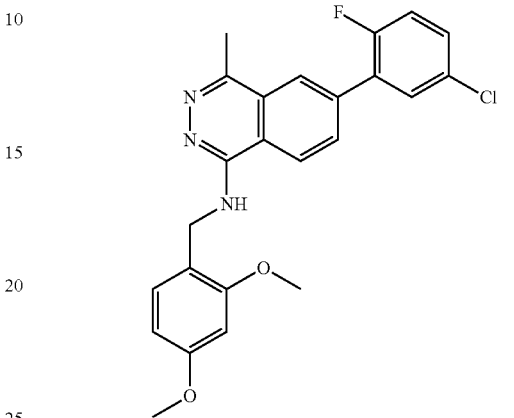

A mixture of 5-chloro-2-fluorobenzeneboronic acid (148.21 mg, 0.850 mmol) and 6-bromo-N-[(2,4-dimethoxyphenyl)methyl]-4-methylphthalazin-1-amine (300.0 mg, 0.770 mmol) in 1,2-dimethoxyethane (4 mL) and aqueous 2N sodium carbonate solution (386.34 uL, 0.770 mmol) was degassed for 10 min with N₂. Then, [1,1'-bis(di-tert-butylphosphino)ferrocene]dichloropalladium(II) (50.51 mg, 0.080 mmol) was added. The mixture was stirred at 80° C. for 5 hours, then it was cooled to room temperature and filtered over Celite, washing with MeOH. The filtrate was evaporated and the residue was purified by column chromatography (KP-NH silica gel, SNAP 55) eluting with a gradient of EtOAc in cyclohexane from 0% to 100% to give partially pure product. The mixture was purified further by column chromatography (KP-C18-HS, 30 g) eluting with a gradient of CH₃CN in water (+0.1% of HCOOH) from 2% to 95%. Fractions containing the desired compound were collected and evaporated under reduced pressure to give 6-(5-chloro-2-fluorophenyl)-N-[(2,4-dimethoxyphenyl)methyl]-4-methylphthalazin-1-amine (230 mg, 0.525 mmol, 67.98% yield) as a pale-yellow solid. ¹H NMR (400 MHz, DMSO-d₆) δ 2.73 (s, 3H), 3.73 (s, 3H), 3.85 (s, 3H), 4.67 (s, 2H), 6.43 (dd, J=8.36, 2.41 Hz, 1H), 6.59 (d, J=2.37 Hz, 1H), 7.13 (d, J=8.32 Hz, 1H), 7.47 (d, J=10.27 Hz, 1H), 7.55-7.63 (m, 1H), 7.67 (br. s, 1H), 7.87 (dd, J=6.79, 2.71 Hz, 1H), 8.07 (dt, J=8.56, 1.92 Hz, 1H), 8.15 (s, 1H), 8.48 (d, J=8.58 Hz, 1H). LC-MS (Method A): r.t. 0.83 min, MS (ESI) m/z=438.3 [M+H]⁺.

Intermediate 64: [3-[1-[(2,4-dimethoxyphenyl)methylamino]-4-methylphthalazin-6-yl]-4-fluorophenyl] boronic Acid

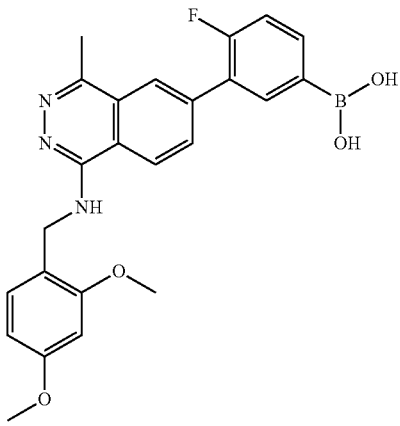 [SMILES: COc1ccc(CNc2nnc(C)c3cc(-c4cc(B(O)O)ccc4F)ccc23)c(OC)c1]

A mixture of 6-(5-chloro-2-fluorophenyl)-N-[(2,4-dimethoxyphenyl)methyl]-4-methylphthalazin-1-amine (230.0 mg, 0.530 mmol), 4,4,5,5-tetramethyl-2-(4,4,5,5-tetramethyl-1,3,2-dioxaborolan-2-yl)-1,3,2-dioxaborolane (400.14 mg, 1.58 mmol), dicyclohexyl-[2-[2,4,6-tri(propan-2-yl)phenyl]phenyl]phosphine (20.03 mg, 0.040 mmol), potassium acetate (154.64 mg, 1.58 mmol) and palladium(II) diacetate (5.9 mg, 0.030 mmol) were dissolved in 1,4-dioxane (5 mL) in a microwave vial and degassed for 10 min with $N_2$. The mixture was stirred at 75° C. for 2 hours, then it was cooled to room temperature and filtered over Celite, washing with MeOH. The filtrate was evaporated and the residue was purified by column chromatography (KP-C18-HS, 30 g) eluting with a gradient of $CH_3CN$ in water from 2% to 95%. Fractions containing the desired compound were collected and evaporated under reduced pressure to give [3-[1-[(2,4-dimethoxyphenyl)methylamino]-4-methylphthalazin-6-yl]-4-fluorophenyl]boronic acid (56 mg, 0.125 mmol, 23.84% yield) as a white vitreous solid. $^1$H NMR (400 MHz, DMSO-$d_6$) δ 2.72 (s, 3H), 3.74 (s, 3H), 3.85 (s, 3H), 4.68 (d, J=5.43 Hz, 2H), 6.44 (dd, J=8.41, 2.36 Hz, 1H), 6.59 (d, J=2.37 Hz, 1H), 7.14 (d, J=8.37 Hz, 1H), 7.32-7.40 (m, 1H), 7.64 (t, J=5.36 Hz, 1H), 7.86-7.96 (m, 1H), 8.00-8.17 (m, 3H), 8.25 (s, 2H), 8.48 (dd, J=8.65, 3.30 Hz, 1H). LC-MS (Method A): r.t. 0.69 min, MS (ESI) m/z=448.3 [M+H]$^+$.

Intermediate 65: (2-chloro-5-methoxyphenyl)methanol

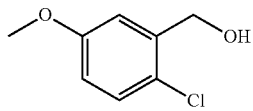

To a solution of 2-chloro-5-methoxybenzoic acid (0.5 g, 2.68 mmol) in THF (15 mL) cooled to 0° C., a 1M solution of $BH_3$ in THF (5.63 mL, 5.63 mmol) was added dropwise. The mixture was stirred at room temperature for 24 h, then cooled again to 0° C. and water (10 mL) was added dropwise, followed by saturated $NaHCO_3$ solution (25 mL). EtOAc (50 mL) was added and the layers were separated. The organic phase was evaporated to obtain (2-chloro-5-methoxyphenyl)methanol (560 mg, 3.244 mmol, 121.07% yield) as a viscous oil. This crude product was used in the next step without further purification. $^1$H NMR (400 MHz, DMSO-$d_6$) δ 3.76 (s, 3H), 4.51 (d, J=5.65 Hz, 2H), 5.39 (t, J=5.65 Hz, 1H), 6.84 (ddt, J=8.74, 3.13, 0.72 Hz, 1H), 7.10 (dt, J=3.19, 0.97 Hz, 1H), 7.29 (d, J=8.74 Hz, 1H). LC-MS (Method A): r.t. 0.81 min, MS (ESI) m/z of product not observed due to poor ionization.

Intermediate 66: (4-bromo-2-chloro-5-methoxyphenyl)methanol

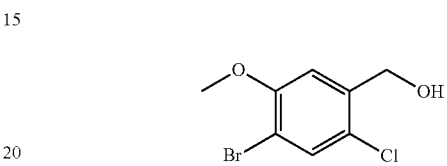

NBS (750.65 mg, 4.22 mmol) was added to a solution of (2-chloro-5-methoxyphenyl)methanol (560.0 mg, 3.24 mmol) in THF (5 mL) and the mixture was stirred at room temperature for 18 h. The mixture was diluted with EtOAc (50 mL) and washed with saturated aqueous $Na_2S_2O_3$ solution and saturated aqueous $NaHCO_3$ solution, dried over $Na_2SO_4$, filtered and the solvent was evaporated. The residue was purified by column chromatography (KP-Sil, SNAP 50 g) eluting with a gradient of EtOAc in cyclohexane from 0% to 20% to give (4-bromo-2-chloro-5-methoxyphenyl)methanol (297 mg, 1.181 mmol, 36.4% yield) as a pale yellow oil. $^1$H NMR (400 MHz, DMSO-$d_6$) δ 3.86 (s, 3H), 4.51 (d, J=5.50 Hz, 2H), 5.53 (t, J=5.50 Hz, 1H), 7.25 (s, 1H), 7.63 (s, 1H). LC-MS (Method A): r.t. 0.98 min, MS (ESI) m/z of product not observed due to poor ionization.

Intermediate 67: 2-[(4-bromo-2-chloro-5-methoxyphenyl)methoxy]oxane

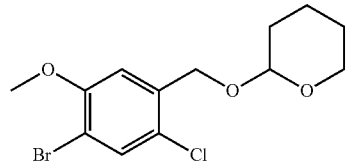 [SMILES: COc1cc(COC2CCCCO2)c(Cl)cc1Br]

To a solution of (4-bromo-2-chloro-5-methoxyphenyl)methanol (297.0 mg, 1.18 mmol) in DCM (4.455 mL) were added 3,4-dihydro-2H-pyran (0.16 mL, 1.77 mmol) and 4-methylbenzenesulfonic acid hydrate (11.23 mg, 0.060 mmol). The mixture was stirred at room temperature for 21 h, diluted with DCM (40 mL) and washed with saturated aqueous $NaHCO_3$ solution. The organic phase was dried over $Na_2SO_4$, filtered and the solvent was evaporated. The residue was purified by column chromatography (KP-Sil, SNAP 25 g) eluting with a gradient of EtOAc in cyclohexane from 0% to 20% to give 2-[(4-bromo-2-chloro-5-methoxyphenyl)methoxy]oxane (227 mg, 0.676 mmol, 57.27% yield) as an oil. NMR analysis showed the product contains some impurities. This mixture was used in the next step without further purification. $^1$H NMR (400 MHz, DMSO-$d_6$) δ 1.41-1.82 (m, 6H), 3.46-3.54 (m, 1H), 3.76-3.84 (m, 1H), 3.87 (s, 3H), 4.49 (d, J=13.00 Hz, 1H), 4.68

(d, J=13.00 Hz, 1H), 4.72-4.76 (m, 1H), 7.21 (s, 1H), 7.69 (s, 1H). LC-MS (Method A): r.t. 1.37 min, MS (ESI) m/z of product not observed due to poor ionization.

Intermediate 68: 6-[5-chloro-2-methoxy-4-(oxan-2-yloxymethyl)phenyl]-N-[(2,4-dimethoxyphenyl)methyl]-4-methylphthalazin-1-amine

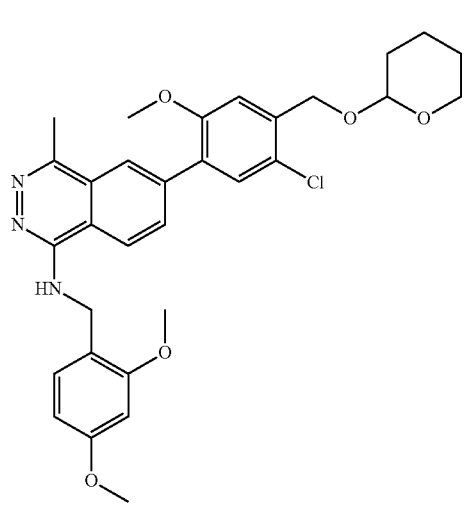 [SMILES: COc1ccc(CNc2nnc(C)c3cc(-c4cc(Cl)c(COC5CCCCO5)cc4OC)ccc23)c(OC)c1]

A mixture of 2-[(4-bromo-2-chloro-5-methoxyphenyl)methoxy]oxane (223.32 mg, 0.670 mmol), [1-[(2,4-dimethoxyphenyl)methylamino]-4-methylphthalazin-6-yl]boronic acid (235.0 mg, 0.670 mmol) and aqueous 2N sodium carbonate solution (332.69 uL, 0.670 mmol) in 1,2-dimethoxyethane (9.4 mL) was degassed for 10 min. Then [1,1'-bis(di-tert-butylphosphino)ferrocene]dichloropalladium(II) (43.5 mg, 0.070 mmol) was added and the resulting reaction mixture was stirred at 85° C. for 6 hours. The mixture was filtered over Celite, washing with EtOAc and the filtrate was concentrated in vacuo. The residue was purified by column chromatography (KP-NH silica gel, SNAP 28 g) eluting with a gradient of DCM/EtOAc (1:1) in cyclohexane from 0% to 100% to give 6-[5-chloro-2-methoxy-4-(oxan-2-yloxymethyl)phenyl]-N-[(2,4-dimethoxyphenyl)methyl]-4-methylphthalazin-1-amine (253 mg, 0.449 mmol, 67.41% yield) as a viscous oil. $^1$H NMR (400 MHz, DMSO-$d_6$) δ 1.45-1.88 (m, 6H), 2.69 (s, 3H), 3.50-3.58 (m, 1H), 3.72 (s, 3H), 3.84 (s, 3H), 3.84 (s, 3H), 3.85-3.89 (m, 1H), 4.60 (d, J=12.97 Hz, 1H), 4.67 (d, J=5.58 Hz, 2H), 4.76-4.84 (m, 2H), 6.42 (dd, J=8.36, 2.42 Hz, 1H), 6.58 (d, J=2.42 Hz, 1H), 7.11 (d, J=8.36 Hz, 1H), 7.31 (s, 1H), 7.50-7.71 (m, 2H), 8.00 (dd, J=8.58, 1.70 Hz, 1H), 8.04 (d, J=1.70 Hz, 1H), 8.38 (d, J=8.58 Hz, 1H). LC-MS (Method A): r.t. 0.95 min, MS (ESI) m/z=564.4 [M+H]$^+$.

Intermediate 69: N-[(2,4-dimethoxyphenyl)methyl]-6-[2-methoxy-4-(oxan-2-yloxymethyl)-5-(4,4,5,5-tetramethyl-1,3,2-dioxaborolan-2-yl)phenyl]-4-methylphthalazin-1-amine

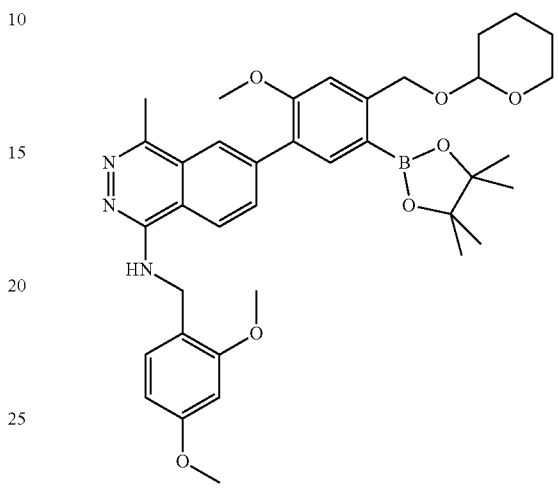

Palladium(II) diacetate (4.98 mg, 0.020 mmol), 6-[5-chloro-2-methoxy-4-(oxan-2-yloxymethyl)phenyl]-N-[(2,4-dimethoxyphenyl)methyl]-4-methylphthalazin-1-amine (250.0 mg, 0.440 mmol), dicyclohexyl-[2-[2,4,6-tri(propan-2-yl)phenyl]phenyl]phosphine (16.9 mg, 0.040 mmol), potassium acetate (130.49 mg, 1.33 mmol) and 4,4,5,5-tetramethyl-2-(4,4,5,5-tetramethyl-1,3,2-dioxaborolan-2-yl)-1,3,2-dioxaborolane (337.64 mg, 1.33 mmol) were dissolved in 1,4-dioxane (13.6 mL). The mixture was degassed with Ar for 10 min, then stirred at 80° C. for 9 hours. The mixture was filtered over a pad of Celite, washing with EtOAc and the filtrate was concentrated in vacuo. The residue was purified by column chromatography (KP-C18-HS, SNAP 30 g) eluting with a gradient of CH$_3$CN in water from 1% to 95% to give N-[(2,4-dimethoxyphenyl)methyl]-6-[2-methoxy-4-(oxan-2-yloxymethyl)-5-(4,4,5,5-tetramethyl-1,3,2-dioxaborolan-2-yl)phenyl]-4-methylphthalazin-1-amine (133 mg, 0.203 mmol, 45.77% yield) as a pale yellow solid. $^1$H NMR (400 MHz, DMSO-$d_6$) δ 1.28 (s, 12H), 1.41-1.89 (m, 6H), 2.67 (s, 3H), 3.38 (s, 3H), 3.46-3.55 (m, 1H), 3.72 (s, 3H), 3.84 (s, 3H), 3.81-3.89 (m, 1H), 4.66 (d, J=5.56 Hz, 2H), 4.73-4.81 (m, 2H), 4.88 (d, J=12.36 Hz, 1H), 6.42 (dd, J=8.38, 2.39 Hz, 1H), 6.57 (d, J=2.39 Hz, 1H), 7.11 (d, J=8.38 Hz, 1H), 7.25 (s, 1H), 7.56 (t, J=5.78 Hz, 1H), 7.65 (s, 1H), 7.91 (dd, J=8.60, 1.72 Hz, 1H), 7.96 (d, J=1.72 Hz, 1H), 8.37 (d, J=8.60 Hz, 1H). LC-MS (Method A): r.t. 1.03 min, MS (ESI) m/z=656.4 [M+H]$^+$.

Intermediate 70: 6-(5-chloro-2-methoxyphenyl)-N-[(2,4-dimethoxyphenyl)methyl]-3-methylisoquinolin-1-amine

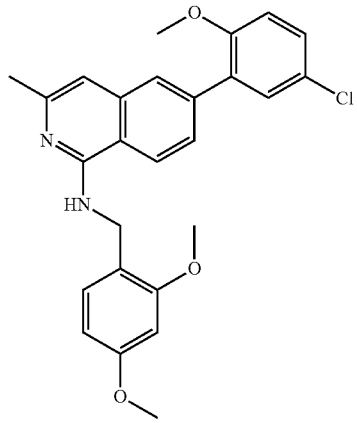 [SMILES: COc1ccc(CNc2nc(C)cc3cc(-c4cc(Cl)ccc4OC)ccc23)c(OC)c1]

A mixture of 6-bromo-N-[(2,4-dimethoxyphenyl) methyl]-3-methylisoquinolin-1-amine (405.0 mg, 1.04 mmol) and 5-chloro-2-methoxyphenylboronic acid (192.98 mg, 1.04 mmol) in 1,2-dimethoxyethane (6.739 mL) and aqueous 2N sodium carbonate solution (0.518 mL) was degassed for 10 min, then [1,1'-bis(di-tert-butylphosphino) ferrocene]dichloropalladium(II) (67.69 mg, 0.100 mmol) was added. The mixture was degassed for 10 min and then stirred at 70° C. for 90 min. The mixture was left to reach room temperature, then it was diluted with EtOAc and filtered. The volatiles were removed and the residue was purified by column chromatography (KP-Sil silica gel, 2×SNAP 25 in series) eluting with a gradient of EtOAc in cyclohexane from 5% to 35% to give 6-(5-chloro-2-methoxyphenyl)-N-[(2,4-dimethoxyphenyl)methyl]-3-methylisoquinolin-1-amine (224 mg, 0.499 mmol, 48.19% yield) as a yellowish foam. $^1$H NMR (400 MHz, DMSO-$d_6$) δ 2.32 (s, 3H), 3.73 (s, 3H), 3.80 (s, 3H), 3.85 (s, 3H), 4.66 (d, J=5.50 Hz, 2H), 6.44 (dd, J=8.36, 2.42 Hz, 1H), 6.57 (d, J=2.42 Hz, 1H), 6.75 (s, 1H), 7.14-7.21 (m, 2H), 7.41-7.47 (m, 2H), 7.50 (dd, J=8.58, 1.76 Hz, 1H), 7.57 (t, J=5.72 Hz, 1H), 7.68 (d, J=1.76 Hz, 1H), 8.27 (d, J=9.02 Hz, 1H). LC-MS (Method A): r.t. 0.90 min, MS (ESI) m/z=449.31 [M+H]$^+$.

Intermediate 71: N-[(2,4-dimethoxyphenyl)methyl]-6-[2-methoxy-5-(4,4,5,5-tetramethyl-1,3,2-dioxaborolan-2-yl)phenyl]-3-methylisoquinolin-1-amine

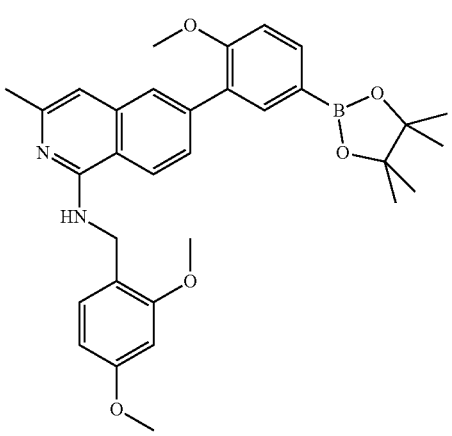

A mixture of potassium acetate (144.28 mg, 1.47 mmol), 4,4,5,5-tetramethyl-2-(4,4,5,5-tetramethyl-1,3,2-dioxaborolan-2-yl)-1,3,2-dioxaborolane (373.32 mg, 1.47 mmol) and 6-(5-chloro-2-methoxyphenyl)-N-[(2,4-dimethoxyphenyl) methyl]-3-methylisoquinolin-1-amine (220.0 mg, 0.490 mmol) in 1,4-dioxane (4.125 mL) was degassed for 10 min. Dicyclohexyl-[2-[2,4,6-tri(propan-2-yl)phenyl]phenyl] phosphine (18.69 mg, 0.040 mmol) and palladium(II) diacetate (5.5 mg, 0.020 mmol) were added and the reaction was stirred at 70° C. for 1.5 h, then it was left to reach room temperature. EtOAc was added and the mixture was filtered, then the volatiles were evaporated. The residue was purified by column chromatography (KP-C18-HS, 30) eluting with a gradient of MeCN in water from 2% to 100% to give N-[(2,4-dimethoxyphenyl)methyl]-6-[2-methoxy-5-(4,4,5,5-tetramethyl-1,3,2-dioxaborolan-2-yl)phenyl]-3-methylisoquinolin-1-amine (159 mg, 0.294 mmol, 60.03% yield) as a white solid. $^1$H NMR (400 MHz, DMSO-$d_6$) δ 1.30 (s, 12H), 2.32 (s, 3H), 3.74 (s, 3H), 3.82 (s, 3H), 3.85 (s, 3H), 4.66 (d, J=5.72 Hz, 2H), 6.45 (dd, J=8.36, 2.42 Hz, 1H), 6.57 (d, J=2.42 Hz, 1H), 6.78 (s, 1H), 7.15-7.20 (m, 2H), 7.47 (dd, J=8.58, 1.76 Hz, 1H), 7.54 (t, J=5.72 Hz, 1H), 7.61-7.65 (m 2H), 7.72 (dd, J=8.14, 1.76 Hz, 1H), 8.25 (d, J=8.58 Hz, 1H). LC-MS (Method A): r.t. 0.99 min, MS (ESI) m/z=541.5 [M+H]$^+$.

Intermediate 72: 6-(4-chloropyrazol-1-yl)-N-[(2,4-dimethoxyphenyl)methyl]-4-methylphthalazin-1-amine

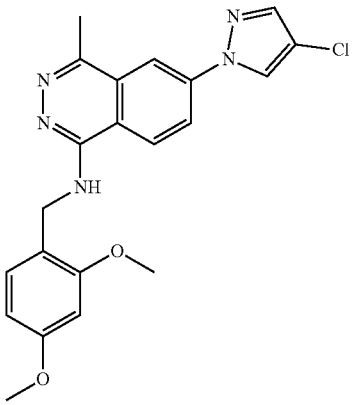 [SMILES: COc1ccc(CNc2nnc(C)c3cc(-n4cc(Cl)cn4)ccc23)c(OC)c1]

A mixture of 6-bromo-N-[(2,4-dimethoxyphenyl) methyl]-4-methylphthalazin-1-amine (200.0 mg, 0.490 mmol), 4-chloro-1H-pyrazole (75.25 mg, 0.730 mmol), (1R, 2R)-cyclohexane-1,2-diamine (23.5 uL, 0.200 mmol), copper (I) iodide (18.64 mg, 0.100 mmol) and potassium carbonate (135.27 mg, 0.980 mmol) were dissolved in DMSO (12 mL) in a microwave vial. The mixture was heated under microwave irradiation at 160° C. for 1.5 hours in a microwave reactor, then it was cooled to room temperature, water was added and the precipitate was filtered on a Hirsch funnel. The collected solid was purified by column chromatography (KP-NH silica gel, SNAP 55) eluting with a gradient of EtOAc in cyclohexane from 2% to 90% to give 6-(4-chloropyrazol-1-yl)-N-[(2,4-dimethoxyphenyl) methyl]-4-methylphthalazin-1-amine (110 mg, 0.268 mmol, 54.84% yield) as a yellow powder. $^1$H NMR (400 MHz, DMSO-$d_6$) δ 2.72 (s, 3H), 3.73 (s, 3H), 3.84 (s, 3H), 4.66 (d, J=5.40 Hz, 2H), 6.43 (dd, J=8.36, 2.40 Hz, 1H), 6.58 (d, J=2.38 Hz, 1H), 7.14 (d, J=8.33 Hz, 1H), 7.64 (t, J=5.69 Hz, 1H), 8.02 (d, J=0.62 Hz, 1H), 8.29 (d, J=2.26 Hz, 1H), 8.36 (dd, J=8.98, 2.27 Hz, 1H), 8.54 (d, J=9.01 Hz, 1H), 9.14 (d, J=0.69 Hz, 1H). LC-MS (Method A): r.t. 0.74 min, MS (ESI) m/z=410.3 [M+H]$^+$.

Intermediate 73: [1-[1-[(2,4-dimethoxyphenyl)methylamino]-4-methylphthalazin-6-yl]pyrazol-4-yl]boronic Acid

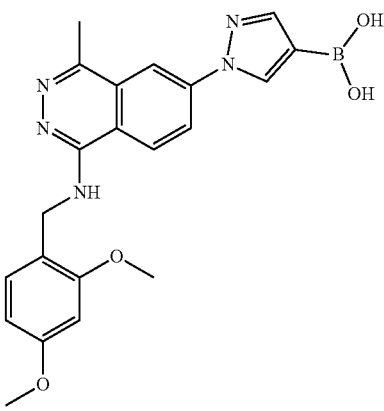 [SMILES: COc1ccc(CNc2nnc(C)c3cc(-n4cc(B(O)O)cn4)ccc23)c(OC)c1]

A mixture of 6-(4-chloropyrazol-1-yl)-N-[(2,4-dimethoxyphenyl)methyl]-4-methylphthalazin-1-amine (110.0 mg, 0.270 mmol), 4,4,5,5-tetramethyl-2-(4,4,5,5-tetramethyl-1,3,2-dioxaborolan-2-yl)-1,3,2-dioxaborolane (204.46 mg, 0.810 mmol), dicyclohexyl-[2-[2,4,6-tri(propan-2-yl)phenyl]phenyl]phosphine (10.24 mg, 0.020 mmol), potassium acetate (79.02 mg, 0.810 mmol) and palladium(II) diacetate (3.01 mg, 0.010 mmol) were dissolved in 1,4-dioxane (3 mL) in a microwave vial and degassed for 10 min with N$_2$. The mixture was stirred at 75° C. for 2 hours, then it was cooled to room temperature and filtered over Celite, washing with MeOH. The filtrate was evaporated and the residue was purified by column chromatography (KP-C18-HS, 30 g) eluting with a gradient of CH$_3$CN in water from 2% to 95%. Fractions containing the desired compound were collected and evaporated under reduced pressure to give [1-[1-[(2,4-dimethoxyphenyl)methylamino]-4-methylphthalazin-6-yl]pyrazol-4-yl]boronic acid (56 mg, 0.134 mmol, 49.77% yield) as a pale-yellow solid containing ~10% of N-[(2,4-dimethoxyphenyl)methyl]-4-methyl-6-(1H-pyrazol-1-yl)phthalazin-1-amine. $^1$H NMR (400 MHz, DMSO-d$_6$) δ 2.83 (s, 3H), 3.78 (s, 3H), 3.81 (s, 3H), 4.67 (d, J=5.14 Hz, 2H), 6.53 (dd, J=8.36, 2.38 Hz, 1H), 6.65 (d, J=2.36 Hz, 1H), 7.25 (d, J=8.36 Hz, 1H), 8.13 (s, 1H), 8.56 (d, J=2.24 Hz, 1H), 8.66 (dd, J=9.11, 2.16 Hz, 1H), 8.87 (d, J=9.08 Hz, 1H), 9.02 (s, 1H). LC-MS (Method A): r.t. 0.57 min, MS (ESI) m/z=420.4 [M+H]$^+$.

Intermediate 74: tert-butyl N-[2-[2-[2-(2-bromo-4-chlorophenoxy)ethoxy]ethoxy]ethyl]carbamate

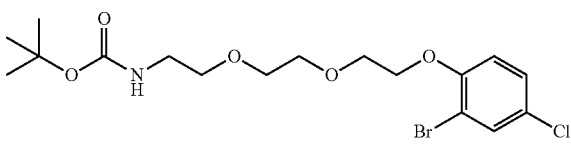 [SMILES: CC(C)(C)OC(=O)NCCOCCOCCOc1ccc(Cl)cc1Br]

(NE)-N-Ethoxycarbonyliminocarbamic acid ethyl ester (0.57 mL, 3.62 mmol) was added to a solution of 2-bromo-4-chlorophenol (750.0 mg, 3.62 mmol), tert-butyl (2-(2-(2-hydroxyethoxy)ethoxy)ethyl)carbamate (901.3 mg, 3.62 mmol) and triphenylphosphine (1043.09 mg, 3.98 mmol) in THF (8.001 mL) at 0° C. The resulting mixture was stirred for 4 hours at room temperature then it was diluted with EtOAc. The organic phase was washed with water and brine, dried over sodium sulfate, filtered and concentrated under reduced pressure. The residue was purified by column chromatography (KP-C18-HS, 120 g) eluting with a gradient of CH$_3$CN in water (+0.1% of HCOOH) from 5% to 80%. Fractions containing the desired compound were collected and lyophilised to give tert-butyl N-[2-[2-[2-(2-bromo-4-chlorophenoxy)ethoxy]ethoxy]ethyl]carbamate (1.306 g, 2.977 mmol, 82.34% yield) as a white solid. $^1$H NMR (400 MHz, Chloroform-d) δ 1.46 (s, 9H), 3.34 (q, J=5.31 Hz, 2H), 3.57 (t, J=5.17 Hz, 2H), 3.63-3.70 (m, 2H), 3.76-3.82 (m, 2H), 3.89-3.96 (m, 2H), 4.19 (dd, J=5.44, 4.21 Hz, 2H), 5.00 (s, 1H), 6.87 (d, J=8.80 Hz, 1H), 7.24 (dd, J=8.78, 2.54 Hz, 1H), 7.55 (d, J=2.54 Hz, 1H). LC-MS (Method A): r.t. 1.28 min, MS (ESI) m/z=438.2 and 440.2 [M+H]$^+$.

Intermediate 75: tert-butyl N-[2-[2-[2-(2-bromo-4-chlorophenoxy)ethoxy]ethoxy]ethyl]carbamate

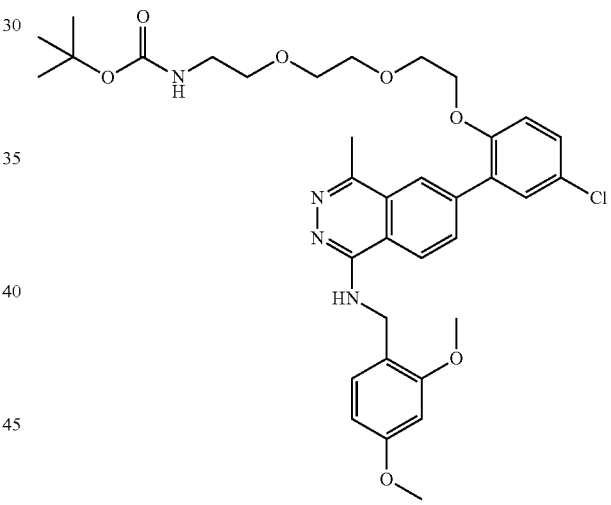

A mixture of tert-butyl N-[2-[2-[2-(2-bromo-4-chlorophenoxy)ethoxy]ethoxy]ethyl]carbamate (329.45 mg, 0.750 mmol), and [1-[(2,4-dimethoxyphenyl)methylamino]-4-methylphthalazin-6-yl]boronic acid (240.0 mg, 0.580 mmol) in 1,2-dimethoxyethane (4 mL) and aqueous 2N sodium carbonate solution (580 uL, 1.17 mmol) was degassed for 10 minutes with N$_2$. Then [1,1'-bis(di-tert-butylphosphino)ferrocene]dichloropalladium(II) (38.14 mg, 0.060 mmol) was added and the resulting reaction mixture was stirred at 70° C. for 2 hours. It was then cooled to room temperature and filtered over Celite, washing with EtOAc. The filtrate was evaporated and the residue was purified by column chromatography (KP-NH silica gel, SNAP 55) eluting with a gradient of MeOH in dichloromethane from 1% to 10% to give tert-butyl N-[2-[2-[2-[4-chloro-2-[1-[(2,4-dimethoxyphenyl)methylamino]-4-methylphthalazin-6-yl]phenoxy] ethoxy]ethoxy]ethyl]carbamate (322 mg, 0.483 mmol, 83.55% yield) as a yellow solid. $^1$H NMR (400 MHz, DMSO-$d_6$) δ 1.34 (s, 9H), 2.71 (s, 3H), 2.99 (q, J=5.99 Hz, 2H), 3.26-3.31 (m, 2H), 3.41-3.46 (m, 2H), 3.47-3.53 (m, 2H), 3.67-3.73 (m, 2H), 3.73 (s, 3H), 3.85 (s, 3H), 4.15-4.22 (m, 2H), 4.67 (d, J=5.66 Hz, 2H), 6.43 (dd, J=8.36, 2.42 Hz, 1H), 6.58 (d, J=2.42 Hz, 1H), 6.69 (t, J=5.47 Hz, 1H), 7.12 (d, J=8.34 Hz, 1H), 7.24 (d, J=8.90 Hz, 1H), 7.47 (dd, J=8.82, 2.68 Hz, 1H), 7.57-7.62 (m, 2H), 8.08 (dd, J=8.58, 1.76 Hz, 1H), 8.14 (d, J=1.72 Hz, 1H), 8.39 (d, J=8.58 Hz, 1H). LC-MS (Method A): r.t. 0.93 min, MS (ESI) m/z=668.1 [M+H]$^+$.

Intermediate 76: [3-[1-[(2,4-dimethoxyphenyl)methylamino]-4-methylphthalazin-6-yl]-4-[2-[2-[2-[(2-methylpropan-2-yl)oxycarbonylamino]ethoxy]ethoxy]ethoxy]phenyl]boronic Acid

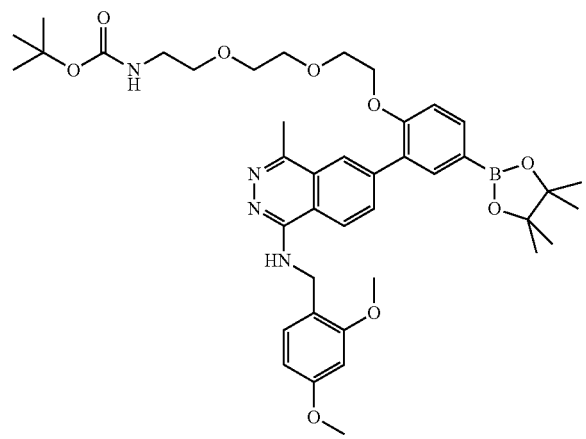 [SMILES: COc1ccc(CNc2nnc(C)c3cc(-c4cc(B5OC(C)(C)C(C)(C)O5)ccc4OCCOCCOCCNC(=O)OC(C)(C)C)ccc23)c(OC)c1]

Palladium(II) diacetate (2.93 mg, 0.010 mmol), tert-butyl N-[2-[2-[2-[4-chloro-2-[1-[(2,4-dimethoxyphenyl)methylamino]-4-methylphthalazin-6-yl]phenoxy]ethoxy]ethoxy]ethyl]carbamate (185.0 mg, 0.260 mmol), dicyclohexyl-[2-[2,4,6-tri(propan-2-yl)phenyl]phenyl]phosphine (12.43 mg, 0.030 mmol), potassium acetate (76.74 mg, 0.780 mmol) and 4,4,5,5-tetramethyl-2-(4,4,5,5-tetramethyl-1,3,2-dioxaborolan-2-yl)-1,3,2-dioxaborolane (198.56 mg, 0.780 mmol) were dissolved in 1,4-dioxane (2.6 mL) in a microwave vial. The resulting mixture was degassed for 10 minutes under $N_2$ and then stirred at 75° C. for 2 hours. It was then cooled to room temperature and filtered over Celite, washing with EtOAc. The filtrate was evaporated and the residue was combined with a similar residue obtained from a separate reaction performed with the same procedure but starting from 100 mg of tert-butyl N-[2-[2-[2-[4-chloro-2-[1-[(2,4-dimethoxyphenyl)methylamino]-4-methylphthalazin-6-yl]phenoxy]ethoxy]ethoxy]ethyl]carbamate. The combined residues were purified by column chromatography (KP-C18-HS, 30 g) eluting with a gradient of $CH_3CN$ in water (+0.1% of HCOOH) from 1% to 80%. Fractions containing the desired compound were collected and evaporated under reduced pressure to give tert-butyl N-[2-[2-[2-[2-[1-[(2,4-dimethoxyphenyl)methylamino]-4-methylphthalazin-6-yl]-4-(4,4,5,5-tetramethyl-1,3,2-dioxaborolan-2-yl)phenoxy]ethoxy]ethoxy]ethyl]carbamate (184 mg, 0.243 mmol, 59.3% yield) as a colourless oil. $^1$H NMR (400 MHz, DMSO-$d_6$) δ 1.31 (s, 12H), 1.34 (s, 9H), 2.70 (s, 3H), 2.99 (q, J=6.21 Hz, 2H), 3.27-3.31 (m, 2H), 3.39-3.47 (m, 2H), 3.47-3.57 (m, 2H), 3.68-3.75 (m, 5H), 3.85 (s, 3H), 4.14-4.25 (m, 2H), 4.67 (d, J=5.38 Hz, 2H), 6.43 (dd, J=8.36, 2.39 Hz, 1H), 6.58 (d, J=2.39 Hz, 1H), 6.68 (t, J=5.74 Hz, 1H), 7.13 (d, J=8.36 Hz, 1H), 7.22 (d, J=8.30 Hz, 1H), 7.57 (t, J=5.66 Hz, 1H), 7.70 (d, J=1.66 Hz, 1H), 7.74 (dd, J=8.24, 1.67 Hz, 1H), 8.01 (dd, J=8.56, 1.73 Hz, 1H), 8.09 (d, J=1.74 Hz, 1H), 8.38 (d, J=8.62 Hz, 1H). LC-MS (Method A): r.t. 1.00 min, MS (ESI) m/z=759.71 [M+H]$^+$.

Intermediate 77: 6-[2-[2-[2-(2-aminoethoxy)ethoxy]ethoxy]-5-(4,4,5,5-tetramethyl-1,3,2-dioxaborolan-2-yl)phenyl]-4-methylphthalazin-1-amine trifluoroacetic Acid Salt

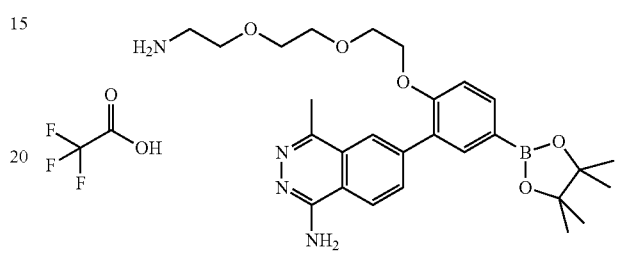

A solution of tert-butyl N-[2-[2-[2-[2-[1-[(2,4-dimethoxyphenyl)methylamino]-4-methylphthalazin-6-yl]-4-(4,4,5,5-tetramethyl-1,3,2-dioxaborolan-2-yl)phenoxy]ethoxy]ethoxy]ethyl]carbamate (184.0 mg, 0.240 mmol) in DCM (2.5 mL) and trifluoroacetic acid (2.5 mL) was stirred at room temperature for 1 hour then it was concentrated under reduced pressure. The pale-pink residue was dissolved in dichloromethane/methanol (4:1) and filtered over a pad of Celite. The organic phase was concentrated under reduced pressure to give 6-[2-[2-[2-(2-aminoethoxy)ethoxy]ethoxy]-5-(4,4,5,5-tetramethyl-1,3,2-dioxaborolan-2-yl)phenyl]-4-methylphthalazin-1-amine trifluoroacetic acid salt (184 mg, 0.296 mmol, 121.89% yield) as a colourless oil. $^1$H NMR (400 MHz, DMSO-$d_6$) δ 1.31 (s, 12H), 2.75 (s, 3H), 2.93 (m, J=5.74 Hz, 2H), 3.50-3.60 (m, 6H), 3.74 (m, J=5.75 Hz, 2H), 4.26 (dd, J=5.64, 3.67 Hz, 2H), 7.27 (d, J=8.42 Hz, 1H), 7.72 (br. s, 2H), 7.77 (d, J=1.64 Hz, 1H), 7.80 (dd, J=8.30, 1.69 Hz, 1H), 8.31 (d, J=8.37 Hz, 1H), 8.38 (s, 1H), 8.68 (d, J=8.55 Hz, 1H), 9.16 (s, 2H). LC-MS (Method A): r.t. 0.56 min, MS (ESI) m/z=623.4 [M+H]$^+$.

Intermediate 78: 5-[(3aS,4S,6aR)-2-oxo-hexahydro-1H-thieno[3,4-d]imidazol-4-yl]-N-[2-(2-{2-[2-(1-amino-4-methylphthalazin-6-yl)-4-(4,4,5,5-tetramethyl-1,3,2-dioxaborolan-2-yl)phenoxy]ethoxy}ethoxy)ethyl]pentanamide

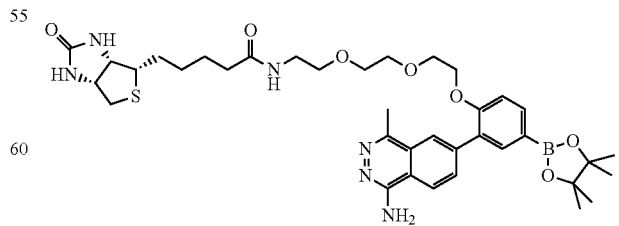

To a solution of 6-[2-[2-[2-(2-aminoethoxy)ethoxy]ethoxy]-5-(4,4,5,5-tetramethyl-1,3,2-dioxaborolan-2-yl)phenyl]-4-methylphthalazin-1-amine trifluoroacetic acid salt (50.0 mg, 0.100 mmol) and triethylamine (20.56 uL, 0.150 mmol) in DMF (1.104 mL), biotin-OSu (33.57 mg, 0.100 mmol) was added. The resulting mixture was stirred at room temperature for 1 hour. Water and dichloromethane were added and the phases were separated. The aqueous phase was extracted further with dichloromethane. The combined organic phases were washed with water and brine, dried over sodium sulfate, filtered and concentrated in vacuum to give 5-[(3aS,4S,6aR)-2-oxo-hexahydro-1H-thieno[3,4-d]imidazol-4-yl]-N-[2-(2-{2-[2-(1-amino-4-methylphthalazin-6-yl)-4-(4,4,5,5-tetramethyl-1,3,2-dioxaborolan-2-yl)phenoxy]ethoxy}ethoxy)ethyl]pentanamide (65 mg, 0.088 mmol, 89.96% yield) as a yellow vitreous oil. LC-MS (Method A): r.t. 0.74 min, MS (ESI) m/z=735.7 [M+H]$^+$.

Intermediate 79: 6-(5-chloro-4-fluoro-2-methoxyphenyl)-N-[(2,4-dimethoxyphenyl)methyl]-4-methylphthalazin-1-amine

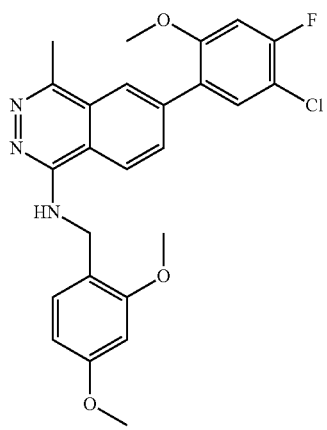 [SMILES: COc1ccc(CNc2nnc(C)c3cc(-c4cc(Cl)c(F)cc4OC)ccc23)c(OC)c1]

A mixture of (5-chloro-4-fluoro-2-methoxyphenyl)boronic acid (210.57 mg, 1.03 mmol), 6-bromo-N-[(2,4-dimethoxyphenyl)methyl]-4-methylphthalazin-1-amine (400.0 mg, 1.03 mmol) and [1,1'-bis(di-tert-butylphosphino)ferrocene]dichloropalladium(II) (67.35 mg, 0.100 mmol) in 1,2-dimethoxyethane (8 mL) and aqueous 2N sodium carbonate solution (1.03 mL, 2.06 mmol) was degassed for 10 min with Ar. The mixture was stirred at 85° C. for 1 hour, then cooled to room temperature and filtered over Celite, washing with EtOAc. The solvent was evaporated and the residue was purified by column chromatography (KP-NH silica gel SNAP 55 g) eluting with a gradient of EtOAc in cyclohexane from 0% to 100% giving 6-(5-chloro-4-fluoro-2-methoxyphenyl)-N-[(2,4-dimethoxyphenyl)methyl]-4-methylphthalazin-1-amine (315 mg, 0.673 mmol, 65.34% yield) as a yellow oil. $^1$H NMR (400 MHz, DMSO-d$_6$) δ 2.69 (s, 3H), 3.72 (s, 3H), 3.84 (s, 6H), 4.66 (d, J=5.54 Hz, 2H), 6.42 (dd, J=8.32, 2.39 Hz, 1H), 6.57 (d, J=2.39 Hz, 1H), 7.11 (d, J=8.32 Hz, 1H), 7.35 (d, J=11.65 Hz, 1H), 7.58 (t, J=5.75 Hz, 1H), 7.72 (d, J=8.58 Hz, 1H), 7.97 (dd, J=8.58, 1.70 Hz, 1H), 8.02 (d, J=1.68 Hz, 1H), 8.38 (d, J=8.58 Hz, 1H). LC-MS (Method A): r.t. 0.87 min, MS (ESI) m/z=468.4 [M+H]$^+$.

Intermediate 80: [5-[1-[(2,4-dimethoxyphenyl)methylamino]-4-methylphthalazin-6-yl]-2-fluoro-4-methoxyphenyl]boronic Acid

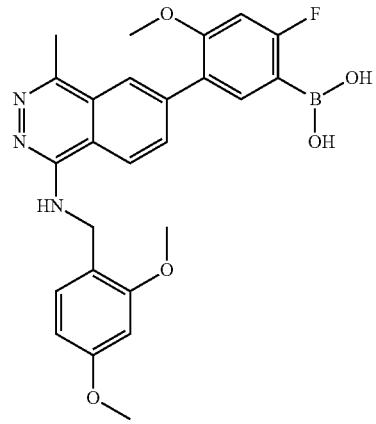 [SMILES: COc1ccc(CNc2nnc(C)c3cc(-c4cc(B(O)O)c(F)cc4OC)ccc23)c(OC)c1]

Palladium(II) diacetate (7.44 mg, 0.030 mmol), 6-(5-chloro-4-fluoro-2-methoxyphenyl)-N-[(2,4-dimethoxyphenyl)methyl]-4-methylphthalazin-1-amine (310.0 mg, 0.660 mmol), dicyclohexyl-[2-[2,4,6-tri(propan-2-yl)phenyl]phenyl]phosphine (25.27 mg, 0.050 mmol), potassium acetate (195.06 mg, 1.99 mmol) and 4,4,5,5-tetramethyl-2-(4,4,5,5-tetramethyl-1,3,2-dioxaborolan-2-yl)-1,3,2-dioxaborolane (504.71 mg, 1.99 mmol) were dissolved in 1,4-dioxane (16.85 mL). The mixture was degassed with Ar for 10 min, then stirred at 80° C. for 5 hours. The mixture was filtered over a pad of Celite, washing with EtOAc and the filtrate was concentrated in vacuo. The residue was purified by column chromatography (KP-C18-HS, SNAP 30 g), eluting with a gradient of CH$_3$CN in water from 1% to 95% to give [5-[1-[(2,4-dimethoxyphenyl)methylamino]-4-methylphthalazin-6-yl]-2-fluoro-4-methoxyphenyl]boronic acid (286 mg, 0.599 mmol, 90.45% yield) as a pale yellow solid. LC-MS (Method A): r.t. 0.63 min, MS (ESI) m/z=478.4 [M+H]$^+$.

Intermediate 81: 2-[2-(4-bromo-2-chlorophenyl)ethoxy]oxane

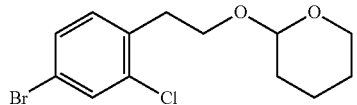 [SMILES: Clc1cc(Br)ccc1CCOC1CCCCO1]

Step 1: A 1M solution of BH$_3$ in THF (16.83 mL, 16.83 mmol) was added dropwise to a solution of 2-(4-bromo-2-chlorophenyl)acetic acid (2.0 g, 8.02 mmol) in THF (30 mL) cooled to 0° C. The mixture was stirred at room temperature for 18 h, then cooled again at 0° C. and water (25 mL) was added dropwise, followed by saturated aqueous NaHCO$_3$ solution (25 mL, dropwise). EtOAc (50 mL) was added and the layers were separated. The organic phase was washed with brine, and filtered over a short pad of silica gel, eluting with EtOAc and the volatiles were evaporated.

Step 2: The oil obtained in Step 1 was dissolved in DCM (0.038 mL) and 3,4-dihydro-2H-pyran (1.45 mL, 15.92 mmol) and 4-methylbenzenesulfonic acid hydrate (0.1 g, 0.530 mmol) were added. The mixture was stirred at room temperature for 8 h. DCM (40 mL) was added and the organics were washed with saturated aquoes NaHCO₃ solution, dried over Na₂SO₄, filtered and the solvent was evaporated. The residue was purified by column chromatography (KP-Sil, SNAP 25 g) eluting with a gradient of EtOAc in cyclohexane from 0% to 20% to give 2-[2-(4-bromo-2-chlorophenyl)ethoxy]oxane in a mixture with side-products derived from 3,4-dihydro-2H-pyran (2.5 g) as an oil. This material was used in the next step without further purification. LC-MS (Method A): r.t. 1.45 min, MS (ESI) m/z of product not observed due to poor ionization.

Intermediate 82: 6-[3-chloro-4-[2-(oxan-2-yloxy)ethyl]phenyl]-N-[(2,4-dimethoxyphenyl)methyl]-4-methylphthalazin-1-amine

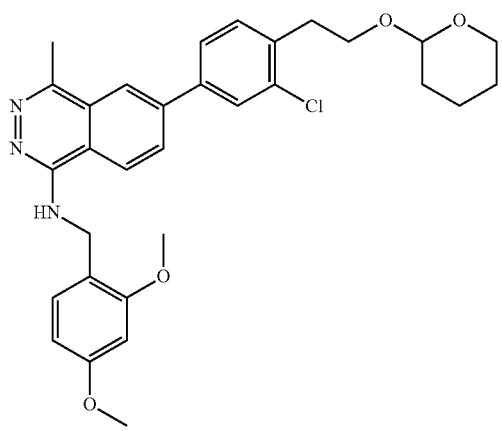 [SMILES: COc1ccc(CNc2nnc(C)c3cc(-c4ccc(CCOC5CCCCO5)c(Cl)c4)ccc23)c(OC)c1]

A mixture of 2-[2-(4-bromo-2-chlorophenyl)ethoxy]oxane (380.09 mg, 1.19 mmol), [1-[(2,4-dimethoxyphenyl)methylamino]-4-methylphthalazin-6-yl]boronic acid (350.0 mg, 0.990 mmol) and aqueous 2N sodium carbonate solution (991.0 uL, 1.98 mmol) in 1,2-dimethoxyethane (14.02 mL) was degassed with Ar for 10 min. Then [1,1'-bis(di-tert-butylphosphino)ferrocene]dichloropalladium(II) (64.79 mg, 0.100 mmol) was added and the resulting reaction mixture was stirred at 85° C. for 6 hours. The mixture was filtered over Celite, washing with EtOAc. The filtrate was concentrated in vacuo and the residue was purified by column chromatography (KP-NH silica gel, SNAP 28 g) eluting with a gradient of EtOAc in cyclohexane from 0% to 100% to give 6-[3-chloro-4-[2-(oxan-2-yloxy)ethyl]phenyl]-N-[(2,4-dimethoxyphenyl)methyl]-4-methylphthalazin-1-amine (233 mg, 0.425 mmol, 42.9% yield) as a viscous oil. LC-MS (Method A): r.t. 0.95 min, MS (ESI) m/z=548.5 [M+H]⁺.

Intermediate 83: 2 N-[(2,4-dimethoxyphenyl)methyl]-4-methyl-6-[4-[2-(oxan-2-yloxy)ethyl]-3-(4,4,5,5-tetramethyl-1,3,2-dioxaborolan-2-yl)phenyl]phthalazin-1-amine

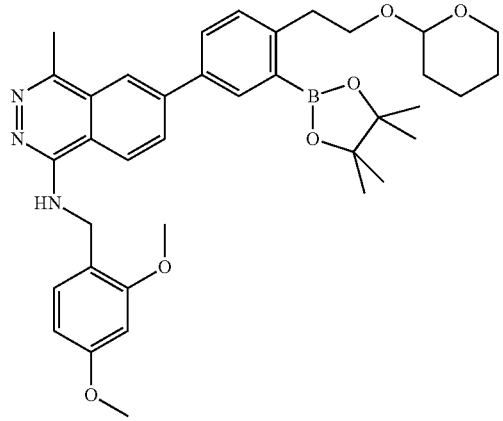 [SMILES: COc1ccc(CNc2nnc(C)c3cc(-c4ccc(CCOC5CCCCO5)c(B5OC(C)(C)C(C)(C)O5)c4)ccc23)c(OC)c1]

Palladium(II) diacetate (4.77 mg, 0.020 mmol), 6-[3-chloro-4-[2-(oxan-2-yloxy)ethyl]phenyl]-N-[(2,4-dimethoxyphenyl)methyl]-4-methylphthalazin-1-amine (233.0 mg, 0.430 mmol), dicyclohexyl-[2-[2,4,6-tri(propan-2-yl)phenyl]phenyl]phosphine (16.21 mg, 0.030 mmol), potassium acetate (125.17 mg, 1.28 mmol) and 4,4,5,5-tetramethyl-2-(4,4,5,5-tetramethyl-1,3,2-dioxaborolan-2-yl)-1,3,2-dioxaborolane (323.87 mg, 1.28 mmol) were dissolved in 1,4-dioxane (12.66 mL). The mixture was degassed with Ar for 10 min, then stirred at 80° C. for 9 hours. The mixture was filtered over a pad of Celite, washing with EtOAc and the filtrate was concentrated in vacuo. The residue was purified by column chromatography (KP-C18-HS, SNAP 30 g) eluting with a gradient of CH₃CN in water from 1% to 95% to give N-[(2,4-dimethoxyphenyl)methyl]-4-methyl-6-[4-[2-(oxan-2-yloxy)ethyl]-3-(4,4,5,5-tetramethyl-1,3,2-dioxaborolan-2-yl)phenyl]phthalazin-1-amine (54 mg, 0.084 mmol, 19.86% yield) as a pale yellow solid. LC-MS (Method A): r.t. 1.06 min, MS (ESI) m/z=640.6 [M+H]⁺.

Intermediate 84: tert-butyl N-[2-[2-[2-[2-(2-bromo-4-chlorophenoxy)ethoxy]ethoxy]ethoxy]ethyl]carbamate

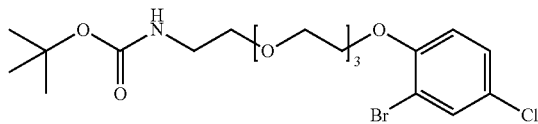

To a suspension of 2-bromo-4-chlorophenol (320.0 mg, 1.54 mmol) and potassium carbonate (426.39 mg, 3.09 mmol) in DMF (3.548 mL), tert-butyl N-[2-[2-[2-(2-bromoethoxy)ethoxy]ethyl]carbamate (604.48 mg, 1.7 mmol) was added. The resulting mixture was stirred at 50° C. overnight then it was concentrated under reduced pressure and the residue was taken up with EtOAc. The organic phase was washed with water and brine, dried over sodium sulfate, filtered and concentrated under reduced pressure to give tert-butyl N-[2-[2-[2-[2-(2-bromo-4-chlorophenoxy)ethoxy]ethoxy]ethoxy]ethyl]carbamate (680 mg, 1.408 mmol, 91.31% yield) as a yellow oil. ¹H NMR (400 MHz, Chloroform-d) δ 1.47 (d, J=2.93 Hz, 9H), 3.21-3.42 (m, 2H), 3.56 (t, J=5.10 Hz, 2H), 3.60-3.73 (m, 6H), 3.78-3.83 (m, 2H), 3.90-3.95 (m, 2H), 4.19 (t, J=4.85 Hz, 2H), 5.05 (s, 1H), 6.87 (d, J=8.77 Hz, 1H), 7.24 (dd, J=8.76, 2.53 Hz, 1H), 7.55 (d, J=2.53 Hz, 1H). LC-MS (Method A): r.t. 1.29 min, MS (ESI) m/z=482.3 and 484.3 [M+H]⁺.

Intermediate 85: tert-butyl N-[2-[2-[2-[2-[4-chloro-2-[4-[(2,4-dimethoxyphenyl)methylamino]cinnolin-7-yl]phenoxy]ethoxy]ethoxy]ethoxy]ethyl]carbamate

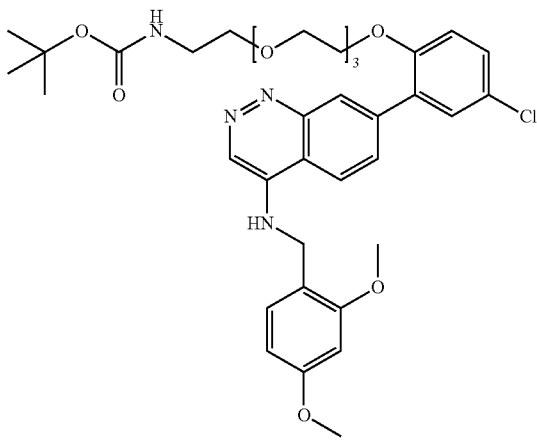

A mixture of tert-butyl N-[2-[2-[2-[2-(2-bromo-4-chlorophenoxy)ethoxy]ethoxy]ethoxy]ethyl]carbamate (427.06 mg, 0.880 mmol), [4-[(2,4-dimethoxyphenyl)methylamino]cinnolin-7-yl]boronic acid (500.0 mg, 0.740 mmol), [1,1'-bis(di-tert-butylphosphino)ferrocene]dichloropalladium(II) (48.68 mg, 0.070 mmol) in 1,2-dimethoxyethane (12.41 mL) and aqueous 2N sodium carbonate solution (0.74 mL, 1.49 mmol) was degassed for 10 min under N₂. The mixture was stirred at 70° C. for 2 hours, then it was cooled to room temperature and filtered over Celite, washing with EtOAc. The filtrate was evaporated and the residue was purified by column chromatography (KP-NH silica gel, SNAP 55) eluting with a gradient of EtOAc in dichloromethane from 5% to 50% to give tert-butyl N-[2-[2-[2-[2-[4-chloro-2-[4-[(2,4-dimethoxyphenyl)methylamino]cinnolin-7-yl]phenoxy]ethoxy]ethoxy]ethyl]carbamate (350 mg, 0.502 mmol, 68.1% yield) as yellow oil. LC-MS (Method A): r.t. 1.14 min, MS (ESI) m/z=697.44 [M+H]⁺.

Intermediate 86: 7-[2-[2-(2-{2-[2-(2-aminoethoxy)ethoxy]ethoxy}ethoxy)-5-(4,4,5,5-tetramethyl-1,3,2-dioxaborolan-2-yl)phenyl]cinnolin-4-amine trifluoroacetic Acid

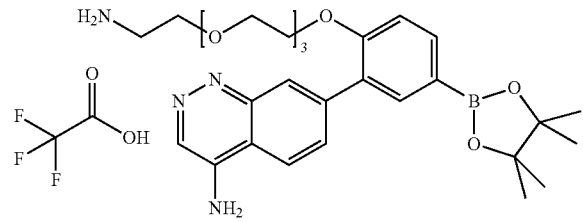

Palladium(II) diacetate (4.51 mg, 0.020 mmol), tert-butyl N-[2-[2-[2-[2-[4-chloro-2-[4-[(2,4-dimethoxyphenyl)methylamino]cinnolin-7-yl]phenoxy]ethoxy]ethoxy]ethoxy]ethyl]carbamate (350.0 mg, 0.400 mmol), dicyclohexyl-[2-[2,4,6-tri(propan-2-yl)phenyl]phenyl]phosphine (19.14 mg, 0.040 mmol), potassium acetate (118.24 mg, 1.2 mmol) and 4,4,5,5-tetramethyl-2-(4,4,5,5-tetramethyl-1,3,2-dioxaborolan-2-yl)-1,3,2-dioxaborolane (305.94 mg, 1.2 mmol) were dissolved in 1,4-dioxane (2.61 mL) in a microwave vial. The resulting mixture was degassed for 10 minutes under N₂ and then stirred at 75° C. for 2 h. It was then cooled to room temperature and filtered over Celite, washing with EtOAc. The filtrated was evaporated and the residue was purified by column chromatography (KP-C18-HS, 30 g) eluting with a gradient of CH₃CN in water from 1% to 80%. Fractions containing the desired compound were collected and evaporated under reduced pressure to give tert-butyl N-[2-[2-[2-[2-[4-[(2,4-dimethoxyphenyl)methylamino]cinnolin-7-yl]-4-(4,4,5,5-tetramethyl-1,3,2-dioxaborolan-2-yl)phenoxy]ethoxy]ethoxy]ethoxy]ethyl]carbamate (90 mg, 0.114 mmol, 28.41% yield) as a colourless oil and [3-[4-[(2,4-dimethoxyphenyl)methylamino]cinnolin-7-yl]-4-[2-[2-[2-[(2-methylpropan-2-yl)oxycarbonylamino]ethoxy]ethoxy]ethoxy]phenyl]boronic acid (120 mg, 0.170 mmol, 42.29% yield) as a white powder. These intermediates were combined and solubilized in dichloromethane (2.5 mL) and then 2,3-dimethylbutane-2,3-diol (52.68 mg, 0.450 mmol) was added. After 1 hour trifluoroacetic acid (2.5 mL) was added and the resulting mixture was stirred at room temperature for 4 hours then it was evaporated and stripped with toluene three times to give crude 7-[2-[2-[2-[2-(2-aminoethoxy)ethoxy]ethoxy]ethoxy]-5-(4,4,5,5-tetramethyl-1,3,2-dioxaborolan-2-yl)phenyl]cinnolin-4-amine trifluoroacetic acid salt (159.9 mg) as a yellow solid. The crude product was used in the next step without further purification. LC-MS (Method A): r.t. 0.54 min, MS (ESI) m/z=539.44 [M+H]⁺.

Intermediate 87: 5-[(3aS,4S,6aR)-2-oxo-hexahydro-1H-thieno[3,4-d]imidazol-4-yl]-N-{2-[2-(2-{2-[2-(4-aminocinnolin-7-yl)-4-(4,4,5,5-tetramethyl-1,3,2-dioxaborolan-2-yl)phenoxy]ethoxy}ethoxy)ethoxy]ethyl}pentanamide

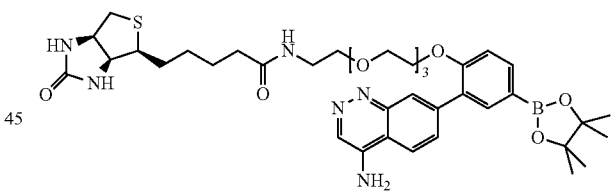

To a solution of 7-[2-[2-[2-[2-(2-aminoethoxy)ethoxy]ethoxy]ethoxy]-5-(4,4,5,5-tetramethyl-1,3,2-dioxaborolan-2-yl)phenyl]cinnolin-4-amine trifluoroacetic acid salt (150.0 mg) and triethylamine (20.56 uL, 0.150 mmol) in DMF (3 mL), biotin-OSu (95.1 mg, 0.280 mmol) was added. The resulting mixture was stirred at room temperature for 1 hour. Water and dichloromethane were added and the phases were separated. The aqueous phase was extracted further with dichloromethane. The combined organic phases were washed with water and brine, dried over sodium sulfate, filtered and concentrated in vacuum to give 5-[(3aS,4S,6aR)-2-oxo-hexahydro-1H-thieno[3,4-d]imidazol-4-yl]-N-{2-[2-(2-{2-[2-(4-aminocinnolin-7-yl)-4-(4,4,5,5-tetramethyl-1,3,2-dioxaborolan-2-yl)phenoxy]ethoxy}ethoxy)ethoxy]ethyl}pentanamide (200 mg) as a yellow vitreous oil. LC-MS (Method A): r.t. 0.72 min, MS (ESI) m/z=765.74 [M+H]⁺.

Intermediate 88: 6-(5-chloro-2-methoxy-4-methylphenyl)-N-[(2,4-dimethoxyphenyl)methyl]-4-methylphthalazin-1-amine

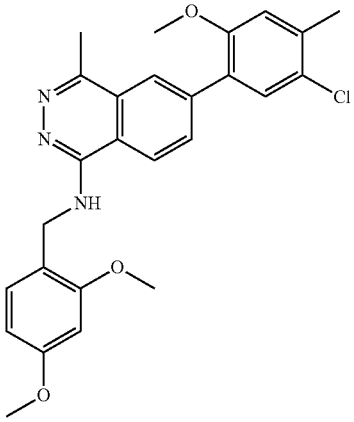 [SMILES: COc1ccc(CNc2nnc(C)c3cc(-c4cc(Cl)c(C)cc4OC)ccc23)c(OC)c1]

A mixture of 2-(5-chloro-2-methoxy-4-methylphenyl)-4,4,5,5-tetramethyl-1,3,2-dioxaborolane (240.17 mg, 0.850 mmol) and 6-bromo-N-[(2,4-dimethoxyphenyl)methyl]-4-methylphthalazin-1-amine (300.0 mg, 0.770 mmol) in 1,2-dimethoxyethane (4 mL) and aqueous 2N sodium carbonate solution (386.34 uL, 0.770 mmol) was degassed for 10 min with $N_2$. Then, [1,1'-bis(di-tert-butylphosphino)ferrocene]dichloropalladium(II) (50.51 mg, 0.080 mmol) was added. The mixture was stirred at 80° C. for 5 hours, then it was cooled to room temperature and filtered over Celite, washing with MeOH. The filtrate was evaporated and the residue was purified by column chromatography (KP-NH silica gel, SNAP 28) eluting with a gradient of MeOH in DCM from 0% to 3% to give 6-(5-chloro-2-methoxy-4-methylphenyl)-N-[(2,4-dimethoxyphenyl)methyl]-4-methylphthalazin-1-amine (335 mg, 0.722 mmol, 93.45% yield) as a brown oil. $^1$H NMR (400 MHz, DMSO-$d_6$) δ 2.41 (s, 3H), 2.70 (s, 3H), 3.73 (s, 3H), 3.82 (s, 3H), 3.85 (s, 3H), 4.67 (d, J=5.58 Hz, 2H), 6.43 (dd, J=8.36, 2.38 Hz, 1H), 6.58 (d, J=2.37 Hz, 1H), 7.12 (d, J=8.33 Hz, 1H), 7.21 (s, 1H), 7.53 (s, 1H), 7.57 (t, J=5.76 Hz, 1H), 7.96-8.03 (m, 2H), 8.38 (d, J=8.52 Hz, 1H). LC-MS (Method A): r.t. 0.91 min, MS (ESI) m/z=464.4 [M+H]$^+$.

Intermediate 89: N-[(2,4-dimethoxyphenyl)methyl]-6-[2-methoxy-4-methyl-5-(4,4,5,5-tetramethyl-1,3,2-dioxaborolan-2-yl)phenyl]-4-methylphthalazin-1-amine

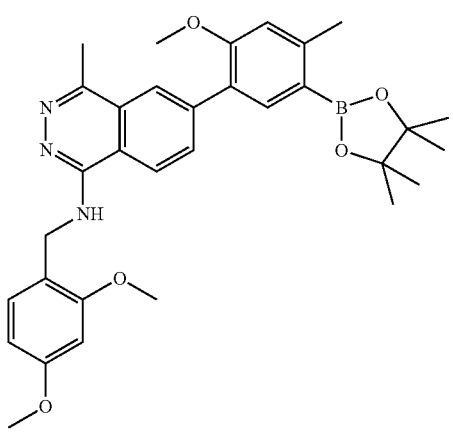

A mixture of 6-(5-chloro-2-methoxy-4-methylphenyl)-N-[(2,4-dimethoxyphenyl)methyl]-4-methylphthalazin-1-amine (335.0 mg, 0.720 mmol), 4,4,5,5-tetramethyl-2-(4,4,5,5-tetramethyl-1,3,2-dioxaborolan-2-yl)-1,3,2-dioxaborolane (550.07 mg, 2.17 mmol), dicyclohexyl-[2-[2,4,6-tri(propan-2-yl)phenyl]phenyl]phosphine (27.54 mg, 0.060 mmol), potassium acetate (212.58 mg, 2.17 mmol) and palladium (II) diacetate (8.11 mg, 0.040 mmol) were dissolved in 1,4-dioxane (7 mL) in a microwave vial and degassed for 10 min with $N_2$. The mixture was stirred at 85° C. for 4 hours, then it was cooled to room temperature and filtered over Celite, washing with MeOH. The filtrate was evaporated and the residue was purified by column chromatography (KP-C18-HS, 30 g) eluting with a gradient of $CH_3CN$ in water from 5% to 95%. Fractions containing the desired compound were collected and evaporated under reduced pressure to give N-[(2,4-dimethoxyphenyl)methyl]-6-[2-methoxy-4-methyl-5-(4,4,5,5-tetramethyl-1,3,2-dioxaborolan-2-yl)phenyl]-4-methylphthalazin-1-amine (139 mg, 0.250 mmol, 34.66% yield) as a white solid. $^1$H NMR (400 MHz, DMSO-$d_6$) δ 1.30 (s, 12H), 2.56 (s, 3H), 2.68 (s, 3H), 3.73 (s, 3H), 3.83 (s, 3H), 3.85 (s, 3H), 4.67 (d, J=5.47 Hz, 2H), 6.43 (dd, J=8.35, 2.40 Hz, 1H), 6.58 (d, J=2.40 Hz, 1H), 7.02 (s, 1H), 7.12 (d, J=8.34 Hz, 1H), 7.56 (t, J=5.79 Hz, 1H), 7.62 (s, 1H), 7.89 (dd, J=8.50, 1.72 Hz, 1H), 7.94 (d, J=1.66 Hz, 1H), 8.38 (d, J=8.57 Hz, 1H). LC-MS (Method A): r.t. 1.02 min, MS (ESI) m/z=556.5 [M+H]$^+$.

Intermediate 90: 6-[2-methoxy-4-methyl-5-(4,4,5,5-tetramethyl-1,3,2-dioxaborolan-2-yl)phenyl]-4-methylphthalazin-1-amine trifluoroacetic Acid Salt

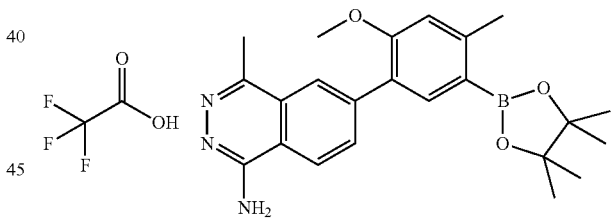

A solution of N-[(2,4-dimethoxyphenyl)methyl]-6-[2-methoxy-4-methyl-5-(4,4,5,5-tetramethyl-1,3,2-dioxaborolan-2-yl)phenyl]-4-methylphthalazin-1-amine (139.0 mg, 0.250 mmol) in DCM (1.5 mL) and trifluoroacetic acid (1.5 mL) was stirred for 1 hour at room temperature then was concentrated under reduced pressure. The residue was suspended in $Et_2O$, stirred for 30 min, filtered on a Hirsch funnel and dried to give 6-[2-methoxy-4-methyl-5-(4,4,5,5-tetramethyl-1,3,2-dioxaborolan-2-yl)phenyl]-4-methylpht halazin-1-amine trifluoroacetic acid salt (143 mg, 0.275 mmol, 110.04% yield) as a pale-pink powder. $^1$H NMR (400 MHz, DMSO-$d_6$) δ 1.30 (s, 12H), 2.58 (s, 3H), 2.73 (s, 3H), 3.84 (s, 3H), 7.07 (s, 1H), 7.65 (s, 1H), 8.18 (dd, J=8.49, 1.68 Hz, 1H), 8.22 (d, J=1.65 Hz, 1H), 8.65 (d, J=8.56 Hz, 1H), 9.07 (br. s, 2H). LC-MS (Method A): r.t. 0.86 min, MS (ESI) m/z=406.3 [M+H]$^+$.

Intermediate 91: 4-chloro-2-[1-[(2,4-dimethoxyphenyl)methylamino]-4-methylphthalazin-6-yl]benzonitrile Formic Acid Salt

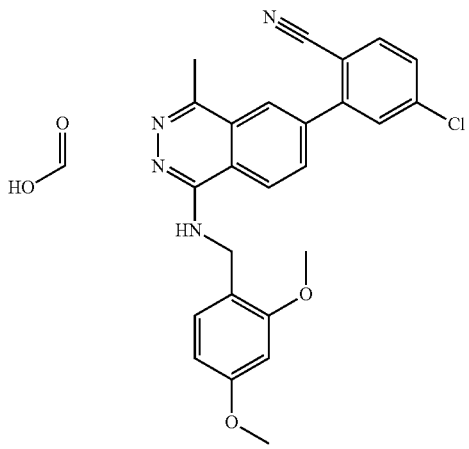 [SMILES: O=CO ; COc1ccc(CNc2nnc(C)c3cc(-c4cc(Cl)ccc4C#N)ccc23)c(OC)c1]

A mixture of [1-[(2,4-dimethoxyphenyl)methylamino]-4-methylphthalazin-6-yl]boronic acid (300.0 mg, 0.770 mmol) and 2-bromo-4-chlorobenzonitrile (167.32 mg, 0.770 mmol) in 1,2-dimethoxyethane (7.28 mL) and aqueous 2N sodium carbonate solution (0.39 mL, 0.770 mmol) was degassed for 10 min. [1,1'-Bis(di-tert-butylphosphino)ferrocene]dichloropalladium(II) (50.53 mg, 0.080 mmol) was added and the mixture was degassed for 10 min, then it was stirred at 75° C. for 4 h. The mixture was left to reach room temperature, then diluted with EtOAc, filtered and concentrated. The residue was purified by column chromatography (KP-C18-HS, SNAP30) eluting with a gradient of MeCN (+0.1% of HCOOH) in water (+0.1% of HCOOH) from 2% to 40% to give 4-chloro-2-[1-[(2,4-dimethoxyphenyl)methylamino]-4-methylphthalazin-6-yl]benzonitrile formic acid salt (111 mg, 0.226 mmol, 29.25% yield) as a brownish foam. $^1$H NMR (400 MHz, DMSO-$d_6$) δ 2.73 (s, 3H), 3.74 (s, 3H), 3.85 (s, 3H), 4.66-4.71 (m, 2H), 6.44 (dd, J=8.36, 2.42 Hz, 1H), 6.59 (d, J=2.20 Hz, 1H), 7.14 (d, J=8.36 Hz, 1H), 7.69-7.74 (m, 1H), 7.79 (dd, J=8.36, 1.98 Hz, 1H), 8.00 (d, J=1.98 Hz, 1H), 8.09 (d, J=8.36 Hz, 1H), 8.14 (dd, J=8.58, 1.76 Hz, 1H), 8.16 (s, 1H from HCOOH), 8.25 (d, J=1.54 Hz, 1H), 8.54 (d, J=8.58 Hz, 1H). LC-MS (Method A): r.t. 0.79 min, MS (ESI) m/z=445.23 [M+H]$^+$.

Intermediate 92: [4-cyano-3-[1-[(2,4-dimethoxyphenyl)methylamino]-4-methylphthalazin-6-yl]phenyl]boronic Acid

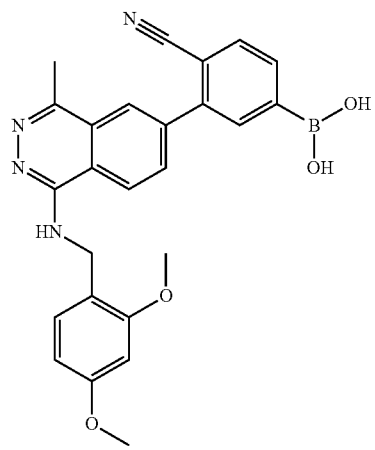 [SMILES: COc1ccc(CNc2nnc(C)c3cc(-c4cc(B(O)O)ccc4C#N)ccc23)c(OC)c1]

Palladium(II) diacetate (2.8 mg, 0.010 mmol), potassium acetate (73.45 mg, 0.750 mmol), 4,4,5,5-tetramethyl-2-(4,4,5,5-tetramethyl-1,3,2-dioxaborolan-2-yl)-1,3,2-dioxaborolane (190.07 mg, 0.750 mmol), dicyclohexyl-[2-[2,4,6-tri(propan-2-yl)phenyl]phenyl]phosphine (9.51 mg, 0.020 mmol) and 4-chloro-2-[1-[(2,4-dimethoxyphenyl)methylamino]-4-methylphthalazin-6-yl]benzonitrile (111.0 mg, 0.250 mmol) were dissolved in 1,4-dioxane (4.856 mL). The mixture was degassed with Ar for 10 min, then stirred at 75° C. for 3 hours. The mixture was left to reach room temperature, then diluted with EtOAc and filtered. The volatiles were removed and the residue was purified by column chromatography (KP-C18-HS, 2×SNAP12 in series) eluting with a gradient of MeCN in water from 2% to 100%, and then MeCN+0.1% TFA to give [4-cyano-3-[1-[(2,4-dimethoxyphenyl)methylamino]-4-methylphthalazin-6-yl]phenyl]boronic acid (35 mg, 0.077 mmol, 30.88% yield) as a brownish solid. LC-MS (Method A): r.t. 0.67 min, MS (ESI) m/z=455.35[M+H]$^+$.

Intermediate 93: 3-bromo-5-chloro-2-methoxypyridine

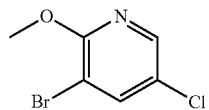

To a solution of 3-bromo-5-chloro-2-fluoropyridine (1.0 g, 4.75 mmol) in methanol (4 mL) was added 25% w/w solution of sodium methoxide in MeOH (1.3 mL, 5.7 mmol) and the mixture was stirred at 50° C. for 5 h. The volatiles were evaporated and the solid residue was partionated between EtOAc (100 mL) and water (50 mL). The organic phases was washed with brine, dried over Na$_2$SO$_4$, filtered and the solvent was evaporated to give 3-bromo-5-chloro-2-methoxypyridine (980 mg, 4.405 mmol, 92.7% yield) as a white solid. $^1$H NMR (400 MHz, DMSO-$d_6$) δ 3.93 (s, 3H), 8.24-8.26 (m, 1H), 8.26-8.28 (m, 1H). LC-MS (Method A): r.t. 1.17 min, MS (ESI) m/z of product not observed due to poor ionization.

Intermediate 94: 6-(5-chloro-2-methoxypyridin-3-yl)-N-[(2,4-dimethoxyphenyl)methyl]-4-methylphthalazin-1-amine

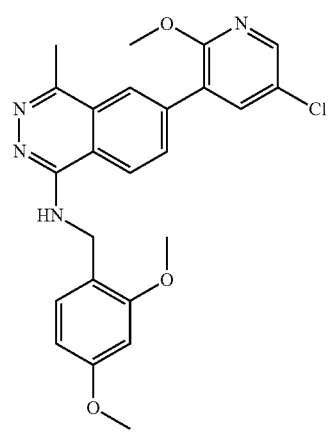

A mixture of 3-bromo-5-chloro-2-methoxypyridine (188.97 mg, 0.850 mmol) and [1-[(2,4-dimethoxyphenyl)methylamino]-4-methylphthalazin-6-yl]boronic acid (300.0 mg, 0.850 mmol) in 1,2-dimethoxyethane (8 mL) and aqueous 2N sodium carbonate solution (0.42 mL, 0.850 mmol) was degassed for 10 min. [1,1'-Bis(di-tert-butylphosphino)ferrocene]dichloropalladium(II) (55.53 mg, 0.080 mmol) was added and the mixture was degassed for 10 min, then it was stirred at 80° C. for 4 h. The mixture was left to reach room temperature, then diluted with EtOAc, filtered and concentrated. The residue was purified by column chromatography (KP-NH silica gel, SNAP 28) eluting with a gradient of EtOAc in cyclohexane from 10% to 60% to give 6-(5-chloro-2-methoxypyridin-3-yl)-N-[(2,4-dimethoxyphenyl)methyl]-4-methylphthalazin-1-amine (140 mg, 0.310 mmol, 36.55% yield) as a brownish foam. $^1$H NMR (400 MHz, DMSO-$d_6$) δ 2.71 (s, 3H), 3.73 (s, 3H), 3.85 (s, 3H), 3.94 (s, 3H), 4.67 (d, J=5.28 Hz, 2H), 6.43 (dd, J=8.36, 2.42 Hz, 1H), 6.58 (d, J=2.42 Hz, 1H), 7.12 (d, J=8.36 Hz, 1H), 7.62 (t, J=5.72 Hz, 1H), 8.10 (dd, J=8.58, 1.76 Hz, 1H), 8.14 (d, J=2.64 Hz, 1H), 8.16 (d, J=1.54 Hz, 1H), 8.33 (d, J=2.42 Hz, 1H), 8.42 (d, J=8.58 Hz, 1H). LC-MS (Method A): r.t. 0.82 min, MS (ESI) m/z=451.33 [M+H]$^+$.

Intermediate 95: [5-[1-[(2,4-dimethoxyphenyl)methylamino]-4-methylphthalazin-6-yl]-6-methoxypyridin-3-yl]boronic Acid

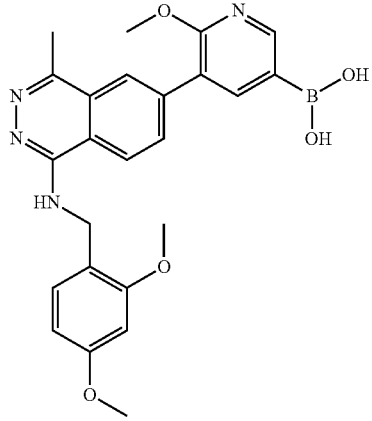 [SMILES: COc1ccc(CNc2nnc(C)c3cc(-c4cc(B(O)O)cnc4OC)ccc23)c(OC)c1]

Palladium(II) diacetate (3.35 mg, 0.010 mmol), 6-(5-chloro-2-methoxypyridin-3-yl)-N-[(2,4-dimethoxyphenyl)methyl]-4-methylphthalazin-1-amine (140.0 mg, 0.300 mmol), dicyclohexyl-[2-[2,4,6-tri(propan-2-yl)phenyl]phenyl]phosphine (11.37 mg, 0.020 mmol), potassium acetate (87.75 mg, 0.890 mmol) and 4,4,5,5-tetramethyl-2-(4,4,5,5-tetramethyl-1,3,2-dioxaborolan-2-yl)-1,3,2-dioxaborolane (227.07 mg, 0.890 mmol) were dissolved in 1,4-dioxane (5.88 mL). The mixture was degassed for 10 min, then stirred at 75° C. for 3 hours. The mixture was left to reach room temperature, diluted with EtOAc and filtered. The volatiles were removed and the residue was purified by column chromatography (KP-C18-HS, SNAP 30) eluting with a gradient of MeCN (+0.1% of HCOOH) in water (+0.1% of HCOOH) from 2% to 100% and then MeOH to give [5-[1-[(2,4-dimethoxyphenyl)methylamino]-4-methylphthalazin-6-yl]-6-methoxypyridin-3-yl]boronic acid (54 mg, 0.117 mmol, 39.36% yield) as a brownish solid. LC-MS (Method A): r.t. 0.65 min, MS (ESI) m/z=461.35 [M+H]$^+$.

Intermediate 96: 1-(2-amino-4-bromo-6-fluorophenyl)ethanone

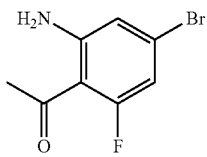

A stirred solution of 3-bromo-5-fluoroaniline (2 g, 10.53 mmol) and dry acetonitrile (5.5 mL, 105.26 mmol) in dry toluene (14 mL) was cooled to 0° C. A 1M solution of trichloroborane in DCM (12.8 mL, 12.8 mmol) was added dropwise, while keeping the temperature below 10° C. Next, trichloroalumane (1.895 g, 14.21 mmol) was added in small portions at 0° C. The reaction mixture was heated to 100° C. overnight. The reaction mixture was cooled to room temperature and then quenched with 20 mL of 2M HCl solution. The mixture was heated to 50° C. for 1 hour then cooled to room temperature and the phases were separated. The aqueous phase was extracted with EtOAc. The combined organic phases were collected, filtered through a phase separator cartridge and concentrated under reduced pressure. The residue was purified by column chromatography (KP silica gel, SNAP 100) eluting with a gradient of EtOAc in cyclohexane from 1% to 25% to give 1-(2-amino-4-bromo-6-fluorophenyl)ethanone (594 mg, 0.862 mmol, 24.3% yield) as a yellow powder. $^1$H NMR (400 MHz, Chloroform-d) δ 2.60 (d, J=8.26 Hz, 3H), 6.40 (s, 2H), 6.54 (dd, J=11.64, 1.88 Hz, 1H), 6.63 (dd, J=1.90, 1.25 Hz, 1H). LC-MS (Method A): r.t. 1.08 min, MS (ESI) m/z=232.03 and 234.03 [M+H]$^+$.

Intermediate 97: 7-bromo-5-fluorocinnolin-4-ol hydrochloride

1-(2-Amino-4-bromo-6-fluorophenyl)ethanone (200.0 mg, 0.860 mmol) was dissolved in 12M hydrochloric acid solution (4.98 mL, 59.78 mmol) and water (2 mL), then the mixture was cooled to −5° C. in an ice/brine bath. A solution of sodium nitrite (62.36 mg, 0.900 mmol) in water (4 mL) was added slowly. The reaction mixture was stirred for one hour, then the temperature was raised to 60° C., stirred for 2 hours and then cooled to room temperature. The resulting precipitate was filtered, washed with water, dried and collected to give 7-bromo-5-fluorocinnolin-4-ol hydrochloride (130 mg, 0.465 mmol, 53.97% yield) as an off white solid. $^1$H NMR (400 MHz, DMSO-$d_6$) δ 6.60 (dd, J=11.95, 1.94 Hz, 1H), 6.85 (dd, J=1.98, 1.20 Hz, 1H), 7.47 (s, 2H). LC-MS (Method A): r.t. 0.67 min, MS (ESI) m/z=279.4 and 281.4 [M+H]$^+$.

Intermediate 98: 7-bromo-4-chloro-5-fluorocinnoline

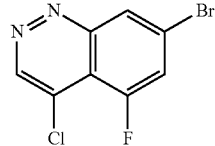 [SMILES: Fc1cc(Br)cc2nncc(Cl)c12]

A solution of 7-bromo-5-fluorocinnolin-4-ol hydrochloride (189.75 mg, 0.680 mmol) in phosphorus oxychloride (0.5 mL, 0.680 mmol) was stirred at 90° C. for 2 hours. The reaction mixture was cooled to room temperature then the excess of phosphorus oxychloride was removed in vacuo. The residue was dissolved in DCM and washed with a saturated aqueous solution of $NaHCO_3$ and brine. The organic layer was dried over sodium sulfate, filtered and concentrated under reduce pressure to give 7-bromo-4-chloro-5-fluorocinnoline (198 mg, 0.757 mmol, 111.53% yield) as a brown solid. LC-MS (Method A): r.t. 1.03 min, MS (ESI) m/z=260.99 and 263.04 [M+H]+.

Intermediate 99: 7-bromo-N-[(2,4-dimethoxyphenyl)methyl]-5-fluorocinnolin-4-amine

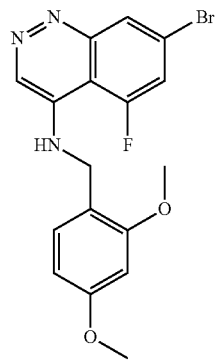 [SMILES: COc1ccc(CNc2cnnc3cc(Br)cc(F)c23)c(OC)c1]

(2,4-Dimethoxyphenyl)methanamine (0.2 mL, 1.33 mmol) was added to a solution of 7-bromo-4-chloro-5-fluorocinnoline (173.77 mg, 0.660 mmol) in ethanol (2.172 mL) and the resulting mixture was stirred at 90° C. for 2 hours. The reaction mixture was cooled to room temperature and concentrated under reduced pressure. The residue was taken up with EtOAc and the resulting suspension was filtered on a Hirsch funnel to give 7-bromo-N-[(2,4-dimethoxyphenyl)methyl]-5-fluorocinnolin-4-amine (145 mg, 0.370 mmol, 55.63% yield) as an off white solid. LC-MS (Method A): r.t. 0.69 min, MS (ESI) m/z=392.1 and 394.1 [M+H]+.

Intermediate 100: 7-(5-chloro-2-methoxyphenyl)-N-[(2,4-dimethoxyphenyl)methyl]-5-fluorocinnolin-4-amine

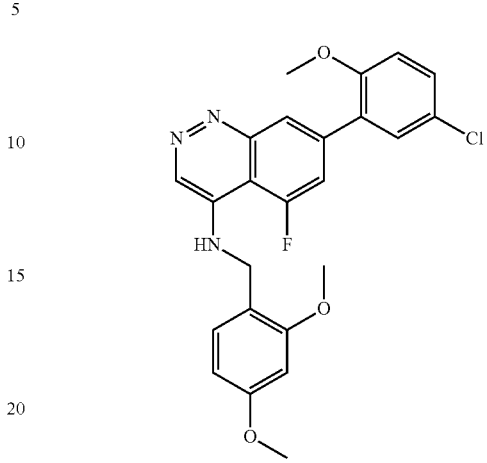

A mixture of 5-chloro-2-methoxyphenyl boronic acid (73.19 mg, 0.390 mmol) and 7-bromo-N-[(2,4-dimethoxyphenyl)methyl]-5-fluorocinnolin-4-amine (140.0 mg, 0.360 mmol) in 1,2-dimethoxyethane (3.267 mL) and aqueous 2N sodium carbonate solution (360 uL, 0.71 mmol) was degassed for 10 minutes with $N_2$. Then [1,1'-bis(di-tert-butylphosphino)ferrocene]dichloropalladium(II) (23.34 mg, 0.040 mmol) was added and the resulting reaction mixture was stirred at 75° C. for 3 hours. It was then cooled to room temperature and filtered over Celite, washing with EtOAc. The filtrate was evaporated and the residue was purified by column chromatography (KP silica gel, SNAP 25) eluting with a gradient of EtOAc in dichloromethane from 5% to 40% to give 7-(5-chloro-2-methoxyphenyl)-N-[(2,4-dimethoxyphenyl)methyl]-5-fluorocinnolin-4-amine (124 mg, 0.273 mmol, 76.54% yield) as a yellow solid. $^1$H NMR (400 MHz, DMSO-$d_6$) δ 3.00 (s, 3H), 3.08 (s, 3H), 3.13 (s, 3H), 3.83 (s, 2H), 5.72 (d, J=8.81 Hz, 1H), 5.82 (s, 1H), 6.35 (d, J=8.86 Hz, 1H), 6.47 (d, J=8.33 Hz, 1H), 6.62 (dd, J=8.84, 2.59 Hz, 1H), 6.67 (d, J=2.63 Hz, 1H), 6.72 (d, J=14.22 Hz, 1H), 7.20 (s, 1H), 7.79 (s, 1H). LC-MS (Method A): r.t. 0.86 min, MS (ESI) m/z=454.89 [M+H]+.

Intermediate 101: Give N-[(2,4-dimethoxyphenyl)methyl]-5-fluoro-7-[2-methoxy-5-(4,4,5,5-tetramethyl-1,3,2-dioxaborolan-2-yl)phenyl]cinnolin-4-amine

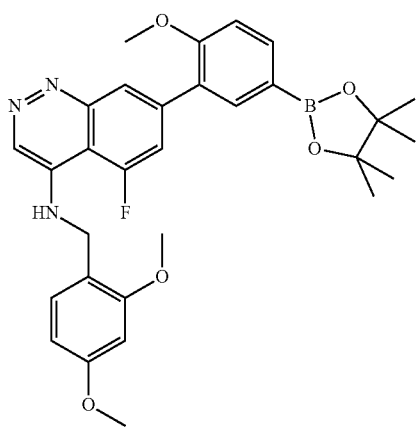 [SMILES: COc1ccc(CNc2cnnc3cc(-c4cc(B5OC(C)(C)C(C)(C)O5)ccc4OC)cc(F)c23)c(OC)c1]

Palladium(II) diacetate (3.09 mg, 0.010 mmol), 7-(5-chloro-2-methoxyphenyl)-N-[(2,4-dimethoxyphenyl)methyl]-5-fluorocinnolin-4-amine (125.0 mg, 0.280 mmol), dicyclohexyl-[2-[2,4,6-tri(propan-2-yl)phenyl]phenyl]phosphine (13.13 mg, 0.030 mmol), potassium acetate (81.08 mg, 0.830 mmol) and 4,4,5,5-tetramethyl-2-(4,4,5,5-tetramethyl-1,3,2-dioxaborolan-2-yl)-1,3,2-dioxaborolane (209.8 mg, 0.830 mmol) were dissolved in 1,4-dioxane (2.754 mL) in a microwave vial. The resulting mixture was degassed for 10 minutes under $N_2$ and then stirred at 80° C. for 2 hours. It was then cooled to room temperature and filtered over Celite, washing with EtOAc. The filtrate was evaporated and the residue was purified by column chromatography (KP silica gel, SNAP 25) eluting with a gradient of EtOAc/methanol (90:10) in dichloromethane from 0% to 100% to give N-[(2,4-dimethoxyphenyl)methyl]-5-fluoro-7-[2-methoxy-5-(4,4,5,5-tetramethyl-1,3,2-dioxaborolan-2-yl)phenyl]cinnolin-4-amine (95 mg, 0.174 mmol, 63.25% yield) as a yellow solid. LC-MS (Method A): r.t. 0.95 min, MS (ESI) m/z=456.41 [M+H]$^+$.

Intermediate 102:
1-chloro-4-methoxy-2-(2-methoxyethenyl)benzene

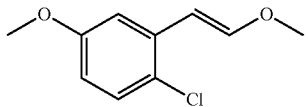

To a solution of methoxymethyl(triphenyl)phosphonium chloride (1205.7 mg, 3.52 mmol) in THF (15 mL), cooled to 0° C., potassium tert-butoxide (427.55 mg, 3.81 mmol) was added and the mixture was stirred for 20 min. 2-Chloro-5-methoxybenzaldehyde (0.5 g, 2.93 mmol) was added and the mixture was stirred at room temperature for 16 h. Saturated aqueous $NH_4Cl$ solution (50 mL) was added and the aqueous phase was extracted with EtOAc (3×50 mL). The combined organic phases were dried over $Na_2SO_4$, filtered and the solvent was evaporated. The residue was purified by column chromatography (KP-Sil, SNAP 50 g) eluting with a gradient of EtOAc in cyclohexane from 0% to 40% to give 1-chloro-4-methoxy-2-(2-methoxyethenyl)benzene (650 mg, 3.272 mmol, 111.64% yield) as a mixture of isomers. LC-MS (Method A): r.t. (isomer 1) 1.19 min and r.t. (isomer 2) 1.20 min, MS (ESI) m/z=199.0 [M+H]$^+$.

Intermediate 103:
2-(2-chloro-5-methoxyphenyl)ethanol

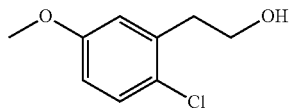

Step 1: 6 M Hydrochloric acid solution (5.0 mL, 30 mmol) was added to a solution of 1-chloro-4-methoxy-2-(2-methoxyethenyl)benzene (650.0 mg, 3.27 mmol) in THF (10 mL) and the mixture was heated to reflux for 1 h then cooled to room temperature. EtOAc was added and the layers were separated. The organic layer was washed with saturated aqueous $NaHCO_3$ solution and brine, dried over $Na_2SO_4$, filtered and the solvent was evaporated under reduced pressure.

Step 2: The crude compound obtained in Step 1 (610 mg, 3.3 mmol) was dissolved in methanol (5 mL) and sodium borohydride (112.49 mg, 2.97 mmol) was added portion wise. The mixture was stirred under Ar for 2 h and water (20 mL) was carefully added. The aqueous layer was extracted with $Et_2O$ (80 mL) and the organic phase was dried over $Na_2SO_4$, filtered and the solvent was evaporated. The residue was purified by column chromatography (KP-Sil, SNAP 25 g) eluting with a gradient of EtOAc in cyclohexane from 0% to 40% to obtain 2-(2-chloro-5-methoxyphenyl)ethanol (391 mg, 2.095 mmol, 64% yield over two steps) as an oil. $^1$H NMR (400 MHz, DMSO-d$_6$) δ 2.81 (t, J=7.13 Hz, 2H), 3.59 (td, J=7.11, 5.33 Hz, 2H), 4.71 (t, J=5.33 Hz, 1H), 6.81 (dd, J=8.78, 3.07 Hz, 1H), 6.92 (d, J=3.07 Hz, 1H), 7.29 (d, J=8.78 Hz, 1H). LC-MS (Method A): r.t. 0.85 min, MS (ESI) m/z of product not observed due to poor ionization.

Intermediate 104:
2-(4-bromo-2-chloro-5-methoxyphenyl)ethanol

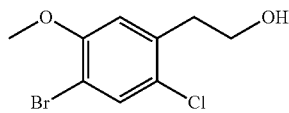

NBS (398.61 mg, 2.24 mmol) was added to a solution of 2-(2-chloro-5-methoxyphenyl)ethanol (380.0 mg, 2.04 mmol) in THF (3 mL) and the mixture was stirred at room temperature for 18 h. Another aliquot of NBS (108.71 mg, 0.610 mmol) was added and the mixture was stirred at room temperature for another 6 h. The mixture was diluted with EtOAc washed with saturated aqueous $Na_2S_2O_3$ solution, saturated aqueous $NaHCO_3$ solution and brine, dried over $Na_2SO_4$, filtered and the solvent was evaporated. The residue was purified by column chromatography (KP-Sil, SNAP 25 g) eluting with a gradient of EtOAc in cyclohexane from 0% to 40% to give 2-(4-bromo-2-chloro-5-methoxyphenyl)ethanol (160 mg, 0.603 mmol, 29.6% yield) as an oil. $^1$H NMR (400 MHz, DMSO-d$_6$) δ 2.83 (t, J=7.01 Hz, 2H), 3.61 (td, J=7.01, 5.51 Hz, 2H), 3.84 (s, 3H), 4.74 (t, J=5.37 Hz, 1H), 7.10 (s, 1H), 7.62 (s, 1H). LC-MS (Method A): r.t. 1.00 min, MS (ESI) m/z of product not observed due to poor ionization.

Intermediate 105: 2-[2-(4-bromo-2-chloro-5-methoxyphenyl)ethoxy]oxane

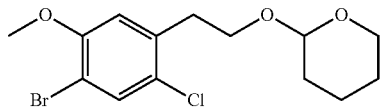 [SMILES: COc1cc(CCOC2CCCCO2)c(Cl)cc1Br]

To a solution of 2-(4-bromo-2-chloro-5-methoxyphenyl)ethanol (160.0 mg, 0.600 mmol) in DCM (5 mL), 3,4-dihydro-2H-pyran (82.46 uL, 0.900 mmol) and 4-methylbenzenesulfonic acid hydrate (5.73 mg, 0.030 mmol) were added. The mixture was stirred at room temperature for 48 h, diluted with DCM (40 mL) and washed with saturated aqueous $NaHCO_3$ solution. The organic phases was dried over $Na_2SO_4$, filtered and the solvent was evaporated. The residue was purified by column chromatography (KP-Sil, SNAP 25 g) eluting with a gradient of EtOAc in cyclohexane from 0% to 20% to give 2-[2-(4-bromo-2-chloro-5-methoxyphenyl)ethoxy]oxane (130 mg, 0.372 mmol, 61.7% yield) as an oil. NMR analysis showed the product contained some impurities. This material was used in the next step without further purification. $^1$H NMR (400 MHz, DMSO-$d_6$) δ 1.10-2.13 (m, 6H), 2.93 (td, J=6.85, 1.73 Hz, 2H), 3.36-3.47 (m, 1H), 3.54-3.67 (m, 2H), 3.77-3.87 (m, 1H), 3.84 (s, 3H), 4.59 (t, J=3.48 Hz, 1H), 7.17 (s, 1H), 7.64 (s, 1H). LC-MS (Method A): r.t. 1.41 min, MS (ESI) m/z of product not observed due to poor ionization.

Intermediate 106: 6-[5-chloro-2-methoxy-4-[2-(oxan-2-yloxy)ethyl]phenyl]-N-[(2,4-dimethoxyphenyl)methyl]-4-methylphthalazin-1-amine

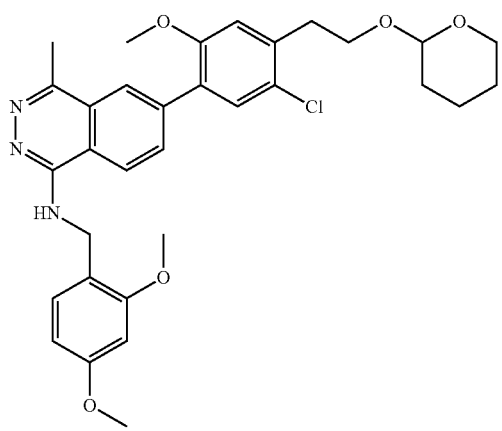

A mixture of 2-[2-(4-bromo-2-chloro-5-methoxyphenyl)ethoxy]oxane (128.7 mg, 0.370 mmol), [1-[(2,4-dimethoxyphenyl)methylamino]-4-methylphthalazin-6-yl]boronic acid (130.0 mg, 0.370 mmol) and aqueous 2N sodium carbonate solution (368.08 uL, 0.740 mmol) in 1,2-dimethoxyethane (6.008 mL) was degassed with Ar for 10 min. Then [1,1'-bis(di-tert-butylphosphino)ferrocene]dichloropalladium(II) (24.06 mg, 0.040 mmol) was added and the resulting reaction mixture was stirred at 90° C. for 6 hours. The mixture was filtered over Celite, washing with EtOAc and the filtrate was concentrated in vacuo. The residue was purified by column chromatography (KP-NH silica gel, SNAP 28 g) eluting with a gradient of EtOAc in cyclohexane from 0% to 100% to give 6-[5-chloro-2-methoxy-4-[2-(oxan-2-yloxy)ethyl]phenyl]-N-[(2,4-dimethoxyphenyl)methyl]-4-methylphthalazin-1-amine (94 mg, 0.163 mmol, 44.18% yield) as a viscous oil. LC-MS (Method A): r.t. 0.97 min, MS (ESI) m/z=578.5 [M+H]$^+$.

Intermediate 107: N-[(2,4-dimethoxyphenyl)methyl]-6-[2-methoxy-4-[2-(oxan-2-yloxy)ethyl]-5-(4,4,5,5-tetramethyl-1,3,2-dioxaborolan-2-yl)phenyl]-4-methylphthalazin-1-amine

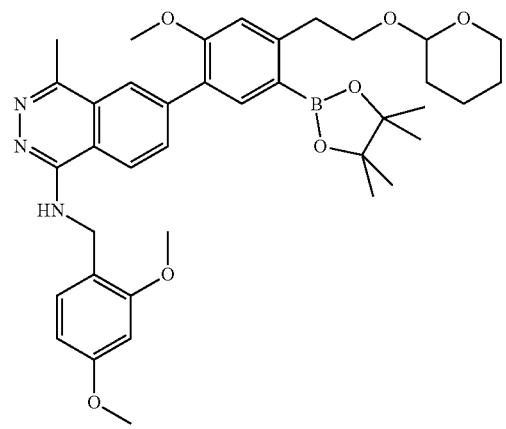 [SMILES: COc1ccc(CNc2nnc(C)c3cc(-c4cc(B5OC(C)(C)C(C)(C)O5)c(CCOC5CCCCO5)cc4OC)ccc23)c(OC)c1]

Palladium(II) diacetate (1.83 mg, 0.010 mmol), 6-[5-chloro-2-methoxy-4-[2-(oxan-2-yloxy)ethyl]phenyl]-N-[(2,4-dimethoxyphenyl)methyl]-4-methylphthalazin-1-amine (94.0 mg, 0.160 mmol), dicyclohexyl-[2-[2,4,6-tri(propan-2-yl)phenyl]phenyl]phosphine (6.2 mg, 0.010 mmol), potassium acetate (47.87 mg, 0.490 mmol) and 4,4,5,5-tetramethyl-2-(4,4,5,5-tetramethyl-1,3,2-dioxaborolan-2-yl)-1,3,2-dioxaborolane (123.87 mg, 0.490 mmol) were dissolved in 1,4-dioxane (5.109 mL). The mixture was degassed with Ar for 10 min, then stirred at 90° C. for 18 hours. The mixture was filtered over a pad of Celite, washing with EtOAc and the filtrate was concentrated in vacuo. The residue was purified by column chromatography (KP-C18-HS, SNAP 30 g) eluting with a gradient of CH$_3$CN in water from 1% to 95% to give N-[(2,4-dimethoxyphenyl)methyl]-6-[2-methoxy-4-[2-(oxan-2-yloxy)ethyl]-5-(4,4,5,5-tetramethyl-1,3,2-dioxaborolan-2-yl)phenyl]-4-methylphthalazin-1-amine (11 mg, 0.016 mmol, 10.1% yield) as a pale yellow solid. LC-MS (Method A): r.t. 1.06 min, MS (ESI) m/z=670.7 [M+H]$^+$.

Intermediate 108: tert-butyl N-[2-[2-[2-[2-[2-(2-hydroxyethoxy)ethoxy]ethoxy]ethoxy]ethyl]carbamate

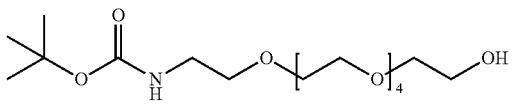

To a stirred solution of 2-[2-[2-[2-[2-(2-aminoethoxy)ethoxy]ethoxy]ethoxy]ethanol (500.0 mg, 1.78 mmol) in THF (10 mL) at 0° C., di-tert-butyl dicarbonate (465.43 mg, 2.13 mmol) was added portionwise. The mixture was stirred at room temperature for 5 hours. The reaction mixture was diluted with water and extracted with EtOAc. The combined organic phases were washed with brine, dried over sodium sulphate and concentrated under reduced pressure. The residue was purified by column chromatography (KP-Sil silica gel, SNAP 25) eluting with EtOAc to give tert-butyl N-[2-[2-[2-[2-[2-(2-hydroxyethoxy)ethoxy]ethoxy]ethoxy]ethoxy]ethyl]carbamate (680 mg, 1.783 mmol, 100.31% yield) as a colorless oil. ¹H NMR (400 MHz, DMSO-d₆) δ 1.38 (s, 9H), 3.06 (q, J=6.03 Hz, 2H), 3.35-3.44 (m, 4H), 3.51 (dd, J=5.82, 0.98 Hz, 18H), 4.56 (br. s, 1H), 6.74 (s, 1H).

Intermediate 109: tert-butyl N-[2-[2-[2-[2-[2-(2-bromoethoxy)ethoxy]ethoxy]ethoxy]ethoxy]ethyl]carbamate

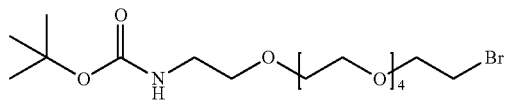

To a stirred solution of tert-butyl N-[2-[2-[2-[2-[2-(2-hydroxyethoxy)ethoxy]ethoxy]ethoxy]ethoxy]ethyl]carbamate (380.0 mg, 1 mmol) and triphenylphosphine (313.54 mg, 1.2 mmol) in dry CH₃CN (2.49 mL) at 0° C., tetrabromomethane (396.43 mg, 1.2 mmol) was added portionwise. The resulting solution was slowly warmed to room temperature and stirred overnight. The reaction mixture was diluted with DCM and washed with water and brine, dried over sodium sulphate and concentrated under reduced pressure to give tert-butyl N-[2-[2-[2-[2-[2-(2-bromoethoxy)ethoxy]ethoxy]ethoxy]ethoxy]ethyl]carbamate in a mixture with triphenylphosphine oxide (840 mg) as a colourless oil. This material was progressed without further purification. ¹H NMR (400 MHz, DMSO-d₆) δ 1.38 (s, 9H), 3.06 (q, J=6.03 Hz, 2H), 3.38 (t, J=6.15 Hz, 2H), 3.47-3.61 (m, 18H), 3.74 (t, J=5.78 Hz, 2H).

Intermediate 110: tert-butyl N-[2-[2-[2-[2-[2-[2-(2-bromo-4-chlorophenoxy)ethoxy]ethoxy]ethoxy]ethoxy]ethoxy]ethyl]carbamate

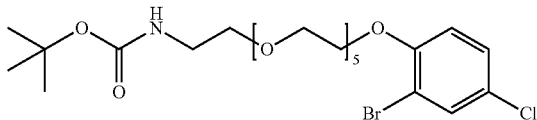

A mixture of tert-butyl N-[2-[2-[2-[2-[2-(2-bromoethoxy)ethoxy]ethoxy]ethoxy]ethoxy]ethyl]carbamate (840 mg), 2-bromo-4-chlorophenol (180.0 mg, 0.870 mmol) and potassium carbonate (239.84 mg, 1.74 mmol) in dry DMF (2.41 mL) was stirred at 50° C. for 8 hours. The reaction mixture was diluted with water and extracted with EtOAc. The combined organic phases were washed with brine, dried over sodium sulphate and concentrated under reduced pressure. The residue was combined with a similar residue obtained from a separate reaction performed with the same procedure but starting from 50 mg of 2-bromo-4-chlorophenol. The combined residues were purified by column chromatography (KP-NH silica gel, SNAP 28) eluting with a gradient of EtOAc in cyclohexane from 5% to 95% to give partially pure product. The mixture was purified further by column chromatography (KP-C18-HS, 2×30 g in series) eluting with a gradient of CH₃CN in water (+0.1% of HCOOH) from 5% to 95%. Fractions containing the desired compound were collected and evaporated under reduced pressure to give tert-butyl N-[2-[2-[2-[2-[2-[2-(2-bromo-4-chlorophenoxy)ethoxy]ethoxy]ethoxy]ethoxy]ethoxy]ethyl]carbamate (450 mg, 0.788 mmol, 61.8% yield over 2 steps) as a colourless oil. ¹H NMR (400 MHz, DMSO-d₆) δ 1.37 (s, 9H), 3.06 (q, J=6.03 Hz, 2H), 3.37 (t, J=6.14 Hz, 2H), 3.45-3.57 (m, 14H), 3.60-3.66 (m, 2H), 3.72-3.81 (m, 2H), 4.13-4.23 (m, 2H), 6.73 (t, J=5.55 Hz, 1H), 7.16 (d, J=8.90 Hz, 1H), 7.41 (dd, J=8.85, 2.58 Hz, 1H), 7.69 (d, J=2.58 Hz, 1H). LC-MS (Method A): r.t. 1.26 min, MS (ESI) m/z=570.5 and 572.4 [M+H]⁺.

Intermediate 111: tert-butyl N-[2-[2-[2-[2-[2-[2-[4-chloro-2-[4-[(2,4-dimethoxyphenyl)methylamino]cinnolin-7-yl]phenoxy]ethoxy]ethoxy]ethoxy]ethoxy]ethoxy]ethyl]carbamate

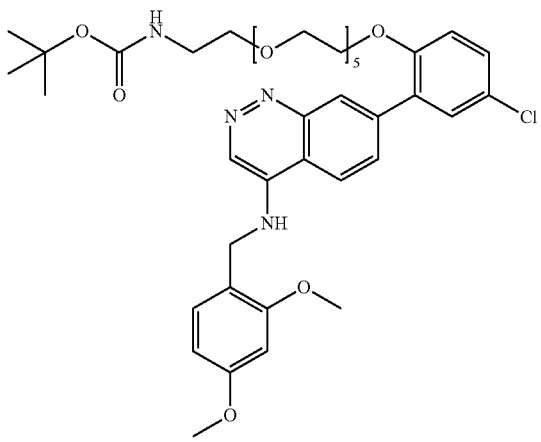

A mixture of [4-[(2,4-dimethoxyphenyl)methylamino]cinnolin-7-yl]boronic acid (356.44 mg, 0.530 mmol) and tert-butyl N-[2-[2-[2-[2-[2-[2-(2-bromo-4-chlorophenoxy)ethoxy]ethoxy]ethoxy]ethoxy]ethoxy]ethyl]carbamate (300.0 mg, 0.530 mmol) in 1,2-dimethoxyethane (5.26 mL) and aqueous 2N sodium carbonate solution (525.49 uL, 1.05 mmol) was degassed for 10 min with N₂. Then, [1,1'-bis(di-tert-butylphosphino)ferrocene]dichloropalladium(II) (34.35 mg, 0.050 mmol) was added. The mixture was stirred at 80° C. for 20 hours, then it was cooled to room temperature and filtered over Celite, washing with MeOH. The filtrate was evaporated and the residue was purified by column chromatography (KP-NH silica gel, SNAP 55) eluting with a gradient of EtOAc in cyclohexane from 0% to 100% to give tert-butyl N-[2-[2-[2-[2-[2-[2-[4-chloro-2-[4-[(2,4-dimethoxyphenyl)methylamino]cinnolin-7-yl]phenoxy]ethoxy]ethoxy]ethoxy]ethoxy]ethoxy]ethyl]carbamate (85 mg, 0.108 mmol, 20.6% yield) as a brown oil. ¹H NMR (400 MHz, DMSO-d₆) δ 1.36 (s, 9H), 3.04 (q, J=6.02 Hz, 2H), 3.35 (t, J=6.17 Hz, 2H), 3.38-3.49 (m, 14H), 3.49-3.53 (m, 2H), 3.68-3.72 (m, 2H), 3.74 (s, 3H), 3.89 (s, 3H), 4.19 (dd, J=5.67, 3.58 Hz, 2H), 4.52 (d, J=5.83 Hz, 2H), 6.48 (dd, J=8.36, 2.42 Hz, 1H), 6.64 (d, J=2.39 Hz, 1H), 6.72 (t, J=5.87 Hz, 1H), 7.16 (d, J=8.42 Hz, 1H), 7.24 (d, J=8.91 Hz, 1H), 7.45 (dd, J=8.80, 2.67 Hz, 1H), 7.55 (d, J=2.70 Hz, 1H), 7.86 (dd, J=8.79, 1.84 Hz, 1H), 8.01 (t, J=5.97 Hz, 1H), 8.25 (d, J=1.81 Hz, 1H), 8.35 (d, J=8.85 Hz, 1H), 8.48 (s, 1H). LC-MS (Method A): r.t. 0.84 min, MS (ESI) m/z=700.6 [M+H]⁺.

Intermediate 112: tert-butyl N-[2-[2-[2-[2-[2-[2-[2-[4-[(2,4-dimethoxyphenyl)methylamino]cinnolin-7-yl]-4-(4,4,5,5-tetramethyl-1,3,2-dioxaborolan-2-yl)phenoxy]ethoxy]ethoxy]ethoxy]ethoxy]ethoxy]ethyl]carbamate

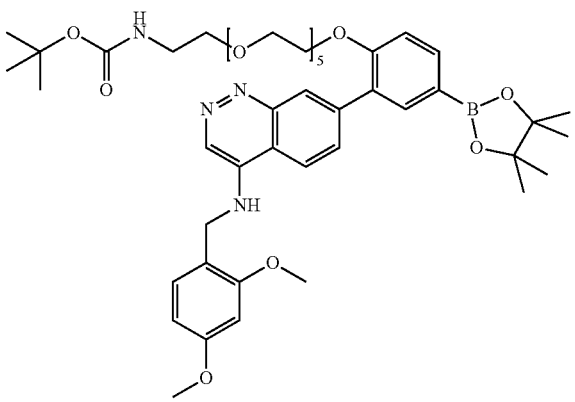

A mixture of N-[2-[2-[2-[2-[2-[2-[4-chloro-2-[4-[(2,4-dimethoxyphenyl)methylamino]cinnolin-7-yl]phenoxy]ethoxy]ethoxy]ethoxy]ethoxy]ethoxy]ethyl]carbamate (85.0 mg, 0.108 mmol), 4,4,5,5-tetramethyl-2-(4,4,5,5-tetramethyl-1,3,2-dioxaborolan-2-yl)-1,3,2-dioxaborolane (111.56 mg, 0.440 mmol), dicyclohexyl-[2-[2,4,6-tri(propan-2-yl)phenyl]phenyl]phosphine (6.98 mg, 0.010 mmol), potassium acetate (43.11 mg, 0.440 mmol) and palladium(II) diacetate (1.64 mg, 0.010 mmol) were dissolved in 1,4-dioxane (1.5 mL) in a microwave vial and degassed for 10 min with $N_2$. The mixture was stirred at 75° C. for 2 hours, then it was cooled to room temperature and filtered over Celite, washing with MeOH. The filtrate was evaporated and the residue was purified by column chromatography (KP-C18-HS, 30 g) eluting with a gradient of $CH_3CN$ in water from 2% to 95%. Fractions containing the desired compound were collected and evaporated under reduced pressure to give N-[2-[2-[2-[2-[2-[2-[2-[4-[(2,4-dimethoxyphenyl)methylamino]cinnolin-7-yl]-4-(4,4,5,5-tetramethyl-1,3,2-dioxaborolan-2-yl)phenoxy]ethoxy]ethoxy]ethoxy]ethoxy]ethyl]carbamate (58 mg, 0.066 mmol, 45.17% yield) as a colourless oil. $^1$H NMR (400 MHz, DMSO-$d_6$) δ 1.31 (s, 12H), 1.36 (s, 9H), 3.04 (q, J=6.03 Hz, 2H), 3.33-3.49 (m, 16H), 3.53 (t, J=3.28 Hz, 2H), 3.66-3.79 (m, 5H), 3.89 (s, 3H), 4.24 (t, J=4.67 Hz, 2H), 4.52 (d, J=5.85 Hz, 2H), 6.48 (dd, J=8.42, 2.40 Hz, 1H), 6.64 (d, J=2.38 Hz, 1H), 6.68-6.75 (m, 1H), 7.17 (d, J=8.37 Hz, 1H), 7.22 (d, J=8.76 Hz, 1H), 7.69-7.77 (m, 2H), 7.85 (dd, J=8.80, 1.83 Hz, 1H), 8.00 (t, J=5.94 Hz, 1H), 8.18 (d, J=1.78 Hz, 1H), 8.34 (d, J=8.86 Hz, 1H), 8.47 (s, 1H). LC-MS (Method A): r.t. 1.00 min, MS (ESI) m/z=877.9 [M+H]$^+$.

Intermediate 113: 7-[2-[2-[2-[2-[2-[2-(2-aminoethoxy)ethoxy]ethoxy]ethoxy]ethoxy]-5-(4,4,5,5-tetramethyl-1,3,2-dioxaborolan-2-yl)phenyl]cinnolin-4-amine trifluoroacetic Acid Salt

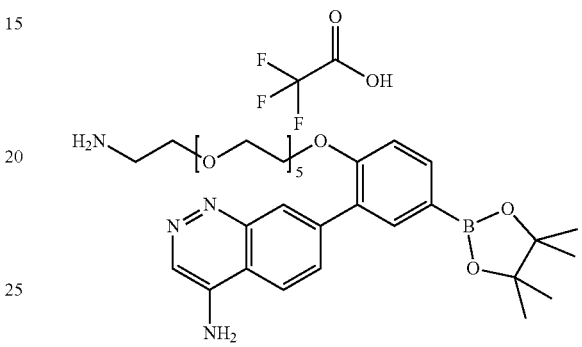

A solution of tert-butyl N-[2-[2-[2-[2-[2-[2-[2-[4-[(2,4-dimethoxyphenyl)methylamino]cinnolin-7-yl]-4-(4,4,5,5-tetramethyl-1,3,2-dioxaborolan-2-yl)phenoxy]ethoxy]ethoxy]ethoxy]ethoxy]ethyl]carbamate (55.0 mg, 0.060 mmol) in DCM (0.5 mL) and trifluoroacetic acid (0.5 mL) was stirred for 1 hour at room temperature then it was concentrated under reduced pressure. The residue was dissolved in DCM/MeOH (1/1) and filtered over Celite. The organic phase was evaporated to give 7-[2-[2-[2-[2-[2-[2-(2-aminoethoxy)ethoxy]ethoxy]ethoxy]ethoxy]phenyl]-5-(4,4,5,5-tetramethyl-1,3,2-dioxaborolan-2-yl)phenyl]cinnolin-4-amine trifluoroacetic acid salt (50 mg, 0.074 mmol, 100% yield) as a pale-yellow oil. $^1$H NMR (400 MHz, DMSO-$d_6$) δ 1.31 (s, 12H), 2.97 (q, J=5.53 Hz, 2H), 3.37-3.59 (m, 18H), 3.75 (dd, J=5.55, 3.28 Hz, 2H), 4.23-4.30 (m, 2H), 7.28 (d, J=8.36 Hz, 1H), 7.71-7.81 (m, 4H), 8.00 (d, J=1.65 Hz, 1H), 8.07 (dd, J=8.91, 1.64 Hz, 1H), 8.45 (d, J=8.97 Hz, 1H), 8.50 (s, 1H), 9.75 (br.s, 1H), 9.89 (br.s, 1H). LC-MS (Method A): r.t. 0.57 min, MS (ESI) m/z=627.6 [M+H]$^+$.

Intermediate 114: 5-[(3aS,4S,6aR)-2-oxo-hexahydro-1H-thieno[3,4-d]imidazol-4-yl]-N-{17-[2-(4-aminocinnolin-7-yl)-4-(4,4,5,5-tetramethyl-1,3,2-dioxaborolan-2-yl)phenoxy]-3,6,9,12,15-pentaoxaheptadecan-1-yl}pentanamide

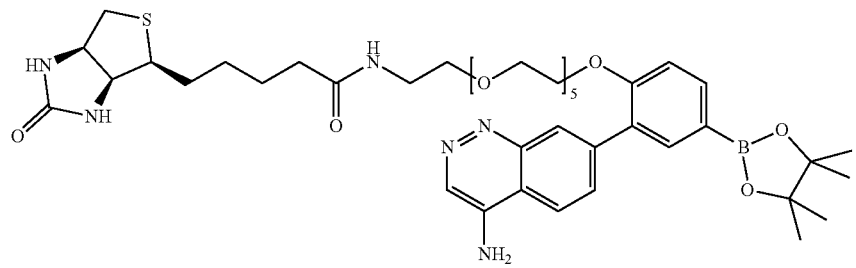

A mixture of 7-[2-[2-[2-[2-[2-[2-(2-aminoethoxy)ethoxy]ethoxy]ethoxy]ethoxy]ethoxy]-5-(4,4,5,5-tetramethyl-1,3,2-dioxaborolan-2-yl)phenyl]cinnolin-4-amine trifluoroacetic acid salt (50.0 mg, 0.080 mmol) and biotin-OSu (27.24 mg, 0.080 mmol) in dry DMF (1 mL) was stirred at room temperature for 1 hour. The reaction mixture was diluted with water and extracted with DCM. The combined organic phases were washed with brine, dried over sodium sulphate and concentrated under reduced pressure to give 5-[(3aS,4S,6aR)-2-oxo-hexahydro-1H-thieno[3,4-d]imidazol-4-yl]-N-{17-[2-(4-aminocinnolin-7-yl)-4-(4,4,5,5-tetramethyl-1,3,2-dioxaborolan-2-yl)phenoxy]-3,6,9,12,15-pentaoxaheptadecan-1-yl}pentanamide (60 mg, 0.070 mmol, 88.16% yield) as a yellow vitreous oil. $^1$H NMR (400 MHz, DMSO-$d_6$) δ 1.31 (s, 12H), 1.40-1.54 (m, 4H), 1.55-1.70 (m, 2H), 2.06 (t, J=7.41 Hz, 2H), 2.78-2.83 (m, 2H), 3.04-3.13 (m, 2H), 3.17 (q, J=5.86 Hz, 2H), 3.37 (t, J=5.92 Hz, 2H), 3.39-3.65 (m, 15H), 3.74-3.78 (m, 2H), 4.07-4.19 (m, 1H), 4.22-4.35 (m, 3H), 7.27 (d, J=8.30 Hz, 1H), 7.74 (d, J=1.66 Hz, 1H), 7.78 (dd, J=8.28, 1.65 Hz, 1H), 7.82 (t, J=5.73 Hz, 1H), 8.02-8.08 (m, 2H), 8.52 (d, J=8.31 Hz, 2H), 9.87 (s, 1H), 10.00 (s, 1H). LC-MS (Method A): r.t. 0.73 min, MS (ESI) m/z=853.9 [M+H]$^+$.

Intermediate 115: 6-(3-chloro-2-fluoro-6-methoxyphenyl)-N-[(2,4-dimethoxyphenyl)methyl]-4-methylphthalazin-1-amine

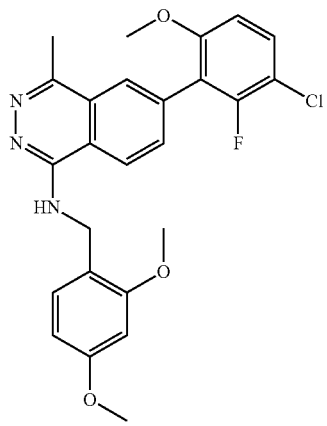

A mixture of 1-chloro-2-fluoro-3-iodo-4-methoxybenzene (233.6 mg, 0.820 mmol), [1-[(2,4-dimethoxyphenyl)methylamino]-4-methylphthalazin-6-yl]boronic acid (300.0 mg, 0.820 mmol) and aqueous 2N sodium carbonate solution (815.45 uL, 1.63 mmol) in 1,2-dimethoxyethane (6 mL) was degassed for 10 min. Then [1,1'-bis(di-tert-butylphosphino)ferrocene]dichloropalladium(II) (53.31 mg, 0.080 mmol) was added and the resulting mixture was stirred at 85° C. for 6 hours. The mixture was filtered over Celite, washing with EtOAc. The filtrate was concentrated in vacuo and the residue was purified by column chromatography (KP-NH silica gel, SNAP 28 g) eluting with a gradient of EtOAc in cyclohexane from 0% to 100% to give 6-(3-chloro-2-fluoro-6-methoxyphenyl)-N-[(2,4-dimethoxyphenyl)methyl]-4-methylphthalazin-1-amine (233 mg, 0.498 mmol, 61.06% yield) as a viscous oil. $^1$H NMR (400 MHz, DMSO-$d_6$) δ 2.65 (s, 3H), 3.73 (s, 3H), 3.78 (s, 3H), 3.84 (s, 3H), 4.67 (d, J=5.61 Hz, 2H), 6.43 (dd, J=8.37, 2.38 Hz, 1H), 6.58 (d, J=2.38 Hz, 1H), 7.09 (dd, J=9.14, 1.46 Hz, 1H), 7.13 (d, J=8.36 Hz, 1H), 7.59-7.68 (m, 2H), 7.78-7.92 (m, 1H), 7.98 (t, J=1.29 Hz, 1H), 8.43 (d, J=8.49 Hz, 1H). LC-MS (Method A): r.t. 0.86 min, MS (ESI) m/z=468.3 [M+H]$^+$.

Intermediate 116: 1-bromo-4-(difluoromethyl)-2-methoxybenzene

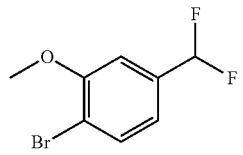

DAST (0.52 mL, 3.95 mmol) was added dropwise to a solution of 4-bromo-3-methoxybenzaldehyde (500 mg, 2.325 mmol) in dichloromethane (2.325 mL) at 0° C. After addition was complete the reaction mixture was allowed to warm to room temperature and stirred overnight. It was then quenched with a saturated solution of NaHCO$_3$ and extracted three times with EtOAc. The combined organic phases were washed with brine, dried over sodium sulfate, filtered and concentrated under reduced pressure. The residue was purified by column chromatography (KP silica gel, SNAP 50) eluting with a gradient of EtOAc in cyclohexane from 1% to 30% to give 1-bromo-4-(difluoromethyl)-2-methoxybenzene (520 mg, 2.194 mmol, 94.35% yield) as a colourless oil. $^1$H NMR (400 MHz, Chloroform-d) δ 3.96 (s, 3H), 6.63 (t, J=56.35 Hz, 1H), 6.99 (dd, J=8.11, 1.65 Hz, 1H), 7.05 (d, J=1.77 Hz, 1H), 7.64 (dd, J=8.03, 1.25 Hz, 1H). LC-MS (Method A): r.t. 1.11 min, MS (ESI) m/z of product not observed due to poor ionization.

Intermediate 117: 1-bromo-5-chloro-4-(difluoromethyl)-2-methoxybenzene

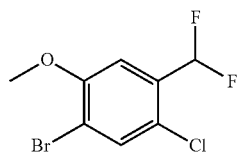

To a solution of 1-bromo-4-(difluoromethyl)-2-methoxybenzene (520.0 mg, 2.19 mmol) in trifluoroacetic acid (5 mL) and DMF (8 mL), 1-chloropyrrolidine-2,5-dione (292.93 mg, 2.19 mmol) was added. The resulting mixture was stirred at 60° C. for 3 days then it was cooled to room temperature and quenched with a saturated solution of Na$_2$S$_2$O$_3$. The mixture was extracted three times with EtOAc. The combined organic phases were washed with water and brine, dried over sodium sulfate, filtered and concentrated in vacuo. The residue was purified by column chromatography (KP-C18-HS, 60 g) eluting with a gradient of CH$_3$CN in water (+0.1% of HCOOH) from 1% to 90%. Fractions containing the desired compound were collected and evaporated under reduced pressure to give 1-bromo-5-chloro-4-(difluoromethyl)-2-methoxybenzene (90 mg, 0.332 mmol, 15.11% yield) as a white solid. $^1$H NMR (400 MHz, Chloroform-d) δ 3.96 (s, 3H), 6.92 (t, J=54.85 Hz, 1H), 7.17 (s, 1H), 7.64 (d, J=1.33 Hz, 1H). LC-MS (Method A): r.t. 1.24 min, MS (ESI) m/z of product not observed due to poor ionization.

Intermediate 118: 6-[5-chloro-4-(difluoromethyl)-2-methoxyphenyl]-N-[(2,4-dimethoxyphenyl)methyl]-4-methylphthalazin-1-amine

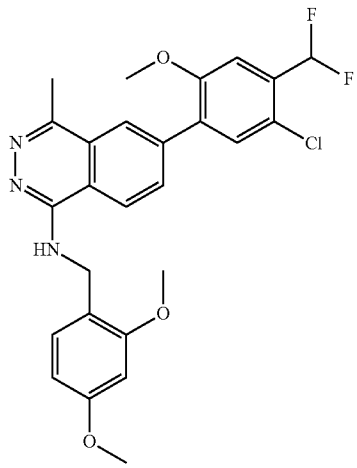 [SMILES: COc1ccc(CNc2nnc(C)c3cc(-c4cc(Cl)c(C(F)F)cc4OC)ccc23)c(OC)c1]

A mixture of 1-bromo-5-chloro-4-(difluoromethyl)-2-methoxybenzene (80.0 mg, 0.290 mmol) and [1-[(2,4-dimethoxyphenyl)methylamino]-4-methylphthalazin-6-yl]boronic acid (122.44 mg, 0.290 mmol) in 1,2-dimethoxyethane (1.228 mL) and aqueous 2N sodium carbonate solution (290 uL, 0.590 mmol) was degassed for 10 minutes with $N_2$. Then [1,1'-bis(di-tert-butylphosphino)ferrocene]dichloropalladium(II) (19.26 mg, 0.030 mmol) was added and the resulting reaction mixture was stirred at 80° C. for 3 hours. It was then cooled to room temperature and filtered over Celite, washing with EtOAc. The filtrate was evaporated and the residue was purified by column chromatography (KP silica gel, SNAP 25) eluting with a gradient of EtOAc in dichloromethane from 5% to 50% to give 6-[5-chloro-4-(difluoromethyl)-2-methoxyphenyl]-N-[(2,4-dimethoxyphenyl)methyl]-4-methylphthalazin-1-amine (60 mg, 0.120 mmol, 40.73% yield) as a viscous oil. LC-MS (Method B): r.t. 1.14 min, MS (ESI) m/z=500.8 [M+H]$^+$.

Intermediate 119: 4-chloro-2-[1-[(2,4-dimethoxyphenyl)methylamino]-4-methylphthalazin-6-yl]-6-fluorobenzonitrile

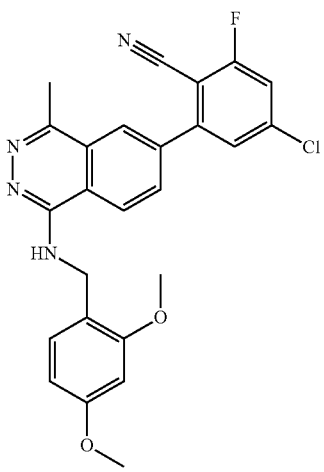 [SMILES: COc1ccc(CNc2nnc(C)c3cc(-c4cc(Cl)cc(F)c4C#N)ccc23)c(OC)c1]

A microwave vial was charged with [1-[(2,4-dimethoxyphenyl)methylamino]-4-methylphthalazin-6-yl]boronic acid (150.0 mg, 0.370 mmol), 2-bromo-4-chloro-6-fluorobenzonitrile (94.2 mg, 0.400 mmol) and [1,1'-bis(di-tert-butylphosphino)ferrocene]dichloropalladium(II) (23.88 mg, 0.040 mmol) in 1,2-dimethoxyethane (3.653 mL) and aqueous 2N sodium carbonate solution (0.37 mL, 0.730 mmol). The resulting mixture was degassed with $N_2$ for 10 min and then stirred at 70° C. for 3 hours. It was then cooled to room temperature and filtered over Celite, washing with EtOAc. The filtrate was evaporated and the residue was purified by column chromatography (KP silica gel, SNAP 25) eluting with a gradient of EtOAc in dichloromethane from 5% to 80% to give 4-chloro-2-[1-[(2,4-dimethoxyphenyl)methylamino]-4-methylphthalazin-6-yl]-6-fluorobenzonitrile (110 mg, 0.238 mmol, 65.06% yield) as a yellow solid. $^1$H NMR (400 MHz, DMSO-$d_6$) δ 2.73 (s, 3H), 3.73 (s, 3H), 3.85 (s, 3H), 4.68 (d, J=5.58 Hz, 2H), 6.44 (dd, J=8.36, 2.42 Hz, 1H), 6.59 (d, J=2.39 Hz, 1H), 7.14 (d, J=8.34 Hz, 1H), 7.72 (t, J=5.64 Hz, 1H), 7.90 (dd, J=1.94, 0.87 Hz, 1H), 7.98 (dd, J=9.25, 1.91 Hz, 1H), 8.16 (dd, J=8.50, 1.85 Hz, 1H), 8.29 (d, J=1.82 Hz, 1H), 8.55 (d, J=8.57 Hz, 1H). LC-MS (Method A): r.t. 0.80 min, MS (ESI) m/z=463.9 [M+H]$^+$.

Intermediate 120: [4-cyano-3-[1-[(2,4-dimethoxyphenyl)methylamino]-4-methylphthalazin-6-yl]-5-fluorophenyl]boronic Acid

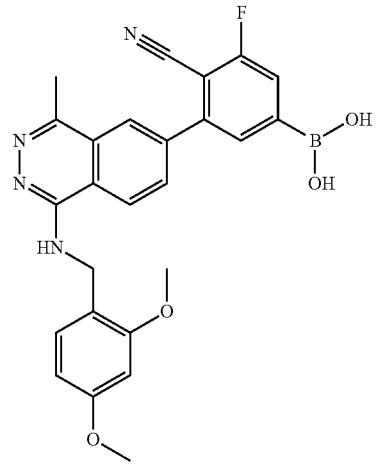 [SMILES: COc1ccc(CNc2nnc(C)c3cc(-c4cc(B(O)O)cc(F)c4C#N)ccc23)c(OC)c1]

Palladium(II) diacetate (2.55 mg, 0.010 mmol), 4-chloro-2-[1-[(2,4-dimethoxyphenyl)methylamino]-4-methylphthalazin-6-yl]-6-fluorobenzonitrile (105.0 mg, 0.230 mmol), potassium acetate (66.78 mg, 0.680 mmol), dicyclohexyl-[2-[2,4,6-tri(propan-2-yl)phenyl]phenyl]phosphine (10.80 mg, 0.020 mmol) and 4,4,5,5-tetramethyl-2-(4,4,5,5-tetramethyl-1,3,2-dioxaborolan-2-yl)-1,3,2-dioxaborolane (172.8 mg, 0.680 mmol) were dissolved in 1,4-dioxane (2.181 mL) in a microwave vial. The resulting mixture was degassed for 10 minutes with $N_2$ and stirred at 75° C. for 2 hours. It was then cooled to room temperature and filtered over Celite, washing with EtOAc. The filtrate was evaporated and the residue was purified by column chromatography (KP-C18-HS, 30 g) eluting with a gradient of $CH_3CN$ in water (+0.1% of HCOOH) from 1% to 70%. Fractions containing the desired compound were collected and evaporated under reduced pressure to give [4-cyano-3-[1-[(2,4-dimethoxyphenyl)methylamino]-4-methylphthalazin-6-yl]-5-fluorophe-

Intermediate 121: 1-chloro-5-iodo-4-methoxy-2-(trifluoromethyl)benzene

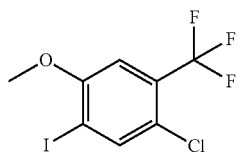

To a solution of 1-chloro-4-methoxy-2-(trifluoromethyl)benzene (1.0 g, 4.75 mmol) in DCM (15 mL), silver trifluoromethanesulfonate (1.46 g, 5.7 mmol) and iodine (1.32 g, 5.22 mmol) were added. The mixture was stirred at room temperature for 2 h. The mixture was diluted with DCM (50 mL) and washed with 20% aqueous $Na_2S_2O_3$ solution, saturated aqueous $NaHCO_3$ solution and brine. The organic phase was dried over $Na_2SO_4$, filtered and the solvent was evaporated to give crude 1-chloro-5-iodo-4-methoxy-2-(trifluoromethyl)benzene (780 mg, 2.31 mmol, 48.8% yield) which was used in the next step without further purification. $^1$H NMR (400 MHz, DMSO-$d_6$) δ 3.93 (s, 3H), 7.28 (s, 1H), 8.13 (d, J=0.82 Hz, 1H).

Intermediate 122: 6-[5-chloro-2-methoxy-4-(trifluoromethyl)phenyl]-N-[(2,4-dimethoxyphenyl)methyl]-4-methylphthalazin-1-amine

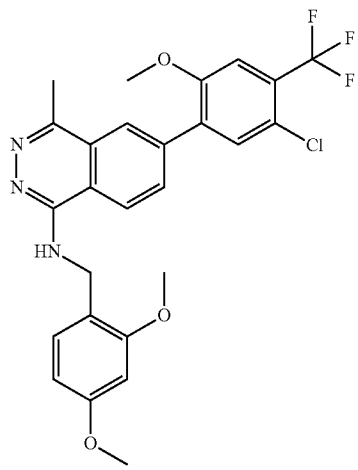 [SMILES: COc1ccc(CNc2nnc(C)c3cc(-c4cc(Cl)c(C(F)(F)F)cc4OC)ccc23)c(OC)c1]

A mixture of 1-chloro-5-iodo-4-methoxy-2-(trifluoromethyl)benzene (381.09 mg, 1.13 mmol), [1-[(2,4-dimethoxyphenyl)methylamino]-4-methylphthalazin-6-yl]boronic acid (400.0 mg, 1.13 mmol) and aqueous 2N sodium carbonate solution (1132.57 uL, 2.27 mmol) in 1,2-dimethoxyethane (8.333 mL) was degassed for 10 min. Then [1,1'-bis(di-tert-butylphosphino)ferrocene]dichloropalladium(II) (74.04 mg, 0.110 mmol) was added and the resulting reaction mixture was stirred at 85° C. for 6 hours. The mixture was filtered over Celite, washing with EtOAc. The filtrate was concentrated in vacuo and the residue was purified by column chromatography (KP-NH silica gel, SNAP 28 g) eluting with a gradient of EtOAc in cyclohexane from 0% to 100% to give 6-[5-chloro-2-methoxy-4-(trifluoromethyl)phenyl]-N-[(2,4-dimethoxyphenyl)methyl]-4-methylphthalazin-1-amine (237 mg, 0.458 mmol, 40.4% yield) as a viscous oil. $^1$H NMR (400 MHz, DMSO-$d_6$) δ 2.70 (s, 3H), 3.73 (s, 3H), 3.84 (s, 3H), 3.91 (s, 3H), 4.67 (d, J=5.60 Hz, 2H), 6.42 (dd, J=8.39, 2.41 Hz, 1H), 6.58 (d, J=2.40 Hz, 1H), 7.11 (d, J=8.39 Hz, 1H), 7.53 (s, 1H), 7.62 (t, J=5.74 Hz, 1H), 7.86 (d, J=0.82 Hz, 1H), 8.03 (dd, J=8.53, 1.74 Hz, 1H), 8.10 (d, J=1.74 Hz, 1H), 8.42 (d, J=8.53 Hz, 1H). LC-MS (Method A): r.t. 0.93 min, MS (ESI) m/z=518.3 [M+H]$^+$.

Intermediate 123: 6-[3-chloro-5-(trifluoromethyl)phenyl]-N-[(2,4-dimethoxyphenyl)methyl]-4-methylphthalazin-1-amine

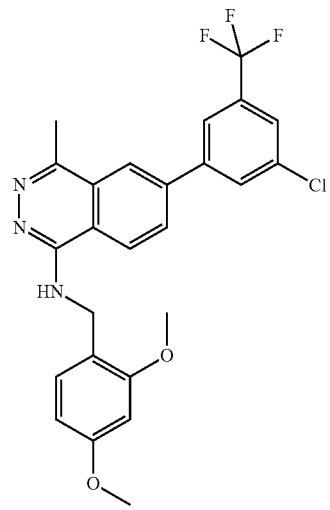 [SMILES: COc1ccc(CNc2nnc(C)c3cc(-c4cc(Cl)cc(C(F)(F)F)c4)ccc23)c(OC)c1]

A mixture of 3-bromo-5-chlorobenzotrifluoride (183.65 mg, 0.710 mmol), [1-[(2,4-dimethoxyphenyl)methylamino]-4-methylphthalazin-6-yl]boronic acid (250.0 mg, 0.710 mmol) and aqueous 2N sodium carbonate solution (707.85 uL, 1.42 mmol) in 1,2-dimethoxyethane (6 mL) was degassed for 10 min. Then [1,1'-bis(di-tert-butylphosphino)ferrocene]dichloropalladium(II) (46.28 mg, 0.070 mmol) was added and the resulting reaction mixture was stirred at 80° C. for 6 hours. The mixture was filtered over Celite, washing with EtOAc. The filtrate was concentrated in vacuo and the residue was purified by column chromatography (KP-NH silica gel, SNAP 28 g) with a gradient from of EtOAc in cyclohexane 0% to 100% to give 6-[3-chloro-5-(trifluoromethyl)phenyl]-N-[(2,4-dimethoxyphenyl)methyl]-4-methylphthalazin-1-amine (156 mg, 0.320 mmol, 45.17% yield) as a viscous oil. $^1$H NMR (400 MHz, DMSO-$d_6$) δ 2.78 (s, 3H), 3.73 (s, 3H), 3.84 (s, 3H), 4.66 (d, J=5.5 Hz, 2H), 6.43 (dd, J=8.4, 2.4 Hz, 1H), 6.58 (d, J=2.4 Hz, 1H), 7.12 (d, J=8.4 Hz, 1H), 7.67 (t, J=5.5 Hz, 1H), 8.00-7.89 (m, 1H), 8.24 (td, J=1.7, 0.8 Hz, 1H), 8.34-8.29 (m, 2H), 8.36 (d, J=1.9 Hz, 1H), 8.62-8.44 (m, 1H). LC-MS (Method A): r.t. 0.92 min, MS (ESI) m/z=488.32 [M+H]$^+$.

Intermediate 124: [3-[1-[(2,4-dimethoxyphenyl)methylamino]-4-methylphthalazin-6-yl]-5-(trifluoromethyl)phenyl]boronic Acid

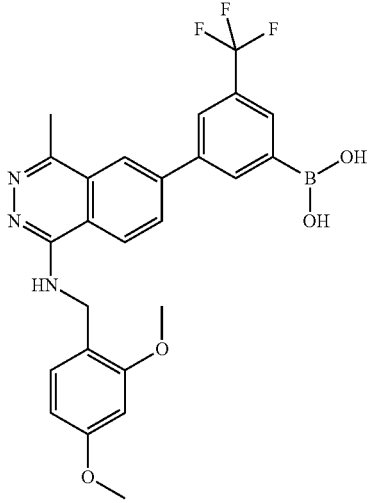 [SMILES: COc1ccc(CNc2nnc(C)c3cc(-c4cc(B(O)O)cc(C(F)(F)F)c4)ccc23)c(OC)c1]

Palladium(II) diacetate (3.59 mg, 0.020 mmol), 6-[3-chloro-5-(trifluoromethyl)phenyl]-N-[(2,4-dimethoxyphenyl)methyl]-4-methylphthalazin-1-amine (156.0 mg, 0.320 mmol), dicyclohexyl-[2-[2,4,6-tri(propan-2-yl)phenyl]phenyl]phosphine (12.19 mg, 0.030 mmol), potassium acetate (94.14 mg, 0.960 mmol) and 4,4,5,5-tetramethyl-2-(4,4,5,5-tetramethyl-1,3,2-dioxaborolan-2-yl)-1,3,2-dioxaborolane (243.58 mg, 0.960 mmol) were dissolved in 1,4-dioxane (8.478 mL). The mixture was degassed for 10 min with Ar, then stirred at 90° C. for 18 hours. The mixture was filtered over a pad of Celite, washing with EtOAc. The filtrate was concentrated in vacuo and the residue was purified by column chromatography (KP-C18-HS, SNAP 30 g) eluting with a gradient of $CH_3CN$ in water from 1% to 95% to give [3-[1-[(2,4-dimethoxyphenyl)methylamino]-4-methylphthalazin-6-yl]-5-(trifluoromethyl)phenyl]boronic acid (90 mg, 0.181 mmol, 56.61% yield) as a pale yellow solid. LC-MS (Method A): r.t. 0.79 min, MS (ESI) m/z=498.37 $[M+H]^+$.

Intermediate 125: 6-[5-chloro-2-(trifluoromethyl)phenyl]-N-[(2,4-dimethoxyphenyl)methyl]-4-methylphthalazin-1-amine

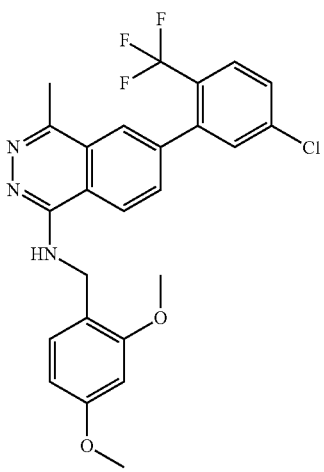 [SMILES: COc1ccc(CNc2nnc(C)c3cc(-c4cc(Cl)ccc4C(F)(F)F)ccc23)c(OC)c1]

A microwave vial was charged with [1-[(2,4-dimethoxyphenyl)methylamino]-4-methylphthalazin-6-yl]boronic acid (150.0 mg, 0.420 mmol), 2-bromo-4-chlorobenzotrifluoride (110.19 mg, 0.420 mmol), [1,1'-bis(di-tert-butylphosphino)ferrocene]dichloropalladium(II) (27.77 mg, 0.040 mmol) and aqueous 2N sodium carbonate solution (0.42 mL, 0.850 mmol) in 1,2-dimethoxyethane (6.229 mL) and the mixture was degassed with $N_2$ for 10 min and then stirred at 70° C. for 3 h. It was then cooled to room temperature and filtered over Celite, washing with EtOAc. The filtrate was evaporated and the residue was purified by column chromatography (KP silica gel, SNAP50) eluting with a gradient of methanol in dichloromethane from 1% to 15% to give 6-[5-chloro-2-(trifluoromethyl)phenyl]-N-[(2,4-dimethoxyphenyl)methyl]-4-methylphthalazin-1-amine (240 mg, 0.89 mmol, 56.95% yield) as a colourless oil. $^1$H NMR (400 MHz, DMSO-$d_6$) δ 2.67 (s, 3H), 3.74 (s, 3H), 3.85 (s, 3H), 4.68 (d, J=5.56 Hz, 2H), 6.44 (dd, J=8.35, 2.39 Hz, 1H), 6.59 (d, J=2.42 Hz, 1H), 7.15 (d, J=8.30 Hz, 1H), 7.64-7.72 (m, 2H), 7.79 (ddd, J=8.55, 2.20, 0.91 Hz, 1H), 7.83-7.90 (m, 1H), 7.95 (d, J=8.56 Hz, 2H), 8.45 (d, J=8.56 Hz, 1H). LC-MS (Method A): r.t. 0.89 min, MS (ESI) m/z=488.3 $[M+H]^+$.

Intermediate 126: [3-[1-[(2,4-dimethoxyphenyl)methylamino]-4-methylphthalazin-6-yl]-4-(trifluoromethyl)phenyl]boronic Acid

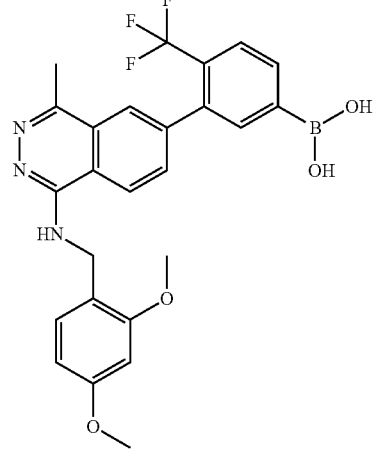

Palladium(II) diacetate (2.876 mg, 0.013 mmol), 6-[5-chloro-2-(trifluoromethyl)phenyl]-N-[(2,4-dimethoxyphenyl)methyl]-4-methylphthalazin-1-amine (125.0 mg, 0.256 mmol), potassium acetate (75.43 mg, 0.769 mmol), dicyclohexyl-[2-[2,4,6-tri(propan-2-yl)phenyl]phenyl]phosphine (12.21 mg, 0.026 mmol), and 4,4,5,5-tetramethyl-2-(4,4,5,5-tetramethyl-1,3,2-dioxaborolan-2-yl)-1,3,2-dioxaborolane (195.18 mg, 0.769 mmol) were dissolved in 1,4-dioxane (2.597 mL) in a microwave vial. The resulting mixture was degassed for 10 minutes with $N_2$ and stirred at 75° C. for 2 h. It was then cooled to room temperature and filtered over Celite, washing with EtOAc. The filtrate was evaporated and the residue was purified by column chromatography (KP-C18-HS, 30 g) eluting with a gradient of $CH_3CN$ in water (+0.1% of HCOOH) from 1% to 70%. Fractions containing the desired compound were collected and evaporated under reduced pressure to give [3-[1-[(2,4-dimethoxyphenyl)methylamino]-4-methylphthalazin-6-yl]-

4-(trifluoromethyl)phenyl]boronic acid (95 mg, 0.191 mmol, 74.57% yield) as a white solid. $^1$H NMR (400 MHz, DMSO-$d_6$) δ 2.66 (s, 3H), 3.73 (s, 3H), 3.84 (s, 3H), 4.67 (d, J=5.53 Hz, 2H), 6.44 (dd, J=8.36, 2.42 Hz, 1H), 6.58 (d, J=2.41 Hz, 1H), 7.14 (d, J=8.27 Hz, 1H), 7.63-7.71 (m, 1H), 7.84-7.94 (m, 3H), 8.04 (d, J=7.87 Hz, 1H), 8.44-8.49 (m, 2H). LC-MS (Method A): r.t. 0.78 min, MS (ESI) m/z=498.3 [M+H]$^+$.

Intermediate 127:
1-bromo-3-chloro-5-dimethylphosphorylbenzene

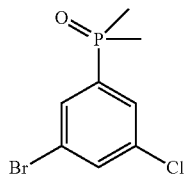

1-Bromo-3-chloro-5-iodobenzene (500.0 mg, 1.58 mmol), dimethylphosphine oxide (122.97 mg, 1.58 mmol), triethylamine (0.22 mL, 1.58 mmol), (1E,4E)-1,5-diphenyl-3-penta-1,4-dienone palladium (144.28 mg, 0.160 mmol) and (5-diphenylphosphino-9,9-dimethyl-4-xanthenyl)-diphenylphosphine (91.16 mg, 0.160 mmol) were dissolved in 1,4-dioxane (5.901 mL) in a microwave vial. The mixture was degassed with N$_2$ for 10 minutes and stirred at room temperature for 24 hours. It was then cooled to room temperature and filtered over Celite, washing with EtOAc. The filtrate was evaporated and the residue was purified by column chromatography (KP silica gel, SNAP 50) eluting with a gradient of methanol in dichloromethane from 1% to 15% to give 1-bromo-3-chloro-5-dimethylphosphorylbenzene (240 mg, 0.897 mmol, 56.95% yield) as a colourless oil. $^1$H NMR (400 MHz, DMSO-$d_6$) δ 1.68 (s, 3H), 1.71 (s, 3H), 7.83 (ddd, J=11.09, 1.97, 1.15 Hz, 1H), 7.87-7.97 (m, 2H). LC-MS (Method A): r.t. 0.75 min, MS (ESI) m/z=267.06 and 269.06 [M+H]$^+$.

Intermediate 128: 6-(3-chloro-5-dimethylphosphorylphenyl)-N-[(2,4-dimethoxyphenyl)methyl]-4-methylphthalazin-1-amine

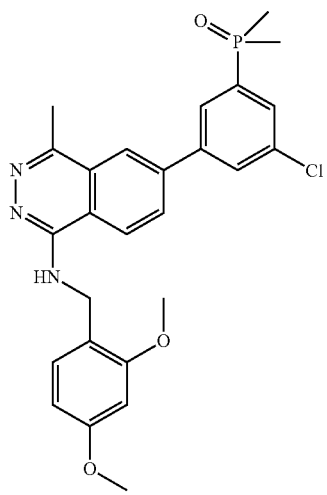 [SMILES: COc1ccc(CNc2nnc(C)c3cc(-c4cc(Cl)cc(P(C)(C)=O)c4)ccc23)c(OC)c1]

[1-[(2,4-Dimethoxyphenyl)methylamino]-4-methylphthalazin-6-yl]boronic acid (200.0 mg, 0.510 mmol), 1-bromo-3-chloro-5-dimethylphosphorylbenzene (149.96 mg, 0.560 mmol) and [1,1'-bis(di-tert-butylphosphino)ferrocene] dichloropalladium(II) (33.32 mg, 0.050 mmol) were dissolved in 1,2-dimethoxyethane (5.097 mL) and aqueous 2N sodium carbonate solution (0.51 mL, 1.02 mmol). The mixture was degassed with N$_2$ for 10 minutes and stirred at 70° C. for 3 hours. It was then cooled to room temperature and filtered over Celite, washing with EtOAc. The filtrate was evaporated and the residue was purified by column chromatography (KP silica gel, SNAP 50) eluting with a gradient of methanol in dichloromethane from 1% to 15% to give 6-(3-chloro-5-dimethylphosphorylphenyl)-N-[(2,4-dimethoxyphenyl)methyl]-4-methylphthalazin-1-amine (110 mg, 0.222 mmol, 43.52% yield) as a yellow solid. LC-MS (Method A): r.t. 0.68 min, MS (ESI) m/z=496.4 [M+H]$^+$.

Intermediate 129: [3-[1-[(2,4-dimethoxyphenyl)methylamino]-4-methylphthalazin-6-yl]-5-dimethylphosphorylphenyl]boronic Acid

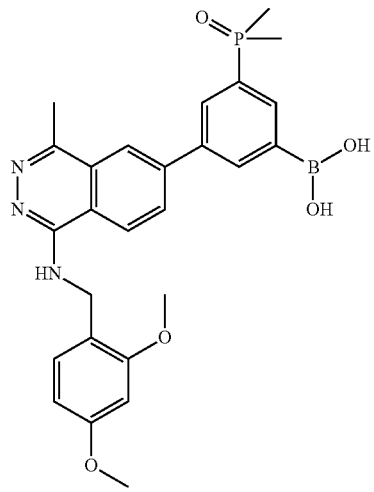 [SMILES: COc1ccc(CNc2nnc(C)c3cc(-c4cc(B(O)O)cc(P(C)(C)=O)c4)ccc23)c(OC)c1]

Palladium(II) diacetate (2.49 mg, 0.010 mmol), 6-(3-chloro-5-dimethylphosphorylphenyl)-N-[(2,4-dimethoxyphenyl)methyl]-4-methylphthalazin-1-amine (110.0 mg, 0.220 mmol), dicyclohexyl-[2-[2,4,6-tri(propan-2-yl)phenyl]phenyl]phosphine (10.57 mg, 0.020 mmol), potassium acetate (65.3 mg, 0.670 mmol) and 4,4,5,5-tetramethyl-2-(4,4,5,5-tetramethyl-1,3,2-dioxaborolan-2-yl)-1,3,2-dioxaborolane (168.97 mg, 0.670 mmol) were dissolved in 1,4-dioxane (2.285 mL) in a microwave vial. The resulting mixture was degassed for 10 minutes with N$_2$ and stirred at 75° C. for 2 h. It was then cooled to room temperature and filtered over Celite, washing with EtOAc. The filtrate was evaporated and the residue was purified by column chromatography (KP-C18-HS, 30 g), eluting with a gradient of CH$_3$CN in water (+0.1% of HCOOH) from 1% to 70%. Fractions containing the desired compound were collected and evaporated under reduced pressure to give [3-[1-[(2,4-dimethoxyphenyl)methylamino]-4-methylphthalazin-6-yl]-5-dimethylphosphorylphenyl]boronic acid (94 mg, 0.186 mmol, 83.87% yield) as a white solid. LC-MS (Method A): r.t. 0.57 min, MS (ESI) m/z=506.4 [M+H]$^+$.

Intermediate 130:
1-bromo-5-chloro-2-iodo-4-methylbenzene

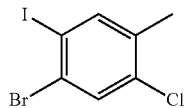

4-Bromo-2-chloro-1-methylbenzene (2.0 g, 9.73 mmol) was dissolved in trifluoroacetic acid (10 mL) and NIS (2.19 g, 9.73 mmol) was added. The mixture was stirred at room temperature for 3 days, observing the formation of a precipitate. The precipitate was filtered off, then dissolved in EtOAc and washed with aqueous $Na_2S_2O_3$ solution, aqueous $NaHCO_3$ solution and water. The organic phase was dried over $Na_2SO_4$, filtered and the solvent was evaporated to give 1-bromo-5-chloro-2-iodo-4-methylbenzene (2.67 g, 8.057 mmol, 82.78% yield) as a pale yellow solid. $^1$H NMR (400 MHz, DMSO-$d_6$) δ 2.24 (d, J=0.77 Hz, 3H), 7.76 (s, 1H), 7.93 (d, J=0.83 Hz, 1H).

Intermediate 131:
2-bromo-4-chloro-5-methylbenzaldehyde

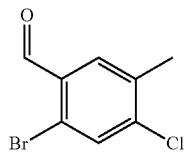

To a solution of 1-bromo-5-chloro-2-iodo-4-methylbenzene (2.67 g, 8.06 mmol) in THF (100 mL) cooled to −78° C., under nitrogen, was added dropwise a 1.6M solution of n-butyllithium in hexanes (6.04 mL, 9.67 mmol) The mixture was stirred for 20 min at −78° C. then N,N-dimethylformamide (0.87 mL, 11.28 mmol) was added and the mixture was stirred at room temperature for 1 h. Saturated aqueous $NH_4Cl$ solution was added dropwise and the aqueous layer was extracted with $Et_2O$ (3×50 mL). The combined organic phases were dried over $Na_2SO_4$, filtered and the solvent was evaporated. The residue was purified by column chromatography (KP-Sil, SNAP 100 g) eluting with a gradient of EtOAc in cyclohexane from 0% to 20% to give 2-bromo-4-chloro-5-methylbenzaldehyde (1.05 g, 4.497 mmol, 55.81% yield, purity 80%) as an oil. $^1$H NMR (400 MHz, DMSO-$d_6$) δ 2.37 (s, 3H), 7.82-7.85 (m, 1H), 7.94 (s, 1H), 10.15 (s, 1H).

Intermediate 132:
2-bromo-4-chloro-5-methylbenzonitrile

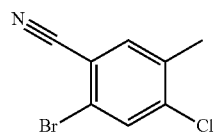

Step 1: To a solution of 2-bromo-4-chloro-5-methylbenzaldehyde (1.05 g, 4.5 mmol) in methanol (25 mL), sodium acetate trihydrate (1223.9 mg, 8.99 mmol) was added followed by hydroxylamine hydrochloride (437.49 mg, 6.3 mmol). The mixture was stirred at room temperature for 16 h and the volatiles were evaporated. The solid residue was taken up in DCM (50 mL) and washed with water and brine, dried over $Na_2SO_4$, filtered and the solvent was evaporated.

Step 2: The crude material from Step 1 was dissolved in DCM (25 mL), and triethylamine (1.73 mL, 12.43 mmol) was added. The mixture was cooled to 0° C. and triflic anhydride (0.84 mL, 4.97 mmol) was added dropwise. The mixture was stirred at room temperature for 16 h then diluted with DCM (50 mL) and washed with saturated aqueous $NaHCO_3$ solution and brine, dried over $Na_2SO_4$, filtered and the solvent was evaporated. The residue was purified by column chromatography (KP-Sil, SNAP 50 g) eluting with a gradient of EtOAc in cyclohexane from 0% to 10% to give 2-bromo-4-chloro-5-methylbenzonitrile (567 mg, 2.46 mmol, 54.6% yield over two steps) as a yellow solid. $^1$H NMR (400 MHz, DMSO-$d_6$) δ 2.33 (s, 3H), 8.01 (s, 1H), 8.06 (s, 1H). $^{13}$C NMR (101 MHz, DMSO-$d_6$) δ 140.09, 137.35, 136.97, 133.32, 122.56, 117.21, 113.66, 19.33.

Intermediate 133: 4-chloro-2-[1-[(2,4-dimethoxyphenyl)methylamino]-4-methylphthalazin-6-yl]-5-methylbenzonitrile

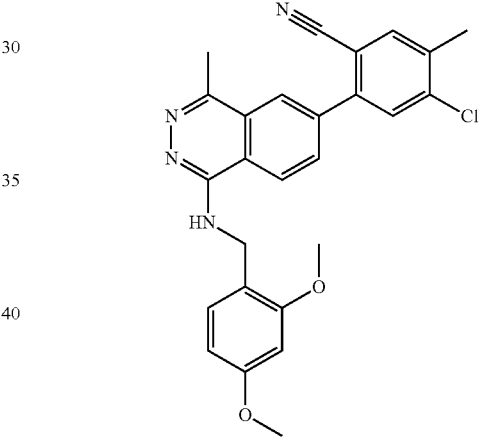

A mixture of 2-bromo-4-chloro-5-methylbenzonitrile (228.41 mg, 0.990 mmol), [1-[(2,4-dimethoxyphenyl)methylamino]-4-methylphthalazin-6-yl]boronic acid (350.0 mg, 0.990 mmol) and aqueous 2N sodium carbonate solution (991.0 uL, 1.98 mmol) in 1,2-dimethoxyethane (8.4 mL) was degassed for 10 min. Then [1,1'-bis(di-tert-butylphosphino)ferrocene]dichloropalladium(II) (64.79 mg, 0.100 mmol) was added and the resulting reaction mixture was stirred at 80° C. for 6 hours. The mixture was filtered over Celite, washing with EtOAc. The filtrate was concentrated in vacuo and the residue was purified by column chromatography (KP-NH silica gel, SNAP 28 g) eluting with a gradient of EtOAc in cyclohexane from 0% to 100% to give 4-chloro-2-[1-[(2,4-dimethoxyphenyl)methylamino]-4-methylphthalazin-6-yl]-5-methylbenzonitrile (210 mg, 0.458 mmol, 46.17% yield) as a viscous oil. $^1$H NMR (500 MHz, DMSO-$d_6$) δ 2.45 (s, 3H), 2.72 (s, 3H), 3.72 (s, 3H), 3.84 (s, 3H), 4.67 (d, J=5.5 Hz, 2H), 6.43 (dd, J=8.4, 2.3 Hz, 1H), 6.58 (d, J=2.3 Hz, 1H), 7.12 (d, J=8.4 Hz, 1H), 7.71 (t, J=5.6 Hz, 1H), 7.86-7.99 (m, 1H), 8.07-8.14 (m, 1H), 8.09-8.13 (m, 1H), 8.18-8.24 (m, 1H), 8.52 (d, J=8.6 Hz, 1H). LC-MS (Method A): r.t.=0.85 min, MS (ESI) m/z=459.28 [M+H]$^+$.

Intermediate 134: 2-[1-[(2,4-dimethoxyphenyl)methylamino]-4-methylphthalazin-6-yl]-5-methyl-4-(4,4,5,5-tetramethyl-1,3,2-dioxaborolan-2-yl)benzonitrile

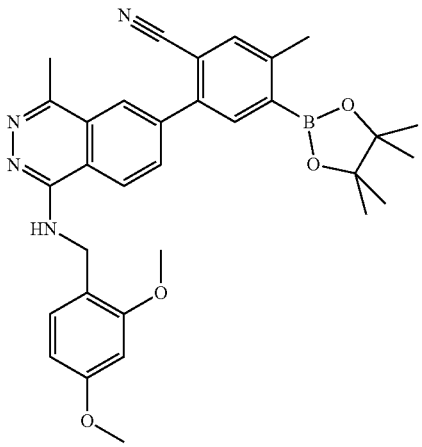 [SMILES: COc1ccc(CNc2nnc(C)c3cc(-c4cc(B5OC(C)(C)C(C)(C)O5)c(C)cc4C#N)ccc23)c(OC)c1]

Palladium(II) diacetate (5.14 mg, 0.020 mmol), 4-chloro-2-[1-[(2,4-dimethoxyphenyl)methylamino]-4-methylphthalazin-6-yl]-5-methylbenzonitrile (210.0 mg, 0.460 mmol), dicyclohexyl-[2-[2,4,6-tri(propan-2-yl)phenyl]phenyl]phosphine (17.45 mg, 0.040 mmol), potassium acetate (134.72 mg, 1.37 mmol) and 4,4,5,5-tetramethyl-2-(4,4,5,5-tetramethyl-1,3,2-dioxaborolan-2-yl)-1,3,2-dioxaborolane (348.59 mg, 1.37 mmol) were dissolved in 1,4-dioxane (11.4 mL). The mixture was degassed for 10 min with Ar, then stirred at 90° C. for 18 hours. The mixture was filtered over a pad of Celite, washing with EtOAc and concentrated in vacuo. The residue was purified by column chromatography (KP-C18-HS, SNAP 30 g) eluting with a gradient of $CH_3CN$ in water from 1% to 95% to give 2-[1-[(2,4-dimethoxyphenyl)methylamino]-4-methylphthalazin-6-yl]-5-methyl-4-(4,4,5,5-tetramethyl-1,3,2-dioxaborolan-2-yl)benzonitrile (105 mg, 0.191 mmol, 41.69% yield) as a mixture of boronic ester and boronic acid. LC-MS (Method A): r.t. (boronic acid) =0.70 min, MS (ESI) m/z=469.38 [M+H]$^+$. r.t. (boronic ester)=1.00 min; MS (ESI) m/z=551.49 [M+H]$^+$.

Intermediate 135: 6-(5-chloro-2-methoxy-3-methylphenyl)-N-[(2,4-dimethoxyphenyl)methyl]-4-methylphthalazin-1-amine

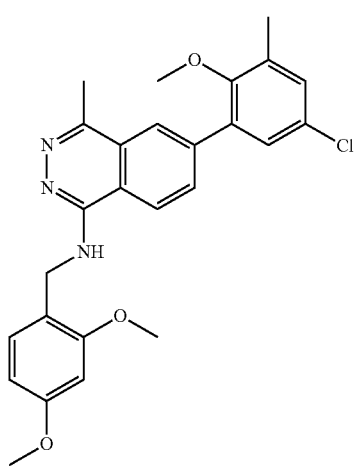 [SMILES: COc1ccc(CNc2nnc(C)c3cc(-c4cc(Cl)cc(C)c4OC)ccc23)c(OC)c1]

A mixture of [1-[(2,4-dimethoxyphenyl)methylamino]-4-methylphthalazin-6-yl]boronic acid (374.91 mg, 1.06 mmol) and 1-bromo-5-chloro-2-methoxy-3-methylbenzene (250.0 mg, 1.06 mmol) in 1,2-dimethoxyethane (9 mL) and aqueous 2N sodium carbonate solution (1061.53 uL, 2.12 mmol) was degassed for 10 min with $N_2$. Then, [1,1'-bis(di-tert-butylphosphino)ferrocene]dichloropalladium(II) (69.4 mg, 0.110 mmol) was added. The mixture was stirred at 80° C. for 20 hours, then it was cooled to room temperature and filtered over Celite, washing with MeOH. The filtrate was evaporated and the residue was purified by column chromatography (KP-NH silica gel, 2×SNAP 28 in series) eluting with a gradient of EtOAc in cyclohexane from 0% to 50% to give 6-(5-chloro-2-methoxy-3-methylphenyl)-N-[(2,4-dimethoxyphenyl)methyl]-4-methylphthalazin-1-amine (250 mg, 0.539 mmol, 50.76% yield) as a yellow/brown powder. $^1$H NMR (400 MHz, DMSO-d$_6$) δ 2.32 (s, 3H), 2.70 (s, 3H), 3.31 (s, 3H), 3.72 (s, 3H), 3.84 (s, 3H), 4.66 (d, J=5.54 Hz, 2H), 6.43 (dd, J=8.36, 2.42 Hz, 1H), 6.58 (d, J=2.39 Hz, 1H), 7.13 (d, J=8.33 Hz, 1H), 7.41 (dd, J=2.69, 0.84 Hz, 1H), 7.46 (d, J=2.71 Hz, 1H), 7.62 (t, J=5.80 Hz, 1H), 8.04 (dd, J=8.50, 1.74 Hz, 1H), 8.10 (d, J=1.75 Hz, 1H), 8.43 (d, J=8.64 Hz, 1H). LC-MS (Method A): r.t. 0.91 min, MS (ESI) m/z=464.3 [M+H]$^+$.

Intermediate 136: N-[(2,4-dimethoxyphenyl)methyl]-6-[2-methoxy-3-methyl-5-(4,4,5,5-tetramethyl-1,3,2-dioxaborolan-2-yl)phenyl]-4-methylphthalazin-1-amine

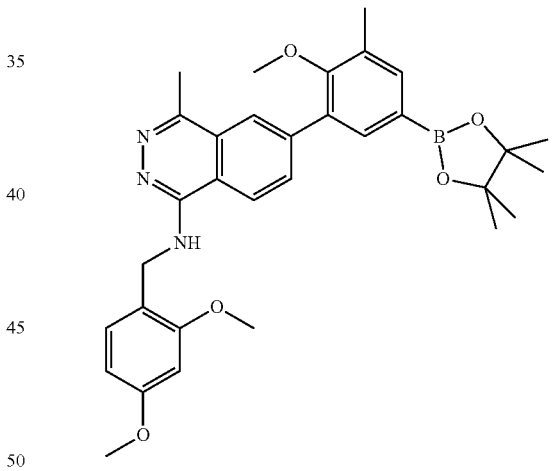

A mixture of 6-(5-chloro-2-methoxy-3-methylphenyl)-N-[(2,4-dimethoxyphenyl)methyl]-4-methylphthalazin-1-amine (250.0 mg, 0.460 mmol), 4,4,5,5-tetramethyl-2-(4,4,5,5-tetramethyl-1,3,2-dioxaborolan-2-yl)-1,3,2-dioxaborolane (348.92 mg, 1.37 mmol), dicyclohexyl-[2-[2,4,6-tri(propan-2-yl)phenyl]phenyl]phosphine (17.47 mg, 0.040 mmol), potassium acetate (134.85 mg, 1.37 mmol) and palladium (II) diacetate (5.14 mg, 0.020 mmol) were dissolved in 1,4-dioxane (5 mL) in a microwave vial and degassed for 10 min with $N_2$. The mixture was stirred at 75° C. for 1.5 hours, then it was cooled to room temperature and filtered over Celite, washing with MeOH. The filtrate was evaporated and the residue was purified by column chromatography (KP-C18-HS, 2×30 g in series) eluting with a gradient of $CH_3CN$ in water from 5% to 95%. Fractions containing the desired compound were collected and evaporated under reduced pressure to give N-[(2,4-dimethoxyphenyl)methyl]-6-[2-methoxy-3-methyl-5-(4,4,5,5-tetramethyl-1,3,2-dioxaborolan-2-yl)phenyl]-4-methylphthalazin-1-amine (118 mg, 0.212 mmol, 46.38% yield). ¹H NMR (400 MHz, DMSO-d₆) δ 1.30 (s, 12H), 2.34 (s, 3H), 2.70 (s, 3H), 3.35 (s, 3H), 3.74 (s, 3H), 3.85 (s, 3H), 4.68 (d, J=5.52 Hz, 2H), 6.44 (dd, J=8.36, 2.41 Hz, 1H), 6.59 (d, J=2.40 Hz, 1H), 7.16 (d, J=8.31 Hz, 1H), 7.56 (d, J=1.63 Hz, 1H), 7.58-7.65 (m, 2H), 7.99 (dd, J=8.54, 1.72 Hz, 1H), 8.05 (d, J=1.70 Hz, 1H), 8.44 (d, J=8.56 Hz, 1H). LC-MS (Method A): r.t. 1.00 min, MS (ESI) m/z=556.5 [M+H]⁺.

Intermediate 137: 6-[2-methoxy-3-methyl-5-(4,4,5,5-tetramethyl-1,3,2-dioxaborolan-2-yl)phenyl]-4-methylphthalazin-1-amine trifluoroacetic Acid Salt

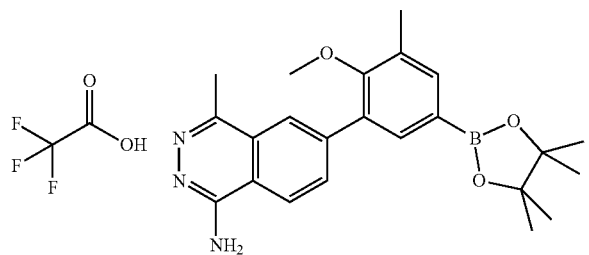

A solution of N-[(2,4-dimethoxyphenyl)methyl]-6-[2-methoxy-3-methyl-5-(4,4,5,5-tetramethyl-1,3,2-dioxaborolan-2-yl)phenyl]-4-methylphthalazin-1-amine (115.0 mg, 0.210 mmol) in DCM (8 mL) and trifluoroacetic acid (8 mL) was stirred for 3.5 hours at room temperature then it was concentrated under reduced pressure. The residue was dissolved in DCM/MeOH (1/1) and filtered over Celite. The organic phase was evaporated to give 6-[2-methoxy-3-methyl-5-(4,4,5,5-tetramethyl-1,3,2-dioxaborolan-2-yl)phenyl]-4-methylphthalazin-1-amine trifluoroacetic acid salt (94 mg, 0.232 mmol, 100% yield) as a pale-pink vitreous solid. ¹H NMR (400 MHz, DMSO-d₆) δ 1.30 (s, 12H), 2.35 (s, 3H), 2.75 (s, 3H), 3.38 (s, 3H), 7.60 (s, 1H), 7.68 (s, 1H), 8.27 (d, J=8.39 Hz, 1H), 8.32 (s, 1H), 8.71 (d, J=8.56 Hz, 1H), 9.19 (br. s, 2H). LC-MS (Method A): r.t. 0.84 min, MS (ESI) m/z=406.3 [M+H]⁺.

Intermediate 138: 1-bromo-5-chloro-4-cyclopropyl-2-methoxybenzene

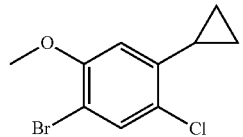

A mixture of 1-bromo-5-chloro-4-iodo-2-methoxybenzene (500.0 mg, 1.44 mmol), tripotassium phosphate (929.63 mg, 4.32 mmol) and cyclopropylboronic acid (123.64 mg, 1.44 mmol) in 1,4-dioxane (7.197 mL) was degassed with N₂ for 10 min. Then [1,1'-bis(diphenylphosphino)ferrocene]dichloropalladium(II) (105.61 mg, 0.140 mmol) was added and the resulting reaction mixture was stirred at 90° C. overnight. It was then cooled to room temperature and filtered over Celite, washing with EtOAc. The filtrate was evaporated and the residue was purified by column chromatography (KP silica gel, SNAP 50) eluting with a gradient of EtOAc in cyclohexane from 1% to 25% to give 1-bromo-5-chloro-4-cyclopropyl-2-methoxybenzene (270 mg, 1.032 mmol, 71.72% yield) as a colourless oil. The product was isolated in a mixture with 1-bromo-5-chloro-4-iodo-2-methoxybenzene (~30%). The mixture was used in the next step without further purification. ¹H NMR (400 MHz, Chloroform-d) δ 0.66-0.72 (m, 2H), 1.03-1.08 (m, 2H), 2.16 (tt, J=8.35, 5.34 Hz, 1H), 3.87 (s, 3H), 6.48 (s, 1H), 7.53 (s, 1H). LC-MS (Method A): r.t. 1.39 min, MS (ESI) m/z of product not observed due to poor ionization.

Intermediate 139: 6-(5-chloro-4-cyclopropyl-2-methoxyphenyl)-N-[(2,4-dimethoxyphenyl)methyl]-4-methylphthalazin-1-amine

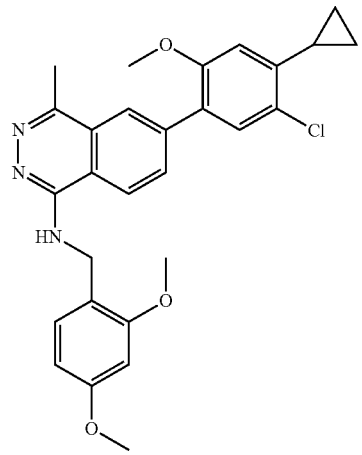 [SMILES: COc1ccc(CNc2nnc(C)c3cc(-c4cc(Cl)c(C5CC5)cc4OC)ccc23)c(OC)c1]

[1-[(2,4-Dimethoxyphenyl)methylamino]-4-methylphthalazin-6-yl]boronic acid (200.0 mg, 0.570 mmol), 1-bromo-5-chloro-4-cyclopropyl-2-methoxybenzene (211.58 mg, 0.570 mmol), and [1,1'-bis(di-tert-butylphosphino)ferrocene]dichloropalladium(II) (37.02 mg, 0.060 mmol) were dissolved in 1,2-dimethoxyethane (4.247 mL) and aqueous 2N sodium carbonate solution (0.57 mL, 1.13 mmol). The mixture was degassed with N₂ for 10 minutes and stirred at 70° C. for 3 hours. It was then cooled to room temperature and filtered over Celite, washing with EtOAc. The filtrate was evaporated and the residue was purified by column chromatography (KP silica gel, SNAP 25) eluting with a gradient of EtOAc in cyclohexane from 10% to 90% to give 6-(5-chloro-4-cyclopropyl-2-methoxyphenyl)-N-[(2,4-dimethoxyphenyl)methyl]-4-methylphthalazin-1-amine (140 mg, 0.286 mmol, 50.46% yield) as a white foam. ¹H NMR (400 MHz, DMSO-d₆) δ 0.83-0.91 (m, 2H), 1.07 (td, J=6.19, 5.54, 3.09 Hz, 2H), 2.22 (tt, J=8.38, 5.24 Hz, 1H), 2.69 (s, 3H), 3.73 (s, 3H), 3.81 (s, 3H), 3.85 (s, 3H), 4.67 (d, J=5.62 Hz, 2H), 6.43 (dd, J=8.36, 2.42 Hz, 1H), 6.58 (d, J=2.38 Hz, 1H), 6.72 (s, 1H), 7.11 (d, J=8.37 Hz, 1H), 7.54 (s, 1H), 7.57 (t, J=5.57 Hz, 1H), 7.98 (dd, J=8.59, 1.75 Hz, 1H), 8.01 (d, J=1.71 Hz, 1H), 8.37 (d, J=8.61 Hz, 1H). LC-MS (Method A): r.t. 0.96 min, MS (ESI) m/z=490.3 [M+H]⁺.

Intermediate 140: 1-bromo-2-methoxy-4-(trifluoromethoxy)benzene

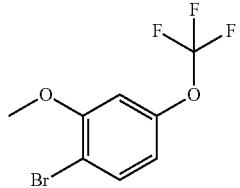

To a solution of 2-bromo-5-(trifluoromethoxy)phenol (1.0 g, 3.89 mmol) in DMF (23 mL), potassium carbonate (806.67 mg, 5.84 mmol) and iodomethane (0.36 mL, 5.84 mmol) were added in this order at 0° C. The reaction mixture was stirred at room temperature for 12 hours. Then it was diluted with EtOAc and washed with water twice and brine, dried over $Na_2SO_4$, filtered and evaporated. The residue was purified by column chromatography (KP-Sil silica gel, SNAP 50) eluting with a gradient of EtOAc in cyclohexane from 0% to 10% to give tert-butyl 1-bromo-2-methoxy-4-(trifluoromethoxy)benzene (950 mg, 3.505 mmol, 90.08% yield) as a colourless oil. $^1$H NMR (400 MHz, DMSO-$d_6$) δ 3.88 (s, 3H), 6.89-6.96 (m, 1H), 7.14 (d, J=2.63 Hz, 1H), 7.70 (d, J=8.67 Hz, 1H). LC-MS (Method A): r.t. 1.26 min, MS (ESI) m/z of product not observed due to poor ionization.

Intermediate 141: 1-bromo-5-chloro-2-methoxy-4-(trifluoromethoxy)benzene

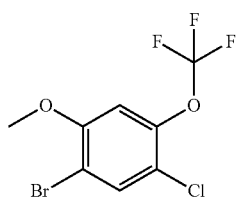

To a solution of 1-bromo-2-methoxy-4-(trifluoromethoxy)benzene (700.0 mg, 2.58 mmol) and 1-chloropyrrolidine-2,5-dione (517.31 mg, 3.87 mmol) in DMF (11 mL), trifluoroacetic acid (3 mL) was added dropwise. The reaction mixture was stirred at 70° C. for 24 hours, then it was diluted with DCM and washed with three times with brine, dried over $Na_2SO_4$, filtered and evaporated. The residue was purified by column chromatography (KP-Sil silica gel, SNAP 50) eluting with a gradient of EtOAc in cyclohexane from 0% to 5% to give 1-bromo-5-chloro-2-methoxy-4-(trifluoromethoxy)benzene (345 mg, 1.113 mmol, 43.09% yield) as a colourless oil. $^1$H NMR (400 MHz, DMSO-$d_6$) δ 3.91 (s, 3H), 7.31 (d, J=1.13 Hz, 1H), 8.01 (s, 1H). LC-MS (Method A): r.t. 1.37 min, MS (ESI) m/z of product not observed due to poor ionization.

Intermediate 142: 6-[5-chloro-2-methoxy-4-(trifluoromethoxy)phenyl]-N-[(2,4-dimethoxyphenyl)methyl]-4-methylphthalazin-1-amine

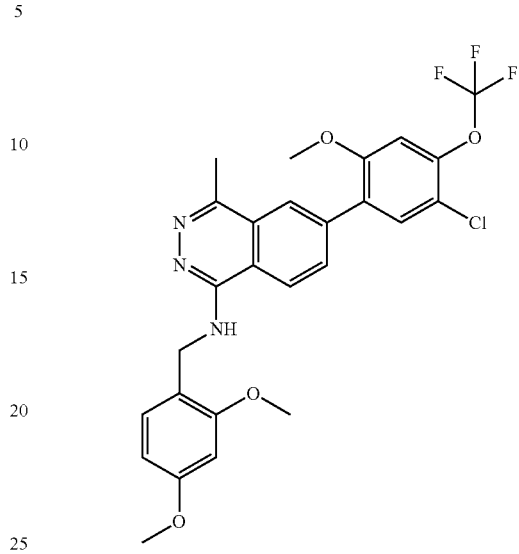

A mixture of [1-[(2,4-dimethoxyphenyl)methylamino]-4-methylphthalazin-6-yl]boronic acid (398.87 mg, 1.13 mmol) and 1-bromo-5-chloro-2-methoxy-4-(trifluoromethoxy)benzene (345.0 mg, 1.13 mmol) in 1,2-dimethoxyethane (9 mL) and aqueous 2N sodium carbonate solution (1129.37 uL, 2.26 mmol) was degassed for 10 min with $N_2$. Then, [1,1'-bis(di-tert-butylphosphino)ferrocene]dichloropalladium(II) (73.83 mg, 0.110 mmol) was added. The mixture was stirred at 80° C. for 7 hours, then it was cooled to room temperature and filtered over Celite, washing with MeOH. The filtrate was evaporated and the residue was purified by column chromatography (2×KP-NH silica gel, SNAP 28) eluting with a gradient of EtOAc in cyclohexane from 0% to 80% to give 6-[5-chloro-2-methoxy-4-(trifluoromethoxy)phenyl]-N-[(2,4-dimethoxyphenyl)methyl]-4-methylphthalazin-1-amine (205 mg, 0.384 mmol, 34% yield) as a brown powder. $^1$H NMR (400 MHz, DMSO-$d_6$) δ 2.70 (s, 3H), 3.73 (s, 3H), 3.85 (s, 3H), 3.87 (s, 3H), 4.67 (d, J=5.57 Hz, 2H), 6.43 (dd, J=8.37, 2.38 Hz, 1H), 6.58 (d, J=2.37 Hz, 1H), 7.12 (d, J=8.34 Hz, 1H), 7.37 (q, J=1.22 Hz, 1H), 7.60 (t, J=5.78 Hz, 1H), 7.83 (s, 1H), 8.01 (dd, J=8.58, 1.76 Hz, 1H), 8.07 (d, J=1.68 Hz, 1H), 8.41 (d, J=8.62 Hz, 1H). LC-MS (Method A): r.t. 0.96 min, MS (ESI) m/z=534.3 [M+H]$^+$.

Intermediate 143: 6-[2-methoxy-5-(4,4,5,5-tetramethyl-1,3,2-dioxaborolan-2-yl)-4-(trifluoromethoxy)phenyl]-4-methylphthalazin-1-amine trifluoroacetic Acid Salt

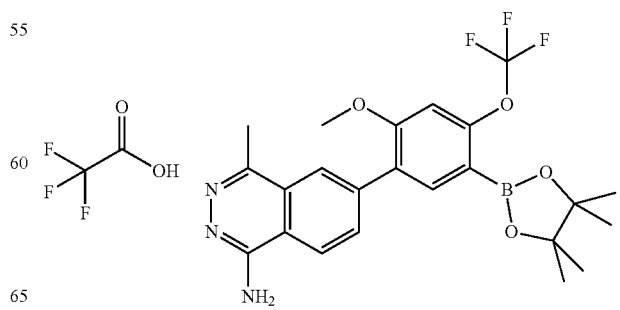

A mixture of 6-[5-chloro-2-methoxy-4-(trifluoromethoxy)phenyl]-N-[(2,4-dimethoxyphenyl)methyl]-4-methylphthalazin-1-amine (110.0 mg, 0.210 mmol), 4,4,5,5-tetramethyl-2-(4,4,5,5-tetramethyl-1,3,2-dioxaborolan-2-yl)-1,3,2-dioxaborolane (156.95 mg, 0.620 mmol), dicyclohexyl-[2-[2,4,6-tri(propan-2-yl)phenyl]phenyl]phosphine (7.86 mg, 0.020 mmol), potassium acetate (60.66 mg, 0.620 mmol) and palladium(II) diacetate (2.31 mg, 0.010 mmol) were dissolved in 1,4-dioxane (2 mL) in a microwave vial and degassed for 15 min with $N_2$. The mixture was stirred at 80° C. for 9 hours, then it was cooled to room temperature and filtered over Celite, washing with MeOH. The filtrate was evaporated and the residue was used in the next reaction without further purification. The crude was dissolved in DCM (5 mL) and trifluoroacetic acid (3 mL) and stirred for 2 hours at room temperature then was concentrated under reduced pressure. The residue was suspended in $Et_2O$, stirred for 30 min, filtered on a Hirsch funnel and dried to give 6-[2-methoxy-5-(4,4,5,5-tetramethyl-1,3,2-dioxaborolan-2-yl)-4-(trifluoromethoxy)phenyl]-4-methylphthalazin-1-amine trifluoroacetic acid salt (180 mg, 0.379 mmol, 67.8% yield) as an orange oil. LC-MS (Method A): r.t. 0.89 min, MS (ESI) m/z=476.3 [M+H]$^+$. Purity 48%.

Intermediate 144:
5-bromo-1-chloro-2-methoxy-3-methylbenzene

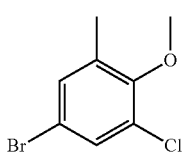

To a solution of 4-bromo-2-chloro-6-methylphenol (1.5 g, 6.77 mmol) in DMF (10 mL), potassium carbonate (1123.25 mg, 8.13 mmol) was added and the mixture was stirred at room temperature for 10 min. Iodomethane (0.46 mL, 7.45 mmol) was added and the mixture was stirred at room temperature for 20 h. The mixture was diluted with $Et_2O$ (100 mL) and washed with saturated aqueous $NH_4Cl$ solution and brine. The organic phase was dried over $Na_2SO_4$, filtered and the solvent was evaporated to give crude 5-bromo-1-chloro-2-methoxy-3-methylbenzene (1.5 g, 6.369 mmol, 94.04% yield) as a brown oil. $^1$H NMR (400 MHz, DMSO-$d_6$) δ 2.26 (t, J=0.7 Hz, 3H), 3.74 (s, 3H), 7.43 (dd, J=2.4, 0.8 Hz, 1H), 7.55 (dd, J=2.4, 0.7 Hz, 1H). LC-MS (Method A): r.t. 1.34 min, MS (ESI) m/z of product not observed due to poor ionization.

Intermediate 145: 6-(3-chloro-4-methoxy-5-methylphenyl)-N-[(2,4-dimethoxyphenyl)methyl]-4-methylphthalazin-1-amine

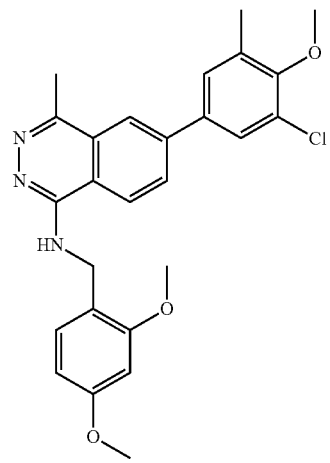 [SMILES: COc1ccc(CNc2nnc(C)c3cc(-c4cc(C)c(OC)c(Cl)c4)ccc23)c(OC)c1]

A mixture of 5-bromo-1-chloro-2-methoxy-3-methylbenzene (233.39 mg, 0.990 mmol), [1-[(2,4-dimethoxyphenyl)methylamino]-4-methylphthalazin-6-yl]boronic acid (350.0 mg, 0.990 mmol) and aqueous 2N sodium carbonate solution (991.0 uL, 1.98 mmol) in 1,2-dimethoxyethane (8.4 mL) was degassed for 10 min. Then [1,1'-bis(di-tert-butylphosphino)ferrocene]dichloropalladium(II) (64.79 mg, 0.100 mmol) was added and the resulting reaction mixture was stirred at 85° C. for 6 hours. The mixture was filtered over a short pad of Celite, washing with EtOAc. The filtrate was concentrated in vacuo and the residue was purified by column chromatography (KP-NH silica gel, SNAP 28 g) eluting with a gradient of EtOAc in cyclohexane from 0% to 100% to give 6-(3-chloro-4-methoxy-5-methylphenyl)-N-[(2,4-dimethoxyphenyl)methyl]-4-methylphthalazin-1-amine (233 mg, 0.502 mmol, 50.68% yield) as a viscous oil. $^1$H NMR (400 MHz, DMSO-$d_6$) δ 2.40 (s, 3H), 2.76 (s, 3H), 3.73 (s, 3H), 3.82 (s, 3H), 3.85 (s, 3H), 4.66 (d, J=5.58 Hz, 2H), 6.43 (dd, J=8.35, 2.40 Hz, 1H), 6.58 (d, J=2.39 Hz, 1H), 7.12 (d, J=8.31 Hz, 1H), 7.61 (t, J=5.62 Hz, 1H), 7.77 (dd, J=2.39, 0.83 Hz, 1H), 7.83-7.94 (m, 1H), 8.11-8.23 (m, 2H), 8.38-8.51 (m, 1H). LC-MS (Method A): r.t. 0.89 min, MS (ESI) m/z=464.32 [M+H]$^+$.

Intermediate 146: [5-[1-[(2,4-dimethoxyphenyl)methylamino]-4-methylphthalazin-6-yl]-2-methoxy-3-methylphenyl]boronic Acid

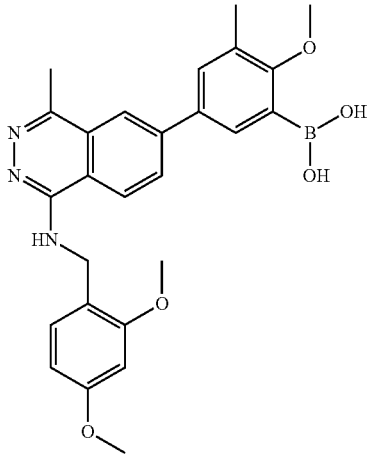 [SMILES: COc1ccc(CNc2nnc(C)c3cc(-c4cc(C)c(OC)c(B(O)O)c4)ccc23)c(OC)c1]

Palladium(II) diacetate (5.64 mg, 0.030 mmol), 6-(3-chloro-4-methoxy-5-methylphenyl)-N-[(2,4-dimethoxyphenyl)methyl]-4-methylphthalazin-1-amine (233.0 mg, 0.500 mmol), dicyclohexyl-[2-[2,4,6-tri(propan-2-yl)phenyl]phenyl]phosphine (19.15 mg, 0.040 mmol), potassium acetate (147.86 mg, 1.51 mmol) and 4,4,5,5-tetramethyl-2-(4,4,5,5-tetramethyl-1,3,2-dioxaborolan-2-yl)-1,3,2-dioxaborolane (382.58 mg, 1.51 mmol) were dissolved in 1,4-dioxane (12.66 mL). The mixture was degassed with Ar for 10 min, then stirred at 90° C. for 18 hours. The mixture was filtered over a pad of Celite, washing with EtOAc and the filtrate was concentrated in vacuo. The residue was purified by column chromatography (KP-C18-HS, SNAP 30 g) eluting with a gradient of $CH_3CN$ in water from 1% to 95% to give [5-[1-[(2,4-dimethoxyphenyl)methylamino]-4-methylphthalazin-6-yl]-2-methoxy-3-methylphenyl]boronic acid (41 mg, 0.087 mmol, 17.25% yield) as a pale yellow solid. LC-MS (Method A): r.t. 0.74 min, MS (ESI) m/z=474.36 [M+H]+.

Intermediate 147: 7-[5-chloro-2-methoxy-4-[2-(oxan-2-yloxy)ethyl]phenyl]-N-[(2,4-dimethoxyphenyl)methyl]cinnolin-4-amine

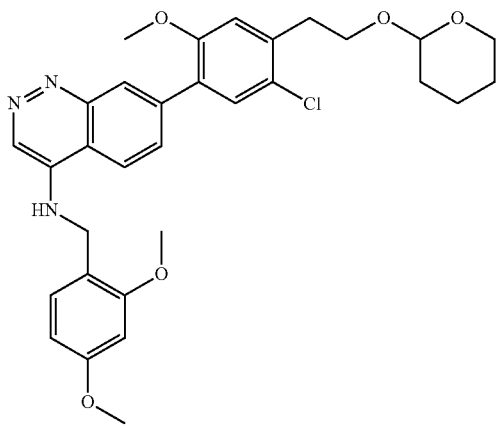 [SMILES: COc1ccc(CNc2cnnc3cc(-c4cc(Cl)c(CCOC5CCCCO5)cc4OC)ccc23)c(OC)c1]

A mixture of 2-[2-(4-bromo-2-chloro-5-methoxyphenyl)ethoxy]oxane (184.34 mg, 0.530 mmol), [4-[(2,4-dimethoxyphenyl)methylamino]cinnolin-7-yl]boronic acid (298.0 mg, 0.530 mmol) and aqueous 2N sodium carbonate solution (527.2 uL, 1.05 mmol) in 1,2-dimethoxyethane (5.545 mL) was degassed for 10 min. Then [1,1'-bis(di-tert-butylphosphino)ferrocene]dichloropalladium(II) (34.47 mg, 0.050 mmol) was added and the resulting reaction mixture was stirred at 90° C. for 6 hours. The mixture was filtered over Celite, washing with EtOAc and the filtrate was concentrated in vacuo. The residue was purified by column chromatography (KP-NH silica gel, SNAP 28 g) eluting with a gradient of EtOAc in cyclohexane from 0% to 100% to give 7-[5-chloro-2-methoxy-4-[2-(oxan-2-yloxy)ethyl]phenyl]-N-[(2,4-dimethoxyphenyl)methyl]cinnolin-4-amine (189 mg, 0.335 mmol, 63.56% yield) as a viscous oil. $^1$H NMR (400 MHz, DMSO-$d_6$) δ 1.36-1.81 (m, 6H), 3.03 (t, J=6.79 Hz, 2H), 3.39-3.48 (m, 1H), 3.63-3.71 (m, 2H), 3.74 (s, 3H), 3.83 (s, 3H), 3.88 (s, 3H), 3.89-3.94 (m, 1H), 4.51 (d, J=6.25 Hz, 2H), 4.63-4.70 (m, 1H), 6.47 (dd, J=8.43, 2.41 Hz, 1H), 6.63 (d, J=2.41 Hz, 1H), 7.14 (d, J=8.43 Hz, 1H), 7.25 (s, 1H), 7.51 (s, 1H), 7.76 (dd, J=8.79, 1.83 Hz, 1H), 8.02 (t, J=5.97 Hz, 1H), 8.17 (d, J=1.83 Hz, 1H), 8.35 (d, J=8.75 Hz, 1H), 8.46 (s, 1H). LC-MS (Method A): r.t. 0.94 min, MS (ESI) m/z=564.4 [M+H]+.

Intermediate 148: 4-chloro-5-fluoro-2-iodoaniline

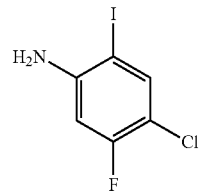

1-Iodopyrrolidine-2,5-dione (850.09 mg, 3.78 mmol) was slowly added under argon to vigorously stirred DMF (1.5 mL), followed by methanesulfonic acid (2.3 mL, 35.44 mmol). The mixture was stirred for 5 min, until a clear solution was observed. Separately, 4-chloro-3-fluoroaniline (500.0 mg, 3.44 mmol) was dissolved in DMF (9 mL) and the solution was cooled to 0° C. The mixture was stirred at 0° C. and the above described solution of 1-iodopyrrolidine-2,5-dione in DMF was added dropwise, at 0° C., over 30 min. The reaction mixture was stirred at 0° C. for 2.5 hours and then a saturated aqueous solution of sodium thiosulfate was added. The phases were separated and the aqueous phase was extracted with EtOAc. The organic phases were combined, washed with water, dried over $Na_2SO_4$, filtered and concentrated under reduced pressure. The residue was purified by column chromatography (KP silica gel, SNAP 50) eluting with a gradient of EtOAc in cyclohexane 5% to 40% to give 4-chloro-5-fluoro-2-iodoaniline (485 mg, 1.787 mmol, 52.01% yield) as a yellow solid. $^1$H NMR (400 MHz, DMSO-$d_6$) δ 5.63 (s, 2H), 6.68 (d, J=12.0 Hz, 1H), 7.67 (d, J=8.2 Hz, 1H). LC-MS (Method A): r.t. 1.15 min, MS (ESI) m/z=272.0 [M+H]+.

Intermediate 149: 2-bromo-4-chloro-3-fluoro-6-iodoaniline

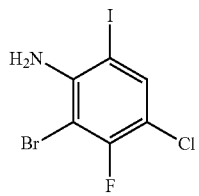 [SMILES: Nc1c(I)cc(Cl)c(F)c1Br]

1-Bromopyrrolidine-2,5-dione (349.78 mg, 1.97 mmol) was dissolved in DMF (2 mL) and acetic acid (0.500 mL), and stirred for 5 min until a clear solution was observed. Separately, 4-chloro-5-fluoro-2-iodoaniline (485.0 mg, 1.79 mmol) was dissolved in acetic acid (1 mL) and DMF (4 mL). The solution was cooled to 0° C. and the above described solution of 1-bromopyrrolidine-2,5-dione in DMF was added dropwise, at 0° C., over 20 min. The reaction mixture was stirred at 0° C. for 30 min, and then at room temperature for 5 h. Subsequently water was added and the aqueous phase was extracted three times with EtOAc. The organic phases were combined and washed with brine, dried over $Na_2SO_4$ and concentrated under reduced pressure. The residue was purified by column chromatography (KP silica gel, SNAP 50) eluting with a gradient of EtOAc in cyclohexane from 1% to 40% to give 2-bromo-4-chloro-3-fluoro-6-iodoaniline (505 mg, 1.441 mmol, 80.68% yield) as a yellow solid. $^1$H NMR (400 MHz, DMSO-$d_6$) δ 5.64 (s, 2H), 7.84 (d, J=8.0 Hz, 1H). LC-MS (Method A): r.t. 1.31 min, MS (ESI) m/z=349.93 and 352.08 [M+H]$^+$.

Intermediate 150: 1-bromo-3-chloro-2-fluoro-5-iodobenzene

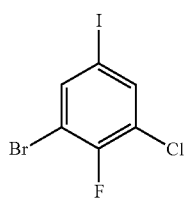

To a stirred solution of nitrous acid 3-methylbutyl ester (0.11 mL, 0.860 mmol) in DMF (3 mL) at 65° C., a solution of 2-bromo-4-chloro-3-fluoro-6-iodoaniline (100.0 mg, 0.290 mmol) in DMF (2 mL) was added dropwise over 40 min. The reaction mixture was stirred at 65° C. for 30 min, then cooled to room temperature. EtOAc and 0.5N hydrochloric acid solution were added. The aqueous phase was extracted three times with EtOAc. The organic phases were combined, washed with 2N hydrochloric acid solution and brine, dried over $Na_2SO_4$, filtered and concentrated under reduced pressure. The residue was purified by column chromatography (KP silica gel, SNAP 25) eluting with a gradient of EtOAc in cyclohexane from 5% to 40% to give 1-bromo-3-chloro-2-fluoro-5-iodobenzene (65 mg, 0.194 mmol, 67.91% yield) as an off white solid. $^1$H NMR (400 MHz, DMSO-$d_6$) δ 8.01-8.05 (m, 1H), 8.09 (dd, J=6.0, 2.0 Hz, 1H). LC-MS (Method A): r.t. 1.44 min, MS (ESI) m/z of product not observed due to poor ionization.

Intermediate 151: 1-bromo-3-chloro-5-dimethylphosphoryl-2-fluorobenzene

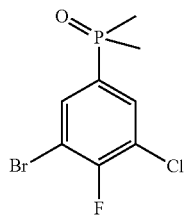

1-Bromo-3-chloro-2-fluoro-5-iodobenzene (360.0 mg, 1.07 mmol), dimethylphosphine oxide (83.79 mg, 1.07 mmol), triethylamine (0.15 mL, 1.07 mmol), (1E,4E)-1,5-diphenyl-3-penta-1,4-dienone palladium (98.31 mg, 0.110 mmol) and (5-diphenylphosphino-9,9-dimethyl-4-xanthenyl)-diphenylphosphine (62.12 mg, 0.110 mmol) were dissolved in 1,4-dioxane (4.249 mL). The mixture was deoxygenated with $N_2$ for 10 minutes, then it was stirred at room temperature for 24 hours. The mixture was filtered over a pad of Celite, washing with EtOAc and concentrated in vacuo. The residue was purified by column chromatography (KP silica gel, SNAP 50) eluting with a gradient of methanol in dichloromethane from 1% to 15% to give 1-bromo-3-chloro-5-dimethylphosphoryl-2-fluorobenzene (115 mg, 0.403 mmol, 37.52% yield) as a colourless oil. $^1$H NMR (400 MHz, Chloroform-d) δ 1.76 (s, 3H), 1.79 (s, 3H), 7.74 (ddd, J=11.2, 6.4, 1.8 Hz, 1H), 7.84 (ddd, J=11.2, 5.8, 1.8 Hz, 1H). LC-MS (Method A): r.t. 0.78 min, MS (ESI) m/z=285.0 and 286.98 [M+H]$^+$.

Intermediate 152: 6-(3-chloro-5-dimethylphosphoryl-2-fluorophenyl)-N-[(2,4-dimethoxyphenyl)methyl]-4-methylphthalazin-1-amine

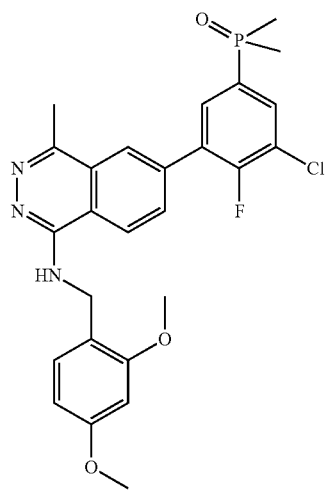 [SMILES: COc1ccc(CNc2nnc(C)c3cc(-c4cc(P(C)(C)=O)cc(Cl)c4F)ccc23)c(OC)c1]

A mixture of 1-bromo-3-chloro-5-dimethylphosphoryl-2-fluorobenzene (115.59 mg, 0.400 mmol) and [1-[(2,4-dimethoxyphenyl)methylamino]-4-methylphthalazin-6-yl]boronic acid (130.0 mg, 0.370 mmol) in 1,2-dimethoxyethane (4.247 mL) and aqueous 2N sodium carbonate solution (0.37 mL, 0.740 mmol) was degassed for 10 minutes with $N_2$. Then [1,1'-bis(di-tert-butylphosphino)ferrocene] dichloropalladium(II) (24.06 mg, 0.040 mmol) was added and the resulting reaction mixture was stirred at 65° C. for 3 hours. It was then cooled to room temperature and filtered over Celite, washing with EtOAc. The filtrate was evaporated under reduced pressure and the residue was purified by column chromatography (KP silica gel, SNAP 50) eluting with a gradient of methanol in dichloromethane from 1% to 15%, giving 6-(3-chloro-5-dimethylphosphoryl-2-fluoro-phenyl)-N-[(2,4-dimethoxyphenyl)methyl]-4-methylphthalazin-1-amine (75 mg, 0.146 mmol, 39.65% yield) as a yellow solid. LC-MS (Method A): r.t. 0.70 min, MS (ESI) m/z=514.3 [M+H]$^+$.

Intermediate 153: 7-(3-chloro-2-fluoro-6-methoxy-phenyl)-N-[(2,4-dimethoxyphenyl)methyl]cinnolin-4-amine

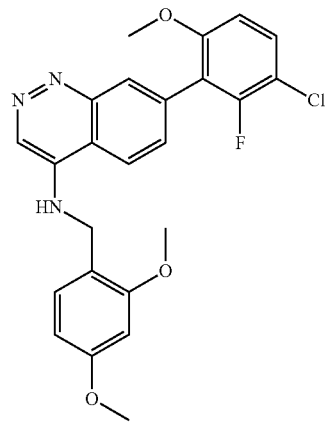 [SMILES: COc1ccc(CNc2cnnc3cc(-c4c(OC)ccc(Cl)c4F)ccc23)c(OC)c1]

A mixture of 1-chloro-2-fluoro-3-iodo-4-methoxybenzene (187.52 mg, 0.650 mmol), [4-[(2,4-dimethoxyphenyl)methylamino]cinnolin-7-yl]boronic acid (370.0 mg, 0.650 mmol) and aqueous 2N sodium carbonate solution (654.58 uL, 1.31 mmol) in 1,2-dimethoxyethane (5 mL) was degassed for 10 min. Then [1,1'-bis(di-tert-butylphosphino)ferrocene]dichloropalladium(II) (42.79 mg, 0.070 mmol) was added and the resulting reaction mixture was stirred at 85° C. for 6 hours. The mixture was filtered over Celite, washing with EtOAc. The filtrate was concentrated in vacuo and the residue was purified by column chromatography (KP-NH silica gel, SNAP 28 g) eluting with a gradient of EtOAc in cyclohexane from 0% to 100% to give 7-(3-chloro-2-fluoro-6-methoxyphenyl)-N-[(2,4-dimethoxyphenyl)methyl]cinnolin-4-amine (184 mg, 0.405 mmol, 61.93% yield) as a viscous oil. $^1$H NMR (400 MHz, DMSO-d$_6$) δ 3.74 (s, 3H), 3.79 (s, 3H), 3.88 (s, 3H), 4.52 (d, J=5.77 Hz, 2H), 6.47 (dd, J=8.40, 2.40 Hz, 1H), 6.63 (d, J=2.42 Hz, 1H), 7.09 (dd, J=9.13, 1.48 Hz, 1H), 7.16 (d, J=8.38 Hz, 1H), 7.61 (dt, J=8.76, 1.49 Hz, 1H), 7.64 (t, J=8.83 Hz, 1H), 8.02-8.09 (m, 2H), 8.39 (d, J=8.77 Hz, 1H), 8.50 (s, 1H). LC-MS (Method A): r.t. 0.93 min, MS (ESI) m/z=454.2 [M+H]$^+$.

Intermediate 154: 2-bromo-4-chloro-6-(trifluoromethyl)phenol

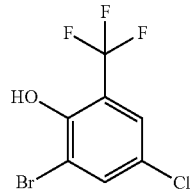 [SMILES: Oc1c(Br)cc(Cl)cc1C(F)(F)F]

To a stirred suspension of 4-chloro-2-(trifluoromethyl)phenol (1.0 g, 5.09 mmol) in acetic acid (7.5 mL) at 0° C. molecular bromine (260.68 uL, 5.09 mmol) was added dropwise. The reaction mixture was stirred at room temperature for 8 hours. DCM was added and the mixture was quenched with saturated sodium thiosulfate solution, filtered over a phase separator cartridge and evaporated. The crude material was purified by column chromatography (KP-Sil silica gel, SNAP 55) eluting with a gradient of EtOAc in cyclohexane from 0% to 30% to give 2-bromo-4-chloro-6-(trifluoromethyl)phenol (830 mg, 3.013 mmol, 59.23% yield) as a pale-yellow crystalline powder. $^1$H NMR (400 MHz, DMSO-d$_6$) δ 7.64 (d, J=2.5 Hz, 1H), 7.99 (d, J=2.6 Hz, 1H), 10.56 (s, 1H). LC-MS (Method A): r.t. 1.21 min, MS (ESI) m/z=272.9 and 274.9 [M+H]$^+$.

Intermediate 155: 1-bromo-5-chloro-2-methoxy-3-(trifluoromethyl)benzene

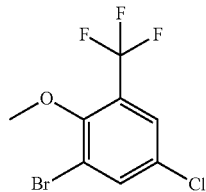

To a solution of 2-bromo-4-chloro-6-(trifluoromethyl)phenol (850.0 mg, 3.09 mmol) in DMF (14 mL), potassium carbonate (639.74 mg, 4.63 mmol) and iodomethane (288.16 uL, 4.63 mmol) were added in this order at 0° C. The resulting reaction mixture was stirred at room temperature overnight, then it was diluted with DCM and washed with water and twice with brine, dried over Na$_2$SO$_4$, filtered and evaporated. The residue was purified by column chromatography (KP-Sil silica gel, SNAP 50) eluting with a gradient of EtOAc in cyclohexane from 0% to 2% to give 1-bromo-5-chloro-2-methoxy-3-(trifluoromethyl)benzene (450 mg, 1.555 mmol, 50.38% yield) as a pale-yellow oil. $^1$H NMR (400 MHz, DMSO-d$_6$) δ 3.88 (s, 3H), 7.81 (d, J=2.5 Hz, 1H), 8.18 (d, J=2.5 Hz, 1H). LC-MS (Method A): r.t. 1.36 min, MS (ESI) m/z of product not observed due to poor ionization.

289

Intermediate 156: 6-[5-chloro-2-methoxy-3-(trifluoromethyl)phenyl]-N-[(2,4-dimethoxyphenyl)methyl]-4-methylphthalazin-1-amine

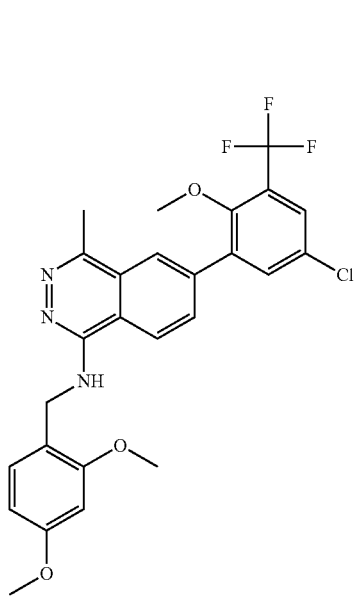 [SMILES: COc1ccc(CNc2nnc(C)c3cc(-c4cc(Cl)cc(C(F)(F)F)c4OC)ccc23)c(OC)c1]

A mixture of 1-bromo-5-chloro-2-methoxy-3-(trifluoromethyl)benzene (235.0 mg, 0.810 mmol), [1-[(2,4-dimethoxyphenyl)methylamino]-4-methylphthalazin-6-yl]boronic acid (286.71 mg, 0.810 mmol) and aqueous 2 N sodium carbonate solution (811.8 uL, 1.62 mmol) in 1,2-dimethoxyethane (9 mL) was degassed for 10 min under $N_2$. Then [1,1'-Bis(di-tert-butylphosphino)ferrocene]dichloropalladium(II) (53.07 mg, 0.080 mmol) was added and the resulting reaction mixture was stirred at 80° C. for 20 hours. The mixture was filtered over a pad of Celite, washing with MeOH. The organic phase was concentrated in vacuo and the residue was purified by column chromatography (KP-Sil silica gel, SNAP 25) eluting with a gradient of EtOAc in cyclohexane from 0% to 80% to give 6-[5-chloro-2-methoxy-3-(trifluoromethyl)phenyl]-N-[(2,4-dimethoxyphenyl) methyl]-4-methylphthalazin-1-amine (200 mg, 0.386 mmol, 47.57% yield) as a brown powder. $^1$H NMR (400 MHz, DMSO-$d_6$) δ 2.72 (s, 3H), 3.31 (s, 2H), 3.73 (s, 3H), 3.84 (s, 3H), 4.66 (s, 2H), 6.43 (dd, J=8.3, 2.4 Hz, 1H), 6.58 (d, J=2.4 Hz, 1H), 7.14 (d, J=8.4 Hz, 1H), 7.67 (t, J=5.7 Hz, 1H), 7.84 (d, J=2.6 Hz, 1H), 8.02 (d, J=2.6 Hz, 1H), 8.09 (dd, J=8.6, 1.8 Hz, 1H), 8.18 (d, J=1.7 Hz, 1H), 8.49 (d, J=8.6 Hz, 1H). LC-MS (Method A): r.t. 0.94 min, MS (ESI) m/z=518.3 [M+H]$^+$.

290

Intermediate 157: N-[(2,4-dimethoxyphenyl)methyl]-6-[2-methoxy-5-(4,4,5,5-tetramethyl-1,3,2-dioxaborolan-2-yl)-3-(trifluoromethyl)phenyl]-4-methylphthalazin-1-amine

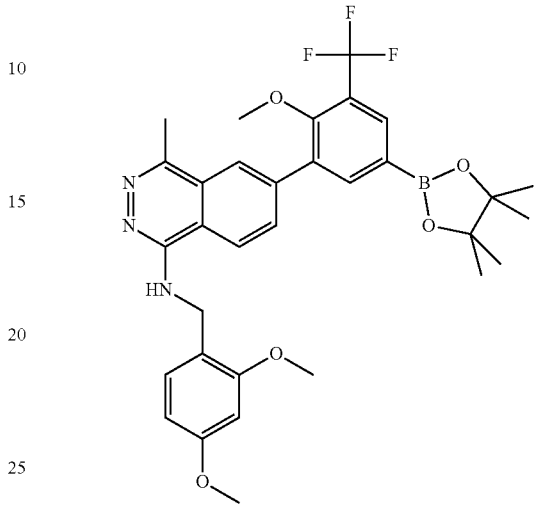

6-[5-Chloro-2-methoxy-3-(trifluoromethyl)phenyl]-N-[(2,4-dimethoxyphenyl)methyl]-4-methylphthalazin-1-amine (200.0 mg, 0.390 mmol), dicyclohexyl-[2-[2,4,6-tri(propan-2-yl)phenyl]phenyl]phosphine (14.73 mg, 0.030 mmol), potassium acetate (113.69 mg, 1.16 mmol), 4,4,5,5-tetramethyl-2-(4,4,5,5-tetramethyl-1,3,2-dioxaborolan-2-yl)-1,3,2-dioxaborolane (294.18 mg, 1.16 mmol) and palladium(II) diacetate (4.33 mg, 0.020 mmol) were dissolved in 1,4-dioxane (4 mL) in a microwave vial and the mixture was deoxygenated with $N_2$ for 10 minutes. The mixture was stirred at 75° C. for 1.5 hours, then it was filtered over a pad of Celite, washing with MeOH and concentrated in vacuo. The resulting crude was purified by column chromatography (KP-C18-HS, 30 g) eluting with a gradient of $CH_3CN$ in water (+0.1% of HCOOH) from 5% to 95%. Fractions containing the desired compound were collected and evaporated under reduced pressure to give N-[(2,4-dimethoxyphenyl)methyl]-6-[2-methoxy-5-(4,4,5,5-tetramethyl-1,3,2-dioxaborolan-2-yl)-3-(trifluoromethyl)phenyl]-4-methylphthalazin-1-amine (145 mg, 0.238 mmol, 61.61% yield) as a white solid. $^1$H NMR (400 MHz, DMSO-$d_6$) δ 1.18 (s, 12H), 2.73 (s, 3H), 3.35 (s, 3H), 3.74 (s, 3H), 3.85 (s, 3H), 4.68 (d, J=5.4 Hz, 2H), 6.45 (dd, J=8.3, 2.4 Hz, 1H), 6.59 (d, J=2.4 Hz, 1H), 7.16 (d, J=8.3 Hz, 1H), 8.09 (dd, J=8.5, 1.7 Hz, 1H), 8.16 (dd, J=6.4, 1.7 Hz, 2H), 8.22 (d, J=1.7 Hz, 1H), 8.42 (s, 1H), 8.52 (d, J=8.6 Hz, 1H). LC-MS (Method A): r.t. 0.79 min, MS (ESI) m/z=528.3 [M-pinacol+H]$^+$.

Intermediate 158: 1-bromo-2-chloro-5-iodo-4-methoxybenzene

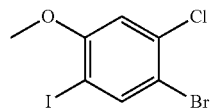

1-Bromo-2-chloro-4-methoxybenzene (2.0 g, 9.03 mmol) was dissolved in trifluoroacetic acid (10 mL) and NIS (2.03 g, 9.03 mmol) was added. The mixture was stirred at room temperature for 28 h, observing the formation of a precipitate. The precipitate was filtered off, then dissolved in DCM and washed with aqueous $Na_2S_2O_3$ solution, aqueous $NaHCO_3$ solution and water. The organic phase was dried over $Na_2SO_4$, filtered and the solvent was evaporated to give 1-bromo-2-chloro-5-iodo-4-methoxybenzene (2.74 g, 7.888 mmol, 87.35% yield) as a white solid. The crude product was used directly in the next step without further purification. $^1H$ NMR (400 MHz, DMSO-$d_6$) δ 3.86 (s, 3H), 7.26 (s, 1H), 8.09 (s, 1H). LC-MS (Method A): r.t. 1.39 min, MS (ESI) m/z of product not observed due to poor ionization.

Intermediate 159: 6-(5-bromo-4-chloro-2-methoxyphenyl)-N-[(2,4-dimethoxyphenyl)methyl]-4-methylphthalazin-1-amine

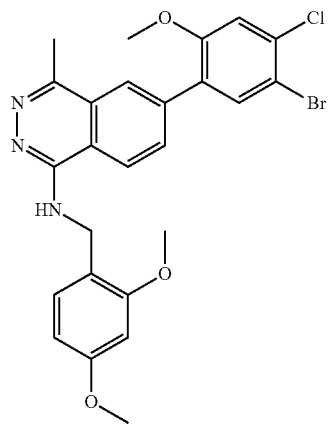 [SMILES: COc1ccc(CNc2nnc(C)c3cc(-c4cc(Br)c(Cl)cc4OC)ccc23)c(OC)c1]

A mixture of palladium(II)triphenylphosphine dichloride (107.32 mg, 0.150 mmol), 1-bromo-2-chloro-5-iodo-4-methoxybenzene (531.13 mg, 1.53 mmol) and [1-[(2,4-dimethoxyphenyl)methylamino]-4-methylphthalazin-6-yl]boronic acid (540.0 mg, 1.53 mmol) in 1,2-dimethoxyethane (5.625 mL) was degassed for 10 min. Then aqueous 2N sodium carbonate solution (1.5 mL, 3.06 mmol) was added and the resulting reaction mixture was stirred at 85° C. for 6 hours. The mixture was filtered over Celite, washing with EtOAc. The filtrate was concentrated in vacuo and the residue was purified by column chromatography (KP-NH silica gel, SNAP 28 g) eluting with a gradient of EtOAc in cyclohexane from 0% to 100% to give 6-(5-bromo-4-chloro-2-methoxyphenyl)-N-[(2,4-dimethoxyphenyl)methyl]-4-methylphthalazin-1-amine (145 mg, 0.274 mmol, 17.93% yield) as a viscous oil. $^1H$ NMR (400 MHz, DMSO-$d_6$) δ 2.70 (s, 3H), 3.72 (s, 3H), 3.84 (s, 3H), 3.85 (s, 3H), 4.66 (d, J=5.60 Hz, 2H), 6.42 (dd, J=8.36, 2.40 Hz, 1H), 6.58 (d, J=2.39 Hz, 1H), 7.11 (d, J=8.37 Hz, 1H), 7.47 (s, 1H), 7.59 (t, J=5.78 Hz, 1H), 7.86 (s, 1H), 7.98 (dd, J=8.53, 1.76 Hz, 1H), 8.03 (d, J=1.73 Hz, 1H), 8.38 (d, J=8.61 Hz, 1H). LC-MS (Method A): r.t. 0.92 min, MS (ESI) m/z=528.2 and 530.2 $[M+H]^+$.

Intermediate 160: 4-(2-bromo-4-chlorophenoxy)oxane

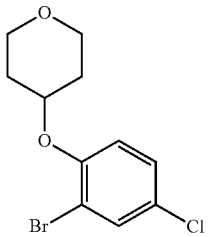 [SMILES: Clc1ccc(OC2CCOCC2)c(Br)c1]

Diisopropyl azodicarboxylate (1.04 mL, 5.3 mmol) was added dropwise to a solution of 2-bromo-4-chlorophenol (1.0 g, 4.82 mmol), 4-oxanol (541.54 mg, 5.3 mmol) and triphenylphosphine (1390.79 mg, 5.3 mmol) in THF (10 mL) cooled to 0° C. The mixture was stirred at room temperature for 5 h, then diluted with EtOAc. The organic phase was washed with saturated aqueous $NH_4Cl$ solution, saturated aqueous $NaHCO_3$ solution and brine, dried over $Na_2SO_4$, filtered and the solvent was evaporated. The residue was purified by column chromatography (KP-Sil, SNAP 50 g) eluting with a gradient of EtOAc in cyclohexane from 0% to 20% to give 4-(2-bromo-4-chlorophenoxy)oxane (980 mg, 3.361 mmol, 69.73% yield) as an oil. $^1H$ NMR (400 MHz, DMSO-$d_6$) δ 1.54-1.71 (m, 2H), 1.86-2.03 (m, 2H), 3.50 (ddd, J=11.44, 8.05, 3.27 Hz, 2H), 3.84 (ddd, J=10.68, 6.30, 3.79 Hz, 2H), 4.66-4.74 (m, 1H), 7.24 (d, J=8.93 Hz, 1H), 7.39 (dd, J=8.92, 2.60 Hz, 1H), 7.69 (d, J=2.60 Hz, 1H).

Intermediate 161: 7-[5-chloro-2-(oxan-4-yloxy)phenyl]-N-[(2,4-dimethoxyphenyl)methyl]cinnolin-4-amine

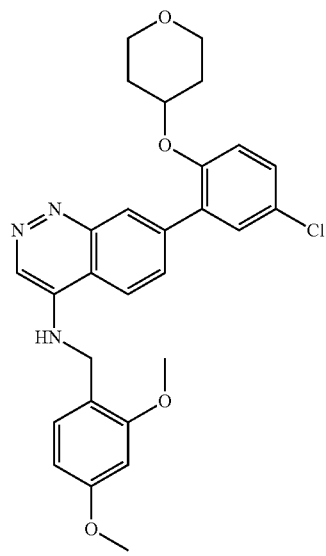 [SMILES: COc1ccc(CNc2cnnc3cc(-c4cc(Cl)ccc4OC4CCOCC4)ccc23)c(OC)c1]

A mixture of 4-(2-bromo-4-chlorophenoxy)oxane (356.78 mg, 1.22 mmol), [4-[(2,4-dimethoxyphenyl)methylamino]cinnolin-7-yl]boronic acid (415.0 mg, 1.22 mmol) and aqueous 2N sodium carbonate solution (1.2 mL, 2.45 mmol) in 1,2-dimethoxyethane (8.646 mL) was degassed for 10 min. Then [1,1'-bis(di-tert-butylphosphino)ferrocene]dichloropalladium(II) (80.0 mg, 0.120 mmol) was added and the resulting reaction mixture was stirred at 85° C. for 6 hours. The mixture was filtered over Celite, washing with EtOAc. The filtrate was concentrated in vacuo and the residue was purified by column chromatography (KP-NH silica gel, SNAP 28 g) eluting with a gradient of EtOAc in cyclohexane from 0% to 100% to give 7-[5-chloro-2-(oxan-4-yloxy)phenyl]-N-[(2,4-dimethoxyphenyl)methyl]cinnolin-4-amine (134 mg, 0.265 mmol, 21.64% yield) as a viscous oil. $^1$H NMR (400 MHz, DMSO-$d_6$) δ 1.47-1.60 (m, 2H), 1.84-1.96 (m, 2H), 3.43 (ddd, J=11.34, 7.85, 3.28 Hz, 2H), 3.65 (ddd, J=10.69, 6.36, 3.75 Hz, 2H), 3.74 (s, 3H), 3.88 (s, 3H), 4.51 (d, J=5.81 Hz, 2H), 4.64-4.72 (m, 1H), 6.48 (dd, J=8.39, 2.40 Hz, 1H), 6.63 (d, J=2.42 Hz, 1H), 7.16 (d, J=8.38 Hz, 1H), 7.29 (d, J=8.92 Hz, 1H), 7.44 (dd, J=8.83, 2.68 Hz, 1H), 7.56 (d, J=2.74 Hz, 1H), 7.81 (dd, J=8.73, 1.84 Hz, 1H), 8.02 (t, J=5.92 Hz, 1H), 8.24 (d, J=1.80 Hz, 1H), 8.37 (d, J=8.86 Hz, 1H), 8.48 (s, 1H). LC-MS (Method A): r.t. 0.84 min, MS (ESI) m/z=506.3 [M+H]$^+$.

Intermediate 162:
3-(3-bromo-5-chlorophenyl)pyridine

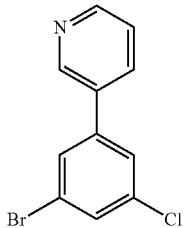 [SMILES: Clc1cc(Br)cc(-c2cccnc2)c1]

A mixture of 1-bromo-3-chloro-5-iodobenzene (500.0 mg, 1.58 mmol), 3-pyridinylboronic acid (213.03 mg, 1.73 mmol) and potassium carbonate (1088.78 mg, 7.88 mmol) in 1,4-dioxane (8 mL) was degassed for 15 min under N$_2$. Then palladium tetrakis triphenylphosphine (91.03 mg, 0.080 mmol) was added and the resulting reaction mixture was stirred at 90° C. for 12 hours. The mixture was cooled to room temperature, filtered over a pad of Celite, washing with MeOH and evaporated. The residue was purified by column chromatography (KP-NH silica gel, 2×SNAP 28 in series) eluting with a gradient of EtOAc in cyclohexane from 0% to 80% to give 3-(3-bromo-5-chlorophenyl)pyridine (300 mg, 1.117 mmol, 70.91% yield) as a white solid. $^1$H NMR (400 MHz, DMSO-$d_6$) δ 7.48-7.52 (m, 1H), 7.77 (t, J=1.8 Hz, 1H), 7.87 (t, J=1.7 Hz, 1H), 7.95 (t, J=1.7 Hz, 1H), 8.14-8.18 (m, 1H), 8.62 (dd, J=4.8, 1.6 Hz, 1H), 8.95 (dd, J=2.5, 0.9 Hz, 1H). LC-MS (Method A): r.t. 1.03 min, MS (ESI) m/z=268.0 and 270.0 [M+H]$^+$.

Intermediate 163: 6-(3-chloro-5-pyridin-3-ylphenyl)-N-[(2,4-dimethoxyphenyl)methyl]-4-methylphthalazin-1-amine

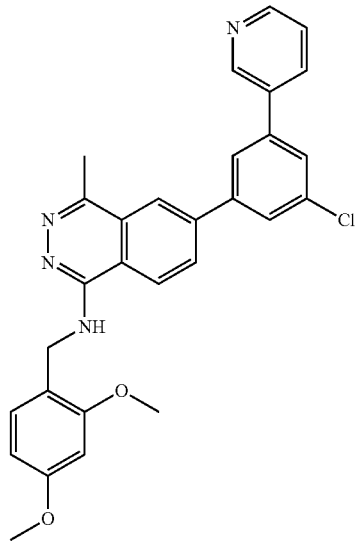 [SMILES: COc1ccc(CNc2nnc(C)c3cc(-c4cc(Cl)cc(-c5cccnc5)c4)ccc23)c(OC)c1]

A mixture of 3-(3-bromo-5-chlorophenyl)pyridine (230.0 mg, 0.860 mmol), [1-[(2,4-dimethoxyphenyl)methylamino]-4-methylphthalazin-6-yl]boronic acid (432.13 mg, 0.860 mmol) and aqueous 2 M sodium carbonate solution (856.48 μL, 1.71 mmol) in 1,2-dimethoxyethane (8.565 mL) was degassed for 10 min under N$_2$. Then [1,1'-bis(di-tert-butylphosphino)ferrocene]dichloropalladium(II) (55.99 mg, 0.090 mmol) was added and the resulting reaction mixture was stirred at 80° C. for 3 hours. The mixture was filtered over a pad of Celite, washing with MeOH. The organic phase was concentrated in vacuo and the residue was purified by column chromatography (KP-NH silica gel, 2×SNAP 28 in series) eluting with a gradient of EtOAc in cyclohexane from 0% to 80% to give 6-(3-chloro-5-pyridin-3-ylphenyl)-N-[(2,4-dimethoxyphenyl)methyl]-4-methylphthalazin-1-amine (145 mg, 0.292 mmol, 34.06% yield) as a yellow oil. $^1$H NMR (400 MHz, DMSO-$d_6$) δ 2.79 (s, 3H), 3.73 (s, 3H), 3.85 (s, 3H), 4.68 (d, J=5.6 Hz, 2H), 6.44 (dd, J=8.4, 2.4 Hz, 1H), 6.59 (d, J=2.4 Hz, 1H), 7.13 (d, J=8.4 Hz, 1H), 7.51-7.59 (m, 1H), 7.66 (t, J=5.7 Hz, 1H), 7.92 (t, J=1.7 Hz, 1H), 8.07 (t, J=1.8 Hz, 1H), 8.19 (t, J=1.6 Hz, 1H), 8.27-8.31 (m, 1H), 8.34 (d, J=1.8 Hz, 1H), 8.37 (dd, J=8.6, 1.9 Hz, 1H), 8.51 (d, J=8.6 Hz, 1H), 8.66 (dd, J=4.8, 1.6 Hz, 1H), 9.10 (dd, J=2.4, 0.9 Hz, 1H). LC-MS (Method A): r.t. 0.77 min, MS (ESI) m/z=497.3 [M+H]$^+$.

Intermediate 164: [3-[1-[(2,4-dimethoxyphenyl)methylamino]-4-methylphthalazin-6-yl]-5-pyridin-3-ylphenyl]boronic Acid

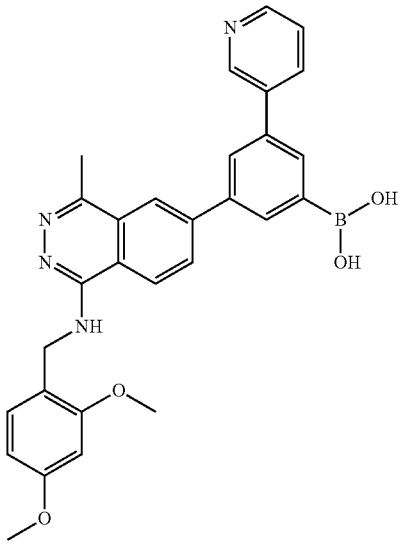 [SMILES: COc1ccc(CNc2nnc(C)c3cc(-c4cc(B(O)O)cc(-c5cccnc5)c4)ccc23)c(OC)c1]

6-(3-Chloro-5-pyridin-3-ylphenyl)-N-[(2,4-dimethoxyphenyl)methyl]-4-methylphthalazin-1-amine (145.0 mg, 0.290 mmol), dicyclohexyl-[2-[2,4,6-tri(propan-2-yl)phenyl]phenyl]phosphine (11.13 mg, 0.020 mmol), potassium acetate (85.9 mg, 0.880 mmol), 4,4,5,5-tetramethyl-2-(4,4,5,5-tetramethyl-1,3,2-dioxaborolan-2-yl)-1,3,2-dioxaborolane (222.27 mg, 0.880 mmol) and palladium(II) diacetate (3.28 mg, 0.010 mmol) were dissolved in 1,4-dioxane (3 mL) in a microwave vial and the mixture was deoxygenated under $N_2$ for 10 minutes. The reaction mixture was stirred at 75° C. for 1.5 hours, then it was left to reach room temperature and filtered over a pad of Celite, washing with MeOH and concentrated in vacuo. The residue was purified by column chromatography (KP-C18-HS, 30 g) eluting with a gradient of $CH_3CN$ in water from 5% to 95% to give [3-[1-[(2,4-dimethoxyphenyl)methylamino]-4-methylphthalazin-6-yl]-5-pyridin-3-ylphenyl]boronic acid (55 mg, 0.109 mmol, 37.23% yield) as a yellow solid. $^1$H NMR (400 MHz, DMSO-$d_6$) δ 2.78 (s, 3H), 3.73 (s, 3H), 3.85 (s, 3H), 4.67 (d, J=5.3 Hz, 2H), 6.43 (dd, J=8.3, 2.4 Hz, 1H), 6.58 (d, J=2.4 Hz, 1H), 7.14 (d, J=8.5 Hz, 1H), 7.50-7.57 (m, 1H), 7.57-7.68 (m, 1H), 7.99 (s, 1H), 8.06-8.11 (m, 1H), 8.18-8.35 (m, 3H), 8.38 (s, 1H), 8.46-8.54 (m, 1H), 8.63 (td, J=4.9, 1.6 Hz, 1H), 9.04-9.08 (m, 1H). LC-MS (Method A): r.t. 0.57 min, MS (ESI) m/z=507.2 [M+H]$^+$.

Intermediate 165: 4-bromo-2-[(2,4-dimethoxyphenyl)methylamino]-6-fluorobenzoate

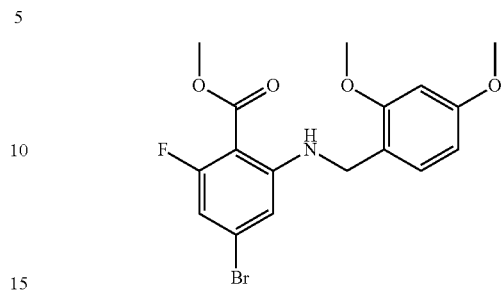

(2,4-Dimethoxyphenyl)methanamine (4.33 g, 25.89 mmol) was added to a stirred solution of methyl 4-bromo-2,6-difluorobenzoate (5.0 g, 19.92 mmol) in ethanol (60 mL). The resulting mixture was heated to 80° C. overnight then it was cooled to room temperature, giving a white precipitate. The precipitated solid was filtered, washed with ethanol, dried and collected to give methyl 4-bromo-2-[(2,4-dimethoxyphenyl)methylamino]-6-fluorobenzoate (5.966 g, 14.98 mmol, 75.21% yield) as a white solid. $^1$H NMR (400 MHz, DMSO-$d_6$) δ 3.76 (s, 3H), 3.82 (s, 3H), 3.84 (s, 3H), 4.29 (d, J=5.7 Hz, 2H), 6.51 (dd, J=8.3, 2.4 Hz, 1H), 6.60 (dd, J=7.1, 2.4 Hz, 1H), 6.67 (dd, J=11.0, 1.8 Hz, 1H), 6.76 (t, J=1.4 Hz, 1H), 7.17 (d, J=8.3 Hz, 1H), 7.84 (t, J=5.7 Hz, 1H). LC-MS (Method A): r.t. 1.44 min. MS (ESI) m/z of product not observed due to poor ionization.

Intermediate 166: methyl 2-amino-4-bromo-6-fluorobenzoate

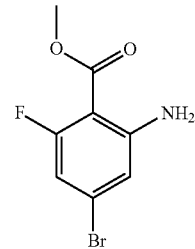

A solution of methyl 4-bromo-2-[(2,4-dimethoxyphenyl)methylamino]-6-fluorobenzoate (5.97 g, 14.98 mmol) in DCM (10 mL) and trifluoroacetic acid (10 mL) was stirred at room temperature for 2 hours then it was cooled to 0° C. The mixture was quenched with water and solid $NaHCO_3$ and then extracted with EtOAc. The combined organic phases were washed with water, dried over $Na_2SO_4$, filtered and concentrated under reduced pressure. The residue was purified by column chromatography (KP-Sil silica gel, SNAP 100) eluting with a gradient of EtOAc in cyclohexane from 5% to 60% to give methyl 2-amino-4-bromo-6-fluorobenzoate (2.2 g, 8.869 mmol, 59.2% yield) as a yellow solid. $^1$H NMR (400 MHz, Chloroform-d) δ 3.92 (s, 3H), 5.83 (s, 2H), 6.56 (dd, J=10.9, 1.9 Hz, 1H), 6.65 (t, J=1.6 Hz, 1H). LC-MS (Method A): r.t. 1.07 min, MS (ESI) m/z=247.98 and 250.04 [M+H]$^+$.

Intermediate 167: methyl 4-bromo-2-fluoro-6-iodobenzoate

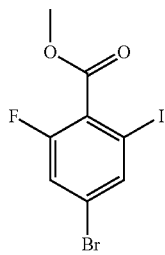

Methyl 2-amino-4-bromo-6-fluorobenzoate (2.0 g, 8.06 mmol) was suspended in acetonitrile (12.5 mL) and H$_2$O (22.5 mL). 12 M Hydrochloric acid solution (6.72 mL, 80.63 mmol) was added and the mixture was cooled in an ice bath. Sodium nitrite (1.11 g, 16.13 mmol) in H$_2$O (1 mL) was added dropwise and the resulting reaction mixture was stirred for 30 minutes. Then potassium iodide (4.02 g, 24.19 mmol) in H$_2$O (1 mL) was added slowly and the reaction was warmed to room temperature for 2 hours. A saturated aqueous solution of Na$_2$S$_2$O$_3$ was added and the mixture was stirred for 30 minutes, then it was extracted with EtOAc. The combined organic phases were washed with brine, dried over Na$_2$SO$_4$, filtered and evaporated in vacuo. The residue was purified by column chromatography (KP-Sil silica gel, SNAP 100) eluting with a gradient of EtOAc in cyclohexane from 5% to 50% to give methyl 4-bromo-2-fluoro-6-iodobenzoate (2.542 g, 7.082 mmol, 87.84% yield) as a colorless oil. $^1$H NMR (400 MHz, Chloroform-d) δ 3.99 (s, 3H), 7.34 (dd, J=8.6, 1.7 Hz, 1H), 7.85 (t, J=1.4 Hz, 1H). LC-MS (Method A): r.t. 1.24 min. MS (ESI) m/z of product not observed due to poor ionization.

Intermediate 168: methyl 2-acetyl-4-bromo-6-fluorobenzoate

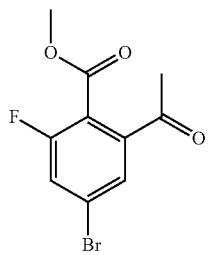

A 2M solution of isopropyl magnesium chloride in THF (4.52 mL, 9.04 mmol) was added to a solution of methyl 4-bromo-2-fluoro-6-iodobenzoate (2.95 g, 8.22 mmol) in THF (32.98 mL) at −78° C. After 30 minutes acetic acid acetyl ester (1.01 mL, 10.68 mmol) was added at the same temperature. After addition was complete the reaction mixture was stirred at room temperature for 2 hours, then it was quenched with a saturated aqueous solution of ammonium chloride and extracted three times with EtOAc. The combined organic phases were washed with brine, dried over Na$_2$SO$_4$, filtered and evaporated in vacuo. The residue was purified by column chromatography (KP-Sil silica gel, SNAP 100) eluting with a gradient of EtOAc in cyclohexane from 5% to 50% to give methyl 2-acetyl-4-bromo-6-fluorobenzoate (1.68 g, 6.108 mmol, 74.31% yield) as a colourless oil. $^1$H NMR (400 MHz, Chloroform-d) δ 2.60 (s, 3H), 3.96 (s, 3H), 7.51 (dd, J=8.3, 1.7 Hz, 1H), 7.69 (dd, J=1.7, 0.9 Hz, 1H). LC-MS (Method A): r.t. 0.99 min, MS (ESI) m/z=274.9 and 276.9 [M+H]$^+$.

Intermediate 169: 6-bromo-8-fluoro-4-methylphthalazin-1-ol

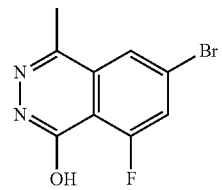

Hydrazine hydrate (139.99 mg, 1.82 mmol) was added to a solution of methyl 2-acetyl-4-bromo-6-fluorobenzoate (500.0 mg, 1.82 mmol) in ethanol (10 mL). The resulting reaction mixture was stirred at room temperature overnight then it was evaporated under reduced pressure. The residue was taken up with ethanol and it was heated to 80° C. for 5 hours, then it was cooled to room temperature and evaporated in vacuo. The residue was triturated with acetonitrile. The resulting solid was filtered and dried to give 6-bromo-8-fluoro-4-methylphthalazin-1-ol (427 mg, 1.661 mmol, 91.38% yield) as a pale yellow solid. $^1$H NMR (400 MHz, DMSO-d$_6$) δ 2.48 (s, 3H), 7.91-8.00 (m, 2H), 12.48 (s, 1H). LC-MS (Method A): r.t. 0.74 min, MS (ESI) m/z=256.8 and 258.86 [M+H]$^+$.

Intermediate 170: 7-bromo-4-chloro-5-fluoro-1-methylphthalazine

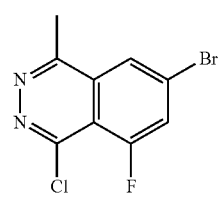

A mixture of POCl$_3$ (2.5 mL, 1.66 mmol) and 6-bromo-8-fluoro-4-methylphthalazin-1-ol (427.0 mg, 1.66 mmol) was stirred at 90° C. for 2 hours. The reaction was cooled to room temperature and the excess of POCl$_3$ was removed in vacuo. The residue was dissolved in DCM, washed with a saturated aqueous solution of NaHCO$_3$ and brine, dried over Na$_2$SO$_4$, filtered and evaporated in vacuo to give 7-bromo-4-chloro-5-fluoro-1-methylphthalazine (418 mg, 1.517 mmol, 91.34% yield) as a red solid. $^1$H NMR (400 MHz, DMSO-d$_6$) δ 2.92 (s, 3H), 8.33 (dd, J=11.14, 1.74 Hz, 1H), 8.40 (dd, J=1.77, 0.98 Hz, 1H). LC-MS (Method A): r.t. 0.94 min, MS (ESI) m/z=274.8 and 276.8 [M+H]$^+$.

Intermediate 171: 6-bromo-N-[(2,4-dimethoxyphenyl)methyl]-8-fluoro-4-methylphthalazin-1-amine

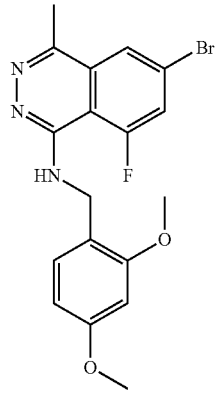 [SMILES: COc1ccc(CNc2nnc(C)c3cc(Br)cc(F)c23)c(OC)c1]

(2,4-Dimethoxyphenyl)methanamine (0.23 mL, 1.52 mmol) was added to a solution of 7-bromo-4-chloro-5-fluoro-1-methylphthalazine (418.0 mg, 1.52 mmol) in ethanol (6.5 mL) and the resulting mixture was stirred at 50° C. for 6 hours. The reaction mixture was cooled to room temperature and evaporated in vacuo. The residue was purified by column chromatography (KP-NH silica gel, SNAP 55) eluting with a gradient of EtOAc in cyclohexane from 5% to 70% to give 6-bromo-N-[(2,4-dimethoxyphenyl)methyl]-8-fluoro-4-methylphthalazin-1-amine (130 mg, 0.320 mmol, 21.09% yield) as an orange solid. $^1$H NMR (400 MHz, DMSO-$d_6$) δ 2.66 (s, 3H), 3.73 (s, 3H), 3.85 (s, 3H), 4.65 (d, J=5.58 Hz, 2H), 6.44 (dd, J=8.36, 2.42 Hz, 1H), 6.59 (d, J=2.39 Hz, 1H), 6.96 (m, 1H), 7.14 (d, J=8.30 Hz, 1H), 8.05 (m, 2H). LC-MS (Method A): r.t. 0.70 min, MS (ESI) m/z=406.2 and 408 [M+H]$^+$.

Intermediate 172: 6-(5-chloro-2-methoxyphenyl)-N-[(2,4-dimethoxyphenyl)methyl]-8-fluoro-4-methylphthalazin-1-amine

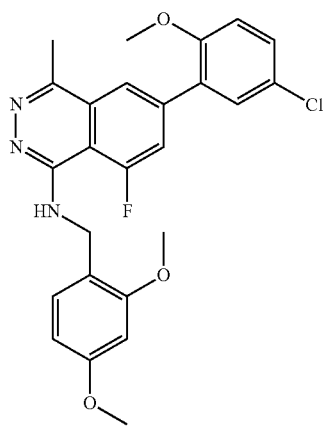 [SMILES: COc1ccc(CNc2nnc(C)c3cc(-c4cc(Cl)ccc4OC)cc(F)c23)c(OC)c1]

A mixture of 6-bromo-N-[(2,4-dimethoxyphenyl)methyl]-8-fluoro-4-methylphthalazin-1-amine (130.0 mg, 0.320 mmol) and 5-chloro-2-methoxyphenylboronic acid (0.07 g, 0.350 mmol) in 1,2-dimethoxyethane (3 mL) and aqueous 2N sodium carbonate solution (320 uL, 0.640 mmol) was degassed for 10 minutes with N$_2$. Then [1,1'-bis(di-tert-butylphosphino)ferrocene]dichloropalladium(II) (20.92 mg, 0.032 mmol) was added and the resulting reaction mixture was stirred at 70° C. for 6 hours. Then it was cooled to room temperature and filtered over Celite, washing with EtOAc. The filtrate was evaporated and the residue was purified by column chromatography (KP-NH silica gel, SNAP 30) eluting with a gradient of EtOAc in cyclohexane from 10% to 90% to give 6-(5-chloro-2-methoxyphenyl)-N-[(2,4-dimethoxyphenyl)methyl]-8-fluoro-4-methylphthalazin-1-amine (130 mg, 0.278 mmol, 86.82% yield) as an orange solid. LC-MS (Method A): r.t. 0.90 min, MS (ESI) m/z=468.15 [M+H]$^+$.

Intermediate 173: ethyl 2-(4-bromo-2-chlorophenyl)acetate

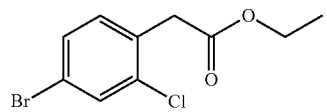

Sulfuric acid (0.75 mL, 14.03 mmol) was added dropwise to a solution of 2-(4-bromo-2-chlorophenyl)acetic acid (700.0 mg, 2.81 mmol) in ethanol (20 mL) and the resulting solution was stirred and heated to reflux for 5 h. The volatiles were evaporated and the residue was diluted with EtOAc, then washed with water and saturated aqueous NaHCO$_3$ solution, dried over Na$_2$SO$_4$, filtered and the solvent was evaporated. The crude ethyl 2-(4-bromo-2-chlorophenyl)acetate (680 mg, 2.45 mmol, 87.32% yield) was used in the next step without further purification. $^1$H NMR (400 MHz, DMSO-$d_6$) δ 1.18 (t, J=7.11 Hz, 3H), 3.79 (s, 2H), 4.10 (q, J=7.11 Hz, 2H), 7.38 (d, J=8.20 Hz, 1H), 7.54 (dd, J=8.20, 2.05 Hz, 1H), 7.73 (d, J=2.05 Hz, 1H). LC-MS (Method A): r.t. 1.25 min, MS (ESI) m/z=276.9 and 278.9 [M+H]$^+$.

Intermediate 174: ethyl 2-[2-chloro-4-[1-[(2,4-dimethoxyphenyl)methylamino]-4-methylphthalazin-6-yl]phenyl]acetate

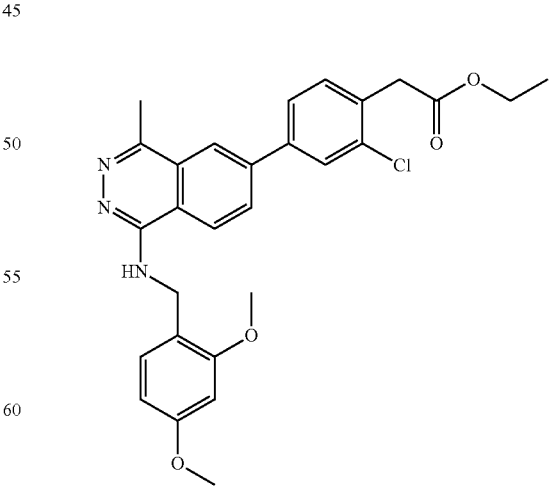

A mixture of K$_3$PO$_4$ (360.61 mg, 1.7 mmol), KH$_2$PO$_4$ (115.6 mg, 0.850 mmol), ethyl 2-(4-bromo-2-chlorophenyl)acetate (235.75 mg, 0.850 mmol) and [1-[(2,4-dimethoxyphenyl)methylamino]-4-methylphthalazin-6-yl]boronic acid (300.0 mg, 0.850 mmol) in 1,4-dioxane (9.574 mL) was degassed for 10 min. Then [1,1'-bis(di-tert-butylphosphino)ferrocene]dichloropalladium(II) (55.53 mg, 0.080 mmol) was added and the resulting reaction mixture was stirred at 85° C. for 6 hours. The mixture was filtered over Celite, washing with EtOAc. The filtrate was concentrated in vacuo and the residue was purified by column chromatography (KP-NH silica gel, SNAP 28 g) eluting with a gradient of EtOAc in cyclohexane from 0% to 100% to give ethyl 2-[2-chloro-4-[1-[(2,4-dimethoxyphenyl)methylamino]-4-methylphthalazin-6-yl]phenyl]acetate (399 mg, 0.789 mmol, 92.83% yield) as a viscous oil. $^1$H NMR (400 MHz, DMSO-$d_6$) δ 1.17 (t, J=7.09 Hz, 3H), 2.76 (s, 3H), 3.73 (s, 3H), 3.84 (s, 3H), 3.89 (s, 2H), 4.03 (q, J=7.09 Hz, 2H), 4.66 (d, J=5.59 Hz, 2H), 6.42 (dd, J=8.37, 2.40 Hz, 1H), 6.58 (d, J=2.40 Hz, 1H), 7.12 (d, J=8.37 Hz, 1H), 7.58 (d, J=8.01 Hz, 1H), 7.60-7.67 (m, 1H), 7.86 (dd, J=7.94, 1.94 Hz, 1H), 8.04 (d, J=1.94 Hz, 1H), 8.20-8.29 (m, 2H), 8.47 (d, J=9.25 Hz, 1H). LC-MS (Method A): r.t. 0.85 min, MS (ESI) m/z=506.1 [M+H]$^+$.

Intermediate 175: ethyl 2-[4-(1-amino-4-methylphthalazin-6-yl)-2-(4,4,5,5-tetramethyl-1,3,2-dioxaborolan-2-yl)phenyl]acetate

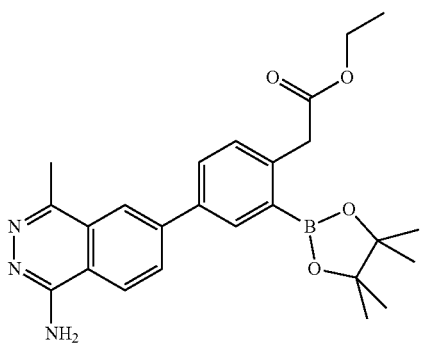 [SMILES: CCOC(=O)Cc1ccc(-c2ccc3c(N)nnc(C)c3c2)cc1B1OC(C)(C)C(C)(C)O1]

Step 1: A mixture of ethyl 2-[2-chloro-4-[1-[(2,4-dimethoxyphenyl)methylamino]-4-methylphthalazin-6-yl]phenyl]acetate (399.0 mg, 0.790 mmol), 4,4,5,5-tetramethyl-2-(4,4,5,5-tetramethyl-1,3,2-dioxaborolan-2-yl)-1,3,2-dioxaborolane (600.74 mg, 2.37 mmol), potassium acetate (232.17 mg, 2.37 mmol), dicyclohexyl-[2-[2,4,6-tri(propan-2-yl)phenyl]phenyl]phosphine (30.07 mg, 0.060 mmol) and palladium(II) diacetate (8.85 mg, 0.040 mmol) in 1,4-dioxane (10 mL) was degassed with Ar for 10 min, then heated at 100° C. for 40 h. A ~1:1 mixture desired product and ethyl 2-[4-(1-{[(2,4-dimethoxyphenyl)methyl]amino}-4-methylphthalazin-6-yl)phenyl]acetate was obtained. The volatiles were evaporated and the crude ethyl 2-[4-[1-[(2,4-dimethoxyphenyl)methylamino]-4-methylphthalazin-6-yl]-2-(4,4,5,5-tetramethyl-1,3,2-dioxaborolan-2-yl)phenyl]acetate (800 mg) was used in the next step without further purification. LC-MS (Method A): r.t. 0.98 min, MS (ESI) m/z=598.2 [M+H]$^+$.

Step 2: The crude material obtained in Step 1 was suspended in DCM (10 mL), then trifluoroacetic acid (10 mL) was added and the mixture was stirred at room temperature for 2 h. The volatiles were evaporated and the residue was purified by column chromatography (KP-C18-HS, SNAP 30 g) eluting with a gradient of CH$_3$CN (+0.1% of HCOOH) in water (+0.1% of HCOOH) from 1% to 50% to give ethyl 2-[4-(1-amino-4-methylphthalazin-6-yl)-2-(4,4,5,5-tetramethyl-1,3,2-dioxaborolan-2-yl)phenyl]acetate (150 mg, 0.335 mmol, 25.04% yield) in a mixture with [5-(1-amino-4-methylphthalazin-6-yl)-2-(2-ethoxy-2-oxo-ethyl)phenyl]boronic acid. LC-MS (Method A): r.t. (boronic ester) 0.79 min, MS (ESI) m/z=448.5 [M+H]$^+$; r.t. (boronic acid) 0.52 min, MS (ESI) m/z=366.5 [M+H]$^+$.

Intermediate 176: 4-bromo-2-fluoro-6-iodophenol

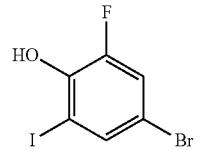

A 2M aqueous solution of sodium hydroxide (5.24 mL, 10.47 mmol) was added to an ice-cooled solution of 4-bromo-2-fluorophenol (1.0 g, 5.24 mmol), potassium iodide (1.3 g, 7.85 mmol) and iodine (1.99 g, 7.85 mmol) in water (13.09 mL). The mixture was left to reach room temperature and stirred for 5 h. An aqueous solution of ammonium chloride was added, followed by solid sodium thiosulfate (until decoloration was achieved). Methyl tert-butyl ether was added and the phases were separated. The organic phase was washed with brine, dried over sodium sulfate, filtered and concentrated. The brownish solid residue was purified by column chromatography (KP-C18-HS, 60 g) eluting with a gradient of CH$_3$CN (+0.1% of HCOOH) in water (+0.1% of HCOOH) from 2% to 50% to give 4-bromo-2-fluoro-6-iodophenol (1.04 g, 3.282 mmol, 62.68% yield) as a white solid. $^1$H NMR (400 MHz, DMSO-$d_6$) δ 7.53 (dd, J=10.1, 2.2 Hz, 1H), 7.68-7.70 (m, 1H), 10.76 (br. s, 1H). LC-MS (Method A): r.t. 1.16 min, MS (ESI) m/z=314.8 and 316.8 [M−H]$^−$.

Intermediate 177: 5-bromo-1-fluoro-3-iodo-2-methoxybenzene

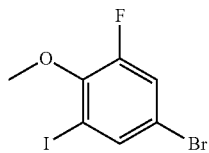

Iodomethane (0.22 mL, 3.61 mmol) was added dropwise to a stirred solution of 4-bromo-2-fluoro-6-iodophenol (1.04 g, 3.28 mmol) and potassium carbonate (544.31 mg, 3.94 mmol) in DMF (5 mL). The reaction mixture was stirred at room temperature for 90 min, then Et$_2$O and a saturated aqueous solution of ammonium chloride were added. The phases were separated, and the organic phase was washed with brine, dried over sodium sulfate, filtered and concentrated to give 5-bromo-1-fluoro-3-iodo-2-methoxybenzene (801 mg, 2.421 mmol, 73.75% yield) as a yellowish oil. $^1$H NMR (400 MHz, DMSO-$d_6$) δ 3.84 (d, J=1.5 Hz, 3H), 7.68 (dd, J=10.8, 2.2 Hz, 1H), 7.82-7.85 (m, 1H). LC-MS (Method A): r.t. 1.34 min, MS (ESI) m/z of product not observed due to poor ionization.

Intermediate 178: 6-(5-bromo-3-fluoro-2-methoxyphenyl)-N-[(2,4-dimethoxyphenyl)methyl]-4-methylphthalazin-1-amine

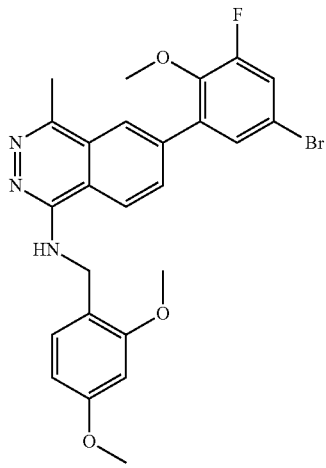 [SMILES: COc1ccc(CNc2nnc(C)c3cc(-c4cc(Br)cc(F)c4OC)ccc23)c(OC)c1]

A mixture of 5-bromo-1-fluoro-3-iodo-2-methoxybenzene (299.83 mg, 0.910 mmol) and [1-[(2,4-dimethoxyphenyl)methylamino]-4-methylphthalazin-6-yl]boronic acid (400.0 mg, 0.910 mmol) in 1,2-dimethoxyethane (8.5 mL) and aqueous 2N sodium carbonate solution (0.45 mL, 0.910 mmol) was degassed for 10 min. [1,1'-Bis(di-tert-butylphosphino)ferrocene]dichloropalladium(II) (59.23 mg, 0.090 mmol) was added and the mixture was degassed for a further 10 min, then it was stirred at 80° C. for 3.5 h. The mixture was left to reach room temperature, diluted with EtOAc, filtered and concentrated. The residue was purified by column chromatography (KP-Sil silica gel SNAP25) eluting with a gradient of EtOAc in cyclohexane from 20% to 100% to give 6-(5-bromo-3-fluoro-2-methoxyphenyl)-N-[(2,4-dimethoxyphenyl)methyl]-4-methylphthalazin-1-amine (45 mg, 0.088 mmol, 9.693% yield) as a brownish foam. LC-MS (Method A): r.t. 0.90 min, MS (ESI) m/z=512.2 [M+H]$^+$.

Intermediate 179: [3-[1-[(2,4-dimethoxyphenyl)methylamino]-4-methylphthalazin-6-yl]-5-fluoro-4-methoxyphenyl]boronic Acid

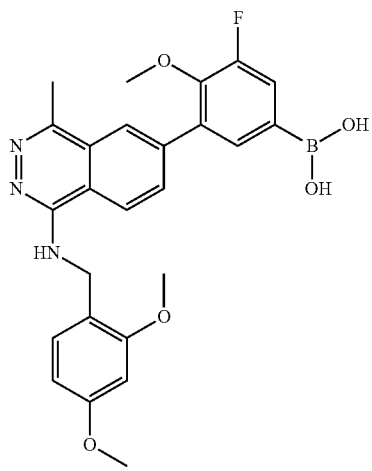 [SMILES: COc1ccc(CNc2nnc(C)c3cc(-c4cc(B(O)O)cc(F)c4OC)ccc23)c(OC)c1]

Palladium(II) diacetate (0.49 mg, 0.002 mmol), potassium acetate (12.93 mg, 0.130 mmol), 4,4,5,5-tetramethyl-2-(4,4,5,5-tetramethyl-1,3,2-dioxaborolan-2-yl)-1,3,2-dioxaborolane (33.45 mg, 0.130 mmol), dicyclohexyl-[2-[2,4,6-tri(propan-2-yl)phenyl]phenyl]phosphine (1.67 mg, 0.004 mmol) and 6-(5-bromo-3-fluoro-2-methoxyphenyl)-N-[(2,4-dimethoxyphenyl)methyl]-4-methylphthalazin-1-amine (45.0 mg, 0.040 mmol) were dissolved in 1,4-dioxane (2.045 mL). The mixture was degassed with Ar for 10 min, then stirred at 75° C. for 2 hours. The mixture was left to reach room temperature, then diluted with EtOAc, filtered and concentrated. The residue was purified by column chromatography (KP-C18-HS, 12 g) eluting with a gradient of $CH_3CN$ (+0.1% of HCOOH) in water (+0.1% of HCOOH) from 2% to 50% to give [3-[1-[(2,4-dimethoxyphenyl)methylamino]-4-methylphthalazin-6-yl]-5-fluoro-4-methoxyphenyl]boronic acid (9 mg, 0.019 mmol, 42.94% yield). LC-MS (Method A): r.t. 0.94 min, MS (ESI) m/z=478.18 [M+H]$^+$.

Intermediate 180: 4-(5-chloro-2-methoxyphenyl)oxan-4-ol

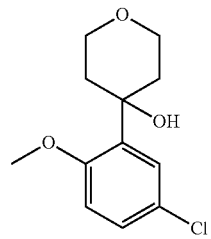 [SMILES: COc1ccc(Cl)cc1C1(O)CCOCC1]

A 2M solution of isopropyl magnesium chloride in THF (2.05 mL, 4.1 mmol) was added to a solution of 4-chloro-2-iodoanisole (1 g, 3.72 mmol) in THF (14.9 mL) at −78° C. After 30 minutes 4-oxanone (0.44 mL, 4.84 mmol) was added at the same temperature. After addition was complete the reaction mixture was stirred at room temperature for 2 hours, then it was quenched with a saturated aqueous solution of ammonium chloride and extracted three times with EtOAc. The combined organic phases were washed with brine, dried over $Na_2SO_4$, filtered and evaporated in vacuo. The residue was purified by column chromatography (KP silica gel, SNAP 50) eluting with a gradient of EtOAc in cyclohexane from 5% to 50% to give 4-(5-chloro-2-methoxyphenyl)oxan-4-ol (450 mg, 1.854 mmol, 49.78% yield) as a colourless oil. $^1$H NMR (400 MHz, Chloroform-d) δ 1.88-1.98 (m, 2H), 2.09-2.21 (m, 2H), 3.82 (t, J=1.05 Hz, 1H), 3.86 (m, 2H), 3.92 (s, 3H), 4.02 (m, 2H), 6.89 (d, J=8.63 Hz, 1H), 7.25 (dd, J=8.65, 2.58 Hz, 1H), 7.28 (s, 1H). LC-MS (Method A): r.t. 0.90 min. MS (ESI) m/z of product not observed due to poor ionization.

Intermediate 181: 4-(5-chloro-2-methoxyphenyl)oxane

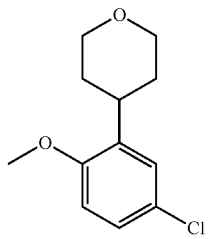

A solution of 4-(5-chloro-2-methoxyphenyl)oxan-4-ol (450.0 mg, 1.85 mmol) and triethylsilane (0.32 mL, 2.04 mmol) in DCM (7 mL) was chilled in an ice bath. Trifluoroacetic acid (1.42 mL, 18.54 mmol) was added in a dropwise manner over 20 minutes. After 1 hour at 0° C. the reaction mixture was warmed to room temperature and stirred for 3 hours. 1N aqueous NaOH solution was added until the aqueous pH was basic and the mixture was extracted three times with dichloromethane. The combined organic phases were dried over $Na_2SO_4$ and concentrated in vacuo. The residue was purified by column chromatography (KP silica gel, SNAP 50) eluting with a gradient of EtOAc in cyclohexane from 5% to 50% to give 4-(5-chloro-2-methoxyphenyl)oxane (296.1 mg, 1.30 mmol, 70% yield) as a colourless oil. $^1$H NMR (400 MHz, Chloroform-d) δ 1.73-1.85 (m, 4H), 3.18 (tt, J=10.67, 5.08 Hz, 1H), 3.57 (m, 2H), 3.84 (s, 3H), 4.04-4.20 (m, 2H), 6.76-6.85 (m, 1H), 7.12-7.22 (m, 2H). LC-MS (Method A): r.t. 1.18 min. MS (ESI) m/z of product not observed due to poor ionization.

Intermediate 182: 4-(3-bromo-5-chloro-2-methoxyphenyl)oxane

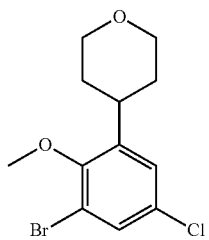 [SMILES: COc1c(Br)cc(Cl)cc1C1CCOCC1]

1-Bromopyrrolidine-2,5-dione (498.14 mg, 2.8 mmol) was added to a solution of 4-(5-chloro-2-methoxyphenyl)oxane (423.0 mg, 1.87 mmol) in DMF (8 mL) at 0° C. The resulting mixture was stirred at 50° C. overnight, then it was cooled to room temperature and quenched with a saturated aqueous solution of $Na_2S_2O_3$. The mixture was extracted three times with EtOAc. The combined organic phases were washed with water and brine, dried over sodium sulfate, filtered and concentrated in vacuo. The residue was purified by column chromatography (KP-Sil silica gel, SNAP 50) eluting with a gradient of EtOAc in cyclohexane from 5% to 50% to give 4-(3-bromo-5-chloro-2-methoxyphenyl)oxane (450 mg, 1.473 mmol, 78.92% yield) as a white solid. $^1$H NMR (400 MHz, Chloroform-d) δ 1.67-1.82 (m, 4H), 3.13-3.26 (m, 1H), 3.57 (m, 2H), 3.85 (s, 3H), 4.06-4.18 (m, 2H), 7.17 (d, J=2.51 Hz, 1H), 7.44 (d, J=2.51 Hz, 1H).

LC-MS (Method A): r.t. 1.3 min. MS (ESI) m/z of product not observed due to poor ionization.

Intermediate 183: 7-[5-chloro-2-methoxy-3-(oxan-4-yl)phenyl]-N-[(2,4-dimethoxyphenyl)methyl]cinnolin-4-amine

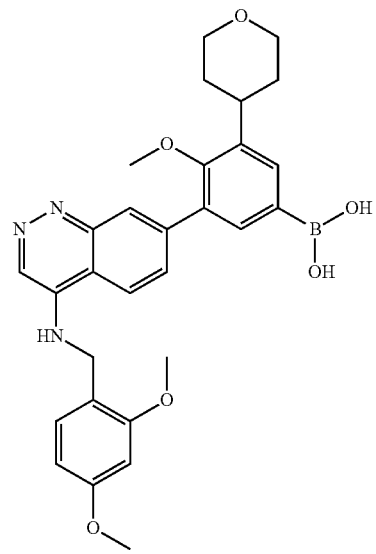 [SMILES: COc1ccc(CNc2cnnc3cc(-c4cc(B(O)O)cc(C5CCOCC5)c4OC)ccc23)c(OC)c1]

A mixture of 4-(3-bromo-5-chloro-2-methoxyphenyl)oxane (0.17 g, 0.550 mmol), [4-[(2,4-dimethoxyphenyl)methylamino]cinnolin-7-yl]boronic acid (340.0 mg, 0.500 mmol) in 1,2-dimethoxyethane (4 mL) and aqueous 2N sodium carbonate solution (500 uL, 1 mmol) was degassed for 10 minutes with $N_2$. Then [1,1'-bis(di-tert-butylphosphino)ferrocene]dichloropalladium(II) (32.77 mg, 0.05 mmol) was added and the resulting reaction mixture was stirred at 75° C. for 6 hours. Then it was cooled to room temperature and filtered over Celite, washing with EtOAc. The filtrate was evaporated and the residue was purified by column chromatography (KP-NH silica gel, SNAP 30) eluting with a gradient of EtOAc in dichloromethane from 2% to 80% to give 7-[5-chloro-2-methoxy-3-(oxan-4-yl)phenyl]-N-[(2,4-dimethoxyphenyl)methyl]cinnolin-4-amine (75 mg, 0.144 mmol, 28.77% yield) as an orange solid. LC-MS (Method A): r.t. 0.85 min, MS (ESI) m/z=520.2 $[M+H]^+$.

Intermediate 184: 2,4-bis(4,4,5,5-tetramethyl-1,3,2-dioxaborolan-2-yl)aniline

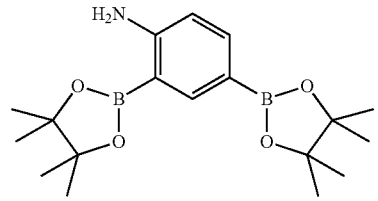

4-(4,4,5,5-Tetramethyl-1,3,2-dioxaborolan-2-yl)aniline (1.5 g, 6.85 mmol) was dissolved in THF (6.6 mL) in a microwawe vial then 4,4,5,5-tetramethyl-1,3,2-dioxaborolane (2.19 mL, 15.06 mmol) was added and the reaction vessel was sealed and stirred at room temperature for 1 h. 3,4,7,8-Tetramethyl-1,10-phenanthroline (48.54 mg, 0.210 mmol) and (1Z,5Z)-cycloocta-1,5-diene iridium methyloxonium (68.49 mg, 0.100 mmol) were added and the reaction vessel was sealed and heated at 80° C. for 16 h. The reaction mixture was allowed to reach room temperature and the reaction mixture was exposed to air, diluted with MeOH and concentrated. The residue was purified by column chromatography (KP-Sil silica gel, SNAP 50) eluting with a gradient of EtOAc in cyclohexane from 5% to 40% to give 2,4-bis(4,4,5,5-tetramethyl-1,3,2-dioxaborolan-2-yl)aniline (1.1 g, 3.188 mmol, 46.56% yield) as a white solid. $^1$H NMR (400 MHz, DMSO-d$_6$) δ 1.25 (s, 12H), 1.30 (s, 12H), 5.85 (s, 2H), 6.55 (d, J=8.36 Hz, 1H), 7.41 (dd, J=8.14, 1.76 Hz, 1H), 7.80 (d, J=1.54 Hz, 1H). LC-MS (Method A): r.t. 1.37 min, MS (ESI) m/z=346.16 [M+H]$^+$.

Intermediate 185: 6-[2-amino-5-(4,4,5,5-tetramethyl-1,3,2-dioxaborolan-2-yl)phenyl]-N-[(2,4-dimethoxyphenyl)methyl]-4-methylphthalazin-1-amine

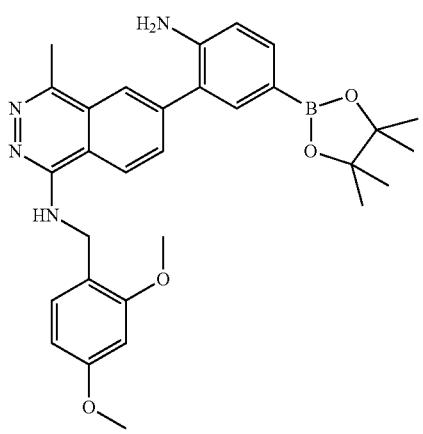 [SMILES: COc1ccc(CNc2nnc(C)c3cc(-c4cc(B5OC(C)(C)C(C)(C)O5)ccc4N)ccc23)c(OC)c1]

A mixture of 6-bromo-N-[(2,4-dimethoxyphenyl) methyl]-4-methylphthalazin-1-amine (93.18 mg, 0.240 mmol), dicesium carbonate (234.59 mg, 0.720 mmol) and 2,4-bis(4,4,5,5-tetramethyl-1,3,2-dioxaborolan-2-yl)aniline (165.62 mg, 0.480 mmol) in 1,4-dioxane (3.735 mL) and water (0.934 mL) was degassed for 10 min. [1,1'-Bis(di-tert-butylphosphino)ferrocene]dichloropalladium(II) (31.38 mg, 0.050 mmol) was added and the mixture was degassed again for 10 min. The reaction mixture was stirred at 55° C. for 1.5 h, then it was allowed to reach to room temperature, diluted with EtOAc and filtered over a pad of Celite. The volatiles were removed and the residue was purified by column chromatography (KP-Sil silica gel, SNAP25) eluting with a gradient of EtOAc in cyclohexane from 50% to 100% and then 5% MeOH in EtOAc to give 6-[2-amino-5-(4,4,5,5-tetramethyl-1,3,2-dioxaborolan-2-yl)phenyl]-N-[(2,4-dimethoxyphenyl)methyl]-4-methylphthalazin-1-amine (97 mg, 0.184 mmol, 76.78% yield) as a brownish foam. $^1$H NMR (400 MHz, DMSO-d$_6$) δ 1.27 (s, 12H), 2.68 (s, 3H), 3.74 (s, 3H), 3.85 (s, 3H), 4.67 (d, J=5.50 Hz, 2H), 5.44 (s, 2H), 6.43 (dd, J=8.25, 2.31 Hz, 1H), 6.59 (d, J=2.42 Hz, 1H), 6.78 (d, J=7.92 Hz, 1H), 7.12 (d, J=8.36 Hz, 1H), 7.37 (d, J=1.32 Hz, 1H), 7.42 (dd, J=8.14, 1.54 Hz, 1H), 7.59 (t, J=5.94 Hz, 1H), 7.85 (dd, J=8.47, 1.65 Hz, 1H), 7.93 (d, J=1.54 Hz, 1H), 8.43 (d, J=8.58 Hz, 1H). LC-MS (Method A): r.t. 0.87 min, MS (ESI) m/z=527.27 [M+H]$^+$.

Intermediate 186: N-[2-[1-[(2,4-dimethoxyphenyl) methylamino]-4-methylphthalazin-6-yl]-4-(4,4,5,5-tetramethyl-1,3,2-dioxaborolan-2-yl)phenyl]-3-methylbutanamide

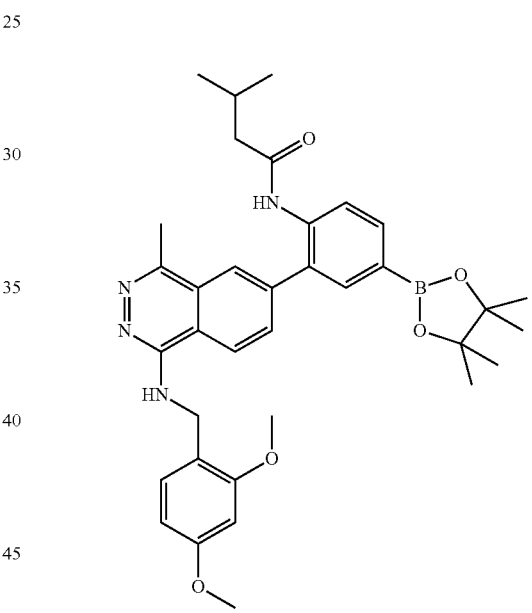

3-Methylbutanoyl chloride (11.45 mg, 0.090 mmol) was added to a stirred solution of 6-[2-amino-5-(4,4,5,5-tetramethyl-1,3,2-dioxaborolan-2-yl)phenyl]-N-[(2,4-dimethoxyphenyl)methyl]-4-methylphthalazin-1-amine (50.0 mg, 0.090 mmol) and triethylamine (0.01 mL, 0.090 mmol) in DCM (0.800 mL). The reaction mixture was stirred at room temperature for 2 h, then water and DCM were added. The phases were separated and the organic phase was washed with water and brine, dried over sodium sulfate, filtered and concentrated to give N-[2-[1-[(2,4-dimethoxyphenyl)methylamino]-4-methylphthalazin-6-yl]-4-(4,4,5,5-tetramethyl-1,3,2-dioxaborolan-2-yl)phenyl]-3-methylbutanamide (47 mg, 0.077 mmol, 81.05% yield) as a yellowish solid. LC-MS (Method A): r.t. 0.89 min, MS (ESI) m/z=611.27 [M+H]$^+$.

Intermediate 187: N-[2-(1-{[(2,4-dimethoxyphenyl)methyl]amino}-4-methylphthalazin-6-yl)-4-(4,4,5,5-tetramethyl-1,3,2-dioxaborolan-2-yl)phenyl]-4-methylpentanamide

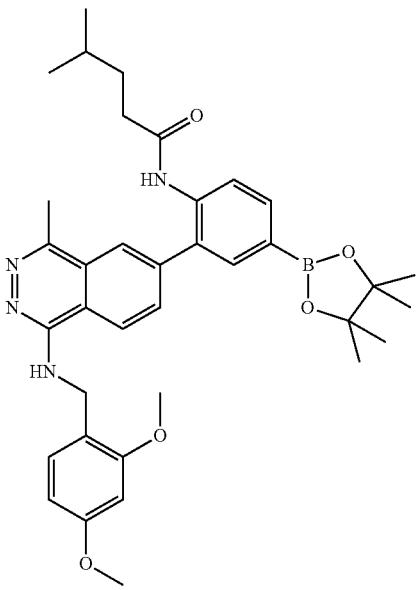 [SMILES: COc1ccc(CNc2nnc(C)c3cc(-c4cc(B5OC(C)(C)C(C)(C)O5)ccc4NC(=O)CCC(C)C)ccc23)c(OC)c1]

4-Methylpentanoyl chloride (0.01 mL, 0.090 mmol) was added to a stirred solution of 6-[2-amino-5-(4,4,5,5-tetramethyl-1,3,2-dioxaborolan-2-yl)phenyl]-N-[(2,4-dimethoxyphenyl)methyl]-4-methylphthalazin-1-amine (50.0 mg, 0.090 mmol) and triethylamine (0.01 mL, 0.090 mmol) in DCM (0.80 mL). The reaction mixture was stirred at room temperature for 2 h, then water and DCM were added. The phases were separated and the organic phase was washed with water and brine, dried over sodium sulfate, filtered and concentrated to give N-[2-[1-[(2,4-dimethoxyphenyl)methylamino]-4-methylphthalazin-6-yl]-4-(4,4,5,5-tetramethyl-1,3,2-dioxaborolan-2-yl)phenyl]-4-methylpentanamide (42 mg, 0.067 mmol, 70.8% yield) as a yellowish solid. LC-MS (Method A): r.t. 0.93 min, MS (ESI) m/z=625.23 [M+H]$^+$.

Intermediate 188: 2-bromo-4-chloro-1-dimethylphosphorylbenzene

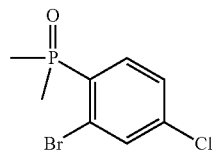

A mixture of 2-bromo-4-chloro-1-iodobenzene (1.0 g, 3.15 mmol), dimethylphosphine oxide (245.94 mg, 3.15 mmol), triethylamine (0.44 mL, 3.15 mmol), (5-diphenylphosphino-9,9-dimethyl-4-xanthenyl)-diphenylphosphine (182.33 mg, 0.320 mmol) and (1E,4E)-1,5-diphenyl-3-penta-1,4-dienone palladium (288.55 mg, 0.320 mmol) was dissolved in 1,4-dioxane (12 mL) and degassed for 10 min with $N_2$. The mixture was stirred at room temperature for 24 hours, then it was diluted with MeOH and filtered over Celite, washing with MeOH. The filtrate was evaporated and the residue was purified by column chromatography (KP-C18-HS, 30 g) eluting with a gradient of $CH_3CN$ in water (+0.1% of HCOOH) from 5 to 95%. Fractions containing the desired compound were collected and evaporated under reduced pressure to give 2-bromo-4-chloro-1-dimethylphosphorylbenzene (431 mg, 1.611 mmol, 51.13% yield) as a white powder. $^1$H NMR (400 MHz, DMSO-$d_6$) δ 1.81 (s, 3H), 1.85 (s, 3H), 7.68 (dq, J=8.27, 2.01, 0.97 Hz, 1H), 7.92-7.99 (m, 2H). LC-MS (Method A): r.t. 0.75 min, MS (ESI) m/z=268.9 [M+H]$^+$.

Intermediate 189: 6-(5-chloro-2-dimethylphosphorylphenyl)-N-[(2,4-dimethoxyphenyl)methyl]-4-methylphthalazin-1-amine

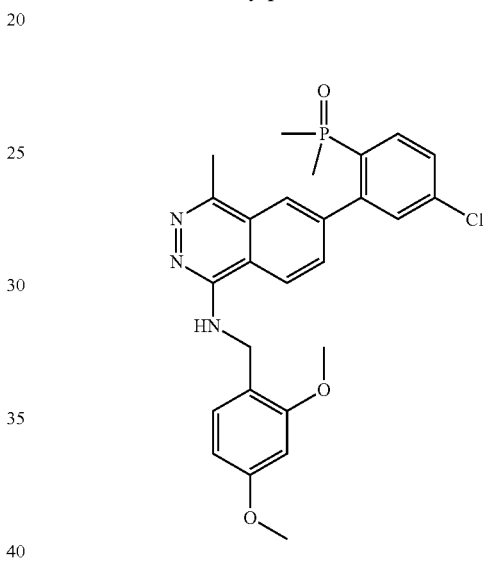

A mixture of 2-bromo-4-chloro-1-dimethylphosphorylbenzene (159.05 mg, 0.590 mmol), [1-[(2,4-dimethoxyphenyl)methylamino]-4-methylphthalazin-6-yl]boronic acid (250.0 mg, 0.500 mmol) and aqueous 2 N sodium carbonate solution (495.5 uL, 0.990 mmol) in 1,2-dimethoxyethane (5 mL) was degassed for 10 min under $N_2$. Then [1,1'-bis(di-tert-butylphosphino)ferrocene]dichloropalladium(II) (32.39 mg, 0.050 mmol) was added and the resulting reaction mixture was stirred at 80° C. for 12 hours. The mixture was filtered over a pad of Celite, washing with MeOH. The filtrate was concentrated in vacuo and the residue was purified by column chromatography (KP-NH silica gel, SNAP 28) eluting with a gradient of MeOH in DCM from 0% to 10% to give 6-(5-chloro-2-dimethylphosphorylphenyl)-N-[(2,4-dimethoxyphenyl)methyl]-4-methylphthalazin-1-amine (210 mg, 0.423 mmol, 85.46% yield) as a brown oil. $^1$H NMR (400 MHz, DMSO-$d_6$) δ 1.36 (s, 3H), 1.39 (s, 3H), 2.67 (s, 3H), 3.74 (s, 3H), 3.85 (s, 3H), 4.68 (d, J=5.58 Hz, 2H), 6.45 (dd, J=8.37, 2.41 Hz, 1H), 6.59 (d, J=2.40 Hz, 1H), 7.15 (d, J=8.34 Hz, 1H), 7.57 (dd, J=3.11, 2.14 Hz, 1H), 7.66 (t, J=5.71 Hz, 1H), 7.70 (dq, J=8.36, 2.18, 1.35 Hz, 1H), 7.95-8.03 (m, 2H), 8.14 (d, J=1.75 Hz, 1H), 8.43 (d, J=8.48 Hz, 1H). LC-MS (Method A): r.t. 0.68 min, MS (ESI) m/z=496.1 [M+H]$^+$.

Intermediate 190: 1-chloro-5-iodo-2-methoxy-4-(trifluoromethyl)benzene

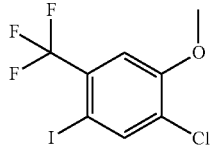

To a solution of 2-chloro-4-iodo-5-(trifluoromethyl)phenol (215.0 mg, 0.670 mmol) in DMF (3 mL), potassium carbonate (184.31 mg, 1.33 mmol) and iodomethane (0.05 mL, 0.730 mmol) were added in this order at 0° C. The resulting reaction mixture was stirred at room temperature overnight. The mixture was diluted with EtOAc and then washed twice with water and brine, dried over $Na_2SO_4$, filtered and evaporated. The residue was purified by column chromatography (KP-Sil silica gel, SNAP 25) eluting with a gradient of EtOAc in cyclohexane from 5% to 50% to give 1-chloro-5-iodo-2-methoxy-4-(trifluoromethyl)benzene (195 mg, 0.580 mmol, 86.92% yield) as a yellow oil. $^1$H NMR (400 MHz, DMSO-$d_6$) δ 3.95 (s, 3H), 7.41 (s, 1H), 8.16 (s, 1H). LC-MS (Method A): r.t. 1.38 min. MS (ESI) m/z of product not observed due to poor ionization.

Intermediate 191: 6-[5-chloro-4-methoxy-2-(trifluoromethyl)phenyl]-N-[(2,4-dimethoxyphenyl)methyl]-4-methylphthalazin-1-amine

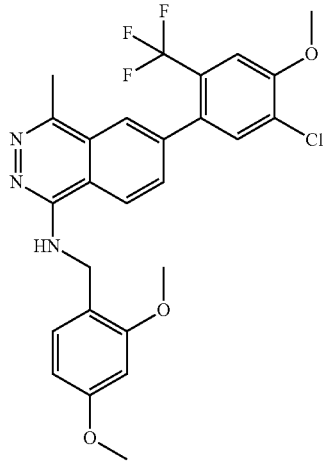 [SMILES: COc1ccc(CNc2nnc(C)c3cc(-c4cc(Cl)c(OC)cc4C(F)(F)F)ccc23)c(OC)c1]

A mixture of 1-chloro-5-iodo-2-methoxy-4-(trifluoromethyl)benzene (220.85 mg, 0.660 mmol) and 1-[(2,4-dimethoxyphenyl)methylamino]-4-methylphthalazin-6-yl]boronic acid (340.71 mg, 0.660 mmol) in 1,2-dimethoxyethane (6.5 mL) and aqueous 2N sodium carbonate solution (660 uL, 1.32 mmol) was degassed for 10 minutes with $N_2$. Then [1,1'-bis(di-tert-butylphosphino)ferrocene]dichloropalladium(II) (42.89 mg, 0.066 mmol) was added and the resulting reaction mixture was stirred at 80° C. for 6 hours. The mixture was cooled to room temperature and filtered over Celite, washing with EtOAc. The filtrate was evaporated and the residue was purified by column chromatography (KP-NH silica gel, SNAP 55) eluting with a gradient of EtOAc in cyclohexane from 10% to 100% to give 6-[5-chloro-4-methoxy-2-(trifluoromethyl)phenyl]-N-[(2,4-dimethoxyphenyl)methyl]-4-methylphthalazin-1-amine (175 mg, 0.338 mmol, 51.51% yield) as a yellow solid. $^1$H NMR (400 MHz, DMSO-$d_6$) δ 2.66 (s, 3H), 3.74 (s, 3H), 3.85 (s, 3H), 4.04 (s, 3H), 4.67 (d, J=5.56 Hz, 2H), 6.44 (dd, J=8.35, 2.39 Hz, 1H), 6.59 (d, J=2.40 Hz, 1H), 7.14 (d, J=8.38 Hz, 1H), 7.56 (s, 1H), 7.65 (t, J=5.68 Hz, 1H), 7.69 (s, 1H), 7.82 (d, J=8.14 Hz, 1H), 7.91 (d, J=1.73 Hz, 1H), 8.43 (d, J=8.51 Hz, 1H). LC-MS (Method A): r.t. 0.89 min, MS (ESI) m/z=518.2 [M+H]$^+$.

Intermediate 192: ethyl 2-(4-bromo-2-chlorophenyl)-2-oxoacetate

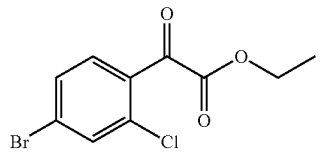

A 2.5M solution of n-butyllithium in hexane (5.99 mL, 14.97 mmol) was added dropwise to a solution of 4-bromo-2-chloroiodobenzene (5.0 g, 15.76 mmol) in THF (40 mL) at −78° C. The reaction mixture was stirred at −78° C. for 1.5 hours, then oxalic acid diethyl ester (6.4 mL, 47.27 mmol) was added dropwise and the mixture stirred overnight at room temperature. Water was added and the two phases were separated. The organic phase was washed with brine, filtered over a hydrophobic frit (Phase Separator) and evaporated. The residue was purified by column chromatography (KP-C18-HS, 120 g) eluting with a gradient of $CH_3CN$ in water (+0.1% of HCOOH) from 5% to 95%. Fractions containing the desired compound were collected and evaporated to give ethyl 2-(4-bromo-2-chlorophenyl)-2-oxoacetate (3.6 g, 12.35 mmol, 78.38% yield) as a yellow oil. $^1$H NMR (400 MHz, DMSO-$d_6$) δ 1.30 (t, J=7.11 Hz, 3H), 4.37 (q, J=7.12 Hz, 2H), 7.72-7.82 (m, 2H), 7.99 (d, J=1.68 Hz, 1H).

Intermediate 193: ethyl 2-(4-bromo-2-chlorophenyl)-2,2-difluoroacetate

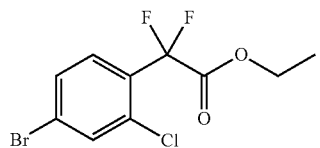 [SMILES: CCOC(=O)C(F)(F)c1ccc(Br)cc1Cl]

(N,N-Diethylamino)sulfur trifluoride (1.27 mL, 9.6 mmol) was added dropwise to a solution of ethyl 2-(4-bromo-2-chlorophenyl)-2-oxoacetate (2.0 g, 6.86 mmol) in DCM (42 mL) at 0° C. The reaction mixture was stirred overnight at room temperature. Aqueous saturated sodium bicarbonate solution was added and the two phases were separated. The aqueous phase was extracted three times with DCM. The combined organic phases was washed with brine, filtered over a hydrophobic frit (Phase Separator) and evaporated. The residue was purified by column chromatography (KP-C18-HS, 120 g) eluting with a gradient of $CH_3CN$ in water (+0.1% of HCOOH) from 5% to 95%. Fractions containing the desired compound were collected and evaporated to give ethyl 2-(4-bromo-2-chlorophenyl)-2,2-difluoroacetate (1.70 g, 5.438 mmol, 79.27% yield) as a colorless oil. $^1$H NMR (400 MHz, DMSO-d$_6$) δ 1.23 (t, J=7.10 Hz, 3H), 4.36 (q, J=7.07 Hz, 2H), 7.70-7.82 (m, 2H), 8.00 (s, 1H). $^{19}$F NMR (377 MHz, DMSO-d$_6$) δ −101.23. LC-MS (Method A): r.t. 1.31 min, MS (ESI) m/z of product not observed due to poor ionization.

Intermediate 194:
2-(4-bromo-2-chlorophenyl)-2,2-difluoroethanol

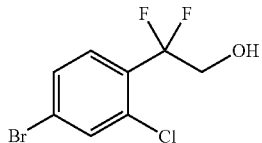

Sodium borohydride (262.44 mg, 6.94 mmol) was added portion-wise to a solution of ethyl 2-(4-bromo-2-chlorophenyl)-2,2-difluoroacetate (1450.0 mg, 4.62 mmol) in ethanol (42 mL). The reaction mixture was stirred for 1.5 hours at room temperature. 1N Hydrochloric acid solution was added and the resulting aqueous mixture was extracted 3 times with DCM. The combined organic phases were washed with brine, filtered over a hydrophobic frit (Phase Separator) and evaporated to give 2-(4-bromo-2-chlorophenyl)-2,2-difluoroethanol (1.244 g, 4.582 mmol, 99.07% yield) as a colorless oil. This material was used in the next step without further purification. $^1$H NMR (400 MHz, DMSO-d$_6$) δ 3.98 (t, J=14.18 Hz, 2H), 5.68 (br. s, 1H), 7.54 (d, J=8.48 Hz, 1H), 7.67-7.72 (m, 1H), 7.88 (d, J=1.96 Hz, 1H). LC-MS (Method A): r.t. 1.04 min, MS (ESI) m/z of product not observed due to poor ionization.

Intermediate 195: [2-(4-bromo-2-chlorophenyl)-2,2-difluoroethoxy]-tert-butyl-dimethylsilane

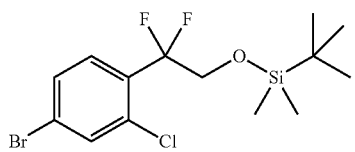 [SMILES: CC(C)(C)[Si](C)(C)OCC(F)(F)c1ccc(Br)cc1Cl]

tert-Butyl(chloro)dimethylsilane (1332.38 mg, 8.84 mmol) was added to a solution of 2-(4-bromo-2-chlorophenyl)-2,2-difluoroethanol (800.0 mg, 2.95 mmol) and imidazole (601.83 mg, 8.84 mmol) in THF (24 mL) under a N$_2$ atmosphere. The reaction mixture was stirred for 3 hours at room temperature. Water was added and the resulting mixture was extracted three times with EtOAc. The combined organic phases were washed with a saturated aqueous solution of sodium bicarbonate and brine, filtered over a hydrophobic frit (Phase Separator) and evaporated. The residue was purified by column chromatography (KP-Sil silica gel, SNAP 50) eluting with a gradient of EtOAc in cyclohexane from 0% to 10% to give [2-(4-bromo-2-chlorophenyl)-2,2-difluoroethoxy]-tert-butyl-dimethylsilane (994 mg, 2.577 mmol, 87.45% yield) as a colorless oil. $^1$H NMR (400 MHz, DMSO-d$_6$) δ −0.02 (s, 6H), 0.76 (s, 9H), 4.20 (t, J=13.42 Hz, 2H), 7.55 (d, J=8.49 Hz, 1H), 7.72 (dd, J=8.47, 1.97 Hz, 1H), 7.91 (dd, J=1.87, 1.01 Hz, 1H). LC-MS (Method A): r.t. 1.67 min, MS (ESI) m/z of product not observed due to poor ionization.

Intermediate 196: 6-[4-[2-[tert-butyl(dimethyl)silyl]oxy-1,1-difluoroethyl]-3-chlorophenyl]-N-[(2,4-dimethoxyphenyl)methyl]-4-methylphthalazin-1-amine

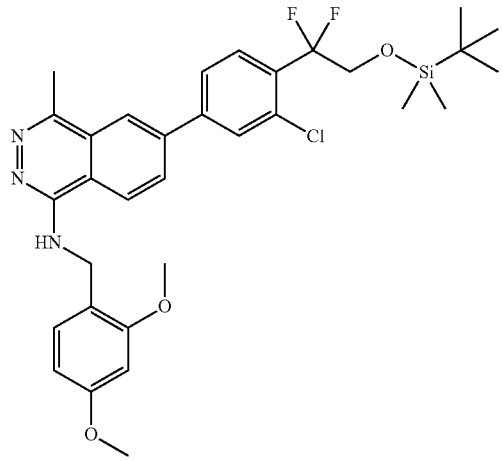 [SMILES: COc1ccc(CNc2nnc(C)c3cc(-c4ccc(C(F)(F)CO[Si](C)(C)C(C)(C)C)c(Cl)c4)ccc23)c(OC)c1]

A mixture of [1-[(2,4-dimethoxyphenyl)methylamino]-4-methylphthalazin-6-yl]boronic acid (91.56 mg, 0.260 mmol) and [2-(4-bromo-2-chlorophenyl)-2,2-difluoroethoxy]-tert-butyl-dimethylsilane (100.0 mg, 0.260 mmol) in 1,2-dimethoxyethane (2.5 mL) and aqueous 2N sodium carbonate solution (259.24 uL, 0.520 mmol) was degassed for 10 min with N$_2$. Then, [1,1'-bis(di-tert-butylphosphino)ferrocene]dichloropalladium(II) (16.95 mg, 0.030 mmol) was added. The mixture was stirred at 80° C. for 3 hours, then it was cooled to room temperature and filtered over Celite, washing with MeOH. The filtrate was evaporated and the residue was purified by column chromatography (KP-Sil silica gel, SNAP 10) eluting with a gradient of EtOAc in cyclohexane from 0% to 100% to give 6-[4-[2-[tert-butyl(dimethyl)silyl]oxy-1,1-difluoroethyl]-3-chlorophenyl]-N-[(2,4-dimethoxyphenyl)methyl]-4-methylphthalazin-1-amine (66 mg, 0.107 mmol, 41.45% yield) as a yellow oil. $^1$H NMR (400 MHz, DMSO-d$_6$) δ 0.03 (s, 6H), 0.80 (s, 9H), 2.77 (s, 3H), 3.73 (s, 3H), 3.85 (s, 3H), 4.28 (t, J=13.52 Hz, 2H), 4.67 (d, J=5.51 Hz, 2H), 6.43 (dd, J=8.37, 2.40 Hz, 1H), 6.59 (d, J=2.40 Hz, 1H), 7.13 (d, J=8.36 Hz, 1H), 7.66 (t, J=5.71 Hz, 1H), 7.77 (d, J=8.36 Hz, 1H), 8.01-8.07 (m, 1H), 8.19 (d, J=1.75 Hz, 1H), 8.25-8.32 (m, 2H), 8.50 (d, J=8.61 Hz, 1H). LC-MS (Method A): r.t. 1.16 min, MS (ESI) m/z=614.2 [M+H]$^+$.

Intermediate 197:
trimethyl(2,2,2-trifluoroethoxy)silane

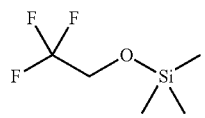

Chloro(trimethyl)silane (3.18 mL, 24.99 mmol) was added dropwise over a period of 2 hours to a solution of 2,2,2-trifluoroethanol (2.5 g, 24.99 mmol) and 1-methylimidazole (2.18 mL, 27.49 mmol) at 0° C. under a N$_2$ atmosphere. Then the temperature was raised at 60° C. and the mixture was stirred for 1 hour. After this time, the upper layer of the biphasic mixture was collected by decantation to give trimethyl(2,2,2-trifluoroethoxy)silane (4 g, 23.23 mmol, 92.94% yield) as a colorless oil. ¹H NMR (400 MHz, DMSO-d₆) δ 0.15 (s, 9H), 4.11 (q, J=9.28 Hz, 2H).

Intermediate 198:
1-(4-bromo-2-methyl-6-nitrophenyl)ethanone

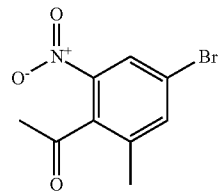

A 2.5M solution of n-butyllithium in hexane (5.85 mL, 14.62 mmol) was added dropwise to a solution of 5-bromo-2-iodo-1-methyl-3-nitrobenzene (5.0 g, 14.62 mmol) in THF (50 mL) at −78° C. The reaction mixture was stirred at −78° C. for 1 hour, then acetic acid acetyl ester (2.07 mL, 21.93 mmol) was added dropwise and the mixture was stirred at this temperature for 20 minutes, then it was warmed to room temperature and stirred for 2 hours. Water and EtOAc were added and the two phases were separated. The organic phase was washed with brine, filtered over a hydrophobic frit (Phase Separator) and evaporated. The residue was purified by column chromatography (KP-Sil silica gel, SNAP 100) eluting with a gradient of EtOAc in cyclohexane from 0% to 40% to give 1-(4-bromo-2-methyl-6-nitrophenyl)ethanone (1.35 g, 5.231 mmol, 35.77% yield) as an orange oil. ¹H NMR (400 MHz, DMSO-d₆) δ 2.30 (s, 3H), 2.52 (s, 3H), 8.05 (dd, J=1.88, 0.82 Hz, 1H), 8.26 (dd, J=1.90, 0.69 Hz, 1H). LC-MS (Method A): r.t. 1.04 min, MS (ESI) m/z=257.94 and 259.96 [M+H]⁺.

Intermediate 199:
1-(2-amino-4-bromo-6-methylphenyl)ethanone

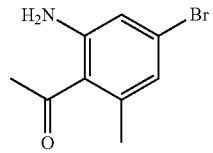

A stirred mixture of iron (1.55 g, 27.71 mmol), ammonium chloride (377.23 mg, 7.05 mmol) and 1-(4-bromo-2-methyl-6-nitrophenyl)ethanone (1.3 g, 5.04 mmol) in ethanol (48 mL) and water (16 mL) was heated to 80° C. for 60 min, then it was left to reach room temperature, diluted with MeOH and filtered over a pad of Celite, washing with MeOH. The volatiles were removed and the residue was purified by column chromatography (KP-sil silica gel, SNAP 100) eluting with a gradient of EtOAc in cyclohexane from 0% to 40% to give 1-(2-amino-4-bromo-6-methylphenyl)ethanone (875 mg, 3.836 mmol, 76.15% yield) as a yellow powder. ¹H NMR (400 MHz, DMSO-d₆) δ 2.16 (s, 3H), 2.42 (s, 3H), 5.63 (s, 2H), 6.59 (dd, J=1.88, 0.78 Hz, 1H), 6.78 (dd, J=1.97, 0.65 Hz, 1H). LC-MS (Method A): r.t. 0.97 min, MS (ESI) m/z=227.9 and 229.9 [M+H]⁺.

Intermediate 200: 7-bromo-5-methylcinnolin-4-ol

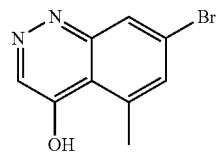

1-(2-Amino-4-bromo-6-methylphenyl)ethanone (871.0 mg, 3.82 mmol) was dissolved in concentrated hydrochloric acid solution (22.07 mL, 264.86 mmol) and water (4 mL) and cooled to −5° C. in an ice/brine bath. After 15 min, a solution of sodium nitrite (276.29 mg, 4 mmol) in water (1 mL) was slowly added dropwise. The reaction mixture was stirred for 1 hour at room temperature and then the temperature was raised to 60° C. The reaction mixture was heated at 60° C. for 2 h, then it was cooled to room temperature and the resulting precipitate was filtered, washed with water and dried in the oven at 50° C. overnight to give 7-bromo-5-methylcinnolin-4-ol (800 mg, 3.346 mmol, 87.63% yield) as a pale-brown solid. LC-MS (Method A): r.t. 0.82 min, MS (ESI) m/z=238.9 and 240.9 [M+H]⁺.

Intermediate 201:
7-bromo-4-chloro-5-methylcinnoline

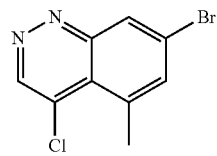

A solution of 7-bromo-5-methylcinnolin-4-ol (800 mg, 3.35 mmol) in phosphorus(V) oxychloride (3.5 mL, 37.44 mmol) was stirred at 50° C. for 2 hours. The reaction was cooled to room temperature and the excess phosphorus(V) oxychloride was removed in vacuo. The residue was dissolved in DCM and a saturated aqueous solution of NaHCO₃ was added dropwise until neutral pH was reached. The phases were separated and the organic phase was washed with brine, dried over Na₂SO₄ sulphate, filtered and evaporated to give 7-bromo-4-chloro-5-methylcinnoline (900 mg, 3.35 mmol, 100% yield) as a brown solid. LC-MS (Method A): r.t. 1.07 min, MS (ESI) m/z=256.9 and 258.9 [M+H]⁺.

Intermediate 202: 7-bromo-N-[(2,4-dimethoxyphenyl)methyl]-5-methylcinnolin-4-amine

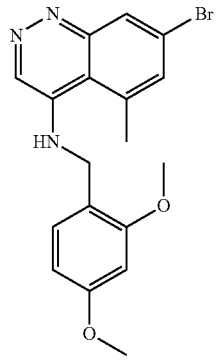 [SMILES: COc1ccc(CNc2cnnc3cc(Br)cc(C)c23)c(OC)c1]

(2,4-Dimethoxyphenyl)methanamine (1.25 mL, 8.35 mmol) was added to a solution of 7-bromo-4-chloro-5-methylcinnoline (860.0 mg, 3.34 mmol) in ethanol (15 mL) and the resulting mixture was stirred at 110° C. for 2 hours. The reaction mixture was cooled to room temperature and concentrated in vacuo. The residue was taken up with EtOAc and the suspension was filtered on a Hirsch funnel. The recovered powder was purified by column chromatography (KP-NH silica gel, SNAP 55) eluting with a gradient of MeOH in DCM from 0% to 10% to give 7-bromo-N-[(2,4-dimethoxyphenyl)methyl]-5-methylcinnolin-4-amine (460 mg, 1.185 mmol, 35.48% yield) as an off-white solid. $^1$H NMR (400 MHz, DMSO-$d_6$) δ 2.92 (s, 3H), 3.75 (s, 3H), 3.89 (s, 3H), 4.53 (d, J=5.84 Hz, 2H), 6.49 (dd, J=8.36, 2.42 Hz, 1H), 6.63 (d, J=2.38 Hz, 1H), 7.05 (t, J=5.93 Hz, 1H), 7.26 (d, J=8.35 Hz, 1H), 7.52-7.54 (m, 1H), 8.10 (dd, J=2.17, 0.62 Hz, 1H), 8.49 (s, 1H). LC-MS (Method A): r.t. 0.68 min, MS (ESI) m/z=388.03 and 390.04 [M+H]$^+$.

Intermediate 203: 7-(5-chloro-2-methoxyphenyl)-N-[(2,4-dimethoxyphenyl)methyl]-5-methylcinnolin-4-amine

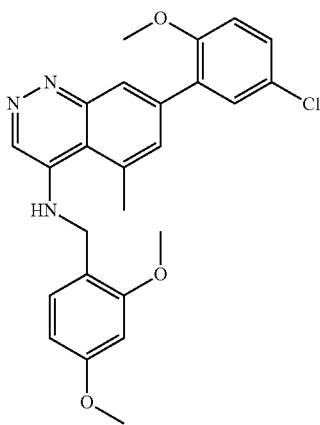 [SMILES: COc1ccc(CNc2cnnc3cc(-c4cc(Cl)ccc4OC)cc(C)c23)c(OC)c1]

A mixture of 5-chloro-2-methoxyphenylboronic acid (105.62 mg, 0.570 mmol) and 7-bromo-N-[(2,4-dimethoxyphenyl)methyl]-5-methylcinnolin-4-amine (200.0 mg, 0.520 mmol) in 1,2-dimethoxyethane (4 mL) and aqueous 2N sodium carbonate solution (257.56 uL, 0.520 mmol) was degassed for 10 min with N$_2$. Then, [1,1'-bis(di-tert-butylphosphino)ferrocene]dichloropalladium(II) (33.68 mg, 0.050 mmol) was added. The mixture was stirred at 80° C. for 6 hours, then it was cooled to room temperature and filtered over Celite, washing with MeOH. The filtrate was evaporated and the residue was purified by column chromatography (KP-NH silica gel, SNAP 28) eluting with a gradient of MeOH in DCM from 0% to 2% to give 7-(5-chloro-2-methoxyphenyl)-N-[(2,4-dimethoxyphenyl)methyl]-5-methylcinnolin-4-amine (205 mg, 0.456 mmol, 88.45% yield) as an orange powder. $^1$H NMR (400 MHz, DMSO-$d_6$) δ 2.97 (s, 3H), 3.74 (s, 3H), 3.81 (s, 3H), 3.90 (s, 3H), 4.53 (d, J=5.79 Hz, 2H), 6.44-6.51 (m, 1H), 6.63 (d, J=2.41 Hz, 1H), 6.96 (t, J=5.96 Hz, 1H), 7.20 (d, J=8.48 Hz, 1H), 7.26 (d, J=8.35 Hz, 1H), 7.43-7.50 (m, 3H), 8.01 (d, J=1.87 Hz, 1H), 8.45 (s, 1H). LC-MS (Method A): r.t. 0.88 min, MS (ESI) m/z=450.1 [M+H]$^+$.

Intermediate 204: 1-(4-bromo-2-chlorophenyl)propan-2-ol (Racemic

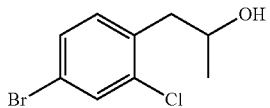

A 2.5M solution of n-butyllithium in hexane (1.51 mL, 3.78 mmol) was added dropwise to a solution of 4-bromo-2-chloroiodobenzene (1.0 g, 3.15 mmol) in THF (25 mL) at −78° C. The reaction mixture was stirred at −78° C. for 1 hour, then 2-methyloxirane (0.23 mL, 3.15 mmol) was added dropwise. Boron trifluoride diethyl etherate (0.33 mL, 3.15 mmol) was added rapidly and the mixture was stirred at this temperature for 30 minutes. A saturated aqueous solution of sodium bicarbonate was added at −78° C. and the reaction mixture was allowed to warm room temperature. EtOAc was added and the two phases were separated. The aqueous phase was extracted three times with EtOAc. The combined organic phases were washed with brine, filtered over a hydrophobic frit (Phase Separator) and evaporated. The residue was purified by column chromatography (KP-sil silica gel, SNAP 50) eluting with a gradient of EtOAc in cyclohexane from 0% to 100% to give 1-(4-bromo-2-chlorophenyl)propan-2-ol (480 mg, 1.924 mmol, 61.06% yield) as a colorless oil. $^1$H NMR (400 MHz, DMSO-$d_6$) δ 1.07 (d, J=6.13 Hz, 3H), 2.65-2.82 (m, 2H), 3.87 (dtd, J=6.93, 6.06, 5.06 Hz, 1H), 4.66 (d, J=5.11 Hz, 1H), 7.30 (d, J=8.23 Hz, 1H), 7.47 (dd, J=8.25, 2.08 Hz, 1H), 7.66 (d, J=2.08 Hz, 1H). LC-MS (Method A): r.t. 1.08 min, MS (ESI) m/z of product not observed due to poor ionization.

Intermediate 205: 1-(4-bromo-2-chlorophenyl)propan-2-yloxy-tert-butyl-dimethylsilane (Racemic

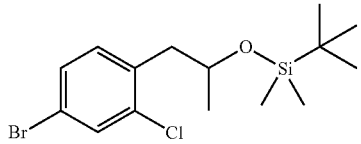 [SMILES: CC(Cc1ccc(Br)cc1Cl)O[Si](C)(C)C(C)(C)C]

tert-Butyl(chloro)dimethylsilane (869.78 mg, 5.77 mmol) was added to a solution of 1-(4-bromo-2-chlorophenyl)

propan-2-ol (480.0 mg, 1.92 mmol) and imidazole (392.88 mg, 5.77 mmol) in THF (14 mL) under a N₂ atmosphere. The reaction mixture was stirred for 24 hours at room temperature. Water was added and the resulting mixture was extracted three times with EtOAc. The combined organic phases were washed with saturated aqueous sodium bicarbonate solution and brine, filtered over a hydrophobic frit (Phase Separator) and evaporated. The residue was purified by column chromatography (KP-Sil silica gel, SNAP 25) eluting with a gradient of EtOAc in cyclohexane from 0% to 5% to give 1-(4-bromo-2-chlorophenyl)propan-2-yloxy-tert-butyl-dimethylsilane (605 mg, 1.663 mmol, 86.45% yield) as a colorless oil. ¹H NMR (400 MHz, DMSO-d₆) δ −0.30 (s, 3H), −0.10 (s, 3H), 0.77 (s, 9H), 1.16 (d, J=6.01 Hz, 3H), 2.65-2.87 (m, 2H), 4.00-4.11 (m, 1H), 7.27 (d, J=8.21 Hz, 1H), 7.48 (dd, J=8.17, 2.07 Hz, 1H), 7.67 (d, J=2.07 Hz, 1H). LC-MS (Method A): r.t. 1.79 min, MS (ESI) m/z of product not observed due to poor ionization.

Intermediate 206: 6-[4-[2-[tert-butyl(dimethyl)silyl]oxypropyl]-3-chlorophenyl]-N-[(2,4-dimethoxyphenyl)methyl]-4-methylphthalazin-1-amine (Racemic

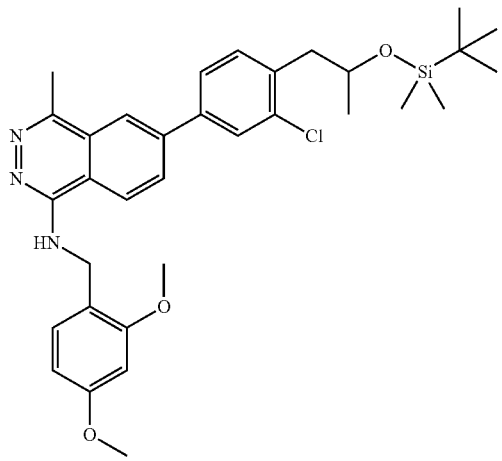 [SMILES: COc1ccc(CNc2nnc(C)c3cc(-c4ccc(CC(C)O[Si](C)(C)C(C)(C)C)c(Cl)c4)ccc23)c(OC)c1]

A mixture of [1-[(2,4-dimethoxyphenyl)methylamino]-4-methylphthalazin-6-yl]boronic acid (404.51 mg, 0.690 mmol) and 1-(4-bromo-2-chlorophenyl)propan-2-yloxy-tert-butyl-dimethylsilane (250.0 mg, 0.690 mmol) in 1,2-dimethoxyethane (7 mL) and aqueous 2N sodium carbonate solution (687.21 uL, 1.37 mmol) was degassed for 10 min with N₂. Then, [1,1'-bis(di-tert-butylphosphino)ferrocene]dichloropalladium(II) (44.93 mg, 0.070 mmol) was added. The mixture was stirred at 80° C. for 12 hours, then it was cooled to room temperature and filtered over Celite, washing with MeOH. The filtrate was evaporated and the residue was purified by column chromatography (KP-NH silica gel, SNAP 28) eluting with a gradient of EtOAc in cyclohexane from 0% to 100% to give 6-[4-[2-[tert-butyl(dimethyl)silyl]oxypropyl]-3-chlorophenyl]-N-[(2,4-dimethoxyphenyl)methyl]-4-methylphthalazin-1-amine (165 mg, 0.279 mmol, 40.54% yield) as a brown oil. ¹H NMR (400 MHz, DMSO-d₆) δ −0.21 (s, 3H), −0.05 (s, 3H), 0.80 (s, 9H), 1.20 (d, J=7.04 Hz, 3H), 2.76 (s, 3H), 2.85-2.92 (m, 2H), 3.73 (s, 3H), 3.85 (s, 3H), 4.10-4.20 (m, 1H), 4.66 (d, J=5.54 Hz, 2H), 6.43 (dd, J=8.39, 2.39 Hz, 1H), 6.58 (d, J=2.38 Hz, 1H), 7.11 (d, J=8.37 Hz, 1H), 7.48 (d, J=8.04 Hz, 1H), 7.64 (t, J=5.76 Hz, 1H), 7.82-7.85 (m, 1H), 8.01 (d, J=1.94 Hz, 1H), 8.18-8.24 (m, 2H), 8.47 (d, J=8.60 Hz, 1H). LC-MS (Method A): r.t. 1.22 min, MS (ESI) m/z=592.3 [M+H]⁺.

Intermediate 207: 7-[2-amino-5-(4,4,5,5-tetramethyl-1,3,2-dioxaborolan-2-yl)phenyl]-N-[(2,4-dimethoxyphenyl)methyl]cinnolin-4-amine

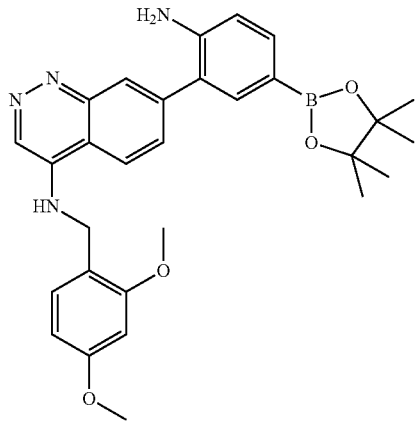 [SMILES: COc1ccc(CNc2cnnc3cc(-c4cc(B5OC(C)(C)C(C)(C)O5)ccc4N)ccc23)c(OC)c1]

A mixture of 7-bromo-N-[(2,4-dimethoxyphenyl)methyl]cinnolin-4-amine (534.61 mg, 0.800 mmol), dicesium carbonate (781.97 mg, 2.4 mmol) and 2,4-bis(4,4,5,5-tetramethyl-1,3,2-dioxaborolan-2-yl)aniline (552.08 mg, 1.6 mmol) in 1,4-dioxane (12 mL) and water (3 mL) was degassed for 10 min. [1,1'-Bis(di-tert-butylphosphino)ferrocene]dichloropalladium(II) (104.6 mg, 0.160 mmol) was added and the mixture was degassed again for 10 min. The reaction mixture was stirred at room temperature for 4 h, then at 55° C. for 1.5 h. The mixture was left to reach room temperature, diluted with EtOAc and filtered. The volatiles were removed and the residue was purified by column chromatography (KP-Sil silica gel, SNAP50) eluting with a gradient of EtOAc in cyclohexane from 50% to 100% and then 5% MeOH in EtOAc to give 7-[2-amino-5-(4,4,5,5-tetramethyl-1,3,2-dioxaborolan-2-yl)phenyl]-N-[(2,4-dimethoxyphenyl)methyl]cinnolin-4-amine (133 mg, 0.260 mmol, 32.44% yield) as a brownish solid. ¹H NMR (400 MHz, DMSO-d₆) δ 1.27 (s, 12H), 3.75 (s, 3H), 3.89 (s, 3H), 4.52 (d, J=5.72 Hz, 2H), 5.42 (s, 2H), 6.48 (dd, J=8.47, 2.31 Hz, 1H), 6.64 (d, J=2.42 Hz, 1H), 6.79 (d, J=8.36 Hz, 1H), 7.15 (d, J=8.36 Hz, 1H), 7.39-7.44 (m, 2H), 7.64-7.69 (m, 1H), 8.00-8.06 (m, 2H), 8.40 (d, J=8.58 Hz, 1H), 8.48 (s, 1H). LC-MS (Method A): r.t. 0.85 min, MS (ESI) m/z=513.22 [M+H]⁺.

Intermediate 208: N-[2-(4-{[(2,4-dimethoxyphenyl)methyl]amino}cinnolin-7-yl)-4-(4,4,5,5-tetramethyl-1,3,2-dioxaborolan-2-yl)phenyl]-3-methylbutanamide

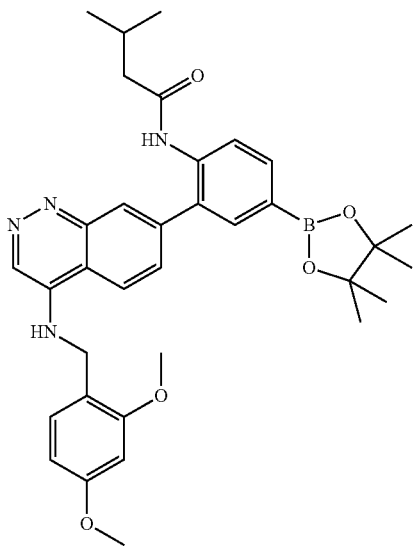 [SMILES: COc1ccc(CNc2cnnc3cc(-c4cc(B5OC(C)(C)C(C)(C)O5)ccc4NC(=O)CC(C)C)ccc23)c(OC)c1]

3-Methylbutanoyl chloride (0.02 mL, 0.120 mmol) was added to a stirred solution of 7-[2-amino-5-(4,4,5,5-tetramethyl-1,3,2-dioxaborolan-2-yl)phenyl]-N-[(2,4-dimethoxyphenyl)methyl]cinnolin-4-amine (64.0 mg, 0.120 mmol) and triethylamine (0.02 mL, 0.120 mmol) in DCM (1.024 mL). The reaction mixture was stirred at room temperature for 2 h, then water and DCM were added. The phases were separated and the organic phase was washed with water and brine, dried over sodium sulfate, filtered and concentrated to give N-[2-[4-[(2,4-dimethoxyphenyl)methylamino]cinnolin-7-yl]-4-(4,4,5,5-tetramethyl-1,3,2-dioxaborolan-2-yl)phenyl]-3-methylbutanamide (54 mg, 0.091 mmol, 72.48% yield) as a yellowish solid. LC-MS (Method A): r.t. 0.87 min, MS (ESI) m/z=597.33 [M+H]$^+$.

Intermediate 209: N-[2-(4-{[(2,4-dimethoxyphenyl)methyl]amino}cinnolin-7-yl)-4-(4,4,5,5-tetramethyl-1,3,2-dioxaborolan-2-yl)phenyl]-4-methylpentanamide

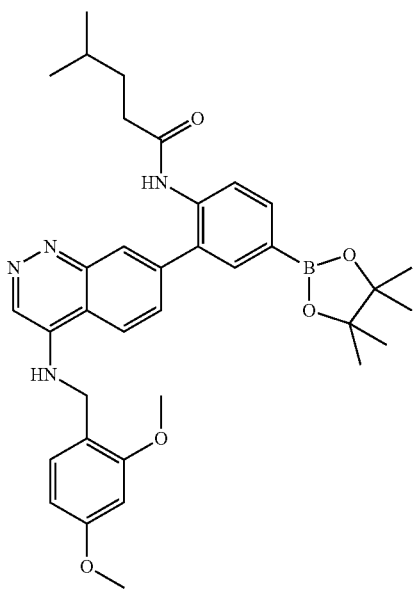 [SMILES: COc1ccc(CNc2cnnc3cc(-c4cc(B5OC(C)(C)C(C)(C)O5)ccc4NC(=O)CCC(C)C)ccc23)c(OC)c1]

4-Methylpentanoyl chloride (0.02 mL, 0.120 mmol) was added to a stirred solution of 7-[2-amino-5-(4,4,5,5-tetramethyl-1,3,2-dioxaborolan-2-yl)phenyl]-N-[(2,4-dimethoxyphenyl)methyl]cinnolin-4-amine (64.0 mg, 0.120 mmol) and triethylamine (0.02 mL, 0.120 mmol) in DCM (1.024 mL). The reaction mixture was stirred overnight at room temperature, then additional triethylamine (0.02 mL, 0.120 mmol) and 4-methylpentanoyl chloride (0.02 mL, 0.120 mmol) were added. The reaction mixture was stirred overnight at room temperature, then water and DCM were added. The phases were separated and the organic phase was washed with water and brine, dried over sodium sulfate, filtered and concentrated to give N-[2-[4-[(2,4-dimethoxyphenyl)methylamino]cinnolin-7-yl]-4-(4,4,5,5-tetramethyl-1,3,2-dioxaborolan-2-yl)phenyl]-4-methylpentanamide (61 mg, 0.100 mmol, 79.99% yield) as a brownish solid. LC-MS (Method A): r.t. 0.90 min, MS (ESI) m/z=611.32 [M+H]$^+$.

Intermediate 210: 1-chloro-2-fluoro-3-iodo-4-(trifluoromethyl)benzene

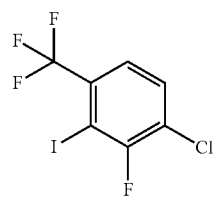 [SMILES: Fc1c(Cl)ccc(C(F)(F)F)c1I]

A 2.5M solution of N-butyllithium in hexane (1.51 mL, 3.78 mmol) was added dropwise over 15 minutes to a solution of 4-chloro-3-fluorobenzotrifluoride (500.0 mg, 2.52 mmol) in THF (8 mL) at −78° C. The mixture was stirred at −78° C. for 1 h then a solution of iodine (0.96 g, 3.78 mmol) in THF (2 mL) was added dropwise. The resulting mixture was stirred at −78° C. for 4 h and then slowly warmed to room temperature. Saturated aqueous NH$_4$Cl solution was added to quench the reaction. Aqueous Na$_2$SO$_3$ solution was then added until the remaining iodine was reduced, and the mixture was extracted with EtOAc. The organic phase was washed with brine, dried over anhydrous sodium sulfate, and then concentrated in vacuo. The residue was purified by column chromatography (KP silica gel, SNAP 50) eluting with a gradient of EtOAc in cyclohexane from 5% to 50% to give 1-chloro-2-fluoro-3-iodo-4-(trifluoromethyl)benzene (744 mg, 2.293 mmol, 91.06% yield) as a colourless oil. $^1$H NMR (400 MHz, DMSO-d$_6$) δ 7.63 (dd, J=8.54, 1.38 Hz, 1H), 7.83 (t, J=7.70 Hz, 1H). LC-MS (Method A): r.t. 1.32 min, MS (ESI) m/z of product not observed due to poor ionization.

Intermediate 211: 6-[3-chloro-2-fluoro-6-(trifluoromethyl)phenyl]-N-[(2,4-dimethoxyphenyl)methyl]-4-methylphthalazin-1-amine

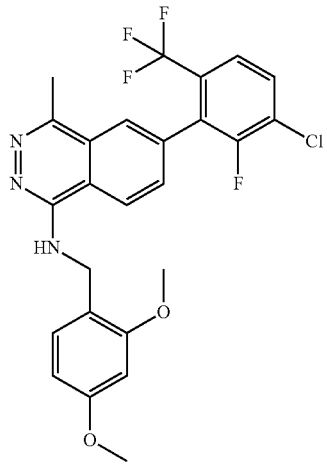 [SMILES: COc1ccc(CNc2nnc(C)c3cc(-c4c(C(F)(F)F)ccc(Cl)c4F)ccc23)c(OC)c1]

A mixture of [1-[(2,4-dimethoxyphenyl)methylamino]-4-methylphthalazin-6-yl]boronic acid (179.62 mg, 0.510 mmol), 1-chloro-2-fluoro-3-iodo-4-(trifluoromethyl)benzene (150.0 mg, 0.460 mmol) in 1,2-dimethoxyethane (5.9 mL) and aqueous 2N sodium carbonate solution (580 uL, 1.16 mmol) was degassed for 10 minutes with $N_2$. Then [1,1'-bis(di-tert-butylphosphino)ferrocene]dichloropalladium(II) (30.23 mg, 0.051 mmol) was added and the resulting reaction mixture was stirred at 75° C. for 2.5 hours. Then it was cooled to room temperature and filtered over Celite, washing with EtOAc. The filtrate was evaporated and the residue was purified by column chromatography (KP-NH silica gel, SNAP 55) eluting with a gradient of EtOAc in cyclohexane from 10% to 100% to give 6-[3-chloro-2-fluoro-6-(trifluoromethyl)phenyl]-N-[(2,4-dimethoxyphenyl)methyl]-4-methylphthalazin-1-amine (120 mg, 0.237 mmol, 51.31% yield) as an off white solid. LC-MS (Method A): r.t. 0.87 min, MS (ESI) m/z=506.1 [M+H]$^+$.

Intermediate 212: 1-(1-hydroxycyclopentyl)cyclopentan-1-ol

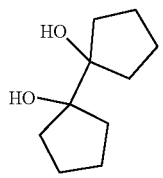

Titanium (IV) chloride (0.42 mL, 3.86 mmol) was added dropwise to a suspension of zinc (505.19 mg, 7.73 mmol) in THF (7.5 mL) under and argon atmosphere, and the mixture was heated to reflux for 1 hour. Then cyclopentanone (0.53 mL, 5.94 mmol) was added and the resulting mixture was stirred overnight at room temperature. The mixture was quenched with water and then filtered over Celite. The filtrate was extracted with EtOAc, the organic phases were combined and washed with brine, dried over $Na_2SO_4$, filtered and evaporated in vacuo. The residue was purified by column chromatography (KP silica gel, SNAP 50) eluting with a gradient of EtOAc in cyclohexane from 5% to 50% to give 1-(1-hydroxycyclopentyl)cyclopentan-1-ol (130 mg, 0.764 mmol, 12.85% yield) as a white solid. $^1$H NMR (400 MHz, DMSO-d$_6$) δ 1.32-1.45 (m, 4H), 1.43-1.58 (m, 4H), 1.62-1.84 (m, 8H), 3.88 (s, 2H).

Intermediate 213: N-(4-bromo-2-chlorophenyl)benzamide

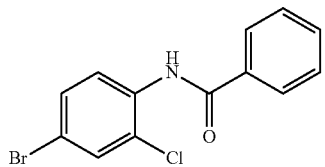 [SMILES: O=C(Nc1ccc(Br)cc1Cl)c1ccccc1]

To a solution of 4-bromo-2-chloroaniline (500.0 mg, 2.42 mmol) in dry THF (10 mL), benzoyl chloride (0.28 mL, 2.42 mmol) and triethylamine (0.34 mL, 2.42 mmol) were added dropwise in this order. The resulting reaction mixture was stirred at room temperature for 3 hours, then water was added and the resulting precipitate was collected by filtration on a Gooch filter, washed with water and dried in the oven at 50° C. overnight to give N-(4-bromo-2-chlorophenyl)benzamide (765 mg, 2.419 mmol, 100% yield) as a white powder. $^1$H NMR (400 MHz, DMSO-d$_6$) δ 7.52-7.62 (m, 4H), 7.62-7.64 (m, 1H), 7.85 (d, J=1.99 Hz, 1H), 7.97-7.99 (m, 1H), 7.99-8.01 (m, 1H), 10.10 (s, 1H). LC-MS (Method A): r.t. 1.23 min, MS (ESI) m/z=309.9 and 311.9 [M+H]$^+$.

Intermediate 214: N-[2-chloro-4-[1-[(2,4-dimethoxyphenyl)methylamino]-4-methylphthalazin-6-yl]phenyl]benzamide

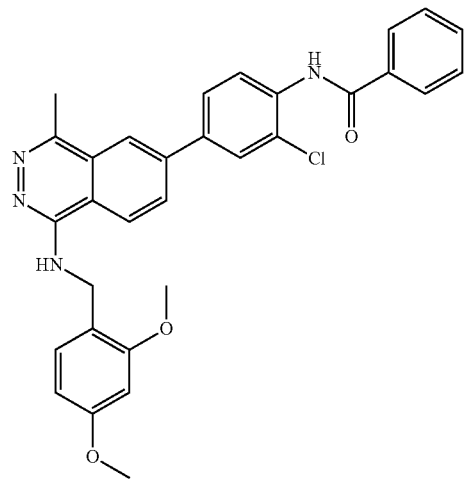 [SMILES: COc1ccc(CNc2nnc(C)c3cc(-c4ccc(NC(=O)c5ccccc5)c(Cl)c4)ccc23)c(OC)c1]

A mixture of [1-[(2,4-dimethoxyphenyl)methylamino]-4-methylphthalazin-6-yl]boronic acid (600.0 mg, 1.7 mmol) and N-(4-bromo-2-chlorophenyl)benzamide (633.13 mg, 2.04 mmol) in 1,2-dimethoxyethane (17 mL) and aqueous 2N sodium carbonate solution (1698.85 uL, 3.4 mmol) was degassed for 10 min with $N_2$. Then, [1,1'-bis(di-tert-butylphosphino)ferrocene]dichloropalladium(II) (111.06 mg, 0.170 mmol) was added. The mixture was stirred at 80°

C. for 5 hours, then it was cooled to room temperature and filtered over Celite, washing with MeOH. The filtrate was evaporated and the residue was purified by column chromatography (KP-NH silica gel, SNAP 55) eluting with a gradient of EtOAc in cyclohexane from 0% to 100% to give N-[2-chloro-4-[1-[(2,4-dimethoxyphenyl)methylamino]-4-methylphthalazin-6-yl]phenyl]benzamide (640 mg, 1.187 mmol, 69.89% yield) as a brown powder. ¹H NMR (400 MHz, DMSO-d₆) δ 2.78 (s, 3H), 3.74 (s, 3H), 3.85 (s, 3H), 4.68 (d, J=5.59 Hz, 2H), 6.44 (dd, J=8.36, 2.39 Hz, 1H), 6.59 (d, J=2.40 Hz, 1H), 7.14 (d, J=8.34 Hz, 1H), 7.53-7.61 (m, 2H), 7.61-7.68 (m, 2H), 7.82 (d, J=8.36 Hz, 1H), 7.95 (dd, J=8.37, 2.17 Hz, 1H), 8.02-8.07 (m, 2H), 8.16 (d, J=2.09 Hz, 1H), 8.24-8.30 (m, 2H), 8.45-8.52 (m, 1H), 10.15 (s, 1H). LC-MS (Method A): r.t. 0.88 min, MS (ESI) m/z=538.2 [M+H]⁺.

Intermediate 215: 3-bromo-5-chloro-6-(trifluoromethyl)pyridin-2-amine

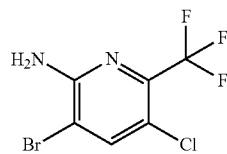 [SMILES: Nc1nc(C(F)(F)F)c(Cl)cc1Br]

1-Bromopyrrolidine-2,5-dione (706.27 mg, 3.97 mmol) was added portionwise to a stirred solution of 5-chloro-6-(trifluoromethyl)pyridin-2-amine (600.0 mg, 3.05 mmol) in DMF (3 mL), at 0° C. The mixture was allowed to warm to room temperature and then stirred for another 18 h. The reaction mixture was diluted with EtOAc, washed with an aqueous solution of sodium thiosulfate, a saturated aqueous solution of NaHCO₃ and twice with brine, dried over Na₂SO₄, filtered and the solvent was evaporated under reduced pressure to give 3-bromo-5-chloro-6-(trifluoromethyl)pyridin-2-amine (823 mg, 2.99 mmol, 97.88% yield) as a pale orange solid. ¹H NMR (400 MHz, DMSO-d₆) δ 7.02 (s, 2H), 8.19 (s, 1H). LC-MS (Method A): r.t. 1.12 min, MS (ESI) m/z=274.92 and 276.9 [M+H]⁺.

Intermediate 216: 5-bromo-3-chloro-2-(trifluoromethyl)pyridine

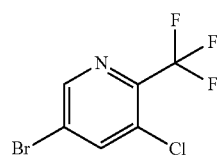 [SMILES: FC(F)(F)c1ncc(Br)cc1Cl]

A solution of nitrous acid 3-methylbutyl ester (0.29 mL, 2.16 mmol) in DMF (2 mL) was stirred and heated under a nitrogen flux at 60° C. for a few minutes, then a solution of 3-bromo-5-chloro-6-(trifluoromethyl)pyridin-2-amine (200.0 mg, 0.720 mmol) in DMF (2.5 mL) was added dropwise over 15 minutes, while maintaining the temperature at 60° C. The mixture was stirred at 60° C. for 1 hour, then cooled to room temperature and partitioned between Et₂O and water. The phases were separated, and the organic phase was washed three times with a saturated aqueous solution of NH₄Cl, dried over Na₂SO₄, filtered and the solvent was evaporated under reduced pressure. The crude 5-bromo-3-chloro-2-(trifluoromethyl)pyridine (190 mg) thus obtained was used in the next step without further purification.

Intermediate 217: 6-[5-chloro-6-(trifluoromethyl)pyridin-3-yl]-N-[(2,4-dimethoxyphenyl)methyl]-4-methylphthalazin-1-amine

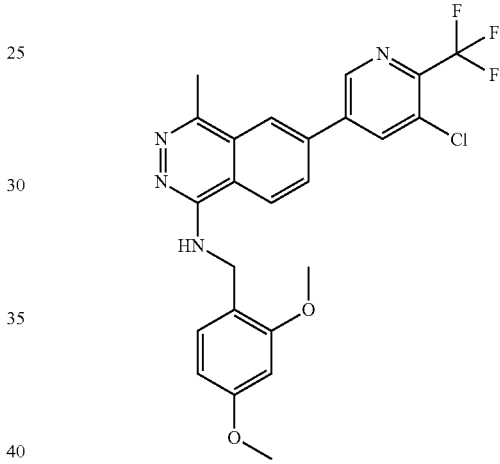

A mixture of 5-bromo-3-chloro-2-(trifluoromethyl)pyridine (182.31 mg, 0.700 mmol), [1-[(2,4-dimethoxyphenyl)methylamino]-4-methylphthalazin-6-yl]boronic acid (247.23 mg, 0.700 mmol) and aqueous 2N sodium carbonate solution (0.7 mL, 1.4 mmol) in 1,4-dioxane (7 mL) was degassed for 10 min. Then [1,1'-bis(di-tert-butylphosphino)ferrocene]dichloropalladium(II) (45.76 mg, 0.070 mmol) was added and the resulting reaction mixture was stirred at 85° C. for 18 hours. The mixture was diluted with MeOH and filtered over a pad of Celite, washing with EtOAc and MeOH. The filtrate was concentrated in vacuo. The residue was purified by column chromatography (Sfar C18 D, 30 g) eluting with a gradient of MeCN (+0.1% HCOOH) in water (+0.1% HCOOH) from 0% to 80% to give partially purified 6-[5-chloro-6-(trifluoromethyl)pyridin-3-yl]-N-[(2,4-dimethoxyphenyl)methyl]-4-methylphthalazin-1-amine (43 mg, 0.088 mmol, 12.56% yield) as a brown solid. This material was used in the next step without further purification. LC-MS (Method A): r.t. 0.84 min, MS (ESI) m/z=489.14 [M+H]⁺.

Intermediate 218: N-[(2,4-dimethoxyphenyl)methyl]-4-methyl-6-[5-(4,4,5,5-tetramethyl-1,3,2-dioxaborolan-2-yl)-6-(trifluoromethyl)pyridin-3-yl]phthalazin-1-amine

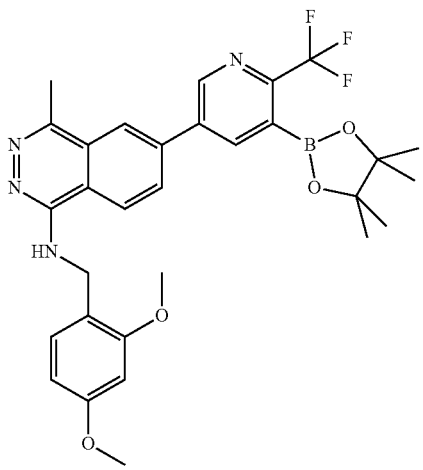 [SMILES: COc1ccc(CNc2nnc(C)c3cc(-c4cnc(C(F)(F)F)c(B5OC(C)(C)C(C)(C)O5)c4)ccc23)c(OC)c1]

A 5 mL microwave vial was charged with dichlorobis(trimethylphosphine)nickel (1.0 mg, 0.004 mmol), 4,4,5,5-tetramethyl-2-(4,4,5,5-tetramethyl-1,3,2-dioxaborolan-2-yl)-1,3,2-dioxaborolane (90.38 mg, 0.360 mmol), cesium fluoride (54.06 mg, 0.360 mmol), 6-[5-chloro-6-(trifluoromethyl)pyridin-3-yl]-N-[(2,4-dimethoxyphenyl)methyl]-4-methylphthalazin-1-amine (87.0 mg, 0.180 mmol), trimethyl (2,2,2-trifluoroethoxy)silane (64.36 mg, 0.370 mmol) and THF (2.121 mL) and the mixture was deoxygenated under N₂ for 10 min. The resulting mixture was heated to 100° C. under microwave irradiation in a microwave reactor for 3 cycles of 2 h 30' each. The mixture was filtered over a pad of Celite, washing with MeOH and the filtrate was evaporated to give N-[(2,4-dimethoxyphenyl)methyl]-4-methyl-6-[5-(4,4,5,5-tetramethyl-1,3,2-dioxaborolan-2-yl)-6-(trifluoromethyl)pyridin-3-yl]phthalazin-1-amine (214 mg, 0.369 mmol, 207.19% yield). This material was used in the next step without further purification. LC-MS (Method A): r.t. 0.94 min, MS (ESI) m/z=581.26 [M+H]⁺.

Intermediate 219: 6-[3-chloro-4-(trifluoromethyl)phenyl]-N-[(2,4-dimethoxyphenyl)methyl]-4-methylphthalazin-1-amine

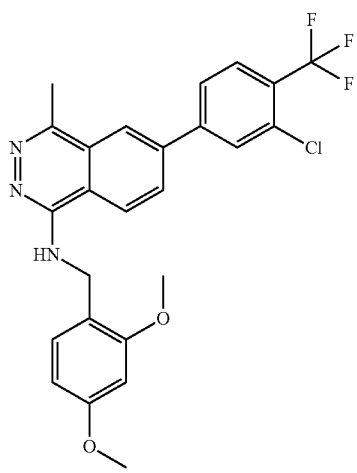 [SMILES: COc1ccc(CNc2nnc(C)c3cc(-c4ccc(C(F)(F)F)c(Cl)c4)ccc23)c(OC)c1]

A mixture of 3-chloro-4-(trifluoromethyl)benzeneboronic acid (254.27 mg, 1.13 mmol) and 6-bromo-N-[(2,4-dimethoxyphenyl)methyl]-4-methylphthalazin-1-amine (400.0 mg, 1.03 mmol) in 1,2-dimethoxyethane (5.292 mL) and aqueous 2N sodium carbonate solution (0.52 mL, 1.03 mmol) was degassed for 10 min. [1,1'-Bis(di-tert-butylphosphino)ferrocene]dichloropalladium(II) (67.35 mg, 0.100 mmol) was added and the mixture was degassed for 10 min, then it was stirred at 80° C. for 2 h. The mixture was left to reach room temperature, diluted with EtOAc, filtered and concentrated. The residue was purified by column chromatography (KP-NH silica gel, 28 g) eluting with a gradient of EtOAc in cyclohexane from 40% to 100% to give 6-[3-chloro-4-(trifluoromethyl)phenyl]-N-[(2,4-dimethoxyphenyl)methyl]-4-methylphthalazin-1-amine (276 mg, 0.566 mmol, 54.91% yield) as a brownish foam. ¹H NMR (400 MHz, DMSO-d₆) δ 2.78 (s, 3H), 3.73 (s, 3H), 3.85 (s, 3H), 4.67 (d, J=5.50 Hz, 2H), 6.43 (dd, J=8.36, 2.42 Hz, 1H), 6.59 (d, J=2.42 Hz, 1H), 7.13 (d, J=8.36 Hz, 1H), 7.68 (t, J=5.83 Hz, 1H), 7.98-8.04 (m, 1H), 8.10 (d, J=7.70 Hz, 1H), 8.28-8.32 (m, 1H), 8.33 (s, 2H), 8.52 (d, J=8.80 Hz, 1H). LC-MS (Method A): r.t. 0.91 min, MS (ESI) m/z=488.12 [M+H]⁺.

Intermediate 220: N-[(2,4-dimethoxyphenyl)methyl]-4-methyl-6-[3-(4,4,5,5-tetramethyl-1,3,2-dioxaborolan-2-yl)-4-(trifluoromethyl)phenyl]phthalazin-1-amine

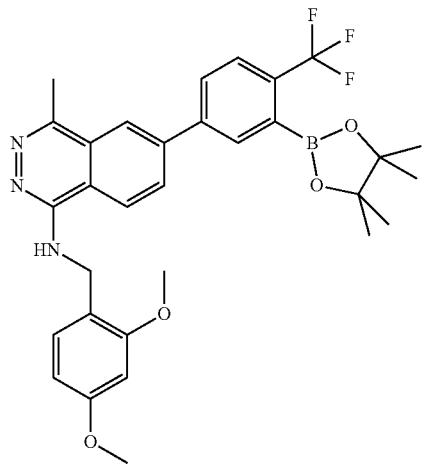

A 5 mL microwave vial was charged with dichlorobis(trimethylphosphine)nickel (1.1 mg, 0.004 mmol), 4,4,5,5-tetramethyl-2-(4,4,5,5-tetramethyl-1,3,2-dioxaborolan-2-yl)-1,3,2-dioxaborolane (108.78 mg, 0.430 mmol), cesium fluoride (59.15 mg, 0.390 mmol), 6-[3-chloro-4-(trifluoromethyl)phenyl]-N-[(2,4-dimethoxyphenyl)methyl]-4-methylphthalazin-1-amine (100.0 mg, 0.190 mmol), trimethyl(2,2,2-trifluoroethoxy)silane (70.42 mg, 0.410 mmol) and THF (1.5 mL) and the mixture was deoxygenated under N₂ for 10 min. The resulting mixture was heated to 100° C. under microwave irradiation in a microwave reactor for 3 hours. The mixture was filtered over a pad of Celite, washing with MeOH and the filtrate was evaporated to give N-[(2,4-dimethoxyphenyl)methyl]-4-methyl-6-[3-(4,4,5,5-tetramethyl-1,3,2-dioxaborolan-2-yl)-4-(trifluoromethyl)phenyl]phthalazin-1-amine (256 mg, 0.442 mmol, 226.91% yield).

This material was used in the next step without further purification. LC-MS (Method A): r.t. 1.00 min, MS (ESI) m/z=580.27 [M+H]⁺.

Intermediate 221: 7-bromo-N-[(2,4-dimethoxyphenyl)methyl]-N-methylcinnolin-4-amine

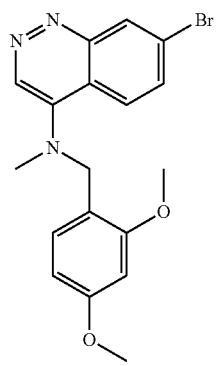 [SMILES: COc1ccc(CN(C)c2cnnc3cc(Br)ccc23)c(OC)c1]

N-(2,4-Dimethoxybenzyl)-N-methylamine (0.96 mL, 5.34 mmol) was added to a solution of 7-bromo-4-chlorocinnoline (1.0 g, 4.11 mmol) in DMSO (8 mL) under a $N_2$ atmosphere and the resulting mixture was stirred at 55° C. overnight. The reaction mixture was cooled to room temperature and the mixture was diluted with EtOAc. The organic phase was washed twice with 1N hydrochloric acid solution and brine, filtered over a hydrophobic frit (Phase Separator) and evaporated to give 7-bromo-N-[(2,4-dimethoxyphenyl)methyl]-N-methylcinnolin-4-amine (940 mg, 2.421 mmol, 58.95% yield) as a yellow powder. ¹H NMR (400 MHz, DMSO-d₆) δ 3.51 (s, 3H), 3.71 (s, 3H), 3.77 (s, 3H), 5.05 (s, 2H), 6.55 (dd, J=8.37, 2.38 Hz, 1H), 6.65 (d, J=2.35 Hz, 1H), 7.27 (d, J=8.37 Hz, 1H), 7.79 (dd, J=9.31, 2.03 Hz, 1H), 8.21 (d, J=9.38 Hz, 1H), 8.29 (d, J=2.03 Hz, 1H), 8.79 (s, 1H). LC-MS (Method A): r.t. 0.67 min, MS (ESI) m/z=388.1 and 390.0 [M+H]⁺.

Intermediate 222: 7-(5-chloro-2-methoxyphenyl)-N-[(2,4-dimethoxyphenyl)methyl]-N-methylcinnolin-4-amine

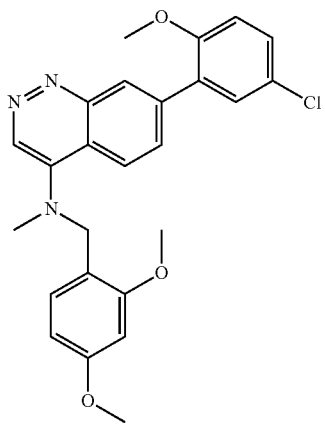 [SMILES: COc1ccc(CN(C)c2cnnc3cc(-c4cc(Cl)ccc4OC)ccc23)c(OC)c1]

A mixture of 5-chloro-2-methoxyphenylboronic acid (132.02 mg, 0.710 mmol) and 7-bromo-N-[(2,4-dimethoxyphenyl)methyl]-N-methylcinnolin-4-amine (250.0 mg, 0.640 mmol) in 1,2-dimethoxyethane (5 mL) and aqueous 2N sodium carbonate solution (321.95 uL, 0.640 mmol) was degassed for 10 min with $N_2$. Then, [1,1'-bis(di-tert-butylphosphino)ferrocene]dichloropalladium(II) (42.1 mg, 0.060 mmol) was added. The mixture was stirred at 80° C. for 6 hours, then it was cooled to room temperature and filtered over Celite, washing with MeOH. The filtrate was evaporated and the residue was purified by column chromatography (KP-NH silica gel, SNAP 28) eluting with a gradient of MeOH in DCM from 0% to 2% to give 7-(5-chloro-2-methoxyphenyl)-N-[(2,4-dimethoxyphenyl)methyl]-N-methylcinnolin-4-amine (210 mg, 0.467 mmol, 72.49% yield) as an orange powder. ¹H NMR (400 MHz, DMSO-d₆) δ 3.07 (s, 3H), 3.61 (s, 3H), 3.76 (s, 3H), 3.82 (s, 3H), 4.65 (s, 2H), 6.54 (dd, J=8.30, 2.38 Hz, 1H), 6.58 (d, J=2.36 Hz, 1H), 7.19-7.25 (m, 2H), 7.47 (dd, J=8.84, 2.68 Hz, 1H), 7.53 (d, J=2.65 Hz, 1H), 7.72 (dd, J=8.91, 1.90 Hz, 1H), 8.05 (d, J=8.93 Hz, 1H), 8.31 (d, J=1.83 Hz, 1H), 8.77 (s, 1H). LC-MS (Method A): r.t. 0.85 min, MS (ESI) m/z=450.1 [M+H]⁺.

Intermediate 223: 2-(2-bromo-4-chlorophenoxy)-N-propan-2-ylacetamide

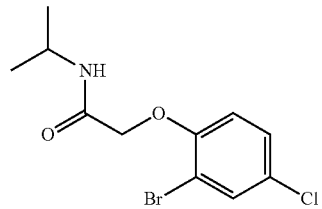 [SMILES: CC(C)NC(=O)COc1ccc(Cl)cc1Br]

To a suspension of 2-bromo-4-chlorophenol (500.0 mg, 2.41 mmol) and potassium carbonate (499.67 mg, 3.62 mmol) in DMF (6 mL), was added N-isopropyl chloroacetamide (392.16 mg, 2.89 mmol). The resulting mixture was stirred at 50° C. for 3 hours. After addition of water and EtOAc the phases were separated and the the aqueous phase was re-extracted with EtOAc. The combined organic layers were washed with brine, dried over anhydrous sodium sulfate and concentrated in vacuo. The residue was purified by column chromatography (KP-NH silica gel, SNAP 55) eluting with a gradient of EtOAc in cyclohexane from 5% to 50% to give 2-(2-bromo-4-chlorophenoxy)-N-propan-2-ylacetamide (600 mg, 1.957 mmol, 81.2% yield) as a colourless oil. ¹H NMR (400 MHz, DMSO-d₆) δ 1.10 (d, J=6.60 Hz, 6H), 3.85-3.97 (m, 1H), 4.57 (s, 2H), 7.01 (d, J=8.91 Hz, 1H), 7.42 (dd, J=8.86, 2.62 Hz, 1H), 7.72 (d, J=2.56 Hz, 1H), 7.75 (d, J=7.90 Hz, 1H). LC-MS (Method A): r.t. 1.14 min, MS (ESI) m/z=307.9 [M+H]⁺.

Intermediate 224: 6-[3-chloro-2-fluoro-6-(trifluoromethyl)phenyl]-N-[(2,4-dimethoxyphenyl)methyl]-4-methylphthalazin-1-amine

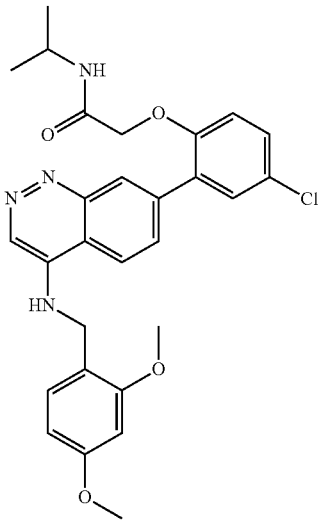 [SMILES: COc1ccc(CNc2cnnc3cc(-c4cc(Cl)ccc4OCC(=O)NC(C)C)ccc23)c(OC)c1]

A mixture of 2-(2-bromo-4-chlorophenoxy)-N-propan-2-ylacetamide (200.0 mg, 0.650 mmol), [4-[(2,4-dimethoxyphenyl)methylamino]cinnolin-7-yl]boronic acid (210.67 mg, 0.980 mmol) in 1,2-dimethoxyethane (6.524 mL) and aqueous 2N sodium carbonate solution (652 uL, 1.305 mmol) was degassed for 10 minutes with $N_2$. Then [1,1'-bis(di-tert-butylphosphino)ferrocene]dichloropalladium(II) (42.65 mg, 0.065 mmol) was added and the resulting reaction mixture was stirred at 75° C. for 2.5 hours. Then it was cooled to room temperature and filtered over Celite, washing with EtOAc. The filtrate was evaporated and the residue was purified by column chromatography (KP-NH silica gel, SNAP 55) eluting with a gradient of EtOAc in cyclohexane from 10% to 100% to give 2-[4-chloro-2-[4-[(2,4-dimethoxyphenyl)methylamino]cinnolin-7-yl]phenoxy]-N-propan-2-ylacetamide (170 mg, 0.326 mmol, 50.02% yield) as an off white solid. $^1$H NMR (400 MHz, Methanol-$d_4$) δ 0.95 (d, J=6.60 Hz, 6H), 3.80 (s, 3H), 3.90-3.95 (m, 4H), 4.53 (s, 2H), 4.65 (s, 2H), 6.50 (dd, J=8.39, 2.39 Hz, 1H), 6.63 (d, J=2.40 Hz, 1H), 7.13 (d, J=8.80 Hz, 1H), 7.22 (d, J=8.38 Hz, 1H), 7.45 (dd, J=8.81, 2.64 Hz, 1H), 7.53 (d, J=2.63 Hz, 1H), 7.89 (dd, J=8.79, 1.77 Hz, 1H), 8.23 (d, J=1.71 Hz, 1H), 8.31 (d, J=8.81 Hz, 1H), 8.57 (s, 1H). LC-MS (Method A): r.t. 0.78 min, MS (ESI) m/z=521.2 [M+H]$^+$.

Intermediate 225: 1-bromo-5-iodo-4-methoxy-2-(trifluoromethyl)benzene

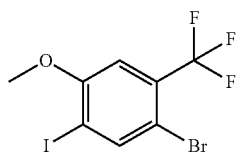

To a solution of 1-bromo-4-methoxy-2-(trifluoromethyl)benzene (2.0 g, 7.84 mmol) in DCM (55.05 mL) were added silver trifluoromethanesulfonate (2.42 g, 9.41 mmol) and iodine (2.19 g, 8.63 mmol). The mixture was stirred at room temperature for 19 h. The mixture was diluted with EtOAc (150 mL) and the organics were washed with saturated aqueous $Na_2S_2O_3$ solution, saturated aqueous $NaHCO_3$ solution and brine. The organic phase was dried over $Na_2SO_4$, filtered and the solvent was evaporated. The residue was purified by column chromatography (KP-sil silica gel, SNAP 100) eluting with a gradient of EtOAc in cyclohexane from 5% to 30% to give 1-bromo-5-iodo-4-methoxy-2-(trifluoromethyl)benzene (2.5 g, 6.563 mmol, 83.69% yield) as a yellow solid. $^1$H NMR (400 MHz, DMSO-$d_6$) δ 3.93 (s, 3H), 7.29 (s, 1H), 8.22-8.30 (m, 1H). LC-MS (Method A): r.t. 1.39 min, MS (ESI) m/z of product not observed due to poor ionization.

Intermediate 226: 7-[5-bromo-2-methoxy-4-(trifluoromethyl)phenyl]-N-[(2,4-dimethoxyphenyl)methyl]cinnolin-4-amine

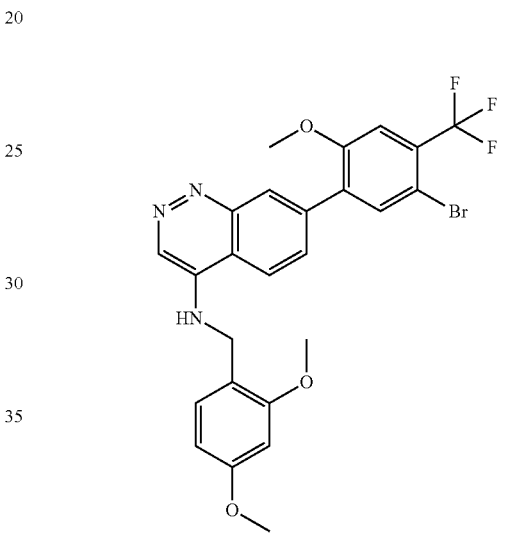

A mixture of aqueous 2N sodium carbonate solution (5.25 mL, 10.5 mmol), [4-[(2,4-dimethoxyphenyl)methylamino]cinnolin-7-yl]boronic acid (1.7 g, 7.88 mmol) and 1-bromo-5-iodo-4-methoxy-2-(trifluoromethyl)benzene (2.0 g, 5.25 mmol) in 1,2-dimethoxyethane (55.13 mL) was degassed for 10 min. Then [1,1'-bis(di-tert-butylphosphino)ferrocene]dichloropalladium(II) (343.24 mg, 0.530 mmol) was added and the resulting reaction mixture was stirred at 80° C. overnight. The mixture was cooled to room temperature and filtered over Celite, washing with MeOH. The filtrate was concentrated and the residue was purified by column chromatography (KP-NH silica gel, SNAP 220) eluting with a gradient of EtOAc in cyclohexane from 2% to 100% to give two batches of 7-[5-bromo-2-methoxy-4-(trifluoromethyl)phenyl]-N-[(2,4-dimethoxyphenyl)methyl]cinnolin-4-amine (1 g, 1.824 mmol, 34.73% yield) as an orange solid and 7-[5-bromo-2-methoxy-4-(trifluoromethyl)phenyl]-N-[(2,4-dimethoxyphenyl)methyl]cinnolin-4-amine (700 mg, 1.277 mmol, 24.31% yield) as a yellowish solid. $^1$H NMR (400 MHz, DMSO-$d_6$) δ 3.74 (s, 3H), 3.88 (s, 3H), 3.92 (s, 3H), 4.52 (d, J=5.83 Hz, 2H), 6.47 (dd, J=8.43, 2.40 Hz, 1H), 6.63 (d, J=2.40 Hz, 1H), 7.15 (d, J=8.37 Hz, 1H), 7.53 (s, 1H), 7.79 (dd, J=8.79, 1.86 Hz, 1H), 7.95 (s, 1H), 8.07 (t, J=6.11 Hz, 1H), 8.24 (d, J=1.78 Hz, 1H), 8.39 (d, J=8.88 Hz, 1H), 8.50 (s, 1H). LC-MS (Method A): r.t. 0.90 min, MS (ESI) m/z=548.0 and 550.1 [M+H]$^+$.

Intermediate 227: tert-butyl 2-[(2-bromo-4-chlorophenoxy)methyl]-4,4-difluoropyrrolidine-1-carboxylate

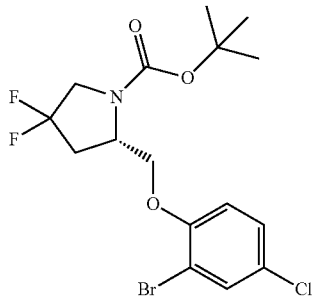 [SMILES: CC(C)(C)OC(=O)N1CC(F)(F)C[C@H]1COc1ccc(Cl)cc1Br]

To a solution of 2-bromo-4-chlorophenol (437.22 mg, 2.11 mmol), triphenylphosphine (608.07 mg, 2.32 mmol) and tert-butyl (2S)-4,4-difluoro-2-(hydroxymethyl)pyrrolidine-1-carboxylate (500.0 mg, 2.11 mmol) in THF (6 mL) was added (NE)-N-ethoxycarbonyliminocarbamic acid ethyl ester (0.37 mL, 2.32 mmol) at room temperature. The resulting mixture was stirred at this temperature for 30 minutes then it was evaporated in vacuo. The residue was purified by column chromatography (KP-sil, SNAP 50) eluting with a gradient of DCM in cyclohexane from 5% to 40% to give tert-butyl 2-[(2-bromo-4-chlorophenoxy)methyl]-4,4-difluoropyrrolidine-1-carboxylate (780 mg, 1.828 mmol, 86.74% yield) as a colourless oil. $^1$H NMR (400 MHz, DMSO-$d_6$) δ 1.40 (s, 9H), 2.45-2.60 (m, 1H), 2.65-2.83 (m, 1H), 3.72 (br. s, 1H), 3.83-3.98 (m, 1H), 4.20 (s, 2H), 4.34 (dq, J=9.26, 4.78 Hz, 1H), 7.21 (d, J=8.81 Hz, 1H), 7.42 (dd, J=8.88, 2.55 Hz, 1H), 7.72 (d, J=2.56 Hz, 1H). LC-MS (Method A): r.t. 1.47 min, MS (ESI) m/z=371.9 [M+H-$C_4H_8$]$^+$ and 327.9 [M+H-Boc]$^+$.

Intermediate 228: tert-butyl (2S)-2-[[4-chloro-2-[4-[(2,4-dimethoxyphenyl)methylamino]cinnolin-7-yl]phenoxy]methyl]-4,4-difluoropyrrolidine-1-carboxylate

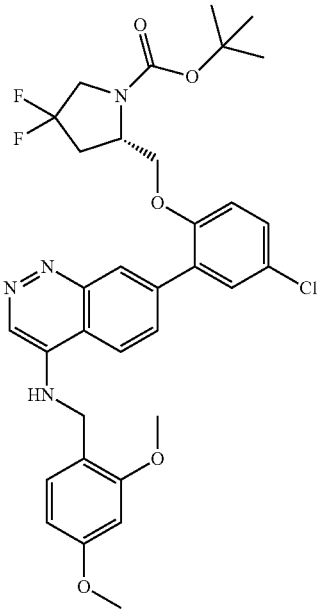 [SMILES: COc1ccc(CNc2cnnc3cc(-c4cc(Cl)ccc4OC[C@@H]4CC(F)(F)CN4C(=O)OC(C)(C)C)ccc23)c(OC)c1]

A mixture of tert-butyl (2S)-2-[(2-bromo-4-chlorophenoxy)methyl]-4,4-difluoropyrrolidine-1-carboxylate (300.0 mg, 0.700 mmol), aqueous 2N sodium carbonate (0.7 mL, 1.41 mmol) and N-[(2,4-dimethoxyphenyl)methyl]-7-(4,4,5,5-tetramethyl-1,3,2-dioxaborolan-2-yl)cinnolin-4-amine (444.33 mg, 1.05 mmol) in 1,2-dimethoxyethane (8.154 mL) in a microwave reaction tube was placed under nitrogen then de-oxygenated with a stream of nitrogen for 10 minutes. [1,1'-Bis(di-tert-butylphosphino)ferrocene]dichloropalladium(II) (45.97 mg, 0.070 mmol) was added and the reaction mixture was heated to 75° C. for 2.5 hours then it was filtered over a pad of Celite, washing with EtOAc. The filtrate was concentrated in vacuo and the residue was purified by column chromatography (KP-NH silica gel, SNAP 55) eluting with a gradient of EtOAc in cyclohexane from 10% to 99% to give tert-butyl (2S)-2-[[4-chloro-2-[4-[(2,4-dimethoxyphenyl)methylamino]cinnolin-7-yl]phenoxy]methyl]-4,4-difluoropyrrolidine-1-carboxylate (370 mg, 0.577 mmol, 82.08% yield) as an off white solid. $^1$H NMR (400 MHz, DMSO-$d_6$) δ 1.07 (s, 9H), 2.22-2.40 (m, 1H), 2.45-2.60 (m, 1H), 3.68 (br. s, 1H), 3.74 (s, 3H), 3.87 (s, 3H), 3.91 (s, 2H), 4.18 (br. s, 2H), 4.51 (d, J=5.72 Hz, 2H), 6.46 (dd, J=8.36, 2.42 Hz, 1H), 6.63 (d, J=2.42 Hz, 1H), 7.14 (d, J=8.36 Hz, 1H), 7.26 (d, J=9.02 Hz, 1H), 7.46 (dd, J=8.80, 2.64 Hz, 1H), 7.55 (d, J=2.42 Hz, 1H), 7.75 (d, J=9.02 Hz, 1H), 8.00-8.07 (m, 1H), 8.16 (d, J=1.32 Hz, 1H), 8.37 (d, J=8.80 Hz, 1H), 8.48 (s, 1H). LC-MS (Method A): r.t. 0.99 min, MS (ESI) m/z=641.14 [M+H]$^+$.

Intermediate 229: 7-bromocinnolin-4-amine

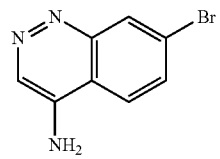 [SMILES: Nc1cnnc2cc(Br)ccc12]

Trifluoroacetic acid (5 mL) was added to a stirred solution of 7-bromo-N-[(2,4-dimethoxyphenyl)methyl]cinnolin-4-amine (1.06 g, 2.83 mmol) in DCM (5 mL). The mixture was stirred at room temperature overnight. The solvent was evaporated and the residue was charged onto an SCX column eluting first with MeOH and then with a 2M methanolic solution of ammonia. The basic fractions were evaporated to give 7-bromocinnolin-4-amine (630 mg, 2.812 mmol, 99.27% yield) as a brown solid. $^1$H NMR (400 MHz, DMSO-$d_6$) δ 7.38 (s, 2H), 7.72 (dd, J=8.97, 2.04 Hz, 1H), 8.17 (d, J=9.01 Hz, 1H), 8.24 (d, J=1.97 Hz, 1H), 8.64 (s, 1H). LC-MS (Method A): r.t. 0.34 min, MS (ESI) m/z=223.97 and 225.94 [M+H]$^+$.

Intermediate 230: 7-bromocinnoline

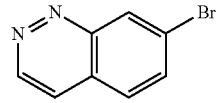 [SMILES: Brc1ccc2ccnnc2c1]

A solution of nitrous acid 3-methylbutyl ester (1.13 mL, 8.44 mmol) in DMF (18.9 mL) was stirred and heated under argon at 65° C. To this solution was added dropwise a solution of 7-bromocinnolin-4-amine (630.0 mg, 2.81 mmol) in DMF (12.6 mL) over 40 min, while maintaining the temperature at 65° C. The mixture was stirred at 65° C. for 1 hour, and then cooled to room temperature. EtOAc/EtOH and 0.5N HCl/H$_2$O were added. The aqueous phase was extracted three times. The combined organic phases were washed with 2N HCl/H$_2$O and brine, dried over Na$_2$SO$_4$, filtered and concentrated. The residue was purified by column chromatography (KP-NH silica gel, SNAP 28) eluting with a gradient of EtOAc in cyclohexane from 0% to 40% to give 7-bromocinnoline (200 mg, 0.957 mmol, 34.03% yield) as a brown solid. $^1$H NMR (400 MHz, DMSO-d$_6$) δ 8.01-8.13 (m, 2H), 8.29 (d, J=5.81 Hz, 1H), 8.73 (d, J=1.91 Hz, 1H), 9.46 (d, J=5.84 Hz, 1H). LC-MS (Method A): r.t. 0.74 min, MS (ESI) m/z=208.92 and 210.89 [M+H]$^+$.

Intermediate 231:
7-(5-chloro-2-methoxyphenyl)cinnoline

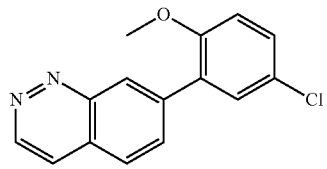 [SMILES: COc1ccc(Cl)cc1-c1ccc2ccnnc2c1]

A mixture of aqueous 2N sodium carbonate solution (478.38 uL, 0.960 mmol), 7-bromocinnoline (200.0 mg, 0.960 mmol) and 5-chloro-2-methoxyphenylboronic acid (196.17 mg, 1.05 mmol) in 1,2-dimethoxyethane (9.568 mL) was degassed for 10 min. Then [1,1'-bis(di-tert-butylphosphino)ferrocene]dichloropalladium(II) (62.55 mg, 0.100 mmol) was added and the resulting reaction mixture was stirred at 80° C. for 4 hours. The mixture was cooled to room temperature and filtered over Celite, washing with MeOH. The filtrate was evaporated and the residue was purified by column chromatography (KP-NH silica gel, SNAP28) eluting with a gradient of EtOAc in cyclohexane from 0% to 80% to give 7-(5-chloro-2-methoxyphenyl)cinnoline (215 mg, 0.794 mmol, 83.01% yield) as a yellow oil. $^1$H NMR (400 MHz, DMSO-d$_6$) δ 3.84 (s, 3H), 7.25 (d, J=8.86 Hz, 1H), 7.51 (dd, J=8.84, 2.72 Hz, 1H), 7.59 (d, J=2.68 Hz, 1H), 8.01 (dd, J=8.59, 1.73 Hz, 1H), 8.10 (d, J=8.56 Hz, 1H), 8.24 (dd, J=5.83, 1.00 Hz, 1H), 8.54 (m, 1H), 9.40 (d, J=5.75 Hz, 1H). LC-MS (Method A): r.t. 1.05 min, MS (ESI) m/z=271.04 [M+H]$^+$.

Intermediate 232: 2-[(2-bromo-4-chlorophenoxy)methyl]oxolane

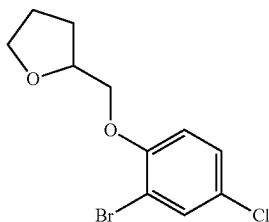 [SMILES: Clc1ccc(OCC2CCCO2)c(Br)c1]

To a suspension of 2-bromo-4-chlorophenol (500.0 mg, 2.41 mmol) and potassium carbonate (499.67 mg, 3.62 mmol) in DMF (6 mL), was added 2-(bromomethyl)tetrahydrofuran (596.64 mg, 3.62 mmol). The resulting mixture was stirred at 80° C. overnight. After addition of water/EtOAc and phase separation, the aqueous phase was re-extracted with EtOAc. The combined organic phases were washed with water, saturated aqueous sodium bicarbonate solution and brine, dried over Na$_2$SO$_4$, filtered and concentrated in vacuum. The residue was purified by column chromatography (KP-sil silica gel, SNAP 50) eluting with a gradient of EtOAc in cyclohexane from 5% to 40% to give 2-[(2-bromo-4-chlorophenoxy)methyl]oxolane (650 mg, 2.229 mmol, 92.49% yield) as a colourless oil. LC-MS (Method A): r.t. 0.67 min, MS (ESI) m/z=290.9 and 293.1 [M+H]$^+$. $^1$H NMR indicated the presence of some aliphatic impurities. This material was used in the next reaction without further purification.

Intermediate 233: 7-[5-chloro-2-(oxolan-2-ylmethoxy)phenyl]-N-[(2,4-dimethoxyphenyl)methyl]cinnolin-4-amine

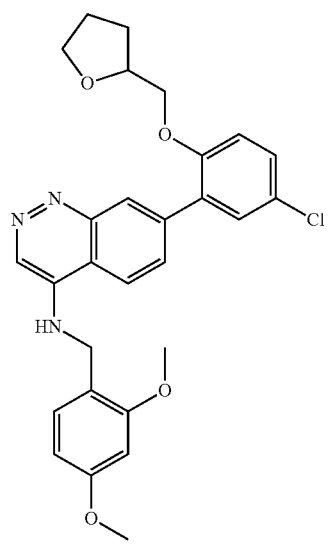 [SMILES: COc1ccc(CNc2cnnc3cc(-c4cc(Cl)ccc4OCC4CCCO4)ccc23)c(OC)c1]

A solution of 2-[(2-bromo-4-chlorophenoxy)methyl]oxolane (450.0 mg, 1.08 mmol), aqueous 2N sodium carbonate solution (1.08 mL, 2.16 mmol) and N-[(2,4-dimethoxyphenyl)methyl]-7-(4,4,5,5-tetramethyl-1,3,2-dioxaborolan-2-yl)cinnolin-4-amine (682.73 mg, 1.62 mmol) in 1,2-dimethoxyethane (10.87 mL) in a microwave reaction tube was placed under nitrogen then de-oxygenated with a stream of nitrogen for 10 min. [1,1'-Bis(di-tert-butylphosphino)ferrocene]dichloropalladium(II) (70.63 mg, 0.110 mmol) was added and the reaction mixture was heated to 75° C. for 2.5 hours then it was filtered over a pad of Celite, washing with EtOAc. The filtrate was concentrated in vacuo and the residue was purified by column chromatography (KP-NH silica gel, SNAP 55) eluting with a gradient of EtOAc in cyclohexane from 10% to 99% to give 7-[5-chloro-2-(oxolan-2-ylmethoxy)phenyl]-N-[(2,4-dimethoxyphenyl)methyl]cinnolin-4-amine (360 mg, 0.711 mmol, 65.86% yield) as an off white solid. $^1$H NMR (400 MHz, DMSO-d$_6$) δ 1.58-1.77 (m, 3H), 1.85-1.95 (m, 1H), 3.59 (q, J=7.02 Hz, 1H), 3.68 (q, J=7.03 Hz, 1H), 3.74 (s, 3H), 3.88 (s, 3H), 4.02-4.14 (m, 3H), 4.51 (d, J=5.75 Hz, 2H), 6.47 (dd, J=8.34, 2.42 Hz, 1H), 6.63 (d, J=2.41 Hz, 1H), 7.15 (d,

337

J=8.29 Hz, 1H), 7.22 (d, J=8.88 Hz, 1H), 7.44 (dd, J=8.84, 2.69 Hz, 1H), 7.54 (d, J=2.67 Hz, 1H), 7.83 (dd, J=8.81, 1.83 Hz, 1H), 8.01 (t, J=6.03 Hz, 1H), 8.23 (d, J=1.77 Hz, 1H), 8.36 (d, J=8.90 Hz, 1H), 8.47 (s, 1H). LC-MS (Method A): r.t. 0.86 min, MS (ESI) m/z=506.2 [M+H]$^+$.

Intermediate 234: 6-[5-chloro-2-(trifluoromethyl) pyridin-3-yl]-N-[(2,4-dimethoxyphenyl)methyl]-4-methylphthalazin-1-amine Formic Acid Salt

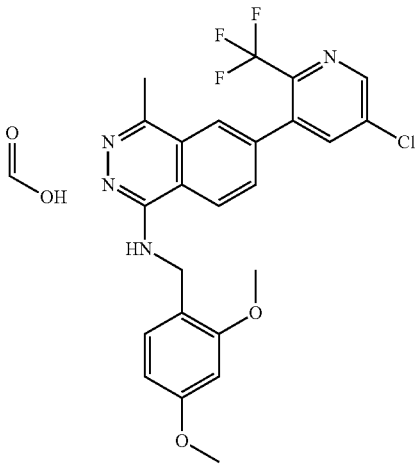 [SMILES: O=CO ; COc1ccc(CNc2nnc(C)c3cc(-c4cc(Cl)cnc4C(F)(F)F)ccc23)c(OC)c1]

A mixture of 3-bromo-5-chloro-2-(trifluoromethyl)pyridine (154.86 mg, 0.590 mmol), [1-[(2,4-dimethoxyphenyl) methylamino]-4-methylphthalazin-6-yl]boronic acid (300.0 mg, 0.590 mmol) and aqueous 2N sodium carbonate solution (0.59 mL, 1.19 mmol) in 1,4-dioxane (7 mL) was degassed for 10 min. Then [1,1'-bis(di-tert-butylphosphino) ferrocene]dichloropalladium(II) (38.87 mg, 0.060 mmol) was added and the resulting reaction mixture was stirred at 85° C. for 18 hours. The mixture was diluted with MeOH and filtered over a pad of Celite, washing with EtOAc and MeOH. The organic solvents were evaporated in vacuo and the residue was purified by column chromatography (Sfar C18 D, 60 g) eluting with a gradient of MeCN (+0.1% HCOOH) in water (+0.1% HCOOH) from 0% to 60% to give 6-[5-chloro-2-(trifluoromethyl)pyridin-3-yl]-N-[(2,4-dimethoxyphenyl)methyl]-4-methylphthalazin-1-amine formic acid salt (170 mg, 0.318 mmol, 53.45% yield) as a light brown solid. $^1$H NMR (400 MHz, DMSO-d$_6$) δ 2.67 (s, 3H), 3.73 (s, 3H), 3.84 (s, 3H), 4.67 (s, 2H), 6.44 (dd, J=8.37, 2.41 Hz, 1H), 6.58 (d, J=2.38 Hz, 1H), 7.14 (d, J=8.36 Hz, 1H), 7.68 (br. s, 1H), 7.91 (dd, J=8.61, 1.74 Hz, 1H), 8.05 (d, J=1.73 Hz, 1H), 8.16 (s, 1H from HCOOH), 8.33 (d, J=2.27 Hz, 1H), 8.47 (d, J=8.50 Hz, 1H), 8.94 (d, J=2.21 Hz, 1H). LC-MS (Method A): r.t. 0.81 min, MS (ESI) m/z=489.10 [M+H]$^+$.

338

Intermediate 235: 2-bromo-4-chloro-1-(difluoromethoxy)benzene

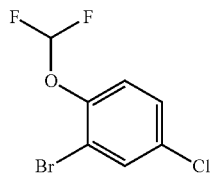 [SMILES: FC(F)Oc1ccc(Cl)cc1Br]

A mixture of 2-bromo-4-chlorophenol (1.0 g, 4.82 mmol), sodium 2-chloro-2,2-difluoroacetate (1690.33 mg, 11.09 mmol) and dicesium carbonate (2198.83 mg, 6.75 mmol) in DMF (5 mL) and water (0.500 mL) was stirred overnight at 100° C., then it was left to reach room temperature. Water and EtOAc were added, the phases were separated and the organic phase was washed with brine, dried over Na$_2$SO$_4$, filtered and concentrated. The residue was purified by column chromatography (KP_sil silica gel, 100 g) eluting with a gradient of EtOAc in cyclohexane from 0% to 10% to give 2-bromo-4-chloro-1-(difluoromethoxy)benzene (715 mg, 2.777 mmol, 57.61% yield) as a colourless oil. $^1$H NMR (400 MHz, DMSO-d$_6$) δ 7.30 (t, J=73.07 Hz, 3H), 7.37 (d, J=8.80 Hz, 1H), 7.55 (dd, J=8.80, 2.42 Hz, 1H), 7.91 (d, J=2.64 Hz, 1H). LC-MS (Method A): r.t. 1.23 min, MS (ESI) m/z of product not observed due to poor ionization.

Intermediate 236: 7-[5-chloro-2-(difluoromethoxy) phenyl]-N-[(2,4-dimethoxyphenyl)methyl]cinnolin-4-amine

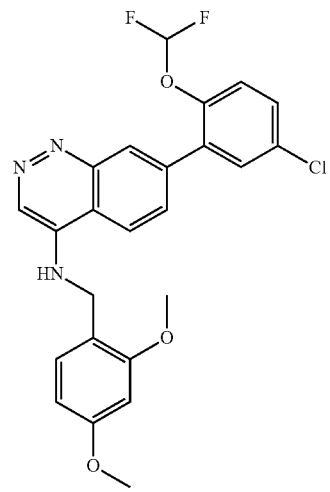

A mixture of N-[(2,4-dimethoxyphenyl)methyl]-7-(4,4,5,5-tetramethyl-1,3,2-dioxaborolan-2-yl)cinnolin-4-amine (319.09 mg, 0.760 mmol) and 2-bromo-4-chloro-1-(difluoromethoxy)benzene (130.0 mg, 0.500 mmol) in aqueous 2N sodium carbonate solution (0.5 mL, 1.01 mmol) and 1,2-dimethoxyethane (10 mL) was degassed for 10 min. [1,1'-Bis(di-tert-butylphosphino)ferrocene]dichloropalladium(II) (33.01 mg, 0.050 mmol) was added and the mixture was degassed for 10 min and then stirred at 85° C. for 90 min. The mixture was left to reach room temperature, diluted with EtOAc and filtered over a pad of Celite, washing with EtOAc. The filtrate was concentrated and the residue was combined with another residue prepared using the same procedure described above but staring with 30 mg of 2-bromo-4-chloro-1-(difluoromethoxy)benzene. The combined residues were purified by column chromatography (KP-NH silica gel, 28 g) eluting with a gradient of EtOAc in cyclohexane from 20% to 75% to give 7-[5-chloro-2-(difluoromethoxy)phenyl]-N-[(2,4-dimethoxyphenyl)methyl]cinnolin-4-amine (233 mg, 0.494 mmol, 97.79% yield) as a yellowish oil. $^1$H NMR (400 MHz, DMSO-d$_6$) δ 3.75 (s, 3H), 3.89 (s, 3H), 4.53 (d, J=5.50 Hz, 2H), 6.49 (dd, J=8.36, 2.42 Hz, 1H), 6.64 (d, J=2.42 Hz, 1H), 7.17 (d, J=8.36 Hz, 1H), 7.23 (t, J=73.30 Hz, 1H), 7.41 (d, J=3.08 Hz, 1H), 7.61 (dd, J=8.80, 2.64 Hz, 1H), 7.73 (d, J=2.64 Hz, 1H), 7.76 (dd, J=8.80, 1.76 Hz, 1H), 8.08 (t, J=5.94 Hz, 1H), 8.20 (d, J=1.76 Hz), 8.42 (d, J=8.80 Hz, 1H), 8.51 (s, 1H) LC-MS (Method A): r.t. 0.83 min, MS (ESI) m/z=472.13 [M+H]$^+$.

Intermediate 237: 7-[3-chloro-4-(trifluoromethyl)phenyl]-N-[(2,4-dimethoxyphenyl)methyl]cinnolin-4-amine

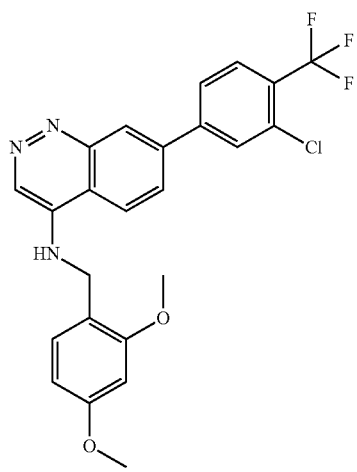 [SMILES: COc1ccc(CNc2cnnc3cc(-c4ccc(C(F)(F)F)c(Cl)c4)ccc23)c(OC)c1]

A mixture of aqueous 2N sodium carbonate solution (801.65 uL, 1.6 mmol), 7-bromo-N-[(2,4-dimethoxyphenyl)methyl]cinnolin-4-amine (300.0 mg, 0.800 mmol) and 3-chloro-4-(trifluoromethyl)benzeneboronic acid (197.85 mg, 0.880 mmol) in 1,2-dimethoxyethane (6 mL) was degassed for 10 min. Then [1,1'-bis(di-tert-butylphosphino)ferrocene]dichloropalladium(II) (52.41 mg, 0.080 mmol) was added and resulting reaction mixture was stirred at 80° C. for 6 hours. The mixture was cooled to room temperature, filtered over Celite, washing with MeOH and the filtrate was evaporated. The residue was purified by column chromatography (KP-NH silica gel, SNAP28) eluting with a gradient of EtOAc in cyclohexane from 2% to 100% to give 7-[3-chloro-4-(trifluoromethyl)phenyl]-N-[(2,4-dimethoxyphenyl)methyl]cinnolin-4-amine (130 mg, 0.274 mmol, 34.22% yield) as an off-white powder. $^1$H NMR (400 MHz, DMSO-d$_6$) δ 3.74 (s, 3H), 3.88 (s, 3H), 4.52 (d, J=5.20 Hz, 2H), 6.47 (dd, J=8.37, 2.40 Hz, 1H), 6.63 (d, J=2.38 Hz, 1H), 7.16 (d, J=8.36 Hz, 1H), 7.99 (d, J=8.32 Hz, 1H), 8.05-8.16 (m, 2H), 8.28 (s, 1H), 8.45-8.55 (m, 3H). LC-MS (Method A): r.t. 0.88 min, MS (ESI) m/z=474.13 [M+H]$^+$.

Intermediate 238: 6-(4-amino-3-chlorophenyl)-N-[(2,4-dimethoxyphenyl)methyl]-4-methylphthalazin-1-amine

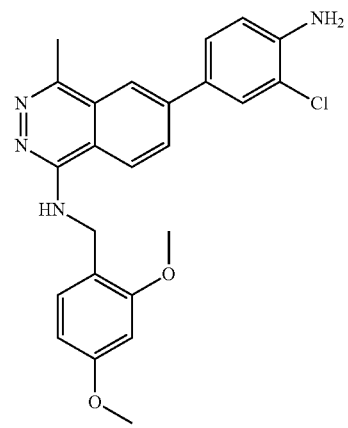 [SMILES: COc1ccc(CNc2nnc(C)c3cc(-c4ccc(N)c(Cl)c4)ccc23)c(OC)c1]

A mixture of aqueous 2N sodium carbonate solution (1931.7 uL, 3.86 mmol), 6-bromo-N-[(2,4-dimethoxyphenyl)methyl]-4-methylphthalazin-1-amine (750.0 mg, 1.93 mmol) and 2-chloro-4-(4,4,5,5-tetramethyl-1,3,2-dioxaborolan-2-yl)aniline (587.69 mg, 2.32 mmol) in 1,2-dimethoxyethane (19 mL) was degassed for 10 min. Then [1,1'-bis(di-tert-butylphosphino)ferrocene]dichloropalladium(II) (126.29 mg, 0.190 mmol) was added and the resulting reaction mixture was stirred at 80° C. for 15 hours. The mixture was cooled to room temperature and filtered over Celite, washing with MeOH. The filtrate and concentrated and the residue was purified by column chromatography (KP-NH silica gel, SNAP55) eluting with a gradient of EtOAc in cyclohexane from 0% to 100% to give 6-(4-amino-3-chlorophenyl)-N-[(2,4-dimethoxyphenyl)methyl]-4-methylphthalazin-1-amine (750 mg, 1.724 mmol, 89.27% yield) as a yellow powder. $^1$H NMR (400 MHz, DMSO-d$_6$) δ 2.73 (s, 3H), 3.73 (s, 3H), 3.84 (s, 3H), 4.65 (d, J=5.41 Hz, 2H), 5.68 (s, 2H), 6.43 (dd, J=8.36, 2.42 Hz, 1H), 6.58 (d, J=2.38 Hz, 1H), 6.94 (d, J=8.46 Hz, 1H), 7.12 (d, J=8.35 Hz, 1H), 7.53 (t, J=5.74 Hz, 1H), 7.63 (dd, J=8.46, 2.19 Hz, 1H), 7.82 (d, J=2.18 Hz, 1H), 8.06 (d, J=1.86 Hz, 1H), 8.12 (dd, J=8.69, 1.88 Hz, 1H), 8.38 (d, J=8.72 Hz, 1H). LC-MS (Method A): r.t. 0.77 min, MS (ESI) m/z=435.14 [M+H]$^+$.

Intermediate 239: [2-amino-5-[1-[(2,4-dimethoxyphenyl)methylamino]-4-methylphthalazin-6-yl]phenyl]boronic Acid

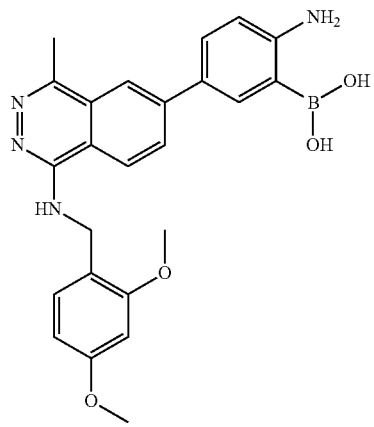 [SMILES: COc1ccc(CNc2nnc(C)c3cc(-c4ccc(N)c(B(O)O)c4)ccc23)c(OC)c1]

A 20 mL microwave vial was charged with dichlorobis(trimethylphosphine)nickel (3.24 mg, 0.010 mmol), 4,4,5,5-tetramethyl-2-(4,4,5,5-tetramethyl-1,3,2-dioxaborolan-2-yl)-1,3,2-dioxaborolane (321.13 mg, 1.26 mmol), cesium fluoride (174.63 mg, 1.15 mmol), 6-(4-amino-3-chlorophenyl)-N-[(2,4-dimethoxyphenyl)methyl]-4-methylphthalazin-1-amine (250.0 mg, 0.570 mmol), trimethyl(2,2,2-trifluoroethoxy)silane (207.89 mg, 1.21 mmol) and THF (5.5 mL) and the mixture was deoxygenated under N₂ for 10 min. The resulting mixture was heated to 100° C. for 5 hours under microwave irradiation in a microwave reactor. The mixture was evaporated, and the residue was solubilized in MeOH and loaded onto an SCX cartridge. The cartridge was eluted first with MeOH and then with a 2M methanolic solution of ammonia. The basic fractions were evaporated to give [2-amino-5-[1-[(2,4-dimethoxyphenyl)methylamino]-4-methylphthalazin-6-yl]phenyl]boronic acid (235 mg, 0.529 mmol, 92.02% yield) as a yellow vitreous solid. This material was used in the next step without further purification. LC-MS (Method A): r.t. 0.64 min, MS (ESI) m/z=445.21 [M+H]⁺.

Intermediate 240: [5-[1-[(2,4-dimethoxyphenyl)methylamino]-4-methylphthalazin-6-yl]-2-(2-methylpropanoylamino)phenyl]boronic Acid

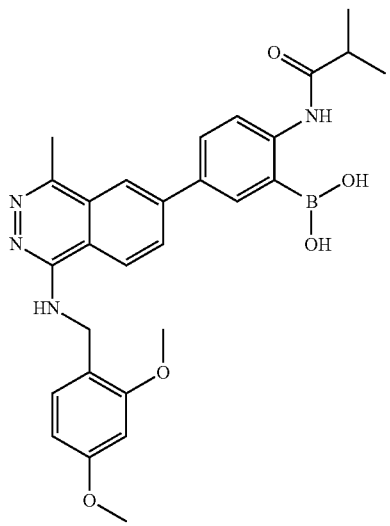 [SMILES: COc1ccc(CNc2nnc(C)c3cc(-c4ccc(NC(=O)C(C)C)c(B(O)O)c4)ccc23)c(OC)c1]

2-Methylpropanoyl chloride (26.16 uL, 0.250 mmol) was added dropwise to a stirred solution of [2-amino-5-[1-[(2,4-dimethoxyphenyl)methylamino]-4-methylphthalazin-6-yl]phenyl]boronic acid (110.0 mg, 0.250 mmol) in dry THF (2.476 mL). Then triethylamine (69.02 uL, 0.500 mmol) was added and the mixture was stirred for 3 hours at room temperature under a N₂ atmosphere. Water was added and the resulting mixture was extracted three times with EtOAc spiked with a drops of MeOH. The combined organic phases were filtered over a hydrophobic frit (Phase separator) and evaporated to give [5-[1-[(2,4-dimethoxyphenyl)methylamino]-4-methylphthalazin-6-yl]-2-(2-methylpropanoylamino)phenyl]boronic acid (56 mg, 0.109 mmol, 43.97% yield) as a yellow oil. This material was used in the next step without further purification. LC-MS (Method A): r.t. 0.58 min, MS (ESI) m/z=515.27 [M+H]⁺.

Intermediate 241: (1R,3S,4R,5R)-3,4,6,6-tetramethylbicyclo[3.1.1]heptane-3,4-diol

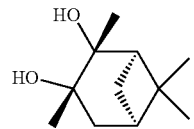

A solution of (1R,4R,5R)-4-hydroxy-4,6,6-trimethylbicyclo[3.1.1]heptan-3-one (250.0 mg, 1.49 mmol) in THF (0.500 mL) was cooled to −78° and then a 3M solution of methylmagnesium chloride in THF (1.09 mL, 3.27 mmol) was added dropwise. After addition was complete the mixture was stirred at room temperature for 1 hour, then quenched with a saturated solution of ammonium chloride and extracted with EtOAc. The organic phase was washed with brine, dried over Na₂SO₄, filtered and evaporated in vacuo. The residue was purified by column chromatography (KP-sil silica gel, SNAP 25) eluting with a gradient of EtOAc in cyclohexane from 5% to 40% to (1R,3S,4R,5R)-3,4,6,6-tetramethylbicyclo[3.1.1]heptane-3,4-diol (130 mg, 0.705 mmol, 47.47% yield) as a white solid. ¹H NMR (400 MHz, DMSO-d₆) δ 0.82 (s, 3H), 1.15 (s, 3H), 1.19 (s, 3H), 1.20 (s, 3H), 1.71-1.84 (m, 4H), 1.89-2.01 (m, 2H), 4.87 (s, 1H), 4.92 (s, 1H).

Intermediate 242: [1-(trifluoromethyl)cyclopropyl]methanol

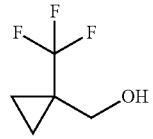

A 2M solution of lithium aluminum hydride in THF (2.11 mL, 4.22 mmol) was added dropwise to a solution of 1-(trifluoromethyl)-1-cyclopropanecarboxylic acid (500.0 mg, 3.24 mmol) in THF (8 mL) cooled to 0° C. The reaction mixture was stirred at room temperature overnight then was quenched with sodium sulfate decahydrate. The resulting suspension was filtered and the filtrate was evaporated in vacuo to give [1-(trifluoromethyl)cyclopropyl]methanol (130 mg, 0.928 mmol, 28.6% yield) as a colourless oil. ¹H NMR (400 MHz, DMSO-d₆) δ 0.75-0.92 (m, 4H), 3.55 (d, J=5.91 Hz, 2H), 4.93 (t, J=6.00 Hz, 1H).

Intermediate 243: 2-bromo-4-chloro-1-[[1-(trifluoromethyl)cyclopropyl]methoxy]benzene

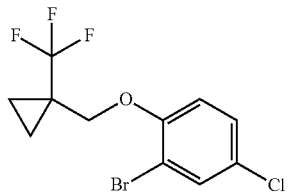 [SMILES: FC(F)(F)C1(COc2ccc(Cl)cc2Br)CC1]

(NE)-N-Ethoxycarbonyliminocarbamic acid ethyl ester (0.16 mL, 1.02 mmol) was added to a solution of 2-bromo-4-chlorophenol (192.49 mg, 0.930 mmol), triphenylphosphine (267.72 mg, 1.02 mmol) and [1-(trifluoromethyl)cyclopropyl]methanol (130.0 mg, 0.930 mmol) in THF (2.651 mL) at room temperature. The resulting mixture was stirred at this temperature for 30 min then evaporated in vacuo. The residue was purified by column chromatography (KP-sil silica gel, SNAP 25) eluting with a gradient of EtOAc in cyclohexane 5% to 40% to give 2-bromo-4-chloro-1-[[1-(trifluoromethyl)cyclopropyl]methoxy]benzene (150 mg, 0.455 mmol, 49.05% yield) as a colourless oil. $^1$H NMR (400 MHz, DMSO-$d_6$) δ 1.01-1.07 (m, 2H), 1.10-1.15 (m, 2H), 4.21 (s, 2H), 7.15 (d, J=8.88 Hz, 1H), 7.42 (dd, J=8.85, 2.58 Hz, 1H), 7.71 (d, J=2.59 Hz, 1H). LC-MS (Method A): r.t. 1.42 min, MS (ESI) m/z of product not observed due to poor ionization.

Intermediate 244: 7-[5-chloro-2-[[1-(trifluoromethyl)cyclopropyl]methoxy]phenyl]-N-[(2,4-dimethoxyphenyl)methyl]cinnolin-4-amine

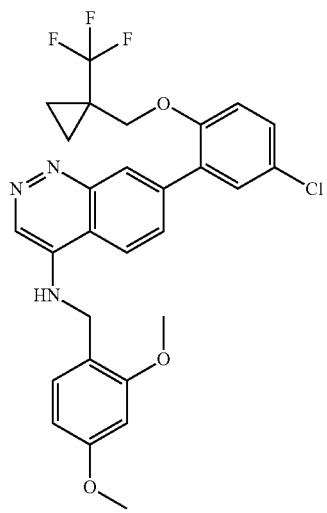 [SMILES: COc1ccc(CNc2cnnc3cc(-c4cc(Cl)ccc4OCC4(C(F)(F)F)CC4)ccc23)c(OC)c1]

A solution of 2-bromo-4-chloro-1-[[1-(trifluoromethyl)cyclopropyl]methoxy]benzene (150.0 mg, 0.460 mmol), aqueous 2N sodium carbonate solution (0.46 mL, 0.910 mmol) and [4-[(2,4-dimethoxyphenyl)methylamino]cinnolin-7-yl]boronic acid (339.62 mg, 0.500 mmol) in 1,2-dimethoxyethane (4.552 mL) in a microwave reaction tube was placed under nitrogen then deoxygenated with a stream of nitrogen for 10 min. [1,1'-Bis(di-tert-butylphosphino)ferrocene]dichloropalladium(II) (29.76 mg, 0.050 mmol) was added and the reaction mixture was heated to 75° C. for 2.5 hours then was filtered over a pad of Celite, washing with EtOAc. The filtrate was concentrated in vacuo and the residue was purified by column chromatography (KP-NH silica gel, SNAP 30) eluting with a gradient of EtOAc in cyclohexane from 10% to 99% to give 7-[5-chloro-2-[[1-(trifluoromethyl)cyclopropyl]methoxy]phenyl]-N-[(2,4-dimethoxyphenyl)methyl]cinnolin-4-amine (115 mg, 0.211 mmol, 46.45% yield) as an off white solid. $^1$H NMR (400 MHz, DMSO-$d_6$) δ 0.89-1.04 (m, 4H), 3.75 (s, 3H), 3.89 (s, 3H), 4.22 (s, 2H), 4.51 (d, J=5.67 Hz, 2H), 6.49 (dd, J=8.37, 2.42 Hz, 1H), 6.64 (d, J=2.42 Hz, 1H), 7.17 (d, J=8.36 Hz, 1H), 7.23 (d, J=8.87 Hz, 1H), 7.47 (dd, J=8.81, 2.70 Hz, 1H), 7.57 (d, J=2.69 Hz, 1H), 7.83 (dd, J=8.79, 1.86 Hz, 1H), 8.01 (t, J=5.83 Hz, 1H), 8.23 (d, J=1.83 Hz, 1H), 8.36 (d, J=8.87 Hz, 1H), 8.49 (s, 1H). LC-MS (Method A): r.t. 0.92 min, MS (ESI) m/z=544.2 [M+H]$^+$.

Intermediate 245: 1-(2-amino-4-bromo-5-fluorophenyl)ethanone

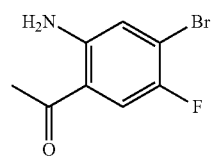

To a stirred 1M solution of trichloroborane in dichloromethane (46.31 mL, 46.31 mmol) was added 3-bromo-4-fluoroaniline (8.0 g, 42.1 mmol) in acetonitrile (100.0 mL, 421.03 mmol) dropwise over 20 min. To this suspension was added trichloroalumane (6.18 g, 46.31 mmol) in three portions. The mixture was then heated to reflux overnight. The mixture was cooled to 0° C. and 4 N aqueous HCl solution was added. The reaction mixture was extracted with DCM. The combined organic layers were washed with aqueous HCl solution, dried over Na$_2$SO$_4$ and concentrated under reduced pressure. The residue was purified by column chromatography (KP silica gel, SNAP 240) eluting with a gradient of EtOAc in cyclohexane from 5% to 40% to give 1-(2-amino-4-bromo-5-fluorophenyl)ethanone (2.5 g, 10.77 mmol, 25.59% yield) as a yellow solid. $^1$H NMR (400 MHz, Chloroform-d) δ 2.56 (s, 3H), 6.17 (s, 2H), 6.90 (d, J=5.78 Hz, 1H), 7.45 (d, J=9.44 Hz, 1H). LC-MS (Method A): r.t. 0.99 min, MS (ESI) m/z=231.9 and 233.9 [M+H]$^+$.

Intermediate 246: 7-bromo-6-fluorocinnolin-4-ol hydrochloride

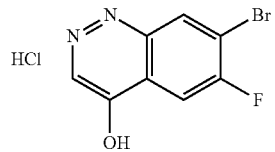

1-(2-Amino-4-bromo-5-fluorophenyl)ethanone (2.5 g, 10.77 mmol) was dissolved in 12M hydrochloric acid solution (62.27 mL, 747.25 mmol) and water (2 mL), then the mixture was cooled to −5° C. in an ice/brine bath. A solution of sodium nitrite (817.71 mg, 11.85 mmol) in water (4 mL) was added slowly dropwise. The reaction was stirred for one hour, then the temperature was raised to 60° C. and the reaction was stirred for 2 h. The reaction mixture was cooled to room temperature and the resulting precipitate was filtered, washed with water, dried and collected to give 7-bromo-6-fluorocinnolin-4-ol hydrochloride (1.7 g, 6.083 mmol, 56.46% yield) as an off white solid. $^1$H NMR (400 MHz, DMSO-$d_6$) δ 7.76 (s, 1H), 7.84 (d, J=8.53 Hz, 1H), 7.94 (d, J=5.81 Hz, 1H), 13.62 (s, 1H). LC-MS (Method A): r.t. 0.7 min, MS (ESI) m/z=242.88 and 244.87 [M+H]$^+$.

Intermediate 247:
7-bromo-4-chloro-6-fluorocinnoline

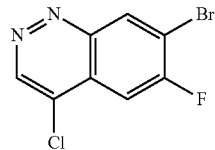 [SMILES: Fc1cc2c(Cl)cnnc2cc1Br]

A solution of 7-bromo-6-fluorocinnolin-4-ol hydrochloride (1.5 g, 0.720 mmol) in phosphorus oxychloride (5 mL, 5.367 mmol) was stirred at 60° C. for 1 hour. The reaction mixture was cooled to room temperature then the excess of phosphorus oxychloride was removed in vacuo. The residue was dissolved in DCM and washed with a saturated aqueous solution of NaHCO$_3$ and brine. The organic layer was dried over Na$_2$SO$_4$, filtered and concentrated under reduce pressure to give 7-bromo-4-chloro-6-fluorocinnoline (1.2 g, 4.589 mmol, 85.5% yield) as a brown solid. $^1$H NMR (400 MHz, DMSO-d$_6$) δ 8.17 (d, J=8.84 Hz, 1H), 9.08 (d, J=6.71 Hz, 1H), 9.65 (s, 1H). LC-MS (Method A): r.t. 1.01 min, MS (ESI) m/z=260.8 and 262.6 [M+H]$^+$.

Intermediate 248:
7-bromo-4-chloro-6-fluorocinnoline

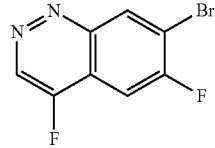 [SMILES: Fc1cc2c(F)cnnc2cc1Br]

A suspension of 7-bromo-4-chloro-6-fluorocinnoline (600.0 mg, 2.29 mmol) and potassium fluoride (133.32 mg, 2.29 mmol) in DMSO (12 mL) was stirred overnight at 110° C. then it was cooled to room temperature. Water was added and the resulting precipitate was filtered, washed with water and dried to give 7-bromo-4,6-difluorocinnoline (400 mg, 1.633 mmol, 71.15% yield) as a pale yellow solid. $^1$H NMR (400 MHz, DMSO-d$_6$) δ 8.26 (d, J=8.47 Hz, 1H), 9.10 (dd, J=6.52, 2.00 Hz, 1H), 9.62 (dd, J=2.95, 0.83 Hz, 1H). LC-MS (Method A): r.t. 1.01 min, MS (ESI) m/z=245.8 and 247.6[M+H]$^+$.

Intermediate 249: 7-bromo-N-[(2,4-dimethoxyphenyl)methyl]-6-fluorocinnolin-4-amine

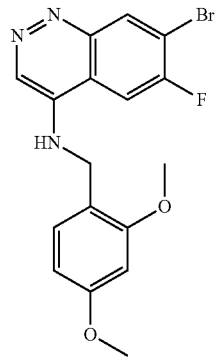 [SMILES: COc1ccc(CNc2cnnc3cc(Br)c(F)cc23)c(OC)c1]

(2,4-Dimethoxyphenyl)methanamine (0.17 mL, 1.14 mmol) was added to a solution of 7-bromo-4,6-difluorocinnoline (400.0 mg, 1.14 mmol) in ethanol (10 mL). The mixture was stirred at 50° C. for 1.5 hours then it was cooled to 0° C. and the resulting precipitate was filtered, washed with ethanol and dried to give 7-bromo-N-[(2,4-dimethoxyphenyl)methyl]-6-fluorocinnolin-4-amine (429 mg, 1.094 mmol, 95.71% yield) as an orange solid. $^1$H NMR (400 MHz, DMSO-d$_6$) δ 3.75 (s, 3H), 3.86 (s, 3H), 4.49 (d, J=5.60 Hz, 2H), 6.49 (dd, J=8.36, 2.42 Hz, 1H), 6.63 (d, J=2.41 Hz, 1H), 7.17 (d, J=8.36 Hz, 1H), 7.98 (t, J=5.77 Hz, 1H), 8.37 (d, J=10.31 Hz, 1H), 8.51 (d, J=6.99 Hz, 1H), 8.54 (s, 1H). LC-MS (Method A): r.t. 0.66 min, MS (ESI) m/z=392.06 and 394.04 [M+H]$^+$.

Intermediate 249: 7-(5-chloro-2-methoxyphenyl)-N-[(2,4-dimethoxyphenyl)methyl]-6-fluorocinnolin-4-amine

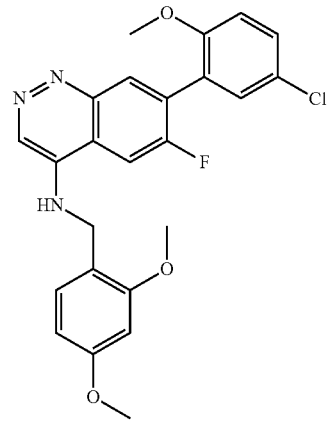 [SMILES: COc1ccc(CNc2cnnc3cc(-c4cc(Cl)ccc4OC)c(F)cc23)c(OC)c1]

A mixture of 7-bromo-N-[(2,4-dimethoxyphenyl)methyl]-6-fluorocinnolin-4-amine (429.0 mg, 1.09 mmol) and 5-chloro-2-methoxyphenylboronic acid (224.27 mg, 1.2 mmol) in 1,2-dimethoxyethane (10.94 mL) and aqueous 2N sodium carbonate solution (1.09 mL, 2.19 mmol) was degassed for 10 minutes with N$_2$. Then [1,1'-bis(di-tert-butylphosphino)ferrocene]dichloropalladium(II) (71.51 mg, 0.110 mmol) was added and the resulting reaction mixture was stirred at 75° C. for 2.5 hours. Then it was cooled to room temperature and filtered over Celite, washing with EtOAc. The filtrate was evaporated and the residue was purified by column chromatography (KP-NH silica gel, SNAP 55) eluting with a gradient of EtOAc in cyclohexane from 10% to 100% to give 7-(5-chloro-2-methoxyphenyl)-N-[(2,4-dimethoxyphenyl)methyl]-6-fluorocinnolin-4-amine (330 mg, 0.727 mmol, 66.47% yield) as a yellow solid. $^1$H NMR (400 MHz, DMSO-d$_6$) δ 3.75 (s, 3H), 3.79 (s, 3H), 3.88 (s, 3H), 4.52 (d, J=5.74 Hz, 2H), 6.49 (dd, J=8.35, 2.40 Hz, 1H), 6.64 (d, J=2.39 Hz, 1H), 7.18 (d, J=8.37 Hz, 1H), 7.21 (d, J=8.86 Hz, 1H), 7.49 (d, J=2.65 Hz, 1H), 7.54 (dd, J=8.81, 2.74 Hz, 1H), 7.90 (t, J=5.84 Hz, 1H), 8.11 (d, J=7.32 Hz, 1H), 8.23 (d, J=11.33 Hz, 1H), 8.49 (s, 1H). LC-MS (Method A): r.t. 0.83 min, MS (ESI) m/z=454.1 [M+H]$^+$.

Intermediate 250: tert-butyl-[1-[2-chloro-4-(4,4,5,5-tetramethyl-1,3,2-dioxaborolan-2-yl)phenyl]propan-2-yloxy]-dimethylsilane

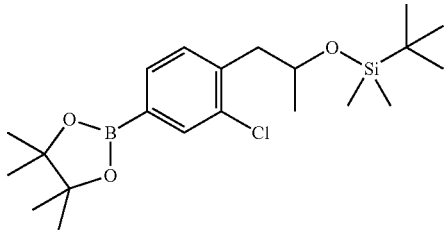 [SMILES: CC(Cc1ccc(B2OC(C)(C)C(C)(C)O2)cc1Cl)O[Si](C)(C)C(C)(C)C]

A stirred suspension of 1-(4-bromo-2-chlorophenyl)propan-2-yloxy-tert-butyl-dimethylsilane (500.0 mg, 1.37 mmol), 4,4,5,5-tetramethyl-2-(4,4,5,5-tetramethyl-1,3,2-dioxaborolan-2-yl)-1,3,2-dioxaborolane (523.53 mg, 2.06 mmol) and potassium acetate (674.43 mg, 6.87 mmol) in 1,4-dioxane (10 mL) was placed under nitrogen then degassed with a stream of nitrogen for 10 min. [1,1'-Bis(diphenylphosphino)ferrocene]dichloropalladium(II) complex with dichloromethane (112.52 mg, 0.140 mmol) was added and the reaction mixture was degassed with a steam of nitrogen for another 10 min, then it was heated to 100° C. for 4 h. The mixture was filtered over Celite, washing with EtOAc. The filtrate was concentrated under reduced pressure and the residue was purified by column chromatography (KP-sil silica gel, SNAP 55) eluting with a gradient of EtOAc in cyclohexane from 0% to 40% to give tert-butyl-[1-[2-chloro-4-(4,4,5,5-tetramethyl-1,3,2-dioxaborolan-2-yl)phenyl]propan-2-yloxy]-dimethylsilane (200 mg, 0.487 mmol, 35.42% yield) as a yellow oil. $^1$H NMR (400 MHz, DMSO-$d_6$) δ −0.28 (s, 3H), −0.10 (s, 3H), 0.77 (s, 9H), 1.15 (d, J=6.02 Hz, 3H), 1.30 (s, 12H), 2.74-2.89 (m, 2H), 4.03-4.17 (m, 1H), 7.33 (d, J=7.48 Hz, 1H), 7.52 (dd, J=7.50, 1.19 Hz, 1H), 7.59 (d, J=1.11 Hz, 1H). LC-MS (Method A): r.t. 1.88 min, MS (ESI) m/z of product not observed due to poor ionization.

Intermediate 251: 7-[4-[2-[tert-butyl(dimethyl)silyl]oxypropyl]-3-chlorophenyl]-N-[(2,4-dimethoxyphenyl)methyl]cinnolin-4-amine (Racemic Method 1: A mixture of 1-(4-bromo-2-chlorophenyl)propan-2-yloxy-tert-butyl-dimethylsilane (237.0 mg, 0.650 mmol), [4-[(2,4-dimethoxyphenyl)methylamino]cinnolin-7-yl]boronic acid (384.25 mg, 0.910 mmol) and aqueous 2 N sodium carbonate solution (651.47 uL, 1.3 mmol) in 1,2-dimethoxyethane (6.5 mL) was degassed for 10 min. Then [1,1'-bis(di-tert-butylphosphino)ferrocene]dichloropalladium(II) (42.59 mg, 0.070 mmol) was added and the resulting reaction mixture was stirred at 80° C. for 12 hours. The mixture was filtered over Celite, washing three times with MeOH. The filtrate was concentrated in vacuo and the residue was purified by column chromatography (KP-NH silica gel, SNAP 28) eluting with a gradient of MeOH in DCM from 0% to 10% to give 7-[4-[2-[tert-butyl(dimethyl)silyl]oxypropyl]-3-chlorophenyl]-N-[(2,4-dimethoxyphenyl)methyl]cinnolin-4-amine (238 mg, 0.412 mmol, 63.18% yield) as a pale-yellow powder.

Method 2: A mixture of tert-butyl-[1-[2-chloro-4-(4,4,5,5-tetramethyl-1,3,2-dioxaborolan-2-yl)phenyl]propan-2-yloxy]-dimethylsilane (200.0 mg, 0.490 mmol), 7-bromo-N-[(2,4-dimethoxyphenyl)methyl]cinnolin-4-amine (260.24 mg, 0.490 mmol) and aqueous 2N sodium carbonate solution (486.78 uL, 0.970 mmol) in 1,2-dimethoxyethane (5 mL) was degassed for 10 min. Then [1,1'-bis(di-tert-butylphosphino)ferrocene]dichloropalladium(II) (31.82 mg, 0.050 mmol) was added and the resulting reaction mixture was stirred at 80° C. for 15 hours. The mixture was filtered over Celite, washing three times with MeOH. The filtrate was concentrated in vacuo and the residue was purified by column chromatography (KP-NH silica gel, SNAP 28) eluting with a gradient of MeOH in DCM from 0% to 5% to give 7-[4-[2-[tert-butyl(dimethyl)silyl]oxypropyl]-3-chlorophenyl]-N-[(2,4-dimethoxyphenyl)methyl]cinnolin-4-amine (240 mg, 0.415 mmol, 85.27% yield) as a brown powder. $^1$H NMR (400 MHz, DMSO-$d_6$) δ −0.22 (s, 3H), −0.05 (s, 3H), 0.80 (s, 9H), 1.20 (d, J=5.96 Hz, 3H), 2.83-2.94 (m, 2H), 3.74 (s, 3H), 3.88 (s, 3H), 4.08-4.21 (m, 1H), 4.52 (d, J=5.75 Hz, 2H), 6.48 (dd, J=8.39, 2.38 Hz, 1H), 6.63 (d, J=2.41 Hz, 1H), 7.16 (d, J=8.36 Hz, 1H), 7.47 (d, J=8.00 Hz, 1H), 7.82 (dd, J=8.00, 1.96 Hz, 1H), 7.95 (d, J=1.95 Hz, 1H), 8.01 (dd, J=8.83, 1.96 Hz, 1H), 8.07 (t, J=6.06 Hz, 1H), 8.35 (d, J=1.93 Hz, 1H), 8.44 (d, J=8.96 Hz, 1H), 8.49 (s, 1H). LC-MS (Method A): r.t. 1.19 min, MS (ESI) m/z=578.31 [M+H]$^+$.

Intermediate 252: N-[(2,4-dimethoxyphenyl)methyl]-7-(4,4,5,5-tetramethyl-1,3,2-dioxaborolan-2-yl)cinnolin-4-amine

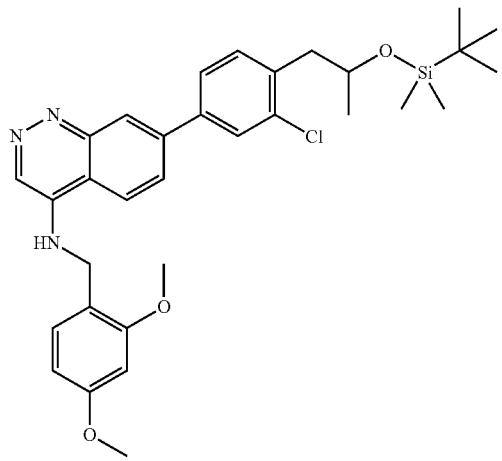 [SMILES: COc1ccc(CNc2cnnc3cc(-c4ccc(CC(C)O[Si](C)(C)C(C)(C)C)c(Cl)c4)ccc23)c(OC)c1]

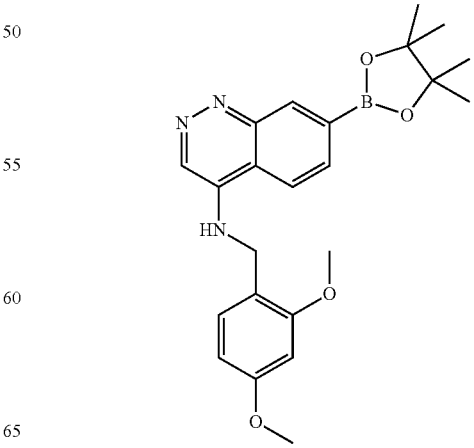

7-Bromo-N-[(2,4-dimethoxyphenyl)methyl]cinnolin-4-amine (50.0 g, 133.61 mmol), potassium acetate (39.34 g, 400.82 mmol), 4,4,5,5-tetramethyl-2-(4,4,5,5-tetramethyl-1,3,2-dioxaborolan-2-yl)-1,3,2-dioxaborolane (101.78 g, 400.82 mmol) were stirred in 1,4-dioxane (1334.9 mL) at room temperature in a 2 L round bottom flask. 3 Cycles of vacuum/$N_2$ (1 full cycle 1 minute, 30 seconds of $N_2$ and 30 seconds of vacuum) were performed on the mixture. Palladium(II) diacetate (1.5 g, 6.68 mmol) and dicyclohexyl-[2-[2,4,6-tri(propan-2-yl)phenyl]phenyl]phosphine (5.1 g, 10.69 mmol) were added and the mixture was deoxygenated by 3 cycles of vacuum/$N_2$ (1 full cycle 1 minute, 30 seconds of $N_2$ and 30 seconds of vacuum). Then, the mixture was stirred at 90° C. for 2 hours. The reaction was cooled to room temperature, filtered over a gooch funnel and the filtrate was concentrated to dryness under reduced pressure. The residue was triturated with EtOAc for 1 hour at room temperature, then filtered and the recovered solid was dried under high vacuum. The trituration procedure was repeated using $Et_2O$ to give N-[(2,4-dimethoxyphenyl)methyl]-7-(4,4,5,5-tetramethyl-1,3,2-dioxaborolan-2-yl)cinnolin-4-amine (30.2 g, 71.68 mmol, 53.65% yield. $^1$H NMR (400 MHz, DMSO-$d_6$) δ 1.16-1.18 (m, 12H), 3.74 (s, 3H), 3.87 (s, 3H), 4.49 (d, J=5.72 Hz, 2H), 6.47 (dd, J=8.36, 2.20 Hz, 1H), 6.63 (d, J=2.20 Hz, 1H), 7.14 (d, J=8.36 Hz, 1H), 7.81 (dd, J=8.36, 1.10 Hz, 1H), 8.02 (t, J=5.72 Hz, 1H), 8.33 (d, J=8.36 Hz, 1H), 8.40 (s, 1H), 8.49 (s, 1H). LC-MS (Method A): r.t. 0.55 min, MS (ESI) m/z=340.3 $[M-C_6H_{10}+H]^+$ (pinacolate ester hydrolyses to boronic acid in HPLC).

Intermediate 253: 4-chloro-3-fluoro-2-iodophenol

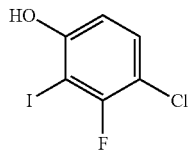

Tribromoborane (10.47 mL, 10.47 mmol) was added to a cold solution (0° C.) of 1-chloro-2-fluoro-3-iodo-4-methoxybenzene (1.0 g, 3.49 mmol) in DCM (20 mL). The reaction mixture was left to reach room temperature and it was stirred overnight. Additional tribromoborane (5.25 mL, 5.25 mmol) was added and the reaction mixture was stirred overnight at room temperature. DCM and ice/water were added. The phases were separated and the organic phase was washed with brine, dried over $Na_2SO_4$, filtered and concentrated to give 4-chloro-3-fluoro-2-iodophenol (794 mg, 2.914 mmol, 83.49% yield) as a black solid. $^1$H NMR (400 MHz, DMSO-$d_6$) δ 6.73 (dd, J=8.80 and 1.10 Hz, 1H), 7.38 (t, J=8.80 Hz, 1H), 10.99 (br. s, 1H). LC-MS (Method A): r.t. 1.07 min, MS (ESI) m/z=271 $[M+H]^+$.

Intermediate 254: 1-chloro-4-(difluoromethoxy)-2-fluoro-3-iodobenzene

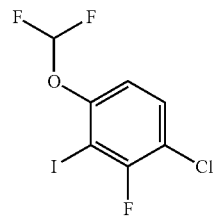

A mixture of 4-chloro-3-fluoro-2-iodophenol (790.0 mg, 2.64 mmol), sodium 2-chloro-2,2-difluoroacetate (925.3 mg, 6.07 mmol) and dicesium carbonate (1203.66 mg, 3.69 mmol) in DMA (10 mL) was stirred overnight at 120° C., then it was allowed to cool to room temperature. EtOAc and water were added. The phases were separated and the organic phase was washed with brine, dried over $Na_2SO_4$, filtered and concentrated. The residue was purified by column chromatography (Sfar D, 2×25 g in series) eluting with a gradient of EtOAc in cyclohexane from 0% to 20% to give 1-chloro-4-(difluoromethoxy)-2-fluoro-3-iodobenzene (390 mg, 1.209 mmol, 45.84% yield) as a colourless oil. $^1$H NMR (400 MHz, DMSO-$d_6$) δ 7.11-7.15 (m, 1H), 7.33 (t, J=72.85 Hz, 1H), 7.72 (t, J=8.69 Hz, 1H). LC-MS (Method A): r.t. 1.24 min, MS (ESI) m/z of product not observed due to poor ionization.

Intermediate 255: 7-[3-chloro-6-(difluoromethoxy)-2-fluorophenyl]-N-[(2,4-dimethoxyphenyl)methyl]cinnolin-4-amine

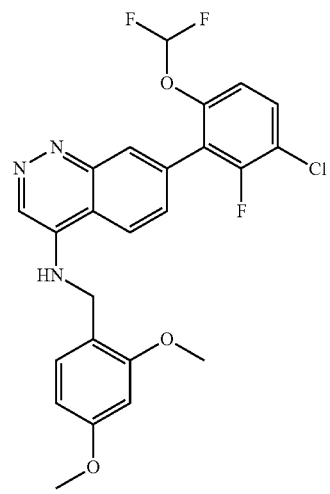 [SMILES: COc1ccc(CNc2cnnc3cc(-c4c(OC(F)F)ccc(Cl)c4F)ccc23)c(OC)c1]

A mixture of 1-chloro-4-(difluoromethoxy)-2-fluoro-3-iodobenzene (200.0 mg, 0.620 mmol) and N-[(2,4-dimethoxyphenyl)methyl]-7-(4,4,5,5-tetramethyl-1,3,2-dioxaborolan-2-yl)cinnolin-4-amine (391.97 mg, 0.930 mmol) in 1,2-dimethoxyethane (12.41 mL) and aqueous 2N sodium carbonate solution (0.62 mL, 1.24 mmol) was degassed for 10 min with Ar. [1,1'-Bis(di-tert-butylphosphino)ferrocene] dichloropalladium(II) (40.55 mg, 0.060 mmol) was added. The mixture was degassed for 10 min and then stirred at 85° C. for 1.5 hours. The mixture was cooled to room temperature and filtered over Celite, washing with EtOAc. The filtrate was concentrated and the residue was purified by column chromatography (KP-NH silica gel, SNAP 55 g) eluting with a gradient of EtOAc in cyclohexane from 20% to 90% to give 7-[3-chloro-6-(difluoromethoxy)-2-fluorophenyl]-N-[(2,4-dimethoxyphenyl)methyl]cinnolin-4-amine (117 mg, 0.239 mmol, 38.51% yield) as a brownish oil. $^1$H NMR (400 MHz, DMSO-$d_6$) δ 3.75 (s, 3H), 3.89 (s, 3H), 4.54 (d, J=5.94 Hz, 2H), 6.49 (dd, J=8.36, 2.42 Hz, 1H), 6.64 (d, J=2.42 Hz, 1H), 7.19 (d, J=8.36 Hz, 1H), 7.25 (t, J=73.07 Hz, 1H), 7.31 (d, J=9.02 Hz, 1H), 7.66 (d, J=9.02 Hz, 1H), 7.80 (t, J=8.80 Hz, 1H), 8.12 (t, J=6.05 Hz, 1H), 8.15 (s, 1H), 8.45 (d, J=8.58 Hz, 1H), 8.54 (s, 1H). LC-MS (Method A): r.t. 0.83 min, MS (ESI) m/z=490.1 [M+H]$^+$.

Intermediate 256: methyl-1,2-thiazole-4-carboxylate

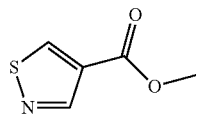

To a solution of 1,2-thiazole-4-carboxylic acid (500 mg, 3.87 mmol) in methanol (8 mL) was added dropwise thionyl chloride (0.42 mL, 5.81 mmol) and the mixture was stirred at reflux for 2 h. The mixture was cooled to room temperature and water was added. The two phases were filtered over a hydrophobic frit (Phase separator) and evaporated to give methyl 1,2-thiazole-4-carboxylate (554 mg, 3.87 mmol, 99.95% yield) as a white powder. $^1$H NMR (400 MHz, DMSO-$d_6$) δ 3.84 (s, 3H), 8.92 (s, 1H), 9.72 (s, 1H). LC-MS (Method A): r.t. 0.60 min, MS (ESI) m/z=144.01[M+H]$^+$.

Intermediate 257: 1,2-thiazol-4-ylmethanol

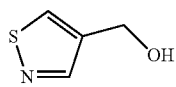

A 2M solution of lithium aluminum hydride in THF (4.45 mL, 8.90 mmol) was added dropwise to a solution of methyl 1,2-thiazole-4-carboxylate (554 mg, 3.87 mmol) in THF (7 mL) cooled to 0° C. The reaction mixture was stirred at 0° C. for 1.5 hours then quenched with sodium sulfate decahydrate. The resulting suspension was filtered and the filtrate was evaporated in vacuo to give 1,2-thiazol-4-ylmethanol (196 mg, 1.70 mmol, 43.98% yield) as a yellow oil. $^1$H NMR (400 MHz, DMSO-$d_6$) δ 4.59 (d, J=5.19 Hz, 2H), 5.27 (t, J=5.59 Hz, 1H), 8.51 (s, 1H), 8.80 (d, J=0.96 Hz, 1H). LC-MS (Method A): r.t. 0.41 min, MS (ESI) m/z=115.94 [M+H]$^+$.

Intermediate 258: 4-[(2-bromo-4-chlorophenoxy)methyl]-1,2-thiazole

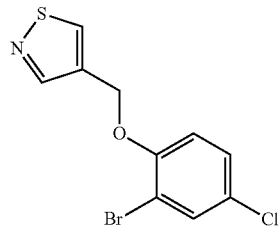 [SMILES: Clc1ccc(OCc2cnsc2)c(Br)c1]

(NE)-N-Ethoxycarbonyliminocarbamic acid ethyl ester (0.34 mL, 1.87 mmol) was added to a solution of 2-bromo-4-chlorophenol (353.11 mg, 1.7 mmol), triphenylphosphine (491.1 mg, 1.87 mmol) and 1,2-thiazol-4-ylmethanol (196 mg, 1.7 mmol) in THF (2.65 mL) at room temperature. The resulting mixture was stirred at this temperature for 30 min then evaporated in vacuo. The residue was purified by column chromatography (KP-NH silica gel, SNAP 30) eluting with a gradient of EtOAc in cyclohexane from 0% to 30% to give 4-[(2-bromo-4-chlorophenoxy)methyl]-1,2-thiazole (225 mg, 0.739 mmol, 43.4% yield) as a white solid. $^1$H NMR (400 MHz, DMSO-$d_6$) δ 5.33 (s, 2H), 7.28 (d, J=8.90 Hz, 1H), 7.45 (dd, J=8.84, 2.58 Hz, 1H), 7.72 (d, J=2.60 Hz, 1H), 8.67 (s, 1H), 9.10 (s, 1H). LC-MS (Method A): r.t. 1.24 min, MS (ESI) m/z=304.03 and 306.05 [M+H]$^+$.

Intermediate 259: 7-[5-chloro-2-(1,2-thiazol-4-ylmethoxy)phenyl]-N-[(2,4-dimethoxyphenyl)methyl]cinnolin-4-amine

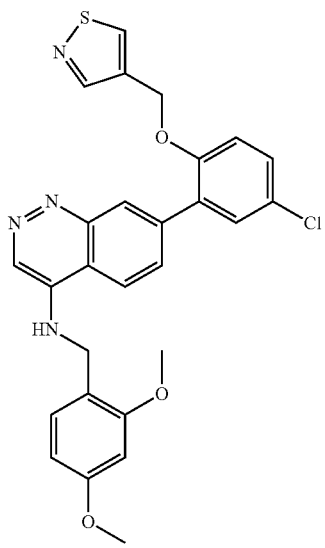 [SMILES: COc1ccc(CNc2cnnc3cc(-c4cc(Cl)ccc4OCc4cnsc4)ccc23)c(OC)c1]

A solution of 4-[(2-bromo-4-chlorophenoxy)methyl]-1,2-thiazole (220.0 mg, 0.720 mmol), aqueous 2N sodium carbonate solution (722.28 uL, 1.44 mmol) and [4-[(2,4-dimethoxyphenyl)methylamino]cinnolin-7-yl]boronic acid (426.02 mg, 1.01 mmol) in 1,2-dimethoxyethane (7 mL) in a microwave reaction tube was placed under nitrogen then deoxygenated with a stream of nitrogen for 10 min. [1,1'-Bis(di-tert-butylphosphino)ferrocene]dichloropalladium(II)

(47.22 mg, 0.070 mmol) was added and the reaction mixture was heated to 80° C. for 8 hours then filtered over a pad of Celite, washing with MeOH. The filtrate was concentrated in vacuo and the residue was purified by column chromatography (KP-NH silica gel, SNAP 28) eluting with a gradient of EtOAc in cyclohexane from 0% to 100% to give 7-[5-chloro-2-(1,2-thiazol-4-ylmethoxy)phenyl]-N-[(2,4-dimethoxyphenyl)methyl]cinnolin-4-amine (244 mg, 0.470 mmol, 65.09% yield) as a pale-brown powder. $^1$H NMR (400 MHz, DMSO-$d_6$) δ 3.74 (s, 3H), 3.88 (s, 3H), 4.51 (d, J=5.60 Hz, 2H), 5.32 (s, 2H), 6.48 (dd, J=8.42, 2.39 Hz, 1H), 6.63 (d, J=2.38 Hz, 1H), 7.15 (d, J=8.39 Hz, 1H), 7.36 (d, J=8.88 Hz, 1H), 7.50 (dd, J=8.81, 2.68 Hz, 1H), 7.57 (d, J=2.65 Hz, 1H), 7.82 (dd, J=8.76, 1.83 Hz, 1H), 8.02 (t, J=5.98 Hz, 1H), 8.22 (d, J=1.80 Hz, 1H), 8.34 (d, J=8.86 Hz, 1H), 8.47 (s, 1H), 8.59 (s, 1H), 8.98 (s, 1H). LC-MS (Method A). r.t. 0.83 min, MS (ESI) m/z=519.20 [M+H]$^+$.

Intermediate 260:
2-(4-bromo-2-chloro-6-fluorophenyl)ethanol

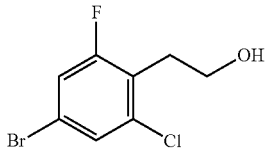

A 2.5M solution of n-butyllithium in hexane (5.73 mL, 14.31 mmol) was added dropwise to a solution of 5-bromo-1-chloro-3-fluoro-2-iodobenzene (4.0 g, 11.93 mmol) in THF (100 mL) at −78° C. The reaction mixture was stirred at −78° C. for 1 hour, then a 2.5M solution of ethylene oxide in THF (4.77 mL, 11.93 mmol) was added dropwise. Boron trifluoride diethyl etherate (1.25 mL, 11.93 mmol) was added rapidly and the mixture was stirred at this temperature for 1 hour. A saturated aqueous solution of sodium bicarbonate was added at −78° C. and the reaction mixture was allowed to warm to room temperature. EtOAc was added and the two phases were separated. The aqueous phase was extracted three times with EtOAc. The combined organic phases were washed with brine, filtered over a hydrophobic frit (Phase Separator) and evaporated. The residue was purified by column chromatography (KP-C18-HS, SNAP 120 g) eluting with a gradient of CH$_3$CN (+0.1% of HCOOH) in water (+0.1% of HCOOH) from 5% to 95% to give 2-(4-bromo-2-chloro-6-fluorophenyl)ethanol (1.6 g, 6.312 mmol, 52.91% yield) as a brownish solid. $^1$H NMR (400 MHz, DMSO-$d_6$) δ 2.86 (td, J=7.05, 2.02 Hz, 2H), 3.50-3.58 (m, 2H), 4.84 (t, J=5.61 Hz, 1H), 7.55 (dd, J=9.06, 1.95 Hz, 1H), 7.60 (t, J=1.70 Hz, 1H). LC-MS (Method A): r.t. 1.02 min, MS (ESI) m/z of product not observed due to poor ionization.

Intermediate 261: 2-(4-bromo-2-chloro-6-fluorophenyl)ethoxy-tert-butyl-dimethylsilane

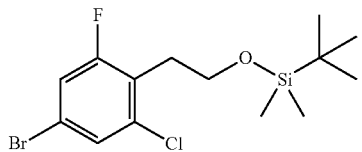 [SMILES: CC(C)(C)[Si](C)(C)OCCc1c(F)cc(Br)cc1Cl]

tert-Butyl(chloro)dimethylsilane (3.39 g, 22.49 mmol) was added to a solution of 2-(4-bromo-2-chloro-6-fluorophenyl)ethanol (1.9 g, 7.5 mmol) and imidazole (1.53 g, 22.49 mmol) in THF (60 mL) under a N$_2$ atmosphere. The reaction mixture was stirred for 1.5 hours at 40° C. Water was added and the resulting mixture was extracted three times with EtOAc. The combined organic phases were washed with saturated aqueous sodium bicarbonate solution and brine, filtered over a hydrophobic frit (Phase Separator) and evaporated. The residue was purified by column chromatography (KP-Sil silica gel, SNAP 50) eluting with a gradient of EtOAc in cyclohexane from 0% to 15% to give 2-(4-bromo-2-chloro-6-fluorophenyl)ethoxy-tert-butyl-dimethylsilane (2.6 g, 7.07 mmol, 94.33% yield) as a pale-yellow oil. $^1$H NMR (400 MHz, DMSO-$d_6$) δ −0.07 (s, 6H), 0.80 (s, 9H), 2.91 (td, J=6.55, 1.97 Hz, 2H), 3.76 (t, J=6.53 Hz, 2H), 7.57 (dd, J=9.07, 1.96 Hz, 1H), 7.62 (t, J=1.67 Hz, 1H). LC-MS (Method A): r.t. 1.79 min, MS (ESI) m/z of product not observed due to poor ionization.

Intermediate 262: 7-[4-[2-[tert-butyl(dimethyl)silyl]oxyethyl]-3-chloro-5-fluorophenyl]-N-[(2,4-dimethoxyphenyl)methyl]cinnolin-4-amine

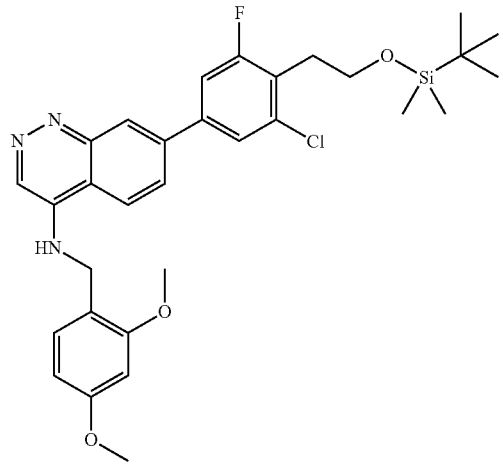 [SMILES: COc1ccc(CNc2cnnc3cc(-c4cc(F)c(CCO[Si](C)(C)C(C)(C)C)c(Cl)c4)ccc23)c(OC)c1]

A mixture of N-[(2,4-dimethoxyphenyl)methyl]-7-(4,4,5,5-tetramethyl-1,3,2-dioxaborolan-2-yl)cinnolin-4-amine (595.7 mg, 1.41 mmol) and 2-(4-bromo-2-chloro-6-fluorophenyl)ethoxy-tert-butyl-dimethylsilane (400.0 mg, 1.09 mmol) in 1,2-dimethoxyethane (11 mL) and aqueous 2N sodium carbonate solution (1.09 mL, 2.18 mmol) was degassed for 10 min with N$_2$. Then, [1,1'-bis(di-tert-butylphosphino)ferrocene]dichloropalladium(II) (71.11 mg, 0.110 mmol) was added. The mixture was stirred at 80° C. for 4 hours, then it was cooled to room temperature and filtered over Celite, washing with MeOH. The filtrate was evaporated and the residue was purified by column chromatography (KP-NH silica gel, SNAP 55) eluting with a gradient of MeOH in DCM from 0% to 5% to give 7-[4-[2-[tert-butyl(dimethyl)silyl]oxyethyl]-3-chloro-5-fluorophenyl]-N-[(2,4-dimethoxyphenyl)methyl]cinnolin-4-amine (332 mg, 0.570 mmol, 52.43% yield) as a white powder. $^1$H NMR (400 MHz, DMSO-$d_6$) δ −0.02 (s, 6H), 0.83 (s, 9H), 3.02 (t, J=6.54 Hz, 2H), 3.74 (s, 3H), 3.83 (t, J=6.74 Hz, 2H), 3.88 (s, 3H), 4.52 (d, J=5.73 Hz, 2H), 6.48 (dd, J=8.39, 2.38 Hz, 1H), 6.63 (d, J=2.38 Hz, 1H), 7.16 (d, J=8.36 Hz, 1H), 7.82 (dd, J=10.70, 1.81 Hz, 1H), 7.90 (s, Intermediate 263: 7-(5-chloro-1-benzofuran-7-yl)-N-[(2,4-dimethoxyphenyl)methyl]cinnolin-4-amine

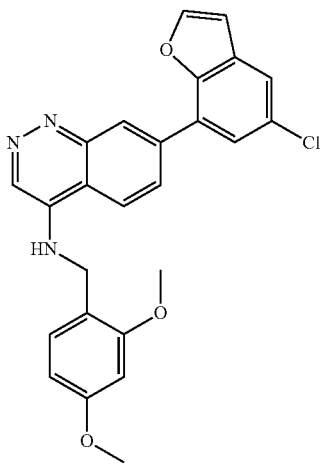 [SMILES: COc1ccc(CNc2cnnc3cc(-c4cc(Cl)cc5ccoc45)ccc23)c(OC)c1]

A mixture of N-[(2,4-dimethoxyphenyl)methyl]-7-(4,4,5,5-tetramethyl-1,3,2-dioxaborolan-2-yl)cinnolin-4-amine (327.62 mg, 0.780 mmol), 7-bromo-5-chloro-1-benzofuran (120.0 mg, 0.520 mmol) and aqueous 2N sodium carbonate solution (0.52 mL, 1.04 mmol) in 1,2-dimethoxyethane (7.4 mL) was degassed for 10 minutes under argon, then [1,1'-bis(di-tert-butylphosphino)ferrocene]dichloropalladium(II) (33.89 mg, 0.050 mmol) was added. The mixture was heated to 85° C. and stirred for 1 hour. The mixture was allowed to cool to room temperature then it was diluted with EtOAc and filtered over Celite, washing with EtOAc and MeOH. The filtrate was concentrated and the residue was purified by colum chromatography (Sfar Amino D, 28 g) eluting with a gradient of EtOAc in cyclohexane from 0% to 100% and then MeOH in EtOAc from 0% to 10% to afford 7-(5-chloro-1-benzofuran-7-yl)-N-[(2,4-dimethoxyphenyl)methyl]cinnolin-4-amine (138 mg, 0.309 mmol, 59.7% yield) as a brown solid. $^1$H NMR (400 MHz, DMSO-$d_6$) δ 3.75 (s, 3H), 3.89 (s, 3H), 4.55 (d, J=5.72 Hz, 2H), 6.49 (dd, J=8.47, 2.31 Hz, 1H), 6.66 (d, J=2.42 Hz, 1H), 7.11 (d, J=2.20 Hz, 1H), 7.18 (d, J=8.36 Hz, 1H), 7.82 (d, J=1.98 Hz, 1H), 7.85 (d, J=1.98 Hz, 1H), 8.09-8.13 (m, 1H), 8.16 (dd, J=8.91, 1.87 Hz, 1H), 8.24 (d, J=2.20 Hz, 1H), 8.50 (d, J=9.02 Hz, 1H), 8.53 (s, 1H), 8.67 (d, J=1.98 Hz, 1H). LC-MS (Method A): r.t. 0.91 min, MS (ESI) m/z=446.2 [M+H]$^+$.

Intermediate 264: (1S,3R,4S,5S)-3,4,6,6-tetramethylbicyclo[3.1.1]heptane-3,4-diol

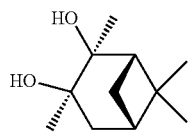

A solution of (1S,4S,5S)-4-hydroxy-4,6,6-trimethylbicyclo[3.1.1]heptan-3-one (1.0 g, 5.94 mmol) in THF (2 mL) was cooled to −78° C. and then a 3M solution of methylmagnesium chloride in THF (4.95 mL, 14.86 mmol) was added dropwise. After addition was complete the mixture was stirred at room temperature for 1 hour, then was quenched with saturated solution of ammonium chloride and extracted with EtOAc. The organic phase was washed with brine, dried over Na$_2$SO$_4$, filtered and evaporated in vacuo. The residue was purified by column chromatography (KP-sil silica gel, SNAP 50) eluting with a gradient of EtOAc in cyclohexane from 0% to 40% to give (1S,3R,4S,5S)-3,4,6,6-tetramethylbicyclo[3.1.1]heptane-3,4-diol (724 mg, 3.929 mmol, 66.09% yield) as a white solid. $^1$H NMR (400 MHz, DMSO-$d_6$) δ 0.83 (s, 3H), 1.16 (s, 3H), 1.21 (d, J=5.50 Hz, 6H), 1.72-1.85 (m, 4H), 1.90-2.02 (m, 2H), 4.88 (s, 1H), 4.93 (s, 1H).

Intermediate 265: 6-(5-chloro-1-benzofuran-7-yl)-N-[(2,4-dimethoxyphenyl)methyl]-4-methylphthalazin-1-amine

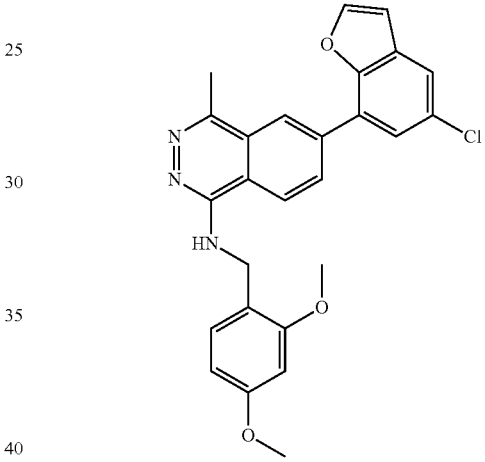

A mixture of 7-bromo-5-chloro-1-benzofuran (130.0 mg, 0.560 mmol) and [1-[(2,4-dimethoxyphenyl)methylamino]-4-methylphthalazin-6-yl]boronic acid (343.82 mg, 0.730 mmol) in 1,2-dimethoxyethane (3.5 mL) and aqueous 2N sodium carbonate solution (0.28 mL, 0.560 mmol) was degassed for 10 min with Ar. [1,1'-Bis(di-tert-butylphosphino)ferrocene]dichloropalladium(II) (36.72 mg, 0.060 mmol) was added and the mixture was degassed for 10 min then stirred at 80° C. for 3 hours. The mixture was cooled to room temperature and filtered over Celite, washing with EtOAc and the filtrate was evaporated. The residue was purified by column chromatography (KP-NH silica gel, SNAP 28 g) eluting with a gradient of EtOAc in DCM from 0% to 90% to give 6-(5-chloro-1-benzofuran-7-yl)-N-[(2,4-dimethoxyphenyl)methyl]-4-methylphthalazin-1-amine (74 mg, 0.161 mmol, 28.65% yield) as a yellowish foam. $^1$H NMR (400 MHz, DMSO-$d_6$) δ 2.77 (s, 3H), 3.74 (s, 3H), 3.86 (s, 3H), 4.69 (d, J=5.28 Hz, 2H), 6.44 (dd, J=8.36, 2.42 Hz, 1H), 6.59 (d, J=2.42 Hz, 1H), 7.09-7.12 (m, 1H), 7.15 (d, J=8.36 Hz, 1H), 7.67 (t, J=5.72 Hz, 1H), 7.83-7.88 (m, 2H), 8.22 (d, J=2.20 Hz, 1H), 8.35-8.41 (m, 1H), 8.44 (d, J=1.76 Hz, 1H), 8.51-8.56 (m, 1H). LC-MS (Method A): r.t. 0.89 min, MS (ESI) m/z=460.2 [M+H]$^+$.

Intermediate 266: 2-bromo-1-(2-bromo-1,1,2,2-tetrafluoroethoxy)-4-chlorobenzene

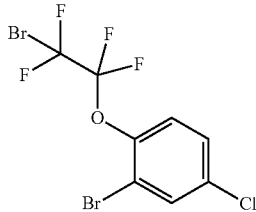 [SMILES: FC(F)(Br)C(F)(F)Oc1ccc(Cl)cc1Br]

1,2-Dibromo-1,1,2,2-tetrafluoroethane (0.35 mL, 2.89 mmol) was added to a solution of 2-bromo-4-chlorophenol (500.0 mg, 2.41 mmol) and dicesium carbonate (1020.89 mg, 3.13 mmol) in DMSO (4 mL). The resulting reaction mixture was stirred at 80° C. overnight then cooled to room temperature, diluted with water and extracted three times with EtOAc. The combined organic phases were washed with water and brine, dried over sodium sulfate, filtered and concentrated under reduced pressure. The residue was purified by column chromatography (KP-Sil silica gel, SNAP 50) eluting with a gradient of EtOAc in cyclohexane from 5% to 40% to give 2-bromo-1-(2-bromo-1,1,2,2-tetrafluoroethoxy)-4-chlorobenzene (500 mg, 1.294 mmol, 53.69% yield) as a yellow oil. $^1$H NMR (400 MHz, DMSO-$d_6$) δ 7.54-7.58 (m, 1H), 7.62 (dd, J=8.83, 2.49 Hz, 1H), 8.02 (d, J=2.45 Hz, 1H). LC-MS (Method A): r.t. 1.49 min. MS (ESI) m/z of product not observed due to poor ionization.

Intermediate 267: 2-bromo-4-chloro-1-(1,1,2,2-tetrafluoroethoxy)benzene

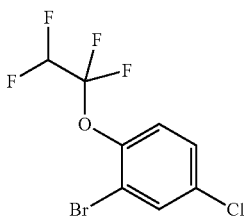 [SMILES: FC(F)C(F)(F)Oc1ccc(Cl)cc1Br]

Zinc powder (338.44 mg, 5.18 mmol) was added to a cold solution of 2-bromo-1-(2-bromo-1,1,2,2-tetrafluoroethoxy)-4-chlorobenzene (500.0 mg, 1.29 mmol) in acetic acid (10.35 mL). The resulting reaction mixture was stirred at 50° C. for one hour then cooled to room temperature, diluted with EtOAc and filtered over a Celite pad. The filtrate was evaporated under reduced pressure and the residue was purified by column chromatography (KP-Sil silica gel, SNAP 50) eluting with a gradient of EtOAc in cyclohexane from 5% to 50% to give 2-bromo-4-chloro-1-(1,1,2,2-tetrafluoroethoxy)benzene (350 mg, 1.138 mmol, 87.96% yield) as an orange oil. $^1$H NMR (400 MHz, DMSO-$d_6$) δ 6.88 (tt, J=51.50, 3.08 Hz, 1H), 7.50 (d, J=9.02 Hz, 1H), 7.58 (dd, J=8.80, 2.42 Hz, 1H), 7.98 (d, J=2.42 Hz, 1H). LC-MS (Method A): r.t. 1.31 min. MS (ESI) m/z of product not observed due to poor ionization

Intermediate 268: 7-[5-chloro-2-(1,1,2,2-tetrafluoroethoxy)phenyl]-N-[(2,4-dimethoxyphenyl)methyl]cinnolin-4-amine

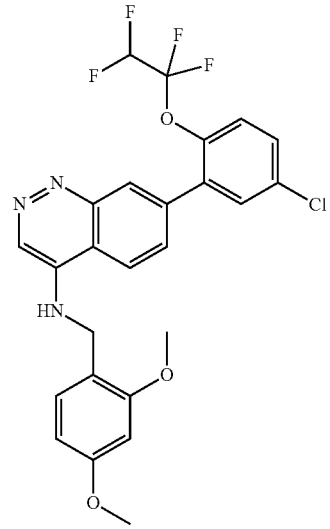 [SMILES: COc1ccc(CNc2cnnc3cc(-c4cc(Cl)ccc4OC(F)(F)C(F)F)ccc23)c(OC)c1]

A mixture of N-[(2,4-dimethoxyphenyl)methyl]-7-(4,4,5,5-tetramethyl-1,3,2-dioxaborolan-2-yl)cinnolin-4-amine (0.41 g, 0.980 mmol), 2-bromo-4-chloro-1-(1,1,2,2-tetrafluoroethoxy)benzene (250.0 mg, 0.810 mmol) in 1,2-dimethoxyethane (11.3 mL) and aqueous 2N sodium carbonate solution (0.81 mL, 1.62 mmol) was degassed for 10 minutes with $N_2$. Then [1,1'-bis(di-tert-butylphosphino)ferrocene]dichloropalladium(II) (0.05 g, 0.080 mmol) was added and the resulting reaction mixture was stirred at 75° C. for two hours. The mixture was cooled to room temperature and filtered over Celite, washing with EtOAc. The filtrate was evaporated and the residue was purified by column chromatography (KP-NH silica gel, SNAP 55) eluting with a gradient of EtOAc in cyclohexane from 10% to 100% to give 7-[5-chloro-2-(1,1,2,2-tetrafluoroethoxy)phenyl]-N-[(2,4-dimethoxyphenyl)methyl]cinnolin-4-amine (250 mg, 0.479 mmol, 58.91% yield) as yellow oil. $^1$H NMR (400 MHz, DMSO-$d_6$) δ 3.74 (s, 3H), 3.88 (s, 3H), 4.51 (d, J=5.66 Hz, 2H), 6.48 (dd, J=8.40, 2.41 Hz, 1H), 6.56-6.65 (m, 2H), 7.16 (d, J=8.43 Hz, 1H), 7.54 (d, J=8.75 Hz, 1H), 7.64 (dd, J=8.77, 2.67 Hz, 1H), 7.71 (dd, J=8.80, 1.84 Hz, 1H), 7.78 (d, J=2.62 Hz, 1H), 8.07 (t, J=5.95 Hz, 1H), 8.17 (d, J=1.77 Hz, 1H), 8.40 (d, J=8.84 Hz, 1H), 8.51 (s, 1H). LC-MS (Method A): r.t. 0.88 min, MS (ESI) m/z=522.2 [M+H]$^+$.

Intermediate 269: 2-bromo-4-chloro-1-(1,2,2,2-tetrafluoroethoxy)benzene

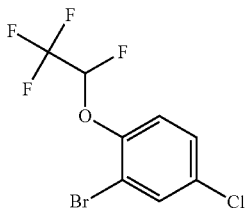 [SMILES: FC(Oc1ccc(Cl)cc1Br)C(F)(F)F]

A mixture of 2-bromo-4-chlorophenol (300.0 mg, 1.45 mmol), dicesium carbonate (612.53 mg, 1.88 mmol) and 1,1,1,2-tetrafluoro-2-iodoethane (0.19 mL, 1.74 mmol) in DMF (3 mL) was stirred at 120° C. for 20 hours. The reaction mixture was quenched with 1N aqueous HCl solution and extracted twice with EtOAc. The combined organic layers were washed with brine, dried over Na$_2$SO$_4$, filtered and evaporated under reduced pressure. The residue was purified by column chromatography (Sfar D, 25 g) eluting with a gradient of EtOAc in cyclohexane from 0% to 10% to give 2-bromo-4-chloro-1-(1,2,2,2-tetrafluoroethoxy)benzene (378 mg, 1.229 mmol, 85.01% yield) as a colourless oil. $^1$H NMR (400 MHz, DMSO-d$_6$) δ 6.96 (dq, J=56.37, 3.01 Hz, 1H), 7.41 (dd, J=8.92, 1.13 Hz, 1H), 7.58 (dd, J=8.87, 2.53 Hz, 1H), 7.90 (d, J=2.51 Hz, 1H). LC-MS (Method A): r.t. 1.33 min, MS (ESI) m/z of product not observed due to poor ionization.

Intermediate 270: 7-[5-chloro-2-(1,2,2,2-tetrafluoroethoxy)phenyl]-N-[(2,4-dimethoxyphenyl)methyl]cinnolin-4-amine

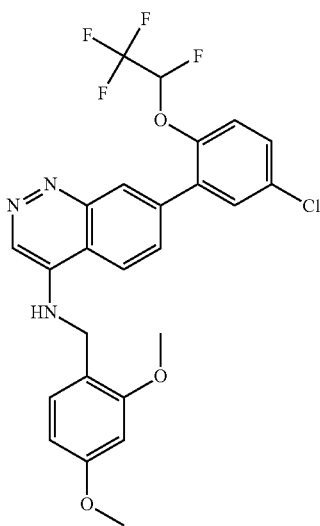 [SMILES: COc1ccc(CNc2cnnc3cc(-c4cc(Cl)ccc4OC(F)C(F)(F)F)ccc23)c(OC)c1]

A mixture of N-[(2,4-dimethoxyphenyl)methyl]-7-(4,4,5,5-tetramethyl-1,3,2-dioxaborolan-2-yl)cinnolin-4-amine (219.23 mg, 0.520 mmol), 2-bromo-4-chloro-1-(1,2,2,2-tetrafluoroethoxy)benzene (160.0 mg, 0.520 mmol) and aqueous 2N sodium carbonate solution (0.35 mL, 0.690 mmol) in 1,4-dioxane (4 mL) was degassed for 10 minutes under argon, then [1,1'-bis(di-tert-butylphosphino)ferrocene]dichloropalladium (II) (22.79 mg, 0.030 mmol) was added. The mixture was heated to 85° C. and stirred for 22 hours. The mixture was allowed to cool, to room temperature then it was diluted with EtOAc and filtered over Celite, washing with EtOAc and MeOH. The filtrate was purified by colum chromatography (Sfar Amino D, 28 g) eluting with a gradient of EtOAc in cyclohexane from 0% to 100% to afford 7-[5-chloro-2-(1,2,2,2-tetrafluoroethoxy)phenyl]-N-[(2,4-dimethoxyphenyl)methyl]cinnolin-4-amine (106 mg, 0.203 mmol, 39.03% yield) as a brown solid. $^1$H NMR (400 MHz, DMSO-d$_6$) δ 3.74 (s, 3H), 3.88 (s, 3H), 4.51 (d, J=5.65 Hz, 2H), 6.48 (dd, J=8.39, 2.39 Hz, 1H), 6.63 (d, J=2.38 Hz, 1H), 6.98 (dq, J=56.40, 3.03 Hz, 1H), 7.16 (d, J=8.39 Hz, 1H), 7.47 (d, J=8.32 Hz, 1H), 7.64 (dd, J=8.82, 2.67 Hz, 1H), 7.71-7.78 (m, 2H), 8.05 (t, J=5.88 Hz, 1H), 8.20 (d, J=1.77 Hz, 1H), 8.40 (d, J=8.83 Hz, 1H), 8.51 (s, 1H). LC-MS (Method A): r.t. 0.89 min, MS (ESI) m/z=522.1 [M+H]$^+$.

Intermediate 271: 2-bromo-4-chloro-1-[2-(2-methoxyethoxy)ethoxy]benzene

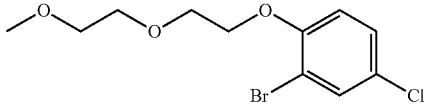 [SMILES: COCCOCCOc1ccc(Cl)cc1Br]

A suspension of 1-(2-bromoethoxy)-2-methoxyethane (485.28 mg, 2.65 mmol), 2-bromo-4-chlorophenol (500.0 mg, 2.41 mmol) and potassium carbonate (666.23 mg, 4.82 mmol) in DMF (7 mL) was stirred at 65° C. overnight. The reaction mixture was diluted with water and extracted with EtOAc. The organic phase was washed with brine, dried over Na$_2$SO$_4$ and concentrated under reduced pressure to give 2-bromo-4-chloro-1-[2-(2-methoxyethoxy)ethoxy]benzene (770 mg, 2.487 mmol, 103.19% yield) as a colourless oil. $^1$H NMR (400 MHz, DMSO-d$_6$) δ 3.24 (s, 3H), 3.41-3.50 (m, 2H), 3.57-3.65 (m, 2H), 3.73-3.79 (m, 2H), 4.15-4.20 (m, 2H), 7.15 (d, J=8.88 Hz, 1H), 7.40 (dd, J=8.86, 2.59 Hz, 1H), 7.68 (d, J=2.56 Hz, 1H). LC-MS (Method A): r.t. 1.17 min, MS (ESI) m/z=309.1 and 311.0 [M+H]$^+$.

Intermediate 272: 7-[5-chloro-2-[2-(2-methoxyethoxy)ethoxy]phenyl]-N-[(2,4-dimethoxyphenyl)methyl]cinnolin-4-amine

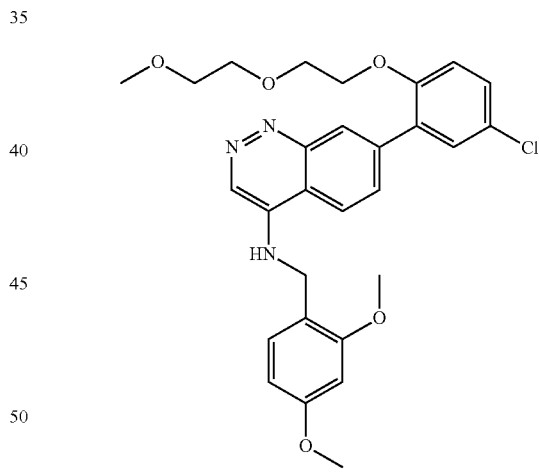

A mixture of 2-bromo-4-chloro-1-[2-(2-methoxyethoxy)ethoxy]benzene (200.0 mg, 0.650 mmol) and [4-[(2,4-dimethoxyphenyl)methylamino]cinnolin-7-yl]boronic acid (326.61 mg, 0.780 mmol) in 1,2-dimethoxyethane (6 mL) and aqueous 2M sodium carbonate solution (0.65 mL, 1.29 mmol) was degassed for 10 min with N$_2$. Then [1,1'-bis(di-tert-butylphosphino)ferrocene]dichloropalladium(II) (42.24 mg, 0.060 mmol) was added and the resulting reaction mixture was stirred at 80° C. for two hours. The mixture was cooled to room temperature and filtered over Celite, washing with MeOH. The filtrate was evaporated and the residue was purified by column chromatography (Sfar Amino D, 28 g) eluting with a gradient of EtOAc in cyclohexane from 5% to 95% to give 7-[5-chloro-2-[2-(2-methoxyethoxy)ethoxy]

phenyl]-N-[(2,4-dimethoxyphenyl)methyl]cinnolin-4-amine (140 mg, 0.267 mmol, 41.36% yield). ¹H NMR (400 MHz, DMSO-d₆) δ 3.14 (s, 3H), 3.35-3.42 (m, 2H), 3.45-3.51 (m, 2H), 3.68-3.72 (m, 2H), 3.75 (s, 3H), 3.89 (s, 3H), 4.17-4.25 (m, 2H), 4.52 (d, J=5.71 Hz, 2H), 6.48 (dd, J=8.35, 2.37 Hz, 1H), 6.64 (d, J=2.43 Hz, 1H), 7.15 (d, J=8.40 Hz, 1H), 7.24 (d, J=8.91 Hz, 1H), 7.46 (dd, J=8.81, 2.67 Hz, 1H), 7.55 (d, J=2.67 Hz, 1H), 7.85 (dd, J=8.80, 1.80 Hz, 1H), 8.02 (t, J=6.00 Hz, 1H), 8.24 (d, J=1.77 Hz, 1H), 8.35 (d, J=8.87 Hz, 1H), 8.48 (s, 1H). LC-MS (Method A): r.t. 0.84 min, MS (ESI) m/z=524.2 [M+H]⁺.

Intermediate 273: 2-bromo-4-chloro-5-methylphenol

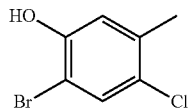

1-Chloropyrrolidine-2,5-dione (1.43 g, 10.69 mmol) was added slowly to a solution of 2-bromo-5-methylphenol (2.0 g, 10.69 mmol) and trifluoroacetic acid (0.500 mL) in DMF (15 mL) at 0° C. The resulting mixture was stirred at 25° C. for 18 hours, then it was quenched with a saturated aqueous solution of Na₂S₂O₃, and extracted three times with EtOAc. The combined organic phases were washed twice with brine, dried over Na₂SO₄, filtered and evaporated in vacuo to obtain a light brown oil that was purified by column chromatography (Sfar D, 50 g) eluting with a gradient of EtOAc in cyclohexane from 0% to 10% to give 2-bromo-4-chloro-5-methylphenol (853 mg, 3.851 mmol, 36.02% yield) as a light yellow solid. ¹H NMR (400 MHz, DMSO-d₆) δ 2.21 (s, 3H), 6.89 (d, J=0.84 Hz, 1H), 7.50 (s, 1H), 10.37 (s, 1H). LC-MS (Method A): r.t. 1.11 min, MS (ESI) m/z=219.1 and 221.2 [M−H]⁺.

Intermediate 274: 1-bromo-5-chloro-2-(difluoromethoxy)-4-methylbenzene

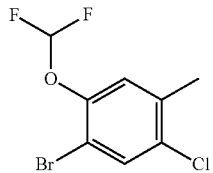

A mixture of 2-bromo-4-chloro-5-methylphenol (400.0 mg, 1.81 mmol), sodium 2-chloro-2,2-difluoroacetate (633.3 mg, 4.15 mmol) and dicesium carbonate (823.82 mg, 2.53 mmol) in DMF (2.5 mL) was stirred at 120° C. for 2 hours, then it was allowed to cool to room temperature. The reaction was quenched with 1N aqueous HCl solution and extracted twice with EtOAc. The combined organic phases were washed with brine, dried over Na₂SO₄, filtered and evaporated under reduced pressure. The residue was purified by column chromatography (Sfar D, 25 g) eluting with a gradient of EtOAc in cyclohexane from 0% to 10% to give 1-bromo-5-chloro-2-(difluoromethoxy)-4-methylbenzene (357 mg, 1.315 mmol, 72.81% yield) as an off-white solid. ¹H NMR (400 MHz, DMSO-d₆) δ 2.32 (s, 3H), 7.25 (t, J=73.07 Hz, 1H), 7.39 (d, J=0.83 Hz, 1H), 7.84 (s, 1H). LC-MS (Method A): r.t. 1.32 min, MS (ESI) m/z of product not observed due to poor ionization Intermediate 275: 7-[5-chloro-2-(difluoromethoxy)-4-methylphenyl]-N-[(2,4-dimethoxyphenyl)methyl]cinnolin-4-amine

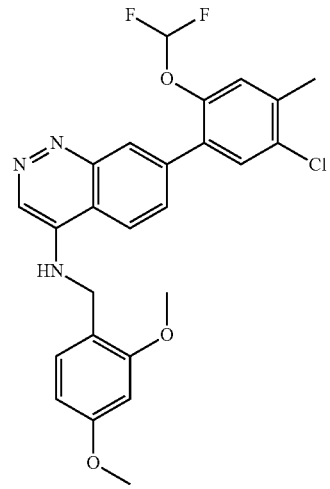 [SMILES: COc1ccc(CNc2cnnc3cc(-c4cc(Cl)c(C)cc4OC(F)F)ccc23)c(OC)c1]

A mixture of N-[(2,4-dimethoxyphenyl)methyl]-7-(4,4,5,5-tetramethyl-1,3,2-dioxaborolan-2-yl)cinnolin-4-amine (200.0 mg, 0.470 mmol), 1-bromo-5-chloro-2-(difluoromethoxy)-4-methylbenzene (128.88 mg, 0.470 mmol) and aqueous 2N sodium carbonate solution (0.47 mL, 0.950 mmol) in 1,4-dioxane (5 mL) was degassed for 10 min, then [1,1'-bis(di-tert-butylphosphino)ferrocene]dichloropalladium(II) (31.04 mg, 0.050 mmol) was added. The resulting mixture was heated to 85° C. and stirred for 22 hours. The mixture was allowed to cool to room temperature, diluted with EtOAc and filtered over Celite, washing with EtOAc and MeOH. The filtrate concentrated in vacuo and the residue was purified by column chromatography (Sfar Amino D, 28 g) eluting with a gradient of EtOAc in cyclohexane from 0% to 100% to give 7-[5-chloro-2-(difluoromethoxy)-4-methylphenyl]-N-[(2,4-dimethoxyphenyl)methyl]cinnolin-4-amine (106 mg, 0.218 mmol, 45.95% yield) as a light brown solid. ¹H NMR (400 MHz, DMSO-d₆) δ 2.43 (s, 3H), 3.74 (s, 3H), 3.88 (s, 3H), 4.52 (d, J=6.03 Hz, 2H), 6.47 (dd, J=8.40, 2.40 Hz, 1H), 6.63 (d, J=2.38 Hz, 1H), 7.16 (d, J=8.37 Hz, 1H), 7.19 (t, J=73.60 Hz, 1H), 7.41 (s, 1H), 7.70 (s, 1H), 7.74 (dd, J=8.75, 1.83 Hz, 1H), 8.06 (t, J=6.00 Hz, 1H), 8.18 (d, J=1.76 Hz, 1H), 8.40 (d, J=8.84 Hz, 1H), 8.50 (s, 1H). LC-MS (Method A): r.t. 0.88 min, MS (ESI) m/z=486.1 [M+H]⁺.

Intermediate 276: 7-bromo-N-[(2,4-dimethoxyphenyl)methyl]quinolin-4-amine

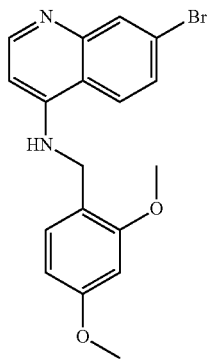 [SMILES: COc1ccc(CNc2ccnc3cc(Br)ccc23)c(OC)c1]

(2,4-Dimethoxyphenyl)methanamine (0.35 mL, 2.35 mmol) was added to a solution of 7-bromo-4-chloroquinoline (380.0 mg, 1.57 mmol) in ethanol (6 mL). The resulting mixture was stirred at 90° C. overnight, then further (2,4-dimethoxyphenyl)methanamine (0.35 mL, 2.35 mmol) was added and the reaction mixture was stirred at 100° C. for 24 hours. The reaction mixture was cooled to room temperature giving a white precipitate. The precipitate was collected by filteration, washed with water and dried to give 7-bromo-N-[(2,4-dimethoxyphenyl)methyl]quinolin-4-amine (440 mg, 1.179 mmol, 75.23% yield) as a white solid. $^1$H NMR (400 MHz, DMSO-$d_6$) δ 3.73 (s, 3H), 3.86 (s, 3H), 4.40 (d, J=5.58 Hz, 2H), 6.31 (d, J=5.41 Hz, 1H), 6.45 (dd, J=8.41, 2.41 Hz, 1H), 6.61 (d, J=2.40 Hz, 1H), 7.08 (d, J=8.36 Hz, 1H), 7.58 (dd, J=8.95, 2.13 Hz, 1H), 7.79 (t, J=5.85 Hz, 1H), 7.95 (d, J=2.08 Hz, 1H), 8.27 (d, J=8.99 Hz, 1H), 8.32 (d, J=5.42 Hz, 1H). LC-MS (Method A): r.t. 0.66 min, MS (ESI) m/z=375.1 [M+H]$^+$.

Intermediate 277: 7-(5-chloro-2-methoxyphenyl)-N-[(2,4-dimethoxyphenyl)methyl]quinolin-4-amine

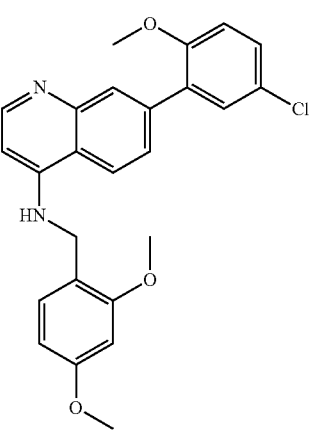 [SMILES: COc1ccc(CNc2ccnc3cc(-c4cc(Cl)ccc4OC)ccc23)c(OC)c1]

A mixture of 7-bromo-N-[(2,4-dimethoxyphenyl)methyl]quinolin-4-amine (440.0 mg, 1.18 mmol) and 5-chloro-2-methoxyphenylboronic acid (263.69 mg, 1.41 mmol) in 1,2-dimethoxyethane (12 mL) and aqueous 2M sodium carbonate solution (1.18 mL, 2.36 mmol) was degassed for 10 min with $N_2$. Then [1,1'-bis(di-tert-butylphosphino)ferrocene]dichloropalladium(II) (77.07 mg, 0.120 mmol) was added and the resulting reaction mixture was stirred at 80° C. for two hours. The mixture was cooled to room temperature and filtered over Celite, washing with MeOH. The filtrate was evaporated and the residue was purified by column chromatography (Sfar Amino D, 12 g) eluting with a gradient of EtOAc in cyclohexane from 5% to 95% to give 7-(5-chloro-2-methoxyphenyl)-N-[(2,4-dimethoxyphenyl)methyl]quinolin-4-amine (520 mg, 1.196 mmol, 101.42% yield) as a yellow powder. $^1$H NMR (400 MHz, DMSO-$d_6$) δ 3.73 (s, 3H), 3.80 (s, 3H), 3.87 (s, 3H), 4.39-4.46 (m, 2H), 6.22-6.30 (m, 1H), 6.40-6.48 (m, 1H), 6.58-6.63 (m, 1H), 7.04-7.13 (m, 1H), 7.16-7.23 (m, 1H), 7.40-7.47 (m, 2H), 7.52-7.58 (m, 1H), 7.59-7.71 (m, 1H), 7.80-7.88 (m, 1H), 8.31 (m, 2H). LC-MS (Method A): r.t. 0.84 min, MS (ESI) m/z=435.2 [M+H]$^+$.

Intermediate 278: 2-[2-(2-bromo-4-chlorophenoxy)ethyl]oxolane

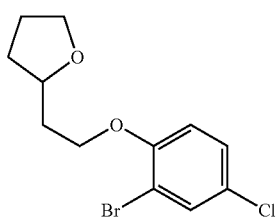 [SMILES: Clc1ccc(OCCC2CCCO2)c(Br)c1]

(NE)-N-Ethoxycarbonyliminocarbamic acid ethyl ester (0.37 mL, 2.32 mmol) was added to a solution of 2-bromo-4-chlorophenol (446.47 mg, 2.15 mmol), triphenylphosphine (620.95 mg, 2.37 mmol) and 2-(oxolan-2-yl)ethanol (250.0 mg, 2.15 mmol) in THF (6 mL) at room temperature. The resulting mixture was stirred at this temperature for 30 minutes then it was evaporated under reduced pressure. The residue was purified by column chromatography (KP-Sil silica gel, SNAP 50) eluting with a gradient of dichloromethane in cyclohexane from 5% to 50% to give 2-[2-(2-bromo-4-chlorophenoxy)ethyl]oxolane (280 mg, 0.916 mmol, 42.6% yield) as a colourless oil. $^1$H NMR (400 MHz, Chloroform-d) δ 1.58-1.68 (m, 2H), 1.87-2.02 (m, 2H), 2.01-2.18 (m, 2H), 3.73-3.80 (m, 1H), 3.84-3.94 (m, 1H), 4.05-4.20 (m, 3H), 6.85 (d, J=8.80 Hz, 1H), 7.23 (dd, J=8.78, 2.55 Hz, 1H), 7.54 (d, J=2.54 Hz, 1H). LC-MS (Method A): r.t. 1.36 min, MS (ESI) m/z of product not observed due to poor ionization.

Intermediate 279: 7-[5-chloro-2-[2-(oxolan-2-yl)ethoxy]phenyl]-N-[(2,4-dimethoxyphenyl)methyl]cinnolin-4-amine

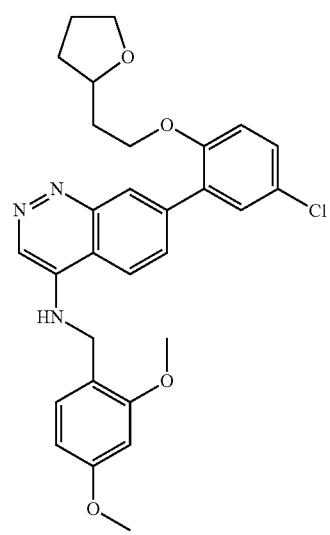 [SMILES: COc1ccc(CNc2cnnc3cc(-c4cc(Cl)ccc4OCCC4CCCO4)ccc23)c(OC)c1]

A mixture of 2-[2-(2-bromo-4-chlorophenoxy)ethyl]oxolane (180.0 mg, 0.590 mmol), N-[(2,4-dimethoxyphenyl)methyl]-7-(4,4,5,5-tetramethyl-1,3,2-dioxaborolan-2-yl)cinnolin-4-amine (322.59 mg, 0.770 mmol) in 1,2-dimethoxyethane (5.9 mL) and aqueous 2N sodium carbonate solution (0.589 mL, 1.18 mmol) was degassed for 10 minutes with $N_2$. Then [1,1'-bis(di-tert-butylphosphino)ferrocene]dichloropalladium(II) (38.51 mg, 0.060 mmol) was added and the resulting reaction mixture was stirred at 75° C. for four hours. The mixture was then cooled to room temperature and filtered over Celite, washing with EtOAc. The filtrate was evaporated and the residue was purified by column chromatography (KP-NH silica gel, SNAP 28) eluting with a gradient of EtOAc in cyclohexane from 10% to 100% to give 7-[5-chloro-2-[2-(oxolan-2-yl)ethoxy]phenyl]-N-[(2,4-dimethoxyphenyl)methyl]cinnolin-4-amine (180 mg, 0.346 mmol, 58.77% yield) as a white powder. $^1$H NMR (400 MHz, DMSO-$d_6$) δ 1.15-1.23 (m, 1H), 1.36-1.48 (m, 1H), 1.71-1.86 (m, 4H), 3.52-3.60 (m, 1H), 3.67-3.76 (m, 1H), 3.75 (s, 3H), 3.78-3.85 (m, 1H), 3.89 (s, 3H), 4.05-4.14 (m, 3H), 4.48-4.54 (m, 2H), 6.48 (dd, J=8.38, 2.42 Hz, 1H), 6.64 (d, J=2.42 Hz, 1H), 7.16 (d, J=8.34 Hz, 1H), 7.22 (d, J=8.90 Hz, 1H), 7.45 (dd, J=8.81, 2.73 Hz, 1H), 7.54 (d, J=2.73 Hz, 1H), 7.80 (dd, J=8.79, 1.86 Hz, 1H), 8.03 (t, J=5.94 Hz, 1H), 8.21 (d, J=1.78 Hz, 1H), 8.36 (d, J=8.91 Hz, 1H), 8.48 (s, 1H). LC-MS (Method A): r.t. 0.88 min, MS (ESI) m/z=520.3 [M+H]$^+$.

Intermediate 280: 6-bromo-4-iodoisoquinoline

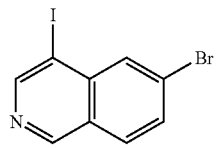 [SMILES: Brc1ccc2cncc(I)c2c1]

A solution of 6-bromoisoquinoline (2.0 g, 9.61 mmol) and 1-iodopyrrolidine-2,5-dione (2.38 g, 10.57 mmol) in acetic acid (19.99 mL) was stirred at 80° C. for 6 hours then evaporated under reduced pressure. The residue was quenched with a saturated aqueous solution of NaHCO$_3$ and extracted three times with EtOAc. The combined organic phases were washed with a saturated aqueous solution of Na$_2$S$_2$O$_4$, water and brine, dried over sodium sulfate, filtered and evaporated. The residue was purified by column chromatography (KP-Sil silica gel, SNAP 100) eluting with a gradient of EtOAc in cyclohexane from 5% to 60% to give 6-bromo-4-iodoisoquinoline (1.85 g, 5.54 mmol, 57.63% yield) as a yellow solid. $^1$H NMR (400 MHz, DMSO-$d_6$) δ 7.96 (dd, J=8.65, 1.89 Hz, 1H), 8.07-8.17 (m, 2H), 8.99 (s, 1H), 9.32 (d, J=0.83 Hz, 1H). LC-MS (Method A): r.t. 1.25 min, MS (ESI) m/z=333.9 and 335.6 [M+H]$^+$.

Intermediate 281: 6-bromo-4-methylisoquinoline

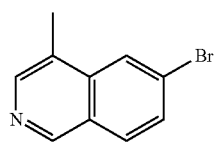

A mixture of 6-bromo-4-iodoisoquinoline (1.7 g, 5.09 mmol), potassium carbonate (2110.71 mg, 15.27 mmol) and 2,4,6-trimethyl-1,3,5,2,4,6-trioxatriborinane (0.36 mL, 2.55 mmol) in 1,2-dimethoxyethane (5.9 mL) was degassed for 10 minutes with $N_2$. Then [1,1'-bis(diphenylphosphino)ferrocene]dichloropalladium(II) (373.51 mg, 0.510 mmol) was added and the resulting reaction mixture was stirred at 80° C. overnight. The mixture was cooled to room temperature and filtered over Celite, washing with EtOAc. The filtrate was evaporated and the residue was purified by column chromatography (KP-NH silica gel, SNAP 55) eluting with a gradient of EtOAc in cyclohexane from 10% to 90% to give 6-bromo-4-methylisoquinoline (710 mg, 3.197 mmol, 62.8% yield) as a colourless oil. $^1$H NMR (400 MHz, DMSO-$d_6$) δ 2.57 (d, J=0.81 Hz, 3H), 7.84 (dd, J=8.70, 1.88 Hz, 1H), 8.10 (d, J=8.21 Hz, 1H), 8.25 (d, J=1.88 Hz, 1H), 8.41 (d, J=1.16 Hz, 1H), 9.19 (s, 1H). LC-MS (Method A): r.t. 0.9 min, MS (ESI) m/z=223.3 and 225.1 [M+H]$^+$.

Intermediate 282: 6-bromo-4-methyl-2-oxidoisoquinolin-2-ium

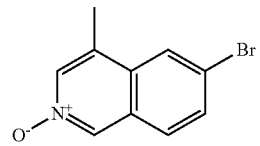

3-Chlorobenzenecarboperoxoic acid (1.66 g, 9.59 mmol) was added to a cold solution of 6-bromo-4-methylisoquinoline (710.0 mg, 3.2 mmol) in DCM (31.97 mL). The resulting mixture was stirred at room temperature for 2 hours. After addition of water/dichloromethane and phase separation, the aqueous phase was re-extracted with dichloromethane. The combined organic phases were washed with water, 2M aqueous NaOH solution and brine, dried over sodium sulfate, filtered and concentrated in vacuo to give 6-bromo-4-methyl-2-oxidoisoquinolin-2-ium (750 mg, 3.15 mmol, 98.53% yield) as an orange oil. LC-MS (Method A): r.t. 0.63 min, MS (ESI) m/z=237.9 and 239.9 [M+H]$^+$.

Intermediate 283: 6-bromo-1-chloro-4-methylisoquinoline

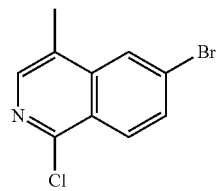

A solution of 6-bromo-4-methyl-2-oxidoisoquinolin-2-ium (750.0 mg, 3.15 mmol) in phosphorus(V) oxychloride (5.0 mL, 53.48 mmol) was stirred at 60° C. for 1 h. The excess of phosphorus(V) oxychloride was removed under reduced pressure. The residue was quenched with 2N aqueous NaOH solution and then it was extracted three times with EtOAc. The combined organic phases were washed with brine, dried over Na$_2$SO$_4$, filtered and evaporated to give 6-bromo-1-chloro-4-methylisoquinoline (780 mg, 3.041 mmol, 96.52% yield) as a red oil. LC-MS (Method A): r.t. 1.24 min, MS (ESI) m/z=256.1 and 258.1 [M+H]+.

Intermediate 284: 6-bromo-N-[(2,4-dimethoxyphenyl)methyl]-4-methylisoquinolin-1-amine

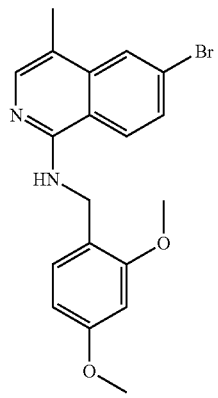 [SMILES: COc1ccc(CNc2ncc(C)c3cc(Br)ccc23)c(OC)c1]

A solution of 6-bromo-1-chloro-4-methylisoquinoline (780.0 mg, 3.04 mmol), (2,4-dimethoxyphenyl)methanamine (1.39 mL, 9.12 mmol) and triethylamine (0.64 mL, 4.56 mmol) in DMSO (6.081 mL) was stirred at 110° C. for 72 hours then cooled to room temperature. After addition of water/EtOAc and phase separation, the aqueous phase was re-extracted with EtOAc. The combined organic phases were washed with water and brine, dried over $Na_2SO_4$, filtered and concentrated under reduced pressure. The residue was purified by column chromatography (KP-NH silica gel, SNAP 55) eluting with a gradient of EtOAc in cyclohexane from 5% to 50% to give 6-bromo-N-[(2,4-dimethoxyphenyl)methyl]-4-methylisoquinolin-1-amine (145 mg, 0.374 mmol, 12.31% yield) as a yellow solid. $^1$H NMR (400 MHz, DMSO-$d_6$) δ 2.31 (d, J=1.10 Hz, 3H), 3.72 (s, 3H), 3.82 (s, 3H), 4.57 (d, J=5.58 Hz, 2H), 6.41 (dd, J=8.36, 2.42 Hz, 1H), 6.56 (d, J=2.40 Hz, 1H), 7.05 (d, J=8.33 Hz, 1H), 7.60-7.69 (m, 2H), 7.71 (s, 1H), 7.94 (d, J=2.00 Hz, 1H), 8.31 (d, J=8.94 Hz, 1H). LC-MS (Method A): r.t. 0.74 min, MS (ESI) m/z=387.1 and 389.1 [M+H]+.

Intermediate 285: 6-(5-chloro-2-methoxyphenyl)-N-[(2,4 dimethoxyphenyl)methyl]-4-methylisoquinolin-1-amine

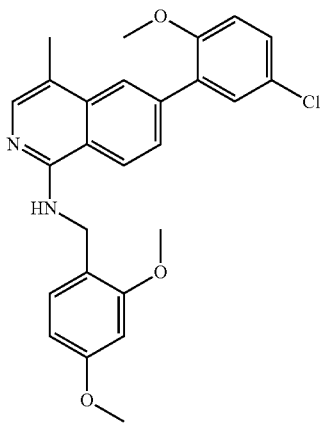 [SMILES: COc1ccc(CNc2ncc(C)c3cc(-c4cc(Cl)ccc4OC)ccc23)c(OC)c1]

A mixture of 6-bromo-N-[(2,4-dimethoxyphenyl)methyl]-4-methylisoquinolin-1-amine (145.0 mg, 0.370 mmol) and 5-chloro-2-methoxyphenylboronic acid (104.69 mg, 0.560 mmol) in 1,2-dimethoxyethane (3.8 mL) and aqueous 2N sodium carbonate solution (0.37 mL, 0.750 mmol) was degassed for 10 minutes with $N_2$. Then [1,1'-bis(di-tert-butylphosphino)ferrocene]dichloropalladium(II) (24.48 mg, 0.040 mmol) was added and the resulting reaction mixture was stirred at 75° C. for five hours. The mixture was cooled to room temperature and filtered over Celite, washing with EtOAc. The filtrate was evaporated and the residue was purified by column chromatography (KP-NH silica gel, SNAP 28) eluting with a gradient of MeOH in dichloromethane from 1% to 10% to give 6-(5-chloro-2-methoxyphenyl)-N-[(2,4-dimethoxyphenyl)methyl]-4-methylisoquinolin-1-amine (120 mg, 0.267 mmol, 71.39% yield) as an orange solid. $^1$H NMR (400 MHz, DMSO-$d_6$) δ 2.35 (s, 3H), 3.71 (s, 3H), 3.80 (s, 3H), 3.83 (s, 3H), 4.60 (d, J=5.62 Hz, 2H), 6.40 (dd, J=8.37, 2.41 Hz, 1H), 6.56 (d, J=2.41 Hz, 1H), 7.06 (d, J=8.35 Hz, 1H), 7.19 (d, J=8.86 Hz, 1H), 7.45 (dd, J=8.74, 2.70 Hz, 1H), 7.49 (d, J=2.67 Hz, 1H), 7.54 (t, J=5.37 Hz, 1H), 7.63 (dd, J=8.66, 1.76 Hz, 1H), 7.67 (s, 1H), 7.81 (d, J=1.77 Hz, 1H), 8.35 (d, J=8.68 Hz, 1H). LC-MS (Method A): r.t. 0.92 min, MS (ESI) m/z=449.2 [M+H]+.

Intermediate 286: 3-[2-(2-bromo-4-chlorophenoxy)ethyl]oxolane

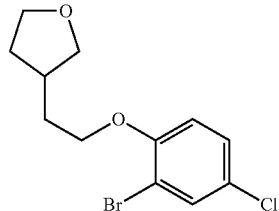 [SMILES: Clc1ccc(OCCC2CCOC2)c(Br)c1]

(NE)-N-Ethoxycarbonyliminocarbamic acid ethyl ester (0.63 mL, 3.98 mmol) was added to a solution of 2-(oxolan-3-yl)ethanol (419.96 mg, 3.62 mmol), triphenylphosphine (1043.09 mg, 3.98 mmol) and 2-bromo-4-chlorophenol (750.0 mg, 3.62 mmol) in THF (10 mL) at room temperature. The resulting mixture was stirred at this temperature for 30 minutes then it was evaporated under reduced pressure. The residue was purified by column chromatography (KP-NH silica gel, SNAP 28) eluting with a gradient of EtOAc in cyclohexane from 0% to 10% to give 3-[2-(2-bromo-4-chlorophenoxy)ethyl]oxolane (1 g, 3.272 mmol, 90.51% yield) as a colourless oil. $^1$H NMR (400 MHz, Chloroform-d) δ 1.62-1.72 (m, 1H), 1.92-2.02 (m, 2H), 2.08-2.25 (m, 1H), 2.44-2.55 (m, 1H), 3.45-3.54 (m, 1H), 3.73-3.85 (m, 1H), 3.87-3.96 (m, 1H), 3.98-4.09 (m, 3H), 6.82 (d, J=8.78 Hz, 1H), 7.24 (dd, J=8.77, 2.55 Hz, 1H), 7.55 (d, J=2.53 Hz, 1H). LC-MS (Method A): r.t. 1.29 min, MS (ESI) m/z=305.0 and 307.1 [M+H]+.

Intermediate 287: 7-[5-chloro-2-[2-(oxolan-3-yl)ethoxy]phenyl]-N-[(2,4-dimethoxyphenyl)methyl]cinnolin-4-amine

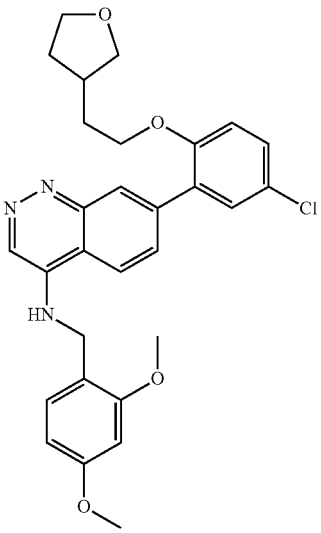 [SMILES: COc1ccc(CNc2cnnc3cc(-c4cc(Cl)ccc4OCCC4CCOC4)ccc23)c(OC)c1]

A mixture of 3-[2-(2-bromo-4-chlorophenoxy)ethyl]oxolane (200.0 mg, 0.650 mmol) and [4-[(2,4-dimethoxyphenyl)methylamino]cinnolin-7-yl]boronic acid (330.86 mg, 0.790 mmol) in 1,2-dimethoxyethane (6 mL) and aqueous 2M sodium carbonate solution (0.65 mL, 1.31 mmol) was degassed for 10 min with $N_2$. Then [1,1'-bis(di-tert-butylphosphino)ferrocene]dichloropalladium(II) (42.79 mg, 0.070 mmol) was added and the resulting reaction mixture was stirred at 80° C. for two hours. The mixture was cooled to room temperature and filtered over Celite, washing with MeOH. The filtrate was evaporated and the residue was purified by column chromatography (Sfar Amino D, 11 g) eluting with a gradient of EtOAc in cyclohexane from 0% to 80% to give 7-[5-chloro-2-[2-(oxolan-3-yl)ethoxy]phenyl]-N-[(2,4-dimethoxyphenyl)methyl]cinnolin-4-amine (150 mg, 0.288 mmol, 44.08% yield). $^1$H NMR (400 MHz, DMSO-$d_6$) δ 1.40-1.52 (m, 1H), 1.69-1.78 (m, 2H), 1.84-1.93 (m, 1H), 2.15-2.24 (m, 1H), 3.13-3.19 (m, 1H), 3.46-3.60 (m, 1H), 3.60-3.71 (m, 2H), 3.74 (s, 3H), 3.89 (s, 3H), 3.99-4.13 (m, 2H), 4.52 (d, J=5.74 Hz, 2H), 6.48 (dd, J=8.39, 2.41 Hz, 1H), 6.64 (d, J=2.41 Hz, 1H), 7.16 (d, J=8.35 Hz, 1H), 7.23 (d, J=8.86 Hz, 1H), 7.46 (dd, J=8.80, 2.72 Hz, 1H), 7.54 (d, J=2.67 Hz, 1H), 7.79 (dd, J=8.80, 1.84 Hz, 1H), 8.02 (t, J=5.96 Hz, 1H), 8.20 (d, J=1.77 Hz, 1H), 8.37 (d, J=8.84 Hz, 1H), 8.49 (s, 1H). LC-MS (Method A): r.t. 0.85 min, MS (ESI) m/z=520.3 [M+H]$^+$.

Intermediate 288: 2-[(2-bromo-4-chlorophenoxy)methyl]-4,4-dimethyloxolane

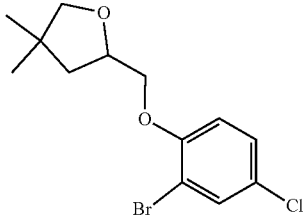 [SMILES: CC1(C)COC(COc2ccc(Cl)cc2Br)C1]

(NE)-N-Ethoxycarbonyliminocarbamic acid ethyl ester (0.54 mL, 2.96 mmol) was added to a solution of 2-bromo-4-chlorophenol (557.75 mg, 2.69 mmol), triphenylphosphine (775.71 mg, 2.96 mmol) and (4,4-dimethyloxolan-2-yl)methanol (350.0 mg, 2.69 mmol) in THF (5 mL) at room temperature. The resulting mixture was stirred at this temperature for 3 hours then evaporated in vacuo. The residue was purified by column chromatography (KP-NH silica gel, SNAP 28) eluting with a gradient of EtOAc in cyclohexane from 0% to 10% to give 2-[(2-bromo-4-chlorophenoxy)methyl]-4,4-dimethyloxolane (381 mg, 1.192 mmol, 44.34% yield) as a colorless oil. $^1$H NMR (400 MHz, DMSO-$d_6$) δ 1.07 (s, 3H), 1.10 (s, 3H), 1.65 (dd, J=12.24, 8.75 Hz, 1H), 1.80 (dd, J=12.22, 7.27 Hz, 1H), 3.40 (d, J=7.81 Hz, 1H), 3.49 (d, J=7.84 Hz, 1H), 4.03 (dd, J=10.40, 5.36 Hz, 1H), 4.11 (dd, J=10.44, 3.38 Hz, 1H), 4.27-4.40 (m, 1H), 7.15 (d, J=8.90 Hz, 1H), 7.40 (dd, J=8.86, 2.58 Hz, 1H), 7.68 (d, J=2.54 Hz, 1H). LC-MS (Method A): r.t. 1.41 min, MS (ESI) m/z=319.00 and 321.06 [M+H]$^+$.

Intermediate 289: 7-[5-chloro-2-[(4,4-dimethyloxolan-2-yl)methoxy]phenyl]-N-[(2,4-dimethoxyphenyl)methyl]cinnolin-4-amine

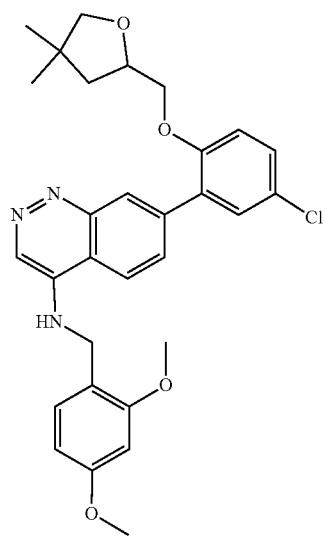 [SMILES: COc1ccc(CNc2cnnc3cc(-c4cc(Cl)ccc4OCC4CC(C)(C)CO4)ccc23)c(OC)c1]

A solution of 2-[(2-bromo-4-chlorophenoxy)methyl]-4,4-dimethyloxolane (180.0 mg, 0.560 mmol), aqueous 2N sodium carbonate solution (563.17 uL, 1.13 mmol) and N-[(2,4-dimethoxyphenyl)methyl]-7-(4,4,5,5-tetramethyl-1,3,2-dioxaborolan-2-yl)cinnolin-4-amine (308.44 mg, 0.730 mmol) in 1,2-dimethoxyethane (6 mL) in a microwave reaction tube was placed under nitrogen then deoxygenated with a stream of nitrogen for 10 min. [1,1'-Bis(di-tert-butylphosphino)ferrocene]dichloropalladium(II) (36.82 mg, 0.060 mmol) was added and the reaction mixture was heated to 80° C. for 4 hours then filtered over a pad of Celite, washing with MeOH. The filtrate was concentrated in vacuo and the residue was purified by column chromatography (KP-NH silica gel, SNAP 28) eluting with a gradient of EtOAc in cyclohexane from 2% to 95% to give 7-[5-chloro-2-[(4,4-dimethyloxolan-2-yl)methoxy]phenyl]-N-[(2,4-dimethoxyphenyl)methyl]cinnolin-4-amine (227 mg, 0.425 mmol, 75.48% yield) as a white powder. $^1$H NMR (400 MHz, DMSO-$d_6$) δ 0.86 (s, 3H), 0.99 (s, 3H), 1.51 (dd, J=12.20, 9.02 Hz, 1H), 1.68 (dd, J=12.16, 6.99 Hz, 1H), 3.29 (s, 2H), 3.74 (s, 3H), 3.88 (s, 3H), 4.02-4.06 (m, 1H), 4.12 (dd, J=10.40, 3.40 Hz, 1H), 4.22-4.31 (m, 1H), 4.52 (d, J=5.81 Hz, 2H), 6.47 (dd, J=8.39, 2.40 Hz, 1H), 6.64 (d, J=2.39 Hz, 1H), 7.14 (d, J=8.37 Hz, 1H), 7.23 (d, J=8.92 Hz, 1H), 7.45 (dd, J=8.82, 2.73 Hz, 1H), 7.54 (d, J=2.70 Hz, 1H), 7.82 (dd, J=8.79, 1.85 Hz, 1H), 8.02 (t, J=5.97 Hz, 1H), 8.21 (d, J=1.74 Hz, 1H), 8.37 (d, J=8.81 Hz, 1H), 8.48 (s, 1H). LC-MS (Method A): r.t. 0.92 min, MS (ESI) m/z=534.30 [M+H]$^+$.

Intermediate 290:
2-bromo-4-chloro-1-(2-cyclopropylethoxy)benzene

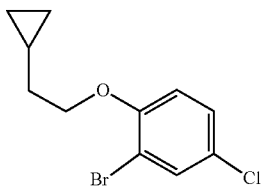 [SMILES: Clc1ccc(OCCC2CC2)c(Br)c1]

(NE)-N-Ethoxycarbonyliminocarbamic acid ethyl ester (0.42 mL, 2.65 mmol) was added dropwise to a solution of 2-cyclopropylethanol (0.21 mL, 2.41 mmol) and triphenylphosphine (695.39 mg, 2.65 mmol) in THF (4 mL). The mixture was stirred at room temperature for 3 hours, then the solvent was evaporated under reduced pressure. The residue was purified by column chromatography (Sfar D, 25 g) eluting with a gradient of EtOAc in cyclohexane from 0% to 10% to give 2-bromo-4-chloro-1-(2-cyclopropylethoxy)benzene (579 mg, 2.101 mmol, 87.17% yield) as a colourless oil. $^1$H NMR (400 MHz, DMSO-$d_6$) δ 0.03-0.24 (m, 2H), 0.35-0.54 (m, 2H), 0.77-0.95 (m, 1H), 1.64 (q, J=6.49 Hz, 2H), 4.10 (t, J=6.34 Hz, 2H), 7.14 (d, J=8.87 Hz, 1H), 7.40 (dd, J=8.84, 2.59 Hz, 1H), 7.67 (d, J=2.56 Hz, 1H). LC-MS (Method A): r.t. 1.49 min, MS (ESI) m/z of product not observed due to poor ionization.

Intermediate 291: 7-[5-chloro-2-(2-cyclopropylethoxy)phenyl]-N-[(2,4-dimethoxyphenyl)methyl]cinnolin-4-amine

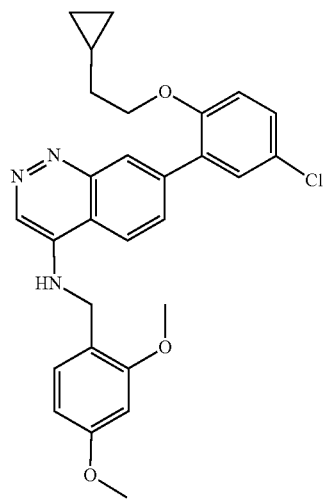 [SMILES: COc1ccc(CNc2cnnc3cc(-c4cc(Cl)ccc4OCCC4CC4)ccc23)c(OC)c1]

A mixture of N-[(2,4-dimethoxyphenyl)methyl]-7-(4,4,5,5-tetramethyl-1,3,2-dioxaborolan-2-yl)cinnolin-4-amine (450.0 mg, 1.07 mmol), 2-bromo-4-chloro-1-(2-cyclopropylethoxy)benzene (294.34 mg, 1.07 mmol) and aqueous 2M sodium carbonate solution (1.07 mL) in 1,4-dioxane (6 mL) was degassed for 10 min under argon, then [1,1'-bis(di-tert-butylphosphino)ferrocene]dichloropalladium (II) (69.83 mg, 0.110 mmol) was added and the mixture heated at 85° C. for 2 hours. The mixture was allowed to cool to room temperature then diluted with EtOAc and filtered over Celite, washing with EtOAc and MeOH. The filtrate was concentrated under reduced pressure and the residue was purified by column chromatography (Sfar Amino D, 28 g), eluting with a gradient of EtOAc in cyclohexane from 0% to 100% to give 7-[5-chloro-2-(2-cyclopropylethoxy)phenyl]-N-[(2,4-dimethoxyphenyl)methyl]cinnolin-4-amine (300 mg, 0.612 mmol, 57.32% yield) as a light brown solid. $^1$H NMR (400 MHz, DMSO-$d_6$) δ −0.03-0.16 (m, 2H), 0.29-0.54 (m, 2H), 0.75 (ddt, J=12.66, 7.61, 4.68 Hz, 1H), 1.56 (q, J=6.44 Hz, 2H), 3.74 (s, 3H), 3.88 (s, 3H), 4.09 (t, J=6.30 Hz, 2H), 4.51 (d, J=5.77 Hz, 2H), 6.47 (dd, J=8.36, 2.41 Hz, 1H), 6.63 (d, J=2.39 Hz, 1H), 7.15 (d, J=8.40 Hz, 1H), 7.22 (d, J=8.94 Hz, 1H), 7.45 (dd, J=8.80, 2.67 Hz, 1H), 7.54 (d, J=2.66 Hz, 1H), 7.81 (dd, J=8.78, 1.81 Hz, 1H), 8.00 (t, J=5.95 Hz, 1H), 8.22 (d, J=1.76 Hz, 1H), 8.35 (d, J=8.89 Hz, 1H), 8.47 (s, 1H). LC-MS (Method A): r.t. 0.96 min, MS (ESI) m/z=490.3 [M+H]$^+$.

Intermediate 292:
4-bromo-2-chloro-5-methoxybenzaldehyde

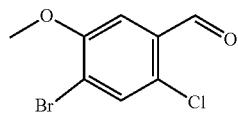

A 2.0 M solution of isopropylmagnesium chloride in THF (1.17 mL, 2.34 mmol) was added dropwise to a stirred solution of 2-bromo-4-chloro-5-iodoanisole (1.25 g, 2.34 mmol) in THF (20 mL) at −78° C., and the mixture was stirred at −78° C. for 1 hour. Then N,N-dimethylformamide (0.18 mL, 2.34 mmol) was added and the mixture was allowed to warm to room temperature over 2 hours. The reaction mixture was quenched with saturated aqueous NH$_4$Cl solution and extracted twice with EtOAc. The combined organic phases were dried over Na$_2$SO$_4$, filtered and evaporated under reduced pressure. The residue was purified by column chromatography (Sfar D, 25 g) eluting with a gradient of EtOAc in cyclohexane from 0% to 10% to give 4-bromo-2-chloro-5-methoxybenzaldehyde (538 mg, 2.156 mmol, 92.2% yield) as a white solid. $^1$H NMR (400 MHz, DMSO-d$_6$) δ 3.94 (s, 3H), 7.44 (s, 1H), 7.97 (s, 1H), 10.27 (s, 1H). LC-MS (Method A): r.t. 1.16 min, MS (ESI) m/z=249.0 [M+H]$^+$.

Intermediate 293: (E)-N-[(4-bromo-2-chloro-5-methoxyphenyl)methylidene]hydroxylamine

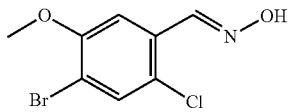

To a stirred solution of 4-bromo-2-chloro-5-methoxybenzaldehyde (535.0 mg, 2.14 mmol) in methanol (13 mL), sodium acetate trihydrate (583.61 mg, 4.29 mmol) was added followed by hydroxylamine hydrochloride (208.62 mg, 3 mmol). The mixture was stirred at room temperature for 3 hours, then the volatiles were evaporated under reduced pressure. The white solid thus obtained was taken up in DCM and washed with water, then brine. The organic phase was dried over Na$_2$SO$_4$, filtered and evaporated under reduced pressure to give (E)-N-[(4-bromo-2-chloro-5-methoxyphenyl)methylidene]hydroxylamine (410 mg, 1.55 mmol, 72.29% yield) as a white solid. $^1$H NMR (400 MHz, DMSO-d$_6$) δ 3.88 (s, 3H), 7.40 (s, 1H), 7.79 (s, 1H), 8.29 (s, 1H), 11.80 (s, 1H). LC-MS (Method A): r.t. 1.11 min, MS (ESI) m/z=263.9 and 266.0 [M+H]$^+$.

Intermediate 294: 4-bromo-2-chloro-5-methoxybenzonitrile

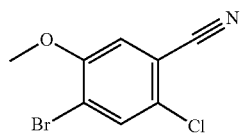

To a stirred solution of (E)-N-[(4-bromo-2-chloro-5-methoxyphenyl)methylidene]hydroxylamine (408.0 mg, 1.54 mmol) in DCM (10 mL), triethylamine (0.64 mL, 4.63 mmol) was added and the mixture cooled to 0° C. Trifluoromethanesulfonic acid trifluoromethylsulfonyl ester (0.31 mL, 1.85 mmol) was then added dropwise and the mixture stirred at room temperature for 4 hours. The mixture was diluted with DCM, washed with saturated aqueous NaHCO$_3$ solution and brine, dried over Na$_2$SO$_4$, filtered and the solvent evaporated under reduced pressure. The residue was purified by column chromatography (Sfar D, 25 g) eluting with a gradient of EtOAc in cyclohexane from 0% to 10% to give 4-bromo-2-chloro-5-methoxybenzonitrile (350 mg, 1.42 mmol, 92.05% yield) as an off-white solid. $^1$H NMR (400 MHz, DMSO-d$_6$) δ 3.92 (s, 3H), 7.74 (s, 1H), 8.08 (s, 1H). LC-MS (Method A): r.t. 1.15 min, MS (ESI) m/z=245.8 and 247.8 [M+H]$^+$.

Intermediate 295: 2-chloro-4-[1-[(2,4-dimethoxyphenyl)methylamino]-4-methylphthalazin-6-yl]-5-methoxybenzonitrile

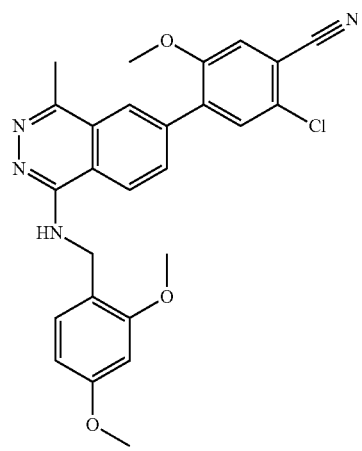 [SMILES: COc1ccc(CNc2nnc(C)c3cc(-c4cc(Cl)c(C#N)cc4OC)ccc23)c(OC)c1]

A mixture of 4-bromo-2-chloro-5-methoxybenzonitrile (150.75 mg, 0.610 mmol), [1-[(2,4-dimethoxyphenyl)methylamino]-4-methylphthalazin-6-yl]boronic acid (240.0 mg, 0.610 mmol) and aqueous 2 M sodium carbonate solution (0.61 mL, 1.22 mmol) in 1,4-dioxane (6 mL) was degassed under Ar for 10 min. Then [1,1'-bis(di-tert-butylphosphino)ferrocene]dichloropalladium(II) (39.98 mg, 0.060 mmol) was added and the resulting mixture was stirred at 85° C. for 16 hours. The mixture was diluted with MeOH and filtered over Celite, washing with EtOAc and MeOH. The filtrate was evaporated in vacuo and the residue was purified by column chromatography (Sfar Amino D, 28 g) eluting with a gradient of EtOAc in cyclohexane from 0% to 100% to give 2-chloro-4-[1-[(2,4-dimethoxyphenyl)methylamino]-4-methylphthalazin-6-yl]-5-methoxybenzonitrile (215 mg, 0.453 mmol, 74.02% yield) as a yellow solid. $^1$H NMR (400 MHz, DMSO-d$_6$) δ 2.70 (s, 3H), 3.72 (s, 3H), 3.84 (s, 3H), 3.88 (s, 3H), 4.66 (d, J=6.01 Hz, 2H), 6.43 (dd, J=8.36, 2.42 Hz, 1H), 6.57 (d, J=2.42 Hz, 1H), 7.11 (d, J=8.36 Hz, 1H), 7.62 (t, J=5.75 Hz, 1H), 7.82 (s, 1H), 7.89 (s, 1H), 8.02 (dd, J=8.56, 1.75 Hz, 1H), 8.10 (d, J=1.78 Hz, 1H), 8.41 (d, J=8.61 Hz, 1H). LC-MS (Method A): r.t. 0.82 min, MS (ESI) m/z=475.2 [M+H]$^+$.

Intermediate 296: 2-bromo-4-chloro-1-cyclobutyloxybenzene

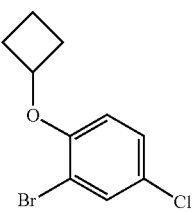 [SMILES: Clc1ccc(OC2CCC2)c(Br)c1]

A mixture of potassium carbonate (499.67 mg, 3.62 mmol), 2-bromo-4-chlorophenol (500.0 mg, 2.41 mmol) and bromocyclobutane (390.46 mg, 2.89 mmol) in DMF (6 mL) was stirred at 110° C. overnight. Then the mixture was diluted with water and extracted three times with EtOAc. The combined organic phases were washed with water and brine, dried over Na$_2$SO$_4$, filtered and concentrated in vacuo. The residue was purified by column chromatography (KP-Sil silica gel, SNAP 25) eluting with a gradient of EtOAc in cyclohexane from 10% to 40% to give 2-bromo-4-chloro-1-cyclobutyloxybenzene (617 mg, 2.359 mmol, 97.88% yield) as a colourless oil. $^1$H NMR (400 MHz, Chloroform-d) δ 1.64-1.78 (m, 1H), 1.84-1.97 (m, 1H), 2.19-2.32 (m, 2H), 2.42-2.52 (m, 2H), 4.65 (q, J=7.13 Hz, 1H), 6.69 (d, J=8.76 Hz, 1H), 7.20 (dd, J=8.79, 2.54 Hz, 1H), 7.54 (d, J=2.53 Hz, 1H). LC-MS (Method A): r.t. 1.44 min, MS (ESI) m/z of product not observed due to poor ionization.

Intermediate 297: 7-(5-chloro-2-cyclobutyloxyphenyl)-N-[(2,4-dimethoxyphenyl)methyl]cinnolin-4-amine

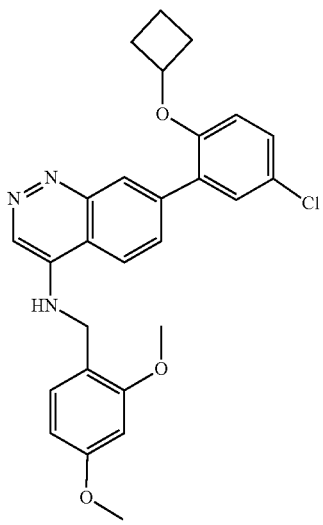 [SMILES: COc1ccc(CNc2cnnc3cc(-c4cc(Cl)ccc4OC4CCC4)ccc23)c(OC)c1]

A mixture of 2-bromo-4-chloro-1-cyclobutyloxybenzene (150.0 mg, 0.570 mmol) and N-[(2,4-dimethoxyphenyl)methyl]-7-(4,4,5,5-tetramethyl-1,3,2-dioxaborolan-2-yl)cinnolin-4-amine (362.44 mg, 0.860 mmol) in 1,2-dimethoxyethane (5.7 mL) and aqueous 2N sodium carbonate solution (0.57 mL, 1.15 mmol) was degassed for 10 minutes with N$_2$. Then [1,1'-bis(di-tert-butylphosphino)ferrocene]dichloropalladium(II) (37.49 mg, 0.060 mmol) was added and the resulting reaction mixture was stirred at 75° C. for five hours. The mixture was cooled to room temperature and filtered over Celite, washing with EtOAc. The filtrate was evaporated and the residue was purified by column chromatography (KP-NH silica gel, SNAP 28) eluting with a gradient of EtOAc in cyclohexane from 10% to 100% to give 7-(5-chloro-2-cyclobutyloxyphenyl)-N-[(2,4-dimethoxyphenyl)methyl]cinnolin-4-amine (140 mg, 0.294 mmol, 51.29% yield) as a white powder. $^1$H NMR (400 MHz, DMSO-d$_6$) δ 1.53-1.71 (m, 1H), 1.71-1.83 (m, 1H), 1.92-2.10 (m, 2H), 2.35-2.48 (m, 2H), 3.75 (s, 3H), 3.89 (s, 3H), 4.52 (d, J=5.74 Hz, 2H), 4.77 (q, J=7.11 Hz, 1H), 6.48 (dd, J=8.37, 2.41 Hz, 1H), 6.64 (d, J=2.41 Hz, 1H), 7.03 (d, J=8.84 Hz, 1H), 7.16 (d, J=8.36 Hz, 1H), 7.42 (dd, J=8.80, 2.70 Hz, 1H), 7.55 (d, J=2.67 Hz, 1H), 7.82 (dd, J=8.78, 1.85 Hz, 1H), 8.03 (t, J=5.98 Hz, 1H), 8.24 (d, J=1.83 Hz, 1H), 8.37 (d, J=8.88 Hz, 1H), 8.48 (s, 1H). LC-MS (Method A): r.t. 0.94 min, MS (ESI) m/z=476.3 [M+H]$^+$.

Intermediate 298: 2-bromo-4-chloro-1-(2,2,2-trifluoroethoxy)benzene

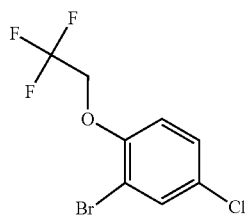 [SMILES: FC(F)(F)COc1ccc(Cl)cc1Br]

A suspension of 1,1,1-trifluoro-2-iodoethane (607.2 mg, 2.89 mmol), 2-bromo-4-chlorophenol (500.0 mg, 2.41 mmol) and potassium carbonate (666.23 mg, 4.82 mmol) in DMF (8 mL) was stirred at 80° C. for 24 hours. Then the reaction mixture was diluted with water and extracted with EtOAc. The organic phase was washed with brine, dried over Na$_2$SO$_4$ and concentrated under reduced pressure. The residue was purified by column chromatography (Sfar D silica gel, 25 g) eluting with a gradient of EtOAc in cyclohexane from 0% to 50% to give 2-bromo-4-chloro-1-(2,2,2-trifluoroethoxy)benzene (450 mg, 1.555 mmol, 64.5% yield). $^1$H NMR (400 MHz, DMSO-d$_6$) δ 4.88 (q, J=8.77 Hz, 2H), 7.28 (d, J=8.89 Hz, 1H), 7.49 (dd, J=8.86, 2.59 Hz, 1H), 7.77 (d, J=2.58 Hz, 1H). LC-MS (Method A): r.t. 1.29 min, MS (ESI) m/z of product not observed due to poor ionization.

Intermediate 299: 7-[5-chloro-2-(2,2,2-trifluoroethoxy)phenyl]-N-[(2,4-dimethoxyphenyl)methyl]cinnolin-4-amine

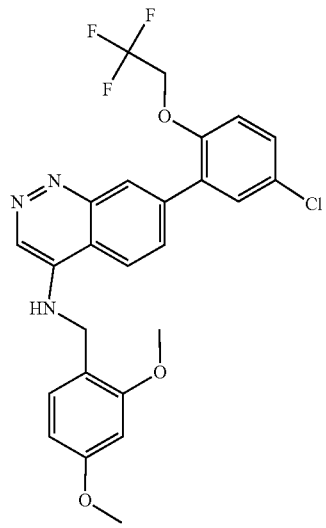 [SMILES: COc1ccc(CNc2cnnc3cc(-c4cc(Cl)ccc4OCC(F)(F)F)ccc23)c(OC)c1]

A mixture of 2-bromo-4-chloro-1-(2,2,2-trifluoroethoxy) benzene (180.0 mg, 0.620 mmol), [4-[(2,4-dimethoxyphenyl)methylamino]cinnolin-7-yl]boronic acid (314.36 mg, 0.750 mmol) in 1,2-dimethoxyethane (6 mL) and aqueous 2M sodium carbonate solution (0.62 mL, 1.24 mmol) was degassed for 10 min with $N_2$. Then [1,1'-bis(di-tert-butylphosphino)ferrocene]dichloropalladium(II) (40.65 mg, 0.060 mmol) was added and the resulting reaction mixture was stirred at 80° C. for three hours. The mixture was cooled to room temperature and filtered over Celite, washing with MeOH. The filtrate was evaporated and the residue was purified by column chromatography (Sfar Amino D, 11 g) eluting with a gradient of EtOAc in cyclohexane from 0% to 60% to 7-[5-chloro-2-(2,2,2-trifluoroethoxy)phenyl]-N-[(2,4-dimethoxyphenyl)methyl]cinnolin-4-amine (118 mg, 0.234 mmol, 37.66% yield). $^1$H NMR (400 MHz, DMSO-$d_6$) δ 3.75 (s, 3H), 3.89 (s, 3H), 4.52 (d, J=5.79 Hz, 2H), 4.86 (q, J=8.80 Hz, 2H), 6.49 (dd, J=8.39, 2.39 Hz, 1H), 6.64 (d, J=2.38 Hz, 1H), 7.17 (d, J=8.36 Hz, 1H), 7.35 (d, J=8.90 Hz, 1H), 7.54 (dd, J=8.86, 2.66 Hz, 1H), 7.62 (d, J=2.64 Hz, 1H), 7.78 (dd, J=8.80, 1.86 Hz, 1H), 8.03 (t, J=5.93 Hz, 1H), 8.22 (d, J=1.81 Hz, 1H), 8.38 (d, J=8.75 Hz, 1H), 8.50 (s, 1H). LC-MS (Method A): r.t. 0.87 min, MS (ESI) m/z=504.2 [M+H]$^+$.

Intermediate 300:
4-bromo-6-chloro-2-methyl-1,3-benzoxazole

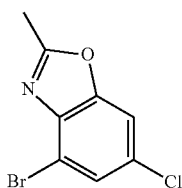

A mixture of 4-methylbenzenesulfonic acid hydrate (39.48 mg, 0.2 mmol), 2-amino-3-bromo-5-chlorophenol (450.0 mg, 2.02 mmol) and 1,1,1-triethoxyethane (3.5 mL, 2.02 mmol) was stirred at 135° C. for 90 min, then it was concentrated. The residue was purified by column chromatography (KP-Sil, SNAP 10 g+10 g in series) eluting with a gradient of EtOAc in cyclohexane from 2% to 20% to give 4-bromo-6-chloro-2-methyl-1,3-benzoxazole (314 mg, 1.274 mmol, 63% yield) as a whitish solid. $^1$H NMR (400 MHz, DMSO-$d_6$) δ 2.65 (s, 3H), 7.70-7.72 (m, 1H), 7.95-7.97 (m, 1H). LC-MS (Method A): r.t. 1.11 min, MS (ESI) m/z=245.9 and 247.9 [M+H]$^+$.

Intermediate 301: 7-(6-chloro-2-methyl-1,3-benzoxazol-4-yl)-N-[(2,4-dimethoxyphenyl)methyl]cinnolin-4-amine Formic Acid Salt

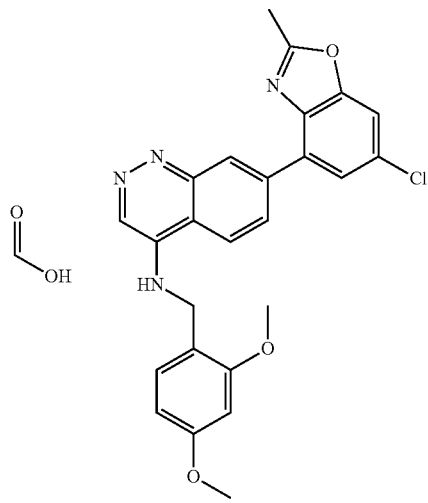 [SMILES: O=CO ; COc1ccc(CNc2cnnc3cc(-c4cc(Cl)cc5oc(C)nc45)ccc23)c(OC)c1]

A mixture of N-[(2,4-dimethoxyphenyl)methyl]-7-(4,4,5,5-tetramethyl-1,3,2-dioxaborolan-2-yl)cinnolin-4-amine (461.48 mg, 1.1 mmol) and aqueous 2N sodium carbonate solution (0.73 mL, 1.46 mmol) in 1,2-dimethoxyethane (17.53 mL) was degassed for 10 min with Ar. Then 4-bromo-6-chloro-2-methyl-1,3-benzoxazole (200.0 mg, 0.730 mmol) and [1,1'-bis(di-tert-butylphosphino)ferrocene]dichloropalladium(II) (47.74 mg, 0.070 mmol) were added. The mixture was degassed for 10 min and then stirred at 85° C. for 4 hours. The mixture was cooled to room temperature and filtered over Celite, washing with EtOAc. The filtrate was evaporated and the residue was purified by column chromatography (KP-C18-HS, 30 g) eluting with a gradient of $CH_3CN$ (+0.1% of HCOOH) in water (+0.1% of HCOOH) from 2% to 60% to give 7-(6-chloro-2-methyl-1,3-benzoxazol-4-yl)-N-[(2,4-dimethoxyphenyl)methyl]cinnolin-4-amine formic acid salt (136 mg, 0.268 mmol, 36.74% yield) as a yellow solid. $^1$H NMR (400 MHz, DMSO-$d_6$) δ 2.72 (s, 3H), 3.75 (s, 3H), 3.89 (s, 3H), 4.54 (d, J=5.50 Hz, 2H), 6.49 (dd, J=8.36, 2.42 Hz, 1H), 6.64 (d, J=2.42 Hz, 1H), 7.18 (d, J=8.36 Hz, 1H), 7.92 (d, J=1.76 Hz, 1H), 7.98 (d, J=1.98 Hz, 1H), 8.09 (t, J=6.05 Hz, 1H), 8.17 (s, 1H from HCOOH), 8.27 (dd, J=8.91, 1.87 Hz, 1H), 8.48 (d, J=9.02 Hz, 1H), 8.52 (s, 1H), 8.90 (d, J=1.76 Hz, 1H). LC-MS (Method A). r.t. 0.82 min, MS (ESI) m/z=461.2 [M+H]$^+$.

Intermediate 302: methyl 4-chloro-2-iodobenzoate

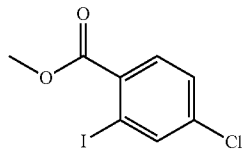

2-Amino-4-chlorobenzoic acid methyl ester (5.0 g, 26.94 mmol) was suspended in acetonitrile (38 mL) and $H_2O$ (69 mL). 12 M Hydrochloric acid solution (22.45 mL, 269.38 mmol) was added and the mixture was cooled in an ice bath.

A solution of sodium nitrite (3.72 g, 53.88 mmol) in H₂O (3 mL) was added dropwise and the resulting reaction mixture was stirred for 30 minutes. Then a solution of potassium iodide (13.42 g, 80.81 mmol) in H₂O (3 mL) was added slowly and the reaction mixture was warmed to room temperature for 2 hours. A saturated aqueous solution of Na₂S₂O₃ was added and the mixture was stirred for 10 minutes, then extracted 3 times with DCM. The combined organic phases were washed with brine, dried over Na₂SO₄, filtered and evaporated in vacuo. The residue was purified by column chromatography (KP-Sil silica gel, SNAP 100) eluting with a gradient of EtOAc in cyclohexane from 0% to 30% to give methyl 4-chloro-2-iodobenzoate (7.76 g, 26.17 mmol, 97.16% yield) as a yellow oil. ¹H NMR (400 MHz, DMSO-d₆) δ 3.86 (s, 3H), 7.61 (dd, J=8.38, 2.10 Hz, 1H), 7.74 (d, J=8.37 Hz, 1H), 8.11 (d, J=2.07 Hz, 1H). LC-MS (Method A): r.t. 1.22 min, MS (ESI) m/z=296.98 [M–H]⁺.

Intermediate 303: methyl 4-chloro-2-[4-[(2,4-dimethoxyphenyl)methylamino]cinnolin-7-yl]benzoate

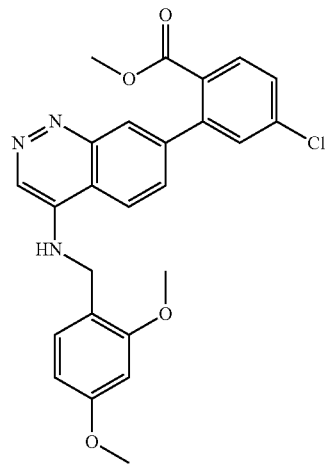 [SMILES: COC(=O)c1ccc(Cl)cc1-c1ccc2c(NCc3ccc(OC)cc3OC)cnnc2c1]

A mixture of methyl 4-chloro-2-iodobenzoate (500.0 mg, 1.69 mmol), aqueous 2N sodium carbonate solution (1.69 mL, 3.37 mmol) and N-[(2,4-dimethoxyphenyl)methyl]-7-(4,4,5,5-tetramethyl-1,3,2-dioxaborolan-2-yl)cinnolin-4-amine (994.67 mg, 2.36 mmol) in 1,2-dimethoxyethane (17 mL) in a microwave reaction tube was placed under nitrogen then deoxygenated with a stream of nitrogen for 10 min. [1,1'-Bis(di-tert-butylphosphino)ferrocene]dichloropalladium(II) (110.25 mg, 0.170 mmol) was added and the reaction mixture was heated to 70° C. for 8 hours then filtered over a pad of Celite, washing with MeOH. The filtrate was concentrated in vacuo and the residue was purified by column chromatography (KP-NH silica gel, SNAP 55) eluting with a gradient of EtOAc in cyclohexane from 0% to 100% to give partially purified product. The material was purified further by column chromatography (KP-C18-HS, 60 g) eluting with a gradient of CH₃CN (+0.1% of HCOOH) in water (+0.1% of HCOOH) from 5% to 95%. Appropriate fractions were collected and lyophilized to give methyl 4-chloro-2-[4-[(2,4-dimethoxyphenyl)methylamino]cinnolin-7-yl]benzoate (630 mg, 1.358 mmol, 80.53% yield) as a yellow powder. ¹H NMR (400 MHz, DMSO-d₆) δ 3.61 (s, 3H), 3.75 (s, 3H), 3.89 (s, 3H), 4.53 (s, 2H), 6.49 (dd, J=8.36, 2.40 Hz, 1H), 6.64 (d, J=2.37 Hz, 1H), 7.17 (d, J=8.37 Hz, 1H), 7.58 (dd, J=8.72, 1.89 Hz, 1H), 7.63-7.70 (m, 2H), 7.91 (dd, J=7.90, 0.86 Hz, 1H), 8.00 (d, J=1.79 Hz, 1H), 8.07 (s, 1H), 8.37 (d, J=8.76 Hz, 1H), 8.51 (s, 1H). LC-MS (Method A): r.t. 0.79 min, MS (ESI) m/z=464.22 [M+H]⁺.

Intermediate 304: 4-chloro-2-[4-[(2,4-dimethoxyphenyl)methylamino]cinnolin-7-yl]benzoic Acid

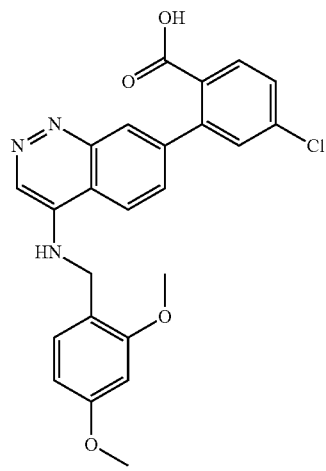 [SMILES: COc1ccc(CNc2cnnc3cc(-c4cc(Cl)ccc4C(=O)O)ccc23)c(OC)c1]

To a solution of methyl 4-chloro-2-[4-[(2,4-dimethoxyphenyl)methylamino]cinnolin-7-yl]benzoate (630 mg, 1.36 mmol) in THF (15 mL) and water (5 mL), lithium hydroxide hydrate (68.38 mg, 1.63 mmol) was added and the reaction mixture was stirred at room temperature for 24 hours. The reaction mixture was diluted with water and partially evaporated under reduced pressure to remove the THF. The residue was neutralized with 1N HCl solution and the resulting precipitate was filtered on a Hirsch funnel to give 4-chloro-2-[4-[(2,4-dimethoxyphenyl)methylamino]cinnolin-7-yl]benzoic acid (520 mg, 1.16 mmol, 85.11% yield) as a pale-brown solid. ¹H NMR (400 MHz, DMSO-d₆) δ 3.75 (s, 3H), 3.89 (s, 3H), 4.53 (d, J=4.82 Hz, 2H), 6.49 (d, J=8.32 Hz, 1H), 6.64 (s, 1H), 7.17 (d, J=8.35 Hz, 1H), 7.56-7.70 (m, 3H), 7.88 (d, J=8.55 Hz, 1H), 8.02 (s, 1H), 8.11 (br. s, 1H), 8.36 (d, J=8.79 Hz, 1H), 8.50 (s, 1H). LC-MS (Method A): r.t. 0.74 min, MS (ESI) m/z=450.22 [M+H]⁺.

Intermediate 305: 4-chloro-2-[4-[(2,4-dimethoxyphenyl)methylamino]cinnolin-7-yl]-N-propan-2-ylbenzamide Formic Acid Salt

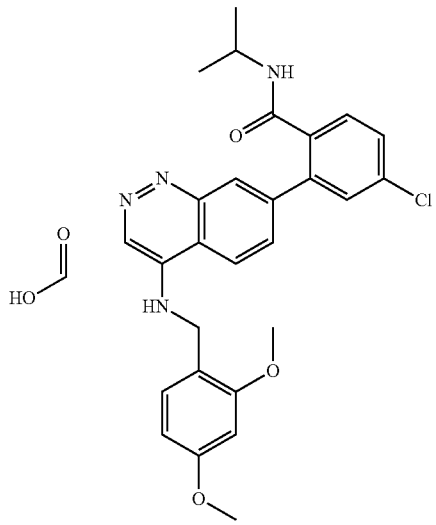

A solution of 4-chloro-2-[4-[(2,4-dimethoxyphenyl)methylamino]cinnolin-7-yl]benzoic acid (150 mg, 0.330 mmol), [dimethylamino(3-triazolo[4,5-b]pyridinyloxy)methylidene]-dimethylammonium hexafluorophosphate (190.16 mg, 0.500 mmol), 2-propanamine (31.24 uL, 0.370 mmol), and N,N-diisopropylethylamine (174.22 uL, 1 mmol) in DMF (1.5 mL) was stirred at room temperature for 2 hours. The mixture was diluted with EtOAc and washed with water. The aqueous layer was extracted with EtOAc and the combined organic layers were dried over $Na_2SO_4$, filtered and concentrated. The residue was purified by column chromatography (KP-NH silica gel, SNAP 28) eluting with a gradient of EtOAc in cyclohexane from 0% to 80% to give partially pure product. This material was purified further by column chromatography (KP-C18-HS, 12 g) eluting with a gradient of $CH_3CN$ (+0.1% of HCOOH) in water (+0.1% of HCOOH) from 2% to 45%. Appropriate fractions were collected and evaporated under reduced pressure to give 4-chloro-2-[4-[(2,4-dimethoxyphenyl)methylamino]cinnolin-7-yl]-N-propan-2-ylbenzamide formic acid salt (90 mg, 0.183 mmol, 54.98% yield) as a yellow oil. $^1$H NMR (400 MHz, DMSO-$d_6$) δ 0.93 (d, J=6.60 Hz, 6H), 3.74 (s, 3H), 3.79-3.86 (m, 1H), 3.87 (s, 3H), 4.51 (s, 2H), 6.47 (dd, J=8.38, 2.40 Hz, 1H), 6.62 (d, J=2.39 Hz, 1H), 7.14 (d, J=8.38 Hz, 1H), 7.49 (d, J=8.15 Hz, 1H), 7.56 (dd, J=8.17, 2.12 Hz, 1H), 7.62-7.68 (m, 2H), 8.02 (br. s, 1H), 8.11 (d, J=1.76 Hz, 1H), 8.14 (s, 0.9H from HCOOH) 8.21 (d, J=7.96 Hz, 1H), 8.36 (d, J=8.77 Hz, 1H), 8.48 (s, 1H). LC-MS (Method A). r.t. 0.72 min, MS (ESI) m/z=491.25 [M+H]$^+$.

Intermediate 306: (2R,4s,6S)-4-(2-bromo-4-chlorophenoxy)-2,6-dimethyloxane

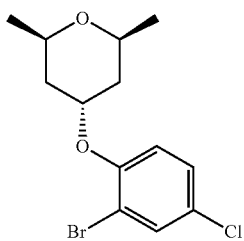 [SMILES: C[C@@H]1C[C@@H](Oc2ccc(Cl)cc2Br)C[C@H](C)O1]

(NE)-N-Ethoxycarbonyliminocarbamic acid ethyl ester (0.58 mL, 3.71 mmol) was added dropwise to a solution of 2-bromo-4-chlorophenol (700.0 mg, 3.37 mmol), triphenylphosphine (973.55 mg, 3.71 mmol) and (2R,4r,6S)-2,6-dimethyloxan-4-ol (439.27 mg, 3.37 mmol) in THF (7 mL). The resulting mixture was stirred at room temperature for 1 hour, then it was concentrated under reduced pressure. The residue was purified by column chromatography (KP-Sil, SNAP 25 g+25 g in series) eluting with a gradient of EtOAc in cyclohexane from 2% to 20% to give (2R,4s,6S)-4-(2-bromo-4-chlorophenoxy)-2,6-dimethyloxane (798 mg, 2.497 mmol, 74.0% yield) as a yellow oil. $^1$H NMR (400 MHz, DMSO-$d_6$) δ 1.08 (d, J=6.38 Hz, 6H), 1.37-1.44 (m, 2H), 1.79 (dd, J=14.64, 2.53 Hz, 2H), 3.83-3.93 (m, 2H), 4.90-4.96 (m, 1H), 7.19 (d, J=9.24 Hz, 1H), 7.40 (dd, J=8.80, 2.64 Hz, 1H), 7.69 (d, J=2.64 Hz, 1H). LC-MS (Method A): r.t. 1.42 min, MS (ESI) m/z=319.1 and 321.0 [M+H]$^+$.

Intermediate 307: 7-(5-chloro-2-{[(2R,4s,6S)-2,6-dimethyloxan-4-yl]oxy}phenyl)-N-[(2,4-dimethoxyphenyl)methyl]cinnolin-4-amine

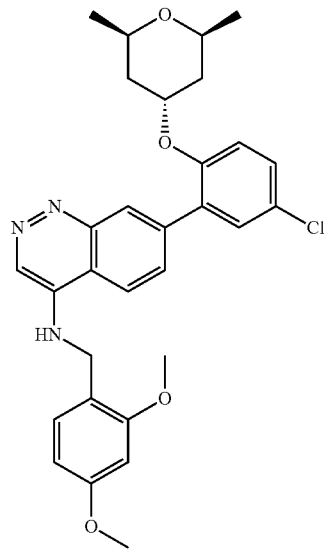 [SMILES: COc1ccc(CNc2cnnc3cc(-c4cc(Cl)ccc4O[C@@H]4C[C@@H](C)O[C@@H](C)C4)ccc23)c(OC)c1]

A mixture of N-[(2,4-dimethoxyphenyl)methyl]-7-(4,4,5,5-tetramethyl-1,3,2-dioxaborolan-2-yl)cinnolin-4-amine (494.3 mg, 1.17 mmol) and (2R,4s,6S)-4-(2-bromo-4-chlorophenoxy)-2,6-dimethyloxane (250.0 mg, 0.780 mmol) in 1,2-dimethoxyethane (24.8 mL) and aqueous 2N sodium carbonate solution (0.78 mL, 1.56 mmol) was degassed for 10 min with Ar. [1,1'-Bis(di-tert-butylphosphino)ferrocene]dichloropalladium(II) (51.14 mg, 0.080 mmol) was added and the mixture was degassed for 10 min then stirred at 85° C. for 90 minutes. The reaction mixture was cooled to room temperature and filtered over Celite, washing with EtOAc and the solvent was evaporated. The residue was purified by column chromatography (KP-C18-HS, 30 g) eluting with a gradient of $CH_3CN$ (+0.1% of HCOOH) in water (+0.1% of HCOOH) from 2% to 50% to give 7-(5-chloro-2-{[(2R,4s,6S)-2,6-dimethyloxan-4-yl]oxy}phenyl)-N-[(2,4-dimethoxyphenyl)methyl]cinnolin-4-amine (211 mg, 0.395 mmol, 50.51% yield) as a brownish foam. $^1$H NMR (400 MHz, DMSO-$d_6$) δ 0.96 (d, J=6.16 Hz, 6H), 1.29-1.41 (m, 2H), 1.78 (d, J=12.32 Hz, 2H), 3.47-3.57 (m, 2H), 3.75 (s, 3H), 3.89 (s, 3H), 4.52 (d, J=5.28 Hz, 2H), 4.81-4.86 (m, 1H), 6.49 (dd, J=8.36, 2.42 Hz, 1H), 6.64 (d, J=2.42 Hz, 1H), 7.18 (d, J=8.36 Hz, 1H), 7.24 (d, J=9.02 Hz, 1H), 7.45 (dd, J=8.91, 2.75 Hz, 1H), 7.56 (d, J=2.86 Hz, 1H), 7.83 (dd, J=8.80, 1.98 Hz, 1H), 8.02 (t, J=5.94 Hz, 1H), 8.25 (d, J=1.76 Hz, 1H), 8.38 (d, J=8.80 Hz, 1H), 8.50 (s, 1H). LC-MS (Method A). r.t. 0.88 min, MS (ESI) m/z=534.3 [M+H]$^+$.

Intermediate 308: 7-bromo-5-chloro-2-methyl-1,3-benzoxazole

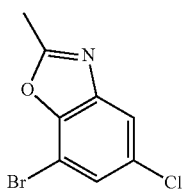

A mixture of 4-methylbenzenesulfonic acid hydrate (34.2 mg, 0.180 mmol), 2-amino-6-bromo-4-chlorophenol (400.0 mg, 1.8 mmol) and 1,1,1-triethoxyethane (3.0 mL, 1.8 mmol) was stirred at 135° C. for 90 minutes, then it was concentrated. The residue was purified by column chromatography (KP-Sil, SNAP 10 g+10 g in series) eluting with a gradient of EtOAc in cyclohexane from 2% to 20% to give 7-bromo-5-chloro-2-methyl-1,3-benzoxazole (311 mg, 1.262 mmol, 70.17% yield) as a yellowish solid. $^1$H NMR (400 MHz, DMSO-$d_6$) δ 2.66 (s, 3H), 7.71 (d, J=1.98 Hz, 1H), 7.82 (d, J=1.98 Hz, 1H). LC-MS (Method A): r.t. 1.16 min, MS (ESI) m/z=246.0 and 247.9 [M+H]$^+$.

Intermediate 309: 7-(5-chloro-2-methyl-1,3-benzoxazol-7-yl)-N-[(2,4-dimethoxyphenyl)methyl]cinnolin-4-amine

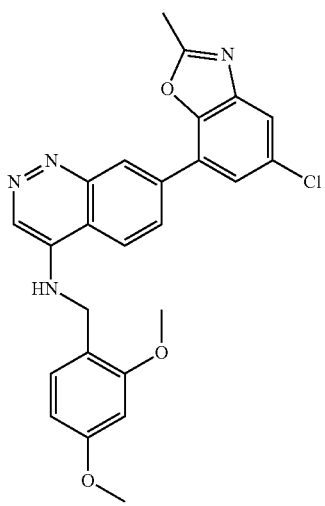 [SMILES: COc1ccc(CNc2cnnc3cc(-c4cc(Cl)cc5nc(C)oc45)ccc23)c(OC)c1]

A mixture N-[(2,4-dimethoxyphenyl)methyl]-7-(4,4,5,5-tetramethyl-1,3,2-dioxaborolan-2-yl)cinnolin-4-amine (487.12 mg, 1.16 mmol) and 7-bromo-5-chloro-2-methyl-1,3-benzoxazole (190.0 mg, 0.770 mmol) in 1,2-dimethoxyethane (19.5 mL) and aqueous 2N sodium carbonate solution (0.77 mL, 1.54 mmol) was degassed for 10 min with Ar. [1,1'-Bis(di-tert-butylphosphino)ferrocene]dichloropalladium(II) (50.39 mg, 0.080 mmol) was added and the mixture was degassed for 10 min then stirred at 85° C. for 5 hours. The reaction mixture was cooled to room temperature and filtered over Celite, washing with EtOAc and the solvent was evaporated. The residue was purified by column chromatography (KP-C18-HS, 30 g) eluting with a gradient of CH$_3$CN (+0.1% of HCOOH) in water (+0.1% of HCOOH) from 2% to 50% to give to give 7-(5-chloro-2-methyl-1,3-benzoxazol-7-yl)-N-[(2,4-dimethoxyphenyl)methyl]cinnolin-4-amine (27 mg, 0.059 mmol, 7.6% yield) as a yellow foam. $^1$H NMR (400 MHz, DMSO-$d_6$) δ 2.72 (s, 3H), 3.75 (s, 3H), 3.89 (s, 3H), 4.54 (d, J=5.28 Hz, 2H), 6.49 (dd, J=8.36, 2.42 Hz, 1H), 6.64 (d, J=2.20 Hz, 1H), 7.18 (d, J=8.14 Hz, 1H), 7.87 (d, J=1.98 Hz, 1H), 7.93 (d, J=1.98 Hz, 1H), 8.10-8.28 (m, 2H), 8.52 (d, J=9.02 Hz, 1H), 8.54 (s, 1H), 8.68 (d, J=1.76 Hz, 1H). LC-MS (Method A): r.t. 0.77 min, MS (ESI) m/z=463.2 [M+H]$^+$.

Intermediate 310: (2R,4s,6S)-2,6-dimethyloxan-4-yl 4-nitrobenzoate

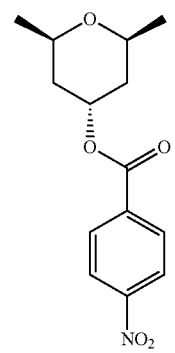

(NE)-N-Ethoxycarbonyliminocarbamic acid ethyl ester (0.63 mL, 3.98 mmol) was added dropwise to a solution of (2R,4r,6S)-2,6-dimethyloxan-4-ol (450.0 mg, 3.46 mmol), 4-nitrobenzoic acid (577.69 mg, 3.46 mmol) and triphenylphosphine (1042.67 mg, 3.98 mmol) in THF (10 mL). The resulting mixture was stirred at room temperature for 4 hours, then it was concentrated. The residue was purified by column chromatography (KP-Sil, SNAP 25 g+25 g in series) eluting with a gradient of EtOAc in cyclohexane from 0% to 40% to give (2R,4s,6S)-2,6-dimethyloxan-4-yl 4-nitrobenzoate (909 mg, 3.255 mmol, 94.15% yield) as a yellowish solid. $^1$H NMR (400 MHz, DMSO-$d_6$) δ 1.12 (d, J=6.16 Hz, 6H), 1.50 (ddd, J=14.31, 11.66, 2.86 Hz, 2H), 1.85 (dd, J=14.42, 2.31 Hz, 2H), 3.83-3.94 (m, 2H), 5.36 (quin, J=2.81 Hz, 1H), 8.24-8.29 (m, 2H), 8.32-8.38 (m, 2H). LC-MS (Method A): r.t. 1.13 min, MS (ESI) m/z of product not observed due to poor ionization.

Intermediate 311: (2R,4s,6S)-2,6-dimethyloxan-4-ol

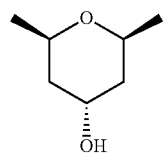

A solution of lithium hydroxide (389.75 mg, 16.27 mmol) in water (14 mL) was added to a stirred solution of (2R,4s,6S)-2,6-dimethyloxan-4-yl 4-nitrobenzoate (909.0 mg, 3.25 mmol) in THF (47 mL). The reaction mixture was stirred overnight at room temperature, then it was partially concentrated. Water was added, followed by EtOAc and the phases were separated. The organic phase was dried over Na$_2$SO$_4$, filtered and concentrated to give (2R,4s,6S)-2,6-dimethyl-oxan-4-ol (261 mg, 2.005 mmol, 61.6% yield) as a yellowish oil. ¹H NMR (400 MHz, DMSO-d₆) δ 1.03 (d, J=6.16 Hz, 6H), 1.19-1.26 (m, 2H), 1.52 (dd, J=13.86, 3.08 Hz, 2H), 3.74-3.83 (m, 2H), 3.96-4.00 (m, 1H), 4.51 (d, J=2.86 Hz, 1H). LC-MS (Method A): r.t. 0.41 min, MS (ESI) m/z=131 [M+H]⁺.

Intermediate 312: (2R,4R,6S)-4-2-bromo-4-chloro-phenoxy)-2,6-dimethyloxane

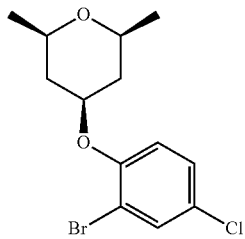 [SMILES: C[C@@H]1C[C@H](Oc2ccc(Cl)cc2Br)C[C@H](C)O1]

(NE)-N-ethoxycarbonyliminocarbamic acid ethyl ester (0.35 mL, 2.21 mmol) was added dropwise to a solution of 2-bromo-4-chlorophenol (415.94 mg, 2.01 mmol), triphenylphosphine (578.48 mg, 2.21 mmol) and (2R,6S)-2,6-dimethyloxan-4-ol (261.01 mg, 2.01 mmol) in THF (4.2 mL). The resulting mixture was stirred at room temperature for 1 hour, then it was concentrated. The residue was purified by column chromatography (KP-Sil, SNAP 25 g) eluting with a gradient of EtOAc in cyclohexane from 2% to 20% to give (2R,4r,6S)-4-(2-bromo-4-chlorophenoxy)-2,6-dimethyloxane (380 mg, 1.189 mmol, 59.3% yield) as a yellow solid. 1H NMR (400 MHz, DMSO-d₆) δ 1.11-1.20 (m, 8H), 2.03-2.10 (m, 2H), 3.48-3.57 (m, 2H), 4.54-4.64 (m, 1H), 7.27 (d, J=9.02 Hz, 1H), 7.39 (dd, J=8.80, 2.64 Hz, 1H), 7.69 (d, J=2.42 Hz, 1H). LC-MS (Method A): r.t. 1.41 min, MS (ESI) m/z of product not observed due to poor ionization.

Intermediate 313: 7-(5-chloro-2-{[(2R,4R,6S)-2,6-dimethyloxan-4-yl]oxy}phenyl)-N-[(2,4-dimethoxy-phenyl)methyl]cinnolin-4-amine Formic Acid Salt

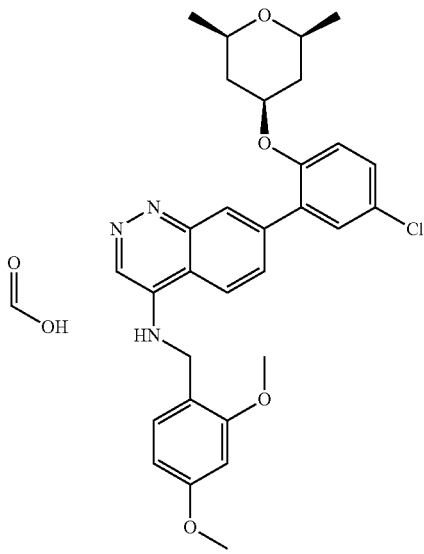 [SMILES: O=CO ; COc1ccc(CNc2cnnc3cc(-c4cc(Cl)ccc4O[C@H]4C[C@@H](C)O[C@@H](C)C4)ccc23)c(OC)c1]

A mixture of N-[(2,4-dimethoxyphenyl)methyl]-7-(4,4,5,5-tetramethyl-1,3,2-dioxaborolan-2-yl)cinnolin-4-amine (494.3 mg, 1.17 mmol) and (2R,4r,6S)-4-(2-bromo-4-chlorophenoxy)-2,6-dimethyloxane (250.0 mg, 0.780 mmol) in 1,2-dimethoxyethane (37.7 mL) and aqueous 2N sodium carbonate solution (0.78 mL, 1.56 mmol) was degassed for 10 min with Ar. [1,1'-Bis(di-tert-butylphosphino)ferrocene]dichloropalladium(II) (51.14 mg, 0.080 mmol) was added and the mixture was degassed for 10 min then stirred at 85° C. for 90 minutes. The reaction mixture was cooled to room temperature and filtered over Celite, washing with EtOAc and the solvent was evaporated. The residue was purified by column chromatography (KP-C18-HS, 30 g+30 g in series) eluting with a gradient of CH₃CN (+0.1% of HCOOH) in water (+0.1% of HCOOH) from 2% to 50% to give 7-(5-chloro-2-{[(2R,4r,6S)-2,6-dimethyloxan-4-yl]oxy}phenyl)-N-[(2,4-dimethoxyphenyl)methyl]cinnolin-4-amine formic acid salt (140 mg, 0.241 mmol, 30.86% yield) as a brownish foam. ¹H NMR (400 MHz, DMSO-d₆) δ 0.99-1.12 (m, 8H), 2.03-2.08 (m, 2H), 3.52 (dd, J=9.79, 6.49 Hz, 2H), 3.75 (s, 3H), 3.89 (s, 3H), 4.52 (d, J=5.28 Hz, 2H), 4.59-4.67 (m, 1H), 6.48 (dd, J=8.47, 2.31 Hz, 1H), 6.64 (d, J=2.42 Hz, 1H), 7.17 (d, J=8.36 Hz, 1H), 7.34 (d, J=9.02 Hz, 1H), 7.43 (dd, J=9.02, 2.64 Hz, 1H), 7.55 (d, J=2.64 Hz, 1H), 7.79 (dd, J=8.80, 1.76 Hz, 1H), 8.02 (br s, 1H), 8.18 (1H from HCOOH), 8.20 (d, J=1.54 Hz, 1H), 8.36 (d, J=8.80 Hz, 1H), 8.49 (s, 1H). LC-MS (Method A): r.t. 0.90 min, MS (ESI) m/z=534.2 [M+H]⁺.

Intermediate 314: [4-chloro-2-[4-[(2,4-dimethoxy-phenyl)methylamino]cinnolin-7-yl]phenyl]-pyrrolidin-1-ylmethanone

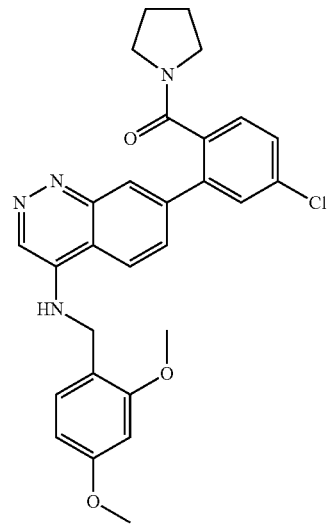 [SMILES: COc1ccc(CNc2cnnc3cc(-c4cc(Cl)ccc4C(=O)N4CCCC4)ccc23)c(OC)c1]

A solution of 4-chloro-2-[4-[(2,4-dimethoxyphenyl)methylamino]cinnolin-7-yl]benzoic acid (130 mg, 0.290 mmol), [dimethylamino(3-triazolo[4,5-b]pyridinyloxy)methylidene]-dimethylammonium hexafluorophosphate (153.82 mg, 0.400 mmol), pyrrolidine (26.53 uL, 0.320 mmol), and N,N-diisopropylethylamine (150 uL, 0.870 mmol) in DMF (1.15 mL) was stirred at room temperature for 3 hours. The mixture was diluted with EtOAc and washed with water. The aqueous layer was extracted with EtOAc and the combined organic layers were dried over Na₂SO₄, filtered and concentrated. The residue was purified by column chromatography (KP-sil silica gel, SNAP 25) eluting with a gradient of EtOAc in cyclohexane from 0% to 80% to give [4-chloro-2-[4-[(2,4-dimethoxyphenyl)methylamino]cinnolin-7-yl]phenyl]-pyrrolidin-1-ylmethanone (145 mg, 0.288 mmol, 99.76% yield) as a yellow oil. ¹H NMR (400 MHz, DMSO-d$_6$) δ 1.48-1.66 (m, 4H), 2.94 (t, J=6.18 Hz, 2H), 3.25 (t, J=6.82 Hz, 2H), 3.75 (s, 3H), 3.88 (s, 3H), 4.48-4.56 (m, 2H), 6.49 (dd, J=8.40, 2.39 Hz, 1H), 6.63 (d, J=2.39 Hz, 1H), 7.17 (d, J=8.36 Hz, 1H), 7.50 (d, J=8.22 Hz, 1H), 7.60 (dd, J=8.17, 2.10 Hz, 1H), 7.69 (dd, J=8.78, 1.94 Hz, 1H), 7.74 (d, J=2.13 Hz, 1H), 8.06 (t, J=5.94 Hz, 1H), 8.12 (d, J=1.87 Hz, 1H), 8.40 (d, J=8.80 Hz, 1H), 8.51 (s, 1H). LC-MS (Method A): r.t. 0.73 min, MS (ESI) m/z=503.26 [M+H]⁺.

Intermediate 315: 6-(6-chloro-2-methyl-1,3-benzoxazol-4-yl)-N-[(2,4-dimethoxyphenyl)methyl]-4-methylphthalazin-1-amine

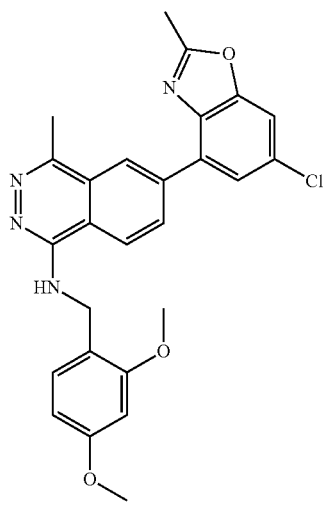 [SMILES: COc1ccc(CNc2nnc(C)c3cc(-c4cc(Cl)cc5oc(C)nc45)ccc23)c(OC)c1]

A mixture [1-[(2,4-dimethoxyphenyl)methylamino]-4-methylphthalazin-6-yl]boronic acid (245.02 mg, 0.620 mmol) and 4-bromo-6-chloro-2-methyl-1,3-benzoxazole (114.0 mg, 0.420 mmol) in 1,2-dimethoxyethane (2.7 mL) and aqueous 2N sodium carbonate solution (0.21 mL, 0.420 mmol) was degassed for 10 min with Ar. [1,1'-Bis(di-tert-butylphosphino)ferrocene]dichloropalladium(II) (27.21 mg, 0.040 mmol) was added and the mixture was degassed for 10 min then stirred at 85° C. for 6 hours. The reaction mixture was cooled to room temperature and filtered over Celite, washing with EtOAc and the solvent was evaporated. The residue was purified by column chromatography (KP-C18-HS, 30 g) eluting with a gradient of CH$_3$CN (+0.1% of HCOOH) in water (+0.1% of HCOOH) from 2% to 50% to give 6-(6-chloro-2-methyl-1,3-benzoxazol-4-yl)-N-[(2,4-dimethoxyphenyl)methyl]-4-methylphthalazin-1-amine (86 mg, 0.181 mmol, 43.5% yield) as a brownish foam. ¹H NMR (400 MHz, DMSO-d$_6$) δ 2.71 (s, 3H), 2.77 (s, 3H), 3.74 (s, 3H), 3.86 (s, 3H), 4.69 (d, J=5.28 Hz, 2H), 6.44 (dd, J=8.36, 2.42 Hz, 1H), 6.59 (d, J=2.42 Hz, 1H), 7.15 (d, J=8.36 Hz, 1H), 7.64 (t, J=5.50 Hz, 1H), 7.95-8.01 (m, 2H), 8.48-8.54 (m, 2H), 8.61 (s, 1H). LC-MS (Method A): r.t. 0.86 min, MS (ESI) m/z=375.2 [M+H]⁺.

Intermediate 316: 5-(2-bromo-4-chlorophenoxy)piperidin-2-one

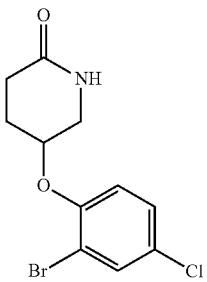 [SMILES: O=C1CCC(Oc2ccc(Cl)cc2Br)CN1]

Triphenylphosphine (417.24 mg, 1.59 mmol) was added to a solution of 2-bromo-4-chlorophenol (300.0 mg, 1.45 mmol), diisopropyl azodicarboxylate (0.31 mL, 1.59 mmol) and 5-hydroxypiperidin-2-one (199.79 mg, 1.74 mmol) in THF (2.892 mL) at room temperature. The resulting mixture was stirred at room temperature for 30 minutes then evaporated in vacuo. The residue was purified by flash chromatography (KP-Sil silica gel, SNAP 50) eluting with a gradient of DCM in cyclohexane from 5% to 40% to give 5-(2-bromo-4-chlorophenoxy)piperidin-2-one (400 mg, 1.313 mmol, 90.8% yield) as a colourless oil. ¹H NMR (400 MHz, DMSO-d$_6$) δ 1.97-2.07 (m, 2H), 2.15-2.26 (m, 1H), 2.29-2.41 (m, 1H), 3.26-3.35 (m, 1H obscured by water signal), 3.44 (ddd, J=13.45, 3.60, 1.48 Hz, 1H), 4.90 (quin, J=3.73 Hz, 1H), 7.28 (d, J=8.91 Hz, 1H), 7.38 (s, 1H), 7.42 (dd, J=8.85, 2.59 Hz, 1H), 7.71 (d, J=2.56 Hz, 1H). LC-MS (Method A): r.t. 0.90 min, MS (ESI) m/z=304.0 and 306.0 [M+H]⁺.

Intermediate 317: 5-[4-chloro-2-[4-[(2,4-dimethoxyphenyl)methylamino]cinnolin-7-yl]phenoxy]piperidin-2-one

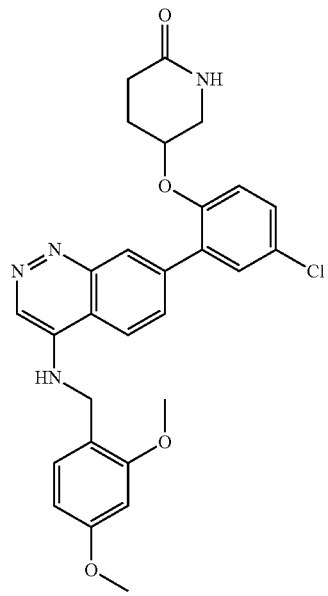 [SMILES: COc1ccc(CNc2cnnc3cc(-c4cc(Cl)ccc4OC4CCC(=O)NC4)ccc23)c(OC)c1]

A mixture of 5-(2-bromo-4-chlorophenoxy)piperidin-2-one (150.0 mg, 0.490 mmol), N-[(2,4-dimethoxyphenyl)methyl]-7-(4,4,5,5-tetramethyl-1,3,2-dioxaborolan-2-yl)cinnolin-4-amine (311.23 mg, 0.740 mmol) in 1,2- dimethoxyethane (4.9 mL) and aqueous 2N sodium carbonate solution (492.5 uL, 0.980 mmol) was degassed for 10 minutes with $N_2$. Then [1,1'-bis(di-tert-butylphosphino)ferrocene]dichloropalladium(II) (32.2 mg, 0.050 mmol) was added and the resulting reaction mixture was stirred at 75° C. for four hours. The reaction mixture was cooled to room temperature and filtered over Celite, washing with EtOAc. The filtrate was evaporated and the residue was purified by column chromatography (KP-NH silica gel, SNAP 28) eluting with a gradient of EtOAc in cyclohexane from 10% to 100% to give 5-[4-chloro-2-[4-[(2,4-dimethoxyphenyl)methylamino]cinnolin-7-yl]phenoxy]piperidin-2-one (170 mg, 0.328 mmol, 66.51% yield) as a white powder. $^1$H NMR (400 MHz, DMSO-$d_6$) δ 1.91-2.05 (m, 2H), 2.08-2.15 (m, 2H), 3.22-3.35 (m, 1H obscured by water signal), 3.35-3.46 (m, 1H), 3.74 (s, 3H), 3.86 (s, 3H), 4.57 (d, J=5.34 Hz, 2H), 4.82-4.88 (m, 1H), 6.49 (dd, J=8.43, 2.39 Hz, 1H), 6.63 (d, J=2.38 Hz, 1H), 7.18 (d, J=8.36 Hz, 1H), 7.26-7.37 (m, 2H), 7.48 (dd, J=8.86, 2.69 Hz, 1H), 7.57 (d, J=2.71 Hz, 1H), 7.79 (dd, J=8.82, 1.79 Hz, 1H), 8.14 (s, 1H), 8.37 (d, J=8.88 Hz, 1H), 8.48-8.57 (m, 2H). LC-MS (Method A): r.t. 0.74 min, MS (ESI) m/z=519.2 [M+H]$^+$.

Intermediate 318: tert-butyl 2-(2-bromo-4-chlorophenyl)acetate

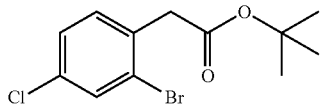 [SMILES: CC(C)(C)OC(=O)Cc1ccc(Cl)cc1Br]

2-(2-Bromo-4-chlorophenyl)acetic acid (3.0 g, 12.02 mmol), di-tert-butyl dicarbonate (5.51 g, 25.25 mmol) and N,N-dimethyl-4-pyridinamine (440.71 mg, 3.61 mmol) were dissolved in tert-butanol (28 mL). The mixture was stirred at 30° C. for 7 hours. The solvent was evaporated under reduced pressure and the residue was purified by column chromatography (Sfar D, 50 g) eluting with a gradient of EtOAc in cyclohexane from 0% to 10% to give tert-butyl 2-(2-bromo-4-chlorophenyl)acetate (3.5 g, 11.45 mmol, 95.25% yield) as a light yellow oil. $^1$H NMR (400 MHz, DMSO-$d_6$) δ 1.40 (s, 9H), 3.71 (s, 2H), 7.42 (d, J=8.36 Hz, 1H), 7.45 (dd, J=8.14, 1.98 Hz, 1H), 7.74 (d, J=1.97 Hz, 1H). LC-MS (Method A): r.t. 1.40 min, MS (ESI) m/z=248.9 and 250.9 [M-tBu+H]$^+$.

Intermediate 319: tert-butyl 2-{4-chloro-2-[(1S,2S,6R,8S)-2,9,9-trimethyl-3,5-dioxa-4-boratricyclo[6.1.1.0$^{2,6}$]decan-4-yl]phenyl}acetate

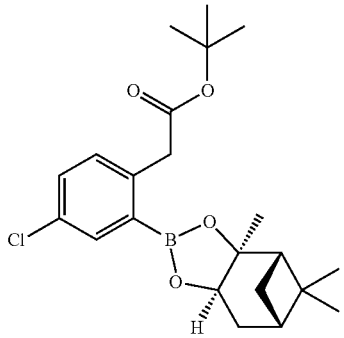 [SMILES: CC(C)(C)OC(=O)Cc1ccc(Cl)cc1B1O[C@@H]2C[C@@H]3C[C@@H](C3(C)C)[C@]2(C)O1]

tert-Butyl 2-(2-bromo-4-chlorophenyl)acetate (1.36 g, 4.45 mmol), potassium acetate (2.206 g, 22.25 mmol) and bis[(+)-pinanediolato]diboron (4.781 g, 13.35 mmol) were mixed in 1,4-dioxane (22 mL) and the solution was degassed for 10 min under argon. Then [1,1'-bis(diphenylphosphino)ferrocene]dichloropalladium(II) (326.52 mg, 0.450 mmol) was added and the mixture was heated at 100° C. for 3 hours. The mixture was allowed to cool to room temperature and filtered over Celite, washing with EtOAc. The filtrate was concentrated under reduced pressure and the residue was purified by column chromatography (Sfar D, 50 g) eluting with a gradient of EtOAc in cyclohexane from 0% to 10% to give tert-butyl 2-{4-chloro-2-[(1S,2S,6R,8S)-2,9,9-trimethyl-3,5-dioxa-4-boratricyclo[6.1.1.0$^{2,6}$]decan-4-yl]phenyl}acetate in a mixture with pinanediolate containing side-products (3.3 g) as a white solid. This crude material was used in the next step without further purification. LC-MS (Method A): r.t. 1.70 min, MS (ESI) m/z of product not observed due to poor ionization.

Intermediate 320: 3-bromo-5-chlorobenzene-1,2-diol

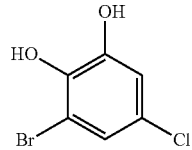

To a stirred suspension of 3-bromo-5-chloro-2-hydroxybenzaldehyde (2.5 g, 10.62 mmol) in 0.5 M aqueous sodium hydroxide solution (25.48 mL, 12.74 mmol) at 40° C. was added dropwise 35% hydrogen peroxide solution (1.26 mL, 11.15 mmol) over a period of 15 minutes. The reaction mixture was stirred at 40° C. for 12 hours, then it was cooled to room temperature, diluted with 1M aqueous NaOH solution and washed with diethyl ether. The aqueous layer was acidified to pH 2 with 2N HCl solution and extracted with Et$_2$O. The organic extracts were combined, washed with brine, dried over Na$_2$SO$_4$, filtered and concentrated in vacuo to afford 3-bromo-5-chlorobenzene-1,2-diol (2.25 g, 10.07 mmol, 94.84% yield) as a red/brown solid. $^1$H NMR (400 MHz, DMSO-$d_6$) δ 6.79 (d, J=2.47 Hz, 1H), 6.98 (d, J=2.50 Hz, 1H), 9.37 (s, 1H), 10.26 (s, 1H). LC-MS (Method A): r.t. 0.91 min, MS (ESI) m/z=221.05 and 223.09 [M+H]$^+$.

Intermediate 321: 4-bromo-6-chloro-1,3-benzodioxole-2-thione

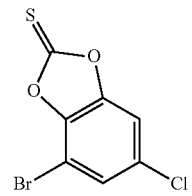 [SMILES: S=c1oc2cc(Cl)cc(Br)c2o1]

3-Bromo-5-chlorobenzene-1,2-diol (1.25 g, 5.59 mmol) and carbonothioic dichloride (0.46 mL, 6.04 mmol) were combined in chloroform (7.5 mL) at 0° C. and treated dropwise over 20 min with 10% sodium hydroxide solution in water (895.05 mg, 22.38 mmol) with vigorous stirring. After stirring for 12 hours at room temperature, the chloroform was removed under vacuo and the solid that formed was filtered off and dried in an oven to give 4-bromo-6-chloro-1,3-benzodioxole-2-thione (1.15 g, 4.331 mmol, 77.43% yield) as a brownish solid. This material was used in the next step without further purification. $^1$H NMR (400 MHz, DMSO-$d_6$) δ 7.82 (d, J=1.92 Hz, 1H), 7.92 (d, J=1.90

Hz, 1H). LC-MS (Method A): r.t. 1.26 min, MS (ESI) m/z of product not observed due to poor ionization.

Intermediate 322:
4-bromo-6-chloro-2,2-difluoro-1,3-benzodioxole

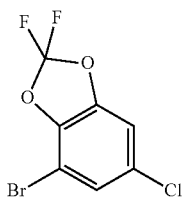 [SMILES: FC1(F)Oc2cc(Cl)cc(Br)c2O1]

4-Bromo-6-chloro-1,3-benzodioxole-2-thione (1.1 g, 4.14 mmol) was dissolved in DCM (41 mL). The solution was cooled to −40° C. and pyridine hydrofluoride (4.18 mL, 41.43 mmol) was added. Then 1-iodopyrrolidine-2,5-dione (2.98 g, 13.26 mmol) was added portionwise. The reaction was warmed from −40 to 0° C. over 30 min. The cooling bath was removed and the reaction mixture was allowed to warm to 25° C. over 30 min and stirred for 3 hours. The reaction mixture was treated with $Na_2S_2O_3$ in water and stirred for 15 min. The mixture was further diluted with water to dissolve solids. The organic phase was washed with brine, filtered over a hydrophobic frit (Phase Separator) and concentrated. The residue was purified by column chromatography (KP-NH silica gel, SNAP 28) eluting with a gradient of EtOAc in cyclohexane from 0% to 10% to give 4-bromo-6-chloro-2,2-difluoro-1,3-benzodioxole (700 mg, 2.579 mmol, 62.25% yield) as a yellow oil. $^1$H NMR (400 MHz, DMSO-$d_6$) δ 7.64 (d, J=1.95 Hz, 1H), 7.72 (d, J=1.95 Hz, 1H). $^{19}$F NMR (377 MHz, DMSO-$d_6$) δ −48.32. LC-MS (Method A): r.t. 1.34 min, MS (ESI) m/z of product not observed due to poor ionization Intermediate 323: 7-(6-chloro-2,2-difluoro-1,3-benzodioxol-4-yl)-N-[(2,4-dimethoxyphenyl)methyl]cinnolin-4-amine

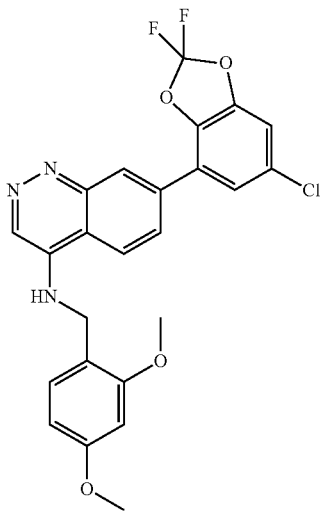 [SMILES: COc1ccc(CNc2cnnc3cc(-c4cc(Cl)cc5c4OC(F)(F)O5)ccc23)c(OC)c1]

A mixture of 4-bromo-6-chloro-2,2-difluoro-1,3-benzodioxole (160 mg, 0.590 mmol), N-[(2,4-dimethoxyphenyl) methyl]-7-(4,4,5,5-tetramethyl-1,3,2-dioxaborolan-2-yl)cinnolin-4-amine (322.84 mg, 0.770 mmol) and aqueous 2 N sodium carbonate solution (0.59 mL, 1.18 mmol) in 1,2-dimethoxyethane (6.07 mL) was degassed for 10 min under $N_2$. Then [1,1'-bis(di-tert-butylphosphino)ferrocene]dichloropalladium(II) (38.54 mg, 0.060 mmol) was added and the resulting reaction mixture was stirred at 80° C. for 8 hours. The mixture was filtered over a pad of Celite, washing with MeOH. The filtrate was concentrated in vacuo and the residue was purified by column chromatography (KP-NH silica gel, SNAP 28) eluting with a gradient of EtOAc in cyclohexane from 0% to 40% to give 7-(6-chloro-2,2-difluoro-1,3-benzodioxol-4-yl)-N-[(2,4-dimethoxyphenyl)methyl]cinnolin-4-amine (202 mg, 0.416 mmol, 70.53% yield) as an orange oil. $^1$H NMR (400 MHz, DMSO-$d_6$) δ 3.74 (s, 3H), 3.87 (s, 3H), 4.53 (d, J=5.59 Hz, 2H), 6.48 (dd, J=8.38, 2.40 Hz, 1H), 6.63 (d, J=2.38 Hz, 1H), 7.16 (d, J=8.37 Hz, 1H), 7.76 (d, J=1.98 Hz, 1H), 7.84 (d, J=2.20 Hz, 1H), 8.02 (dd, J=8.83, 1.96 Hz, 1H), 8.14 (t, J=5.95 Hz, 1H), 8.44-8.55 (m, 3H). LC-MS (Method A): r.t. 0.89 min, MS (ESI) m/z=486.17 [M+H]$^+$.

Intermediate 324: 6-bromo-N-[(2,4-dimethoxyphenyl)methyl]quinolin-4-amine Formic Acid Salt

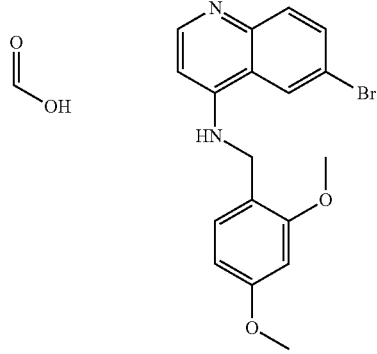 [SMILES: O=CO ; COc1ccc(CNc2ccnc3ccc(Br)cc23)c(OC)c1]

(2,4-Dimethoxyphenyl)methanamine (2.48 mL, 16.49 mmol) was added to a stirred solution of 6-bromo-4-chloroquinoline (2.0 g, 8.25 mmol) in EtOH (30 mL). The mixture was stirred overnight at 100° C. Further (2,4-dimethoxyphenyl)methanamine (2.48 mL, 16.49 mmol) was added and the mixture was stirred at 100° C. for another 48 hours, then it was left to reach room temperature. The volatiles were removed and the residue was purified by column chromatography (KP-NH silica gel, SNAP 110 g+110 g in series) eluting with a gradient of EtOAc in cyclohexane from 20% to 100% to give 6 g of partially purified product which was purified further by column chromatography (KP-C18-HS, 120 g+120 g in series) eluting with a gradient of $CH_3CN$ (+0.1% of HCOOH) in water (+0.1% of HCOOH) from 2% to 90% to give 6-bromo-N-[(2,4-dimethoxyphenyl)methyl]quinolin-4-amine formic acid salt (3.688 g, 9.881 mmol, 106.7% yield) as a yellowish foam. $^1$H NMR (400 MHz, DMSO-$d_6$) δ 3.73 (s, 3H), 3.86 (s, 3H), 4.38 (d, J=5.50 Hz, 2H), 6.31 (d, J=5.50 Hz, 1H), 6.45 (dd, J=8.36, 2.42 Hz, 1H), 6.60 (d, J=2.42 Hz, 1H), 7.09 (d, J=8.36 Hz, 1H), 7.67-7.79 (m, 3H), 8.15 (s, 1H from HCOOH), 8.33 (d, J=5.28 Hz, 1H), 8.59 (s, 1H). LC-MS (Method A): r.t. 0.76 min, MS (ESI) m/z=373.1 and 375.1 [M+H]$^+$.

Intermediate 325: 6-(5-chloro-2-methoxyphenyl)-N-[(2,4-dimethoxyphenyl)methyl]quinolin-4-amine

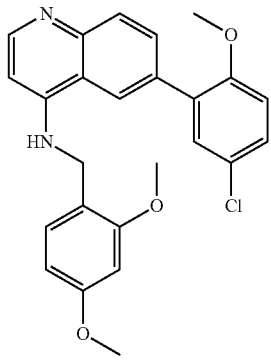 [SMILES: COc1ccc(CNc2ccnc3ccc(-c4cc(Cl)ccc4OC)cc23)c(OC)c1]

A mixture of 6-bromo-N-[(2,4-dimethoxyphenyl)methyl] quinolin-4-amine formic acid salt (600.0 mg, 1.43 mmol) and 5-chloro-2-methoxyphenylboronic acid (329.61 mg, 1.77 mmol) in 1,2-dimethoxyethane (15.3 mL) and aqueous 2N sodium carbonate solution (1.61 mL, 3.22 mmol) was degassed for 10 min with Ar. [1,1'-Bis(di-tert-butylphosphino)ferrocene]dichloropalladium(II) (105.09 mg, 0.160 mmol) was added and the mixture was degassed for 10 min then stirred at 80° C. for 1 hour. The reaction mixture was cooled to room temperature and filtered over Celite, washing with EtOAc and the solvent was evaporated. The residue was purified by column chromatography (KP-NH silica gel, SNAP 55 g) eluting with a gradient of EtOAc in cyclohexane from 20% to 60% to give 6-(5-chloro-2-methoxyphenyl)-N-[(2,4-dimethoxyphenyl)methyl]quinolin-4-amine (590 mg, 1.357 mmol, 94.9% yield) as a brownish solid. $^1$H NMR (400 MHz, DMSO-$d_6$) δ 3.72 (s, 3H), 3.80 (s, 3H), 3.86 (s, 3H), 4.40 (d, J=5.72 Hz, 2H), 6.27 (d, J=5.28 Hz, 1H), 6.44 (dd, J=8.25, 2.31 Hz, 1H), 6.60 (d, J=2.20 Hz, 1H), 7.10 (d, J=8.36 Hz, 1H), 7.18 (d, J=8.80 Hz, 1H), 7.41-7.45 (m, 1H), 7.48 (d, J=2.64 Hz, 1H), 7.71-7.77 (m, 3H), 8.31 (d, J=5.50 Hz, 1H), 8.34 (s, 1H). LC-MS (Method A): r.t. 0.86 min, MS (ESI) m/z=435.2 [M+H]$^+$.

Intermediate 326: 3-bromo-8-chloro-1,7-naphthyridine

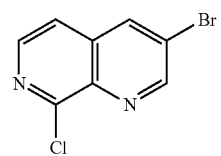 [SMILES: Clc1nccc2cc(Br)cnc12]

A solution of 3-bromo-1,7-naphthyridin-8-ol (390.0 mg, 1.73 mmol) in phosphorus(V) oxychloride (1.29 mL, 13.86 mmol) was stirred at 70° C. for 2 hours. The reaction mixture was cooled to room temperature and concentrated in vacuo. The residue was dissolved in DCM and washed with saturated aqueous NaHCO$_3$ solution and brine. The organic layer was dried over Na$_2$SO$_4$, filtered and concentrated to give 3-bromo-8-chloro-1,7-naphthyridine (400 mg, 1.643 mmol, 94.79% yield) as a brown solid. LC-MS (Method A): r.t. 0.88 min, MS (ESI) m/z=242.9 and 245.0 [M+H]$^+$.

Intermediate 327: 3-bromo-N-[(2,4-dimethoxyphenyl)methyl]-1,7-naphthyridin-8-amine

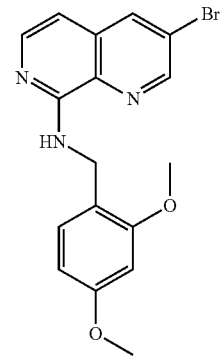 [SMILES: COc1ccc(CNc2nccc3cc(Br)cnc23)c(OC)c1]

(2,4-Dimethoxyphenyl)methanamine (0.74 mL, 4.93 mmol) was added to a solution of 3-bromo-8-chloro-1,7-naphthyridine (400.0 mg, 1.64 mmol) in EtOH (6 mL). The resulting mixture was stirred at 100° C. overnight then evaporated under reduced pressure. The residue was purified by column chromatography (KP-NH silica gel, 55 g) eluting with a gradient of EtOAc in cyclohexane from 0% to 30% to give 3-bromo-N-[(2,4-dimethoxyphenyl)methyl]-1,7-naphthyridin-8-amine (590 mg, 1.577 mmol, 95.97% yield) as a yellow solid. LC-MS (Method A): r.t. 0.69 min, MS (ESI) m/z=374.1 and 376.1 [M+H]$^+$.

Intermediate 328: 3-(5-chloro-2-methoxyphenyl)-N-[(2,4-dimethoxyphenyl)methyl]-1,7-naphthyridin-8-amine

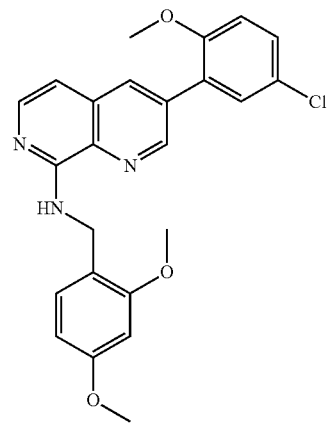 [SMILES: COc1ccc(CNc2nccc3cc(-c4cc(Cl)ccc4OC)cnc23)c(OC)c1]

A mixture of 3-bromo-N-[(2,4-dimethoxyphenyl)methyl]-1,7-naphthyridin-8-amine (290.0 mg, 0.770 mmol) and 5-chloro-2-methoxyphenylboronic acid (173.34 mg, 0.930 mmol) in 1,2-dimethoxyethane (8 mL) and aqueous 2M sodium carbonate solution (0.77 mL, 1.55 mmol) was degassed for 10 min with N$_2$. Then [1,1'-bis(di-tert-butylphosphino)ferrocene]dichloropalladium(II) (50.66 mg, 0.080 mmol) was added and the resulting reaction mixture was stirred at 80° C. for two hours. The mixture was cooled to room temperature and filtered over Celite, washing with MeOH. The filtrate was evaporated and the residue was purified by column chromatography (Sfar Amino D, 11 g)

eluting with a gradient of EtOAc in cyclohexane from 0% to 25% to give 3-(5-chloro-2-methoxyphenyl)-N-[(2,4-dimethoxyphenyl)methyl]-1,7-naphthyridin-8-amine (160 mg, 0.367 mmol, 47.37% yield). ¹H NMR (400 MHz, DMSO-d₆) δ 3.74 (s, 3H), 3.83 (s, 3H), 3.85 (s, 3H), 4.65 (d, J=6.09 Hz, 2H), 6.44 (dd, J=8.34, 2.40 Hz, 1H), 6.59 (d, J=2.38 Hz, 1H), 6.93 (d, J=5.80 Hz, 1H), 7.13 (d, J=8.29 Hz, 1H), 7.24 (d, J=8.89 Hz, 1H), 7.51 (dd, J=8.80, 2.68 Hz, 1H), 7.57 (d, J=2.64 Hz, 1H), 7.67 (t, J=6.09 Hz, 1H), 7.92 (d, J=5.75 Hz, 1H), 8.27 (d, J=2.16 Hz, 1H), 8.90 (d, J=2.12 Hz, 1H). LC-MS (Method A): r.t. 0.87 min, MS (ESI) m/z=436.2 [M+H]⁺.

Intermediate 329: 6-[5-chloro-2-(difluoromethoxy)phenyl]-N-[(2,4-dimethoxyphenyl)methyl]-4-methylphthalazin-1-amine

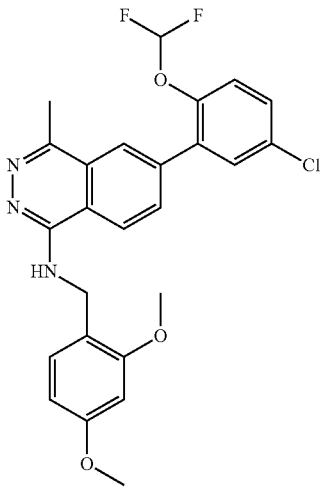 [SMILES: COc1ccc(CNc2nnc(C)c3cc(-c4cc(Cl)ccc4OC(F)F)ccc23)c(OC)c1]

A mixture of 2-bromo-4-chloro-1-(difluoromethoxy)benzene (200.0 mg, 0.780 mmol) and [1-[(2,4-dimethoxyphenyl)methylamino]-4-methylphthalazin-6-yl]boronic acid (365.81 mg, 0.930 mmol) in 1,2-dimethoxyethane (8 mL) and aqueous 2M sodium carbonate solution (0.78 mL, 1.55 mmol) was degassed for 10 min with N₂. Then [1,1'-bis(di-tert-butylphosphino)ferrocene]dichloropalladium(II) (50.79 mg, 0.080 mmol) was added and the resulting reaction mixture was stirred at 80° C. for four hours. The mixture was cooled to room temperature and filtered over Celite, washing with MeOH. The filtrate was evaporated and the residue was purified by column chromatography (Sfar Amino D, 11 g) eluting with a gradient of EtOAc in cyclohexane from 0% to 50% to give 6-[5-chloro-2-(difluoromethoxy)phenyl]-N-[(2,4-dimethoxyphenyl)methyl]-4-methylphthalazin-1-amine (100 mg, 0.206 mmol, 26.49% yield) as a yellow solid. ¹H NMR (400 MHz, DMSO-d₆) δ 2.70 (s, 3H), 3.73 (s, 3H), 3.85 (s, 3H), 4.67 (d, J=5.61 Hz, 2H), 6.44 (dd, J=8.36, 2.42 Hz, 1H), 6.59 (d, J=2.42 Hz, 1H), 7.13 (d, J=8.28 Hz, 1H), 7.24 (t, J=73.51 Hz, 1H), 7.41 (d, J=8.80 Hz, 1H), 7.58-7.68 (m, 2H), 7.77 (d, J=2.65 Hz, 1H), 8.00 (dd, J=8.55, 1.79 Hz, 1H), 8.09 (d, J=1.74 Hz, 1H), 8.45 (d, J=8.61 Hz, 1H). LC-MS (Method A): r.t. 0.86 min, MS (ESI) m/z=486.2 [M+H]⁺.

Intermediate 330: (1R,2S)-1,2-dimethylcyclopentane-1,2-diol

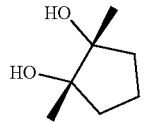

Titanium (IV) chloride (805.22 uL, 4.56 mmol) was added dropwise to a suspension of zinc (596.82 mg, 9.13 mmol) in THF (13.5 mL) under an argon atmosphere and the mixture was refluxed for 1 hour. Heptane-2,6-dione (900.0 mg, 7.02 mmol) in THF (4.5 mL) was added and the resulting mixture was stirred overnight at room temperature. The mixture was quenched with water and then filtered over a pad of Celite. The filtrate was extracted with EtOAc, and the organic phases were combined and washed with brine, dried over Na₂SO₄, filtered and evaporated in vacuo. The residue was purified by column chromatography (KP-Sil silica gel, 2×SNAP 25 g in series) eluting with a gradient of EtOAc in cyclohexane from 5% to 50% to give (1R,2S)-1,2-dimethylcyclopentane-1,2-diol (229 mg, 1.759 mmol, 25.05% yield) as a colourless oil. ¹H NMR (400 MHz, DMSO-d₆) δ 1.03 (s, 6H), 1.32-1.65 (m, 4H), 1.72-1.79 (m, 2H), 3.97 (s, 2H).

Intermediate 331: 1-bromo-5-chloro-2-methoxy-4-methylbenzene

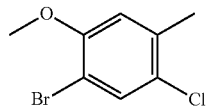

1-Bromopyrrolidine-2,5-dione (2.95 g, 16.6 mmol) was added to a stirred solution of 4-chloro-3-methylanisole in THF (17.9 mL) and the mixture was stirred at room temperature for 48 hours. The mixture was diluted with DCM, then an aqueous solution of sodium thiosulfate was added and the mixture was stirred for 30 minutes at room temperature. The organic phase filtered over a hydrophobic frit (Phase Separator) and evaporated. The residue was purified by column chromatography (KP-Sil, SNAP 100 g) eluting with a gradient of EtOAc in cyclohexane from 0% to 20%. Product containing fractions were collected to give 1.769 g of a pale yellow oil. ¹H NMR analysis of the isolated material is consistent with a ~60:20:20 mixture of 1-bromo-5-chloro-2-methoxy-4-methylbenzene, the regioisomeric product 2-bromo-4-chloro-1-methoxy-3-methylbenzene and unreacted 4-chloro-3-methylanisole. This mixture was used in the next step without further purification. ¹H NMR (400 MHz, DMSO-d₆) only signals from 1-bromo-5-chloro-2-methoxy-4-methylbenzene are reported δ 2.31 (s, 3H), 3.85 (s, 3H), 7.15 (s, 1H), 7.62 (s, 1H). LC-MS (Method A): r.t. 0.1.31 min, MS (ESI) m/z of product not observed due to poor ionization.

Intermediate 332: 2-(5-chloro-2-methoxy-4-methylphenyl)-4,4,5,5-tetramethyl-1,3,2-dioxaborolane

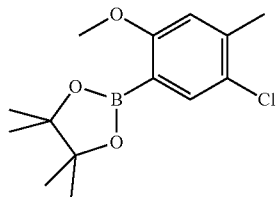 [SMILES: COc1cc(C)c(Cl)cc1B1OC(C)(C)C(C)(C)O1]

[1,1'-Bis(diphenylphosphino)ferrocene]dichloropalladium(II) (548.32 mg, 0.750 mmol), 1-bromo-5-chloro-2-methoxy-4-methylbenzene (1.76 g, ~60% pure), potassium acetate (3.7 g, 37.37 mmol) and 4,4,5,5-tetramethyl-2-(4,4,5,5-tetramethyl-1,3,2-dioxaborolan-2-yl)-1,3,2-dioxaborolane (2.85 g, 11.21 mmol) were dissolved in 1,4-dioxane (32.7 mL) and the mixture was degassed with Ar for 10 minutes. The mixture was then stirred at 105° C. for 24 hours, then filtered over Celite, washing with MeOH. The filtrate was concentrated and the residue was purified by column chromatography (KP-Sil, SNAP 100 g) eluting with a gradient of EtOAc in cyclohexane from 0% to 40%. Product containing fractions were collected to give 1.034 g of a whitish solid. $^1$H NMR analysis of the isolated material is consistent with a ~2:5 mixture of 2-(5-chloro-2-methoxy-4-methylphenyl)-4,4,5,5-tetramethyl-1,3,2-dioxaborolane and 2,3-dimethylbutane-2,3-diol. This mixture was used in the next step without further purification. $^1$H NMR (400 MHz, DMSO-$d_6$) only signals from 2-(5-chloro-2-methoxy-4-methylphenyl)-4,4,5,5-tetramethyl-1,3,2-dioxaborolane are reported δ 1.27 (m, 12H), 2.34 (s, 3H), 3.74 (s, 3H), 6.99 (s, 1H), 7.44 (s, 1H). LC-MS (Method A): r.t. 1.36 min, MS (ESI) m/z=238.2 [M+H]$^+$.

Intermediate 333: 7-(5-chloro-2-methoxy-4-methylphenyl)-N-[(2,4-dimethoxyphenyl)methyl]cinnolin-4-amine

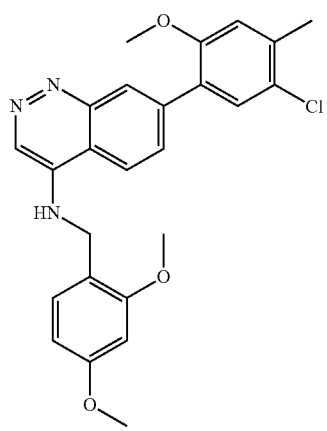 [SMILES: COc1ccc(CNc2cnnc3cc(-c4cc(Cl)c(C)cc4OC)ccc23)c(OC)c1]

A mixture of 7-bromo-N-[(2,4-dimethoxyphenyl)methyl]cinnolin-4-amine (1.0 g, 2.14 mmol) and 2-(5-chloro-2-methoxy-4-methylphenyl)-4,4,5,5-tetramethyl-1,3,2-dioxaborolane (820.32 mg) in 1,2-dimethoxyethane (20 mL) and aqueous 2N sodium carbonate solution (1068.86 uL, 2.14 mmol), was degassed for 10 min with Ar. [1,1'-Bis(di-tert-butylphosphino)ferrocene]dichloropalladium(II) (139.76 mg, 0.210 mmol) was added and the mixture was degassed for 10 min then stirred overnight at 80° C. The reaction mixture was cooled to room temperature and filtered over Celite, washing with EtOAc and MeOH and the solvent was evaporated. The residue was purified by column chromatography (KP-NH silica gel, SNAP 110 g) eluting with a gradient of EtOAc in cyclohexane from 20% to 100% to give 7-(5-chloro-2-methoxy-4-methylphenyl)-N-[(2,4-dimethoxyphenyl)methyl]cinnolin-4-amine (337 mg, 0.749 mmol, 35.04% yield) as a yellow powder. $^1$H NMR (400 MHz, DMSO-$d_6$) δ 2.42 (s, 3H), 3.75 (s, 3H), 3.83 (s, 3H), 3.89 (s, 3H), 4.52 (d, J=5.94 Hz, 2H), 6.48 (dd, J=8.36, 2.42 Hz, 1H), 6.64 (d, J=2.42 Hz, 1H), 7.13-7.18 (m, 1H), 7.22 (s, 1H), 7.50 (s, 1H), 7.76 (dd, J=8.80, 1.76 Hz, 1H), 8.02 (t, J=5.94 Hz, 1H), 8.17 (d, J=1.76 Hz, 1H), 8.35 (d, J=8.80 Hz, 1H), 8.47 (s, 1H). LC-MS (Method A): r.t. 0.88 min, MS (ESI) m/z=450.3 [M+H]$^+$.

Intermediate 334: tricyclo[3.3.1.0$^{3,7}$]nonane-3,7-diol

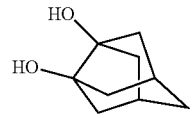

Titanium (IV) chloride (92.4 uL, 0.840 mmol) was added dropwise to a suspension of zinc (111.69 mg, 1.71 mmol) in THF (3 mL) under an argon atmosphere and the mixture was refluxed for 1 hour. Bicyclo[3.3.1]nonane-3,7-dione (200.0 mg, 1.31 mmol) in THF (1 mL) was added and the resulting mixture was stirred overnight at 50° C. The mixture was quenched with water and then filtered over a pad of Celite. The filtrate was extracted with EtOAc, and the organic phases were combined and washed with brine, dried over Na$_2$SO$_4$, filtered and evaporated in vacuo. The residue was purified by column chromatography (KP-Sil silica gel, 2×SNAP 10 g in series) eluting with a gradient of EtOAc in cyclohexane from 5% to 30% to give three batches of tricyclo[3.3.1.0$^{3,7}$]nonane-3,7-diol (32 mg, 0.208 mmol, 15.79% yield, 19 mg, 0.123 mmol, 9.376% yield and 23 mg, 0.149 mmol, 11.35% yield) as white solids. $^1$H NMR (400 MHz, DMSO-$d_6$) δ 1.36 (s, 2H), 1.65-1.72 (m, 4H), 1.72-1.79 (m, 4H), 2.12 (br. s, 2H), 4.32 (s, 2H).

Intermediate 335: cyclooctane-1,5-diol

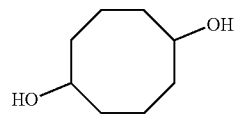

A 1.0 M solution of borane-THF complex (1:1) in THF (10 mL, 10 mmol) was cooled to 0° C. in a dried flask fitted with a condenser and a dropping funnel. To this cooled solution was slowly added a solution of (1Z,5Z)-cycloocta-1,5-diene (1.13 mL, 9.24 mmol) in THF (2 mL). After addition was complete, the clear solution was refluxed for 1 h then allowed to cool to room temperature. To this mixture was slowly added 3 M aqueous sodium hydroxide solution (3 mL, 9 mmol), followed by 35% hydrogen peroxide solution (2 mL, 9.24 mmol) which was added dropwise at a rate which caused the solution to reflux gently. The mixture was allowed to cool to room temperature for 30 minutes and saturated with solid potassium carbonate. The layers were separated and the aqueous phase was extracted with DCM. The combined organic layers were filtered through a hydrophobic frit (Phase Separator) and evaporated to give cyclooctane-1,5-diol (1.33 g, 9.22 mmol, 99.77% yield) as a cloudy oil. $^1$H NMR (400 MHz, Chloroform-d) δ 1.26-1.98 (m, 12H), 3.60-3.72 (m, 1H), 3.76-3.87 (m, 1H).

Intermediate 336: cyclooctane-1,5-dione

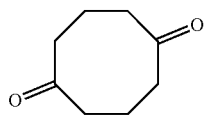

Cyclooctane-1,5-diol (1.33 g, 9.22 mmol) was dissolved in DCM (60 mL) in a flask equipped with a condenser. To this solution was cautiously added pyridine trioxochromium hydrochloride (13.0 g, 60.31 mmol) in small portions with stirring. The solution became black and was refluxed at 40° C. for 24 hours. The black mixture was cooled and filtered over a Gooch funnel packed with silica-gel/Florisil (1:1) washing with cyclohexane and then with cyclohexane/EtOAc (1:1). The filtrate was evaporated to give cyclooctane-1,5-dione (496 mg, 3.538 mmol, 38.37% yield) as a semi-solid opalescent mass. $^1$H NMR (400 MHz, Chloroform-d) δ 2.13-2.21 (m, 4H), 2.49-2.58 (m, 8H).

Intermediate 337: 1,2,3,4,5,6-hexahydropentalene-3a,6a-diol

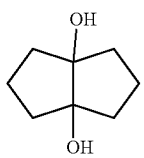

Titanium (IV) chloride (61.35 uL, 0.350 mmol) was added dropwise to a suspension to a suspension of zinc (45.47 mg, 0.700 mmol) in THF (1 mL) under an argon atmosphere and the mixture was heated to reflux for 1 hour. Then a solution of cyclooctane-1,5-dione (75 mg, 0.540 mmol) in THF (350 uL) was added and the resulting mixture was stirred at room temperature overnight. The mixture was quenched with water and then filtered over Celite. The filtrate was extracted with EtOAc, and the organic phases were combined and washed with brine, dried over Na$_2$SO$_4$, filtered and evaporated in vacuo. The residue was purified by column chromatography (KP-Sil silica gel, SNAP 25) eluting with a gradient of EtOAc in cyclohexane from 0% to 60% to give crude 1,2,3,4,5,6-hexahydropentalene-3a,6a-diol (76 mg, 0.540 mmol, 100% yield) as a colorless oil. This material was used in the next step without further purification. $^1$H NMR (400 MHz, Chloroform-d) δ 1.36-1.96 (m, 12H).

Intermediate 338: (2-chloro-5-methoxyphenyl)methanol

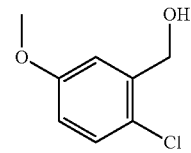

Sodium borohydride (620.93 mg, 16.41 mmol) was added portionwise to a solution of 2-chloro-5-methoxybenzaldehyde (2.0 g, 11.72 mmol) in EtOH (58 mL). The reaction mixture was stirred for 1.5 hours at room temperature. 1N Hydrochloric acid solution was added and the resulting aqueous mixture was extracted 3 times with DCM. The combined organic phases were washed with brine, filtered over a hydrophobic frit (Phase Separator) and evaporated in vacuo. The residue was purified by column chromatography (KP-Sil silica gel, SNAP 100) eluting with a gradient of EtOAc in cyclohexane from 0% to 30% to give (2-chloro-5-methoxyphenyl)methanol (1.32 g, 7.647 mmol, 65.23% yield) as a pale-yellow oil. $^1$H NMR (400 MHz, DMSO-d$_6$) δ 3.76 (s, 3H), 4.51 (d, J=5.52 Hz, 2H), 5.38 (t, J=5.64 Hz, 1H), 6.83 (dd, J=8.71, 3.15 Hz, 1H), 7.10 (d, J=3.12 Hz, 1H), 7.28 (d, J=8.66 Hz, 1H). LC-MS (Method A): r.t. 0.80 min, MS (ESI) m/z of product not observed due to poor ionization.

Intermediate 339: 1-chloro-4-methoxy-2-(methoxymethyl)benzene

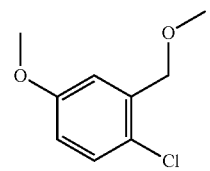

Sodium hydride (60% dispersion in mineral oil, 361.51 mg, 9.04 mmol) was added portionwise to a solution of (2-chloro-5-methoxyphenyl)methanol (1.3 g, 7.53 mmol) in THF (25 mL) at 0° C. The mixture was stirred at 0° C. for 1 hour, then iodomethane (1.41 mL, 22.59 mmol) was added and the reaction was stirred at room temperature for 2 hours. The reaction mixture was quenched with a saturated aqueous solution of NH$_4$Cl and extracted with EtOAc three times. The combined organic phases were washed with brine, dried over Na$_2$SO$_4$, filtered and concentrated in vacuo. The residue was purified by column chromatography (KP-Sil silica gel, SNAP 100) eluting with a gradient of EtOAc in cyclohexane from 0% to 25% to give 1-chloro-4-methoxy-2-(methoxymethyl)benzene (1.29 g, 6.912 mmol, 91.77% yield) as a pale-yellow oil. $^1$H NMR (400 MHz, DMSO-d$_6$) δ 3.37 (s, 3H), 3.77 (s, 3H), 4.45 (s, 2H), 6.90 (dd, J=8.76, 3.14 Hz, 1H), 7.03 (d, J=3.13 Hz, 1H), 7.35 (d, J=8.77 Hz, 1H). LC-MS (Method A): r.t. 1.07 min, MS (ESI) m/z of product not observed due to poor ionization.

Intermediate 340: 1-bromo-5-chloro-2-methoxy-4-(methoxymethyl)benzene

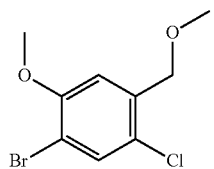

Molecular bromine (150.99 uL, 2.95 mmol) was added dropwise to a stirred suspension of 1-chloro-4-methoxy-2-(methoxymethyl)benzene (500.0 mg, 2.68 mmol) in acetic acid (7 mL) at 0° C. The reaction mixture was stirred at room temperature for 1 hour. DCM was added and the mixture was quenched with saturated sodium thiosulfate solution, filtered over a hydrophobic frit (Phase Separator). The filtrate was and evaporated and the residue was purified by column chromatography (KP-Sil silica gel, SNAP 25) eluting with a gradient of EtOAc in cyclohexane from 0% to 25% to give 1-bromo-5-chloro-2-methoxy-4-(methoxymethyl)benzene (450 mg, 1.695 mmol, 63.26% yield) as a white powder. $^1$H NMR (400 MHz, DMSO-d$_6$) δ 3.38 (s, 3H), 3.87 (s, 3H), 4.45 (d, J=0.61 Hz, 2H), 7.18 (s, 1H), 7.69 (s, 1H). LC-MS (Method A): r.t. 1.23 min, MS (ESI) m/z=272.9 and 274.9 [M+H]$^+$.

Intermediate 341: 7-[5-chloro-2-methoxy-4-(methoxymethyl)phenyl]-N-[(2,4-dimethoxyphenyl)methyl]cinnolin-4-amine

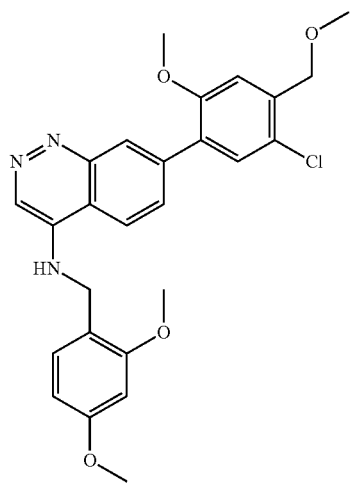 [SMILES: COCc1cc(OC)c(-c2ccc3c(NCc4ccc(OC)cc4OC)cnnc3c2)cc1Cl]

A mixture of 1-bromo-5-chloro-2-methoxy-4-(methoxymethyl)benzene (175.0 mg, 0.660 mmol), N-[(2,4-dimethoxyphenyl)methyl]-7-(4,4,5,5-tetramethyl-1,3,2-dioxaborolan-2-yl)cinnolin-4-amine (360.96 mg, 0.860 mmol) and aqueous 2 N sodium carbonate solution (0.66 mL, 1.32 mmol) in 1,2-dimethoxyethane (7 mL) was degassed for 10 min under N$_2$. Then [1,1'-bis(di-tert-butylphosphino)ferrocene]dichloropalladium(II) (43.09 mg, 0.070 mmol) was added and the resulting reaction mixture was stirred at 80° C. for 7 hours. The mixture was filtered over a pad of Celite, washing with MeOH. The filtrate was concentrated in vacuo and the residue was purified by column chromatography (KP-Sil silica gel, SNAP 50) eluting with a gradient of MeOH in DCM from 0% to 10% to give 7-[5-chloro-2-methoxy-4-(methoxymethyl)phenyl]-N-[(2,4-dimethoxyphenyl)methyl]cinnolin-4-amine (215 mg, 0.448 mmol, 67.97% yield) as an orange oil. $^1$H NMR (400 MHz, DMSO-d$_6$) δ 3.44 (s, 3H), 3.74 (s, 3H), 3.85 (s, 3H), 3.89 (s, 3H), 4.52 (d, J=5.79 Hz, 2H), 4.56 (s, 2H), 6.48 (dd, J=8.43, 2.40 Hz, 1H), 6.64 (d, J=2.40 Hz, 1H), 7.16 (d, J=8.37 Hz, 1H), 7.28 (s, 1H), 7.55 (s, 1H), 7.78 (dd, J=8.77, 1.84 Hz, 1H), 8.03 (t, J=6.02 Hz, 1H), 8.20 (d, J=1.77 Hz, 1H), 8.37 (d, J=8.87 Hz, 1H), 8.48 (s, 1H). LC-MS (Method A): r.t. 0.84 min, MS (ESI) m/z=480.28 [M+H]$^+$.

Intermediate 342: 7-bromo-5-chloro-2,3-dihydro-1-benzofuran

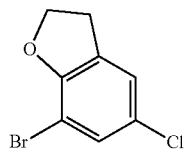 [SMILES: Clc1cc(Br)c2c(c1)CCO2]

Molecular bromine (215.44 uL, 4.2 mmol) was added dropwise to a stirred suspension of 5-chloro-2,3-dihydro-1-benzofuran (500.0 mg, 3.23 mmol) in acetic acid (8 mL) at 0° C. The reaction mixture was stirred at room temperature for 2 hours. DCM was added and the mixture was quenched with saturated sodium thiosulfate solution, filtered over a hydrophobic frit (Phase Separator). The filtrate was evaporated and the residue was purified by column chromatography (KP-Sil silica gel, SNAP 25) eluting with a gradient of EtOAc in cyclohexane from 0% to 35% to give 7-bromo-5-chloro-2,3-dihydro-1-benzofuran (225 mg, 0.964 mmol, 29.79% yield) as a yellow oil. $^1$H NMR (400 MHz, DMSO-d$_6$) δ 3.22-3.36 (m, 2H), 4.65 (t, J=8.81 Hz, 2H), 7.30-7.33 (m, 1H), 7.38-7.42 (m, 1H). LC-MS (Method A): r.t. 1.23 min, MS (ESI) m/z of product not observed due to poor ionization.

Intermediate 343: 7-(5-chloro-2,3-dihydro-1-benzofuran-7-yl)-N-[(2,4-dimethoxyphenyl)methyl]cinnolin-4-amine

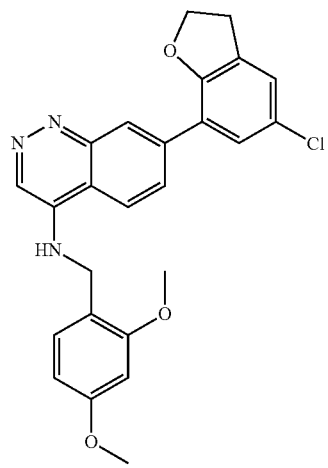 [SMILES: COc1ccc(CNc2cnnc3cc(-c4cc(Cl)cc5c4OCC5)ccc23)c(OC)c1]

A mixture of 7-bromo-5-chloro-2,3-dihydro-1-benzofuran (140.0 mg, 0.600 mmol), N-[(2,4-dimethoxyphenyl)methyl]-7-(4,4,5,5-tetramethyl-1,3,2-dioxaborolan-2-yl)cinnolin-4-amine (328.39 mg, 0.780 mmol) and aqueous 2 N sodium carbonate solution (0.6 mL, 1.2 mmol) in 1,2-dimethoxyethane (6 mL) was degassed for 10 min under $N_2$. Then [1,1'-bis(di-tert-butylphosphino)ferrocene]dichloropalladium(II) (39.2 mg, 0.060 mmol) was added and the resulting reaction mixture was stirred at 80° C. for 7 hours. The mixture was filtered over a pad of Celite, washing with MeOH. The filtrate was concentrated in vacuo and the residue was purified by column chromatography (KP-Sil silica gel, SNAP 50) eluting with a gradient of MeOH in DCM from 0% to 10% to give 7-(5-chloro-2,3-dihydro-1-benzofuran-7-yl)-N-[(2,4-dimethoxyphenyl)methyl]cinnolin-4-amine (145 mg, 0.324 mmol, 53.99% yield) as an orange powder. $^1$H NMR (400 MHz, DMSO-$d_6$) δ 3.27-3.33 (m, 2H), 3.73 (s, 3H), 3.87 (s, 3H), 4.51 (d, J=5.83 Hz, 2H), 4.70 (t, J=8.78 Hz, 2H), 6.47 (dd, J=8.37, 2.41 Hz, 1H), 6.62 (d, J=2.37 Hz, 1H), 7.15 (d, J=8.35 Hz, 1H), 7.34-7.39 (m, 1H), 7.58 (d, J=2.23 Hz, 1H), 7.97 (dd, J=8.89, 1.89 Hz, 1H), 8.03 (t, J=6.00 Hz, 1H), 8.39 (d, J=8.91 Hz, 1H), 8.47 (s, 2H). LC-MS (Method A): r.t. 0.85 min, MS (ESI) m/z=448.24 [M+H]$^+$.

Intermediate 344: 3,8-dibromo-1,7-naphthyridine

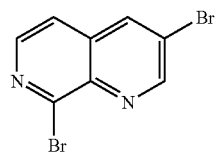 [SMILES: Brc1cnc2c(Br)nccc2c1]

Phosphorus(V) oxybromide (1.27 g, 4.44 mmol) was added to a solution of 3-bromo-1,7-naphthyridin-8(7H)-one (500.0 mg, 2.22 mmol) in DCE (2 mL). The resulting reaction mixture was stirred at 85° C. overnight then it was cooled to room temperature and concentrated under reduced pressure. The residue was dissolved in DCM and washed with saturated aqueous $NaHCO_3$ solution and brine. The organic layer was dried over $Na_2SO_4$, filtered and concentrated to give 3,8-dibromo-1,7-naphthyridine (250 mg, 0.868 mmol, 39.08% yield) as a yellow solid. $^1$H NMR (400 MHz, DMSO-$d_6$) δ 7.94 (d, J=5.50 Hz, 1H), 8.46 (d, J=5.47 Hz, 1H), 8.92 (d, J=2.28 Hz, 1H), 9.22 (d, J=2.28 Hz, 1H). LC-MS (Method A): r.t. 0.92 min, MS (ESI) m/z=289.0 [M+H]$^+$.

Intermediate 345: 3-bromo-1,7-naphthyridine

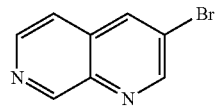 [SMILES: Brc1cnc2cnccc2c1]

Palladium tetrakis triphenylphosphine (80.26 mg, 0.070 mmol) was added to a degassed suspension of 3,8-dibromo-1,7-naphthyridine (250.0 mg, 0.870 mmol) and ammonium formate (109.5 mg, 1.74 mmol) in DMF (2 mL). The resulting reaction mixture was stirred at 50° C. overnight then it was poured into water and extracted with EtOAc three times. The combined organic phases were washed with brine, dried over $Na_2SO_4$, filtered and evaporated under reduced pressure. The residue was purified by column chromatography (Sfar D silica gel, 10 g) eluting with a gradient of EtOAc in cyclohexane from 0% to 60% to give crude 3-bromo-1,7-naphthyridine (95 mg, 0.454 mmol, 52.34% yield) as a brown solid. This material was used in the next step without further purification. LC-MS (Method A): r.t. 0.64 min, MS (ESI) m/z=211.0 [M+H]$^+$.

Intermediate 346:
3-(5-chloro-2-methoxyphenyl)-1,7-naphthyridine

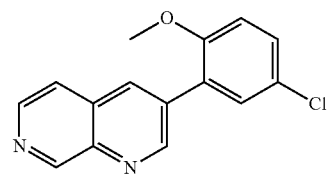 [SMILES: COc1ccc(Cl)cc1-c1cnc2cnccc2c1]

A mixture of 3-bromo-1,7-naphthyridine (95.0 mg, 0.450 mmol) and 5-chloro-2-methoxyphenylboronic acid (101.65 mg, 0.550 mmol) in 1,2-dimethoxyethane (4 mL) and aqueous 2M sodium carbonate solution (0.45 mL, 0.910 mmol) was degassed for 10 min with $N_2$. Then [1,1'-bis(di-tert-butylphosphino)ferrocene]dichloropalladium(II) (29.71 mg, 0.050 mmol) was added and the resulting reaction mixture was stirred at 80° C. for four hours. The mixture was cooled to room temperature and filtered over Celite, washing with MeOH. The filtrate was evaporated and the residue was purified by column chromatography (Sfar Amino D, 11 g) eluting with a gradient of EtOAc in cyclohexane from 0% to 50% to give 3-(5-chloro-2-methoxyphenyl)-1,7-naphthyridine (20 mg, 0.074 mmol, 16.26% yield). $^1$H NMR (400 MHz, DMSO-$d_6$) δ 3.85 (s, 3H), 7.27 (d, J=8.88 Hz, 1H), 7.50-7.57 (m, 1H), 7.62 (d, J=2.67 Hz, 1H), 7.96 (dd, J=5.60, 1.04 Hz, 1H), 8.56 (dd, J=2.19, 0.86 Hz, 1H), 8.66 (d, J=5.55 Hz, 1H), 9.19 (d, J=2.20 Hz, 1H), 9.43 (d, J=1.00 Hz, 1H). LC-MS (Method A): r.t. 0.94 min, MS (ESI) m/z=271.1 [M+H]$^+$.

Intermediate 347: 7-[2-(difluoromethoxy)-4-methyl-5-[(1S,2S,6R,8S)-2,9,9-trimethyl-3,5-dioxa-4-boratricyclo[6.1.1.0$^{2,6}$]decan-4-yl]phenyl]cinnolin-4-amine

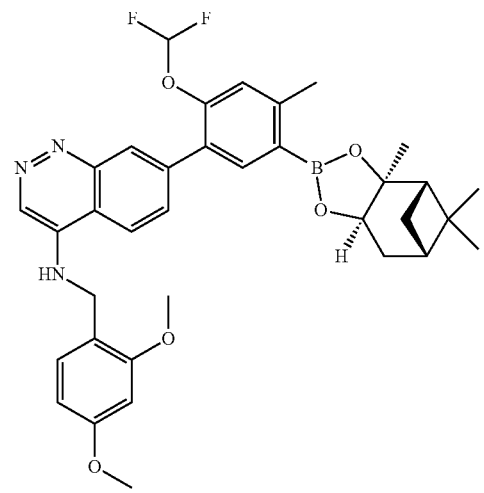 [SMILES: COc1ccc(CNc2cnnc3cc(-c4cc(B5O[C@@H]6C[C@@H]7C[C@@H](C7(C)C)[C@]6(C)O5)c(C)cc4OC(F)F)ccc23)c(OC)c1]

A mixture of 7-[5-chloro-2-(difluoromethoxy)-4-methylphenyl]-N-[(2,4-dimethoxyphenyl)methyl]cinnolin-4- amine (490.0 mg, 1.01 mmol), bis[(+)-pinanediolatio]diboron (361.1 mg, 1.01 mmol) and potassium acetate (296.9 mg, 3.03 mmol)) in 1,4-dioxane (10 mL) was degassed under Ar for 10 min, then dicyclohexyl-[2-[2,4,6-tri(propan-2-yl)phenyl]phenyl]phosphine (38.46 mg, 0.080 mmol) and palladium(II) diacetate (11.32 mg, 0.050 mmol) were added and the mixture was refluxed for 18 hours. The reaction mixture was allowed to cool to room temperature, diluted with EtOAc and filtered over Celite, washing with MeOH and EtOAc. The filtrate was concentrated to give crude 7-[2-(difluoromethoxy)-4-methyl-5-[(1S,2S,6R,8S)-2,9,9-trimethyl-3,5-dioxa-4-boratricyclo[6.1.1.0$^{2,6}$]decan-4-yl]phenyl]cinnolin-4-amine (850 mg), which was used in the next step without further purification. LC-MS (Method A): r.t. 1.13 min, MS (ESI) m/z=630.5 [M+H]$^+$.

Intermediate 348:
3-(2-bromo-4-chlorophenoxy)cyclobutan-1-one

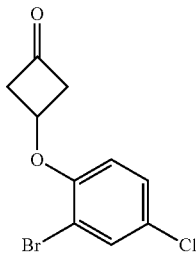 [SMILES: O=C1CC(Oc2ccc(Cl)cc2Br)C1]

Sodium hydride (550.0 mg, 13.75 mmol) was added to a cold (0° C.) solution of 2-bromo-4-chlorophenol (2.59 g, 12.5 mmol) in DMF (22 mL). The mixture was stirred at 0° C. for 30 minutes, then 3-bromocyclobutanone (2.23 g, 15 mmol) in DMF (3 mL) was added. The mixture was left to reach room temperature and stirred for 4 hours. Water and EtOAc were added and the phases were separated. The organic phase was washed with brine, dried over Na$_2$SO$_4$, filtered and concentrated. The residue was purified by column chromatography (KP silica gel, SNAP 100 g) eluting with a gradient of EtOAc in cyclohexane from 0% to 30% to give 3-(2-bromo-4-chlorophenoxy)cyclobutan-1-one (345 mg, 1.252 mmol, 10.02% yield) as a colourless oil. $^1$H NMR (400 MHz, DMSO-d$_6$) δ 3.17-3.25 (m, 2H), 3.57-3.65 (m, 2H), 5.11 (tt, J=6.74, 4.15 Hz, 1H), 7.09 (d, J=8.80 Hz, 1H), 7.44 (dd, J=8.91, 2.53 Hz, 1H), 7.74 (d, J=2.64 Hz, 1H). LC-MS (Method A): r.t. 1.01 min, MS (ESI) m/z=207 [M+H]$^+$.

Intermediate 349: 2-bromo-4-chloro-1-(3,3-difluorocyclobutoxy)benzene

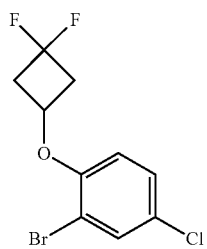 [SMILES: FC1(F)CC(Oc2ccc(Cl)cc2Br)C1]

DAST (301.09 uL, 2.28 mmol) was added to a cold (0° C.) solution of 3-(2-bromo-4-chlorophenoxy)cyclobutan-1-one (345.0 mg, 1.14 mmol) in DCM (7 mL). The mixture was stirred at room temperature for 3 hours, then cooled again to 0° C. and further DAST (301.09 uL, 2.28 mmol) was added. The mixture was stirred overnight at room temperature then cooled to 0° C. and a saturated aqueous solution of NaHCO$_3$ was added, followed by DCM. The phases were separated, and the organic phase was washed with brine, dried over Na$_2$SO$_4$, filtered and concentrated. The residue was purified by column chromatography (KP silica gel, SNAP 25 g) eluting with a gradient of EtOAc in cyclohexane from 0% to 15% to give 2-bromo-4-chloro-1-(3,3-difluorocyclobutyl)oxybenzene (130 mg, 0.437 mmol, 38.35% yield) as a yellowish oil. $^1$H NMR (400 MHz, DMSO-d$_6$) δ 2.67-2.79 (m, 2H), 3.16-3.27 (m, 2H), 4.81-4.92 (m, 1H), 7.05 (d, J=9.02 Hz, 1H), 7.41 (dd, J=8.80, 2.64 Hz, 1H), 7.74 (d, J=2.42 Hz, 1H). LC-MS (Method A): r.t. 1.34 min, MS (ESI) m/z of product not observed due to poor ionization.

Intermediate 350: 7-[5-chloro-2-(3,3-difluorocyclobutoxy)phenyl]-N-[(2,4-dimethoxyphenyl)methyl]cinnolin-4-amine A mixture of N-[(2,4-dimethoxyphenyl)methyl]-7-(4,4,5,5-tetramethyl-1,3,2-dioxaborolan-2-yl)cinnolin-4-amine (325.49 mg, 0.770 mmol) and 2-bromo-4-chloro-1-(3,3-difluorocyclobutyl)oxybenzene (153.24 mg, 0.520 mmol) in 1,2-dimethoxyethane (14.5 mL) and aqueous 2N sodium carbonate solution (0.52 mL, 1.03 mmol) was degassed for 10 min with Ar. [1,1'-Bis(di-tert-butylphosphino)ferrocene]dichloropalladium(II) (33.67 mg, 0.050 mmol) was added and the mixture was degassed for 10 min then stirred at 80° C. for 2 hours. The reaction mixture was cooled to room temperature and filtered over Celite, washing with EtOAc and the solvent was evaporated. The residue was purified by column chromatography (KP-NH silica gel, SNAP 25 g+25 g in series) eluting with a gradient of EtOAc in cyclohexane from 20% to 80% to give 7-[5-chloro-2-(3,3-difluorocyclobutyl)oxyphenyl]-N-[(2,4-dimethoxyphenyl)methyl]cinnolin-4-amine (152 mg, 0.297 mmol, 57.64% yield) as a brownish foam. $^1$H NMR (400 MHz, DMSO-d$_6$) δ 2.60-2.74

(m, 2H), 3.15-3.27 (m, 2H), 3.75 (s, 3H), 3.89 (s, 3H), 4.52 (d, J=5.72 Hz, 2H), 4.80-4.91 (m, 1H), 6.48 (dd, J=8.36, 2.42 Hz, 1H), 6.64 (d, J=2.42 Hz, 1H), 7.10 (d, J=9.02 Hz, 1H), 7.16 (d, J=8.36 Hz, 1H), 7.46 (dd, J=8.80, 2.64 Hz, 1H), 7.58 (d, J=2.64 Hz, 1H), 7.82 (dd, J=8.80, 1.98 Hz, 1H), 8.02 (t, J=5.94 Hz, 1H), 8.22 (d, J=1.76 Hz, 1H), 8.37 (d, J=8.80 Hz, 1H), 8.49 (s, 1H). LC-MS (Method A): r.t. 0.89 min, MS (ESI) m/z=512.2 [M+H]$^+$.

Intermediate 351:
1-(5-bromo-3-fluoropyridin-2-yl)ethanone

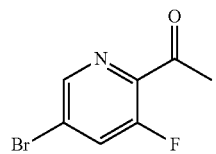

A solution of methylmagnesium chloride (22% w/w in THF, 13.27 mL, 39.8 mmol) was added dropwise to a solution of 5-bromo-3-fluoropyridine-2-carbonitrile (4.0 g, 19.9 mmol) in toluene (50 mL) under argon at −10° C., and the mixture was stirred for 1 hour. Then 3N aqueous HCl solution (49.75 mL, 149.25 mmol) was added slowly and the resulting mixture was stirred at room temperature for 5 hours. The reaction mixture was quenched with 0.5 M aqueous NaHCO$_3$ solution and the resulting mixture was stirred at room temperature for 30 minutes. The two layers were separated and the organic phase was washed with water, then brine, dried over Na$_2$SO$_4$, filtered and evaporated under reduced pressure. The residue was purified by column chromatography (Sfar D, 50 g), eluting with a gradient of EtOAc in cyclohexane from 0% to 50% to give 1-(5-bromo-3-fluoropyridin-2-yl)ethanone (3.2 g, 14.68 mmol, 73.75% yield) as a yellow solid. $^1$H NMR (400 MHz, DMSO-d$_6$) δ 2.59 (d, J=0.77 Hz, 3H), 8.37 (dd, J=10.58, 1.79 Hz, 1H), 8.72 (dd, J=1.81, 1.10 Hz, 1H). LC-MS (Method A): r.t. 0.84 min, MS (ESI) m/z=217.9 [M+H]$^+$.

Intermediate 352: 1-[5-bromo-3-[(2,4-dimethoxyphenyl)methylamino]pyridin-2-yl]ethanone

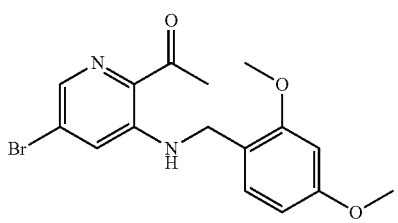 [SMILES: COc1ccc(CNc2cc(Br)cnc2C(C)=O)c(OC)c1]

In a microwave vial 1-(5-bromo-3-fluoropyridin-2-yl)ethanone (4.5 g, 20.64 mmol) and (2,4-dimethoxyphenyl)methanamine (3.1 mL, 20.64 mmol) were dissolved in DMF (9.5 mL) and the reaction mixture was stirred under microwave irradiation at 120° C. for 15 minutes. The mixture was concentrated under reduced pressure, then the residue was triturated with MeOH. The yellow solid was filtered off to give 1-[5-bromo-3-[(2,4-dimethoxyphenyl)methylamino] pyridin-2-yl]ethanone (3.97 g, 10.87 mmol, 52.66% yield) as a bright yellow solid. $^1$H NMR (400 MHz, DMSO-d$_6$) δ 2.55 (s, 3H), 3.75 (s, 3H), 3.83 (s, 3H), 4.35 (d, J=5.90 Hz, 2H), 6.49 (dd, J=8.30, 2.42 Hz, 1H), 6.60 (d, J=2.42 Hz, 1H), 7.18 (d, J=8.31 Hz, 1H), 7.56 (d, J=1.92 Hz, 1H), 7.93 (d, J=1.93 Hz, 1H), 8.87 (t, J=5.91 Hz, 1H). LC-MS (Method A): r.t. 1.36 min, MS (ESI) m/z=365.1 [M+H]$^+$.

Intermediate 353:
1-(3-amino-5-bromopyridin-2-yl)ethanone

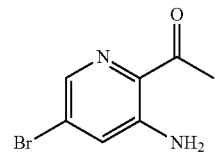

Trifluoroacetic acid (2.5 mL, 32.61 mmol) was added to a solution of 1-[5-bromo-3-[(2,4-dimethoxyphenyl)methylamino]pyridin-2-yl]ethanone (3.97 g, 10.87 mmol) in DCM (38 mL) and the resulting mixture was stirred at room temperature for 2 hours, after which the solvent was removed in vacuo. The resulting solid was triturated with diethyl ether, the white solid was filtered off and the filtrate washed with saturated aqueous Na$_2$CO$_3$ solution, dried over Na$_2$SO$_4$ and the solvent removed under reduced pressure to give 1-(3-amino-5-bromopyridin-2-yl)ethanone (2.33 g, 10.83 mmol, 99.67% yield) as a yellow solid. $^1$H NMR (400 MHz, DMSO-d$_6$) δ 2.53 (s, 3H), 7.28 (s, 2H), 7.48 (d, J=2.07 Hz, 1H), 7.92 (d, J=2.06 Hz, 1H). LC-MS (Method A): r.t. 0.89 min, MS (ESI) m/z=215.0 [M+H]$^+$.

Intermediate 354:
7-bromopyrido[3,2-c]pyridazin-4-ol

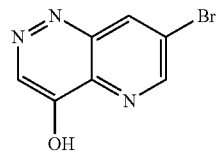 [SMILES: Oc1cnnc2cc(Br)cnc12]

An ice-cold solution of sodium nitrite (755.07 mg, 10.94 mmol) in water (14 mL) was added dropwise to a solution of 1-(3-amino-5-bromopyridin-2-yl)ethanone (2.33 g, 10.83 mmol) in ethanol (50 mL) and 37% w/w aquoeus HCl solution (28.0 mL, 336 mmol) at −10° C. The reaction mixture was stirred for 1 hour at −10° C., then a solution of NaOH (4.32 g) in water (65 mL)/EtOH (125 mL) was added dropwise until pH=8 was reached. The reaction mixture was stirred at −5° C. for 4 hours, then the pH was increased to 14 by addition of the NaOH solution in EtOH/water and the mixture was allowed to warm to room temperature. The reaction mixture was diluted with water (60 mL), washed with Et$_2$O and acidified with 1M aqueous HCl solution until pH=5 was reached. Then the resulting mixture was washed twice with EtOAc and the orange precipitate was filtered off to give 7-bromopyrido[3,2-c]pyridazin-4-ol (812 mg, 3.592 mmol, 33.16% yield) as an orange solid. $^1$H NMR (400 MHz, DMSO-d$_6$) δ 7.93 (s, 1H), 8.23 (d, J=2.08 Hz, 1H), 8.79 (d, J=2.09 Hz, 1H), 13.54 (s, 1H). LC-MS (Method A): r.t. 0.44 min, MS (ESI) m/z=225.9 and 228.0 [M+H]$^+$.

Intermediate 355: 7-bromo-4-chloropyrido[3,2-c]pyridazine

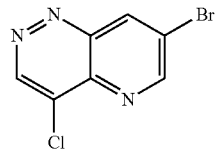 [SMILES: Clc1cnnc2cc(Br)cnc12]

A solution of 7-bromopyrido[3,2-c]pyridazin-4-ol (800.0 mg, 3.54 mmol) in phosphorus(V) oxychloride (4.0 mL, 3.54 mmol) was stirred at 60° C. for 2 hours. The reaction mixture was cooled to room temperature and concentrated in vacuo. The residue was dissolved in DCM and washed with saturated aqueous NaHCO$_3$ solution and brine. The organic layer was dried over Na$_2$SO$_4$, filtered and concentrated to give 7-bromo-4-chloropyrido[3,2-c]pyridazine (110 mg, 0.450 mmol, 12.71% yield) as a dark blue solid. $^1$H NMR (400 MHz, DMSO-d$_6$) δ 9.35 (d, J=2.20 Hz, 1H), 9.45 (d, J=2.20 Hz, 1H), 9.89 (s, 1H). LC-MS (Method A): r.t. 0.76 min, MS (ESI) m/z=243.9 and 245.9 [M+H]$^+$.

Intermediate 356: 7-bromo-N-[(2,4-dimethoxyphenyl)methyl]pyrido[3,2-c]pyridazin-4-amine

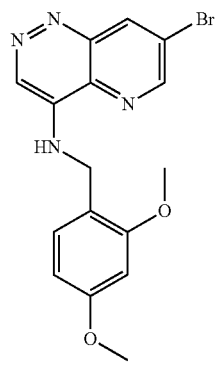 [SMILES: COc1ccc(CNc2cnnc3cc(Br)cnc23)c(OC)c1]

(2,4-Dimethoxyphenyl)methanamine (0.14 mL, 0.900 mmol) was added to a solution of 7-bromo-4-chloropyrido[3,2-c]pyridazine (110.0 mg, 0.450 mmol) in ethanol (1.5 mL) and the resulting mixture was stirred at 90° C. for 90 minutes. The reaction mixture was cooled to room temperature and evaporated in vacuo. The residue was triturated with EtOAc, the insolubles were filtered off, and the filtrate was evaporated under reduced pressure. The residue was purified by column chromatography (Sfar D, 25 g) eluting with a gradient of MeOH in DCM from 0% to 10% to give 7-bromo-N-[(2,4-dimethoxyphenyl)methyl]pyrido[3,2-c]pyridazin-4-amine in a ~3:1 mixture with 7-chloro-N-[(2,4-dimethoxyphenyl)methyl]pyrido[3,2-c]pyridazin-4-amine (126 mg, 0.336 mmol, 74.63% yield) as a dark brown solid. $^1$H NMR (400 MHz, DMSO-d$_6$) only signals from 7-bromo-N-[(2,4-dimethoxyphenyl)methyl]pyrido[3,2-c]pyridazin-4-amine are reported δ 3.73 (s, 3H), 3.86 (s, 3H), 4.55 (d, J=6.43 Hz, 2H), 6.46 (dd, J=8.38, 2.40 Hz, 1H), 6.61 (d, J=2.38 Hz, 1H), 7.17 (d, J=8.37 Hz, 1H), 8.22 (t, J=6.47 Hz, 1H), 8.74-8.79 (m, 2H), 9.02 (d, J=2.19 Hz, 1H). LC-MS (Method A): r.t. 0.64 min, MS (ESI) m/z=375.1 and 377.1 [M+H]$^+$.

Intermediate 357: 4-(2-bromo-4-chlorophenyl)morpholine

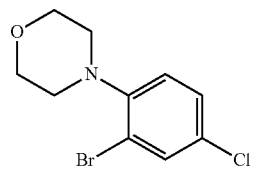 [SMILES: Clc1ccc(N2CCOCC2)c(Br)c1]

Sodium hydride (60% dispersion in mineral oil, 387.47 mg, 9.69 mmol) was added portionwise to a solution of 2-bromo-4-chloroaniline (500.0 mg, 2.42 mmol) in DMSO (24 mL) at 0° C. Then 1-bromo-2-(2-bromoethoxy)ethane (0.31 mL, 2.42 mmol) was added and the reaction was stirred at room temperature for 1.5 hours. Then water and EtOAc were added and the two phases were separated. The organic phase was washed with brine, dried over Na$_2$SO$_4$, filtered and concentrated in vacuo. The residue was purified by column chromatography (KP-Sil silica gel, SNAP 50) eluting with a gradient of EtOAc in cyclohexane from 0% to 20% to give 4-(2-bromo-4-chlorophenyl)morpholine (480 mg, 1.736 mmol, 71.67% yield) as a white powder. $^1$H NMR (400 MHz, DMSO-d$_6$) δ 2.91-2.98 (m, 4H), 3.70-3.77 (m, 4H), 7.18 (d, J=8.62 Hz, 1H), 7.43 (dd, J=8.62, 2.48 Hz, 1H), 7.70 (d, J=2.46 Hz, 1H). LC-MS (Method A): r.t. 1.25 min, MS (ESI) m/z=275.98 and 277.98 [M+H]$^+$.

Intermediate 358: 7-(5-chloro-2-morpholin-4-ylphenyl)-N-[(2,4-dimethoxyphenyl)methyl]cinnolin-4-amine

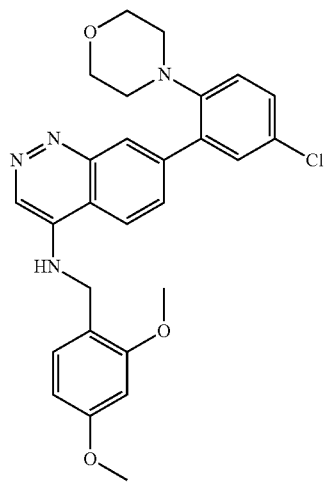 [SMILES: COc1ccc(CNc2cnnc3cc(-c4cc(Cl)ccc4N4CCOCC4)ccc23)c(OC)c1]

A mixture of 4-(2-bromo-4-chlorophenyl)morpholine (150.0 mg, 0.540 mmol), N-[(2,4-dimethoxyphenyl)methyl]-7-(4,4,5,5-tetramethyl-1,3,2-dioxaborolan-2-yl)cinnolin-4-amine (297.05 mg, 0.710 mmol) and aqueous 2 N sodium carbonate solution (0.54 mL, 1.08 mmol) in 1,2-dimethoxyethane (6 mL) was degassed for 10 min under N$_2$. Then [1,1'-bis(di-tert-butylphosphino)ferrocene]dichloropalladium(II) (35.46 mg, 0.050 mmol) was added and the resulting reaction mixture was stirred at 80° C. for 7 hours. The mixture was filtered over a pad of Celite, washing with MeOH. The filtrate was concentrated in vacuo and the residue was purified by column chromatography (KP-Sil silica gel, SNAP 25) eluting with a gradient of EtOAc in cyclohexane from 0% to 100% to give 7-(5-chloro-2-morpholin-4-ylphenyl)-N-[(2,4-dimethoxyphenyl)methyl]cinnolin-4-amine (104 mg, 0.212 mmol, 39.05% yield) as a brown powder. $^1$H NMR (400 MHz, DMSO-$d_6$) δ 2.77 (t, J=4.59 Hz, 4H), 3.47 (t, J=4.33 Hz, 4H), 3.75 (s, 3H), 3.89 (s, 3H), 4.52 (d, J=5.73 Hz, 2H), 6.49 (dd, J=8.41, 2.39 Hz, 1H), 6.64 (d, J=2.39 Hz, 1H), 7.15-7.22 (m, 2H), 7.42-7.48 (m, 2H), 7.95-8.03 (m, 2H), 8.29 (d, J=1.76 Hz, 1H), 8.37 (d, J=8.84 Hz, 1H), 8.49 (s, 1H). LC-MS (Method A): r.t. 0.83 min, MS (ESI) m/z=491.27 [M+H]$^+$.

Intermediate 359: 7-(5-chloro-2-methoxyphenyl)-N-[(2,4-dimethoxyphenyl)methyl]pyrido[3,2-c]pyridazin-4-amine

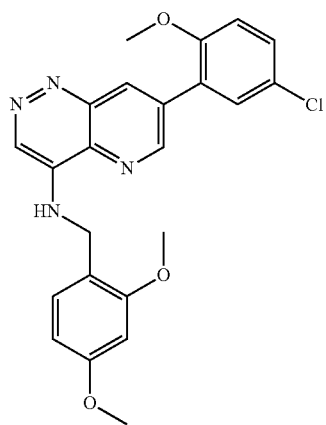 [SMILES: COc1ccc(CNc2cnnc3cc(-c4cc(Cl)ccc4OC)cnc23)c(OC)c1]

A mixture of 7-bromo-N-[(2,4-dimethoxyphenyl)methyl]pyrido[3,2-c]pyridazin-4-amine (125.0 mg, 0.330 mmol), aqueous 2M sodium carbonate solution (0.17 mL, 0.330 mmol) and 5-chloro-2-methoxyphenylboronic acid in 1,2-dimethoxyethane (3.5 mL) was degassed for 10 minutes under argon, then [1,1'-bis(di-tert-butylphosphino)ferrocene]dichloropalladium(II) (21.78 mg, 0.030 mmol) was added and the reaction mixture was heated to 85° C. for 1 h. The reaction mixture was filtered over Celite, washing with EtOAc and MeOH. The filtrate was concentrated under reduced pressure and the residue was purified by flash chromatography (Sfar Amino D, 28 g) eluting with a gradient of MeOH in DCM from 0% to 10% to give 7-(5-chloro-2-methoxyphenyl)-N-[(2,4-dimethoxyphenyl)methyl]pyrido[3,2-c]pyridazin-4-amine (54 mg, 0.124 mmol, 37.1% yield) as a brownish solid. $^1$H NMR (400 MHz, DMSO-$d_6$) δ 3.73 (s, 3H), 3.84 (s, 3H), 3.88 (s, 3H), 4.56 (d, J=6.49 Hz, 2H), 6.47 (dd, J=8.38, 2.42 Hz, 1H), 6.62 (d, J=2.38 Hz, 1H), 7.19 (d, J=8.36 Hz, 1H), 7.27 (d, J=9.02 Hz, 1H), 7.53 (dd, J=8.86, 2.72 Hz, 1H), 7.67 (d, J=2.66 Hz, 1H), 8.07 (t, J=6.51 Hz, 1H), 8.54 (d, J=2.12 Hz, 1H), 8.74 (s, 1H), 9.07 (d, J=2.13 Hz, 1H). LC-MS (Method A): r.t. 0.83 min, MS (ESI) m/z=437.2 [M+H]$^+$. $^1$H NMR (400 MHz, DMSO-$d_6$) δ 7.19 (d, J=8.36 Hz, 1H) 7.27 (d, J=9.02 Hz, 1H)

Intermediate 360: 6-chloro-3,4-dihydro-2H-chromen-4-ol

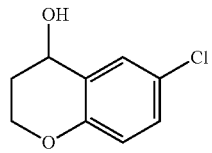 [SMILES: OC1CCOc2ccc(Cl)cc21]

Sodium borohydride (277.89 mg, 6.02 mmol) was added to a cold (0° C.) solution of 6-chloro-2,3-dihydrochromen-4-one (1.0 g, 5.48 mmol) in methanol (15 mL). The mixture was stirred at 0° C. for 30 minutes, then it was stirred at room temperature for 30 minutes. The volatiles were removed and water was added, followed by 6N aqueous HCl solution and DCM. The phases were separated and the organic phase was dried over Na$_2$SO$_4$, filtered and concentrated to give 6-chloro-3,4-dihydro-2H-chromen-4-ol (884 mg, 4.788 mmol, 87.4% yield) as a white solid. $^1$H NMR (400 MHz, DMSO-$d_6$) δ 1.81-1.89 (m, 1H), 1.95-2.05 (m, 1H), 4.16-4.23 (m, 2H), 4.62 (q, J=5.14 Hz, 1H), 5.49 (d, J=5.28 Hz, 1H), 6.78 (d, J=8.80 Hz, 1H), 7.17 (dd, J=8.69, 2.75 Hz, 1H), 7.32 (d, J=2.64 Hz, 1H). LC-MS (Method A): r.t. 0.83 min, MS (ESI) m/z=167.0 [M+H]$^+$.

Intermediate 361: 6-chloro-3,4-dihydro-2H-chromene

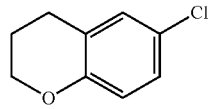

Triethylsilane (27.38 mL, 172.9 mmol) and boron trifluoride diethyl etherate (6.1 mL, 49.4 mmol) were added successively dropwise to a solution of 6-chloro-3,4-dihydro-2H-chromen-4-ol (2.28 g, 12.35 mmol) in DCM (120 mL) at −78° C. The mixture was stirred at −78° C. for 2 hours, then it was stirred at room temperature for 30 minutes. The reaction mixture was concentrated and the residue was purified by column chromatography (KP silica gel, SNAP 100 g) eluting with a gradient of EtOAc in cyclohexane from 0% to 10% to give 6-chloro-3,4-dihydro-2H-chromene (1.882 g, 11.16 mmol, 90.38% yield) as a colourless oil. $^1$H NMR (400 MHz, DMSO-$d_6$) δ 1.86-1.95 (m, 2H), 2.73 (t, J=6.38 Hz, 2H), 4.13 (t, J=5.06 Hz, 2H), 6.74 (d, J=8.58 Hz, 1H), 7.08 (dd, J=8.58, 2.64 Hz, 1H), 7.11-7.14 (m, 1H). LC-MS (Method A): r.t. 1.18 min, MS (ESI) m/z of product not observed due to poor ionization.

Intermediate 362: 8-bromo-6-chloro-3,4-dihydro-2H-chromene

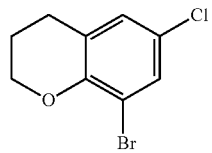 [SMILES: Clc1cc(Br)c2c(c1)CCCO2]

Molecular bromine (727.79 uL, 14.2 mmol) was added dropwise to a cold (0° C.) solution of 6-chloro-3,4-dihydro-2H-chromene (1.88 g, 10.93 mmol) in acetic acid (28.34 mL). The mixture was stirred at room temperature overnight. DCM was added and the reaction mixture was quenched with a saturated aqueous solution of sodium thiosulfate, then filtered over a hydrophobic frit (Phase separator). The filtrate was evaporated and the residue was purified by column chromatography (KP silica gel, SNAP 100 g) eluting with a gradient of EtOAc in cyclohexane from 0% to 10% to give 8-bromo-6-chloro-3,4-dihydro-2H-chromene (1.94 g, 7.838 mmol, 71.73% yield) as a yellowish oil. $^1$H NMR (400 MHz, DMSO-$d_6$) δ 1.87-1.95 (m, 2H), 2.78 (t, J=6.49 Hz, 2H), 4.24 (t, J=5.06 Hz, 2H), 7.18-7.21 (m, 1H), 7.46 (d, J=2.42 Hz, 1H). LC-MS (Method A): r.t. 1.30 min, MS (ESI) m/z of product not observed due to poor ionization.

Intermediate 363: 7-(6-chloro-3,4-dihydro-2H-chromen-8-yl)-N-[(2,4-dimethoxyphenyl)methyl]cinnolin-4-amine

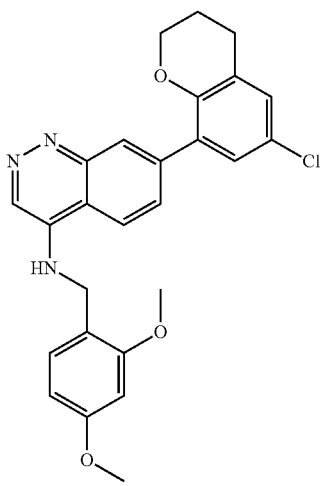 [SMILES: COc1ccc(CNc2cnnc3cc(-c4cc(Cl)cc5c4OCCC5)ccc23)c(OC)c1]

A mixture of N-[(2,4-dimethoxyphenyl)methyl]-7-(4,4,5,5-tetramethyl-1,3,2-dioxaborolan-2-yl)cinnolin-4-amine (400.71 mg, 0.950 mmol) and 8-bromo-6-chloro-3,4-dihydro-2H-chromene (215.0 mg, 0.630 mmol) in 1,2-dimethoxyethane (20.7 mL) and aqueous 2N sodium carbonate solution (0.63 mL, 1.27 mmol) was degassed for 10 min with Ar. [1,1'-Bis(di-tert-butylphosphino)ferrocene]dichloropalladium(II) (41.45 mg, 0.060 mmol) was added and the mixture was degassed for 10 min then stirred at 80° C. for 4 hours. The reaction mixture was cooled to room temperature and filtered over Celite, washing with EtOAc, and the solvent was evaporated. The residue was purified by column chromatography (KP-NH silica gel, SNAP 25 g+25 g in series) eluting with a gradient of EtOAc in cyclohexane from 20% to 100% to give 7-(6-chloro-3,4-dihydro-2H-chromen-8-yl)-N-[(2,4-dimethoxyphenyl)methyl]cinnolin-4-amine (90 mg, 0.195 mmol, 30.73% yield) as a yellowish solid. $^1$H NMR (400 MHz, DMSO-$d_6$) δ 1.94-2.03 (m, 2H), 2.86 (t, J=6.27 Hz, 2H), 3.74 (s, 3H), 3.89 (s, 3H), 4.15-4.23 (m, 2H), 4.52 (d, J=5.72 Hz, 2H), 6.48 (dd, J=8.36, 2.42 Hz, 1H), 6.63 (d, J=2.42 Hz, 1H), 7.15 (d, J=8.36 Hz, 1H), 7.24 (d, J=2.64 Hz, 1H), 7.32 (d, J=2.86 Hz, 1H), 7.76 (dd, J=8.80, 1.76 Hz, 1H), 8.01 (t, J=5.94 Hz, 1H), 8.17 (d, J=1.76 Hz, 1H), 8.35 (d, J=9.02 Hz, 1H), 8.48 (s, 1H). LC-MS (Method A): r.t. 0.90 min, MS (ESI) m/z=462.3 [M+H]$^+$.

Intermediate 364: 6-bromo-4-chloro-3-iodo-1H-indazole

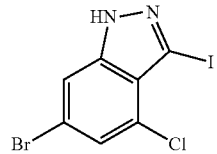 [SMILES: Clc1cc(Br)cc2[nH]nc(I)c12]

Iodine (447.54 uL, 8.64 mmol) was added to a stirred suspension of 6-bromo-4-chloro-1H-indazole (1.0 g, 4.32 mmol) and powdered potassium hydroxide (605.99 mg, 10.8 mmol) in DMF (21 mL). The resulting mixture was stirred at room temperature overnight then it was diluted with EtOAc and quenched with saturated aqueous Na$_2$S$_2$O$_3$ solution and brine. The organic phase was separated, filtered over a hydrophobic frit (Phase Seperator) and concentrated under reduced pressure. The resulting powder was suspended in DCM and sonicated, then the solid was filtered off on a Gooch funnel and rinsed with DCM to give 6-bromo-4-chloro-3-iodo-1H-indazole (1.04 g, 2.91 mmol, 67.36% yield) as a whitish powder. $^1$H NMR (400 MHz, DMSO-$d_6$) δ 7.40 (d, J=1.44 Hz, 1H), 7.85 (d, J=1.46 Hz, 1H). LC-MS (Method A): r.t. 1.23 min, MS (ESI) m/z=356.8 and 358.8 [M+H]$^+$.

Intermediate 365: 6-bromo-1-chloro-4-methylisoquinoline

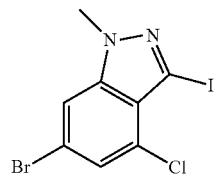

Potassium hydroxide (332.4 mg, 5.82 mmol) was added to a solution of 6-bromo-4-chloro-3-iodo-1H-indazole (1.04 g, 2.91 mmol) in acetone (5 mL) at 0° C. After 5 minutes, iodomethane (0.22 mL, 3.49 mmol) was added dropwise. The resulting mixture was stirred at room temperature until the starting material was consumed as determined by UPLC reaction monitoring. The mixture was then evaporated under reduced pressure, and the residue was taken up with EtOAc, washed with water and brine, dried over Na$_2$SO$_4$, filtered and evaporated in vacuo. The residue was submitted to semi-preparative HPLC purification (Chiralpak AD-H (25× 0.46 cm), 5 μm, n-hexane/(EtOH+0.1% isopropylamine) 80/20% v/v). Appropriate fractions were collected and concentrated to give 6-bromo-4-chloro-3-iodo-1-methylindazole (685 mg, 1.844 mmol, 63.38% yield) as a white solid. $^1$H NMR (400 MHz, DMSO-$d_6$) δ 4.05 (s, 3H), 7.42 (d, J=1.3 Hz, 1H), 8.11 (d, J=1.4 Hz, 1H). LC-MS (Method A): r.t. 1.36 min, MS (ESI) m/z=371.0 and 372.9 [M+H]$^+$.

Intermediate 366: 6-bromo-N-[(2,4-dimethoxyphenyl)methyl]-4-methylisoquinolin-1-amine

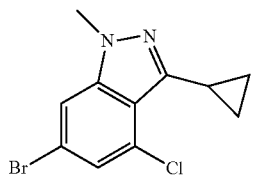

A mixture of 6-bromo-4-chloro-3-iodo-1-methylindazole (215.0 mg, 0.580 mmol), cyclopropylboronic acid (74.59 mg, 0.870 mmol) and tripotassium phosphate (373.89 mg, 1.74 mmol) in 1,4-dioxane (4.5 mL) was degassed for 10 minutes with N₂. Then [1,1'-bis(diphenylphosphino)ferrocene]dichloropalladium(II) (42.47 mg, 0.060 mmol) was added and the resulting reaction mixture was stirred at 90° C. for 15 hours. The mixture was cooled to room temperature and filtered over Celite, washing with methanol. The filtrate was evaporated and the residue was purified by column chromatography (Sfar Amino D, 11 g) eluting with a gradient of EtOAc in cyclohexane from 0% to 5% to give 6-bromo-4-chloro-3-cyclopropyl-1-methylindazole (115 mg, 0.403 mmol, 69.56% yield). ¹H NMR (400 MHz, DMSO-d₆) δ 0.87-0.93 (m, 2H), 0.96-1.02 (m, 2H), 2.52-2.58 (m, 1H), 3.92 (s, 3H), 7.33 (d, J=1.40 Hz, 1H), 7.92 (d, J=1.43 Hz, 1H). LC-MS (Method A): r.t. 1.41 min, MS (ESI) m/z=285.1 and 287.1 [M+H]⁺.

Intermediate 367: 7-(4-chloro-3-cyclopropyl-1-methylindazol-6-yl)-N-[(2,4-dimethoxyphenyl)methyl]cinnolin-4-amine

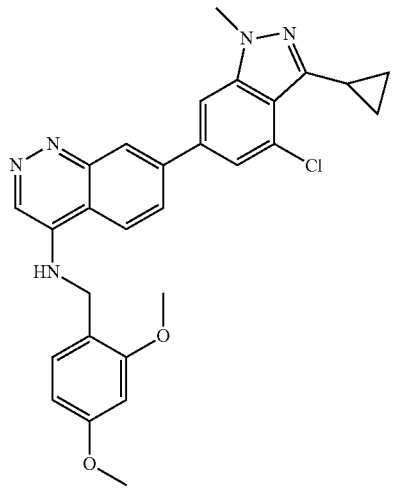 [SMILES: COc1ccc(CNc2cnnc3cc(-c4cc(Cl)c5c(C6CC6)nn(C)c5c4)ccc23)c(OC)c1]

A mixture of 6-bromo-4-chloro-3-cyclopropyl-1-methylindazole (215.0 mg, 0.750 mmol) and N-[(2,4-dimethoxyphenyl)methyl]-7-(4,4,5,5-tetramethyl-1,3,2-dioxaborolan-2-yl)cinnolin-4-amine (348.91 mg, 0.830 mmol) in 1,2-dimethoxyethane (7.5 mL) and aqueous 2N sodium carbonate solution (159.6 mg, 1.51 mmol) was degassed for 10 minutes with N₂. Then [1,1'-bis(di-tert-butylphosphino)ferrocene]dichloropalladium(II) (49.22 mg, 0.080 mmol) was added and the resulting reaction mixture was stirred at 80° C. for two hours. The mixture was cooled to room temperature and filtered over Celite, washing with MeOH. The filtrate was concentrated and the residue was purified by column chromatography (Sfar Amino D, 11 g) eluting with a gradient of MeOH in EtOAc from 0% to 10% to give 7-(4-chloro-3-cyclopropyl-1-methylindazol-6-yl)-N-[(2,4-dimethoxyphenyl)methyl]cinnolin-4-amine (120 mg, 0.240 mmol, 31.88% yield) as a brown solid. ¹H NMR (400 MHz, DMSO-d₆) δ 0.93-1.05 (m, 4H), 2.58-2.65 (m, 1H), 3.74 (s, 3H), 3.88 (s, 3H), 4.05 (s, 3H), 4.53 (d, J=5.72 Hz, 2H), 6.48 (dd, J=8.14, 2.42 Hz, 1H), 6.63 (d, J=2.42 Hz, 1H), 7.17 (d, J=8.36 Hz, 1H), 7.68 (d, J=0.88 Hz, 1H), 8.05-8.19 (m, 3H), 8.48 (d, J=8.81 Hz, 1H), 8.50 (s, 1H), 8.53 (d, J=1.94 Hz, 1H). LC-MS (Method A): r.t. 0.91 min, MS (ESI) m/z=500.3 [M+H]⁺.

Intermediate 368: 1-[4-chloro-2-[4-[(2,4-dimethoxyphenyl)methylamino]cinnolin-7-yl]phenyl]-N-methylpyrazole-4-carboxamide

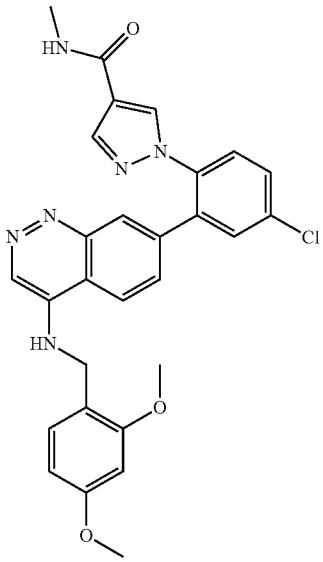 [SMILES: CNC(=O)c1cnn(-c2ccc(Cl)cc2-c2ccc3c(NCc4ccc(OC)cc4OC)cnnc3c2)c1]

A solution of 1-[4-chloro-2-[4-[(2,4-dimethoxyphenyl)methylamino]cinnolin-7-yl]phenyl]pyrazole-4-carboxylic acid (130.0 mg, 0.250 mmol), [dimethylamino(3-triazolo[4,5-b]pyridinyloxy)methylidene]-dimethylammonium hexafluorophosphate (143.71 mg, 0.380 mmol), a 2M solution of methanamine in THF (138.58 uL, 0.280 mmol), and N,N-diisopropylethylamine (131.66 uL, 0.760 mmol) in DMF (2 mL) was stirred at room temperature for 4 hours, then the mixture was diluted with EtOAc and washed with water. The aqueous layer was extracted with EtOAc and the organic layers were combined, dried over Na₂SO₄, filtered and concentrated. The residue was purified by column chromatography (KP-NH silica gel, SNAP 28) eluting with a gradient of MeOH in DCM from 0% to 10% to give 1-[4-chloro-2-[4-[(2,4-dimethoxyphenyl)methylamino]cinnolin-7-yl]phenyl]-N-methylpyrazole-4-carboxamide (85 mg, 0.161 mmol, 63.77% yield) as a colorless oil. ¹H NMR (400 MHz, DMSO-d₆) δ 2.65 (d, J=4.57 Hz, 3H), 3.74 (s, 3H), 3.87 (s, 3H), 4.49 (d, J=5.74 Hz, 2H), 6.47 (dd, J=8.39, 2.41 Hz, 1H), 6.62 (d, J=2.38 Hz, 1H), 7.13 (d, J=8.38 Hz, 1H), 7.18 (dd, J=8.75, 1.88 Hz, 1H), 7.65-7.74 (m, 2H), 7.83 (d, J=2.24 Hz, 1H), 7.90-8.04 (m, 4H), 8.14 (d, J=0.67 Hz, 1H), 8.21 (d, J=8.80 Hz, 1H), 8.48 (s, 1H). LC-MS (Method A): r.t. 0.69 min, MS (ESI) m/z=529.29 [M+H]⁺.

Intermediate 369: 2-(2-bromo-4-chlorophenyl)-N-methoxy-N-methylacetamide

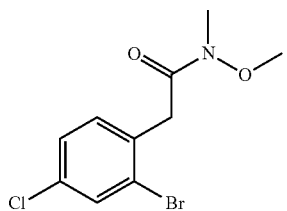

N-Methoxymethanamine hydrochloride (5.88 g, 60.24 mmol) was added to a solution of 2-(2-bromo-4-chlorophenyl)acetic acid (10.0 g, 40.16 mmol), 3-(ethyliminomethylideneamino)-N,N-dimethyl-1-propanamine hydrochloride (11.55 g, 60.24 mmol) and triethylamine (16.79 mL, 120.48 mmol) in DCM (150 mL) at room temperature. The resulting mixture was stirred at this temperature overnight. Water and DCM were added, the phases were separated and the aqueous phase was re-extracted with DCM. The combined organic phases were washed with water, 1N aqueous HCl solution, saturated aqueous NaHCO₃ solution and brine, dried over Na₂SO₄, filtered and concentrated in vacuo. The residue was treated with diethyl ether and filtered. The filtrate was concentrated to give 2-(2-bromo-4-chlorophenyl)-N-methoxy-N-methylacetamide (6.1 g, 20.85 mmol, 51.92% yield) as a pale yellow oil. ¹H NMR (400 MHz, DMSO-d₆) δ 3.13 (s, 3H), 3.75 (s, 3H), 3.90 (s, 2H), 7.39 (d, J=8.10 Hz, 1H), 7.44 (dd, J=8.36, 2.20 Hz, 1H), 7.72 (d, J=2.20 Hz, 1H). LC-MS (Method A): r.t. 1.05 min, MS (ESI) m/z=292.1 and 294.0 [M+H]⁺.

Intermediate 370: 2-(2-bromo-4-chlorophenyl)-1-cyclopropylethanone

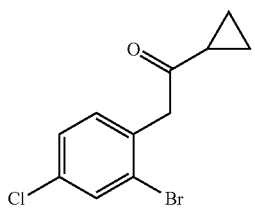 [SMILES: O=C(Cc1ccc(Cl)cc1Br)C1CC1]

A 1M solution of cyclopropylmagnesium bromide in 2-methyltetrahydrofuran (12.82 mL, 12.82 mmol) was added slowly to a solution of 2-(2-bromo-4-chlorophenyl)-N-methoxy-N-methylacetamide (2.5 g, 8.55 mmol) in anhydrous THF (25 mL) at 0° C. under argon. The reaction was stirred for 2 hours at 25° C., then additional 1M solution of cyclopropylmagnesium bromide in 2-methyltetrahydrofuran (4.0 mL, 4 mmol) was added, the temperature was raised to 40° C. and the mixture was stirred for 2 hours. The reaction mixture was quenched with saturated aqueous ammonium chloride solution and extracted with EtOAc. The organic phase was washed with brine, dried over Na₂SO₄, filtered and evaporated under reduced pressure. The residue was purified by flash chromatography (Sfar D, 50 g) eluting with a gradient of EtOAc in cyclohexane from 0% to 10% to give 2-(2-bromo-4-chlorophenyl)-1-cyclopropylethanone (192 mg, 0.702 mmol, 8.2% yield) as a yellowish oil. ¹H NMR (400 MHz, Chloroform-d) δ 0.92 (dt, J=8.10, 3.53 Hz, 2H), 1.06-1.13 (m, 2H), 1.99 (tt, J=7.84, 4.53 Hz, 1H), 3.97 (s, 2H), 7.16 (d, J=8.19 Hz, 1H), 7.21-7.37 (m, 1H), 7.59 (d, J=2.04 Hz, 1H). LC-MS (Method A): r.t. 1.20 min, MS (ESI) m/z=272.9 and 275.0 [M+H]⁺.

Intermediate 371: 2-(2-bromo-4-chlorophenyl)-1-cyclopropylethanol

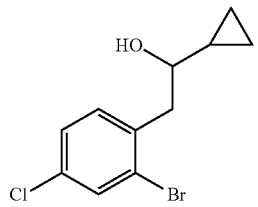 [SMILES: OC(Cc1ccc(Cl)cc1Br)C1CC1]

Sodium borohydride (49.07 mg, 1.3 mmol) was added portionwise to a cold solution of 2-(2-bromo-4-chlorophenyl)-1-cyclopropylethanone (384.0 mg, 1.18 mmol) in methanol (2 mL) and the resulting mixture was stirred at room temperature for 30 minutes. The reaction was quenched with water and the mixture was extracted three times with diethyl ether. The combined organic phases were dried over anhydrous Na₂SO₄, filtered and concentrated under reduced pressure to give 2-(2-bromo-4-chlorophenyl)-1-cyclopropylethanol (348 mg, 1.263 mmol, 107.1% yield) as a yellowish solid, which was used in the next step without further purification. ¹H NMR (400 MHz, DMSO-d₆) δ 0.00-0.12 (m, 1H), 0.25 (ddt, J=8.90, 4.17, 2.08 Hz, 1H), 0.26-0.44 (m, 2H), 0.86 (qt, J=8.08, 4.98 Hz, 1H), 2.82 (dd, J=13.47, 8.16 Hz, 1H), 2.93 (dd, J=13.47, 4.70 Hz, 1H), 3.10 (tt, J=7.88, 5.01 Hz, 1H), 4.64 (d, J=5.29 Hz, 1H), 7.36-7.40 (m, 2H), 7.67 (t, J=1.21 Hz, 1H). LC-MS (Method A): r.t. 1.18 min, MS (ESI) m/z=256.9 and 258.9 [M−H₂O+H]⁺.

Intermediate 372: [2-(2-bromo-4-chlorophenyl)-1-cyclopropylethoxy]-tert-butyl-dimethylsilane

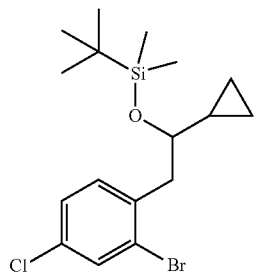 [SMILES: CC(C)(C)[Si](C)(C)OC(Cc1ccc(Cl)cc1Br)C1CC1]

tert-Butyl-chloro-dimethylsilane (0.57 g, 3.79 mmol) was added to a solution of 2-(2-bromo-4-chlorophenyl)-1-cyclopropylethanol (348.0 mg, 1.26 mmol) and imidazole (0.26 g, 3.79 mmol) in THF (8 mL) under a nitrogen atmosphere. The reaction mixture was stirred at 40° C. for 15 hours, then further tert-butyl-chloro-dimethylsilane (285.5 mg, 1.89 mmol) and imidazole (128.96 mg, 1.89 mmol) were added and the mixture was stirred for an additional 5 hours. Water was added and the mixture was extracted with EtOAc. The organic phase was washed sequentially with saturated aqueous NaHCO₃ solution and brine, dried over Na₂SO₄, filtered and evaporated to give [2-(2-bromo-4-chlorophenyl)-1-cyclopropylethoxy]-tert-butyl-dimethylsilane in a mixture with a tert-butyl-dimethylsilyl based side-product (815 mg, 2.091 mmol, 165.55% yield) as a colourless oil, which was used in the next step without further purification. ¹H NMR (400 MHz, Chloroform-d) δ −0.27 (s, 3H), −0.01 (s, 3H), 0.14-0.21 (m, 1H), 0.27-0.35 (m, 1H), 0.36-0.51 (m, 2H), 0.82 (s, 9H), 0.85-0.93 (m, 1H), 2.90 (dd, J=13.30, 7.90 Hz, 1H), 3.01 (dd, J=13.34, 4.97 Hz, 1H), 3.42 (td, J=7.53, 4.97 Hz, 1H), 7.19 (br. s, 2H), 7.50-7.54 (m, 1H). LC-MS (Method A): r.t. 1.89 min, MS (ESI) m/z of product not observed due to poor ionization.

Intermediate 373: tert-butyl(2-{4-chloro-2-[(1S,2S, 6R,8S)-2,9,9-trimethyl-3,5-dioxa-4-boratricyclo [6.1.1.0²,⁶]decan-4-yl]phenyl}-1-cyclopropylethoxy) dimethylsilane

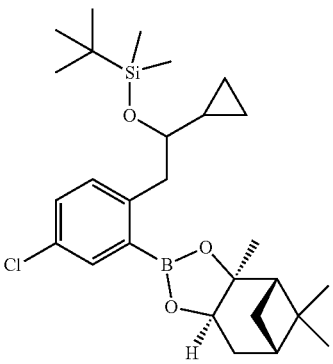 [SMILES: CC1(C)[C@@H]2C[C@H]3OB(c4cc(Cl)ccc4CC(O[Si](C)(C)C(C)(C)C)C4CC4)O[C@@]3(C)[C@H]1C2]

[2-(2-Bromo-4-chlorophenyl)-1-cyclopropylethoxy]-tert-butyl-dimethylsilane (491.19 mg, 1.26 mmol), potassium acetate (0.625 g, 6.3 mmol) and bis[(+)-pinanediolato]diboron (1.35 g, 3.78 mmol) were dissolved in 1,4-dioxane (7 mL) and the solution was degassed for 10 minutes under argon. Then [1,1'-bis(diphenylphosphino)ferrocene]dichloropalladium(II) (92.45 mg, 0.130 mmol) was added and the solution was heated at 100° C. for 3 hours. The mixture was diluted with EtOAc and filtered over Celite, washing with EtOAc. The filtrate was concentrated under reduced pressure and the residue was purified by column chromatography (Sfar D, 25 g) eluting with a gradient of EtOAc in cyclohexane from 0% to 5% to give tert-butyl(2-{4-chloro-2-[(1S,2S,6R,8S)-2,9,9-trimethyl-3,5-dioxa-4-boratricyclo [6.1.1.0²,⁶]decan-4-yl]phenyl}-1-cyclopropylethoxy)dimethylsilane in a mixture with aliphatic impurities (226 mg, 0.462 mmol, 36.68% yield) as a colourless oil. This material was used in the next step without further purification.

Intermediate 374: 7-(7-chloro-1-benzofuran-5-yl)-N-[(2,4-dimethoxyphenyl)methyl]cinnolin-4-amine

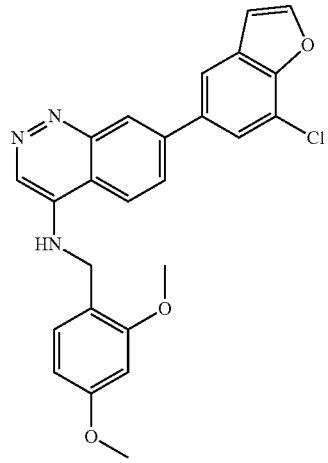 [SMILES: COc1ccc(CNc2cnnc3cc(-c4cc(Cl)c5occc5c4)ccc23)c(OC)c1]

A mixture of N-[(2,4-dimethoxyphenyl)methyl]-7-(4,4,5, 5-tetramethyl-1,3,2-dioxaborolan-2-yl)cinnolin-4-amine (325.49 mg, 0.770 mmol) and 5-bromo-7-chloro-1-benzofuran (150.0 mg, 0.650 mmol) in 1,2-dimethoxyethane (20 mL) and aqueous 2N sodium carbonate solution (0.65 mL, 1.3 mmol) was degassed for 10 min with Ar. [1,1'-Bis(di-tert-butylphosphino)ferrocene]dichloropalladium(II) (42.37 mg, 0.060 mmol) was added, then the mixture was degassed for 10 min and it was stirred at 85° C. for 1.5 hour. The mixture was cooled to room temperature and filtered over Celite, washing with EtOAc and the filtrate was evaporated. The residue was purified by column chromatography (KP-NH silica gel, 2×SNAP 25 in series) eluting with a gradient of EtOAc in cyclohexane from 20% to 100% and then 5% MeOH in EtOAc to give 7-(7-chloro-1-benzofuran-5-yl)-N-[(2,4-dimethoxyphenyl)methyl]cinnolin-4-amine (110 mg, 0.247 mmol, 38.07% yield) as a brownish solid. LC-MS (Method A): r.t. 0.88 min, MS (ESI) m/z=446.2 [M+H]⁺.

Intermediate 375: 1-(2-bromo-4-chlorophenyl)pyrrolidine

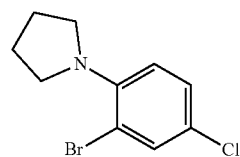 [SMILES: Clc1ccc(N2CCCC2)c(Br)c1]

A mixture of 2-bromo-4-chloro-1-fluorobenzene (1.16 mL, 9.55 mmol), pyrrolidine (0.4 mL, 5.73 mmol) and dicesium carbonate (5.29 g, 16.23 mmol) in DMF (18 mL) was stirred at 120° C. for 18 hours. Additional pyrrolidine (0.94 mL, 11.46 mmol) was added and the mixture was stirred for a further 6 hours, then it was allowed to cool to room temperature. The mixture was partitioned between EtOAc and water, the two phases were separated and the organic phase was washed twice with brine, dried over Na₂SO₄, filtered and concentrated. The residue was purified by column chromatography (Sfar D silica gel, 25 g) eluting with a gradient of EtOAc in cyclohexane from 0% to 10% to give 1-(2-bromo-4-chlorophenyl)pyrrolidine (549 mg, 2.107 mmol, 22.06% yield) as a colourless oil. $^1$H NMR (400 MHz, Chloroform-d) δ 1.87-2.02 (m, 4H), 3.25-3.43 (m, 4H), 6.81 (d, J=8.76 Hz, 1H), 7.14 (dd, J=8.78, 2.47 Hz, 1H), 7.49 (d, J=2.59 Hz, 1H). LC-MS (Method A): r.t. 1.46 min, MS (ESI) m/z=260.0 and 262.0 [M+H]$^+$.

Intermediate 376: 7-[5-chloro-2-(pyrrolidin-1-yl) phenyl]-N-[(2,4-dimethoxyphenyl)methyl]cinnolin-4-amine

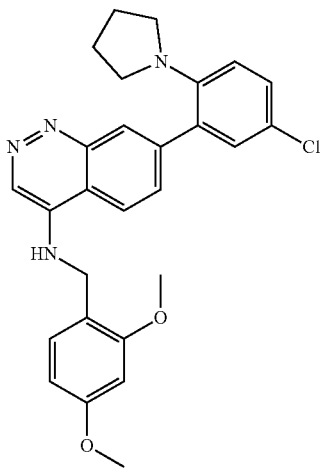 [SMILES: COc1ccc(CNc2cnnc3cc(-c4cc(Cl)ccc4N4CCCC4)ccc23)c(OC)c1]

A mixture of N-[(2,4-dimethoxyphenyl)methyl]-7-(4,4,5,5-tetramethyl-1,3,2-dioxaborolan-2-yl)cinnolin-4-amine (350.0 mg, 0.830 mmol), 1-(2-bromo-4-chlorophenyl)pyrrolidine (309.23 mg, 0.830 mmol) and aqueous 2M sodium carbonate solution (0.83 mL, 1.66 mmol) in 1,2-dimethoxyethane (10 mL) was degassed for 10 minutes under argon. [1,1'-Bis(di-tert-butylphosphino)ferrocene]dichloropalladium(II) (54.31 mg, 0.080 mmol) was added and the mixture was heated to 90° C. and stirred for 4 hours. The mixture was then allowed to cool to room temperature and filtered over Celite, washing with MeOH and EtOAc. The filtrate was concentrated and the residue was purified by column chromatography (Sfar C18 D, 30 g) eluting with a gradient of MeCN (+0.1% of HCOOH) in water (+0.1% of HCOOH) from 2% to 45%. The appropriate fractions were lyophilized to give 7-[5-chloro-2-(pyrrolidin-1-yl)phenyl]-N-[(2,4-dimethoxyphenyl)methyl]cinnolin-4-amine (53 mg, 0.112 mmol, 13.43% yield) as a dark yellow solid. $^1$H NMR (400 MHz, DMSO-d$_6$) δ 1.66-1.75 (m, 4H), 2.82-2.89 (m, 4H), 3.75 (s, 3H), 3.89 (s, 3H), 4.51 (d, J=5.72 Hz, 2H), 6.49 (dd, J=8.47, 2.31 Hz, 1H), 6.64 (d, J=2.42 Hz, 1H), 6.97 (d, J=8.58 Hz, 1H), 7.18 (d, J=8.58 Hz, 1H), 7.26 (d, J=2.64 Hz, 1H), 7.30 (dd, J=8.80, 2.64 Hz, 1H), 7.69 (dd, J=8.80, 1.76 Hz, 1H), 8.02 (d, J=1.76 Hz, 1H), 8.33 (d, J=8.58 Hz, 1H), 8.45-8.48 (m, 1H), 8.49 (s, 1H). LC-MS (Method A): r.t. 0.94 min, MS (ESI) m/z=475.3 [M+H]$^+$.

Intermediate 377: nonane-3,7-dione

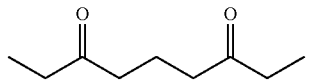

Thionyl dichloride (4.14 mL, 56.77 mmol) was added to a suspension of pentanedioic acid (1.5 g, 11.35 mmol) in toluene (6.75 mL) and the mixture was stirred at 110° C. for 3 hours, then it was allowed to cool to room temperature and the solvent was evaporated under reduced pressure. The residue was dissolved in THF (100 mL) and iron (III) acetylacetonate (120.25 mg, 0.340 mmol) was added under an argon atmosphere, then a 1M solution of ethylmagnesium bromide solution in THF (22.7 mL, 22.7 mmol) was added dropwise over 30 minutes at room temperature. The mixture was stirred for 30 minutes, then the reaction was quenched with aqueous 1M HCl solution and extracted with EtOAc. The organic phase was washed with saturated NaHCO$_3$ solution, then with brine, dried over Na$_2$SO$_4$, filtered and evaporated under reduced pressure. The residue was purified by column chromatography (Sfar D silica gel, 25 g) eluting with a gradient of EtOAc in cyclohexane from 0% to 40% to give nonane-3,7-dione (400 mg, 2.56 mmol, 22.56% yield) as an off-white solid. $^1$H NMR (400 MHz, Chloroform-d) δ 1.05 (t, J=7.34 Hz, 6H), 1.85 (quin, J=7.09 Hz, 2H), 2.35-2.47 (m, 8H).

Intermediate 378: (1R,2S)-1,2-diethylcyclopentane-1,2-diol

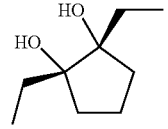

Titanium (IV) chloride (182.48 uL, 1.66 mmol) was added dropwise to a suspension of zinc (217.63 mg, 3.33 mmol) in THF (6 mL) under an argon atmosphere, and the mixture was heated to reflux for 1 hour. Then a solution of nonane-3,7-dione (400.0 mg, 2.56 mmol) in THF (2 mL) was added and the resulting mixture was stirred for 3 hours at room temperature. The mixture was quenched with saturated Na$_2$CO$_3$ solution and then filtered over Celite. The filtrate was extracted three times with ethyl acetate. The combined organic phases were washed with brine, dried over Na$_2$SO$_4$, filtered and evaporated under reduced pressure. The residue was purified by column chromatography (Sfar D silica gel, 25 g) eluting with a gradient of EtOAc in cyclohexane from 20% to 80% to give (1R,2S)-1,2-diethylcyclopentane-1,2-diol (84 mg, 0.531 mmol, 20.73% yield) as a colourless oil. $^1$H NMR (400 MHz, DMSO-d$_6$) δ 0.88 (t, J=7.38 Hz, 6H), 1.15-1.30 (m, 2H), 1.32-1.45 (m, 2H), 1.46-1.69 (m, 6H), 3.81 (s, 2H).

Intermediate 379: 2-(2-bromo-4-chlorophenyl)acetyl chloride

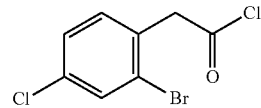 [SMILES: O=C(Cl)Cc1ccc(Cl)cc1Br]

2-(2-Bromo-4-chlorophenyl)acetic acid (1.5 g, 6.01 mmol) was dissolved in thionyl chloride (7.0 mL, 95.97 mmol) and the mixture was stirred at 60° C. for 1.5 hours. The mixture was evaporated in vacuo. The residue was taken up twice in DCM and evaporated to remove the majority of the excess thionyl chloride. The crude product was used in the next step without further purification. LC-MS (Method A): r.t. 1.15 min, MS (ESI) m/z=263.0 and 264.95 [M+H]$^+$.

Intermediate 380:
1-(2-bromo-4-chlorophenyl)-3-methylbutan-2-one

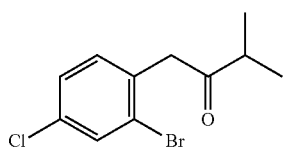

A 0.75M solution of isopropylmagnesium bromide in THF (10.35 mL, 7.76 mmol) was added dropwise over a period of 30 min, under nitrogen, to a stirred solution of 2-(2-bromo-4-chlorophenyl)acetyl chloride (1.6 g, 5.97 mmol) and iron(III) acetylacetonate (63.27 mg, 0.180 mmol) in dry THF (60 mL) at room temperature. After complete addition, stirring was continued for 30 min at the same temperature. Then, the reaction mixture was quenched with 1M aqueous HCl solution and extracted with EtOAc. The organic phase was washed with saturated aqueous NaHCO$_3$ solution and brine, filtered over a hydrophobic frit (Phase Separator) and evaporated in vacuo. The residue was purified by column chromatography (KP-sil silica gel, SNAP 50) eluting with a gradient of EtOAc in cyclohexane from 0% to 60% to give 1-(2-bromo-4-chlorophenyl)-3-methylbutan-2-one (300 mg, 1.089 mmol, 18.23% yield) as a brown oil. $^1$H NMR (400 MHz, DMSO-d$_6$) δ 1.10 (d, J=6.82 Hz, 1H), 2.78 (sept, J=6.93 Hz, 1H), 4.03 (s, 2H), 7.34 (d, J=8.25 Hz, 1H), 7.43 (dd, J=8.24, 2.21 Hz, 1H), 7.73 (d, J=2.20 Hz, 1H). LC-MS (Method A): r.t. 1.25 min, MS (ESI) m/z=275.02 and 277.01 [M+H]$^+$.

Intermediate 381:
1-(2-bromo-4-chlorophenyl)-3-methylbutan-2-ol

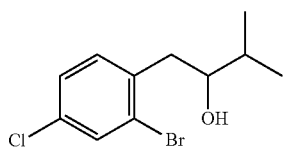

Sodium borohydride (57.66 mg, 1.52 mmol) was added portionwise to a solution of 1-(2-bromo-4-chlorophenyl)-3-methylbutan-2-one (300.0 mg, 1.09 mmol) in ethanol (11 mL). The reaction mixture was stirred for 1.5 hours at room temperature. 1N Hydrochloric acid solution was added and the resulting aqueous mixture was extracted 3 times with DCM. The combined organic phases were washed with brine, filtered over a hydrophobic frit (Phase Separator) and evaporated in vacuo. The residue was purified by column chromatography (KP-Sil silica gel, SNAP 25) eluting with a gradient of EtOAc in cyclohexane from 0% to 30% to give 1-(2-bromo-4-chlorophenyl)-3-methylbutan-2-ol (232 mg, 0.836 mmol, 76.77% yield) as a white powder. $^1$H NMR (400 MHz, DMSO-d$_6$) δ 0.93 (d, J=6.82 Hz, 1H), 1.55-1.68 (m, 1H), 2.56 (dd, J=13.65, 9.42 Hz, 1H), 2.87 (dd, J=13.64, 3.26 Hz, 1H), 3.37-3.49 (m, 1H), 4.46 (d, J=6.15 Hz, 1H), 7.36-7.39 (m, 2H), 7.68 (d, J=1.69 Hz, 1H). LC-MS (Method A): r.t. 1.29 min, MS (ESI) m/z of product not observed due to poor ionization.

Intermediate 382: [1-(2-bromo-4-chlorophenyl)-3-methylbutan-2-yl]oxy-tert-butyl-dimethylsilane (Racemic

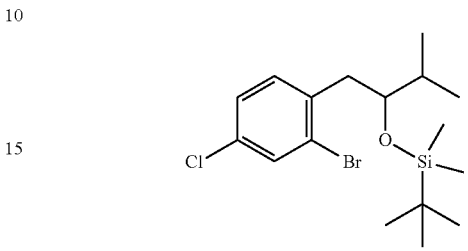

tert-Butyl(chloro)dimethylsilane (377.9 mg, 2.51 mmol) was added to a solution of 1-(2-bromo-4-chlorophenyl)-3-methylbutan-2-ol (232.0 mg, 0.840 mmol) and imidazole (170.7 mg, 2.51 mmol) in THF (8 mL) under a N$_2$ atmosphere. The reaction mixture was stirred for 15 hours at 55° C. Water was added and the resulting mixture was extracted three times with EtOAc. The combined organic phases were washed with saturated aqueous sodium bicarbonate solution and brine, filtered over a hydrophobic frit (Phase Separator) and evaporated. The residue was purified by column chromatography (KP-Sil silica gel, SNAP 25) eluting with a gradient of EtOAc in cyclohexane from 0% to 5% to give 2 [1-(2-bromo-4-chlorophenyl)-3-methylbutan-2-yl]oxy-tert-butyl-dimethylsilane (171 mg, 0.436 mmol, 52.21% yield) as a colorless oil. $^1$H NMR (400 MHz, DMSO-d$_6$) δ −0.46 (s, 3H), −0.10 (s, 3H), 0.79 (s, 9H), 0.92 (d, J=6.82 Hz, 3H), 0.97 (d, J=6.90 Hz, 3H), 1.66-1.78 (m, 1H), 2.67 (dd, J=13.35, 9.10 Hz, 1H), 2.84 (dd, J=13.34, 3.94 Hz, 1H), 3.78-3.91 (m, 1H), 7.31 (d, J=8.22 Hz, 1H), 7.40 (dd, J=8.24, 2.19 Hz, 1H), 7.70 (d, J=2.17 Hz, 1H). LC-MS (Method A): r.t. 1.97 min, MS (ESI) m/z of product not observed due to poor ionization.

Intermediate 383: tert-butyl[(1-{4-chloro-2-[(1S,2S, 6R,8S)-2,9,9-trimethyl-3,5-dioxa-4-boratricyclo [6.1.1.0$^{2,6}$]decan-4-yl]phenyl}-3-methylbutan-2-yl) oxy]dimethylsilane (Racemic

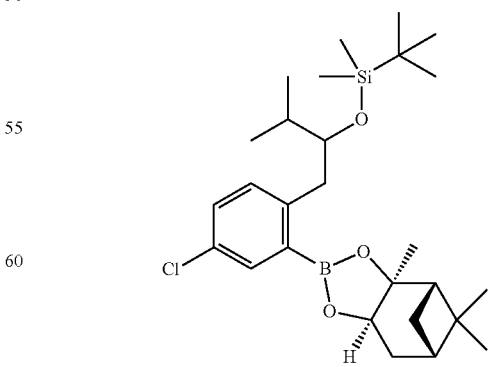

A mixture of [1-(2-bromo-4-chlorophenyl)-3-methylbutan-2-yl]oxy-tert-butyl-dimethylsilane (171.0 mg, 0.440 mmol), potassium acetate (0.22 g, 2.18 mmol) and bis[(+)-pinanendiolato]diboron (468.8 mg, 1.31 mmol) in 1,2-dimethoxyethane (2.44 mL) was degassed for 10 min under N$_2$. Then [1,1'-bis(diphenylphosphino)ferrocene]dichloropalladium(II) (32.02 mg, 0.040 mmol) was added and the resulting reaction mixture was stirred at 100° C. for 2.5 hours. The mixture was filtered over a pad of Celite, washing with EtOAc. The filtrate was concentrated in vacuo and the residue was purified by column chromatography (Sfar D silica gel, 25 g) eluting with a gradient of EtOAc in cyclohexane from 0% to 1% to give tert-butyl[(1-{4-chloro-2-[(1S,2S,6R,8S)-2,9,9-trimethyl-3,5-dioxa-4-boratricyclo[6.1.1.0$^{2,6}$]decan-4-yl]phenyl}-3-methylbutan-2-yl)oxy]dimethylsilane (126 mg, 0.257 mmol, 58.8% yield) as a colourless oil. $^1$H NMR (400 MHz, DMSO-d$_6$) δ −0.64 (s, 3H one diastereoisomer), −0.60 (s, 3H one diastereoisomer), −0.20 (s, 3H one diastereoisomer), −0.18 (s, 3H one diastereoisomer), 0.74 (s, 9H one diastereoisomer), 0.75 (s, 9H one diastereoisomer), 0.87 (s, 3H both diastereoisomers), 0.88-0.96 (m, 6H both diastereoisomers), 1.09-1.16 (m, 1H both diastereoisomers), 1.29 (s, 3H both diastereoisomers), 1.44-1.45 (m, 3H both diastereoisomers), 1.67-1.78 (m, 1H both diastereoisomers), 1.80-1.97 (m, 2H both diastereoisomers), 2.09 (t, J=5.35 Hz, 1H both diastereoisomers), 2.17-2.29 (m, 1H both diastereoisomers), 2.35-2.45 (m, 1H both diastereoisomers), 2.67-2.75 (m, 2H both diastereoisomers), 2.96-3.03 (m, 1H both diastereoisomers), 3.65-3.82 (m, 1H both diastereoisomers), 4.44-4.58 (m, 1H both diastereoisomers), 7.18-7.24 (m, 1H both diastereoisomers), 7.42 (dd, J=8.24, 2.46 Hz, 1H both diastereoisomers), 7.62 (d, J=2.20 Hz, 1H both diastereoisomers).

Intermediate 384: 1-[(2,4-dimethoxyphenyl)methyl]-4-(hydroxymethyl)pyrrolidin-2-one

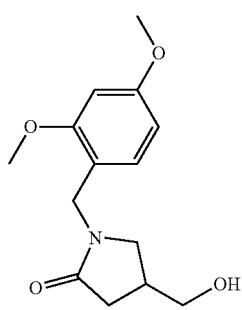 [SMILES: COc1ccc(CN2CC(CO)CC2=O)c(OC)c1]

A solution of (2,4-dimethoxyphenyl)methanamine (500.0 mg, 2.99 mmol) and 2-methylenebutanedioic acid dimethyl ester (567.49 mg, 3.59 mmol) in MeOH (7 mL) was stirred at room temperature for two hours then evaporated in vacuo. The residue was taken up with methanol (7 mL) and sodium borohydride (113.12 mg, 2.99 mmol) was added in portions. The resulting mixture was stirred at room temperature overnight then evaporated under reduced pressure. The residue was purified by column chromatography (KP-Sil silica gel, SNAP 50) eluting with a gradient of MeOH in dichloromethane from 1% to 15% to give 1-[(2,4-dimethoxyphenyl)methyl]-4-(hydroxymethyl)pyrrolidin-2-one (406 mg, 1.53 mmol, 51.18% yield) as a colourless oil. $^1$H NMR (400 MHz, Chloroform-d) δ 2.16-2.31 (m, 1H), 2.46-2.60 (m, 2H), 3.01-3.19 (m, 1H), 3.34-3.45 (m, 1H), 3.51-3.68 (m, 2H), 3.82 (s, 3H), 3.82 (s, 3H), 4.44 (s, 2H), 6.44-6.50 (m, 2H), 7.13-7.18 (m, 1H). LC-MS (Method A): r.t. 0.65 min, MS (ESI) m/z=266.2 [M+H]$^+$.

Intermediate 385: 4-(2-bromo-4-chlorophenoxymethyl)pyrrolidin-2-one

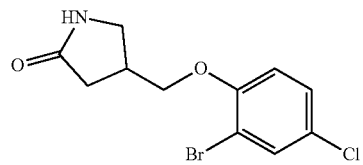 [SMILES: O=C1CC(COc2ccc(Cl)cc2Br)CN1]

Diisopropyl azodicarboxylate (0.31 mL, 1.59 mmol) was added to a solution of 2-bromo-4-chlorophenol (140.75 mg, 0.680 mmol), triphenylphosphine (195.75 mg, 0.750 mmol) and 1-[(2,4-dimethoxyphenyl)methyl]-4-(hydroxymethyl)pyrrolidin-2-one (180.0 mg, 0.680 mmol) in THF (3 mL) at room temperature. The resulting mixture was stirred at this temperature for 30 minutes then evaporated under reduced pressure. The residue was dissolved in dichloromethane (1 mL) and trifluoroacetic acid (1 mL) and the resulting mixture was stirred at 50° C. for 2 hours then evaporated in vacuo. The residue was quenched with saturated aqueous NaHCO$_3$ solution and extracted three times with EtOAc. The combined organic layers were washed with water and brine, dried over Na$_2$SO$_4$, filtered and evaporated. The residue was purified by column chromatography (KP-Sil silica gel, SNAP 25) eluting with a gradient of dichloromethane in cyclohexane from 5% to 50% to give 4-[(2-bromo-4-chlorophenoxy)methyl]pyrrolidin-2-one (150 mg, 0.492 mmol, 72.59% yield) as a colourless oil. $^1$H NMR (400 MHz, DMSO-d$_6$) δ 2.08 (dd, J=16.68, 6.77 Hz, 1H), 2.32 (dd, J=16.70, 9.03 Hz, 1H), 2.77-2.95 (m, 1H), 3.14 (dd, J=9.74, 5.62 Hz, 1H), 3.35-3.45 (m, 1H), 3.94-4.15 (m, 2H), 7.16 (d, J=8.88 Hz, 1H), 7.42 (dd, J=8.83, 2.57 Hz, 1H), 7.57 (s, 1H), 7.70 (d, J=2.59 Hz, 1H). LC-MS (Method A): r.t. 0.94 min, MS (ESI) m/z=304.1 and 306.1 [M+H]$^+$.

Intermediate 386: 4-[[4-chloro-2-[4-[(2,4-dimethoxyphenyl)methylamino]cinnolin-7-yl]phenoxy]methyl]pyrrolidin-2-one

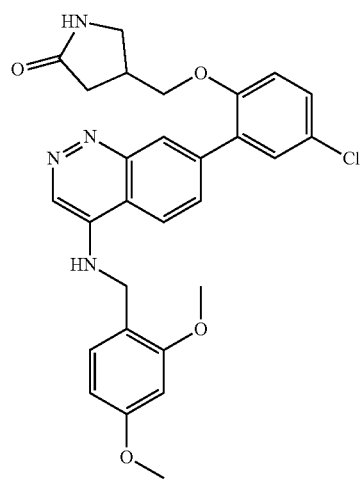 [SMILES: COc1ccc(CNc2cnnc3cc(-c4cc(Cl)ccc4OCC4CNC(=O)C4)ccc23)c(OC)c1]

A mixture of 4-[(2-bromo-4-chlorophenoxy)methyl]pyrrolidin-2-one (150.0 mg, 0.490 mmol) and N-[(2,4-dimethoxyphenyl)methyl]-7-(4,4,5,5-tetramethyl-1,3,2-dioxaborolan-2-yl)cinnolin-4-amine (269.74 mg, 0.640 mmol) in 1,2-dimethoxyethane (4.925 mL) and aqueous 2M sodium carbonate solution (492.5 uL, 0.980 mmol) was degassed for 10 min with $N_2$. Then [1,1'-bis(di-tert-butylphosphino)ferrocene]dichloropalladium(II) (32.2 mg, 0.050 mmol) was added and the resulting reaction mixture was stirred at 75° C. for four hours. The mixture was cooled to room temperature and filtered over Celite, washing with EtOAc. The filtrate was evaporated and the residue was purified by column chromatography (KP-NH silica gel, SNAP 28) eluting with a gradient EtOAc in cyclohexane from 10% to 100% to give 4-[[4-chloro-2-[4-[(2,4-dimethoxyphenyl)methylamino]cinnolin-7-yl]phenoxy]methyl]pyrrolidin-2-one (180 mg, 0.347 mmol, 70.42% yield) as a white powder. $^1$H NMR (400 MHz, DMSO-$d_6$) δ 1.96-2.09 (m, 1H), 2.23 (dd, J=16.67, 9.04 Hz, 1H), 2.71-2.80 (m, 1H), 3.04 (dd, J=9.75, 6.09 Hz, 1H), 3.24-3.28 (m, 1H), 3.76 (s, 3H), 3.87 (s, 3H), 3.97-4.12 (m, 2H), 4.61 (d, J=5.05 Hz, 2H), 6.51 (dd, J=8.39, 2.39 Hz, 1H), 6.64 (d, J=2.40 Hz, 1H), 7.22 (d, J=8.38 Hz, 1H), 7.25 (d, J=8.94 Hz, 1H), 7.49 (m, 2H), 7.57 (d, J=2.72 Hz, 1H), 7.86 (dd, J=8.83, 1.82 Hz, 1H), 8.17 (d, J=1.84 Hz, 1H), 8.44 (d, J=8.87 Hz, 1H), 8.57 (s, 1H), 8.66 (s, 1H). LC-MS (Method A): r.t. 0.77 min, MS (ESI) m/z=519.8 [M+H]$^+$.

Intermediate 387:
7-chloro-1-hydroxy-2,3,1-benzoxazaborinine

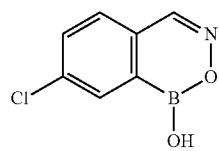 [SMILES: OB1ON=Cc2ccc(Cl)cc21]

A 50% w/w aqueous solution of hydroxylamine (132.94 uL, 2.17 mmol) was added to a stirred mixture of (5-chloro-2-formylphenyl)boronic acid in aqueous pH7 buffer solution (10 mL): the reaction mixture was stirred at room temperature for 2 h. The reaction mixture was filtrered collecting the solid which was washed with water to give 7-chloro-1-hydroxy-2,3,1-benzoxazaborinine (217 mg, 1.196 mmol, 55.15% yield) as a white solid. $^1$H NMR (400 MHz, DMSO-$d_6$) δ 7.81 (d, J=8.36 Hz, 1H), 7.89 (dd, J=8.14, 1.98 Hz, 1H), 8.08 (d, J=2.20 Hz, 1H), 8.69 (s, 1H), 9.55 (s, 1H). LC-MS (Method A): r.t. 0.85 min, MS (ESI) m/z=182.0 [M+H]$^+$.

Intermediate 388: N-[(2,4-dimethoxyphenyl)methyl]-7-(1-hydroxy-2,3,1-benzoxazaborinin-7-yl)cinnolin-4-amine

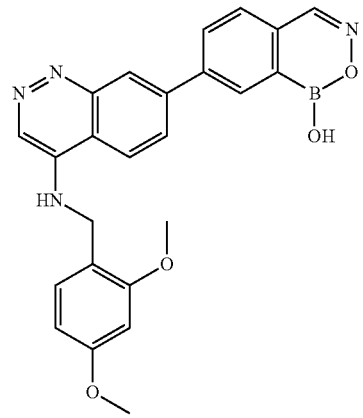 [SMILES: COc1ccc(CNc2cnnc3cc(-c4ccc5c(c4)B(O)ON=C5)ccc23)c(OC)c1]

A mixture of N-[(2,4-dimethoxyphenyl)methyl]-7-(4,4,5,5-tetramethyl-1,3,2-dioxaborolan-2-yl)cinnolin-4-amine (649.21 mg, 1.54 mmol), 7-chloro-1-hydroxy-2,3,1-benzoxazaborinine (215.0 mg, 1.19 mmol) and aqueous 2N sodium carbonate solution (1.19 mL, 2.37 mmol) in 1,4-dioxane (30 mL) was degassed for 10 minutes under argon, then (XPhos) palladium(II) phenethylamine chloride (87.57 mg, 0.120 mmol) was added and the mixture was degassed again for 10 minutes. The mixture was heated to 90° C. and stirred for 6 hours. The mixture was allowed to cool to room temperature then it was diluted with EtOAc and filtered over Celite, washing with EtOAc and MeOH. The filtrate was concentrated and the residue was purified by column chromatography (KP-C18-HS, 2×SNAP 30 g in series) eluting with a gradient of MeCN (+0.1% of HCOOH) in water (+0.1% of HCOOH) from 2% to 50%. Appropriate fractions were lyophilized to give N-[(2,4-dimethoxyphenyl)methyl]-7-(1-hydroxy-2,3,1-benzoxazaborinin-7-yl)cinnolin-4-amine (113 mg, 0.257 mmol, 21.65% yield) as a yellowish solid. $^1$H NMR (400 MHz, DMSO-$d_6$) δ 3.75 (s, 3H), 3.89 (s, 3H), 4.54 (d, J=5.50 Hz, 2H), 6.49 (dd, J=8.36, 2.42 Hz, 1H), 6.64 (d, J=2.20 Hz, 1H), 7.18 (d, J=8.36 Hz, 1H), 7.80 (d, J=8.14 Hz, 1H), 7.85-7.90 (m, 1H), 7.93 (d, J=8.14 Hz, 1H), 8.06-8.18 (m, 2H), 8.39 (dd, J=8.25, 1.87 Hz, 1H), 8.47-8.51 (m, 1H), 8.52 (s, 1H), 8.64-8.69 (m, 1H) 8.75 (s, 1H). LC-MS (Method A): r.t. 0.66 min, MS (ESI) m/z=441.3 [M+H]$^+$.

Intermediate 389: 2-bromo-4-chloro-5-methylphenol

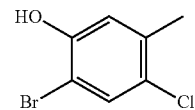

To a mixture of 2-bromo-5-methylphenol (5.0 g, 26.73 mmol) in DMF (37.5 mL) and trifluoroacetic acid (1.25 mL) was added 1-chloropyrrolidine-2,5-dione (3.57 g, 26.73 mmol). The reaction mixture was stirred overnight at room temperature, then a saturated aqueous solution of $Na_2S_2O_3$ was added, followed by EtOAc. The phases were separated and the organic phase was washed with brine, dried over Na$_2$SO$_4$, filtered and concentrated. The residue was purified by column chromatography (Sfar D, 100 g+50 g in series) eluting with a gradient of EtOAc in cyclohexane from 0% to 10% to give 2-bromo-4-chloro-5-methylphenol (3.27 g, 14.76 mmol, 55.23% yield) as a yellowish solid. $^1$H NMR (400 MHz, DMSO-d$_6$) δ 2.22 (s, 3H), 6.90 (d, J=0.66 Hz, 1H), 7.51 (s, 1H), 10.36 (s, 1H). LC-MS (Method A): r.t. 1.11 min, MS (ESI) m/z=219.0 and 221.2 [M−H]$^−$.

Intermediate 390: 1-bromo-5-chloro-2-(2,2-diethoxyethoxy)-4-methylbenzene

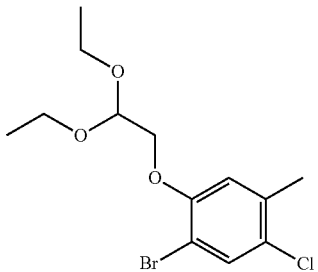 [SMILES: CCOC(COc1cc(C)c(Cl)cc1Br)OCC]

To a mixture of 2-bromo-4-chloro-5-methylphenol (3.27 g, 13.88 mmol) and potassium carbonate (2.88 g, 20.82 mmol) in DMF (23.05 mL) was added 2-bromo-1,1-diethoxyethane (2.53 mL, 16.65 mmol). The reaction mixture was stirred overnight at 100° C., then it was allowed to cool to room temperature. Water and EtOAc were added, the phases were separated and the organic phase was washed with brine, dried over Na$_2$SO$_4$, filtered and concentrated. The residue was purified by column chromatography (Sfar D, 100 g+50 g in series) eluting with a gradient of EtOAc in cyclohexane from 0% to 10% to give 1-bromo-5-chloro-2-(2,2-diethoxyethoxy)-4-methylbenzene (3.28 g, 9.714 mmol, 70% yield) as a yellowish oil. $^1$H NMR (400 MHz, DMSO-d$_6$) δ 1.15 (t, J=7.04 Hz, 6H), 2.29 (s, 3H), 3.55-3.65 (m, 2H), 3.66-3.75 (m, 2H), 4.02 (d, J=5.28 Hz, 2H), 4.83 (t, J=5.28 Hz, 1H), 7.21 (s, 1H), 7.63 (s, 1H). LC-MS (Method A): r.t. 1.46 min, MS (ESI) m/z of product not observed due to poor ionization.

Intermediate 391: 7-bromo-5-chloro-4-methyl-1-benzofuran

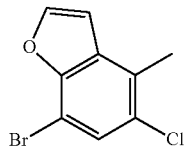

A mixture of 1-bromo-5-chloro-2-(2,2-diethoxyethoxy)-4-methylbenzene (2.3 g, 6.81 mmol) and polyphosphoric acid (2.3 g, 9.59 mmol) in toluene (50.6 mL) was stirred overnight at 110° C. The mixture was left to reach room temperature and water and EtOAc were added. The phases were separated and the organic phase was washed with 1N aqueous NaOH solution, dried over Na$_2$SO$_4$, filtered and concentrated. The residue was purified by column chromatography (KP-Sil silica gel, SNAP 100 g) eluting with a gradient of EtOAc in cyclohexane from 0% to 25% to give 7-bromo-5-chloro-4-methyl-1-benzofuran (580 mg, 2.363 mmol, 34.68% yield) as a white solid. $^1$H NMR (400 MHz, DMSO-d$_6$) δ 2.49 (s, 3H), 7.27 (d, J=2.20 Hz, 1H), 7.65 (s, 1H), 8.17 (d, J=2.42 Hz, 1H). LC-MS (Method A): r.t. 0.39 min, MS (ESI) m/z of product not observed due to poor ionization.

Intermediate 392: 7-(5-chloro-4-methyl-1-benzofuran-7-yl)-N-[(2,4-dimethoxyphenyl)methyl]cinnolin-4-amine

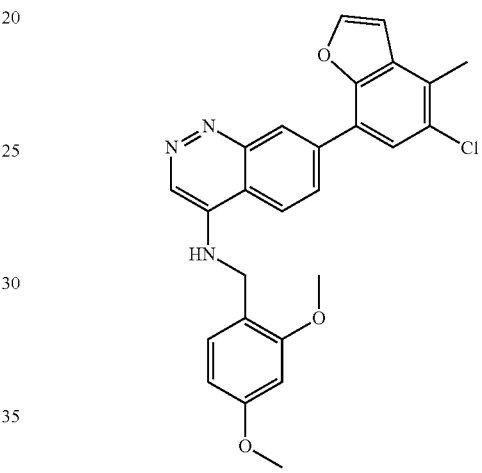

A mixture of N-[(2,4-dimethoxyphenyl)methyl]-7-(4,4,5,5-tetramethyl-1,3,2-dioxaborolan-2-yl)cinnolin-4-amine (463.34 mg, 1.1 mmol), 7-bromo-5-chloro-4-methyl-1-benzofuran (180.0 mg, 0.730 mmol) and aqueous 2N sodium carbonate solution (0.73 mL, 1.47 mmol) in 1,2-dimethoxyethane (12.41 mL) was degassed for 10 minutes under argon, then [1,1′-bis(di-tert-butylphosphino)ferrocene]dichloropalladium (II) (47.93 mg, 0.070 mmol) was added. The mixture was heated to 85° C. and stirred for 1 hour. The mixture was allowed to cool to room temperature then it was diluted with EtOAc and filtered over Celite, washing with EtOAc and MeOH. The filtrate was concentrated and the residue was purified by column chromatography (KP-C18-HS, 2×30 g in series) eluting with a gradient of CH$_3$CN (+0.1% of HCOOH) in water (+0.1% of HCOOH) from 2% to 50% to give 7-(5-chloro-4-methyl-1-benzofuran-7-yl)-N-[(2,4-dimethoxyphenyl)methyl]cinnolin-4-amine (127 mg, 0.276 mmol, 37.66% yield) as a brown solid. $^1$H NMR (400 MHz, DMSO-d$_6$) δ 2.60 (s, 3H), 3.74 (s, 3H), 3.89 (s, 3H), 4.54 (d, J=5.50 Hz, 2H), 6.49 (dd, J=8.36, 2.42 Hz, 1H), 6.64 (d, J=2.20 Hz, 1H), 7.18 (d, J=8.36 Hz, 1H), 7.27 (d, J=2.20 Hz, 1H), 7.83 (s, 1H), 8.10 (t, J=6.16 Hz, 1H), 8.15 (dd, J=8.80, 1.98 Hz, 1H), 8.22 (d, J=2.20 Hz, 1H), 8.49 (d, J=8.80 Hz, 1H), 8.52 (s, 1H), 8.66 (d, J=1.76 Hz, 1H). LC-MS (Method A): r.t. 0.90 min, MS (ESI) m/z=460.2 [M+H]$^+$.

Intermediate 393: 1-[4-chloro-2-(4,4,5,5-tetramethyl-1,3,2-dioxaborolan-2-yl)phenyl]ethan-1-one

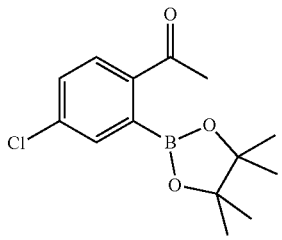 [SMILES: CC(=O)c1ccc(Cl)cc1B1OC(C)(C)C(C)(C)O1]

A mixture of 1-(2-bromo-4-chlorophenyl)ethanone (1.0 g, 4.28 mmol), potassium acetate (1.26 g, 12.85 mmol) and 4,4,5,5-tetramethyl-2-(4,4,5,5-tetramethyl-1,3,2-dioxaborolan-2-yl)-1,3,2-dioxaborolane (1.2 g, 4.71 mmol) in 1,4-dioxane (17 mL) was degassed for 10 minutes under argon, then [1,1-bis(diphenylphosphino)ferrocene]dichloropalladium(II) complex with dichloromethane (105.18 mg, 0.130 mmol) was added and the mixture was stirred at 90° C. for 5 hours. The mixture was allowed to cool to room temperature and filtered over Celite, washing with EtOAc. The filtrate was concentrated and the residue was purified by column chromatography (Sfar D, 50 g) eluting with a gradient of EtOAc in cyclohexane from 0% to 50% to give 1-[4-chloro-2-(4,4,5,5-tetramethyl-1,3,2-dioxaborolan-2-yl)phenyl]ethan-1-one (355 mg, 1.265 mmol, 29.55% yield) as a brownish solid. $^1$H NMR (400 MHz, DMSO-d$_6$) δ 1.33 (s, 12H), 2.59 (s, 3H), 7.43 (d, J=2.19 Hz, 1H), 7.61 (dd, J=8.35, 2.19 Hz, 1H), 8.03 (d, J=8.35 Hz, 1H). LC-MS (Method A): r.t. 1.18 min, MS (ESI) m/z=279.2 [M+H]$^+$.

Intermediate 394: 2-bromo-4-chloro-1-($^2$H$_3$)methoxybenzene

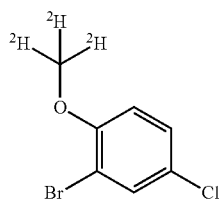 [SMILES: [2H]C([2H])([2H])Oc1ccc(Cl)cc1Br]

Potassium carbonate (2.66 g, 19.28 mmol) and iodo($^2$H$_3$)methane (0.72 mL, 11.57 mmol) were added to a solution of 2-bromo-4-chlorophenol (2.0 g, 9.64 mmol) in acetone (18 mL) at 0° C. The mixture was stirred at room temperature for 6 hours, then diluted with EtOAc and washed with water and brine, dried over Na$_2$SO$_4$, filtered and evaporated under reduced pressure. The residue was purified by column chromatography (Sfar D, 50 g) eluting with a gradient of EtOAc in cyclohexane from 0% to 40% to give 2-bromo-4-chloro-1-($^2$H$_3$)methoxybenzene (1.87 g, 8.33 mmol, 86.4% yield) as a colourless liquid. $^1$H NMR (400 MHz, DMSO-d$_6$) δ 7.13 (d, J=8.84 Hz, 1H), 7.42 (dd, J=8.85, 2.59 Hz, 1H), 7.68 (d, J=2.61 Hz, 1H). LC-MS (Method A): r.t. 1.21 min, MS (ESI) m/z of product not observed due to poor ionization.

Intermediate 395: 7-[5-chloro-2-($^2$H$_3$)methoxyphenyl]-N-[(2,4-dimethoxyphenyl)methyl]cinnolin-4-amine

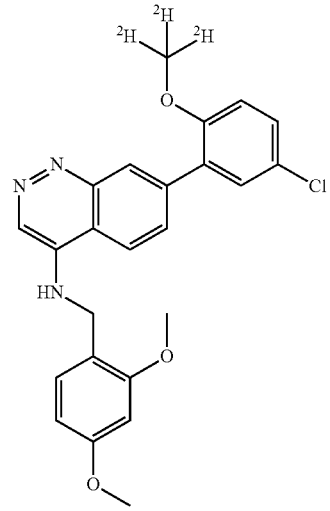 [SMILES: [2H]C([2H])([2H])Oc1ccc(Cl)cc1-c1ccc2c(NCc3ccc(OC)cc3OC)cnnc2c1]

A mixture of 2-bromo-4-chloro-1-(2H$_3$)methoxybenzene (500.0 mg, 2.23 mmol), N-[(2,4-dimethoxyphenyl)methyl]-7-(4,4,5,5-tetramethyl-1,3,2-dioxaborolan-2-yl)cinnolin-4-amine (1.22 g, 2.9 mmol) and an aqueous 2M sodium carbonate solution (2.23 mL, 4.45 mmol) in 1,4-dioxane (20 mL) was degassed for 10 minutes under argon, then [1,1'-bis(di-tert-butylphosphino)ferrocene]dichloropalladium(II) (145.6 mg, 0.220 mmol) was added and the resulting reaction mixture was stirred at 85° C. for 6 hours. The mixture was allowed to cool to room temperature then diluted with MeOH and filtered over Celite, washing with MeOH and EtOAc. The filtrate was concentrated and the residue was purified by column chromatography (Sfar Amino D, 55 g) eluting with a gradient of EtOAc in cyclohexane from 10% to 100% to give 7-[5-chloro-2-($^2$H$_3$)methoxyphenyl]-N-[(2,4-dimethoxyphenyl)methyl]cinnolin-4-amine (691 mg, 1.574 mmol, 70.69% yield) as an off-white solid. $^1$H NMR (400 MHz, DMSO-d$_6$) δ 3.74 (s, 3H), 3.88 (s, 3H), 4.52 (d, J=6.04 Hz, 2H), 6.47 (dd, J=8.38, 2.44 Hz, 1H), 6.63 (d, J=2.43 Hz, 1H), 7.15 (d, J=8.36 Hz, 1H), 7.21 (d, J=8.80 Hz, 1H), 7.47 (dd, J=8.78, 2.70 Hz, 1H), 7.52 (d, J=2.64 Hz, 1H), 7.76 (dd, J=8.76, 1.89 Hz, 1H), 8.02 (t, J=5.99 Hz, 1H), 8.18 (d, J=1.76 Hz, 1H), 8.36 (d, J=8.80 Hz, 1H), 8.48 (s, 1H). LC-MS (Method A): r.t. 0.83 min, MS (ESI) m/z=489.2 [M+H]$^+$.

Intermediate 396: 6-(5-chloro-2-methoxyphenyl)phthalazin-1-ol

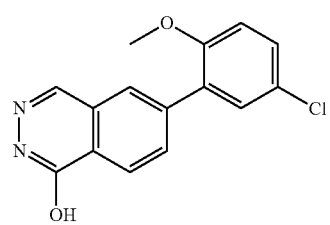 [SMILES: COc1ccc(Cl)cc1-c1ccc2c(O)nncc2c1]

A mixture of 5-chloro-2-methoxyphenylboronic acid (248.49 mg, 1.33 mmol), 6-bromophthalazin-1(2H)-one (200.0 mg, 0.890 mmol) and aqueous 2 M sodium carbonate solution (1.11 mL, 2.22 mmol) in 1,4-dioxane (8.887 mL) was degassed for 10 min. Then [1,1'-bis(di-tert-butylphosphino)ferrocene]dichloropalladium(II) (58.1 mg, 0.090 mmol) was added and resulting reaction mixture was stirred at 80° C. for 4 hours. The mixture was filtered over Celite, washing 3 times with MeOH. The filtrate was concentrated in vacuo and the residue was purified by column chromatography (KP-NH silica gel, SNAP 28) eluting with a gradient of EtOAc in cyclohexane from 2% to 95% to give 6-(5-chloro-2-methoxyphenyl)-2H-phthalazin-1-one (120 mg, 0.419 mmol, 47.09% yield) as a yellow powder. $^1$H NMR (400 MHz, DMSO-$d_6$) δ 3.81 (s, 3H), 7.17-7.27 (m, 1H), 7.46-7.52 (m, 2H), 7.96 (dd, J=8.27, 1.73 Hz, 1H), 8.05 (d, J=1.70 Hz, 1H), 8.23 (d, J=8.25 Hz, 1H), 8.38 (s, 1H), 12.65 (s, 1H). LC-MS (Method A): r.t. 1.00 min, MS (ESI) m/z=287.1 [M+H]$^+$.

Intermediate 397:
7-(5-chloro-2-methoxyphenyl)isoquinoline

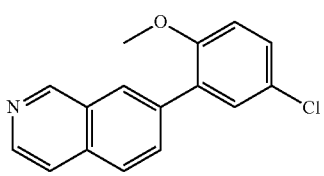 [SMILES: COc1ccc(Cl)cc1-c1ccc2ccncc2c1]

A mixture of 2-bromo-4-chloro-1-methoxybenzene (250.0 mg, 1.13 mmol), isoquinoline-7-boronic acid (292.88 mg, 1.69 mmol) and aqueous 2 M sodium carbonate solution (2.32 mL, 4.63 mmol) in 1,4-dioxane (11.29 mL) was degassed for 10 min. Then [1,1'-bis(di-tert-butylphosphino)ferrocene]dichloropalladium(II) (65.38 mg, 0.100 mmol) was added and the resulting reaction mixture was stirred at 75° C. for 4 hours. The mixture was filtered on Celite, washing with MeOH. The filtrate was concentrated in vacuo and the residue was purified by column chromatography (KP-NH silica gel, SNAP 28) eluting with a gradient of EtOAc in cyclohexane from 2% to 95% to give 7-(5-chloro-2-methoxyphenyl)isoquinoline (198 mg, 0.734 mmol, 65.03% yield) as a yellow powder. $^1$H NMR (400 MHz, DMSO-$d_6$) δ 3.82 (s, 3H), 7.22 (d, J=8.74 Hz, 1H), 7.45-7.51 (m, 2H), 7.86 (d, J=5.66 Hz, 1H), 7.93 (dd, J=8.49, 1.74 Hz, 1H), 8.00 (d, J=8.53 Hz, 1H), 8.23 (t, J=1.27 Hz, 1H), 8.53 (d, J=5.77 Hz, 1H), 9.36 (s, 1H). LC-MS (Method A): r.t. 0.80 min, MS (ESI) m/z=270.1 [M+H]$^+$.

Intermediate 398:
1-(2-amino-4-bromo-6-methoxyphenyl)ethanone

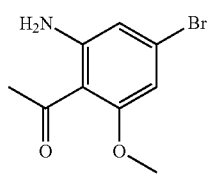

A stirred solution of 3-bromo-5-methoxyaniline (5 g, 24.75 mmol) and dry acetonitrile (15.63 mL, 296.96 mmol) in dry toluene (58 mL) was cooled to 0° C. A 1M solution of trichloroborane in toluene (29.7 mL, 29.7 mmol) was added dropwise, whilst keeping the temperature below 10° C. Then trichloroalumane (4.29 g, 32.17 mmol) was added in small portions at 0° C. The reaction mixture was heated to 100° C. for 4 hours. The reaction mixture was cooled to room temperature and then quenched with 2M aqueous HCl solution (20 mL). The mixture was heated to 50° C. for 30 min then cooled to room temperature and the phases were separated. The aqueous phase was extracted with EtOAc. The combined organic phases were filtered through a hydrophobic frit (Phase Separator) and concentrated under reduced pressure. The residue was purified by column chromatography (Sfar D silica gel, SNAP 200) eluting with a gradient of EtOAc in cyclohexane from 0% to 30% to give 1-(2-amino-4-bromo-6-methoxyphenyl)ethanone (2.7 g, 11.06 mmol, 44.7% yield) as a pale-yellow solid. $^1$H NMR (400 MHz, DMSO-$d_6$) δ 2.43 (s, 3H), 3.82 (s, 3H), 6.35 (d, J=1.85 Hz, 1H), 6.59 (d, J=1.86 Hz, 1H), 6.95 (s, 2H). LC-MS (Method A): r.t. 1.01 min, MS (ESI) m/z=244.01 and 246.03 [M+H]$^+$.

Intermediate 399: 7-bromo-5-methoxycinnolin-4-ol

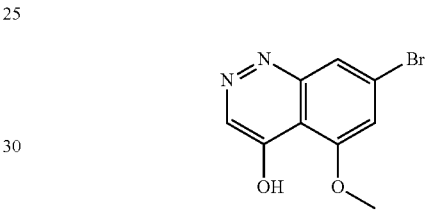

1-(2-Amino-4-bromo-6-methoxyphenyl)ethanone (2.7 g, 11.06 mmol) was dissolved in 12M hydrochloric acid solution (63.94 mL, 767.23 mmol) and water (10 mL), then the mixture was cooled to −5° C. in an ice/brine bath. A solution of sodium nitrite (801.41 mg, 11.61 mmol) in water (6 mL) was added slowly. The reaction mixture was stirred for one hour, then the temperature was raised to 60° C., and the mixture was stirred for 2 hours and then cooled to room temperature. The resulting precipitate was filtered off, washed with water and dried to give 7-bromo-5-methoxycinnolin-4-ol (2.4 g, 9.409 mmol, 85.06% yield) as an off white solid. $^1$H NMR (400 MHz, DMSO-$d_6$) δ 3.87 (s, 3H), 6.95 (d, J=1.70 Hz, 1H), 7.23 (d, J=1.69 Hz, 1H), 7.56 (s, 1H), 13.17 (s, 1H). LC-MS (Method A): r.t. 0.62 min, MS (ESI) m/z=254.97 and 256.97 [M+H]$^+$.

Intermediate 400:
7-bromo-4-chloro-5-methoxycinnoline

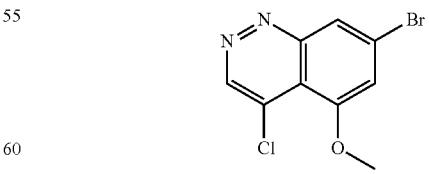

A solution of 7-bromo-5-methoxycinnolin-4-ol (1.0 g, 3.92 mmol) in phosphorus oxychloride (4 mL, 42.78 mmol) was stirred at 90° C. for 4 hours. The reaction mixture was cooled to room temperature then the excess of phosphorus oxychloride was removed in vacuo. The residue was dissolved in EtOAc and neutralized with saturated aqueous NaHCO$_3$ solution. The precipitate was filtered off on a Hirsch funnel, and washed twice with water. The solid was dried in an oven overnight to give 7-bromo-4-chloro-5-methoxycinnoline (706 mg, 2.581 mmol, 65.84% yield) as a brownish solid. $^1$H NMR (400 MHz, DMSO-d$_6$) δ 4.03 (s, 3H), 7.50 (d, J=1.73 Hz, 1H), 8.30 (d, J=1.72 Hz, 1H), 9.44 (s, 1H). LC-MS (Method A): r.t. 1.03 min, MS (ESI) m/z=272.91 and 274.93 [M+H]$^+$.

Intermediate 401: N'-(7-bromo-5-methoxycinnolin-4-yl)-4-methylbenzenesulfonohydrazide

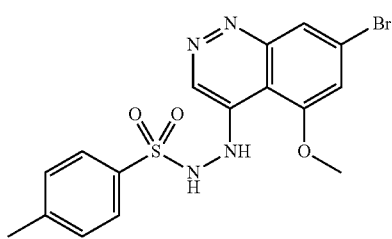 [SMILES: COc1cc(Br)cc2nncc(NNS(=O)(=O)c3ccc(C)cc3)c12]

4-Methylbenzenesulfonohydrazide (1.23 g, 6.58 mmol) was added to a solution of 7-bromo-4-chloro-5-methoxycinnoline (600 mg, 2.19 mmol) in dry chloroform (54 mL) and the resulting mixture was stirred at 85° C. overnight. The reaction mixture was cooled to room temperature and the resulting suspension was filtered on a Gooch funnel to give N'-(7-bromo-5-methoxycinnolin-4-yl)-4-methylbenzenesulfonohydrazide (764 mg, 1.805 mmol, 82.28% yield) as a red powder. LC-MS (Method A): r.t. 0.70 min, MS (ESI) m/z=423.04 and 425.00 [M+H]$^+$.

Intermediate 402: 7-bromo-5-methoxycinnoline

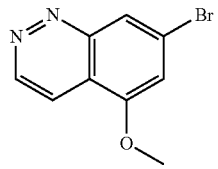

A mixture of N'-(7-bromo-5-methoxycinnolin-4-yl)-4-methylbenzenesulfonohydrazide (700 mg, 1.44 mmol) and aqueous 1M sodium carbonate solution (2.88 mL, 2.88 mmol) was stirred at 100° C. for 2 hours. Then water was added and the resulting precipitate was filtered over a Gooch funnel washing with water. The resulting powder was dried in an oven overnight to give 7-bromo-5-methoxycinnoline (254 mg, 1.062 mmol, 73.84% yield) as a brown powder. $^1$H NMR (400 MHz, DMSO-d$_6$) δ 4.06 (s, 3H), 7.41 (d, J=1.60 Hz, 1H), 8.19-8.27 (m, 2H), 9.41 (d, J=5.77 Hz, 1H). LC-MS (Method A): r.t. 0.85 min, MS (ESI) m/z=238.96 and 240.97 [M+H]$^+$.

Intermediate 403: 7-(5-chloro-2-methoxyphenyl)-5-methoxycinnoline

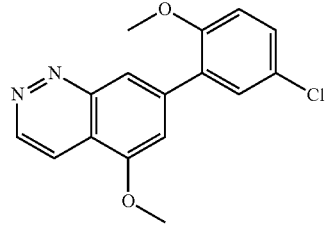 [SMILES: COc1ccc(Cl)cc1-c1cc(OC)c2ccnnc2c1]

A mixture of 5-chloro-2-methoxyphenyl boronic acid (156.0 mg, 0.840 mmol), 7-bromo-5-methoxycinnoline (166.73 mg, 0.700 mmol) and aqueous 2 N sodium carbonate solution (697.42 uL, 1.39 mmol) in 1,2-dimethoxyethane (7 mL) was degassed for 10 min under N$_2$. Then [1,1'-bis(di-tert-butylphosphino)ferrocene]dichloropalladium(II) (45.59 mg, 0.070 mmol) was added and the resulting reaction mixture was stirred at 80° C. for 16 hours. The mixture was filtered over a pad of Celite, washing with MeOH. The filtrate was concentrated in vacuo and the residue was purified by column chromatography (KP-Sil silica gel, SNAP 25) eluting with a gradient of EtOAc in cyclohexane from 0% to 30% to give 7-(5-chloro-2-methoxyphenyl)-5-methoxycinnoline (115 mg, 0.382 mmol, 54.83% yield) as a yellow powder. $^1$H NMR (400 MHz, DMSO-d$_6$) δ 3.84 (s, 3H), 4.07 (s, 3H), 7.24 (d, J=8.86 Hz, 1H), 7.36 (d, J=1.37 Hz, 1H), 7.50 (dd, J=8.82, 2.68 Hz, 1H), 7.61 (d, J=2.69 Hz, 1H), 8.11 (t, J=1.14 Hz, 1H), 8.25 (dd, J=5.85, 0.99 Hz, 1H), 9.37 (d, J=5.86 Hz, 1H). LC-MS (Method A): r.t. 1.12 min, MS (ESI) m/z=301.04 [M+H]$^+$.

Intermediate 404: 2-bromo-4-chloro-1-(1,1-difluoroethoxy)benzene

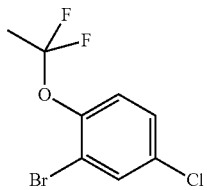

Hydrogen fluoride-pyridine (70% HF, 4.77 mL, 54.82 mmol) and 1-(2-bromo-4-chlorophenyl)ethanone (1.6 g, 6.85 mmol) were added to a stirred mixture of difluoroxenon (2.32 g, 13.71 mmol) in DCM (34 mL). The reaction mixture was stirred at room temperature overnight, then it was cooled at 0° C. and EtOAc and satured aqueous NaHCO$_3$ solution were added to quench the HF. The phases were separated, and the organic phase was washed with brine and dried over Na$_2$SO$_4$. The volatiles were removed and the residue was purified by column chromatography (KP silica gel, SNAP 100) eluting with a gradient of EtOAc in cyclohexane from 0% to 10% to give 2-bromo-4-chloro-1-(1,1-difluoroethoxy)benzene (920 mg, 3.389 mmol, 49.45% yield) as a colourless oil. $^1$H NMR (400 MHz, DMSO-d$_6$) δ 2.01 (t, J=14.01 Hz, 3H), 7.40 (dt, J=8.77, 1.38 Hz, 1H), 7.53 (dd, J=8.80, 2.57 Hz, 1H), 7.89 (d, J=2.55 Hz, 1H).

LC-MS (Method A): r.t. 1.33 min, MS (ESI) m/z of product not observed due to poor ionization.

Intermediate 405: 7-[5-chloro-2-(1,1-difluoroethoxy)phenyl]-N-[(2,4-dimethoxyphenyl)methyl]cinnolin-4-amine

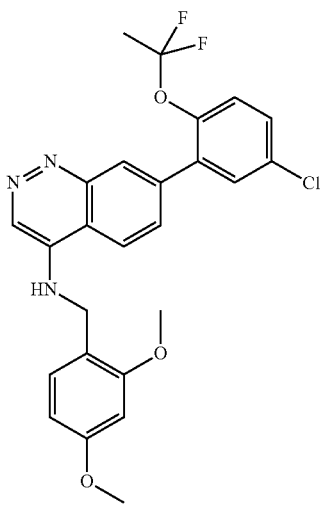 [SMILES: COc1ccc(CNc2cnnc3cc(-c4cc(Cl)ccc4OC(C)(F)F)ccc23)c(OC)c1]

A mixture of 2-bromo-4-chloro-1-(1,1-difluoroethoxy)benzene (150.0 mg, 0.550 mmol), N-[(2,4-dimethoxyphenyl)methyl]-7-(4,4,5,5-tetramethyl-1,3,2-dioxaborolan-2-yl)cinnolin-4-amine (302.6 mg, 0.720 mmol) and aqueous 2 N sodium carbonate solution (552.51 uL, 1.11 mmol) in 1,2-dimethoxyethane (6 mL) was degassed for 10 min under $N_2$. Then [1,1'-bis(di-tert-butylphosphino)ferrocene]dichloropalladium(II) (36.12 mg, 0.060 mmol) was added and the resulting reaction mixture was stirred at 80° C. for 24 hours. The mixture was filtered over a pad of Celite, washing with MeOH. The filtrate was concentrated in vacuo and the residue was purified by column chromatography (KP-NH silica gel, SNAP 28) eluting with a gradient of EtOAc in cyclohexane from 0% to 100% to give 7-[5-chloro-2-(1,1-difluoroethoxy)phenyl]-N-[(2,4-dimethoxyphenyl)methyl]cinnolin-4-amine (150 mg, 0.309 mmol, 55.87% yield) as a yellow oil. $^1$H NMR (400 MHz, DMSO-$d_6$) δ 1.74 (t, J=13.85 Hz, 3H), 3.74 (s, 3H), 3.88 (s, 3H), 4.52 (d, J=5.65 Hz, 2H), 6.48 (dd, J=8.37, 2.42 Hz, 1H), 6.63 (d, J=2.37 Hz, 1H), 7.17 (d, J=8.39 Hz, 1H), 7.46 (d, J=8.80 Hz, 1H), 7.57 (dd, J=8.74, 2.67 Hz, 1H), 7.69-7.77 (m, 2H), 8.07 (t, J=5.84 Hz, 1H), 8.18 (d, J=1.79 Hz, 1H), 8.41 (d, J=8.81 Hz, 1H), 8.51 (s, 1H). $^{19}$F NMR (377 MHz, DMSO-$d_6$) δ −62.14 (q, J=13.95 Hz). LC-MS (Method A). r.t. 0.87 min, MS (ESI) m/z=486.16 [M+H]$^+$.

Intermediate 406: 7-(5-chloro-2-methylsulfonylphenyl)-N-[(2,4-dimethoxyphenyl)methyl]cinnolin-4-amine

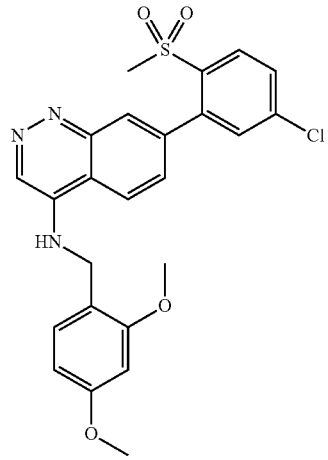 [SMILES: COc1ccc(CNc2cnnc3cc(-c4cc(Cl)ccc4S(C)(=O)=O)ccc23)c(OC)c1]

A mixture of 2-bromo-4-chloro-1-methylsulfonylbenzene (200.0 mg, 0.740 mmol) and N-[(2,4-dimethoxyphenyl)methyl]-7-(4,4,5,5-tetramethyl-1,3,2-dioxaborolan-2-yl)cinnolin-4-amine (0.47 g, 1.11 mmol) in 1,4-dioxane (7.4 mL) and aqueous 2N sodium carbonate solution (0.93 mL, 1.86 mmol) was degassed for 10 minutes with $N_2$. Then [1,1'-bis(di-tert-butylphosphino)ferrocene]dichloropalladium(II) (48.51 mg, 0.070 mmol) was added and the resulting reaction mixture was stirred at 80° C. overnight. The mixture was cooled to room temperature and filtered over Celite, washing with EtOAc. The filtrate was evaporated and the residue was purified by column chromatography (KP-NH silica gel, SNAP 28) eluting with a gradient of EtOAc in cyclohexane from 10% to 100% to give 7-(5-chloro-2-methylsulfonylphenyl)-N-[(2,4-dimethoxyphenyl)methyl]cinnolin-4-amine (285 mg, 0.589 mmol, 79.36% yield) as a yellow powder. $^1$H NMR (400 MHz, DMSO-$d_6$) δ 2.95 (s, 3H), 3.74 (s, 3H), 3.88 (s, 3H), 4.53 (d, J=5.81 Hz, 2H), 6.49 (dd, J=8.39, 2.42 Hz, 1H), 6.63 (d, J=2.41 Hz, 1H), 7.18 (d, J=8.37 Hz, 1H), 7.62-7.68 (m, 2H), 7.84 (dd, J=8.57, 2.23 Hz, 1H), 8.07-8.18 (m, 3H), 8.38 (d, J=8.82 Hz, 1H), 8.53 (s, 1H) LC-MS (Method A): r.t.0.72 min, MS (ESI) m/z=484.1 [M+H]$^+$.

Intermediate 407: tert-butyl N-[(2-bromo-4-chlorophenyl)sulfamoyl]carbamate

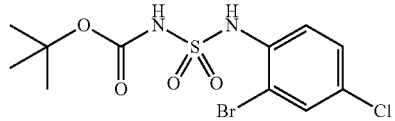 [SMILES: CC(C)(C)OC(=O)NS(=O)(=O)Nc1ccc(Cl)cc1Br]

N-(Oxomethylidene)sulfamoyl chloride (342.74 mg, 2.42 mmol) was added to a solution of tert-butanol (179.49 mg, 2.42 mmol) in DCM (2.5 mL) at 0° C. The mixture was stirred for 5 min and then it was added to a stirred cold (0° C.) mixture of 2-bromo-4-chloroaniline (500.0 mg, 2.42 mmol) and triethylamine (0.34 mL, 2.42 mmol) in DCM (2.5 mL). The reaction mixture was stirred at 0° C. for 30 minutes and at room temperature for 1 hour, then it was diluted with DCM and washed with aqueous 1N HCl solution and brine. The organic phase was dried over Na$_2$SO$_4$, filtered and concentrated under reduced pressure. The residue was purified by column chromatography (Sfar D, 25 g) eluting with a gradient of EtOAc in DCM from 0% to 15% to give tert-butyl N-[(2-bromo-4-chlorophenyl)sulfamoyl]carbamate (789 mg, 2.046 mmol, 84.48% yield) as a white solid. $^1$H NMR (400 MHz, DMSO-d$_6$) δ 1.41 (s, 9H), 7.39 (d, J=8.69 Hz, 1H), 7.54 (dd, J=8.65, 2.43 Hz, 1H), 7.83 (d, J=2.40 Hz, 1H), 9.75 (s, 1H), 11.23 (s, 1H). LC-MS (Method A): r.t. 1.16 min, MS (ESI) m/z=328.9 and 330.9 [M+H-tBu]$^+$.

Intermediate 408: tert-butyl 5-(2-bromo-4-chlorophenyl)-1,1-dioxo-1,2,5-thiadiazolidine-2-carboxylate

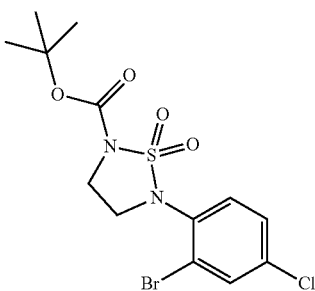 [SMILES: CC(C)(C)OC(=O)N1CCN(c2ccc(Cl)cc2Br)S1(=O)=O]

A suspension of tert-butyl N-[(2-bromo-4-chlorophenyl)sulfamoyl]carbamate (780.0 mg, 2.02 mmol), potassium carbonate (838.59 mg, 6.07 mmol) and 1,2-dibromoethane (0.52 mL, 6.07 mmol) in MeCN (7 mL) was stirred at 80° C. for 24 hours then it was cooled to room temperature. The mixture was quenched with water and extracted three times with EtOAc. The combined organic phases were washed with brine, dried over Na$_2$SO$_4$, filtered and evaporated in vacuo. The residue was purified by column chromatography (Sfar D, 25 g) eluting with a gradient of EtOAc in cyclohexane from 2% to 50% to give tert-butyl 5-(2-bromo-4-chlorophenyl)-1,1-dioxo-1,2,5-thiadiazolidine-2-carboxylate (610 mg, 1.482 mmol, 73.26% yield) as an off-white solid. $^1$H NMR (400 MHz, DMSO-d$_6$) δ 1.48 (s, 9H), 3.88 (t, J=6.47 Hz, 2H), 3.99 (t, J=6.47 Hz, 2H), 7.61 (dd, J=8.57, 2.40 Hz, 1H), 7.68 (d, J=8.61 Hz, 1H), 7.96 (d, J=2.35 Hz, 1H). LC-MS (Method A): r.t. 0.94 min, MS (ESI) m/z=354.8 and 356.8 [M+H-tBu]$^+$.

Intermediate 409: tert-butyl 5-[4-chloro-2-[4-[(2,4-dimethoxyphenyl)methylamino]cinnolin-7-yl]phenyl]-1,1-dioxo-1,2,5-thiadiazolidine-2-carboxylate

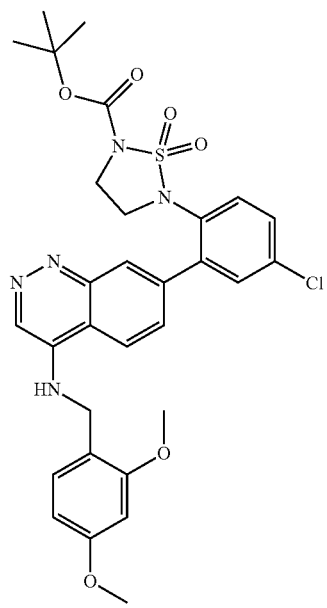 [SMILES: COc1ccc(CNc2cnnc3cc(-c4cc(Cl)ccc4N4CCN(C(=O)OC(C)(C)C)S4(=O)=O)ccc23)c(OC)c1]

A mixture of tert-butyl 5-(2-bromo-4-chlorophenyl)-1,1-dioxo-1,2,5-thiadiazolidine-2-carboxylate (250.0 mg, 0.610 mmol) and N-[(2,4-dimethoxyphenyl)methyl]-7-(4,4,5,5-tetramethyl-1,3,2-dioxaborolan-2-yl)cinnolin-4-amine (0.38 g, 0.910 mmol) in 1,4-dioxane (6.1 mL) and aqueous 2M sodium carbonate solution (0.76 mL, 1.52 mmol) was degassed for 10 min with N$_2$. Then [1,1'-bis(di-tert-butylphosphino)ferrocene]dichloropalladium(II) (39.7 mg, 0.060 mmol) was added and the resulting reaction mixture was stirred at 80° C. for 24 hours. The mixture was cooled to room temperature and filtered over Celite, washing with EtOAc. The filtrate was evaporated and the residue was purified by column chromatography (KP-NH silica gel, SNAP 28) eluting with a gradient of EtOAc in cyclohexane from 10% to 100% to give tert-butyl 5-[4-chloro-2-[4-[(2,4-dimethoxyphenyl)methylamino]cinnolin-7-yl]phenyl]-1,1-dioxo-1,2,5-thiadiazolidine-2-carboxylate (196 mg, 0.313 mmol, 51.55% yield) as a yellow powder. $^1$H NMR (400 MHz, DMSO-d$_6$) δ 1.42 (s, 9H), 3.71-3.74 (m, 2H), 3.75 (s, 3H), 3.76-3.80 (m, 2H), 3.89 (s, 3H), 4.53 (d, J=5.97 Hz, 2H), 6.49 (dd, J=8.40, 2.38 Hz, 1H), 6.64 (d, J=2.40 Hz, 1H), 7.18 (d, J=8.37 Hz, 1H), 7.68 (dd, J=8.58, 2.54 Hz, 1H), 7.73 (d, J=2.44 Hz, 1H), 7.74-7.78 (m, 2H), 8.04 (t, J=5.97 Hz, 1H), 8.19 (d, J=1.81 Hz, 1H), 8.38 (d, J=8.85 Hz, 1H), 8.51 (s, 1H). LC-MS (Method A): r.t. 0.87 min, MS (ESI) m/z=626.1 [M+H]$^+$.

Intermediate 410: 2-bromo-4-chloro-1-(4-fluorophenoxy)benzene

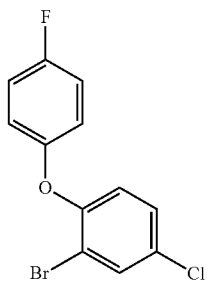 [SMILES: Fc1ccc(Oc2ccc(Cl)cc2Br)cc1]

A mixture of 2-bromo-4-chloro-1-fluorobenzene (889.68 mg, 4.25 mmol), 4-fluorophenol (500.0 mg, 4.46 mmol) and potassium carbonate (1.23 g, 8.92 mmol) in DMSO (5 mL) was stirred at 150° C. for 1.5 hours, then it was allowed to coo to room temperature. EtOAc and water were added, the two phases were separated. The organic phase was washed three times with brine, filtered over a hydrophobic frit (Phase Separator) and concentrated in vacuo. The residue was purified by column chromatography (KP-Sil silica gel, SNAP 50) eluting with a gradient of EtOAc in cyclohexane from 0% to 5% to give 2-bromo-4-chloro-1-(4-fluorophenoxy)benzene (950 mg, 3.15 mmol, 70.63% yield) as a colourless oil. $^1$H NMR (400 MHz, DMSO-$d_6$) δ 7.00-7.09 (m, 3H), 7.19-7.28 (m, 2H), 7.46 (dd, J=8.79, 2.55 Hz, 1H), 7.88 (d, J=2.50 Hz, 1H). LC-MS (Method A): r.t. 1.42 min, no mass detected, MS (ESI) m/z of product not observed due to poor ionization.

Intermediate 411: 7-[5-chloro-2-(4-fluorophenoxy)phenyl]-N-[(2,4-dimethoxyphenyl)methyl]cinnolin-4-amine

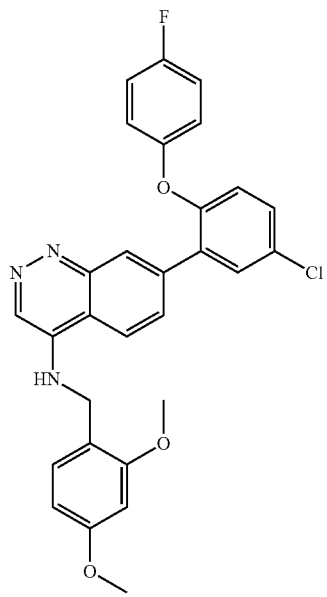 [SMILES: COc1ccc(CNc2cnnc3cc(-c4cc(Cl)ccc4Oc4ccc(F)cc4)ccc23)c(OC)c1]

A mixture of 2-bromo-4-chloro-1-(4-fluorophenoxy)benzene (300.0 mg, 0.970 mmol), N-[(2,4-dimethoxyphenyl)methyl]-7-(4,4,5,5-tetramethyl-1,3,2-dioxaborolan-2-yl)cinnolin-4-amine (691.18 mg, 1.64 mmol) and aqueous 2 N sodium carbonate solution (1.93 mL, 3.86 mmol) in 1,2-dimethoxyethane (10 mL) was degassed for 10 min under $N_2$. Then [1,1'-bis(di-tert-butylphosphino)ferrocene]dichloropalladium(II) (63.09 mg, 0.100 mmol) was added and the resulting reaction mixture was stirred at 80° C. for 12 hours. The mixture was filtered over a pad of Celite, washing with MeOH. The filtrate was concentrated in vacuo and the residue was purified by column chromatography (KP-NH silica gel, SNAP 55) eluting with a gradient of MeOH in DCM from 2% to 100% to give 7-[5-chloro-2-(4-fluorophenoxy)phenyl]-N-[(2,4-dimethoxyphenyl)methyl]cinnolin-4-amine (220 mg, 0.426 mmol, 44.18% yield) as a yellow powder. $^1$H NMR (400 MHz, DMSO-$d_6$) δ 3.74 (s, 3H), 3.87 (s, 3H), 4.51 (d, J=3.96 Hz, 2H), 6.46 (dd, J=8.38, 2.41 Hz, 1H), 6.62 (d, J=2.39 Hz, 1H), 7.01-7.11 (m, 3H), 7.11-7.22 (m, 3H), 7.51 (dd, J=8.79, 2.65 Hz, 1H), 7.74 (d, J=2.64 Hz, 1H), 7.83 (dd, J=8.80, 1.86 Hz, 1H), 8.02 (t, J=6.03 Hz, 1H), 8.26 (d, J=1.82 Hz, 1H), 8.36 (d, J=8.86 Hz, 1H), 8.48 (s, 1H). LC-MS (Method A): r.t. 0.95 min, MS (ESI) m/z=516.15 [M+H]$^+$.

Intermediate 412: 5-(2-bromo-4-chlorophenoxy)-1,3-thiazole

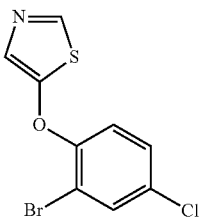 [SMILES: Clc1ccc(Oc2cncs2)c(Br)c1]

2-Bromo-4-chlorophenol (750.0 mg, 3.62 mmol), copper (I) oxide (52.46 mg, 0.360 mmol), 5-bromothiazole (592.99 mg, 3.62 mmol) and dicesium carbonate (2.36 g, 7.23 mmol) were dissolved in DMSO (12.05 mL). The resulting reaction mixture was stirred at 100° C. for 3 hours then it was cooled to room temperature and filtered. The filtrate was diluted with water and extracted 3 times with EtOAc. The combined organic phases were washed with water and brine, dried over $Na_2SO_4$, filtered and evaporated in vacuo. The residue was purified by column chromatography (Sfar D NH, 55 g) eluting with a gradient of EtOAc in cyclohexane from 1% to 35% to give 5-(2-bromo-4-chlorophenoxy)-1,3-thiazole (537 mg, 1.848 mmol, 51.12% yield) as an off-white solid. $^1$H NMR (400 MHz, DMSO-$d_6$) δ 7.26 (d, J=8.79 Hz, 1H), 7.51 (dd, J=8.83, 2.54 Hz, 1H), 7.66 (d, J=0.91 Hz, 1H), 7.91 (d, J=2.52 Hz, 1H), 8.79 (d, J=0.93 Hz, 1H). LC-MS (Method A): r.t. 1.19 min, MS (ESI) m/z=289.88 and 291.88 [M+H]$^+$.

Intermediate 413: 7-[5-chloro-2-(1,3-thiazol-5-yloxy)phenyl]-N-[(2,4-dimethoxyphenyl)methyl]cinnolin-4-amine

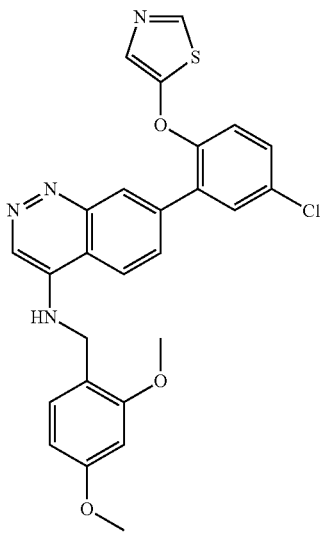 [SMILES: COc1ccc(CNc2cnnc3cc(-c4cc(Cl)ccc4Oc4cncs4)ccc23)c(OC)c1]

A mixture of 5-(2-bromo-4-chlorophenoxy)-1,3-thiazole (150.0 mg, 0.520 mmol), N-[(2,4-dimethoxyphenyl)methyl]-7-(4,4,5,5-tetramethyl-1,3,2-dioxaborolan-2-yl)cinnolin-4-amine (0.33 g, 0.770 mmol) and aqueous 2N sodium carbonate solution (0.83 mL, 1.65 mmol) in 1,2-dimethoxyethane (5.199 mL) was degassed for 10 minutes with $N_2$. Then [1,1'-bis(di-tert-butylphosphino)ferrocene]dichloropalladium(II) (37.49 mg, 0.060 mmol) was added and the resulting reaction mixture was stirred at 75° C. for five hours. The mixture was cooled to room temperature and filtered over Celite, washing with EtOAc. The filtrate was evaporated and the residue was purified by column chromatography (KP-NH silica gel, SNAP 28) eluting with a gradient of EtOAc in cyclohexane from 10% to 100% to give 7-[5-chloro-2-(1,3-thiazol-5-yloxy)phenyl]-N-[(2,4-dimethoxyphenyl)methyl]cinnolin-4-amine (168 mg, 0.333 mmol, 64.44% yield) as a yellow powder. $^1$H NMR (400 MHz, DMSO-$d_6$) δ 3.73 (s, 3H), 3.87 (s, 3H), 4.51 (d, J=5.99 Hz, 2H), 6.47 (dd, J=8.40, 2.41 Hz, 1H), 6.62 (d, J=2.38 Hz, 1H), 7.15 (d, J=8.36 Hz, 1H), 7.30 (d, J=8.82 Hz, 1H), 7.53-7.58 (m, 2H), 7.75 (d, J=2.64 Hz, 1H), 7.81 (dd, J=8.78, 1.86 Hz, 1H), 8.06 (t, J=6.90 Hz, 1H), 8.25 (d, J=1.78 Hz, 1H), 8.40 (d, J=8.83 Hz, 1H), 8.49 (s, 1H), 8.68 (d, J=0.95 Hz, 1H). LC-MS (Method A): r.t. 0.80 min, MS (ESI) m/z=550.09 [M+H]$^+$.

Intermediate 414: 2-(2-bromo-4-chlorophenoxy)-1,3-thiazole

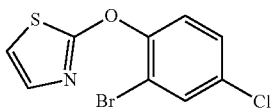 [SMILES: Clc1ccc(Oc2nccs2)c(Br)c1]

A mixture of 2-chlorothiazole (273.78 mg, 2.29 mmol), 2-bromo-4-chlorophenol (500 mg, 2.41 mmol) and potassium carbonate (999.35 mg, 7.23 mmol) in DMSO (5 mL) was stirred at 150° C. for 1.5 hours, then it was left to reach room temperature. EtOAc and water were added, the two phases were separated and the organic phase was washed 3 times with brine, filtered over a hydrophobic frit (Phase Separator) and concentrated in vacuo. The residue was purified by column chromatography (KP-NH silica gel, SNAP 55) eluting with a gradient of EtOAc in cyclohexane from 0% to 25% to give 2-(2-bromo-4-chlorophenoxy)-1,3-thiazole (390 mg, 1.342 mmol, 55.69% yield) as a colourless oil. $^1$H NMR (400 MHz, DMSO-$d_6$) δ 7.25 (d, J=3.74 Hz, 1H), 7.27 (d, J=3.74 Hz, 1H), 7.56-7.58 (m, 2H), 7.95 (dd, J=2.08, 0.71 Hz, 1H) LC-MS (Method A): r.t. 1.22 min, MS (ESI) m/z=289.88 and 291.88 [M+H]$^+$.

Intermediate 415: 7-[5-chloro-2-(1,3-thiazol-2-yloxy)phenyl]-N-[(2,4-dimethoxyphenyl)methyl]cinnolin-4-amine

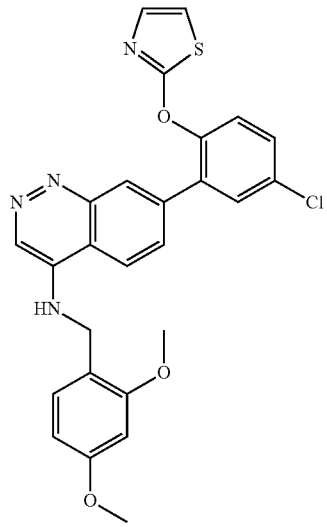 [SMILES: COc1ccc(CNc2cnnc3cc(-c4cc(Cl)ccc4Oc4nccs4)ccc23)c(OC)c1]

A mixture of 2-(2-bromo-4-chlorophenoxy)-1,3-thiazole (150.0 mg, 0.520 mmol), N-[(2,4-dimethoxyphenyl)methyl]-7-(4,4,5,5-tetramethyl-1,3,2-dioxaborolan-2-yl)cinnolin-4-amine (369.74 mg, 0.880 mmol) and aqueous 2 N sodium carbonate solution (0.77 mL, 1.55 mmol) in 1,2-dimethoxyethane (6 mL) was degassed for 10 min under $N_2$. Then [1,1'-bis(di-tert-butylphosphino)ferrocene]dichloropalladium(II) (33.75 mg, 0.050 mmol) was added and the resulting reaction mixture was stirred at 80° C. for 12 hours. The mixture was filtered over a pad of Celite, washing with MeOH. The filtrate was concentrated in vacuo and the residue was purified by column chromatography (KP-NH silica gel, SNAP 55) eluting with a gradient of MeOH in DCM from 0% to 100% to give 7-[5-chloro-2-(1,3-thiazol-2-yloxy)phenyl]-N-[(2,4-dimethoxyphenyl)methyl]cinnolin-4-amine (171 mg, 0.339 mmol, 65.59% yield) as a yellow oil. $^1$H NMR (400 MHz, DMSO-$d_6$) δ 3.74 (s, 3H), 3.87 (s, 3H), 4.50 (d, J=5.84 Hz, 2H), 6.47 (dd, J=8.38, 2.36 Hz, 1H), 6.63 (d, J=2.36 Hz, 1H), 7.11-7.19 (m, 3H), 7.57 (d, J=8.77 Hz, 1H), 7.64 (dd, J=8.71, 2.61 Hz, 1H), 7.75 (dd, J=8.75, 1.87 Hz, 1H), 7.81 (d, J=2.54 Hz, 1H), 8.05 (t, J=5.98 Hz, 1H), 8.19 (d, J=1.80 Hz, 1H), 8.38 (d, J=8.83 Hz, 1H), 8.49 (s, 1H). LC-MS (Method A): r.t. 0.82 min, MS (ESI) m/z=505.14 [M+H]$^+$.

Intermediate 416: 2-bromo-4-chloro-1-(2-methylprop-2-enoxy)benzene

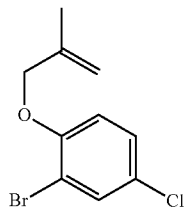

A suspension of 3-bromo-2-methyl-1-propene (0.35 mL, 3.47 mmol), 2-bromo-4-chlorophenol (600.0 mg, 2.89 mmol) and potassium carbonate (599.61 mg, 4.34 mmol) in DMF (5 mL) was stirred at 50° C. overnight. The mixture was cooled to room temperature, diluted with water and extracted three times with EtOAc. The combined organic phases were washed with water and brine, dried over Na$_2$SO$_4$, filtered and evaporated in vacuo. The residue was purified by column chromatography (Sfar D, 25 g) eluting with a gradient of EtOAc in cyclohexane from 0% to 40% to give 2-bromo-4-chloro-1-(2-methylprop-2-enoxy)benzene (736 mg, 2.814 mmol, 97.3% yield) as a colourless oil. $^1$H NMR (400 MHz, DMSO-d$_6$) δ 1.79 (s, 3H), 4.57 (s, 2H), 4.94-5.02 (m, 1H), 5.08-5.17 (m, 1H), 7.13 (d, J=8.90 Hz, 1H), 7.41 (dd, J=8.86, 2.59 Hz, 1H), 7.70 (d, J=2.55 Hz, 1H). LC-MS (Method A): r.t. 1.41 min., MS (ESI) m/z=260.97 and 262.97 [M+H]$^+$.

Intermediate 417: 2-bromo-4-chloro-6-(2-methylprop-2-enyl)phenol

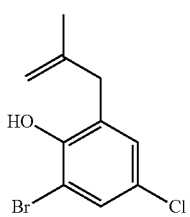

A solution of 2-bromo-4-chloro-1-(2-methylprop-2-enoxy)benzene (686.0 mg, 2.62 mmol) in DMF (13 mL) was stirred under microwave irradiation for ten minutes at 250° C. in a microwave reactor. The mixture was cooled to room temperature, diluted with water and extracted with EtOAc. The organic layer was washed with water and brine, dried over Na$_2$SO$_4$, filtered and evaporated in vacuo. The residue was purified by column chromatography (Sfar D, 25 g) eluting with a gradient of EtOAc in cyclohexane from 0% to 10% to give 2-bromo-4-chloro-6-(2-methylprop-2-enyl)phenol (353 mg, 1.35 mmol, 51.46% yield) as a colourless oil. $^1$H NMR (400 MHz, DMSO-d$_6$) δ 1.67 (t, J=1.06 Hz, 3H), 3.33 (s, 2H), 4.58-4.61 (m, 1H), 4.79-4.81 (m, 1H), 7.10 (d, J=2.62 Hz, 1H), 7.48 (d, J=2.64 Hz, 1H), 9.30 (br. s, 1H). LC-MS (Method A): r.t. 1.32 min., MS (ESI) m/z=259.01 and 261.01 [M+H]$^+$.

Intermediate 418: 7-bromo-5-chloro-2,2-dimethyl-3H-1-benzofuran

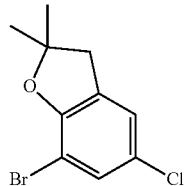

A suspension of 2-bromo-4-chloro-6-(2-methylprop-2-enyl)phenol (300.0 mg, 1.15 mmol) and 4-toluenesulfonic acid (19.75 mg, 0.110 mmol) in chloroform (6 mL) was stirred at 50° C. overnight, then cooled to room temperature and evaporated in vacuo. The residue was purified by column chromatography (Sfar D NH, 28 g) eluting with a gradient of EtOAc in cyclohexane from 1% to 10% to give 7-bromo-5-chloro-2,2-dimethyl-3H-1-benzofuran (295 mg, 1.128 mmol, 98.08% yield) as an off-white solid. $^1$H NMR (400 MHz, DMSO-d$_6$) δ 1.45 (s, 6H), 3.14 (s, 2H), 7.26-7.29 (m, 1H), 7.38-7.40 (m, 1H). LC-MS (Method A): r.t. 1.35 min, MS (ESI) m/z of product not observed due to poor ionization.

Intermediate 419: 7-(5-chloro-2,2-dimethyl-3H-1-benzofuran-7-yl)-N-[(2,4-dimethoxyphenyl)methyl]cinnolin-4-amine

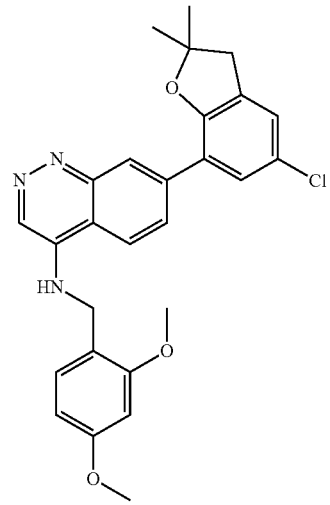 [SMILES: COc1ccc(CNc2cnnc3cc(-c4cc(Cl)cc5c4OC(C)(C)C5)ccc23)c(OC)c1]

A mixture of 7-bromo-5-chloro-2,2-dimethyl-3H-1-benzofuran (150.0 mg, 0.570 mmol) and N-[(2,4-dimethoxyphenyl)methyl]-7-(4,4,5,5-tetramethyl-1,3,2-dioxaborolan-2-yl)cinnolin-4-amine (0.36 g, 0.860 mmol) in 1,2-dimethoxyethane (5.735 mL) and aqueous 2N sodium carbonate solution (0.92 mL, 1.84 mmol) was degassed for 10 minutes with N$_2$. Then [1,1'-bis(di-tert-butylphosphino)ferrocene]dichloropalladium(II) (37.49 mg, 0.060 mmol) was added and the resulting reaction mixture was stirred at 75° C. for 12 hours. The mixture was cooled to room temperature and filtered over Celite, washing with EtOAc. The filtrate was evaporated and the residue was purified by column chromatography (KP-NH silica gel, SNAP 28) eluting with a gradient of EtOAc in cyclohexane from 10% to 100% to give 7-(5-chloro-2,2-dimethyl-3H-1-benzofuran-7-yl)-N-[(2,4-dimethoxyphenyl)methyl]cinnolin-4-amine (151 mg, 0.317 mmol, 55.32% yield) as an off white powder.

¹H NMR (400 MHz, DMSO-d₆) δ 1.51 (s, 6H), 3.13 (s, 2H), 3.75 (s, 3H), 3.89 (s, 3H), 4.52 (d, J=5.86 Hz, 2H), 6.48 (dd, J=8.38, 2.40 Hz, 1H), 6.64 (d, J=2.40 Hz, 1H), 7.16 (d, J=8.37 Hz, 1H), 7.31-7.34 (m, 1H), 7.57 (d, J=2.28 Hz, 1H), 7.96 (dd, J=8.89, 1.89 Hz, 1H), 8.03 (t, J=5.99 Hz, 1H), 8.39 (d, J=8.86 Hz, 1H), 8.47 (d, J=1.89 Hz, 1H), 8.48 (s, 1H). LC-MS (Method A): r.t. 0.92 min, MS (ESI) m/z=476.18 [M+H]⁺.

Intermediate 420:
5-(2-bromo-4-chlorophenoxy)-1,3-thiazole

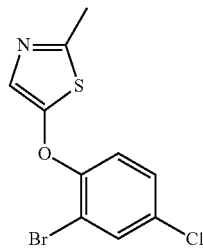

2-Bromo-4-chlorophenol (1.0 g, 4.82 mmol), potassium carbonate (666.23 mg, 4.82 mmol) and 5-bromo-2-methyl-thiazole (944.11 mg, 5.3 mmol) were suspended in DMSO (9.641 mL). The resulting reaction mixture was stirred at 120° C. for 24 hours then cooled to room temperature, diluted with water and extracted three times with EtOAc. The combined organic phases were washed with water and brine, dried over Na₂SO₄, filtered and evaporated in vacuo. The residue was purified by column chromatography (Sfar D NH, 55 g) eluting with a gradient of EtOAc in cyclohexane from 0% to 35% to give 5-(2-bromo-4-chloro-phenoxy)-2-methyl-thiazole (108 mg, 0.355 mmol, 7.356% yield) as an off-white solid. ¹H NMR (400 MHz, DMSO-d₆) δ 2.58 (s, 3H), 7.21 (d, J=8.88 Hz, 1H), 7.39 (s, 1H), 7.48 (dd, J=8.86, 2.53 Hz, 1H), 7.88 (d, J=2.53 Hz, 1H). LC-MS (Method A): r.t. 1.27 min, MS (ESI) m/z=305.95 and 307.95 [M+H]⁺.

Intermediate 421: 7-[5-chloro-2-(2-methylthiazol-5-yl)oxy-phenyl]-N-[(2,4-dimethoxyphenyl)methyl]cinnolin-4-amine

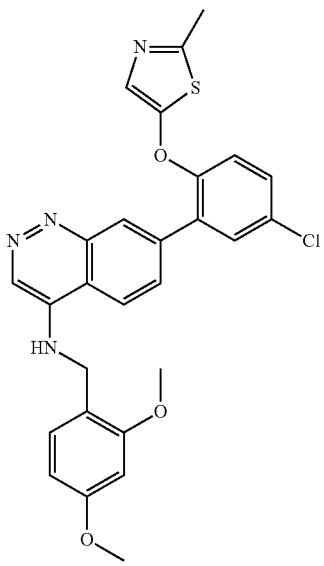 [SMILES: COc1ccc(CNc2cnnc3cc(-c4cc(Cl)ccc4Oc4cnc(C)s4)ccc23)c(OC)c1]

A mixture of 5-(2-bromo-4-chloro-phenoxy)-2-methyl-thiazole (108.0 mg, 0.350 mmol) and N-[(2,4-dimethoxy-phenyl)methyl]-7-(4,4,5,5-tetramethyl-1,3,2-dioxaborolan-2-yl)cinnolin-4-amine (0.22 g, 0.530 mmol) in 1,2-dimethoxyethane (3.743 mL) and aqueous 2N sodium carbonate solution (120.26 mg, 1.13 mmol) was degassed for 10 minutes with N₂. Then [1,1'-bis(di-tert-butylphosphino)ferrocene]dichloropalladium(II) (23.18 mg, 0.040 mmol) was added and the resulting reaction mixture was stirred at 75° C. for six hours. The mixture was cooled to room temperature and filtered over Celite, washing with EtOAc. The filtrate was evaporated and the residue was purified by column chromatography (KP-NH silica gel, SNAP 28) eluting with a gradient of EtOAc in cyclohexane from 10% to 100% to give 7-[5-chloro-2-(2-methylthiazol-5-yl)oxy-phenyl]-N-[(2,4-dimethoxyphenyl)methyl]cinnolin-4-amine (125 mg, 0.241 mmol, 67.92% yield) as a yellow powder. LC-MS (Method A): r.t. 0.82 min, MS (ESI) m/z=519.21 [M+H]⁺.

Example 173: General Procedure for the Conversion of Example Compounds into their Acid Salts (Suitable for Formation of, e.g., Methanesulphonic Acid Salt, Ethane Sulphonic Acid Salt and Maleic Acid Salt Anhydrous acid (1.16 mmol) was added to a stirred solution of the example compound (1.16 mmol) in MeOH (15 mL) and MeCN (5 mL) at room temperature. The resulting mixture was evaporated in vacuo to give the corresponding acid salt.

Example 174 Assays on Exemplary Compounds

In Vitro Hemolysis in Sensitized RBCs

The complement system is a group of proteins that, when activated, leads to target cell lysis and facilitates phagocytosis through opsonisation. Individual complement components can be quantified; however, this does not provide any information as to the activity of the pathway. The in vitro hemolysis assay tests the functional capability of serum complement components of the classical pathway to lyse sheep red blood cells (RBC) pre-coated with rabbit anti-sheep red blood cell antibody (hemolysin). When antibody-coated RBC are incubated with test serum, the classical complement pathway is activated and hemolysis results (Costabile M. Measuring the 50% Haemolytic Complement (CH50) Activity of Serum. (2010) *Journal of Visualized Experiments*. 37:1-3). If a complement component is inhibited, the hemolysis will be inhibited. The in vitro hemolysis of sensitized red blood cells can be induced by human serum (Complement Technology, cat. no NHS or Tebu-Bio, cat. no IPLA-SER), rat serum (Sprague-Dawley, in house or Tebu-Bio, cat. no IRT-COMPL), Cynomolgus serum (in house) or other animal serum/source as specified in the specific experiment.

Sheep Red Blood Cells Sensitization 1 mL of packed Sheep red blood cells ("RBC", 100 packed from Tebu-bio, cat. no IC100-0210) are re-suspended in 40 mL of DPBS (Sigma, cat. no D8537) and centrifuged at 500 g for 10 min (1800 rpm, room temperature, RT). The surnatant is aspirated and RBC are washed another 2-3 times until the surnatant is clear. The RBC are re-suspended in 20 mL of DPBS and sensitized with 1 μL of 0.005% hemolysin (Complement Technology, cat. no hemolysin) for 30 min at 37° C. with gentle shaking. The sensitized RBC (sRBC) are centrifuged as before and re-suspended in the Gelatin Hepes Buffer (GHB: 5 mM Hepes, pH 7.4, 71 mM NaCl, 2.5% Glucose, 0.1% Gelatin) and washed 2-3 times until the surnatant is clear. Sensitized RBC can be stored at 4° C. and should be used within 1 week.

In Vitro Hemolysis Assay

The test item stock solutions are serially diluted 1:3 or 1:4 or as appropriate with DMSO, 11-point curves, in a 384-well compound plate. Nafamostat is the reference control. The assay plate is prepared by copying 1.5 μL from the compound plate into a 384-well PP assay plate (Greiner 781280).

High controls are non-inhibited wells (DMSO), low controls are GHBE obtained with 10 mM final EDTA. The 100% hemolysis is obtained by using water instead of serum and is a control of cell density.

The stimulus consists in 1% of serum, as a 2× concentration and it is prepared in the same GHB as a 25 μL/well. On the day of the experiment sRBC washed once in GHB and the required amount is suspended as 400 Mc/mL of viable cells (Beckman Coulter, ViCell XR), which is 2× of the final assay concentration. 2× of $Ca^{++}$ and $Mg^{++}$ is included in the sRBC suspension (0.15 mM $CaCl_2$ and 0.5 mM $MgCl_2$ final assay concentrations).

The assay starts with the addition of 25 μL of sRBC to the 1.5 μL of compound dilution and 25 μL of serum. The plate is then incubated at 37° C. for 30 min. The reaction is terminated by the plate centrifugation at 1200 rpm for 2 min. The supernatant is transferred into a clear 384-well plate using a Biomek instrument (Beckman-Coulter). The hemolysis is quantified by measuring the absorbance at 415 nm using a ClarioStar plate reader (BMG).

Compound Testing in the C1s Enzymatic Assay

C1s is a serine protease; its enzymatic activity is measured in vitro by the hydrolysis of the synthetic substrate YLGR-Rh110-dPro (Kerr F K, O'Brien G, Quinsey N S, Whisstock J C, Boyd S, de la Banda M G, Kaiserman D, Matthews A Y, Bird P I, Pike R N. Elucidation of the substrate specificity of the C1s protease of the classical complement pathway. J. Biol. Chem. (2005) 280, 39510-39514). The enzyme cleaves the substrate with the release of Rh110 which is highly fluorescent. C1s inhibitors prevent the hydrolysis of the substrate thus resulting in a decrease of the signal. The data is reported as a pIC50, the negative log of the compound concentration at which the enzyme activity is inhibited by 50%.

The C1s enzymatic assay is performed using human C1s protein (Complement Technologies, A104 (examples 2, 9 and 11) or R&D Systems, 2060-SE (all other examples)). The assay buffer composition is: 50 mM HEPES pH 7.5 (Sigma, H3375), 150 mM NaCl (Sigma, S7653), 0.20 PE 8000 (VWR, AA43443-22), 0.01% Pluronic F127 (Sigma, P2243). On the day of the experiment 0.1 mg/mL BSA (Sigma, B4287) is added fresh to the buffer. The test item stock solutions are serially diluted 1:3 or 1:4 or 1:5 with DMSO, 11-point curves, in a 384-well compound plate. Nafamostat concentration curve is always included in the assay plate as a reference control.

The assay plate is prepared by dispensing 0.25 μL from compound plate into a 384-well black assay plate (assay plate, Greiner Fluotrac 200, 781076, VWR 736-0140). The high controls are prepared dispensing in 0.25 μL DMSO in column 23, rows AH or AP and low controls with 0.25 μL of 0.1 μM Nafamostat. C1s solution is prepared as 2× of the final assay concentration (final concentration 2.5 nM for R&D Systems 2060-SE or 5 nM Complement Technologies A104, respectively). The YLGR-Rh 110-dPro substrate is prepared as 2× of the final assay concentration of 20 μM. 5 μL/well of 2× enzyme solution is dispensed and pre-incubated for 15 min with the compounds. The enzymatic reaction is then started with 5 μL/well of the 2× substrate solution. The plate is incubated for 60 min RT in the dark and fluorescence is measured (ex 485/em 535 nm) using an Envision (PerkinElmer) or an equivalent instrument.

TABLE 1 hC1s pIC50 values for exemplary compounds.

| No. | hC1s pIC50 | No. | hC1s pIC50 | No. | hC1s pIC50 |
|---|---|---|---|---|---|
| 1 | 8.93 | 58 | 8.47 | 117 | 9.15 |
| 2 | 8.20 | 59 | 8.49 | 118 | 8.96 |
| 4 | 8.82 | 61 | 8.17 | 119 | 9.19 |
| 5 | 9.23 | 62 | 7.54 | 120 | 7.95 |
| 7 | 9.05 | 63 | 8.67 | 121 | 8.31 |
| 8 | 8.51 | 64 | 7.82 | 122 | 8.93 |
| 9 | 6.29 | 65 | 7.24 | 123 | 9.07 |
| 10 | 8.16 | 66 | 7.76 | 124 | 8.12 |
| 11 | 6.67 | 67 | 7.77 | 125 | 8.49 |
| 12 | 8.09 | 68 | 6.89 | 126 | 8.22 |
| 13 | 7.43 | 70 | 8.42 | 127 | 7.88 |
| 14 | 7.85 | 71 | 8.53 | 128 | 9.26 |
| 15 | 8.77 | 72 | 8.99 | 129 | 5.16 |
| 16 | 8.32 | 73 | 9.04 | 130 | 7.17 |
| 17 | 8.76 | 74 | 8.71 | 131 | 9.21 |
| 18 | 8.26 | 75 | 6.65 | 134 | 8.68 |
| 19 | 8.87 | 76 | 8.54 | 137 | 8.55 |
| 20 | 8.00 | 79 | 9.05 | 138 | 8.79 |
| 22 | 6.57 | 80 | 6.21 | 139 | <4.6 |
| 23 | 6.44 | 81 | 8.34 | 142 | 8.93 |
| 25 | 8.77 | 82 | 9.24 | 143 | 7.24 |
| 26 | 8.66 | 83 | 8.34 | 144 | 7.18 |
| 28 | 8.75 | 84 | 7.93 | 145 | 8.51 |
| 29 | 8.72 | 87 | 4.95 | 146 | 8.28 |
| 30 | 8.69 | 88 | 8.24 | 147 | 8.38 |
| 31 | 7.82 | 89 | 8.23 | 148 | 8.64 |
| 32 | 8.33 | 91 | 8.79 | 149 | 9.22 |
| 34 | 8.99 | 92 | 7.76 | 150 | 7.30 |
| 35 | 8.57 | 93 | 9.00 | 152 | 8.51 |
| 36 | 8.72 | 94 | 8.72 | 153 | 8.78 |
| 37 | 8.80 | 95 | 8.45 | 154 | 8.75 |
| 38 | 8.98 | 97 | 7.93 | 155 | 8.41 |
| 39 | 8.88 | 98 | 9.06 | 156 | 7.26 |
| 40 | 8.99 | 99 | 8.81 | 157 | 9.03 |
| 41 | 8.92 | 100 | 9.11 | 158 | <4.6 |
| 42 | 8.86 | 104 | 9.07 | 159 | 8.90 |
| 43 | 9.00 | 105 | 8.95 | 160 | <4.6 |
| 44 | 9.09 | 106 | 8.99 | 161 | <4.6 |
| 45 | 9.25 | 107 | 9.00 | 162 | <4.6 |
| 46 | 8.13 | 108 | 8.73 | 163 | 8.98 |
| 47 | 7.12 | 109 | 6.06 | 164 | 7.90 |
| 48 | 8.39 | 110 | 9.18 | 165 | 8.13 |
| 49 | 8.72 | 111 | 7.76 | 167 | 8.78 |
| 50 | 9.05 | 112 | 9.11 | 168 | 8.88 |
| 51 | 9.14 | 114 | 8.98 | 169 | 8.84 |
| 55 | 8.18 | 115 | 9.10 | 170 | 8.97 |
| 56 | 8.23 | 116 | 8.65 | 171 | 8.89 |
| 57 | 8.83 | | | | |

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:
1. A compound represented by formula I or II:

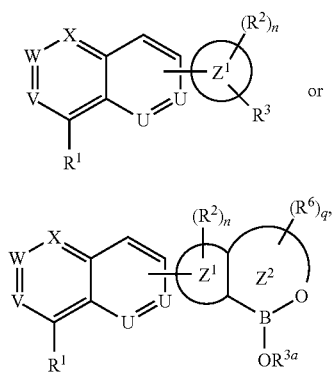

or a pharmaceutically acceptable salt thereof, wherein:
$R^1$ is hydrogen, halogen, amino, hydroxyl, alkoxy, or alkylthio;
W is N;
V and X are selected such that either V is $CR^a$ and X is N, or V is N and X is $CR^b$;
$R^a$ is hydrogen, halogen, nitro, cyano, amino, hydroxyl, alkoxy, alkylthio, or alkyl;
$R^b$ is hydrogen, halogen, nitro, cyano, amino, hydroxyl, alkoxy, alkylthio, alkyl, alkenyl, alkynyl, aralkyl, heteroaralkyl, carbocyclyl, heterocyclyl, aryl, or heteroaryl;
each U independently is N or $CR^c$;
each $R^c$ independently is hydrogen, halogen, alkyl, or alkoxy;
ring $Z^1$ is a five- or six-membered aryl or heteroaryl;
ring $Z^2$ is a five- or six-membered heterocycle;
each $R^2$ independently is halogen, nitro, cyano, amino, acylamino, amido, hydroxyl, alkoxy, alkylthio, acyl, amidino, azido, carbamoyl, carboxyl, carboxyester, guanidine, haloalkyl, haloalkoxy, heteroalkyl, imino, oxime, phosphonate, dialkylphosphine oxide, sulfonyl, sulfonamido, sulfonyl urea, sulfinyl, sulfinic acid, sulfonic acid, thiocyanate, thiocarbonyl, alkyl, aralkyl, heteroaralkyl, alkenyl, alkynyl, carbocyclyl, heterocyclyl, aryl, or heteroaryl; or two vicinal $R^2$, together with the intervening carbon atoms to which they attach, combine to form a 5- or 6-membered carbocycle, 5- or 6-membered heterocycle, 5- or 6-membered aryl, or 5- or 6-membered heteroaryl;
n is 0 or an integer selected from 1-4, as valency permits;
each $R^6$ independently is halogen, nitro, cyano, amino, acylamino, amido, hydroxyl, oxo, carboxyl, alkoxy, alkylthio, acyl, amidino, azido, carbamoyl, carboxyl, carboxyester, guanidine, haloalkyl, haloalkoxy, heteroalkyl, imino, oxime, phosphonate, dialkylphosphine oxide, sulfonyl, sulfonamido, sulfonyl urea, sulfinyl, sulfinic acid, sulfonic acid, thiocyanate, thiocarbonyl, alkyl, alkenyl, alkynyl, aralkyl, heteroaralkyl, carbocyclyl, heterocyclyl, aryl, or heteroaryl; or any two $R^6$, together with the intervening carbon atom(s) to which they attach, combine to form a carbocycle or heterocycle;
q is 0 or an integer selected from 1-4, as valency permits;
$R^3$ is

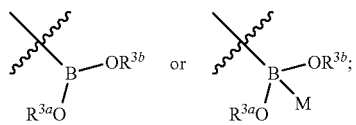

M is $N(R^8)_3$, $N(R^8)_2$, $OR^8$ or $SR^8$;
each $R^8$ is independently hydrogen, alkyl, aralkyl, heteroaralkyl, alkenyl, alkynyl, carbocyclyl, heterocyclyl, aryl, or heteroaryl; and
$R^{3a}$ and $R^{3b}$ independently are hydrogen, alkyl, acyl, alkenyl, alkynyl, aralkyl, heteroaralkyl, carbocyclyl, heterocyclyl, aryl, or heteroaryl; or $R^{3a}$ and $R^{3b}$, together with the boron atom and the two intervening oxygen atoms that separate them, combine to form a monocyclic or polycyclic heterocyclyl; or $R^{3a}$, $R^{3b}$, and M, together with the boron atom and the intervening oxygen atoms, combine to form a polycyclic heterocycle.

2. The compound of claim 1, wherein the compound is represented by formula I-a or II-a:

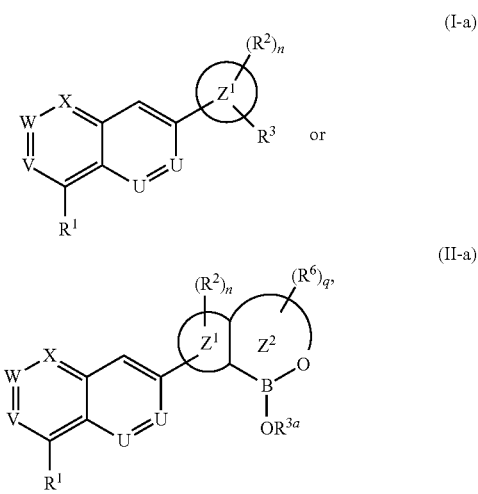

or a pharmaceutically acceptable salt thereof.

3. The compound of claim 1, wherein $R^1$ is hydroxyl, $C_{1-3}$ alkoxy, or amino.

4. The compound of claim 1, wherein each $R^2$ independently is halogen, nitro, cyano, amino, acylamino, amido, hydroxyl, alkoxy, alkylthio, phosphonate, dialkylphosphine oxide, alkyl, aralkyl, heteroaralkyl, alkenyl, alkynyl, carbocyclyl, heterocyclyl, aryl, or heteroaryl; or two vicinal $R^2$, together with the intervening carbon atoms to which they attach, combine to form a 5- or 6-membered carbocycle, 5- or 6-membered heterocycle, 5- or 6-membered aryl, or 5- or 6-membered heteroaryl.

5. The compound of claim 1, wherein each $R^2$ is independently substituted with deuterium.

6. The compound of claim 1, wherein each $R^a$ independently is hydrogen, halogen, amino, hydroxyl, alkoxy or alkyl.

7. The compound of claim 1, wherein $R^b$ is hydrogen, halogen, alkyl, alkenyl, alkynyl, carbocyclyl, heterocyclyl.

8. The compound of claim 1, wherein each $R^c$ independently is hydrogen, halogen, or alkyl.

9. The compound of claim 1, wherein U is $CR^c$.

10. The compound claim 1, wherein ring $Z^1$ is phenyl or a five- or six-membered heteroaryl.

11. The compound of claim 10, wherein ring $Z^1$ is phenyl.

12. The compound of claim 11, wherein the compound is represented by formula I-b or II-b:

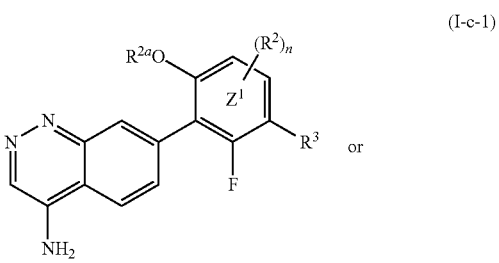

(I-b)

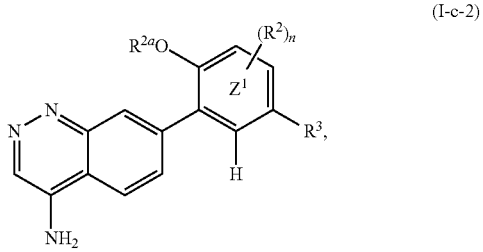

(II-b)

or a pharmaceutically acceptable salt thereof.

13. The compound of claim 12, wherein the compound is a compound represented by formula I-c or II-c:

(I-c)

(II-c)

or a pharmaceutically acceptable salt thereof.

14. The compound of claim 12, wherein the compound is represented by formula I-c-1 or I-c-2:

(I-c-1)

(I-c-2)

or a pharmaceutically acceptable salt thereof, wherein $R^{2a}$ is alkyl, aralkyl, heteroaralkyl, alkenyl, alkynyl, carbocyclyl, heterocyclyl, aryl, or heteroaryl.

15. The compound of claim 14, wherein $R^{2a}$ is methyl, difluoromethyl, $-CF_2CHF_2$, $-CHFCF_3$, $-CH_2CF_3$, $-(CH_2CH_2O)_2CH_3$,

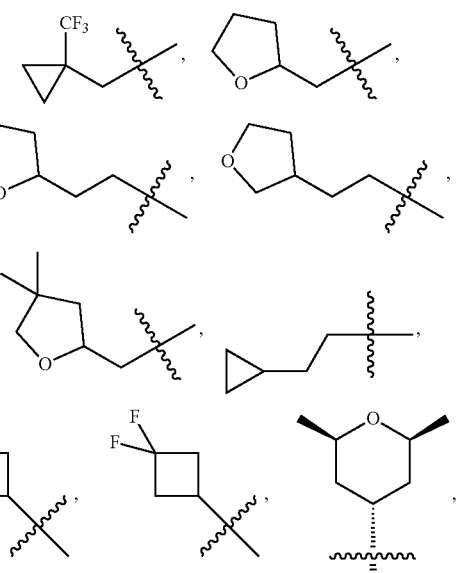

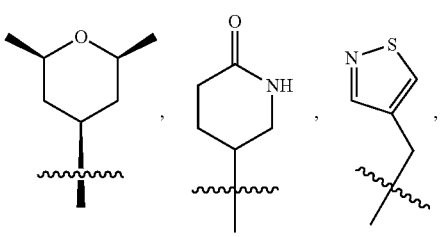

455

-continued

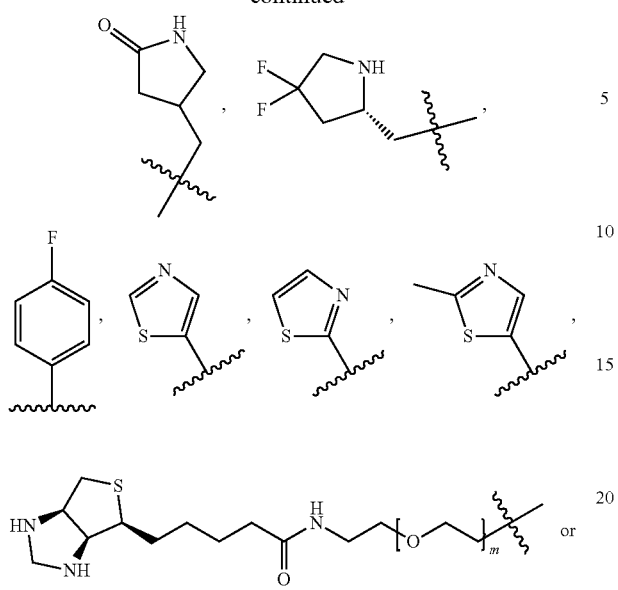

wherein m is an integer from 2 to 6.

16. The compound of claim 14, wherein $R^3$ is

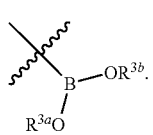

17. The compound of claim 16, wherein $R^{3a}$ and $R^{3b}$ are hydrogen.

18. The compound of claim 16, wherein $R^{3a}$ and $R^{3b}$, together with the boron atom and the two intervening oxygen atoms that separate them, combine such that $R^3$ is a heterocyclyl.

19. The compound of claim 18, wherein $R^3$ is

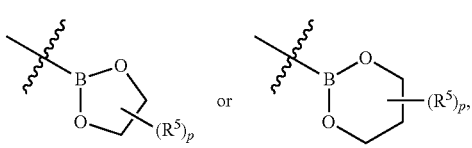

wherein:

each $R^5$ independently is halogen, nitro, cyano, amino, acylamino, amido, hydroxyl, oxo, carboxy, alkoxy, alkylthio, alkyl, aralkyl, heteroaralkyl, alkenyl, alkynyl, carbocyclyl, heterocyclyl, aryl, or heteroaryl; or any two $R^5$, independently, together with the intervening carbon atom(s) to which they attach, combine to form a carbocycle or heterocycle; and p is 0 or an integer selected from 1-6, as valency permits.

456

20. The compound of claim 19, wherein $R^3$ is

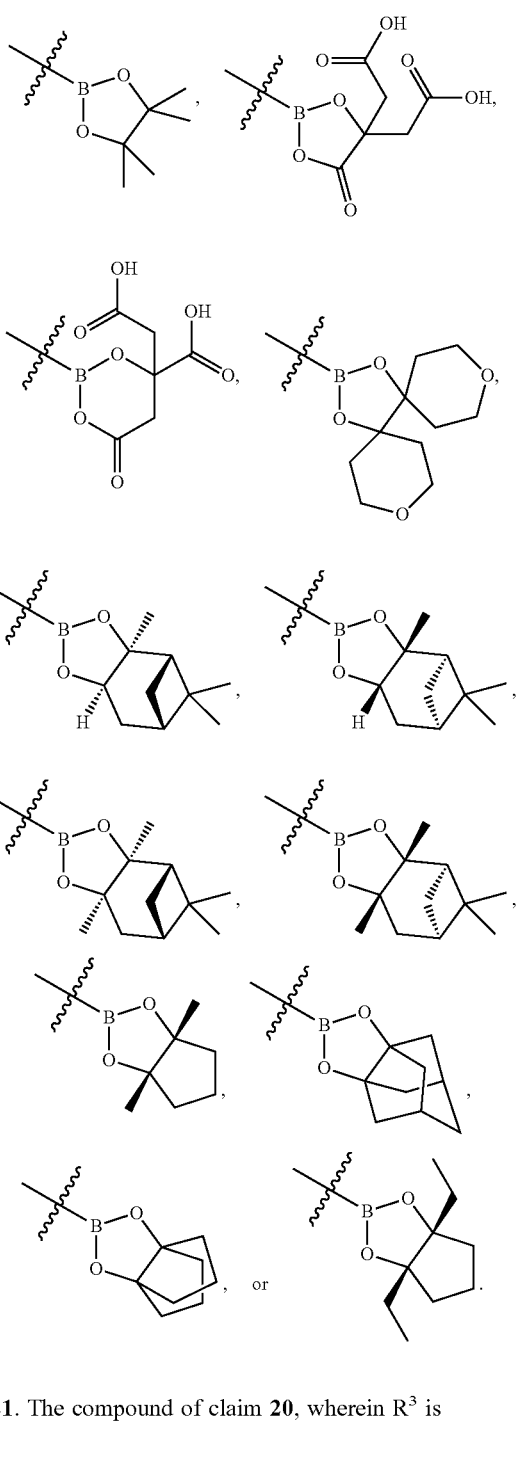

21. The compound of claim 20, wherein $R^3$ is

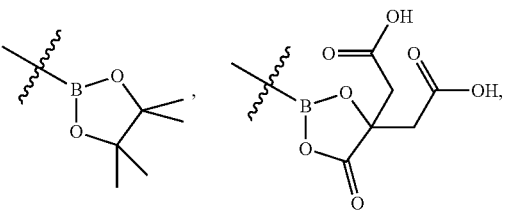

-continued

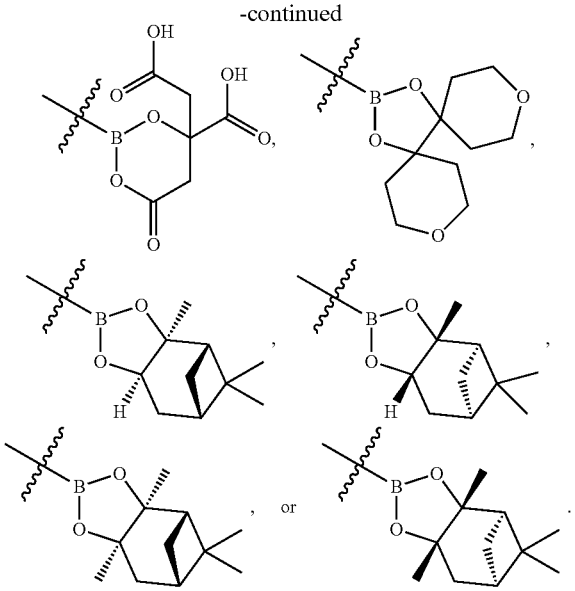

22. The compound of claim 14, wherein $R^3$ is

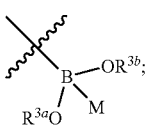

and $R^{3a}$, $R^{3b}$, and M, together with the boron atom and the intervening atoms, combine such that $R^3$ is a polycyclic heterocycle.

23. The compound of claim 22, wherein $R^3$ is

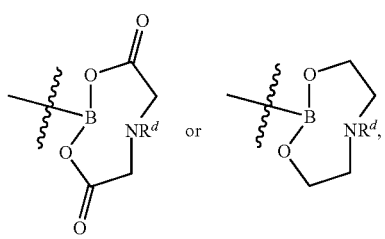

wherein $R^d$ is H or $C_1$-$C_4$ alkyl.

24. The compound of claim 12, wherein the compound is represented by formula II-b-1, II-b-2, or II-b-3:

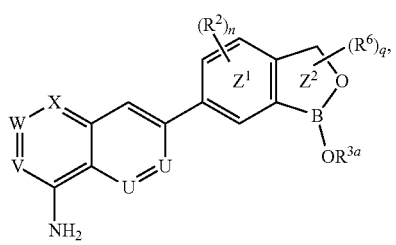

(II-b-1)

-continued

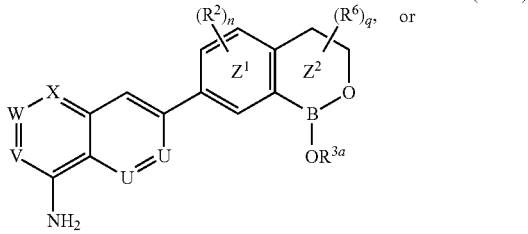

(II-b-2)

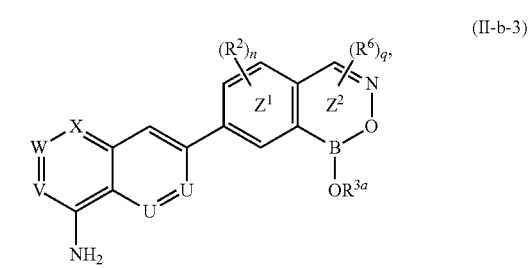

(II-b-3)

or a pharmaceutically acceptable salt thereof.

25. The compound of claim 24, wherein ring $Z^2$ is

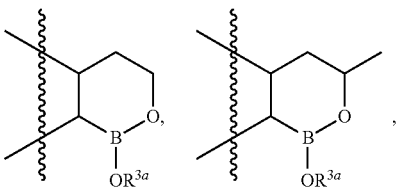

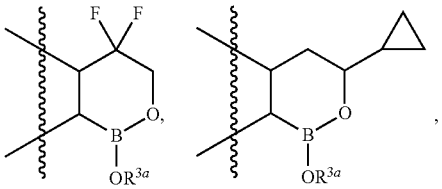

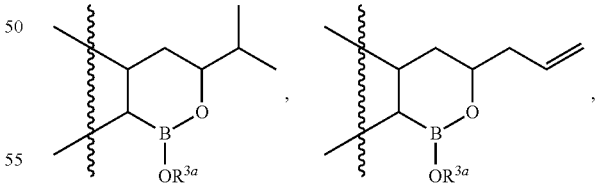

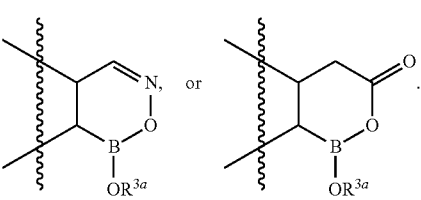

26. The compound of claim 1, wherein the compound is selected from:
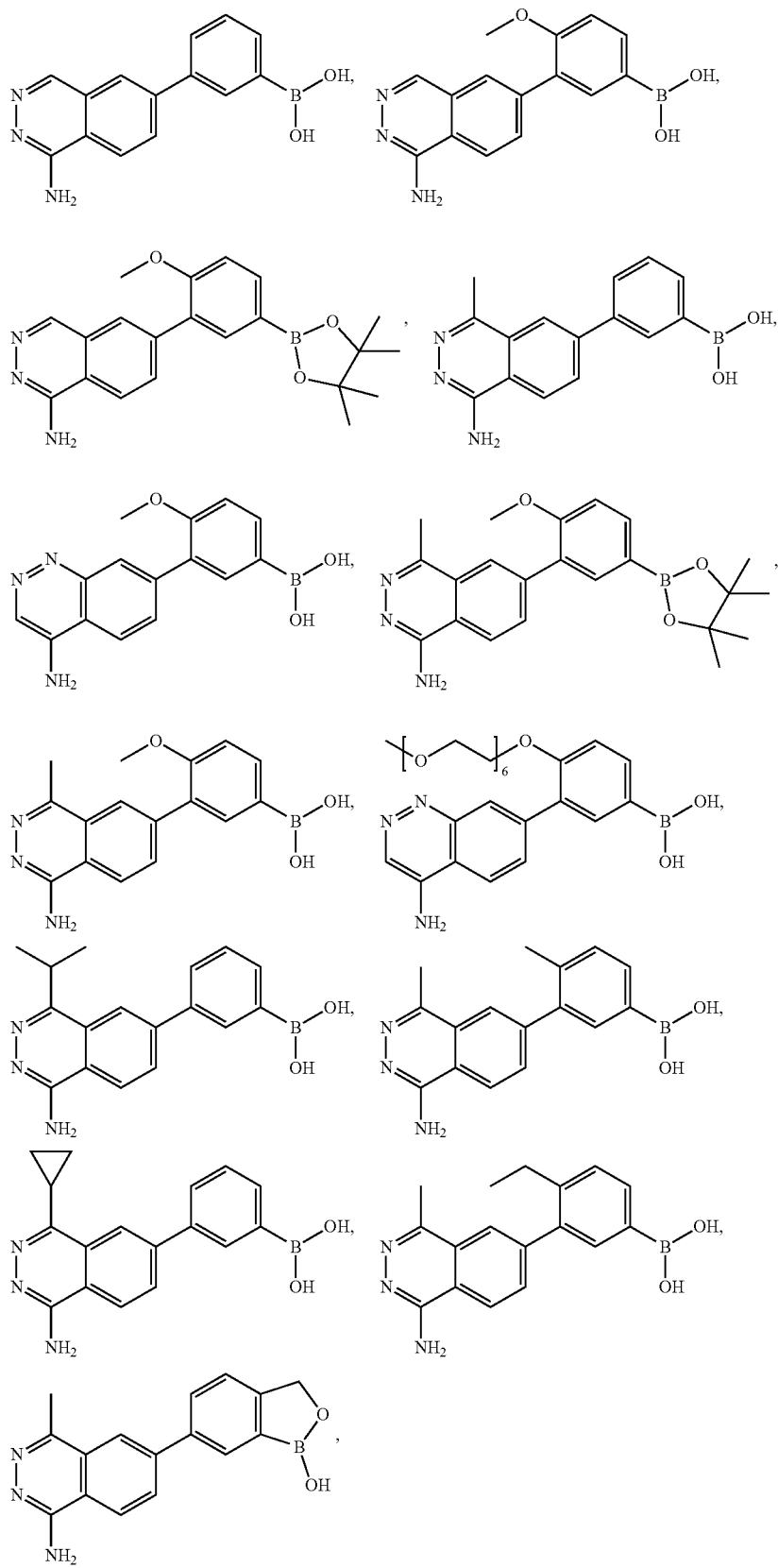

-continued
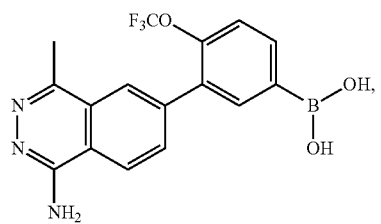
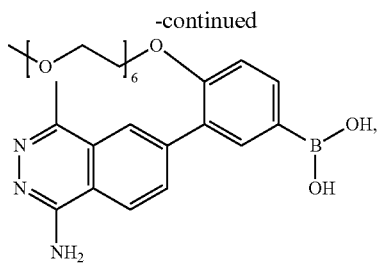
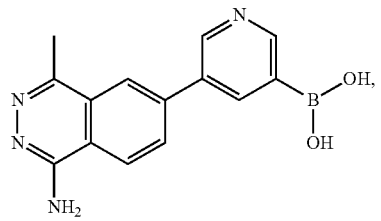
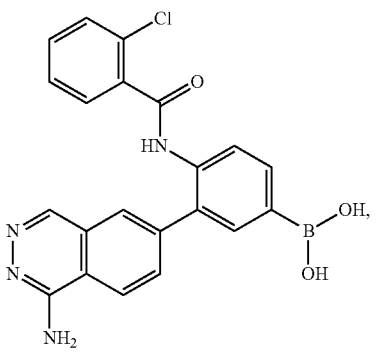
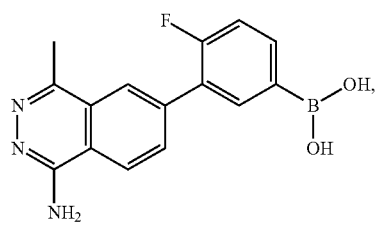
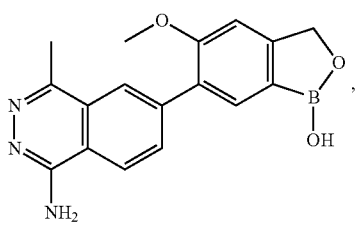
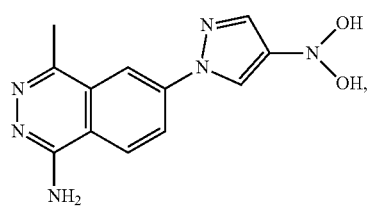
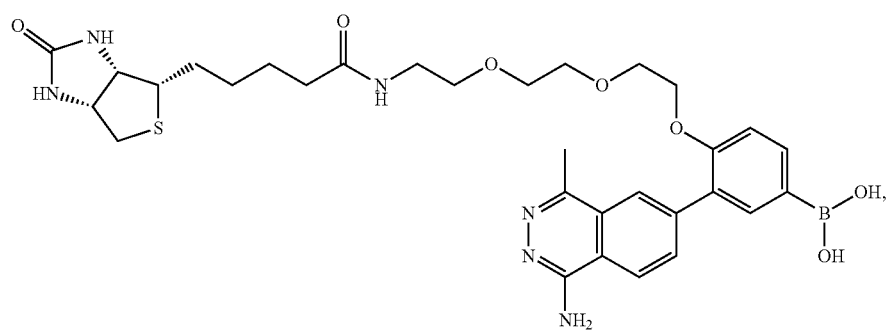
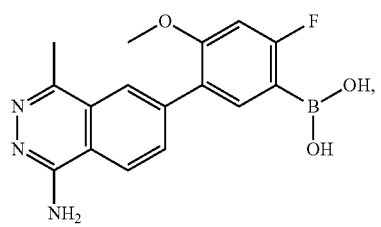
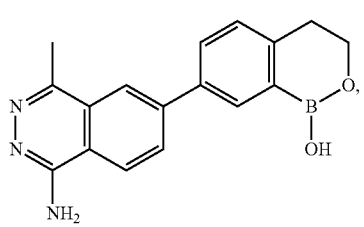

463 464
-continued
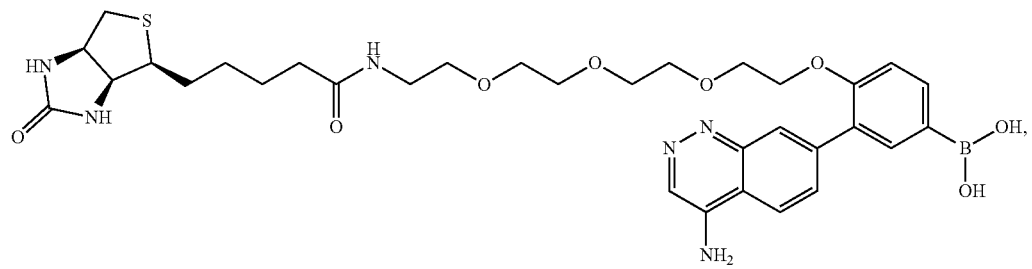
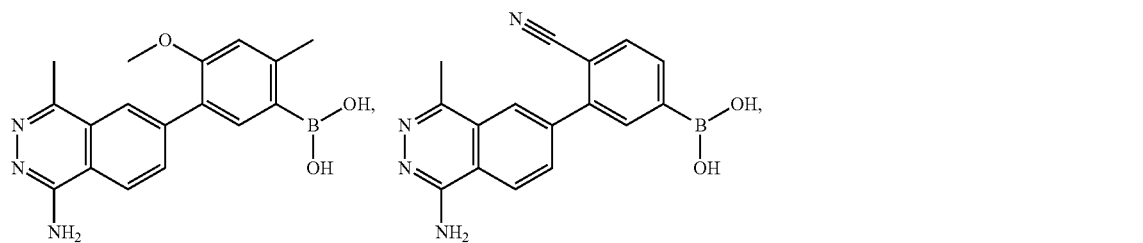
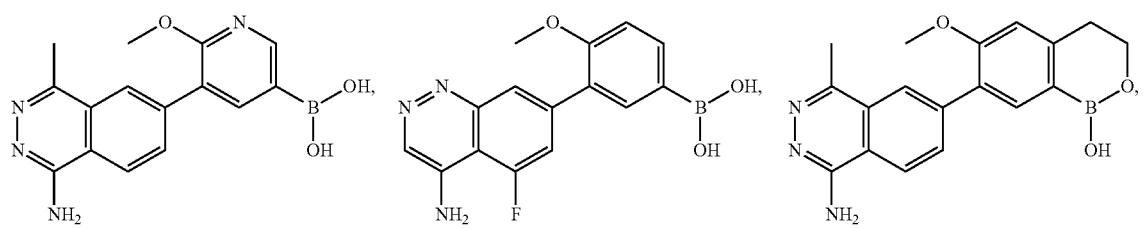
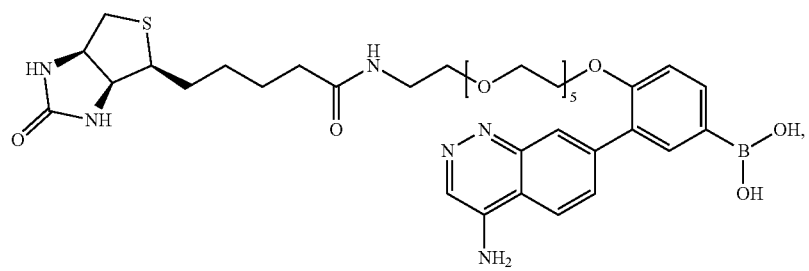
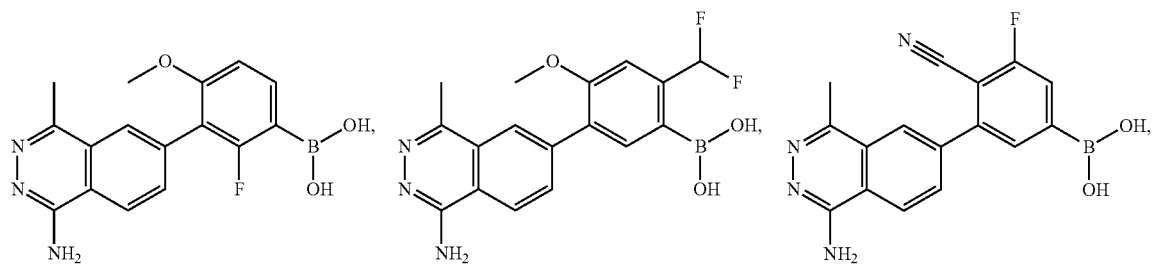
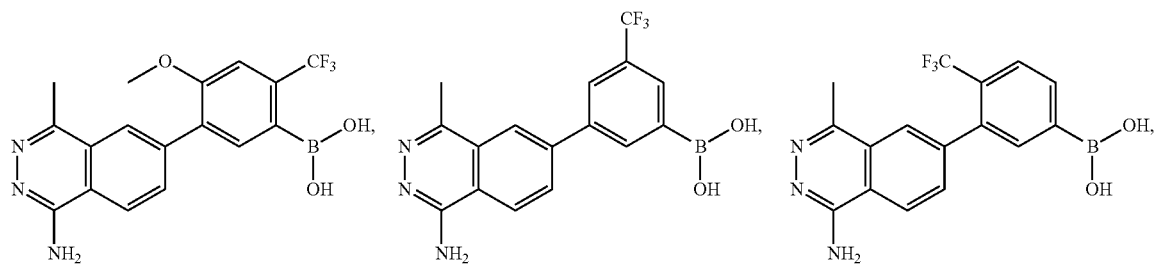

465
466
-continued
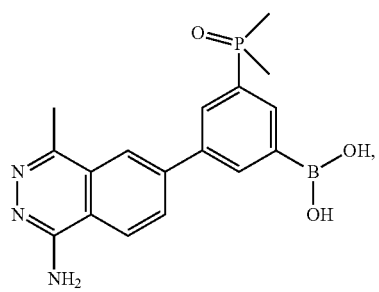
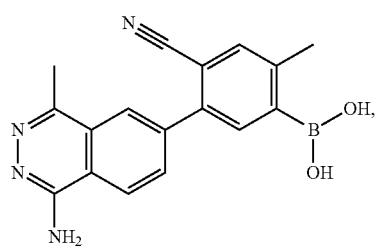
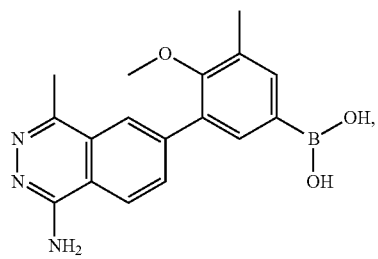
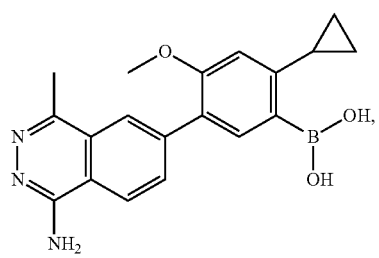
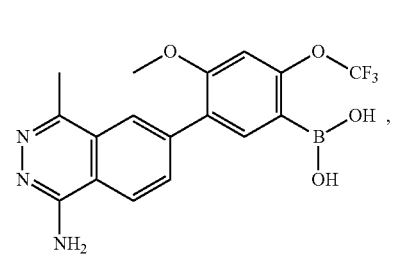
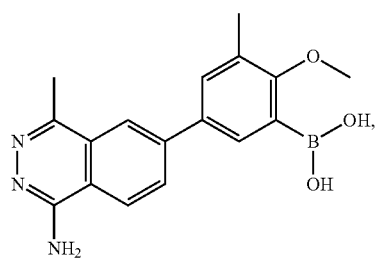
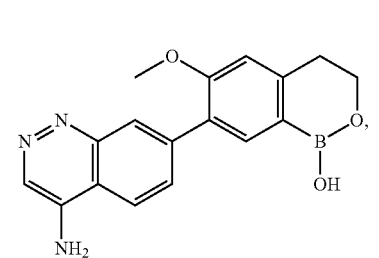
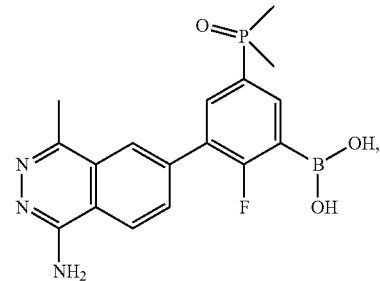
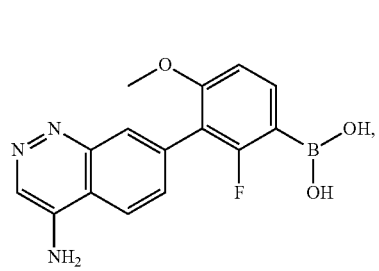
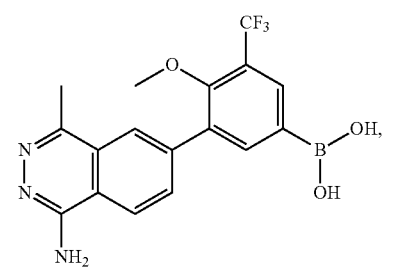
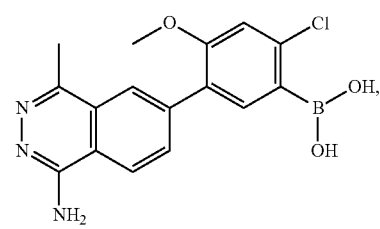
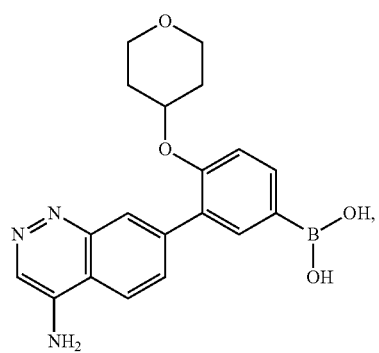
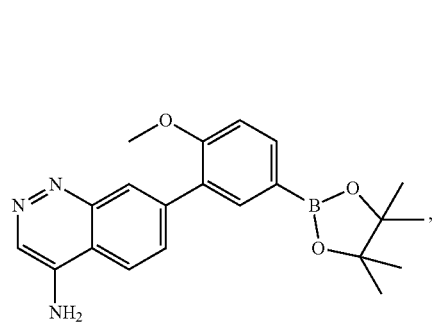
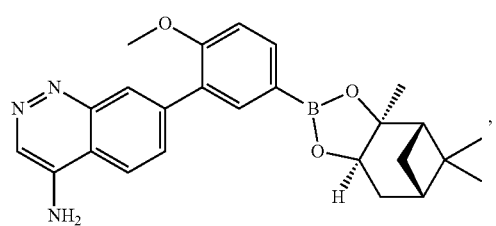

467
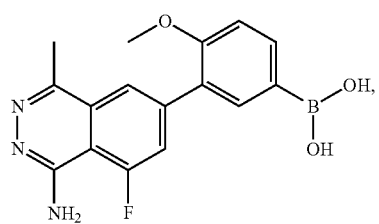
468
-continued
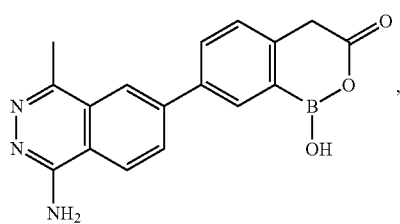
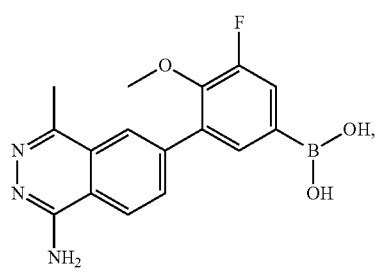
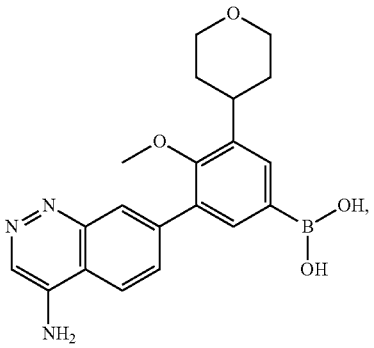
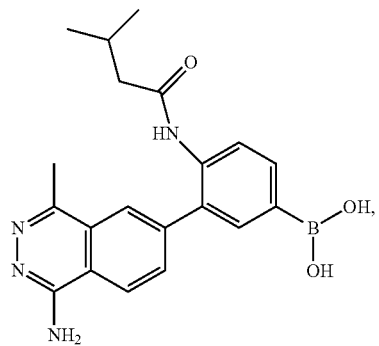
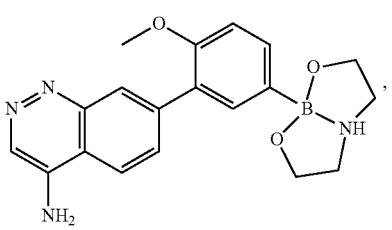
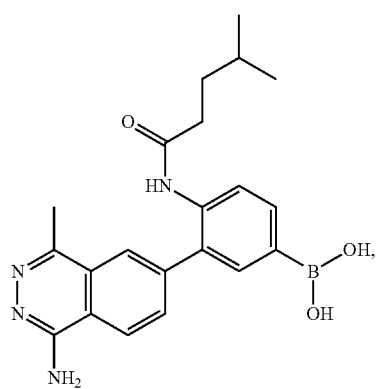
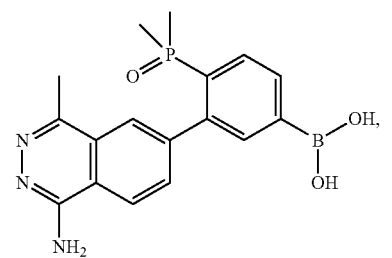
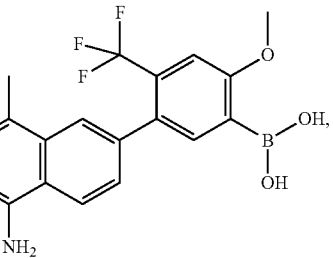
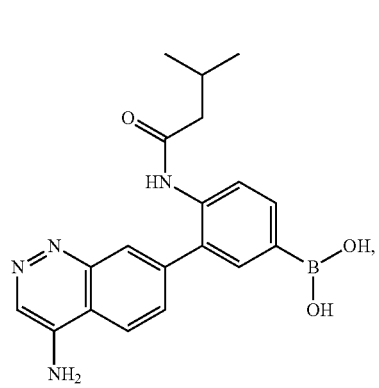
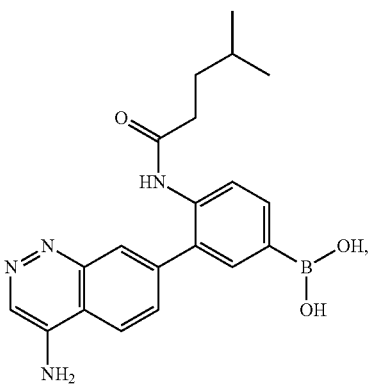

469 470
-continued
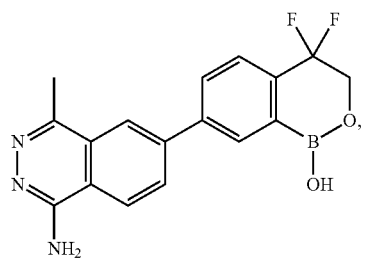
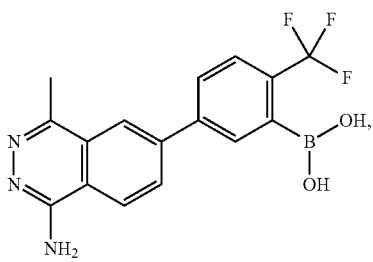
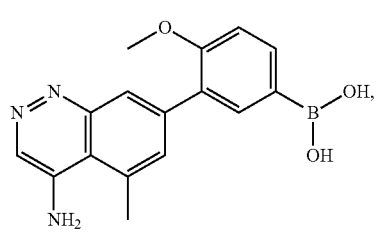
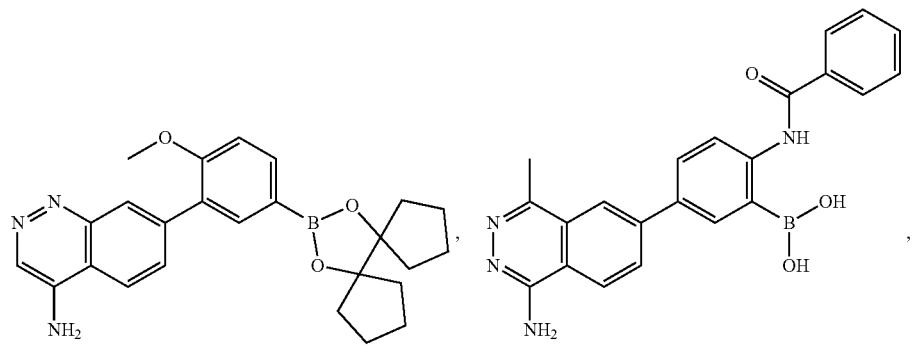
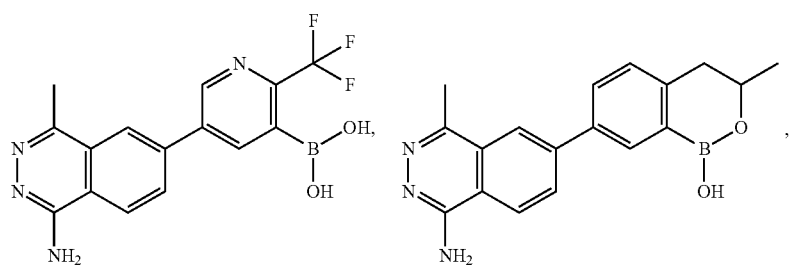
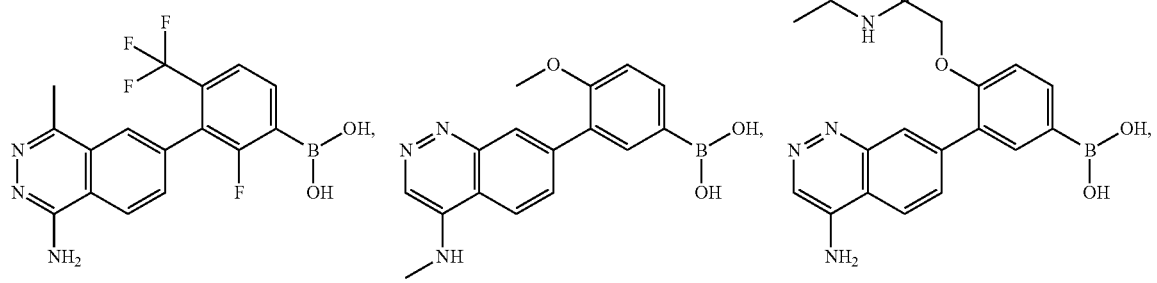
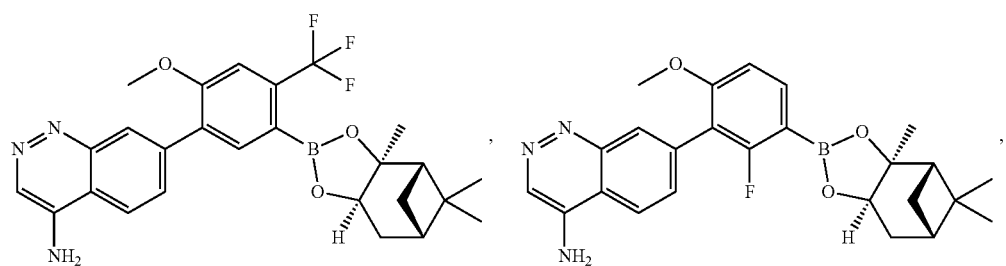

471
-continued
472
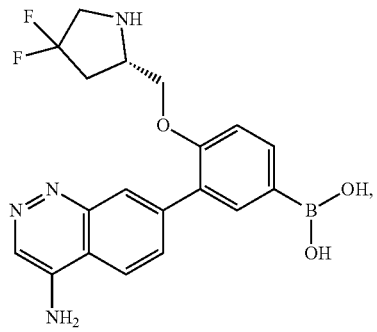
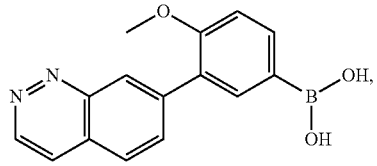
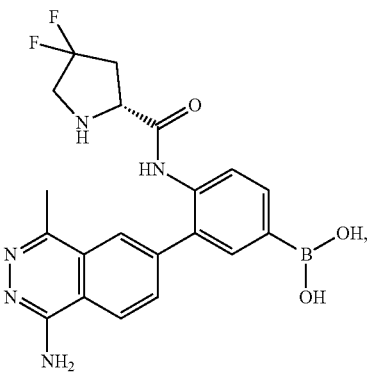
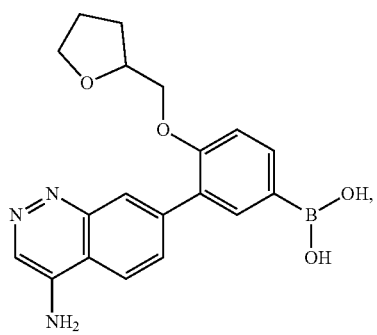
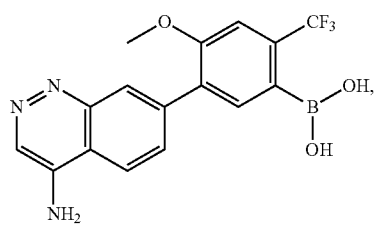
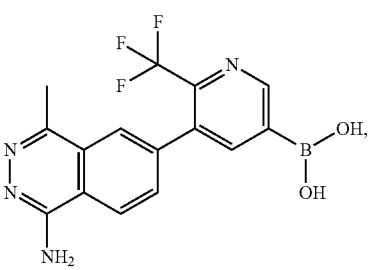
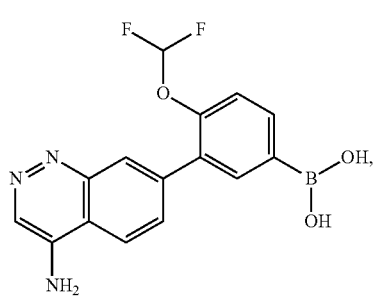
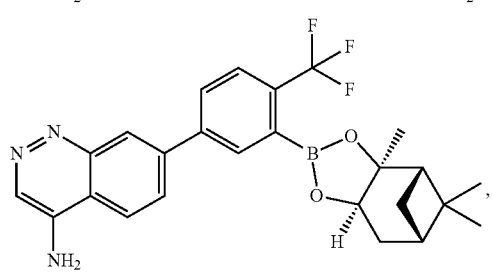
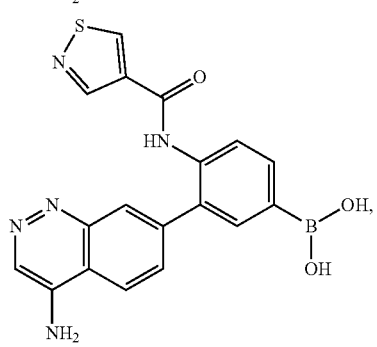
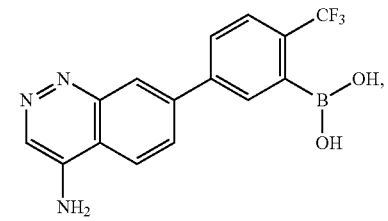
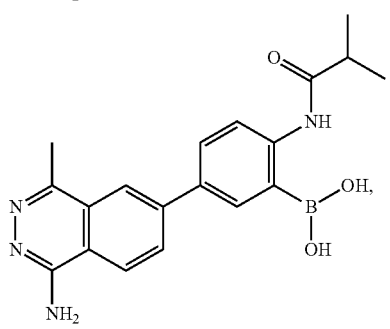
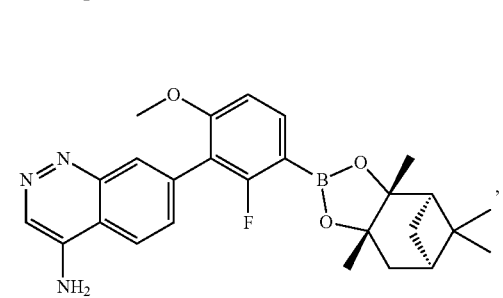

-continued
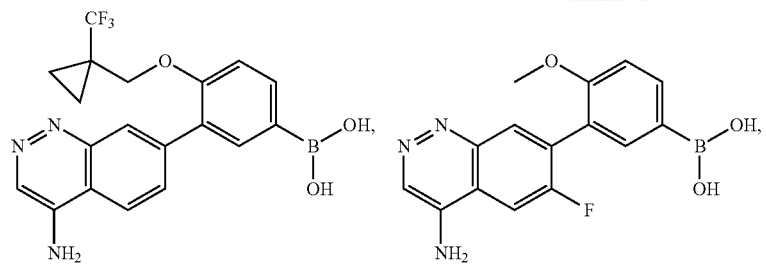
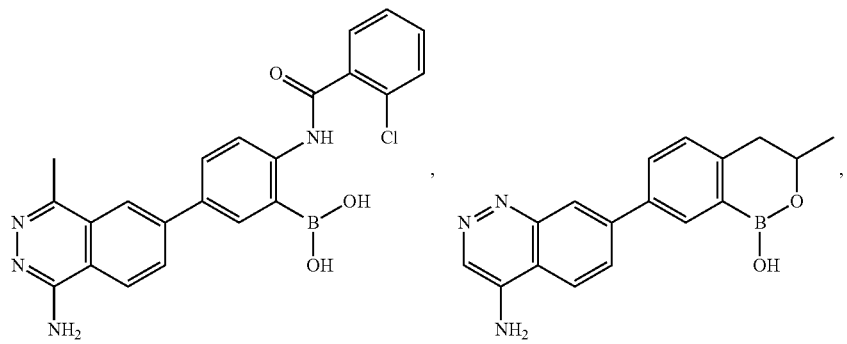
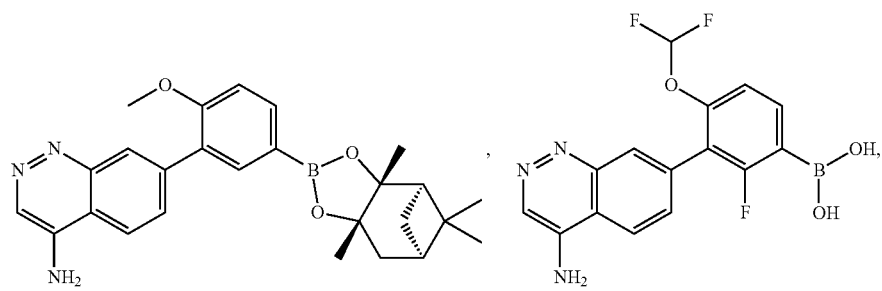
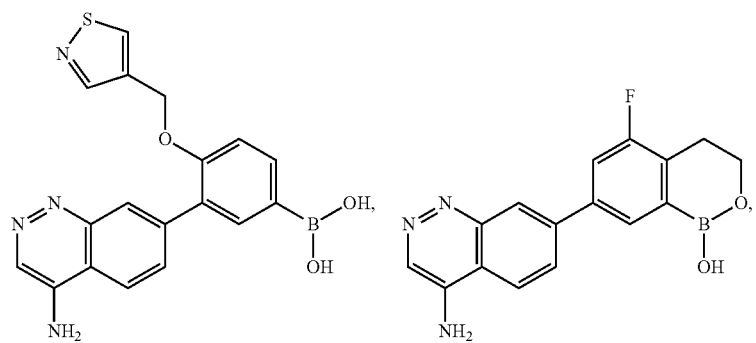
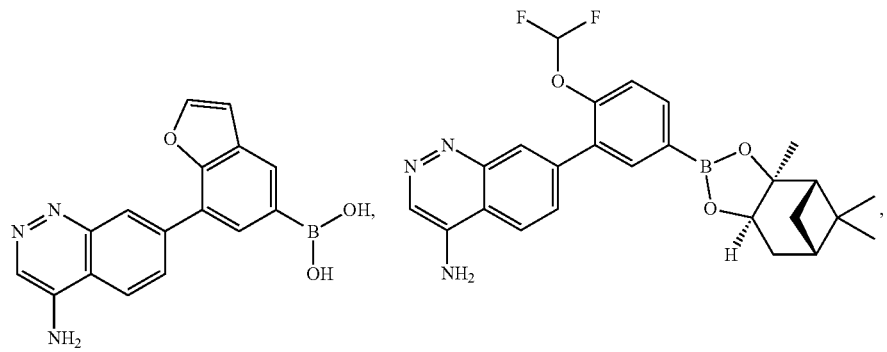

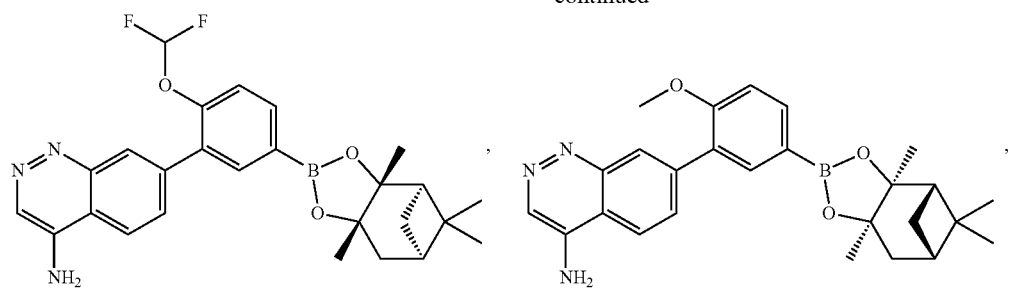
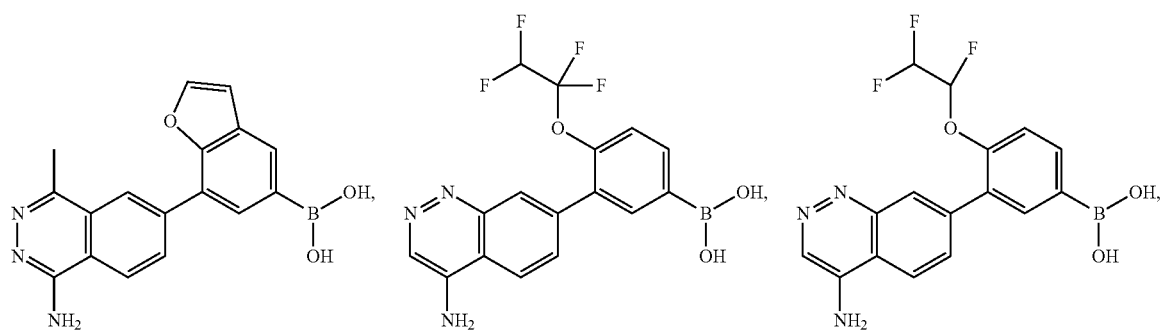
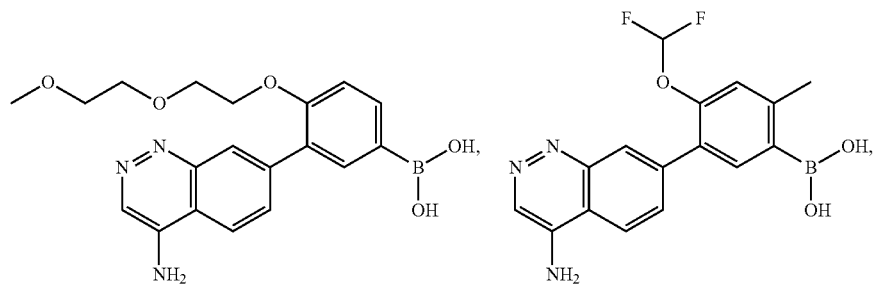
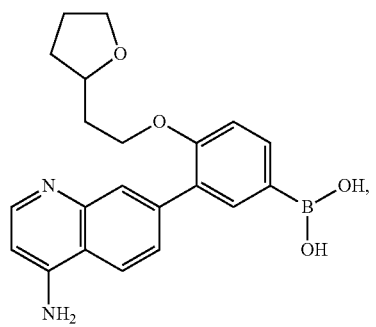
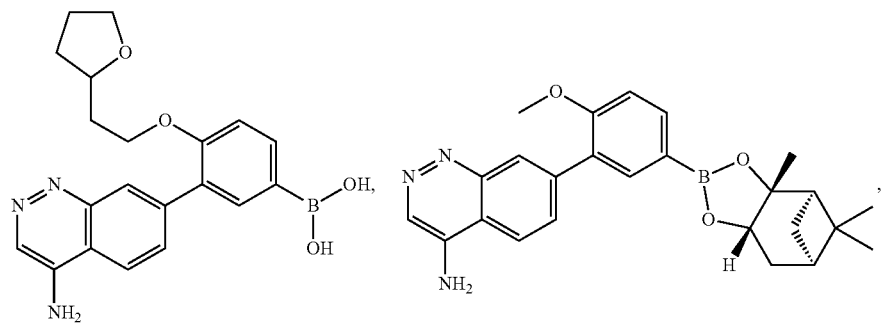

477
478
-continued
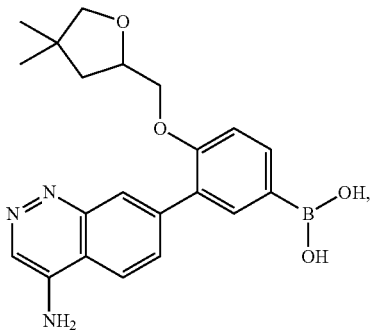 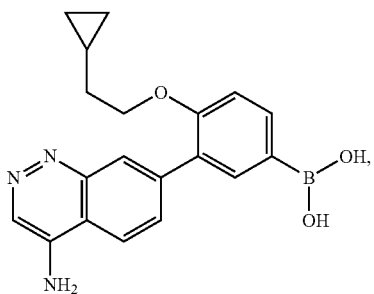
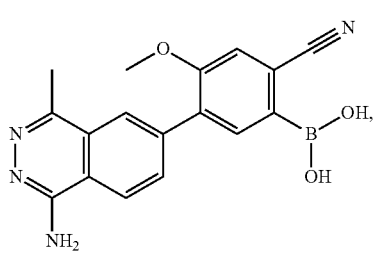 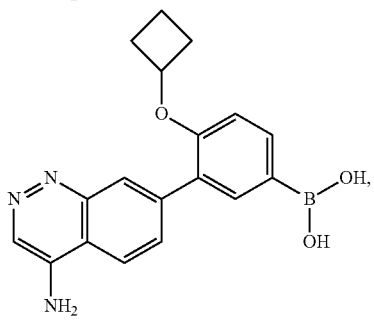 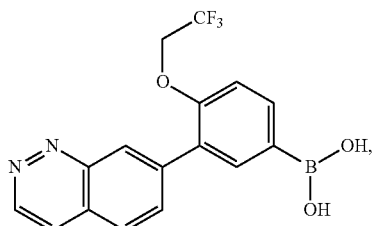
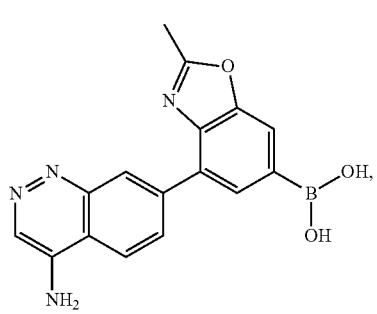 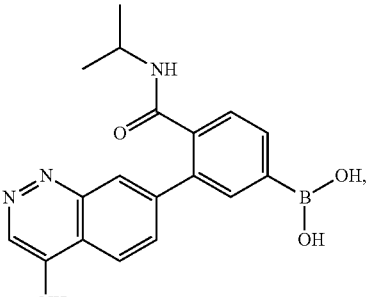 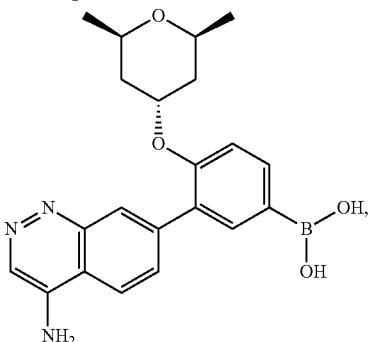
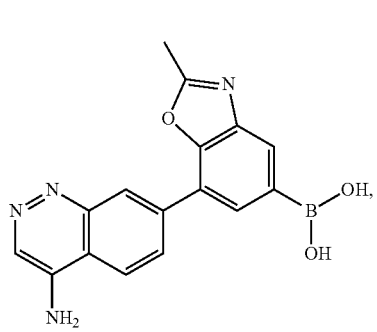 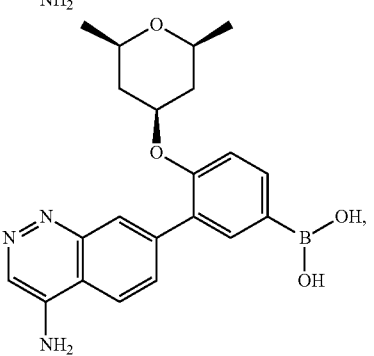 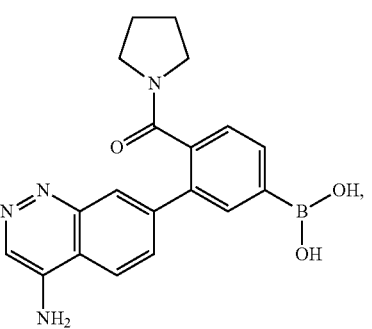
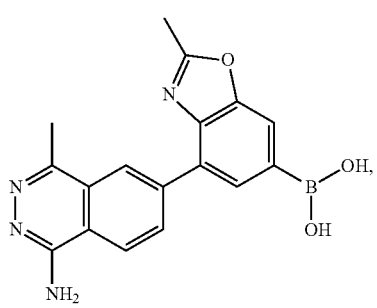 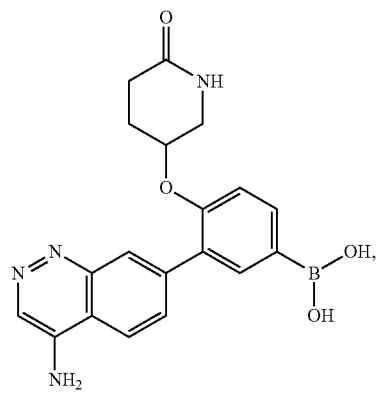

-continued
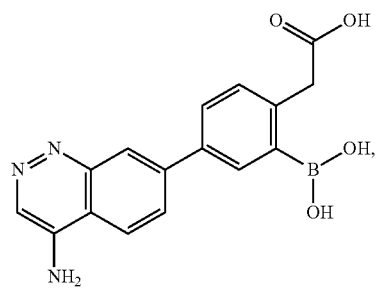
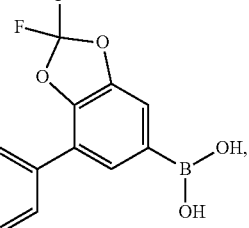
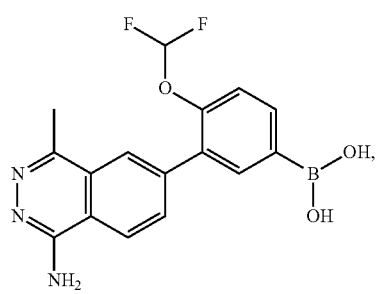
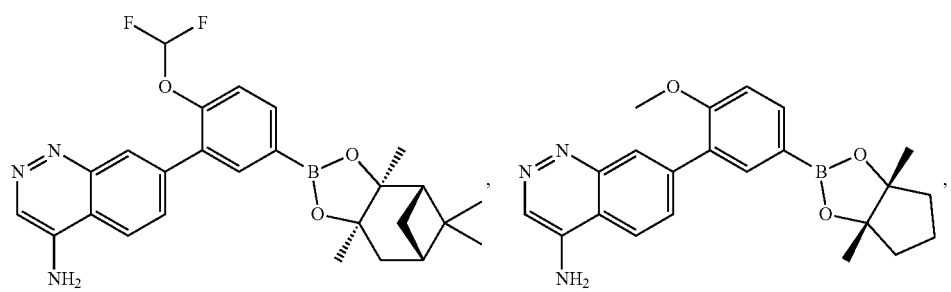
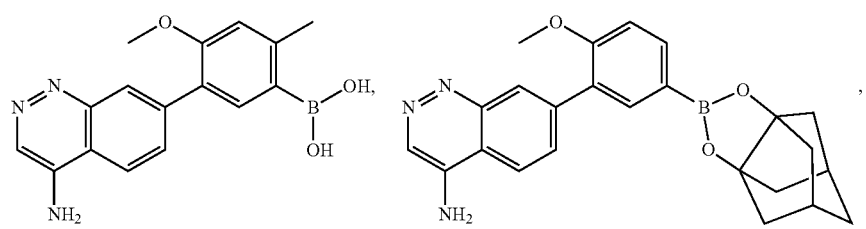
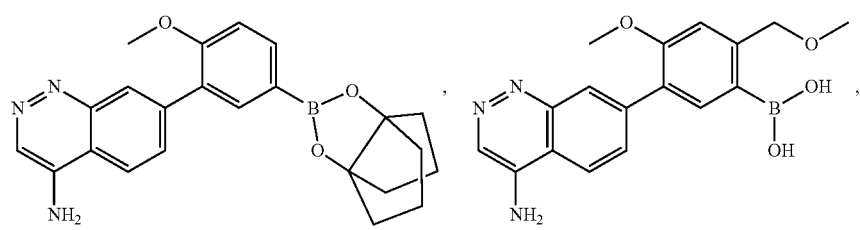
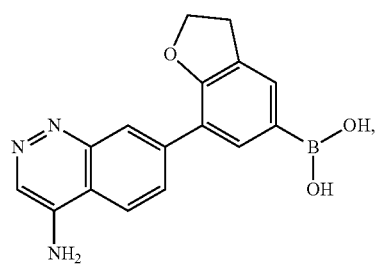

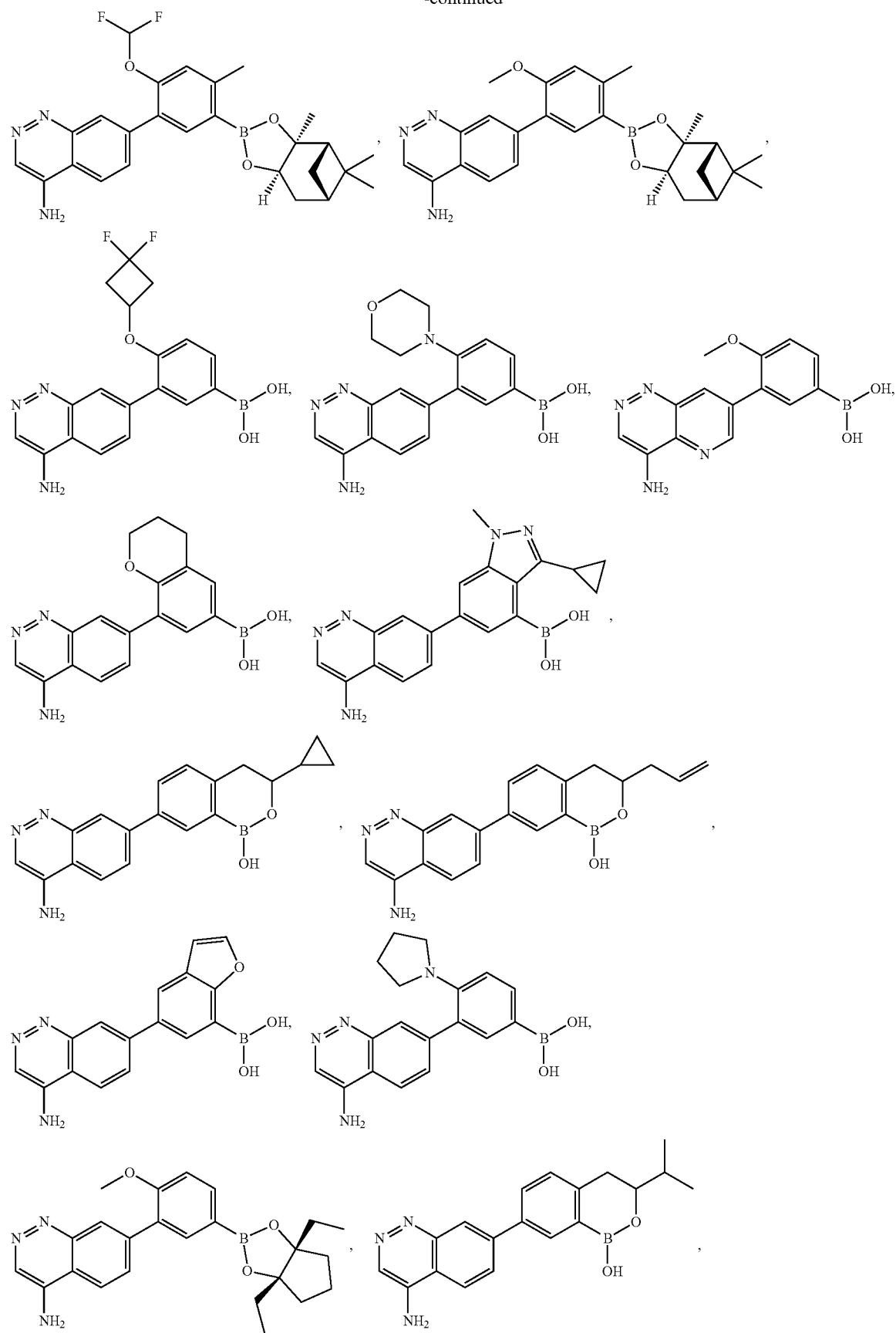

-continued
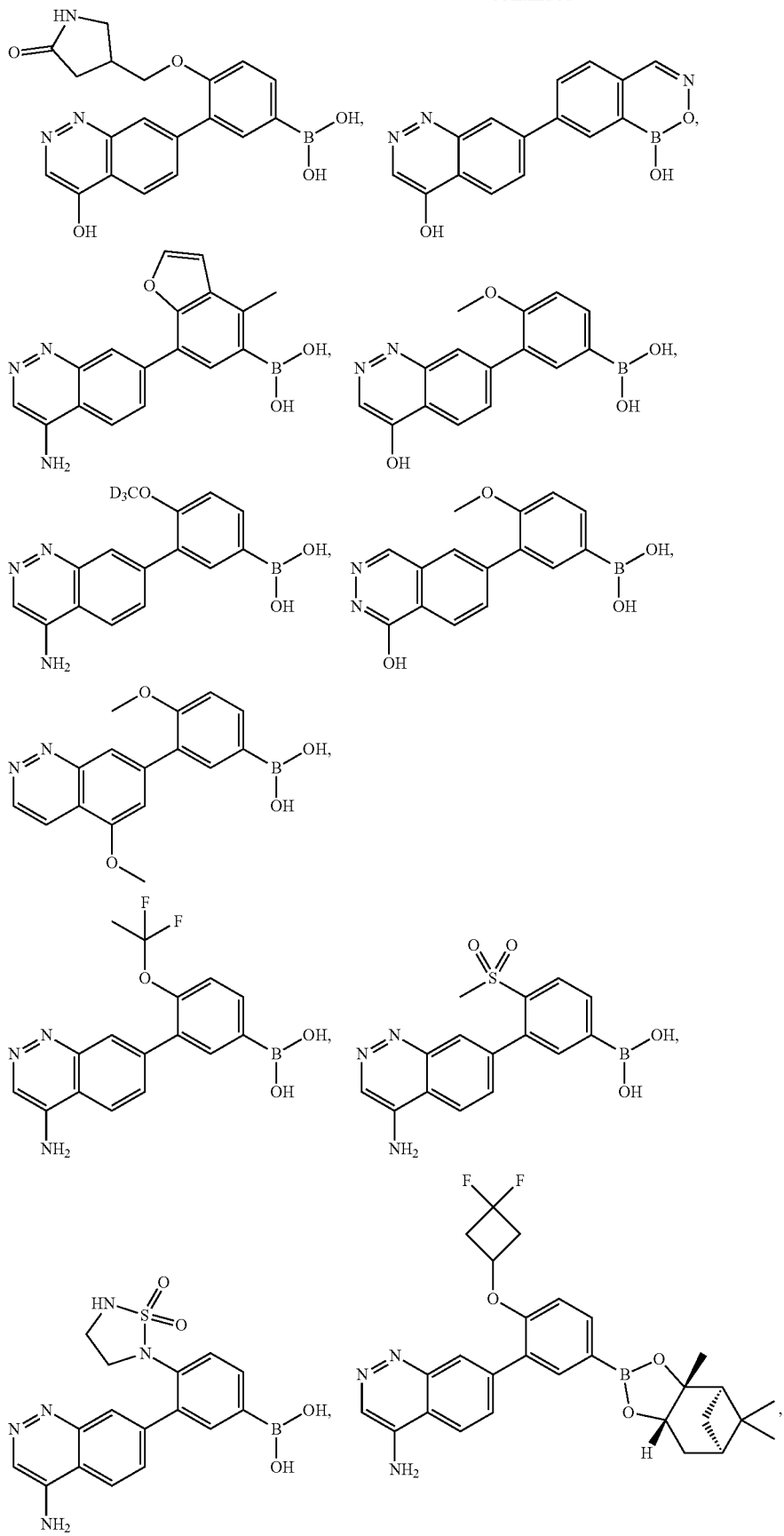

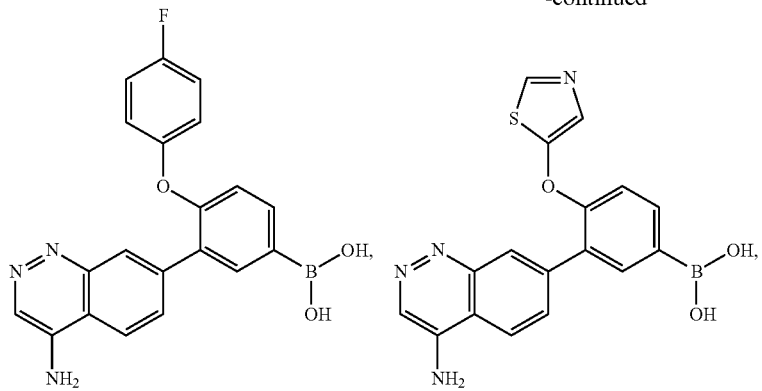

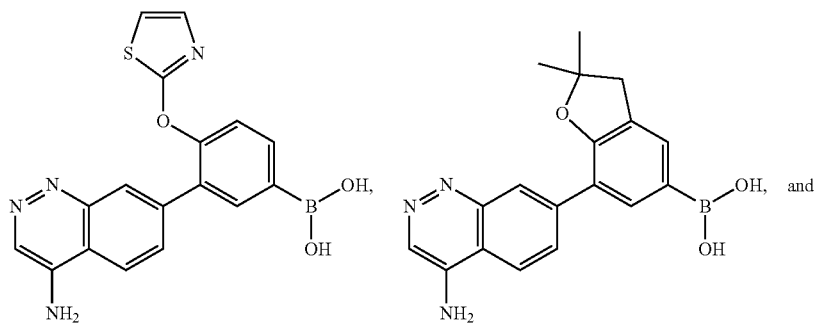

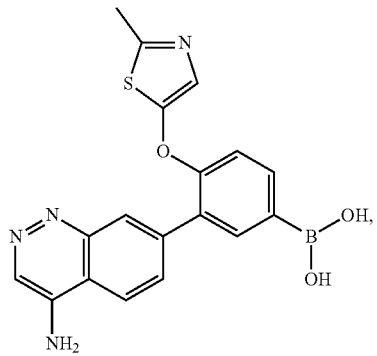

or a pharmaceutically acceptable salt thereof.

27. A pharmaceutical composition, comprising the compound of claim 1 and a pharmaceutically acceptable excipient.

28. The compound according to claim 26, wherein the compound is:

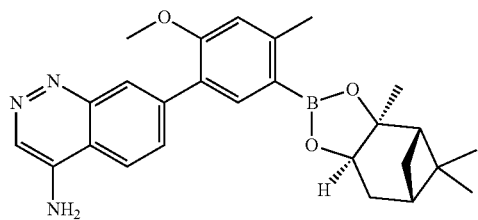

or a pharmaceutically acceptable salt thereof.

29. The compound according to claim 26, wherein the compound is:

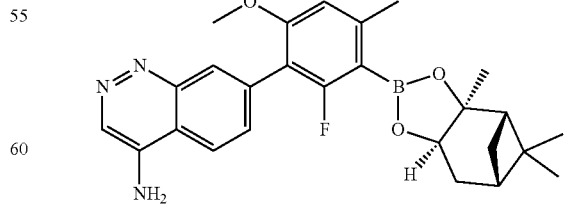

or a pharmaceutically acceptable salt thereof.

30. The compound according to claim 26, wherein the compound is:

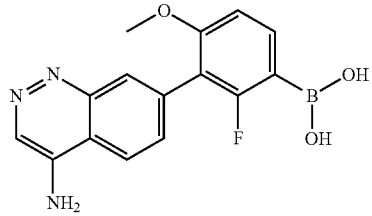 [SMILES: COc1ccc(B(O)O)c(F)c1-c1ccc2c(N)cnnc2c1]

or a pharmaceutically acceptable salt thereof.

31. The compound according to claim 26, wherein the compound is:

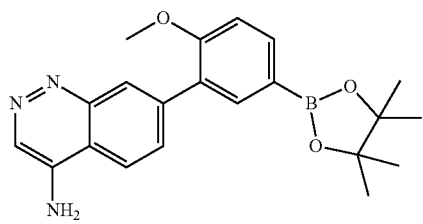 [SMILES: COc1ccc(B2OC(C)(C)C(C)(C)O2)cc1-c1ccc2c(N)cnnc2c1]

or a pharmaceutically acceptable salt thereof.

32. The compound according to claim 26, wherein the compound is:

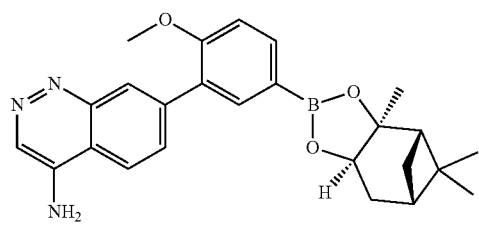 [SMILES: COc1ccc(B2O[C@@H]3C[C@@H]4C[C@@H](C4(C)C)[C@]3(C)O2)cc1-c1ccc2c(N)cnnc2c1]

or a pharmaceutically acceptable salt thereof.

33. The compound according to claim 26, wherein the compound is:

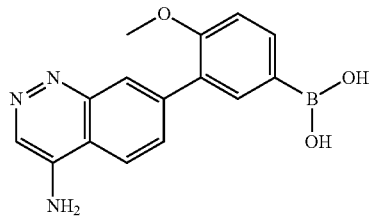 [SMILES: COc1ccc(B(O)O)cc1-c1ccc2c(N)cnnc2c1]

or a pharmaceutically acceptable salt thereof.

34. The compound according to claim 26, wherein the compound is:

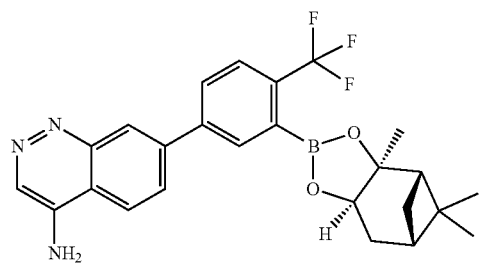 [SMILES: CC1(C)[C@@H]2C[C@H]3OB(c4cc(-c5ccc6c(N)cnnc6c5)ccc4C(F)(F)F)O[C@@]3(C)[C@H]1C2]

or a pharmaceutically acceptable salt thereof.

35. The compound according to claim 26, wherein the compound is:

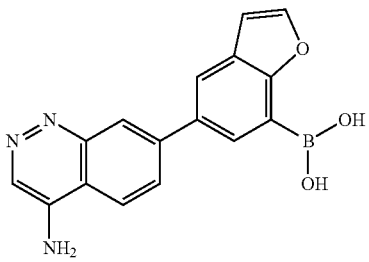 [SMILES: Nc1cnnc2cc(-c3cc(B(O)O)c4occc4c3)ccc12]

or a pharmaceutically acceptable salt thereof.

36. The compound according to claim 26, wherein the compound is:

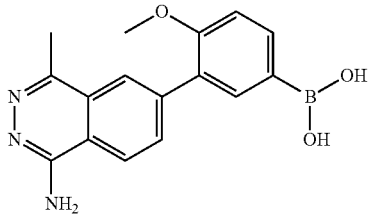 [SMILES: COc1ccc(B(O)O)cc1-c1ccc2c(N)nnc(C)c2c1]

or a pharmaceutically acceptable salt thereof.

37. The compound according to claim 26, wherein the compound is:

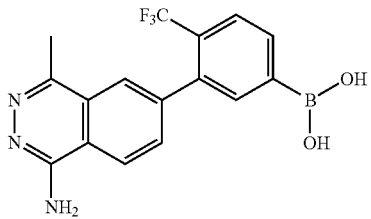 [SMILES: Cc1nnc(N)c2ccc(-c3cc(B(O)O)ccc3C(F)(F)F)cc12]

or a pharmaceutically acceptable salt thereof.

38. The compound according to claim 26, wherein the compound is:

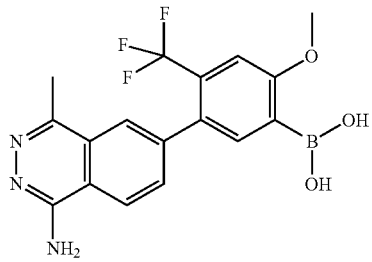 [SMILES: COc1cc(C(F)(F)F)c(-c2ccc3c(N)nnc(C)c3c2)cc1B(O)O]

or a pharmaceutically acceptable salt thereof.

39. The compound according to claim 26, wherein the compound is:

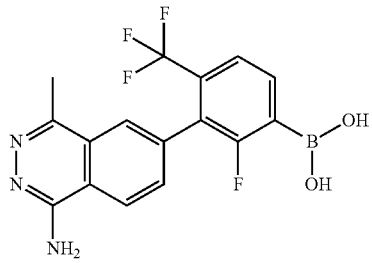 [SMILES: Cc1nnc(N)c2ccc(-c3c(C(F)(F)F)ccc(B(O)O)c3F)cc12]

or a pharmaceutically acceptable salt thereof.

40. The compound according to claim 26, wherein the compound is:

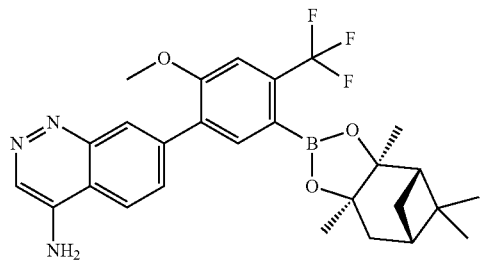 [SMILES: COc1cc(C(F)(F)F)c(B2O[C@]3(C)C[C@@H]4C[C@@H](C4(C)C)[C@]3(C)O2)cc1-c1ccc2c(N)cnnc2c1]

or a pharmaceutically acceptable salt thereof.

41. The compound according to claim 26, wherein the compound is:

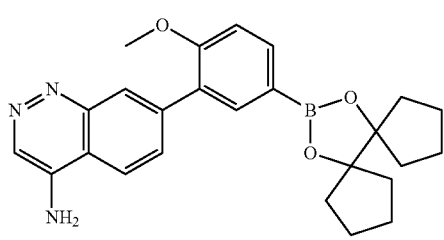 [SMILES: COc1ccc(B2OC3(CCCC3)C3(CCCC3)O2)cc1-c1ccc2c(N)cnnc2c1]

or a pharmaceutically acceptable salt thereof.

42. The compound according to claim 26, wherein the compound is:

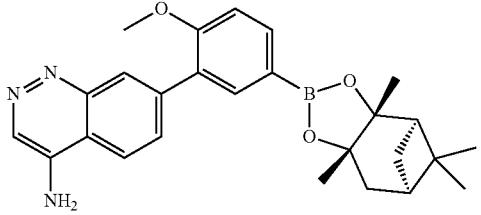 [SMILES: COc1ccc(B2O[C@@]3(C)C[C@H]4C[C@H](C4(C)C)[C@@]3(C)O2)cc1-c1ccc2c(N)cnnc2c1]

or a pharmaceutically acceptable salt thereof.

43. The compound according to claim 26, wherein the compound is:

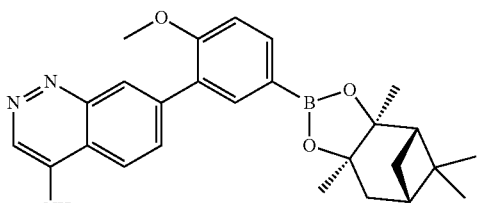

or a pharmaceutically acceptable salt thereof.

44. The compound according to claim 26, wherein the compound is:

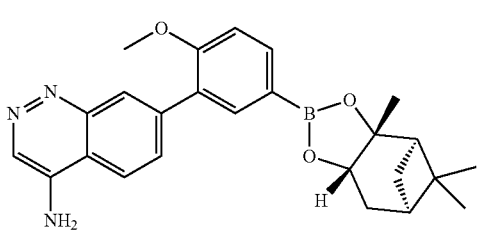 [SMILES: COc1ccc(B2O[C@H]3C[C@H]4C[C@H](C4(C)C)[C@@]3(C)O2)cc1-c1ccc2c(N)cnnc2c1]

or a pharmaceutically acceptable salt thereof.

45. The compound according to claim 26, wherein the compound is:

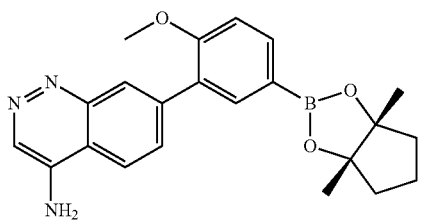 [SMILES: COc1ccc(B2O[C@]3(C)CCC[C@]3(C)O2)cc1-c1ccc2c(N)cnnc2c1]

or a pharmaceutically acceptable salt thereof.

46. The compound according to claim 26, wherein the compound is:

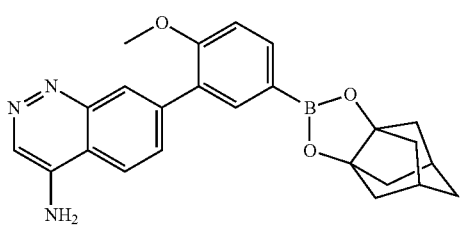 [SMILES: COc1ccc(B2OC34CC5CC(C3)CC4(C5)O2)cc1-c1ccc2c(N)cnnc2c1]

or a pharmaceutically acceptable salt thereof.

47. The compound according to claim 26, wherein the compound is:

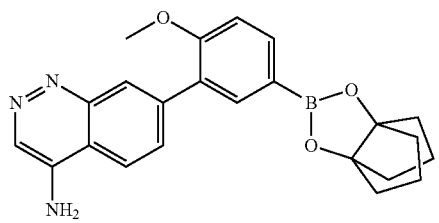 [SMILES: COc1ccc(B2OC34CCCC3(CCC4)O2)cc1-c1ccc2c(N)cnnc2c1]

or a pharmaceutically acceptable salt thereof.

48. The compound according to claim 26, wherein the compound is:

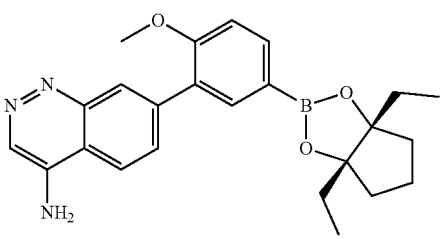 [SMILES: CC[C@@]12CCC[C@]1(CC)OB(c1ccc(OC)c(-c3ccc4c(N)cnnc4c3)c1)O2]

or a pharmaceutically acceptable salt thereof.

* * * * *

UNITED STATES PATENT AND TRADEMARK OFFICE
CERTIFICATE OF CORRECTION

PATENT NO. : 11,814,404 B2
APPLICATION NO. : 17/379334
DATED : November 14, 2023
INVENTOR(S) : Dean R. Artis et al.

Page 1 of 1

It is certified that error appears in the above-identified patent and that said Letters Patent is hereby corrected as shown below:

On the Title Page

At item number (73) Assignees, left column, Line 11, please replace:
"Assignees: ANNEXON, INC., South San Francisco, CA (US); APTUIT (VERONA) SRL, Verona (IT)"
With:
--Assignee: ANNEXON, INC., Brisbane, CA (US)--

In the Claims

At Column 453, Claim 13, Line number 39, please replace:
"13. The compound of claim 12,"
With:
--13. The compound of claim 10,--

Signed and Sealed this
Fourth Day of June, 2024

Katherine Kelly Vidal
*Director of the United States Patent and Trademark Office*